United States Patent
Atamanyuk et al.

(10) Patent No.: US 10,301,305 B2
(45) Date of Patent: May 28, 2019

(54) HETEROAROMATIC DERIVATIVES AND THEIR USE AS PHARMACEUTICALS

(71) Applicant: MUTABILIS, Paris (FR)

(72) Inventors: Dmytro Atamanyuk, Chelles (FR); Francis Chevreuil, Chantilly (FR); Fabien Faivre, Drancy (FR); Nicolas Lecointe, Saint Denis (FR); Benoît Ledoussal, Pommerit Jaudy (FR); Chrystelle Oliveira, Ermont (FR); Christophe Simon, Chevilly la Rue (FR); Vincent Gerusz, Neuvecelle (FR)

(73) Assignee: MUTABILIS, Paris (FR)

( * ) Notice: Subject to any disclaimer, the term of this patent is extended or adjusted under 35 U.S.C. 154(b) by 0 days.

(21) Appl. No.: 15/121,103

(22) PCT Filed: Feb. 24, 2015

(86) PCT No.: PCT/EP2015/053857
§ 371 (c)(1),
(2) Date: Aug. 24, 2016

(87) PCT Pub. No.: WO2015/128333
PCT Pub. Date: Sep. 3, 2015

(65) Prior Publication Data
US 2017/0015661 A1    Jan. 19, 2017

(30) Foreign Application Priority Data

Feb. 27, 2014 (EP) ..................................... 14305285

(51) Int. Cl.
*C07D 471/04* (2006.01)
*A61K 31/437* (2006.01)
(Continued)

(52) U.S. Cl.
CPC ........ *C07D 471/04* (2013.01); *A61K 31/4184* (2013.01); *A61K 31/423* (2013.01); *A61K 31/428* (2013.01); *A61K 31/436* (2013.01); *A61K 31/437* (2013.01); *A61K 31/4355* (2013.01); *A61K 31/4375* (2013.01); *A61K 31/4439* (2013.01); *A61K 31/454* (2013.01); *A61K 31/4545* (2013.01); *A61K 31/4709* (2013.01); *A61K 31/4725* (2013.01); *A61K 31/496* (2013.01); *A61K 31/498* (2013.01); *A61K 31/506* (2013.01); *A61K 31/538* (2013.01); *A61K 31/5383* (2013.01); *A61K 45/06* (2013.01); *C07D 235/04* (2013.01);
(Continued)

(58) Field of Classification Search
CPC .. C07D 235/08; C07D 519/00; C07D 498/06; C07D 491/052; C07D 471/04
USPC ................................................... 514/210.21
See application file for complete search history.

(56) References Cited

U.S. PATENT DOCUMENTS

| 5,523,408 A | 6/1996 | Batt et al. |
| 7,615,628 B2 | 11/2009 | Hirao et al. |

(Continued)

FOREIGN PATENT DOCUMENTS

| GB | 2480816 A | * 12/2011 |
| JP | 2006-199617 A1 | 8/2006 |

(Continued)

OTHER PUBLICATIONS

Chang; J. Med. Chem. 2007, 50, 828-834.*

(Continued)

*Primary Examiner* — Daniel R Carcanague
(74) *Attorney, Agent, or Firm* — Duane Morris LLP

(57) ABSTRACT

The invention relates to the compounds (I) and their acids and bases salts: wherein: Formula (I) the dotted line indicates a double bond; X is N or C—$R_1$ and Y is N or C—$R_2$, X and Y not being simultaneously N; A is selected from the group consisting of phenyl, naphthyl and (5-11) membered monocyclic or bicyclic unsaturated cycle or heterocycle possibly substituted as defined in the application, and A can also comprise either a further (4-7) membered heterocycle, said heterocycle being a monocycle, fused, saturated or unsaturated, the polycyclic system then comprising up to 14 members and up to 5 heteroatoms selected from N, O and S; B is selected from the group of substituents as defined in the application, or B is a 4 or (6-10) membered mono or bicyclic saturated or unsaturated heterocycle containing 1-3 heteroatoms selected from N, O and S, linked by a carbon atom, and possibly substituted as defined in the application; $R_1$ is Hydrogen or a substituent as defined in the application; $R_2$ is Hydrogen or Halogen; their preparation, their use in the antibacterial prevention and therapy, alone or in association with antibacterials, antivirulence agents or drugs reinforcing the host innate immunity, and pharmaceutical compositions and associations containing them.

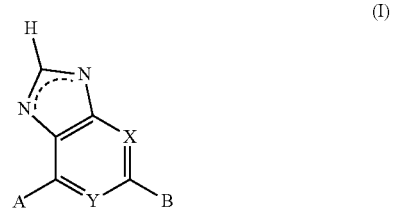

(I)

10 Claims, No Drawings

(51) Int. Cl.

| | | |
|---|---|---|
| A61K 31/4545 | (2006.01) | |
| C07D 519/00 | (2006.01) | |
| C07D 403/14 | (2006.01) | |
| A61K 31/4184 | (2006.01) | |
| C07D 401/14 | (2006.01) | |
| A61K 31/454 | (2006.01) | |
| C07D 487/04 | (2006.01) | |
| C07D 403/04 | (2006.01) | |
| A61K 31/4439 | (2006.01) | |
| C07D 235/08 | (2006.01) | |
| A61K 31/496 | (2006.01) | |
| C07D 401/04 | (2006.01) | |
| C07D 405/14 | (2006.01) | |
| C07D 417/04 | (2006.01) | |
| A61K 31/428 | (2006.01) | |
| A61K 31/4709 | (2006.01) | |
| C07D 491/052 | (2006.01) | |
| A61K 31/436 | (2006.01) | |
| A61K 31/498 | (2006.01) | |
| C07D 413/04 | (2006.01) | |
| A61K 31/538 | (2006.01) | |
| C07D 498/06 | (2006.01) | |
| A61K 31/5383 | (2006.01) | |
| A61K 31/4725 | (2006.01) | |
| A61K 31/423 | (2006.01) | |
| A61K 31/4375 | (2006.01) | |
| A61K 31/4355 | (2006.01) | |
| C07D 491/048 | (2006.01) | |
| A61K 31/506 | (2006.01) | |
| A61K 45/06 | (2006.01) | |
| C07D 235/04 | (2006.01) | |
| C07D 405/04 | (2006.01) | |
| C07D 491/04 | (2006.01) | |

(52) U.S. Cl.
CPC ......... *C07D 235/08* (2013.01); *C07D 401/04* (2013.01); *C07D 401/14* (2013.01); *C07D 403/04* (2013.01); *C07D 403/14* (2013.01); *C07D 405/04* (2013.01); *C07D 405/14* (2013.01); *C07D 413/04* (2013.01); *C07D 417/04* (2013.01); *C07D 487/04* (2013.01); *C07D 491/04* (2013.01); *C07D 491/048* (2013.01); *C07D 491/052* (2013.01); *C07D 498/06* (2013.01); *C07D 519/00* (2013.01)

(56) References Cited

U.S. PATENT DOCUMENTS

| 2004/0186127 A1 | 9/2004 | Daun et al. | |
|---|---|---|---|
| 2006/0247263 A1 | 11/2006 | Siegmund | |
| 2008/0139608 A1* | 6/2008 | Chang | C07D 471/04 514/303 |
| 2011/0105427 A1* | 5/2011 | Daun | C07D 471/04 514/63 |
| 2013/0095057 A1* | 4/2013 | Johnson | A61K 31/424 424/78.1 |

FOREIGN PATENT DOCUMENTS

| JP | 2009046435 A | 3/2009 |
|---|---|---|
| WO | 96/04270 A1 | 2/1996 |
| WO | 2003/057696 A1 | 7/2003 |
| WO | 2006/077816 A1 | 7/2006 |
| WO | 2012/172043 A1 | 12/2012 |
| WO | 2015/004533 | 1/2015 |
| WO | 2015/116886 | 8/2015 |

OTHER PUBLICATIONS

Waldmann; Annu. Rev. Med. 2006, 57, 65-81. (Year: 2006).*
Cox; Inactivation of DltA Modulates Virulence Factor Expression in *Streptococcus* pyogenes. PLoS One 2009, 4(4): e5366. 10 pp. doi:10.1371/journal.pone.0005366. (Year: 2009).*
Unverified Machine Translation of "Notification of Reasons for Rejection dated Sep. 18, 2018 in corresponding Japanese Application No. 2016-554419". (Year: 2018).*
Boman, H.G., "Antibacterial peptides: basic facts and emerging concepts", Journal of Internal Medicine, 2003, 254, 197-215.
Bertsche, U. et al., "Correlation of Daptomycin Resistance in a Clinical *Staphylococcus aureus* Strain with Increased Cell Wall Teichoic Acid Production and D-Alanylation", Antimicrobial Agents and Chemotherapy, Aug. 2011, vol. 55, No. 8, 3922-3928.
May, J.J. et al., "Inhibition of the D-alanine:D-alanyl carrier protein ligase from *Bacillus subtilis* increases the bacterium's susceptibility to antibiotics that target the cell wall", FEBS Journal, 272 (2005) 2993-3003.
Peschel A. et al., "*Staphylococcus aureus* Strains Lacking D-Alanine Modifications of Teichoic Acids are Highly Susceptible to Human Neutrophil Killing and are Virulence Attenuated in Mice", The Journal of Infectious Diseases, 2002, 186, 214-219.
Poyart, C. et al., "Regulation of D-Alanyl-Lipoteichoic Acid Biosynthesis in *Streptococcus agalactiae* Involves a Novel Two-Component Regulatory System", Journal of Bacteriology, Nov. 2001, vol. 183, No. 21, 6324-6334.
Wu, Hsing-Ju et al., "Discovery of virulence factors of pathogenic bacteria", Current Opinion in Chemical Biology, 2008, 12, 93-101.
International Search Report and Written Opinion issued for corresponding International patent application No. PCT/EP2015/053857, dated Jun. 10, 2015, 8 pages.
Notification of Reasons for Rejection dated Sep. 18, 2018 in corresponding Japanese Application No. 2016-554419.

* cited by examiner

HETEROAROMATIC DERIVATIVES AND THEIR USE AS PHARMACEUTICALS

CROSS-REFERENCE TO RELATED APPLICATIONS

The present application is a U.S. national phase application filed under 35 U.S.C. § 371 of International Application No. PCT/EP2015/053857, which was filed Feb. 24, 2015, and which claims priority to European Application No. 14305285.0 filed on Feb. 27, 2014, both of which are incorporated herein by reference in their entirety.

The invention relates to novel heteroaromatic derivatives, their preparation and intermediates, their use as drugs and pharmaceutical compositions containing them.

The invention particularly relates to new compounds capable of inhibiting the activity of the Gram-positive bacterial DltA enzyme and their use to prevent and/or treat Gram-positive bacterial infections in humans or animals.

The emergence of antibiotic-resistant pathogens has become a serious worldwide healthcare problem. Indeed, some infections are now caused by multi-drug resistant organisms that are no longer responsive to currently available treatments. This issue has led to the search for innovative antibacterial approaches with novel modes of action. Among them the inhibition of virulence targets, a concept called antivirulence, is aiming at lessening or inhibiting the pathogenicity of a bacterium to its host (Curr. Opin. Chem. Biol. 2008, 12, 1). Potential advantages of this strategy over classical treatments lay in the preservation of the commensal flora as well as a selection pressure confined to the host tissues where the targeted virulence factor is essential for bacterial survival.

It is known that the extracellular bacteria responsible for serious infections are capable of growth in the extra cellular fluids and are resistant to the bactericidal action of the host innate immunity. This resistance of bacteria to the innate immunity components allows dissemination of the infection, via the blood, to the various tissues. The components of the innate immunity are either circulating molecules such as the complement factors, or the antibacterial peptides such as defensins, which could have bactericidal effects by direct interactions with the bacterium cell wall, or either circulating cells such as the polymorphonuclear leukocytes (PMNs) able to kill invading bacteria.

Among the many virulence factors described to be important for bacteria to resist the innate immunity components are the mechanisms involved in resistance to cationic antimicrobial peptides (CAMP). CAMP play a fundamental role in innate immune defenses, both through direct antimicrobial activity and through immunomodulatory effects (Boman et al., J Intern Med. 2003, 254(3), 197). The CAMP dominating targets are bacterial membranes and CAMP interact with negatively charged bacterial surface. One of the main mechanisms present in bacteria to decrease the negative charge of the cell wall is the addition of positively charged amino acid on structural element of the cell surface.

The dlt operon is responsible for D-alanine modification of cell wall teichoic acids, and its suppression has been linked to attenuated virulence in mice (Peschel et al., J. Infect. Dis. 2002, 186, 214). Among the different proteins expressed by this operon, DltA is a D-alanine:D-alanyl carrier protein ligase acting as the first enzyme controlling the D-alanylation of the teichoic acids as major components of Gram-positive cell wall: the lipoteichoic acids (LTA) and the wall teichoic acids (WTA). Mutant lacking the dltA gene resulted in the absence of D-Ala ester in the LTA (Poyart et al., J Bacteriol. 2001, 183, 6324). As a consequence, D-Ala deficient bacteria displayed a modification in the net charge of their cell surface and an increased susceptibility to various bactericidal compounds including cationic antimicrobial peptides and Vancomycin (FEBS Journal 2005, 272, 2993). Resistance to Daptomycin was shown to correlate with higher dltA expression, and higher level of wall teichoic acids D-Alanylation (Bertsche et al., Antimicrob Agents Chemother. 2011 55, 3922).

Because the dlt operon is conserved in many Gram positive bacteria of medical relevance, such inhibitors would be useful in rendering invading bacteria sensitive to killing by the innate immunity mechanism of the host, allowing eradication or prevention of the infection by a new mechanism of action when compared to current antibiotic treatment.

As antivirulent target, DltA is still largely unexploited at this time since there are no drugs on market nor on advanced clinical phases. Only very few derivatives that display a selective spectrum of activity on species containing DltA have been reported.

The novel compounds of the present invention are based on innovative heteroaromatic bicyclic systems and unexpectedly display an especially interesting spectrum of activity on Gram-positive bacteria. The prior art is essentially constituted by derivatives as those described in WO2012172043A1, JP2009046435A, WO9604270A1, US20060247263, JP5002851, WO2006077816, US20040186127 and WO2003057696. To the knowledge of the applicant, only the purine derivatives described in WO2012172043A1 have been reported in the therapeutic domain of the invention. With respect to these purine derivatives, the level of activity of the compounds of the present invention is significantly higher.

One of the purposes of the present invention is therefore to provide novel compounds active on DltA and related targets. Among other properties, these compounds advantageously modify the surface charge of the Gram-positive cell wall by inhibiting the D-Alanylation of the teichoic acids. As a consequence they can display synergistic effects with components of the innate immune system like CAMP such as alpha-defensins, beta-defensins or peptides of the cathelicidin family. As bacterial cell wall modifiers, they could also be associated and synergize with drugs aiming at treating bacterial infections such as compounds reinforcing the innate immunity of the host, or antibacterials and more specifically with compounds targeting the bacterial cell wall and/or membrane, or for which the bacterial cell wall and/or membrane are a limiting step for penetration. Such compounds include any antibiotics, and more specifically glycopeptides like vancomycin, lipopeptides like daptomycin, antimicrobial peptides like polymixins, cathelicidins, defensins or any synthethic or natural peptide derived from the above listed ones. The association of a DltA inhibitor and an antibacterial could, by lowering the active dose of the antibacterial, expand its therapeutic window.

The invention relates to compounds having the general formula (I)

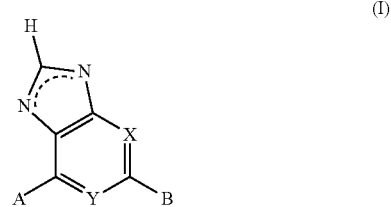

wherein:

the dotted line indicates a double bond in either of the possible positions between C and one N;

X is N or C—$R_1$ and Y is N or C—$R_2$, X and Y not being simultaneously N;

A is selected from the group consisting of phenyl, naphthyl and (5-11) membered monocyclic or bicyclic unsaturated cycle or heterocycle linked by a carbon atom and containing 1-4 heteroatoms selected from N, O and S, all the above members of the group representing A being possibly substituted on carbon or nitrogen atoms by 1-4 identical or different groups $R_3$, and A can also comprise either a further (4-7) membered heterocycle formed with $R_3$, said heterocycle being a monocycle, fused, saturated or unsaturated, and closed with $R_3$ by a simple bond or a double bond, or a further (4-7) membered monocycle formed by two substituents $R_3$ one with the other, said monocycle being then fused, saturated or unsaturated, and the two $R_3$ being linked together by a simple bond or a double bond, the polycyclic system representing A with $R_3$ then comprising up to 14 members and up to 5 heteroatoms selected from N, O and S;

B is selected from the group consisting of Halogen, CN, $NR_4R_5$, $(C_2-C_6)$Alkyl, $(C_3-C_{12})$Cycloalkyl, O—$(C_1-C_6)$Alkyl, O—$(C_1-C_6)$Alkyl-$R_7$, O—$R_7$, O—$(C_3-C_{12})$Cycloalkyl, S—$(C_1-C_6)$Alkyl, S—$(C_3-C_{12})$Cycloalkyl, $(C_2-C_6)$Alkenyl, $(C_6-C_8)$Cycloalkenyl, O—$(C_5-C_8)$Cycloalkenyl and $(C_2-C_6)$Alkynyl, the Alkyl, Cycloalkyl, Alkenyl, Cycloalkenyl and Alkynyl groups being possibly substituted by 1 to 3 identical or different substituents selected from $OR_a$, $C(O)OR_a$, $C(O)NR_aR_b$, $(C_1-C_6)$Alkyl, O—$(C_7-C_{12})$Aralkyl, $(C_1-C_6)$Alkyl-$OR_a$, $(C_1-C_6)$Alkyl-$SR_a$, $(C_1-C_6)$Alkyl-$NR_aR_b$, and $NR_4R_5$;

or B is a 4 or (6-10) membered mono or bicyclic saturated or unsaturated heterocycle containing 1-3 heteroatoms selected from N, O and S, linked by a carbon atom, and possibly substituted by 1 to 3 groups identical or different $R_6$;

$R_1$ is selected from the group consisting of Hydrogen, $NO_2$, $NR_aR_b$, CN, $C(Hal)_n$, $C(S)NR_aR_b$, $S(O)_2NR_aR_b$, $(C_1-C_6)$Alkyl, $(C_3-C_{12})$Cycloalkyl, O—$(C_1-C_6)$Alkyl, O—$(C_3-C_{12})$Cycloalkyl, O—$C(O)OR_a$, $C(O)NR_aR_b$, $C(O)OR_a$, $C(O)R_a$, $C(O)N(R_a)OR_b$, $C(O)N(R_a)NR_bR_c$, $C(O)N(R_a)$ CN, $NR_aC(O)R_b$, $C(O)N(R_a)C(O)R_b$ and $C(O)$Pyrrolidinyl, the Alkyl, Cycloalkyl and Pyrrolidinyl being possibly substituted 1 to 3 identical or different substituents selected from $OR_a$, $NR_aR_b$, CN, $(C_1-C_6)$Alkyl-$OR_a$ and $C(O)NR_aR_b$;

$R_2$ is selected from the group consisting of Hydrogen and Halogen;

$R_3$ is selected from the group consisting of Hydrogen, Hal, CN, $C(Hal)_n$, O—$C(Hal)_n$, $NO_2$, $(C_1-C_6)$Alkyl, $(C_3-C_{12})$Cycloalkyl, =O, =N—O—$(C_1-C_6)$Alkyl, =N—O—$(C_3-C_{12})$Cycloalkyl, $C(O)R_a$, $C(O)OR_a$, $C(=NOR_a)R_b$, $C(O)NR_aR_b$, O—$R_a$, $NR_4R_5$ and $NR_aC(O)R_b$, Alkyl and Cycloalkyl being possibly substituted by 1 to 3 identical or different substituents selected from Halogen, $(C_1-C_6)$Alkyl, $(C_3-C_{12})$Cycloalkyl, $OR_a$ and $NR_4R_5$, or $R_3$ is phenyl or a (4-8) membered monocyclic saturated or unsaturated heterocycle containing 1-3 heteroatoms selected from N, O and S, both possibly substituted by 1 to 3 identical or different substituents selected from $OR_a$, Halogen, $(C_1-C_6)$Alkyl, $NR_4R_5$ and $(C_3-C_{12})$Cycloalkyl, or $R_3$ forms with A, or forms within A with another $R_3$, a cycle defined above;

$R_4$ and $R_5$, identical or different, are selected from the group consisting of Hydrogen, $(C_1-C_6)$Alkyl, $(C_3-C_{12})$Cycloalkyl, $C(O)R_a$, $C(O)NR_aR_b$, $C(O)OR_a$, $S(O)_2(C_1-C_6)$Alkyl, $S(O)_2(C_3-C_{12})$Cycloalkyl and $OR_a$, all the preceeding Alkyl and Cycloalkyl being possibly substituted by 1 to 3 identical or different substituents selected from Halogen, $OR_a$, $NR_aR_b$, $N(R_a)C(O)R_b$, $S(O)_2(C_1-C_6)$Alkyl, $S(O)_2(C_3-C_{12})$Cycloalkyl, $C(O)OR_a$, $C(O)R_a$, and $C(O)NR_aR_b$, or $R_4$ and $R_5$ are selected from the group consisting of $(C_1-C_6)$Alkyl and $(C_3-C_{12})$Cycloalkyl substituted by a (3-10) membered mono or bicyclic saturated or unsaturated heterocycle possibly containing 1-3 heteroatoms selected from N, O and S, and possibly substituted by 1 to 3 identical or different substituents $(C_1-C_6)$Alkyl, $(C_3-C_{12})$Cycloalkyl or $C(O)R_a$, or $R_4$ and $R_5$ form together with N a (4-10) membered saturated or unsaturated mono or bicyclic heterocycle possibly containing another heteroatom selected from N, O and S and possibly substituted by 1 to 3 identical or different groups $R_6$;

$R_6$ is selected from the group consisting of Halogen, $(C_1-C_6)$Alkyl, $(C_3-C_{12})$Cycloalkyl, =O, CN, $C(O)R_a$, $C(O)OR_a$, $C(O)NR_aR_b$, O—$R_a$, $NR_aC(O)R_b$ and $NR_aR_b$, all the Alkyl and Cycloalkyl groups being possibly substituted by 1 to 3 identical or different substituents selected from $OR_a$ and $NR_aR_b$;

$R_7$ is phenyl or (4-10) membered monocyclic or bicyclic saturated or unsaturated heterocycle containing 1-3 heteroatoms selected from N, O and S, both possibly substituted by 1 to 3 identical or different substituents selected from Halogen, $(C_1-C_6)$Alkyl, $(C_3-C_{12})$Cycloalkyl, $NR_aR_b$, $C(O)NR_aR_b$, $C(Hal)$ and $OR_a$;

$R_a$ and $R_b$, identical or different, are selected from the group consisting of Hydrogen, $(C_1-C_6)$Alkyl, and $(C_3-C_{12})$Cycloalkyl, all the Alkyl and Cycloalkyl groups being possibly substituted by 1 to 3 identical or different substituents selected from OH, O—$(C_1-C_6)$Alkyl and O—$(C_3-C_{12})$Cycloalkyl; and n is 1 to 3.

Also included in the invention are the addition salts of the compounds of formula (I) with acids and bases, the tautomeric forms of the compounds of formula (I), as well as the racemic mixtures, the pure enantiomers and the non racemic (scalemic) mixture of enantiomers and diastereoisomers, in case the compounds of formula (I) have one or more chiral centers, both the cis (Z) and trans (E) isomers as well as their mixtures in case the compounds of formula (I) have unsaturated carbon carbon double bonds.

According to the conditions of the medium, the compounds of formula (I) exist under either of the

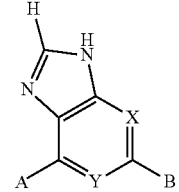

(Ia)

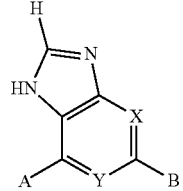

(Ib)

tautomeric forms presented by the following formulae (Ia) and (Ib):

Hereafter in the application, by commodity, the compounds have all been represented under formula (Ia).

Among the acid salts of the compounds of formula (I), there may be cited, among others, those formed with mineral acids, such as hydrochloric, hydrobromic, hydroiodic, sulfuric or phosphoric acid or with organic acids such as formic, acetic, trifluoroacetic, propionic, benzoic, maleic, fumaric, succinic, tartaric, citric, oxalic, glyoxylic, aspartic, alkanesulfonic acids such as methanesulfonic and ethanesulfonic acids, arylsulfonic acids such as benzenesulfonic and paratoluenesulfonic acids.

Among the base salts of the compounds of formula (I), there may be cited, among others, those formed with mineral alkalis such as, for example, sodium, potassium, lithium, calcium, magnesium or ammonium or organic bases such as, for example, methylamine, ethylamine, propylamine, trimethylamine, diethylamine, triethylamine, N,N-dimethylethanolamine, tris(hydroxymethyl)aminomethane, ethanolamine, pyridine, piperidine, piperazine, picoline, dicyclohexylamine, morpholine, benzylamine, procaine, lysine, arginine, histidine, N-methylglucamine.

In the general formula (I), as applied herein and wherever they appear:

"$(C_1-C_6)$Alkyl" or "$(C_2-C_6)$Alkyl" means any linear or branched hydrocarbon groups having 1 (or 2) to 6 carbon atoms and preferably methyl, ethyl, propyl, butyl, pentyl or hexyl, isopropyl, isobutyl, 1-methylbutyl, isopentyl, neopentyl, 2,2-dimethylbutyl, 2-methylpentyl, 3-methylpentyl, isohexyl, sec-butyl, tert-butyl and tert-pentyl;

"$(C_3-C_{12})$Cycloalkyl" means cyclopropyl, cyclobutyl, cyclopentyl, cyclohexyl, cycloheptanyl and tetrahydronaphtyl;

"$(C_7-C_{12})$Aralkyl" means any linear or branched hydrocarbon group substituted by phenyl or naphthyl and preferably benzyl or phenethyl;

"$(C_2-C_6)$Alkenyl" means any linear, i.e—straight-chain, branched hydrocarbon groups of 2 to 6 carbon atoms having at least one double bond and preferably ethenyl, 1-propenyl, 2-propenyl, 2-butenyl, 3-butenyl, 2-methyl-2-butenyl, 3-methyl-2-butenyl, 5-hex enyl and 1,3-pentadienyl;

"$(C_6-C_8)$Cycloalkenyl" means cyclohexenyl, cycloheptenyl and cyclooctenyl;

"$(C_2-C_6)$Alkynyl" means any linear or branched hydrocarbon groups of 2 to 6 carbon atoms, having at least one triple bond and preferably ethynyl, 1-propynyl, 2-propynyl (=propargyl) and 2-butynyl;

"Halogen" or "Hal" means F, Cl, Br or I and preferably F or Cl;

"(5-11) membered monocyclic or bicyclic unsaturated cycle or heterocycle containing 1-4 heteroatoms selected from N, O and S" means any possible cyclic unsaturated, including aromatic, system and preferably azaindolyl, benzimidazolyl, benzodioxanyl, benzodioxolyl, benzofuranyl, benzoisothiazolyl, benzoisoxazolyl, benzopyranyl, benzothiazolyl, benzothiophenyl, benzoxazolyl, benzoxazinyl, cinnolinyl, coumarinyl, dihydropyranopyridinyl, dioxinopyridinyl, furanopyridinyl, furanyl, imidazolyl, imidazopyridinyl, imidazopyrimidinyl, imidazoquinolinyl, imidazoquinoxalinyl, indanyl, indazolyl, indolinyl, indolyl, isoindolyl, isoquinolinyl, isothiazolidinyl, isothiazolopyridinyl, isothiazolopyrimidinyl, isothiazolyl, isoxazolopyridinyl, isoxazolopyrimidinyl, isoxazolyl, naphtyridinyl, oxadiazabenzocycloheptenyl, oxadiazaacenaphtylenyl, oxadiazolyl, oxazolopyridinyl, oxazolopyrimidinyl, oxazolopyrazinyl, oxazolopyridazinyl, oxazolyl, oxoazabenzocycloheptenyl, oxodiazabenzocycloheptenyl, phtalazinyl, pteridinyl, purinyl, pyranopyridazinyl, pyranopyrazinyl, pyranopyridinyl, pyranopyrimidinyl, pyrazinyl, pyrazolopyrazinyl, pyrazolopyridinyl, pyrazolopyrimidinyl, pyrazolotriazinyl, pyrazolyl, pyridazinyl, pyridinyl, pyrimidinyl, pyridoazepinyl, pyridooxazinyl, pyrrolopyridinyl, pyrrolyl, quinolinyl, quinoxalinyl, tetrahydronaphtyl, tetrazolyl, thiadiazolyl, thiatriazaindenyl, thiazolopyridinyl, thiazolopyrimidinyl, thiazolopyrazinyl, thiazolopyridazinyl, thiazolyl, thienopyridinyl, thienopyrimidinyl, thiophenyl, thiopyranyl, triazolyl, triazinyl, triazolopyridinyl, triazolopyrimidinyl, and, if appropriate, their partially saturated analogs;

"(4-7) membered monocyclic saturated or unsaturated heterocycle" means for example azepanyl, azetidinyl, beta-lactamyl, diazepanyl, dihydrofuranonyl, dioxanonyl, dioxanyl, dioxolanyl, 1,1-dioxidethiophenyl, furanonyl, furanyl, imidazolidinonyl, imidazolidinyl, imidazolyl, imidazolonyl, isothiazolidinonyl, isothiazolidinyl, isothiazolonyl, isothiazolyl, isoxazolonyl, isoxazolyl, morpholinyl, oxazolidinonyl, oxazolidinyl, oxazolonyl, oxazolyl, oxepanyl, oxetanyl, perhydroazepinyl, piperazinonyl, piperazinyl, piperidinonyl, piperidinyl, pyranonyl, pyranyl, pyrazinyl, pyrazolonyl, pyrazolyl, pyridazinonyl, pyridazinyl, pyridinonyl, pyridinyl, pyrimidinonyl, pyrimidinyl, pyrrolidinedionyl, pyrrolidinonyl, pyrrolidinyl, pyrrolyl, tetrahydrofuranyl, tetrahydropyranonyl, tetrahydropyranyl, thiazolidinonyl, thiazolidinyl, thiazolonyl, thiazolyl, thiophenyl, thiopyranyl, triazolyl, and if appropriate, their partially saturated analogs;

"Polycyclic system representing A with $R_3$, comprising up to 14 members and up to 5 heteroatoms" or A with two groups $R_3$ means for example diazabenzazulenyl, imidazoquinolinyl, imidazoquinoxalinyl, oxadiazabenzazulenyl, oxadiazaacenaphtylenyl, triazabenzazulenyl, and, if appropriate, their partially saturated analogs;

"4 or (6-10) membered mono or bicyclic saturated or unsaturated heterocycle" in the definition of B means for example azabicyclo[3.2.0]heptanyl, azabicyclo[3.1.0]hexanyl, azabicyclo[3.3.0]octanyl, azepinyl, azetidinyl, azocinyl, diazocinyl, diazepinyl, dioxanyl, morpholinyl, oxepanyl, oxetanyl, piperazinonyl, piperazinyl, piperidinyl, pyranyl, thiomorpholinyl, and, if appropriate, their partially unsaturated analogs;

"(4-8) membered monocyclic saturated or unsaturated heterocycle containing 1-3 heteroatoms selected from N, O and S" in the definition of $R_3$ means for example oxepanyl, oxetanyl, oxocanyl, pyranyl, furanyl;

"(3-10) membered mono or bicyclic saturated or unsaturated heterocycle" as mentioned in the definition of $R_4$ and $R_5$ means for example azepinyl, azetidinyl, benzimidazolyl, benzofuranyl, benzothiazolyl, benzothiophenyl, benzoxazolyl, cyclobutyl, cyclohexyl, cyclopentyl, cyclopropyl, dioxanyl, furanyl, imidazolyl, indolyl, isoindolyl, isoquinolinyl, isothiazolyl, isoxazolyl, morpholinonyl, morpholinyl, oxazolyl, oxetanyl, piperazinyl, piperidinonyl, piperidinyl, pyranyl, pyrazinyl, pyridazinyl, piperidinyl, pyrazolyl, pyridinonyl, pyridinyl, pyrimidinyl, pyrrolidinyl, pyrrolyl, quinolinyl, tetrahydrofuranyl, tetrazolyl, thiazolyl, thiomorpholinyl, thiophenyl, triazolyl, and, if appropriate, their partially saturated or unsaturated analogs;

"(4-10) membered saturated or unsaturated mono or bicyclic heterocycle" as formed by $R_4$ and $R_5$ together with N means for example azabicyclo[3.2.0]heptanyl, azabicyclo[3.1.0]hexanyl, azabicyclo[3.3.0]octanyl azetidinyl, bis-pyrrolidinyl, azetidinyl, azepanyl, morpholinyl, piperazinonyl, piperazinyl, piperidinyl and pyrrolidinyl.

"(4-10) membered monocyclic or bicyclic saturated or unsaturated heterocycle" as mentioned in the definition of $R_7$ means for example azetidinyl, pyrrolidinyl, piperidinyl, pyridinyl, azepanyl, oxetanyl, furanyl, tetrahydrofuranyl, pyranyl, azabicyclo[3.1.0]hexanyl, piperazinyl, imidazolyl, pyrrolyl and pyrazolyl.

According to a particular embodiment, the invention relates to compounds of general formula (I) as defined above, wherein:

X is C—$R_1$, $R_1$ being as defined above,

B is selected from the group consisting of Halogen, CN, $NR_4R_5$, $(C_2-C_6)$Alkyl, $(C_3-C_{12})$Cycloalkyl, O—$(C_1-C_6)$Alkyl, O—$(C_1-C_6)$Alkyl-$R_7$, O—$R_7$, O—$(C_3-C_{12})$Cycloalkyl, O—$(C_5-C_8)$Cycloalkenyl, S—$(C_1-C_6)$Alkyl and S—$(C_3-C_{12})$Cycloalkyl, the Alkyl and Cycloalkyl groups being possibly substituted by 1 to 3 identical or different substituents selected from $OR_a$, $C(O)OR_a$, $(C_1-C_6)$Alkyl, O—$(C_7-C_{12})$Aralkyl, $(C_1-C_6)$Alkyl-$OR_a$, $(C_1-C_6)$Alkyl-$NR_aR_b$, $C(O)NR_aR_b$ and $NR_4R_5$, or B is a 4 or (6-10) membered mono or bicyclic saturated or unsaturated heterocycle containing 1-3 heteroatoms selected from N, O and S, linked by a carbon atom, and possibly substituted by 1 to 3 identical or different substituents $R_6$, all the other definitions being as above.

According to another particular embodiment, the invention relates to compounds of general formula (I) as defined above, wherein $R_1$ is selected from the group consisting of $NO_2$, CN, C(O)OH and $C(O)NR_aR_b$.

According to another particular embodiment, the invention relates to compounds of general formula (I) as defined above, wherein A is selected from the group consisting of phenyl and (5-11) membered monocyclic or bicyclic unsaturated cycle or heterocycle linked by a carbon atom and containing 1-4 heteroatoms selected from N, O and S, all the above members of the group representing A being possibly substituted on carbon or nitrogen atoms by 1-4 identical or different groups $R_3$.

According to another particular embodiment, the invention relates to compounds of general formula (I) as defined above, wherein B is selected from the group consisting of $NR_4R_5$, O—$R_7$ or O—$(C_1-C_6)$Alkyl, the Alkyl group being possibly substituted by $R_7$ or by 1 to 3 identical or different substituents selected from $OR_a$, $C(O)OR_a$, $C(O)NR_aR_b$, $(C_1-C_6)$Alkyl, O—$(C_7-C_{12})$Aralkyl, $(C_1-C_6)$Alkyl-$OR_a$, $(C_1-C_6)$Alkyl-$NR_aR_b$ and $NR_4R_5$.

Among the compounds of the invention, there may be cited the following compounds:
{(S)-1-[7-(1-Cyclohexyl-1H-benzimidazol-5-yl)-3H-imidazo[4,5-b]pyridin-5-yl]-pyrrolidin-3-yl}-methanol,
(3R,4R)-1-[7-(1-Cyclohexyl-1H-benzimidazol-5-yl)-3H-imidazo[4,5-b]pyridin-5-yl]-4-hydroxymethyl-piperidin-3-ol,
{1-[7-(1-Cyclohexyl-1H-benzimidazol-5-yl)-3H-imidazo[4,5-b]pyridin-5-yl]-piperidin-4-yl}-methanol,
2-[7-(1-Cyclohexyl-1H-benzimidazol-5-yl)-3H-imidazo[4,5-b]pyridin-5-ylamino]-ethanol,
{1-[7-(1-Cyclohexyl-1H-benzimidazol-5-yl)-3H-imidazo[4,5-b]pyridin-5-yl]-azetidin-3-yl}-methanol,
{1-[7-(1-Cyclohexyl-1H-benzimidazol-5-yl)-3H-imidazo[4,5-b]pyridin-5-yl]-4-hydroxymethyl-piperidin-4-yl}-methanol,
7-(1-Cyclohexyl-1H-benzimidazol-5-yl)-5-(hexahydro-pyrrolo[3,4-c]pyrrol-2-yl)-3H-imidazo[4,5-b]pyridine,
{(S)-1-[4-(1-Cyclohexyl-3H-benzimidazol-5-yl)-1H-imidazo[4,5-c]pyridin-6-yl]-pyrrolidin-3-yl}-methanol,
{1-[4-(1-Cyclohexyl-1H-benzimidazol-5-yl)-1H-imidazo[4,5-c]pyridin-6-yl]-4-hydroxymethyl-piperidin-4-yl}-methanol,
{1-[4-(1-Cyclohexyl-1H-benzimidazol-5-yl)-1H-imidazo[4,5-c]pyridin-6-yl]-piperidin-4-yl}-methanol,
4-(1-cyclohexyl-1H-benzimidazol-5-yl)-1H-imidazo[4,5-c]pyridine-7-carboxamide,
[(S)-1-(1'-Cyclohexyl-7-nitro-1H,1'H-[4,5]bibenzimidazolyl-6-yl)-pyrrolidin-3-yl]-methanol,
(3R,4R)-1-(1'-Cyclohexyl-7-nitro-1H,1'H-[4,5]bibenzimidazolyl-6-yl)-4-hydroxymethyl-piperidin-3-ol,
(3R,4R)-1-(7-Amino-1'-cyclohexyl-1H,1'H-[4,5]bibenzimidazolyl-6-yl)-4-hydroxymethyl-piperidin-3-ol,
Methyl 1'-Cyclohexyl-6-((S)-3-hydroxymethyl-pyrrolidin-1-yl)-1H,1'H-[4,5']bibenzimidazolyl-7-carboxylate,
1'-Cyclohexyl-6-((S)-3-hydroxymethyl-pyrrolidin-1-yl)-1H,1'H-[4,5']bibenzimidazolyl-7-carboxylic acid,
1'-Cyclohexyl-6-fluoro-1H,1'H-[4,5']bibenzimidazolyl-7-carboxylic acid,
1'-Cyclohexyl-6-((S)-3-hydroxymethyl-pyrrolidin-1-yl)-1H,1'H-[4,5']bibenzimidazolyl-7-carbonitrile,
[(S)-1-(1'-Cyclohexyl-7-trifluoromethyl-1H,1'H-[4,5']]bibenzimidazolyl-6-yl)-pyrrolidin-3-yl]-methanol,
[1-(1'-Cyclohexyl-7-trifluoromethyl-1H,1'H-[4,5']bibenzimidazolyl-6-yl)-piperidin-4-yl]-methanol,
1'-Cyclohexyl-6-(hexahydro-pyrrolo[3,4-c]pyrrol-2-yl)-1H,1'H-[4,5']bibenzimidazolyl-7-carbonitrile,
1'-Cyclohexyl-6-((S)-3-hydroxymethyl-pyrrolidin-1-yl)-1H,1'H-[4,5']bibenzimidazolyl-7-carboxamide,
1'-Cyclohexyl-6-[3-(2-hydroxy-ethyl)-pyrrolidin-1-yl]-1H,1'H-[4,5']bibenzimidazolyl-7-carboxamide,
1'-Cyclohexyl-6-(2-hydroxy-ethylamino)-1H,1'H-[4,5']]bibenzimidazolyl-7-carbonitrile,
N-[2-(7-Cyano-1'-cyclohexyl-1H,1'H-[4,5']]bibenzimidazolyl-6-ylamino)-ethyl]-acetamide,
6-Methoxy-1'-(1-methyl-cyclohexyl)-1H,1'H-[4,5']bibenzimidazolyl-7-carboxamide,
1'-Cyclohexyl-6-piperazin-1-yl-1H,1'H-[4,5']]bibenzimidazolyl-7-carbonitrile,
1'-Cyclohexyl-6-(4-methyl-piperazin-1-yl)-1H,1'H-[4,5']]bibenzimidazolyl-7-carbonitrile,
1'-Cyclohexyl-6-(2-dimethylamino-ethoxy)-1H,1'H-[4,5']]bibenzimidazolyl-7-carbonitrile,
1'-Cyclohexyl-6-[(2-dimethylamino-ethyl)-methyl-amino]-1H,1'H-[4,5']bibenzimidazolyl-7-carboxamide,
1'-Cyclohexyl-6-fluoro-1H,1'H-[4,5']bibenzimidazolyl-N-hydroxy-7-carboxamide,
1'-Cyclohexyl-6-[(2-hydroxy-ethyl)-methyl-amino]-1H,1'H-[4,5']bibenzimidazolyl-7-carboxamide,
6-[(2-dimethylamino-ethyl)-methyl-amino]-1'-(tetrahydro-pyran-3-yl)-1H,1'H-[4,5']bibenzimidazolyl-7-carboxamide,
1'-((1R,2R)-2-fluoro-cyclohexyl)-6-[methyl-(2-methylamino-ethyl)-amino]-1H,1'H-[4,5']bibenzimidazolyl-7-carboxamide,
1'-Cyclohexyl-6-[methyl-(2-pyrrolidin-1-yl-ethyl)-amino]-1H,1'H-[4,5']bibenzimidazolyl-7-carboxamide,
1'-Cyclohexyl-6-[methyl-(1-methyl-pyrrolidin-2-ylmethyl)-amino]-1H,1'H-[4,5']bibenzimidazolyl-7-carboxamide,
1'-Cyclohexyl-6-[(2-diethylamino-ethyl)-methyl-amino]-1H,1'H-[4,5']bibenzimidazolyl-7-carboxamide,
1'-Cyclohexyl-6-[(2-dimethylamino-ethyl)-(2-hydroxy-ethyl)-amino]-1H,1'H-[4,5']bibenzimidazolyl-7-carboxamide,
1'-Cyclohexyl-6-[methyl-(tetrahydro-furan-2-ylmethyl)-amino]-1H,1'H-[45']bibenzimidazolyl-7-carboxamide,
6-[(2-Dimethylamino-ethyl)-methyl-amino]-1'-(2-methoxy-ethyl)-1H,1'H-[4,5']]bibenzimidazolyl-7-carboxamide, rac-1'-((trans)-3-methyl-cyclohexyl)-6-[methyl-(2-methyl-amino-ethyl)-amino]-1H,1'H-[4,5']bibenzimidazolyl-7-carboxamide,
5-[(2-Dimethylamino-ethyl)-methyl-amino]-7-quinolin-7-yl-3H-benzimidazole-4-carboxamide,
1'-Cyclohexyl-6-(2-dimethylamino-ethoxy)-1H,1'H-[4,5']]bibenzimidazolyl-7-carboxamide,
7-(3-Carbamoyl-4-methoxy-phenyl)-5-[(2-dimethylamino-ethyl)-methyl-amino]-3H-benzimidazole-4-carboxamide,
1'-Ethyl-6-[methyl-(2-methylamino-ethyl)-amino]-1H,1'H-[4,5']bibenzimidazolyl-7-carboxamide,
7-(3,4-Dihydro-2H-pyrano[2,3-b]pyridin-6-yl)-5-[(2-dimethylamino-ethyl)-methyl-amino]-3H-benzimidazole-4-carboxamide,
2-(1'-Cyclohexyl-6-fluoro-1H,1'H-[4,5']]bibenzimidazolyl-7-yl)-acetamide,
6-[(2-dimethylamino-ethyl)-methyl-amino]-1H,1'H-[4,5']bibenzimidazolyl-7-carboxamide,
5-[(2-Dimethylamino-ethyl)-methyl-amino]-7-(1-ethyl-2-oxo-1,2-dihydro-pyridin-4-yl)-3H-benzimidazole-4-carboxamide,
6-[(2-dimethylamino-ethyl)-methyl-amino]-1'-ethyl-7'-methoxy-1H,1'H-[4,5']]bibenzimidazolyl-7-carboxamide,
1'-Cyclohexyl-6-(2-pyrrolidin-1-yl-ethoxy)-1H,1'H-[4,5']]bibenzimidazolyl-7-carboxamide,
1'-(4,4-Difluoro-cyclohexyl)-6-[(2-dimethylamino-ethyl)-methyl-amino]-1H,1'H-[4,5']bibenzimidazolyl-7-carboxamide,
1'-(2,2-Difluoro-ethyl)-6-[(2-dimethylamino-ethyl)-methyl-amino]-1H,1'H-[4,5']bibenzimidazolyl-7-carboxamide,
7-(3,4-Dihydro-5-oxa-1,2a-diaza-acenaphthylen-7-yl)-5-[(2-dimethylamino-ethyl)-methyl-amino]-3H-benzimidazole-4-carboxamide,
1'-Cyclohexyl-6-[methyl-(2-piperidin-1-yl-ethyl)-amino]-1H,1'H-[4,5']bibenzimidazolyl-7-carboxamide,
1'-Cyclohexyl-6-(2-hydroxy-ethoxy)-1H,1'H-[4,5']bibenzimidazolyl-7-carboxamide,
1'-((1R,2R)-2-Fluoro-cyclohexyl)-6-[(2-hydroxy-ethyl)-methyl-amino]-1H,1'H-[4,5']]bibenzimidazolyl-7-carboxamide,
1'-Ethyl-7'-methoxy-6-[methyl-(2-pyrrolidin-1-yl-ethyl)-amino]-1H,1'H-[4,5']]bibenzimidazolyl-7-carboxamide,
7-(3,4-Dihydro-2H-pyrano[2,3-b]pyridin-6-yl)-5-[methyl-(2-pyrrolidin-1-yl-ethyl)-amino]-3H-benzimidazole-4-carboxamide,
7-(3,4-Dihydro-2H-pyrano[2,3-b]pyridin-6-yl)-5-(2-dimethylamino-ethoxy)-3H-benzimidazole-4-carboxamide,
6-(2-Dimethylamino-ethoxy)-1'-ethyl-1H,1'H-[4,5']]bibenzimidazolyl-7-carboxamide,
4-(5-cyclopropylpyridin-3-yl)-6-((2-(dimethylamino)ethyl)-(methyl)amino)-1H-benzo[d]imidazole-7-carboxamide,
7-(1-butylbenzimidazol-5-yl)-5-[2-(dimethylamino)ethyl-methyl-amino]-3H-benzimidazole-4-carboxamide,
5-[2-(dimethylamino)ethyl-methyl-amino]-7-(1-ethyl-7-fluoro-benzimidazol-5-yl)-3H-benzimidazole-4-carboxamide,
5-[2-(dimethylamino)ethyl-methyl-amino]-7-(5-pyrrolidin-1-yl-3-pyridyl)-3H-benzimidazole-4-carboxamide,
6-[2-(dimethylamino)ethyl-methyl-amino]-4-(1-ethylbenzimidazol-5-yl)-1H-imidazo[4,5-c]pyridine-7-carboxamide,
7-(3,4-dihydro-2H-pyrano[2,3-b]pyridin-6-yl)-5-[(1-methylpyrrolidin-2-yl)methoxy]-3H-benzimidazole-4-carboxamide,
5-[2-(dimethylamino)ethyl-methyl-amino]-7-(1-phenylbenzimidazol-5-yl)-3H-benzimidazole-4-carboxamide,
7-(3,4-dihydro-2H-pyrano[2,3-b]pyridin-6-yl)-5-[(1-methyl-3-piperidyl)oxy]-3H-benzimidazole-4-carboxamide,
7-(3,4-dihydro-2H-pyrano[2,3-b]pyridin-6-yl)-5-[[(2R)-1-methylpyrrolidin-2-yl]methoxy]-3H-benzimidazole-4-carboxamide,
5-[4,4-bis(hydroxymethyl)-1-piperidyl]-7-(1-cyclohexylbenzimidazol-5-yl)-3H-benzimidazole-4-carboxamide,
7-(3,4-dihydro-2H-pyrano[2,3-b]pyridin-6-yl)-5-(2-pyridylmethoxy)-3H-benzimidazole-4-carboxamide,
5-[2-(dimethylamino)ethyl-methyl-amino]-7-[6-(dimethylamino)-3-pyridyl]-3H-benzimidazole-4-carboxamide,
7-[1-[(1R,2R)-2-fluorocyclohexyl]benzimidazol-5-yl]-5-[[(2R)-pyrrolidin-2-yl]methoxy]-3H-benzimidazole-4-carboxamide,
5-[[(2R)-1-methylpyrrolidin-2-yl]methoxy]-7-(1-tetrahydropyran-3-ylbenzimidazol-5-yl)-3H-benzimidazole-4-carboxamide,
7-(3,4-dihydro-2H-pyrano[2,3-b]pyridin-6-yl)-5-[3-(dimethylamino)-1-piperidyl]-3H-benzimidazole-4-carboxamide,
and their salts, in particular their hydrochlorides, acetates, lactates, tartrates, citrates, 4-toluenesulfonates and methanesulfonates.

As indicated above, the compounds of the invention are active on DltA and related targets which makes them useful as drugs and another object of the invention is the use of the compounds of formula (I) as drugs for preventing or treating human or animal infections by microbial pathogens.

The drugs of the invention are useful as antibacterial agents for the prevention and therapeutical treatment of severe infections due to microbial pathogens, in particular Gram-positive bacteria growing under aerobic or anaerobic conditions. Such drugs are useful against bacteria of the genus *Staphylococcus*, more specifically *S. aureus* and coagulase-negative staphylococci like *S. epidermidis* and *S. saprophyticus* (including multiresistant strains such as methicillin-resistant staphylococci, vancomycin intermediate and vancomycin resistant *Staphylococcus aureus*), *Bacillus* (including *B. anthracis* and *B. cereus*), *Listeria* (including *L. monocytogenes*), *Enterococcus* (including *E. faecalis* and *E. faecium* including vancomycin resistant isolates), *Streptococcus* (including *S. pneumonia, S. agalactiae, S. pyogenes*, and streptococci of the *viridans* group) and *Corynebacterium* (including *C. diphtheriae, C. amicolatum, C. striatum, C. jeikeium, C. urealyticum*, and *C. xerosis*).

The drugs according to the invention are also for use in preventing and treating human or animal bacterial infections, in association with one or more drug(s) and more specifically with one or more antibacterial agent(s) or with one or more antivirulence agent(s) or with one or more drug(s) reinforcing the host innate immunity and this use of the compounds of formula (I) in association constitutes another object of the invention.

The invention relates in particular to the use of the compounds of formula (I) in preventing or treating human or animal bacterial infections in association with one or more antibacterial agent(s) targeting the bacterial cell wall and/or membrane.

The invention relates in particular to the use in preventing or treating human or animal bacterial infections, in association with one or more antibacterial agent(s) of the CAMP type such as, as non-limiting examples, polymyxins, cathelicidins, defensins or any synthethic or natural peptide derived from the above listed ones.

The invention relates in particular to the use in preventing or treating human or animal bacterial infections, in association with one or more antibacterial agent(s) of the glycopeptides type such as, as non-limiting examples, Vancomycin or Teicoplanin.

The invention relates in particular to the use in preventing or treating human or animal bacterial infections, in association with one or more antibacterial agent(s) of the lipopeptides type such as, as non-limiting examples, Daptomycin.

The invention relates in particular to the use in preventing or treating human or animal bacterial infections, in association with one or more drug(s) reinforcing the host innate immunity such as, as non-limiting examples, immunomodulatory peptides.

The invention relates in particular to the use in preventing or treating human or animal bacterial infections, in association with GM-CSF (Granulocyte Macrophage Colony-Stimulating Factor), an approved white blood cell growth factor.

A further object of the invention is therefore the pharmaceutical mixtures or associations of the compounds of formula (I) with the above defined antibacterials and/or antivirulence agents and/or drugs reinforcing the host innate immunity.

The invention also relates to pharmaceutical compositions comprising, as active principle, a therapeutically effective amount of at least one compound of formula (I) such as above defined, as well as pharmaceutical compositions comprising, as active principles, a therapeutically effective amount of at least one compound of formula (I) in association with at least another therapeutically active compound defined above. In the composition of the invention, the active principles are in association with a pharmaceutically acceptable carrier.

Said pharmaceutical compositions are advantageously formulated to be administered under oral, topical, transdermal, sublingual, rectal, parenteral including intravenous, intramuscular, intraperitoneal and subcutaneous routes, with individual doses appropriate for the patient to be treated. The injectable routes are preferred.

The compositions according to the invention can be solid, liquid including solutions, emulsions or suspensions, or in the form of a gel/cream and be presented in the pharmaceutical forms commonly used in human medicine, such as for example, plain or sugar-coated tablets, gelatin capsules, granules, suppositories, injectable preparations, ointments, creams, gels; they are prepared according to the customary methods. The active ingredient/s can be incorporated using excipients which are customarily used in these pharmaceutical compositions, such as talc, gum arabic, lactose, starch, magnesium stearate, aqueous or non-aqueous vehicles, fatty substances of animal or vegetable origin, paraffin derivatives, glycols, various wetting agents, dispersants or emulsifiers, preservatives. These compositions can in particular be presented in the form of a powder intended to be dissolved or suspended extemporaneously in an appropriate vehicle, for example, non-pyrogenic sterile water.

The dose of the compound of formula (I) administered varies according to the condition treated, the patient in question, the administration route and the compound envisaged. It can, for example, be comprised between 0.01 g and 10 g per day in humans. When the compound is administered in association, the dose of the associated active principle is the dose normally prescribed for such compound. For example, the compound of formula (I) can be administered in association with vancomycin at doses of 0.5 to 3 g per day in human (intravenous administration) or colistin at doses of 0.1 to 0.3 g per day in human (intravenous administration).

The compounds of formula (I) and their salts may be prepared by processes illustrated hereafter in the experimental part and more generally by using processes known to the skilled chemist to be applicable for preparing chemically related compounds. Such processes use known starting materials or intermediates which may be obtained by standard procedures of organic chemistry. The following processes provide a variety of non-limiting routes for the production of the compounds of formula (I) and their intermediates. These processes constitute further features of the present invention.

Compounds of formula (I), as defined above, may be prepared by reduction/cyclization of compounds of formula (II):

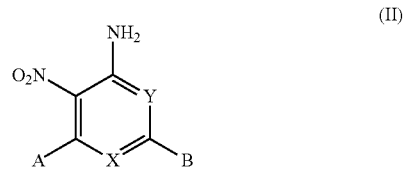

wherein X, Y, A and B are defined above,
in the presence of suitable reduction conditions known to the skilled in the art, non limiting examples comprising the use of a catalyst such as Palladium or iron in an appropriated solvent such as methanol, ethanol, propanol, butanol, ethyl acetate or tetrahydrofuran,
or the presence of suitable cyclization conditions known to the skilled in the art, non limiting examples comprising the use of formic acid, trimethyl orthoformate or triethyl orthoformate.

Compounds of formula (II), as defined above, may be prepared by reacting compounds of formula (III):

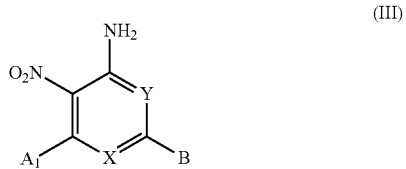

wherein X, Y and B are defined above and $A_1$ represents halogen, triflate or substituted boron, with compounds of formula (IV):

wherein A is defined above and U represents halogen, triflate or substituted boron,
in the presence of suitable metal transition coupling conditions known to the skilled in the art, non limiting examples comprising the use of a Palladium catalyst such as Tetrakis(triphenylphosphine)palladium, Dichloro[1,1'-bis(diphenylphosphino)ferrocene]palladium, Tris(dibenzylideneacetone)dipalladium or Bis(triphenylphosphine)palladium(II) dichloride, a base such as sodium or potassium carbonate, a phosphine ligand such as Xantphos or tricyclohexylphophine in an appropriate solvent such as dimethylformamide, dioxane, tetrahydrofuran or toluene.

Compounds of formula (II), as defined above, may also be prepared by reacting compounds of formula (V):

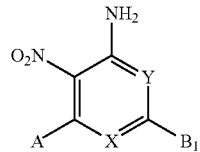

(V)

wherein X, Y and A are defined above and $B_1$ represents halogen,
with compounds of formula (VI):

(VI)

wherein B is defined above,
in the presence of suitable aromatic nucleophilic substitution conditions known to the skilled in the art, non limiting examples comprising the use of a base such as triethylamine, diisopropylethylamine, 1,8-diazabicyclo[5.4.0]undec-7-ene, sodium hydride, sodium or potassium carbonate in an appropriate solvent such as butanol, dimethylformamide, dioxane, dimethylsulfoxide, toluene, acetonitrile or tetrahydrofuran.

Compounds of formula (III), as defined above, may be prepared by reacting compounds of formula (VII):

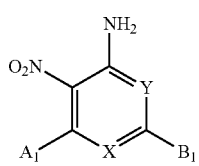

(VII)

Wherein X, Y, A1 and B1 are defined above,
with compounds of formula (VI), as defined above,
in the presence of suitable aromatic nucleophilic substitution conditions known to the skilled in the art, non limiting examples comprising the use of a base such as triethylamine, diisopropylethylamine, 1,8-diazabicyclo[5.4.0]undec-7-ene, sodium hydride, sodium or potassium carbonate in an appropriate solvent such as butanol, dimethylformamide, dioxane, dimethylsulfoxide, toluene, acetonitrile or tetrahydrofuran.

Compounds of formula (V), as defined above, may be prepared by reacting compounds of formula (VII), as defined above,
with compounds of formula (IV), as defined above,
in the presence of suitable metal transition coupling conditions known to the skilled in the art, non limiting examples comprising the use of a Palladium catalyst such as Tetrakis(triphenylphosphine)palladium, Dichloro[1,1'-bis(diphenylphosphino)ferrocene]palladium, Tris(dibenzylideneacetone)dipalladium or Bis(triphenylphosphine)palladium(II) dichloride, a base such as sodium or potassium carbonate, a phosphine ligand such as Xantphos or tricyclohexylphosphine in an appropriate solvent such as dimethylformamide, dioxane, tetrahydrofuran or toluene.

Compounds of formula (I), as defined above, may also be prepared by reacting compounds of formula (VIII):

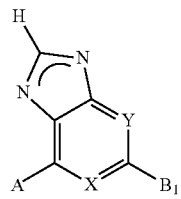

(VIII)

wherein X, Y, A and $B_1$ are defined above,
with compounds of formula (VI), as defined above,
in the presence of suitable aromatic nucleophilic substitution conditions known to the skilled in the art, non limiting examples comprising the use of a base such as triethylamine, diisopropylethylamine, 1,8-diazabicyclo[5.4.0]undec-7-ene, sodium hydride, sodium or potassium carbonate in an appropriate solvent such as butanol, dimethylformamide, dioxane, dimethylsulfoxide, toluene, acetonitrile or tetrahydrofuran.

Compounds of formula (I), as defined above, may also be prepared by reacting compounds of formula (IX):

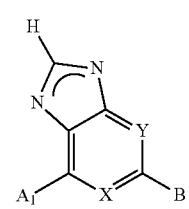

(IX)

wherein X, Y, B and $A_1$ are defined above,
with compounds of formula (IV), as defined above,
in the presence of suitable metal transition coupling conditions known to the skilled in the art, non limiting examples comprising the use of a Palladium catalyst such as Tetrakis(triphenylphosphine)palladium, Dichloro[1,1'-bis(diphenylphosphino)ferrocene]palladium, Tris(dibenzylideneacetone)dipalladium or Bis(triphenylphosphine)palladium(II) dichloride, a base such as sodium or potassium carbonate, a phosphine ligand such as Xantphos or tricyclohexylphopshine in an appropriate solvent such as dimethylformamide, dioxane, tetrahydrofuran or toluene.

Compounds of formula (VIII), as defined above, may also be prepared by reacting compounds of formula (X):

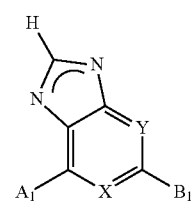

(X)

wherein X, Y, $A_1$ and $B_1$ are defined above,
with compounds of formula (IV), as defined above,
in the presence of suitable metal transition coupling conditions known to the skilled in the art, non limiting examples comprising the use of a Palladium catalyst such as Tetrakis(triphenylphosphine)palladium, Dichloro[1,1'-bis(diphenylphosphino)ferrocene]palladium, Tris(dibenzylideneacetone)dipalladium or Bis(triphenylphosphine)palladium(II)

dichloride, a base such as sodium or potassium carbonate, a phosphine ligand such as Xantphos or tricyclohexylphopshine in an appropriate solvent such as dimethylformamide, dioxane, tetrahydrofuran or toluene.

Compounds of formula (VIII), as defined above, may also be prepared by reacting compounds of formula (X), as defined above,
with compounds of formula (VI), as defined above,
in the presence of suitable aromatic nucleophilic substitution conditions known to the skilled in the art, non limiting examples comprising the use of a base such as triethylamine, diisopropylethylamine, 1,8-diazabicyclo[5.4.0]undec-7-ene, sodium hydride, sodium or potassium carbonate in an appropriate solvent such as butanol, dimethylformamide, dioxane, dimethylsulfoxide, toluene, acetonitrile or tetrahydrofuran.

If appropriate, the reactions previously are followed or preceded by one or more reactions known to the skilled of the art and are performed in an appropriate order to achieve the requisite substitutions on A or/and B, as defined above, to afford other compounds of formula (I). Non-limiting examples of such reactions include:
protection of reactive functions,
deprotection of reactive functions,
condensation reactions,
carbon chain elongation such as Wittig, Grignard, Petasis, Tebbe, Peterson, base-promoted substitution reactions,
halogenation,
dehalogenation,
dealkylation,
dihydroxylation,
epoxydation,
alkylation of amine, aniline, alcohol and phenol,
Mitsunobu reaction on hydroxyl groups,
Cyclization and cycloaddition reactions on appropriate groups,
reduction of nitro, esters, cyano, aldehydes, carboxylic acids, amides or unsaturated bonds,
transition metal-catalyzed coupling reactions,
acylation,
sulfonylation/introduction of sulfonyl groups,
nitration/introduction of nitro groups,
saponification/hydrolysis of esters groups,
amidification or transesterification of ester groups,
amidification or esterificatin of carboxylic groups,
halogen exchange,
nucleophilic substitution with amine, thiol or alcohol,
reductive amination,
oxime formation on carbonyl and hydroxylamine groups,
oxidation reactions on appropriate groups,
salification.

All these reactions and the conditions for performing them are classical and well known to the skilled chemist. General and more specific references can be cited, including, as the general references, Michael B. Smith, Jerry March, March's Advanced Organic Chemistry: Reactions, Mechanisms, and Structure, 6th Edition, Wiley, 2007; Science of Synthesis: Houben-Weyl Methods of Molecular Transformations, Thieme, 2010 and as more specific references illustrating conditions for the above reactions, in particular those listed hereafter:

Protection and deprotection of reactive functions: Peter G. M. Wuts, Theodora W. Greene, Greene's Protective Groups in Organic Synthesis, 4th Edition, Wiley, 2006);
Condensation reactions: Condensations leading to double bonds, in The Chemistry of Carbonyl Group: Volume 1 (1966) (ed S. Patai), Interscience Publishers; J. Alvarez-Builla, J. Jose Vaquero, J. Barluenga, Modern Heterocyclic Chemistry, Wiley, 2011;

Carbon chain elongation such as Wittig, Grignard, Petasis, Tebbe, Peterson, base-promoted substitution reactions: Li, J. J. (ed) Name Reactions for Homologations, John Wiley & Sons, Inc., 2009;

Halogenation reactions: Sasson, Y. Formation of Carbon-Halogen Bonds (Cl, Br, I). In *PATAI'S Chemistry of Functional Groups*, John Wiley & Sons, Ltd: 2009.

Epoxide formation and opening: Crotti, P. and Pineschi, M. (2006) Epoxides in Complex Molecule Synthesis, in Aziridines and Epoxides in Organic Synthesis (ed A. K. Yudin), Wiley-VCH Verlag GmbH & Co. KGaA, Weinheim, FRG; Rosowsky, A. (2008) Ethylene Oxides, in Chemistry of Heterocyclic Compounds: Heterocyclic Compounds with Three- and Four-Membered Rings, Volume 19 (ed A. Weissberger), John Wiley & Sons, Inc., Hoboken, N.J., USA Dihydroxylation reaction of carbon-carbon double bonds: Noe, M. C., Letavic, M. A., Snow, S. L. 2005. Asymmetric dihydroxylation of alkenes: Organic Reactions. 109-625;

Transition metal-catalyzed reactions: Matthias Beller, Carsten Bolm, Transition Metals for Organic Synthesis, Wiley, 2004; Chem. Rev. 2002, 102, 1359 or Tetrahedron 2005, 61, 2245;

Cyclization and cycloaddition reactions on appropriate groups: Cycloaddition Reactions in Organic Synthesis (eds S. Kobayashi and K. A. Jorgensen), Wiley-VCH Verlag GmbH, Weinheim, F R G, 2001.

Synthesis of 1-butyl-5-(4,4,5,5-tetramethyl-1,3,2-dioxaborolan-2-yl)benzimidazole, 1-ethyl-5-(4,4,5,5-tetramethyl-1,3,2-dioxaborolan-2-yl)benzimidazole, 1-cyclohexyl-5-(4,4,5,5-tetramethyl-1,3,2-dioxaborolan-2-yl)benzimidazole, 1-ethyl-7-fluoro-5-(4,4,5,5-tetramethyl-1,3,2-dioxaborolan-2-yl)benzimidazole and 1-[(1 S,3S)-3-methylcyclohexyl]-5-(4,4,5,5-tetramethyl-1,3,2-dioxaborolan-2-yl)benzimidazole are described in WO2012172043.

The conditions for performing the above various reactions are well known to the skilled in the art and several examples are illustrated below in the experimental part.

Experimental Part

This part represents the preparation of the examples (intermediates and final compounds). The following examples are provided for the purpose of illustrating the present invention and by no means should be interpreted to limit the scope of the present invention.

Materials and Procedures

Proton nuclear magnetic resonance ($^1$H NMR) spectra were recorded on either a 300 or 400 MHz Briiker instrument, and chemical shifts are reported in parts per million downfield from the internal standard tetramethylsilane (TMS). Abbreviations for NMR data are as follows: s=singlet, d=doublet, t=triplet, q=quartet, quin=quintet, sex=sextet, sep=septet, m=multiplet, dd=doublet of doublet, dt=doublet of triplet, td=triplet of doublet, tt=triplet of triplet, ddd=doublet of doublet of doublet, qt=quartet of triplet, bs=broad singlet, bd=broad doublet, bt=broad triplet, 2s=two singlets, 2t=two triplets. J indicates the NMR coupling constant measured in Hertz. CDCl$_3$ is deuteriochloroform, DMSO-d$_6$ is hexadeuteriodimethylsulfoxide, and CD$_3$OD is tetradeuteriomethanol. Mass spectra were obtained using electrospray ionization (ESI) techniques on an Agilent 1100 Series LCMS and Waters Acquity UPLC-MS. In the context of mass spectrometry, M refers to the molecular weight, MS refers to mass spectrometer. Analtech Silica Gel GF and E. Merck Silica Gel 60 F-254 thin layer plates were used for thin layer chromatography. Flash chromatography was carried out on Flashsmart Pack cartridge irregular silica 40-60 μm or spherical silica 20-40 μm. Preparative thin layer chromatography was carried out on Analtech Silica Gel GF 1000 μm 20×20 cm.

Abbreviations

Ac refers to acetyl, ACN or $CH_3CN$ refers to acetonitrile, AIBN refers to 2,2'-Azobis(2-methylpropionitrile), Bn refers to benzyl, Boc refers to tert-butylcarboxylate, n-BuOH refers to n-Butanol, n-BuLi refers to n-butyl lithium, BTEAC refers to benzyltriethylammonium chloride, Bu refers to butyl, CDI refers to 1,1'-carbonyldiimidazole, Cbz refers to benzyl carboxylate, DBU refers to 1,8-diazabicyclo[5.4.0]undec-7-ene, DCM refers to dichloromethane, DIAD refers to diisopropyl azodicarboxylate, DIBAL-H refers to diisobutylaluminum hydride, DIPA refers to N,N-diisopropylamine, DIPEA refers to N,N-diisopropylethylamine, DMAP refers to 4-(dimethylamino)pyridine, DME refers to 1,2-dimethoxyethane, DMEDA refers to N,N'-dimethylethylenediamine, DMF refers to N,N-dimethylformamide, DMSO refers to dimethylsulfoxide, DTAD refers to ditertbutyl azodicarboxylate, dppf refers to 1,1'-bis(diphenylphosphino)ferrocene, EDC, EDCI or EDAC refers to N-(3-dimethylaminopropyl)-N'-ethylcarbodiimide hydrochloride, Et refers to ethyl, $Et_2O$ refers to diethyl ether, EtOH refers to ethanol, LDA refers to lithium diisopropylamide, EtOAc refers to ethyl acetate, HATU refers to O-(7-azabenzotriazol-1-yl)-N,N,N',N'-tetramethyluronium hexafluorophosphate, HOBt refers to 1-hydroxybenzotriazole, Me refers to methyl, MeOH refers to methanol, MePhos refers to 2-dicyclohexylphosphino-2'-methylbiphenyl, NBS refers to N-bromosuccinimide, NMO refers to N-methylmorpholine N-oxide, OBn refers to benzyloxy, $Pd(PPh_3)_4$ refers to tetrakis(triphenylphosphine)palladium (0), pH refers to potential of hydrogen, Ph refers to phenyl, PTSA refers to para-toluenesulfonic acid, TBAF refers to tetrabutylammonium fluoride, tBDMS refers to tertbutyldimethylsilyl, tBDPS refers to tertbutyldiphenylsilyl, TEA refers to triethylamine, TFA refers to trifluoroacetic acid, THF refers to tetrahydrofuran, thp refers to tetrahydropyranyl, TMEDA refers to N,N,N',N'-tetramethylethylenediamine, TMS refers to trimethylsilyl, TMSOK refers to potassium trimethylsilanolate, TLC refers to Thin Layer Chromatography, xantphos refers to 4,5-bis(diphenyphosphino)-9,9-dimethylxanthene.

The starting materials are commercially available unless indicated otherwise.

SYNTHETIC EXAMPLES

Example 1

Synthesis of {(S)-1-[7-(1-Cyclohexyl-1H-benzimidazol-5-yl)-3H-imidazo[4,5-b]pyridin-5-yl]-pyrrolidin-3-yl}-methanol

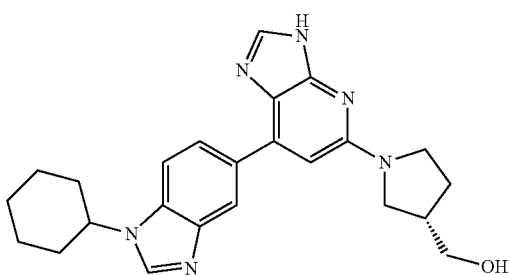

Example 1

Step 1: 4-Bromo-2,6-dichloro-3-nitro-pyridine (1a)

2,6-Dichloro-3-nitro-pyridin-4-ylamine (600 mg, 2.88 mmol) was added slowly to a solution of $CuBr_2$ (965 mg, 4.33 mmol) and tert-butylnitrite (0.52 mL, 4.33 mmol) in $CH_3CN$ (6 mL) at 65° C. The mixture was heated at the same temperature for 2 hours. After cooling at room temperature, a solution of HCl 1N and brine were added. The middle was extracted with AcOEt. The organic layer was dried over sodium sulfate, filtered and concentrated under reduced pressure. The crude was purified by preparative TLC on silica gel (Cyclohexane/EtOAc 92/8) to give compound (1a) as a white solid (605 mg, 2.23 mmol, 78%). $^1$H NMR (400 MHz, $CDCl_3$) δ 7.66 (s, 1H).

Step 2: 1-Cyclohexyl-5-(2,6-dichloro-3-nitro-pyridin-4-yl)-1H-benzimidazole (1b)

Under argon atmosphere, compound (1a) (1.38 g, 5.09 mmol) and 1-Cyclohexyl-5-(4,4,5,5-tetramethyl-1,3,2-dioxaborolan-2-yl)-1H-benzimidazole (1.82 g, 5.60 mmol), potassium carbonate (1.05 g, 7.63 mmol) were dissolved in a mixture of THF (50 mL) and water (10 mL). The solution was degassed under argon for 5 minutes and Tetrakis(triphenylphosphine)palladium(0) (294 mg, 0.25 mmol) was added. The reaction was heated at 85° C. for 7 hours. The middle was diluted with water and ethyl acetate. The organic layer was washed with brine, dried over sodium sulfate, filtered and concentrated under reduced pressure. The crude material was purified by chromatography on silica gel (Cyclohexane to cyclohexane/EtOAc 6/4) to give compound (1b) (1.58 g, 4.05 mmol, 79%). MS m/z ([M+H]$^+$) 391/393/395.

Step 3: 6-Chloro-4-(1-cyclohexyl-1H-benzimidazol-5-yl)-3-nitro-pyridin-2-ylamine (1c)

Compound (1b) (1.58 g, 4.05 mmol) was dissolved in a solution of $NH_3$ (0.5M in dioxane, 30 mL). Ammonium hydroxide (2 mL) was added and the mixture was heated at 110° C. for 3 hours. As starting material remained, ammonium hydroxide (0.5 mL) was added and the mixture was heated at 110° C. for 1 hour more. After cooling, the middle was diluted with water and ethyl acetate. The organic layer was washed with brine, dried over sodium sulfate, filtered and concentrated under reduced pressure. The crude material was purified by chromatography on silica gel (DCM to DCM/MeOH 99/1). The fraction containing desired product was triturated in DCM. Obtained solid was filtered and dried under vacuum to give compound (1c) (644 mg, 1.73 mmol, 44%). $^1$H NMR (400 MHz, $CDCl_3$) δ 1.30-1.44 (m, 1H), 1.45-1.62 (m, 2H), 1.78-1.94 (m, 3H), 1.96-2.08 (m, 2H), 2.20-2.34 (m, 2H), 4.26-4.38 (m, 1H), 6.24 (bs, 1H), 6.71 (bs, 2H), 7.24-7.30 (m, 1H), 7.56 (d, J=8.5 Hz, 1H), 7.90 (d, J=1.2 Hz, 1H), 8.66 (bs, 1H). MS m/z ([M+H]$^+$) 372/374.

Step 4: {(S)-1-[6-Amino-4-(1-cyclohexyl-1H-benzimidazol-5-yl)-5-nitro-pyridin-2-yl]-pyrrolidin-3-yl}-methanol (1d)

Compound (1c) (100 mg, 0.27 mmol) was dissolved in DMSO (1.5 mL). (S)-1-Pyrrolidin-3-yl-methanol (41 mg, 0.40 mmol) was added and the mixture was heated at 50° C. for 1 hour. The middle was diluted with water and ethyl acetate. The organic layer was washed with brine, dried over sodium sulfate, filtered and concentrated under reduced pressure. The crude material was purified by preparative TLC on silica gel (DCM/MeOH 9/1) to give compound (1d) as a yellow solid (115 mg, 0.26 mmol, 99%). $^1$H NMR (400 MHz, CDCl$_3$) δ 1.29-1.41 (m, 1H), 1.48-1.60 (m, 2H), 1.77-1.90 (m, 4H), 1.98-2.06 (m, 2H), 2.10-2.20 (m, 1H), 2.24-2.32 (m, 2H), 2.52-2.62 (m, 1H), 3.55-3.80 (m, 6H), 4.24-4.34 (m, 1H), 5.29 (s, 1H), 5.78 (s, 1H), 6.85 (bs, 2H), 7.20 (d, J=8.3 Hz, 1H), 7.48 (d, J=8.3 Hz, 1H), 7.88 (s, 1H), 8.46 (s, 1H). MS m/z ([M+H]$^+$) 437.

Step 5: (S)-1-[7-(1-cyclohexyl-1H-benzimidazol-5-yl)-3H-imidazo[4,5-b]pyridin-5-yl]-pyrrolidin-3-ylmethyl formate (1e)

Compound (1d) (65 mg, 0.15 mmol) was dissolved in a mixture of n-BuOH (1 mL) and formic acid (1 mL). Iron (84 mg, 1.5 mmol) and ammonium chloride (78 mg, 1.5 mmol) were added and the mixture was heated at 110° C. for 4 hours. After cooling, the middle was filtrated and insoluble was washed with DCM/MeOH. Filtrate was concentrated to give compound (1e) (66.7 mg, 0.15 mmol, 100%). MS m/z ([M+H]$^+$) 445.

Step 6: {(S)-1-[7-(1-Cyclohexyl-1H-benzimidazol-5-yl)-3H-imidazo[4,5-b]pyridin-5-yl]-pyrrolidin-3-yl}-methanol, Example (1)

Compound (1e) (0.15 mmol) was dissolved in EtOH (2 mL). A solution of NaOH 1N (2 mL) was added and the mixture was heated at 60° C. for 30 minutes. The middle was concentrated. DCM and water were added to the middle which was neutralized by addition of HCl 1N. The organic layer was washed with brine, dried over sodium sulfate, filtered and concentrated under reduced pressure. The crude material was purified by preparative TLC on silica gel (DCM/MeOH 85/15). Fraction containing desired product was triturated in hot EtOAc. Obtained solid was filtered and dried under vacuum to give Example (1) as light brown solid (11 mg, 0.026 mmol, 18%). $^1$H NMR (400 MHz, CD$_3$OD) δ 1.41 (qt, J=12.8/3.4 Hz, 1H), 1.55-1.68 (m, 2H), 1.80-2.04 (m, 6H), 2.13-2.26 (m, 3H), 2.58 (sep, J=7.0 Hz, 1H), 3.34-3.40 (m, 1H), 3.52-3.76 (m, 5H), 4.44 (tt, J=11.9/3.7 Hz, 1H), 6.60 (s, 1H), 7.77 (d, 8.4 Hz, 1H), 7.84 (dd, J=8.5/1.6 Hz, 1H), 8.08 (s, 1H), 8.16 (d, J=1.1 Hz, 1H), 8.39 (s, 1H). MS m/z ([M+H]$^+$) 417.

Example 2

Synthesis of (3R,4R)-1-[7-(1-Cyclohexyl-1H-benzimidazol-5-yl)-3H-imidazo[4,5-b]pyridin-5-yl]-4-hydroxymethyl-piperidin-3-ol

Step 1: (3R,4R)-6'-Amino-4'-(1-cyclohexyl-1H-benzimidazol-5-yl)-4-hydroxymethyl-5'-nitro-3,4,5,6-tetrahydro-2H-[1,2']bipyridinyl-3-ol (2a)

Compound (1c) (100 mg, 0.27 mmol) and (3R,4R)-4-Hydroxymethyl-piperidin-3-ol (53 mg, 0.40 mmol) were dissolved in CH$_3$CN (2 mL) and DMSO (0.3 mL). The mixture was heated at 50° C. overnight and 1 h30 at 80° C. to complete the reaction. The middle was diluted with water and ethyl acetate. The organic layer was washed with brine, dried over sodium sulfate, filtered and concentrated under reduced pressure. The crude material was purified by preparative TLC on silica gel (DCM/MeOH 9/1) to give compound (2a) as a yellow solid (115 mg, 0.25 mmol, 92%). $^1$H NMR (400 MHz, CDCl$_3$) δ 1.14-1.36 (m, 2H), 1.42-1.56 (m, 2H), 1.60-1.68 (m, 1H), 1.72-1.86 (m, 4H), 1.92-2.00 (m, 2H), 2.16-2.24 (m, 2H), 2.70-2.88 (m, 2H), 3.60 (td, J=9.9/4.6 Hz, 1H), 3.65-3.72 (m, 1H), 3.78 (dd, J=10.7/4.0 Hz, 1H), 4.12 (bs, 1H), 4.19 (tt, J=11.9/3.5 Hz, 1H), 4.42 (bs, 1H), 4.59 (bs, 1H), 6.00 (s, 1H), 6.72 (bs, 1H), 7.13 (dd, J=8.5/1.3 Hz, 1H), 7.39 (d, J=8.5 Hz, 1H), 7.76 (s, 1H), 8.07 (s, 1H). MS m/z ([M+H]$^+$) 467.

Step 2: (3R,4R)-1-[7-(1-Cyclohexyl-1H-benzimidazol-5-yl)-3H-imidazo[4,5-b]pyridin-5-yl]-4-hydroxymethyl-piperidin-3-ol, Example (2)

Compound (1c) (115 mg, 0.25 mmol) was dissolved in a mixture of n-BuOH (1 mL) and formic acid (1 mL). Iron (138 mg, 2.46 mmol) and ammonium chloride (128 mg, 2.46 mmol) were added and the mixture was heated at 110° C. for 4 hours. After cooling, the mixture was diluted with MeOH and NaOH 1N was added until pH 12-14. The middle was then stirred at room temperature for 30 minutes. Precipitate was filtered. DCM was added and organic layer was washed with brine, dried over sodium sulfate, filtered and concentrated under reduced pressure. The crude material was purified by preparative TLC on silica gel (DCM/MeOH 8/2) to give Example (2) (36 mg, 0.081 mmol, 33%) as a beige solid. $^1$H NMR (400 MHz, DMSO-d$_6$) δ 1.25-1.39 (m, 2H), 1.44-1.60 (m, 3H), 1.70-1.84 (m, 4H), 1.86-1.94 (m, 4H), 2.05-2.12 (m, 2H), 2.56-2.64 (m, 1H), 2.75-2.84 (m, 1H), 3.32-3.43 (m, 2H), 3.62-3.68 (m, 1H), 4.34-4.48 (m, 4H), 4.84 (d, J=5.0 Hz, 1H), 6.99 (s, 1H), 7.75 (d, J=8.5 Hz, 1H), 8.04 (s, 1H), 8.16 (dd, J=8.6/1.5 Hz, 1H), 8.38 (s, 1H), 8.58 (d, J=1.3 Hz, 1H), 12.52 (bs, 1H). MS m/z ([M+H]$^+$) 447.

Example 3

Synthesis of {1-[7-(1-Cyclohexyl-1H-benzimidazol-5-yl)-3H-imidazo[4,5-b]pyridin-5-yl]-piperidin-4-yl}-methanol

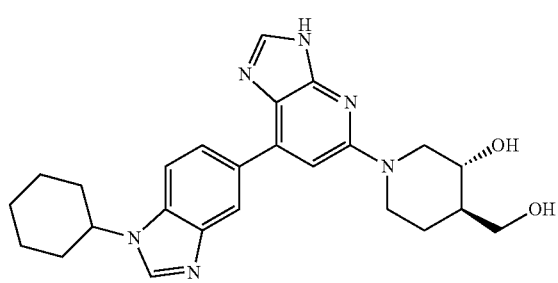

Example 2

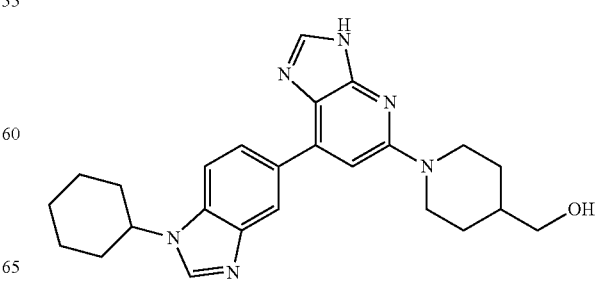

Example 3

Step 1: [6'-Amino-4'-(1-cyclohexyl-1H-benzimidazol-5-yl)-5'-nitro-3,4,5,6-tetrahydro-2H-[1,2']bipyridinyl-4-yl]-methanol (3a)

Compound (1c) (100 mg, 0.27 mmol), piperidin-4-yl-methanol (46 mg, 0.40 mmol) and DIPEA (0.14 mL, 0.8 mmol) were dissolved in n-BuOH (2 mL). The mixture was heated at 110° C. overnight. The middle was concentrated under reduced pressure. The crude material was purified by preparative TLC on silica gel (DCM/MeOH 9/1) to give compound (3a) (115 mg, 0.25 mmol, 95%) as an orange solid. $^1$H NMR (400 MHz, CDCl$_3$) δ 1.25-1.40 (m, 1H), 1.44-1.58 (m, 2H), 1.74-1.87 (m, 6H), 1.94-2.02 (m, 2H), 2.18-2.28 (m, 4H), 2.88-2.97 (m, 2H), 3.51 (d, J=5.9 Hz, 2H), 4.20 (tt, J=12.0/3.7 Hz, 1H), 4.44-4.54 (m, 2H), 6.00 (s, 1H), 6.67 (bs, 2H), 7.16 (dd, J=8.5/1.6 Hz, 1H), 7.40 (d, J=8.5 Hz, 1H), 7.76 (d, J=1.5 Hz, 1H), 8.07 (s, 1H). MS m/z ([M+H]$^+$) 451.

Step 2: {1-[7-(1-Cyclohexyl-1H-benzimidazol-5-yl)-3H-imidazo[4,5-b]pyridin-5-yl]-piperidin-4-yl}-methanol, Example (3)

According to the procedure described in example 2, step 2, compound (3a) (115 mg, 0.25 mmol) was converted, after purification by preparative TLC on silica gel (DCM/MeOH 8/2), to Example (3) (30 mg, 0.069 mmol, 28%) as a beige solid. $^1$H NMR (400 MHz, DMSO-d$_6$) δ 1.15-1.27 (m, 2H), 1.27-1.38 (m, 1H), 1.46-1.59 (m, 2H), 1.60-1.68 (m, 1H), 1.70-1.80 (m, 3H), 1.82-1.94 (m, 4H), 2.05-2.12 (m, 2H), 2.81-2.90 (m, 2H), 3.27-3.30 (m, 2H), 4.37-4.47 (m, 4H), 7.00 (s, 1H), 7.75 (s, J=7.5 Hz, 1H), 8.06 (s, 1H), 8.12 (bs, 1H), 8.40 (s, 1H), 8.55 (bs, 1H), 12.55 (bs, 1H). MS m/z ([M+H]$^+$) 431.

Example 4

Synthesis of 2-[7-(1-Cyclohexyl-1H-benzimidazol-5-yl)-3H-imidazo[4,5-b]pyridin-5-ylamino]-ethanol

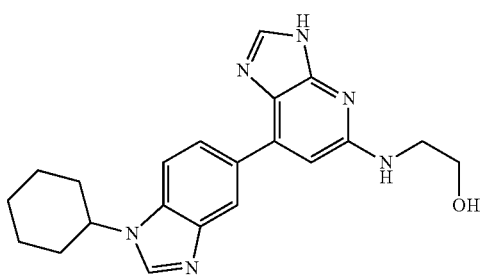

Example 4

Step 1: 2-[6-Amino-4-(1-cyclohexyl-1H-benzimidazol-5-yl)-5-nitro-pyridin-2-ylamino]-ethanol (4a)

According to the procedure described in example 2, step 1, compound (1c) (100 mg, 0.27 mmol) was converted, by reaction with 2-Amino-ethanol (25 mg, 0.40 mmol) and after purification by preparative TLC on silica gel (DCM/MeOH 9/1), to compound (5a) (91 mg, 0.23 mmol, 86%) as a yellow solid. $^1$H NMR (400 MHz, CDCl$_3$) δ 1.25-1.42 (m, 1H), 1.44-1.58 (m, 2H), 1.72-1.88 (m, 3H), 1.92-2.04 (m, 2H), 2.18-2.28 (m, 2H), 3.56-3.63 (m, 2H), 3.83 (t, J=4.8 Hz, 2H), 4.16-4.26 (m, 1H), 5.85 (s, 1H), 6.34 (bs, 1H), 6.75 (bs, 2H), 7.11 (d, J=8.5 Hz, 1H), 7.39 (d, J=8.5 Hz, 1H), 7.68 (s, 1H), 8.13 (bs, 1H). MS m/z ([M+H]$^+$) 397.

Step 2: Preparation of 2-[7-(1-Cyclohexyl-1H-benzimidazol-5-yl)-3H-imidazo[4,5-b]pyridin-5-ylamino]-ethanol, Example (4)

According to the procedure described in example 2, step 2, compound (4a) (91 mg, 0.23 mmol) was converted, after purification by preparative TLC on silica gel (DCM/MeOH 85/15), to Example (4) (13 mg, 0.035 mmol, 15%) as a beige solid. $^1$H NMR (400 MHz, DMSO-d$_6$) δ 1.24-1.38 (m, 1H), 1.46-1.59 (m, 2H), 1.70-1.78 (m, 1H), 1.83-1.95 (m, 4H), 2.04-2.12 (m, 2H), 3.40 (q, J=5.8 Hz, 2H), 3.59 (q, J=5.6 Hz, 2H), 4.36-4.46 (m, 1H), 4.71 (t, J=5.3 Hz, 1H), 6.48 (t, J=5.7 Hz, 1H), 6.77 (s, 1H), 7.75 (d, J=8.6 Hz, 1H), 7.92 (s, 1H), 8.04 (dd, J=8.6/1.2 Hz, 1H), 8.37 (s, 1H), 8.54 (d, J=1.1 Hz, 1H), 12.44 (bs, 1H). MS m/z ([M+H]$^+$) 377.

Example 5

Synthesis of {1-[7-(1-Cyclohexyl-1H-benzimidazol-5-yl)-3H-imidazo[4,5-b]pyridin-5-yl]-azetidin-3-yl}-methanol

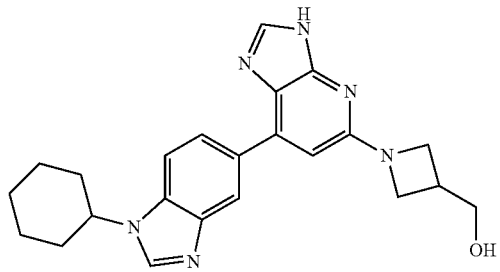

Example 5

Step 1: Preparation of {1-[6-Amino-4-(1-cyclohexyl-1H-benzimidazol-5-yl)-5-nitro-pyridin-2-yl]-azetidin-3-yl}-methanol (5a)

According to the procedure described in example 3, step 1, compound (1c) (100 mg, 0.27 mmol) was converted, by reaction with Azetidin-3-yl-methanol (35 mg, 0.40 mmol) and after purification by preparative TLC on silica gel (DCM/MeOH 9/1), to compound (5a) (105 mg, 0.25 mmol, 93%) as a yellow solid. $^1$H NMR (400 MHz, CDCl$_3$) δ 1.26-1.38 (m, 1H), 1.44-1.58 (m, 2H), 1.74-1.86 (m, 3H), 1.94-2.02 (m, 2H), 2.20-2.26 (m, 2H), 2.87-2.98 (m, 1H), 3.84 (d, J=6.1 Hz, 2H), 3.90-3.96 (m, 2H), 4.12-4.26 (m, 3H), 5.60 (s, 1H), 6.74 (bs, 2H), 7.15 (dd, J=8.5/1.1 Hz, 1H), 7.41 (d, J=8.5 Hz, 1H), 7.75 (s, 1H), 8.15 (s, 1H). MS m/z ([M+H]$^+$) 423.

Step 2: {1-[7-(1-Cyclohexyl-1H-benzimidazol-5-yl)-3H-imidazo[4,5-b]pyridin-5-yl]-azetidin-3-yl}-methanol (Example 5)

According to the procedure described in example 2, step 2, compound (5a) (105 mg, 0.25 mmol) was converted, after purification by preparative TLC on silica gel (DCM/MeOH 8/2+2% NH3 7M in MeOH), to (Example 5) (22 mg, 0.055 mmol, 22%) as a brown solid. ¹H NMR (400 MHz, DMSO-d₆) δ 1.26-1.38 (m, 1H), 1.46-1.60 (m, 2H), 1.70-1.78 (m, 1H), 1.83-1.95 (m, 4H), 2.04-2.12 (m, 2H), 3.20-3.28 (m, 2H), 3.50-3.58 (m, 3H), 4.12 (dd, J=13.6/8.6 Hz, 1H), 4.38-4.48 (m, 1H), 4.65-4.72 (m, 1H), 4.97 (bs, 1H), 6.66 (s, 1H), 7.82 (d, J=8.5 Hz, 1H), 7.87 (bs, 1H), 7.99-8.05 (m, 1H), 8.25 (bs, 1H), 8.43 (s, 1H), 8.53 (bs, 1H). MS m/z ([M+H]⁺) 403.

Example 6

Synthesis of {1-[7-(1-Cyclohexyl-1H-benzimidazol-5-yl)-3H-imidazo[4,5-b]pyridin-5-yl]-4-hydroxymethyl-piperidin-4-yl}-methanol Example 6

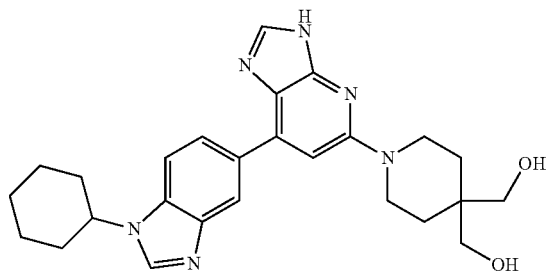

Step 1: [[6'-Amino-4'-(1-cyclohexyl-1H-benzimidazol-5-yl)-4-hydroxymethyl-5'-nitro-3,4,5,6-tetrahydro-2H-[1,2']bipyridinyl-4-yl]-methanol (6a)

According to the procedure described in example 3, step 1, compound (1c) (100 mg, 0.27 mmol) was converted, by reaction with (4-Hydroxymethyl-piperidin-4-yl)-methanol hydrochloride (65 mg, 0.40 mmol) and after purification by preparative TLC on silica gel (DCM/MeOH 9/1), to compound (6a) (130 mg, 0.27 mmol, 100%) as an orange solid. MS m/z ([M+H]⁺) 481.

Step 2: Preparation of {1-[7-(1-Cyclohexyl-1H-benzimidazol-5-yl)-3H-imidazo[4,5-b]pyridin-5-yl]-4-hydroxymethyl-piperidin-4-yl}-methanol, Example (6)

According to the procedure described in example 2, step 2, compound (6a) (130 mg, 0.27 mmol) was converted, after purification by preparative TLC on silica gel (DCM/MeOH 9/1+2% NH3 7M in MeOH), to Example (6) (30 mg, 0.065 mmol, 25%) as a pink solid. ¹H NMR (400 MHz, DMSO-d₆) δ 1.26-1.38 (m, 1H), 1.45-1.60 (m, 6H), 1.71-1.78 (m, 1H), 1.82-1.95 (m, 4H), 2.04-2.12 (m, 2H), 3.37 (d, J=5.2 Hz, 4H), 3.57-3.64 (m, 4H), 4.39 (t, J=5.3 Hz, 2H), 4.40-4.47 (m, 1H), 6.97 (s, 1H), 7.75 (d, J=8.5 Hz, 1H), 8.05 (s, 1H), 8.14 (bs, 1H), 8.39 (s, 1H), 8.58 (bs, 1H), 12.51 (bs, 1H). MS m/z ([M+H]⁺) 461.

Example 7

Synthesis of {syn-1-[7-(1-Cyclohexyl-1H-benzimidazol-5-yl)-3H-imidazo[4,5-b]pyridin-5-yl]-5-methyl-pyrrolidin-3-yl}-methanol Example 7

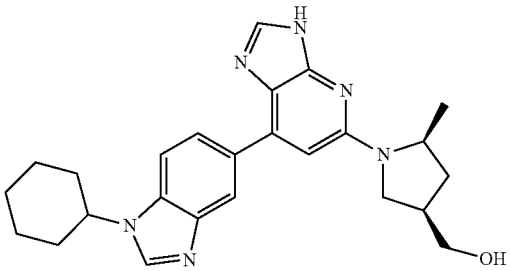

Step 1: Synthesis of 1-Benzyl-5-methyl-pyrrolidin-2-one (7a)

To a suspension of 5-methylpyrrolidin-2-one (4.6 g, 46.4 mmol) in DMF (30 mL) under a nitrogen atmosphere at 0° C., sodium hydride (60% in oil, 2.8 g, 70 mmol) and benzyl bromide (6.6 mL, 55.7 mmol) were added. After 16 hours of stirring at room temperature, the reaction was quenched with a saturated solution of ammonium chloride. Ethyl acetate was added and the organic layer was extracted twice with ethyl acetate, dried over sodium sulfate, filtered and concentrated under reduced pressure. The crude product was purified by flash chromatography on silica gel (cyclohexane/EtOAc 7/3) to give compound (7a) as yellow oil (7.56 g, 40.0 mmol, 88%). ¹H NMR (400 MHz, CDCl₃) δ 1.20 (d, 3H), 1.60 (m, 1H), 2.15 (m, 1H), 2.40 (m, 1H), 2.55 (m, 1H), 3.50 (m, 1H), 4.00 (d, 1H), 5.00 (d, 1H), 7.40-7.20 (m, 5H). MS m/z ([M+H]⁺) 190.

Step 2: Ethyl 1-Benzyl-5-methyl-2-oxo-pyrrolidine-3-carboxylate (7b)

Under a nitrogen atmosphere at −78° C., a solution of butyl lithium (1.6M in hexane, 41 mL, 71.5 mmol)) was added to a solution of diisopropylamine (13.38 mL, 94 mmol) in THF (50 mL). The mixture was stirred 10 minutes at 0° C. and cooled to −78° C. A solution of compound (7a) (5 g, 26 mmol) in THF (50 mL) was then added to the mixture. After 90 minutes at −78° C., ethylchloroformate (2.7 mL, 39 mmol) was added and the reaction was stirred for 30 minutes. The middle was warmed to room temperature and stirred for 2 hours. The reaction was quenched with a saturated solution of ammonium chloride. Ethyl acetate was added and the organic layer was extracted twice with ethyl acetate, dried over sodium sulfate, filtered and concentrated under reduced pressure. The crude product was purified by flash chromatography on silica gel (cyclohexane/EtOAc 7/3) to give compound (7b) as yellow oil (4.70 g, 18.0 mmol, 68%). MS m/z ([M+H]⁺) 262.

Step 3: syn-(1-benzyl-5-methylpyrrolidin-3-yl)methanol (8c) and anti-(1-benzyl-5-methylpyrrolidin-3-yl)methanol (7d)

At 0° C., lithium aluminium hydride (2.5 g, 66 mmol) was added to a suspension of compound (7b) (4.7 g, 18 mmol)

in THF (90 mL). The middle was stirred for 3 hours at room temperature. The reaction was quenched with water and a solution of sodium hydroxide 3M and stirred 1 hour at room temperature. The mixture was filtered and the filtrate was extracted with ethyl acetate. The organic layer was dried over sodium sulfate, filtered and concentrated under reduced pressure. The crude material was purified by flash chromatography on silica gel (DCM/MeOH 95/5 to 90/10+1% Ammonia) to give both diastereoisomers compound (7c) (1.12 g, 5.4 mmol, 30%) and compound (7d) (1.12 g, 5.4 mmol, 30%). Compound (7c): $^1$H NMR (400 MHz, CDCl$_3$) δ 1.20 (d, J=6.1 Hz, 3H), 1.64-1.72 (m, 1H), 1.75-1.81 (m, 1H), 1.99-2.02 (m, 1H), 2.33-2.40 (m, 1H), 2.55-2.62 (m, 1H), 3.05-3.10 (m, 1H), 3.20 (d, J=12.7 Hz, 1H), 3.48-3.60 (m, 2H), 4.03 (d, J=12.7 Hz, 1H), 7.26-7.29 (m, 1H), 7.31-7.35 (m, 4H). MS m/z ([M+H]$^+$) 206. Compound (7d): $^1$H NMR (400 MHz, CDCl$_3$) δ 1.28 (d, J=6.0 Hz, 3H), 1.45-1.51 (m, 1H), 2.19-2.36 (m, 3H), 2.47-2.55 (m, 1H), 2.86 (d, J=9.4 Hz, 1H), 3.08 (d, J=12.9 Hz, 1H), 3.50 (dd, J=2.9/9.9 Hz, 1H), 3.65 (dd, J=3.2/9.9 Hz, 1H), 4.10 (d, J=13.0 Hz, 1H), 7.30-7.35 (m, 5H). MS m/z ([M+H]$^+$) 206.

Step 4: syn-(5-methylpyrrolidin-3-yl)-methanol (7e)

A solution of compound (7c) (1.12 g, 4.8 mmol) in ethanol (35 mL) was purged with argon. Catalyst palladium hydroxyde on carbon (350 mg) was then added and the reaction was stirred under hydrogen atmosphere (atmospheric pression) for 18 hours. The middle was filtered and concentrated under reduced pressure to give compound (7e) as uncolorless oil (630 mg, 4.8 mmol, 100%). $^1$H NMR (400 MHz, CD$_3$OD) δ 1.21-1.25 (m, 3H), 1.47-1.54 (m, 1H), 1.74-1.80 (m, 1H), 2.41-2.48 (m, 1H), 2.60-2.64 (m, 1H), 3.18-3.23 (m, 2H), 3.47-3.59 (m, 2H). MS m/z ([M+H]$^+$) 116.

Step 5: {syn-1-[6-Amino-4-(1-cyclohexyl-1H-benzimidazol-5-yl)-5-nitro-pyridin-2-yl]-5-methyl-pyrrolidin-3-yl}-methanol (7f)

According to the procedure described in example 3, step 1, compound (1c) (100 mg, 0.27 mmol) was converted, by reaction with cis-((3R,5S)-5-Methyl-pyrrolidin-3-yl)-methanol (46 mg, 0.40 mmol) and after purification by preparative TLC on silica gel (DCM/MeOH 92/8), to compound (7f) (106 mg, 0.23 mmol, 88%) as an orange solid. $^1$H NMR (400 MHz, CD$_3$OD) δ 1.29 (d, J=6.1 Hz, 3H), 1.40 (m, 1H), 1.54-1.66 (m, 2H), 1.78-2.03 (m, 7H), 2.16-2.24 (m, 2H), 2.62-2.74 (m, 1H), 3.28-3.34 (m, 2H), 3.56 (dd, J=10.8/6.8 Hz, 1H), 3.64 (dd, J=10.8/6.0 Hz, 1H), 3.68-3.80 (m, 1H), 4.39 (tt, J=12.0/4.1 Hz, 1H), 5.84 (s, 1H), 7.18 (dd, J=8.5/1.6 Hz, 1H), 7.56 (d, J=1.1 Hz, 1H), 7.59 (d, J=8.5 Hz, 1H), 8.28 (s, 1H). MS m/z ([M+H]$^+$) 451.

Step 6: {syn-1-[7-(1-Cyclohexyl-1H-benzimidazol-5-yl)-3H-imidazo[4,5-b]pyridin-5-yl]-5-methyl-pyrrolidin-3-yl}-methanol, Example (7)

According to the procedure described in example 2, step 2, compound (7f) (106 mg, 0.23 mmol) was converted, after purification by preparative TLC on silica gel (DCM/MeOH 9/1+2% NH3 7M in MeOH), to Example (7) (20 mg, 0.046 mmol, 21%) as a beige solid. $^1$H NMR (400 MHz, DMSO-d$_6$) δ 1.25 (d, J=6.2 Hz, 3H), 1.26-1.38 (m, 1H), 1.46-1.60 (m, 2H), 1.70-1.78 (m, 2H), 1.80-1.95 (m, 5H), 2.05-2.12 (m, 2H), 2.58-2.66 (m, 1H), 3.18 (t, J=9.2 Hz, 1H), 3.43-3.53 (m, 2H), 3.67 (dd, J=10.0/7.9 Hz, 1H), 4.27-4.36 (m, 1H), 4.37-4.46 (tt, J=12.1/3.6 Hz, 1H), 4.67 (t, J=5.3 Hz, 1H), 6.57 (s, 1H), 7.75 (d, J=8.5 Hz, 1H), 7.97 (s, 1H), 8.10 (bs, 1H), 8.39 (s, 1H), 8.53 (bs, 1H), 12.50 (bs, 1H). MS m/z ([M+H]$^+$) 431.

Example 8

Synthesis of {anti-1-[7-(1-Cyclohexyl-1H-benzimidazol-5-yl)-3H-imidazo[4,5-b]pyridin-5-yl]-5-methyl-pyrrolidin-3-yl}-methanol

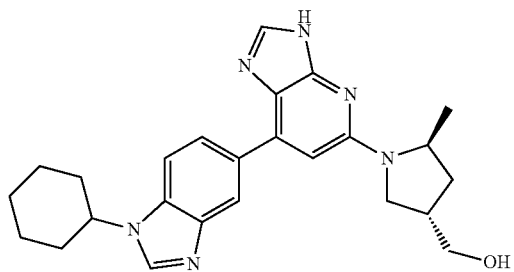

Example 8

Step 1: anti-5-methylpyrrolidin-3-yl methanol (8a)

According to the procedure described in example 8, step 4, compound (7d) (1.12 g, 4.8 mmol) was converted to compound (8a) as yellow oil (630 mg, 4.8 mmol, 100%). $^1$H NMR (400 MHz, CD$_3$OD) δ 1.00-1.08 (m, 1H), 1.22-1.27 (m, 3H), 2.11-2.18 (m, 1H), 2.36-2.47 (m, 1H), 2.86-2.90 (m, 1H), 2.99-3.03 (m, 1H), 3.13-3.21 (m, 1H), 3.49-3.59 (m, 2H). MS m/z ([M+H]$^+$) 116.

Step 2: {anti-1-[6-Amino-4-(1-cyclohexyl-1H-benzimidazol-5-yl)-5-nitro-pyridin-2-yl]-5-methyl-pyrrolidin-3-yl}-methanol (8b)

According to the procedure described in example 3, step 1, compound (1c) (100 mg, 0.27 mmol) was converted, by reaction with compound (8a) (46 mg, 0.40 mmol) and after purification by preparative TLC on silica gel (DCM/MeOH 92/8), to compound (8b) (110 mg, 0.24 mmol, 91%) as an orange solid. $^1$H NMR (400 MHz, CD$_3$OD) δ 1.37 (d, J=6.2 Hz, 3H), 1.40-1.66 (m, 4H), 1.79-2.02 (m, 5H), 2.16-2.24 (m, 2H), 2.34-2.44 (m, 2H), 3.26 (dd, J=11.3/8.4 Hz, 1H), 3.59 (dd, J=10.9/6.9 Hz, 1H), 3.65 (dd, J=10.9/5.5 Hz, 1H), 3.95 (bs, 1H), 4.20-4.30 (m, 1H), 4.38 (tt, J=12.0/3.6 Hz, 1H), 5.86 (s, 1H), 7.18 (dd, J=8.5/1.6 Hz, 1H), 7.56 (d, J=1.1 Hz, 1H), 7.59 (d, J=8.5 Hz, 1H), 8.28 (s, 1H). MS m/z ([M+H]$^+$) 451.

Step 3: {anti-1-[7-(1-Cyclohexyl-1H-benzimidazol-5-yl)-3H-imidazo[4,5-b]pyridin-5-yl]-5-methyl-pyrrolidin-3-yl}-methanol, Example (8)

According to the procedure described in example 2, step 2, compound (8b) (110 mg, 0.24 mmol) was converted, after purification by preparative TLC on silica gel (DCM/MeOH 9/1+2% NH$_3$ 7M in MeOH), to Example (8) (13 mg, 0.030 mmol, 13%) as a white solid. $^1$H NMR (400 MHz, DMSO-d$_6$) δ 1.32 (d, J=6.0 Hz, 3H), 1.28-1.6 (m, 1H), 1.45-1.59 (m, 3H), 1.70-1.78 (m, 1H), 1.82-1.95 (m, 4H), 2.05-2.12 (m, 2H), 2.27-2.37 (m, 2H), 3.33-3.36 (m, 1H), 3.48-3.55 (m, 2H), 3.70-3.78 (m, 1H), 4.14-4.21 (m, 1H), 4.36-4.46 (m, 1H), 4.69 (t, J=5.3 Hz, 1H), 6.62 (s, 1H), 7.75 (d, J=8.6 Hz, 1H), 7.98 (s, 1H), 8.12 (dd, J=8.5/1.2 Hz, 1H), 8.38 (s, 1H), 8.56 (d, J=1.0 Hz, 1H), 12.49 (bs, 1H). MS m/z ([M+H]$^+$) 431.

Example 9

Synthesis of {1-[7-(1-Cyclohexyl-1H-benzimidazol-5-yl)-3H-imidazo[4,5-b]pyridin-5-yl]-piperidin-3-yl}-methanol

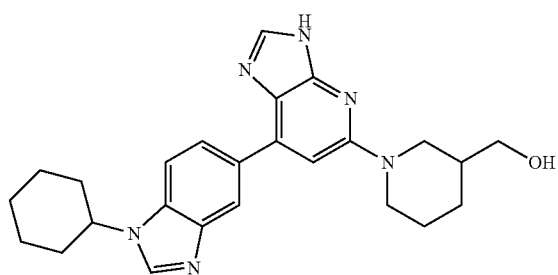

Example 9

Step 1: [6'-Amino-4'-(1-cyclohexyl-1H-benzimidazol-5-yl)-5'-nitro-3,4,5,6-tetrahydro-2H-[1,2']bipyridinyl-3-yl]-methanol (9a)

According to the procedure described in example 3, step 1, compound (1c) (100 mg, 0.27 mmol) was converted, by reaction with Piperidin-3-yl-methanol (46 mg, 0.40 mmol) and after purification by preparative TLC on silica gel (DCM/MeOH 9/1), to compound (9a) (121 mg, 0.27 mmol, 100%) as a yellow solid. $^1$H NMR (400 MHz, CDCl$_3$) δ 1.28-1.44 (m, 2H), 1.45-1.60 (m, 3H), 1.68-1.78 (m, 1H), 1.79-1.92 (m, 4H), 1.95-2.04 (m, 2H), 2.20-2.30 (m, 2H), 2.47 (bs, 2H), 3.25-3.42 (m, 2H), 3.52 (d, J=8.2 Hz, 1H), 3.58 (dd, J=11.0/5.1 Hz, 1H), 3.99 (bs, 1H), 4.06-4.13 (m, 1H), 4.23 (tt, J=12.0/3.7 Hz, 1H), 6.03 (s, 1H), 6.70 (bs, 2H), 7.18 (dd, J=8.5/1.5 Hz, 1H), 7.42 (d, J=8.5 Hz, 1H), 7.82 (s, 1H), 8.19 (bs, 1H). MS m/z ([M+H]$^+$) 451.

Step 2: {(1-[7-(1-Cyclohexyl-1H-benzimidazol-5-yl)-3H-imidazo[4,5-b]pyridin-5-yl]-piperidin-3-yl}-methanol, Example (9)

According to the procedure described in example 2, step 1, compound (9a) (121 mg, 0.27 mmol) was converted, after purification by preparative TLC on silica gel (DCM/MeOH 9/1+1% NH$_3$ 7M in MeOH), to Example (9) (59 mg, 0.137 mmol, 52%) as a white solid. $^1$H NMR (400 MHz, DMSO-d$_6$) δ 1.13-1.24 (m, 1H), 1.25-1.38 (m, 1H), 1.46-1.60 (m, 3H), 1.66-1.81 (m, 4H), 1.82-1.94 (m, 4H), 2.04-2.12 (m, 2H), 2.65 (dd, J=12.7/10.4 Hz, 1H), 2.84-2.93 (m, 1H), 3.31-3.42 (m, 2H), 4.22-4.30 (m, 1H), 4.35-4.47 (m, 2H), 4.55 (t, J=5.4 Hz, 1H), 6.99 (s, 1H), 7.75 (d, J=8.5 Hz, 1H), 8.04 (s, 1H), 8.15 (dd, J=8.3/1.4 Hz, 1H), 8.38 (s, 1H), 8.58 (d, J=1.1 Hz, 1H), 12.53 (bs, 1H). MS m/z ([M+H]$^+$) 431.

Example 10

Synthesis of 2-{1-[7-(1-Cyclohexyl-1H-benzimidazol-5-yl)-3H-imidazo[4,5-b]pyridin-5-yl]-pyrrolidin-3-yl}-ethanol

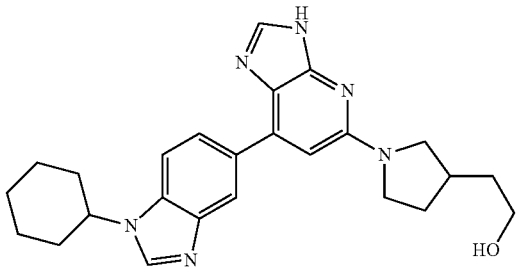

Example 10

Step 1: 2-{1-[6-Amino-4-(1-cyclohexyl-1H-benzimidazol-5-yl)-5-nitro-pyridin-2-yl]-pyrrolidin-3-yl}-ethanol (10a)

According to the procedure described in example 3, step 1, compound (1c) (100 mg, 0.27 mmol) was converted, by reaction with 2-Pyrrolidin-3-yl-ethanol (46 mg, 0.40 mmol) and after purification by preparative TLC on silica gel (DCM/MeOH 9/1), to compound (10a) (121 mg, 0.27 mmol, 100%) as an orange solid. $^1$H NMR (400 MHz, CDCl$_3$) δ 1.25-1.35 (m, 1H), 1.40-1.50 (m, 2H), 1.73 (q, J=6.4 Hz, 2H), 1.76-1.88 (m, 3H), 1.96-2.04 (m, 2H), 2.19 (bs, 1H), 2.22-2.30 (m, 3H), 2.32-2.54 (bs, 3H), 3.00-3.22 (m, 1H), 3.35-3.52 (m, 1H), 3.74 (t, J=6.2 Hz, 2H), 3.82-4.02 (m, 1H), 4.25 (tt, J=12.0/3.6 Hz, 1H), 5.78 (s, 1H), 6.80 (bs, 2H), 7.20 (dd, J=8.5/1.5 Hz, 1H), 7.44 (d, J=8.5 Hz, 1H), 7.83 (d, J=1.0 Hz, 1H), 8.28 (bs, 1H). MS m/z ([M+H]$^+$) 451.

Step 2: 2-{1-[7-(1-Cyclohexyl-1H-benzimidazol-5-yl)-3H-imidazo[4,5-b]pyridin-5-yl]-pyrrolidin-3-yl}-ethanol, Example (10)

According to the procedure described in example 2, step 1, compound (10a) (121 mg, 0.27 mmol) was converted, after purification by preparative TLC on silica gel (DCM/MeOH 9/1+1% NH$_3$ 7M in MeOH), to Example (10) (28 mg, 0.065 mmol, 25%) as a yellow solid. $^1$H NMR (400 MHz, DMSO-d$_6$) δ 1.25-1.38 (m, 1H), 1.46-1.58 (m, 2H), 1.59-1.68 (m, 3H), 1.70-1.79 (m, 1H), 1.82-1.94 (m, 4H), 2.04-2.12 (m, 2H), 2.12-2.19 (m, 1H), 2.32-2.41 (m, 1H), 3.09 (dd, J=9.5/8.7 Hz, 1H), 3.40-3.48 (m, 1H), 3.52 (q, J=6.1 Hz, 2H), 3.59-3.66 (m, 1H), 3.75 (dd, J=9.9/7.3 Hz, 1H), 4.37-4.44 (m, 1H), 4.47 (t, J=5.2 Hz, 1H), 6.60 (s, 1H), 7.75 (d, J=8.6 Hz, 1H), 7.96 (s, 1H), 8.15 (dd, J=8.5/1.5 Hz, 1H), 8.38 (s, 1H), 8.58 (d, J=1.3 Hz, 1H), 12.49 (bs, 1H). MS m/z ([M+H]$^+$) 431.

Example 11

Synthesis of 7-(1-Cyclohexyl-1H-benzimidazol-5-yl)-5-(hexahydro-pyrrolo[3,4-c]pyrrol-2-yl)-3H-imidazo[4,5-b]pyridine

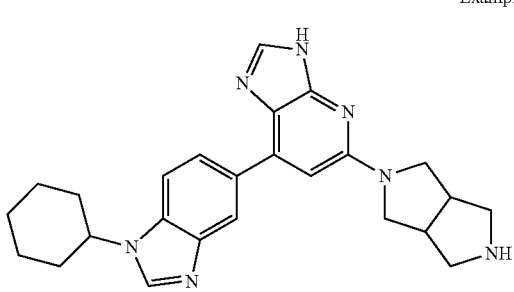

Example 11

Example 12

Synthesis of 1-[7-(1-Cyclohexyl-1H-benzimidazol-5-yl)-3H-imidazo[4,5-b]pyridin-5-yl]-piperidin-4-ol

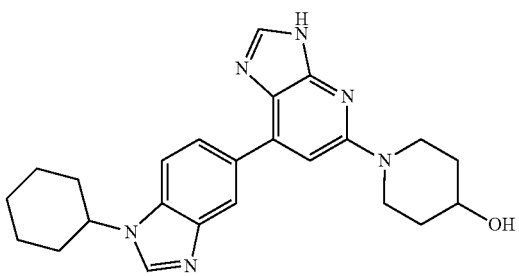

Example 12

Step 1: tert-butyl 5-[6-Amino-4-(1-cyclohexyl-1H-benzimidazol-5-yl)-5-nitro-pyridin-2-yl]-hexahydro-pyrrolo[3,4-c]pyrrole-2-carboxylate (11a)

According to the procedure described in example 3, step 1, compound (1c) (100 mg, 0.27 mmol) was converted, by reaction with tert-butyl Hexahydro-pyrrolo[3,4-c]pyrrole-2-carboxylate (85 mg, 0.40 mmol) and after purification by preparative TLC on silica gel (DCM/MeOH 92/8), to compound (11a) (128 mg, 0.23 mmol, 87%) as an orange solid. $^1$H NMR (400 MHz, CDCl$_3$) δ 1.28-1.42 (m, 2H), 1.45 (s, 9H), 1.48-1.60 (m, 3H), 1.76-1.89 (m, 3H), 1.96-2.05 (m, 2H), 2.22-2.30 (m, 2H), 2.98 (bs, 2H), 3.20-3.38 (m, 2H), 3.60-3.75 (m, 4H), 4.25 (tt, J=12.0/3.5 Hz, 1H), 5.77 (s, 1H), 6.68 (bs, 2H), 7.20 (d, J=8.5 Hz, 1H), 7.44 (d, J=8.5 Hz, 1H), 7.82 (s, 1H), 8.26 (s, 1H). MS m/z ([M+H]$^+$) 548.

Step 2: 7-(1-Cyclohexyl-1H-benzimidazol-5-yl)-5-(hexahydro-pyrrolo[3,4-c]pyrrol-2-yl)-3H-imidazo[4,5-b]pyridine, Example (11)

According to the procedure described in example 2, step 1, compound (11a) (128 mg, 0.23 mmol) was converted, after purification by preparative TLC on silica gel (DCM/MeOH 8/2+3% NH$_3$ 7M in MeOH), to Example (11) (15 mg, 0.035 mmol, 16%) as a white solid. $^1$H NMR (400 MHz, DMSO-d$_6$) δ 1.24-1.38 (m, 1H), 1.46-1.60 (m, 2H), 1.70-1.78 (m, 1H), 1.82-1.94 (m, 4H), 2.04-2.12 (m, 2H), 2.86 (dd, J=11.0/3.5 Hz, 2H), 2.93-3.02 (m, 2H), 3.14-3.22 (m, 2H), 3.45 (dd, J=10.6/2.9 Hz, 2H), 3.62-3.70 (m, 2H), 4.37-4.46 (m, 1H), 6.69 (s, 1H), 7.76 (d, J=8.5 Hz, 1H), 8.03 (s, 1H), 8.13 (bs, 1H), 8.37-8.40 (m, 2H), 8.56 (bs, 1H). MS m/z ([M+H]$^+$) 428.

Step 1: 6'-Amino-4'-(1-cyclohexyl-1H-benzimidazol-5-yl)-5'-nitro-3,4,5,6-tetrahydro-2H-[1,2']bipyridinyl-4-ol (12a)

According to the procedure described in example 3, step 1, compound (1c) (100 mg, 0.27 mmol) was converted, by reaction with Piperidin-4-ol (40 mg, 0.40 mmol) and after purification by preparative TLC on silica gel (DCM/MeOH 9/1), to compound (12a) (108 mg, 0.24 mmol, 93%) as a yellow solid. $^1$H NMR (400 MHz, CDCl$_3$) δ 1.25-1.35 (m, 1H), 1.46-1.62 (m, 4H), 1.76-1.87 (m, 3H), 1.90-2.04 (m, 4H), 2.21-2.30 (m, 2H), 3.36-3.45 (m, 2H), 3.96-4.04 (m, 1H), 4.06-4.14 (m, 2H), 4.21 (tt, J=11.8/3.6 Hz, 1H), 6.02 (s, 1H), 6.63 (bs, 2H), 7.17 (dd, J=8.5/1.5 Hz, 1H), 7.41 (d, J=8.5 Hz, 1H), 7.78 (d, J=1.1 Hz, 1H), 8.07 (s, 1H). MS m/z ([M+H]$^+$) 437.

Step 2: 1-[7-(1-Cyclohexyl-1H-benzimidazol-5-yl)-3H-imidazo[4,5-b]pyridin-5-yl]-piperidin-4-ol, Example (12)

According to the procedure described in example 2, step 1, compound (12a) (108 mg, 0.24 mmol) was converted, after purification by preparative TLC on silica gel (DCM/MeOH 8/2+3% NH$_3$ 7M in MeOH), to Example (12) (41 mg, 0.098 mmol, 41%) as a pale solid. $^1$H NMR (400 MHz, DMSO-d$_6$) δ 1.25-1.38 (m, 1H), 1.39-1.60 (m, 4H), 1.70-1.78 (m, 1H), 1.80-1.95 (m, 6H), 2.05-2.12 (m, 2H), 3.11-3.19 (m, 2H), 3.67-3.76 (m, 1H), 4.08-4.15 (m, 2H), 4.41 (tt, J=11.8/3.7 Hz, 1H), 4.65 (d, J=4.4 Hz, 1H), 7.03 (s, 1H), 7.74 (d, J=8.5 Hz, 1H), 8.04 (s, 1H), 8.17 (dd, J=8.5/1.5 Hz, 1H), 8.38 (s, 1H), 8.60 (d, J=1.5 Hz, 1H), 12.52 (bs, 1H). MS m/z ([M+H]$^+$) 417.

Example 13

Synthesis of 1-[7-(1-Cyclohexyl-1H-benzimidazol-5-yl)-3H-imidazo[4,5-b]pyridin-5-yl]-piperidin-3-ol

Example 14

Synthesis of {syn-1-[7-(1-Cyclohexyl-1H-benzimidazol-5-yl)-3H-imidazo[4,5-b]pyridin-5-yl]-2-methyl-piperidin-4-yl}-methanol

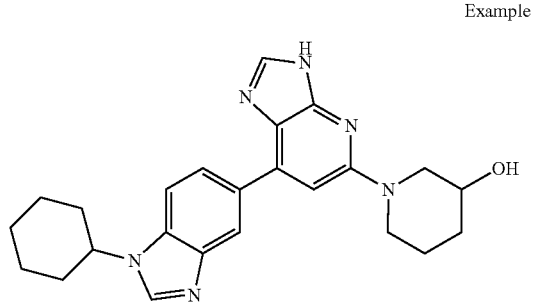

Example 13

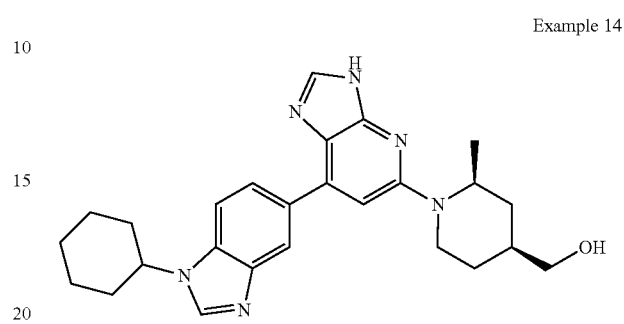

Example 14

Step 1: 6'-Amino-4'-(1-cyclohexyl-1H-benzimidazol-5-yl)-5'-nitro-3,4,5,6-tetrahydro-2H-[1,2']bipyridinyl-3-ol (13a)

According to the procedure described in example 3, step 1, compound (1c) (100 mg, 0.27 mmol) was converted, by reaction with Piperidin-3-ol (40 mg, 0.40 mmol) and after purification by preparative TLC on silica gel (DCM/MeOH 9/1), to compound (13a) (95 mg, 0.21 mmol, 82%) as a yellow solid. $^1$H NMR (400 MHz, CDCl$_3$) δ 1.28-1.42 (m, 1H), 1.46-1.60 (m, 3H), 1.62-1.72 (m, 1H), 1.77-1.92 (m, 4H), 1.93-2.05 (m, 3H), 2.22-2.30 (m, 2H), 3.43-3.58 (m, 2H), 3.74-3.83 (m, 1H), 3.84-3.91 (m, 1H), 4.00 (dd, J=13.1/2.1 Hz, 1H), 4.27 (tt, J=11.8/3.8 Hz, 1H), 6.04 (s, 1H), 6.72 (bs, 2H), 7.22 (dd, J=8.5/1.4 Hz, 1H), 7.46 (d, J=8.5 Hz, 1H), 7.86 (s, 1H), 8.40 (s, 1H). MS m/z ([M+H]$^+$) 437.

Step 2: 1-[7-(1-Cyclohexyl-1H-benzimidazol-5-yl)-3H-imidazo[4,5-b]pyridin-5-yl]-piperidin-3-ol, Example (13)

According to the procedure described in example 2, step 1, compound (13a) (95 mg, 0.21 mmol) was converted, after purification by preparative TLC on silica gel (DCM/MeOH 9/1+1% NH$_3$ 7M in MeOH), to Example (13) (44 mg, 0.106 mmol, 49%) as a white solid. $^1$H NMR (400 MHz, DMSO-d$_6$) δ 1.28-1.42 (m, 2H), 1.46-1.60 (m, 3H), 1.70-1.80 (m, 2H), 1.82-1.96 (m, 5H), 2.05-2.12 (m, 2H), 2.77 (dd, J=12.5/9.1 Hz, 1H), 2.91-3.00 (m, 1H), 3.52-3.61 (m, 1H), 4.07-4.14 (m, 1H), 4.23-4.30 (m, 1H), 4.42 (tt, J=11.8/3.6 Hz, 1H), 4.81 (d, J=4.5 Hz, 1H), 6.98 (s, 1H), 7.75 (d, J=8.5 Hz, 1H), 8.04 (s, 1H), 8.16 (dd, J=8.5/1.6 Hz, 1H), 8.38 (s, 1H), 8.59 (d, J=1.4 Hz, 1H), 12.50 (s, 1H). MS m/z ([M+H]$^+$) 417.

Step 1: tert-butyl 4-{[(tert-butyldimethylsilyl)oxy]methyl}piperidine-1-carboxylate (14a)

To a suspension of 4-hydroxymethyl-1-tert-butoxycarbonylpiperidine (5.40 g, 25 mmol) in DCM (188 mL) under a nitrogen atmosphere, tert-Butyldimethylsilyl chloride (5.55 g, 37 mmol), imidazole (5.1 g, 75 mmol), and 4-dimethylaminopyridine (152 mg, 12 mmol) were added. After stirred 16 hours at room temperature, DCM and water were added. The organic layer was extracted twice with DCM, dried over sodium sulfate, filtered and concentrated under vacuum. The crude product was purified by flash chromatography on silica gel (cyclohexane/EtOAc 9/1) to give compound (14a) as uncolorless oil (6 g, 18.23 mmol, 73%). $^1$H NMR (400 MHz, CDCl$_3$) δ 0.07 (s, 6H), 0.92 (s, 9H), 1.07-1.18 (m, 2H), 1.48 (s, 9H), 1.63-1.71 (m, 4H), 2.67-2.74 (td, J=13.0/2.6 Hz, 2H), 3.58-3.69 (m, 1H), 4.11-4.16 (m, 2H). MS m/z ([M+H]$^+$) 274.

Step 2: tert-butyl4-{[(tert-butyldimethylsilyl)oxy]methyl}-2-methylpiperidine-1-carboxylate (14b)

Under a nitrogen atmosphere at −78° C., compound (14a) (5.68 g, 17 mmol) and N,N,N',N'-tetramethylene diamine (3.23 mL, 21 mmol) were dissolved in diethyl ether (57 mL). Sec-butyl lithium (1.4M in cyclohexane, 16.4 mL, 22 mmol) was then added to the middle. After 3 hours at −78° C., dimethylsulfate (3.4 mL, 34 mmol) was introduced and the reaction mixture was stirred to room temperature for 2 hours. The mixture was quenched with water and the aqueous solution was extracted with ethyl acetate, dried over sodium sulfate, filtered, and concentrated. The crude product was purified by flash chromatography on silica gel (cyclohexane/EtOAc 9/1) to give a mixture of the desired product (14b) and the starting materials (14a) (4.95 g with a ratio 75/25).

Step 3: syn-4-{[(tert-butyldimethylsilyl)oxy]methyl}-2-methylpiperidine (14c)

To a suspension of mixture of (14b) (4.95 g, 14 mmol) in DCM was introduced zinc bromide (7.8 g, 35 mmol). After 16 hours, the middle was quenched with sodium bicarbonate and diluted with DCM. The reaction mixture was filtered and the organic layers was extracted with DCM, dried over sodium sulfate, filtered and concentrated under reduced pressure. The crude product was purified by flash chromatography on silica gel (DCM/MeOH 95/5 to 90/10+1% ammonia). The white powder was washed with pentane to give compound (14c) (360 mg, 1.48 mmol, 10.5%). $^1$H NMR (400 MHz, CDCl$_3$) δ 0.07 (s, 6H), 0.92 (s, 9H), 1.35-1.45 (m, 1H), 1.57 (d, J=6.5 Hz, 3H), 1.60-1.62 (m, 1H), 1.74-1.78 (m, 1H), 1.91-1.95 (m, 2H), 2.85 (td, J=13.0 Hz, J=2.9 Hz, 1H), 3.10-3.15 (m, 1H), 3.48-3.55 (m, 3H).

Step 4: syn-4-(tert-Butyl-dimethyl-silanyloxymethyl)-4'-(1-cyclohexyl-1H-benzimidazol-5-yl)-2-methyl-5'-nitro-3,4,5,6-tetrahydro-2H-[1,2']bipyridinyl-6'-ylamine (14d)

According to the procedure described in example 3, step 1, compound (1c) (100 mg, 0.27 mmol) was converted, by reaction with compound (14c) (97 mg, 0.40 mmol) and after purification by preparative TLC on silica gel (DCM/MeOH 94/6), to compound (14d) (114 mg, 0.19 mmol, 73%) as an orange solid. $^1$H NMR (300 MHz, CDCl$_3$) δ 0.04 (s, 6H), 0.89 (s, 9H), 1.23 (d, J=6.4 Hz, 3H), 1.28-1.42 (m, 3H), 1.43-1.55 (m, 2H), 1.74-2.04 (m, 8H), 2.19-2.29 (m, 2H), 3.02-3.14 (m, 1H), 3.40-3.50 (m, 1H), 3.52-3.60 (m, 1H), 4.13-4.26 (m, 2H), 4.27-4.38 (m, 1H), 5.93 (s, 1H), 6.64 (bs, 2H), 7.15 (dd, J=8.4/1.4 Hz, 1H), 7.39 (d, J=8.4 Hz, 1H), 7.76-7.79 (m, 1H), 8.00 (s, 1H). MS m/z ([M+H]$^+$) 579.

Step 5: {syn-1-[7-(1-Cyclohexyl-1H-benzimidazol-5-yl)-3H-imidazo[4,5-b]pyridin-5-yl]-2-methyl-piperidin-4-yl}-methanol, Example (14)

According to the procedure described in example 2, step 1, compound (14d) (112 mg, 0.19 mmol) was converted, after purification by preparative TLC on silica gel (DCM/MeOH 9/1+2% NH3 7M in MeOH), to Example (14) (50 mg, 0.112 mmol, 59%) as a tan solid. $^1$H NMR (400 MHz, CD$_3$OD) δ 1.19 (d, J=6.2 Hz, 3H), 1.25-1.35 (m, 1H), 1.36-1.50 (m, 2H), 1.56-1.69 (m, 2H), 1.70-1.79 (m, 1H), 1.80-1.88 (m, 1H), 1.90-2.04 (m, 6H), 2.19-2.27 (m, 2H), 3.36-3.44 (m, 1H), 3.44-3.52 (m, 2H), 3.52-3.60 (m, 1H), 3.75-3.84 (m, 1H), 4.40-4.50 (m, 1H), 7.00 (s, 1H), 7.77 (d, J=8.5 Hz, 1H), 7.84-7.92 (m, 1H), 8.13 (s, 1H), 8.19 (bs, 1H), 8.35 (s, 1H). MS m/z ([M+H]$^+$) 445.

Example 15

Synthesis of {anti-1-[7-(1-Cyclohexyl-1H-benzimidazol-5-yl)-3H-imidazo[4,5-b]pyridin-5-yl]-2-methyl-piperidin-4-yl}-methanol Step 1: anti-4-{[(tert-butyldimethylsilyl)oxy]methyl}-2-methylpiperidine (15a)

To a suspension of (14b) (1 g, 4.3 mmol) in DCM was introduced zinc bromide (3.27 g, 1.4 mmol). After 16 hours, middle was quenched with sodium bicarbonate and diluted with diethyl ether. The reaction mixture was filtered and the organic layer was extracted with diethyl ether, dried over sodium sulfate, filtered and concentrated under reduced pressure. The crude product was purified by flash chromatography on silica gel (DCM/MeOH 95/5 to 90/10+5% Ammonia) to give compound (15a) (200 mg, 0.82 mmol, 28%). $^1$H NMR (400 MHz, CDCl$_3$) δ 0.00 (s, 6H), 0.63-0.74 (m, 1H), 0.85 (s, 9H), 0.98-1.04 (m, 4H), 1.51-1.68 (m, 3H), 2.54-2.66 (m, 2H), 3.03-3.09 (m, 1H), 3.37 (d, J=2.1 Hz, 2H).

Step 2: anti-4-(tert-Butyl-dimethyl-silanyloxymethyl)-4'-(1-cyclohexyl-1H-benzimidazol-5-yl)-2-methyl-5'-nitro-3,4,5,6-tetrahydro-2H-[1,2']bipyridinyl-6'-ylamine (15b)

According to the procedure described in example 3, step 1, compound (1c) (100 mg, 0.27 mmol) was converted, by reaction with compound (15a) (97 mg, 0.40 mmol) and after purification by preparative TLC on silica gel (DCM/MeOH 94/6), to compound (15b) (116 mg, 0.197 mmol, 75%) as an orange solid. $^1$H NMR (300 MHz, CDCl$_3$) δ 0.04 (s, 6H), 0.89 (s, 9H), 1.22 (d, J=6.4 Hz, 3H), 1.28-1.42 (m, 3H), 1.43-1.54 (m, 2H), 1.70-2.04 (m, 8H), 2.20-2.29 (m, 2H), 3.02-3.14 (m, 1H), 3.40-3.50 (m, 1H), 3.53-3.60 (m, 1H), 4.14-4.25 (m, 2H), 4.26-4.37 (m, 1H), 5.93 (s, 1H), 6.65 (bs, 2H), 7.15 (dd, J=8.5/1.5 Hz, 1H), 7.39 (d, J=8.5 Hz, 1H), 7.78 (d, J=1.4 Hz, 1H), 8.00 (s, 1H). MS m/z ([M+H]$^+$) 579.

Step 3: {anti-1-[7-(1-Cyclohexyl-1H-benzimidazol-5-yl)-3H-imidazo[4,5-b]pyridin-5-yl]-2-methyl-piperidin-4-yl}-methanol, Example (15)

According to the procedure described in example 2, step 1, compound (15b) (114 mg, 0.197 mmol) was converted, after purification by preparative TLC on silica gel (DCM/MeOH 9/1+2% NH3 7M in MeOH), to Example (15) (51 mg, 0.114 mmol, 59%) as a tan solid. $^1$H NMR (400 MHz, CD$_3$OD) δ 1.19 (d, J=6.2 Hz, 3H), 1.25-1.36 (m, 1H), 1.39-1.50 (m, 2H), 1.56-1.69 (m, 2H), 1.70-1.80 (m, 1H), 1.80-1.88 (m, 1H), 1.90-2.04 (m, 6H), 2.19-2.28 (m, 2H), 3.36-3.44 (m, 1H), 3.44-3.52 (m, 2H), 3.52-3.60 (m, 1H), 3.75-3.85 (m, 1H), 4.40-4.50 (m, 1H), 7.01 (s, 1H), 7.78 (d, J=8.4 Hz, 1H), 7.85-7.91 (m, 1H), 8.14 (s, 1H), 8.19 (bs, 1H), 8.36 (s, 1H). MS m/z ([M+H]$^+$) 445.

Example 16

Synthesis of 5-Chloro-7-(1-cyclohexyl-1H-benzimidazol-5-yl)-3H-imidazo[4,5-b]pyridine

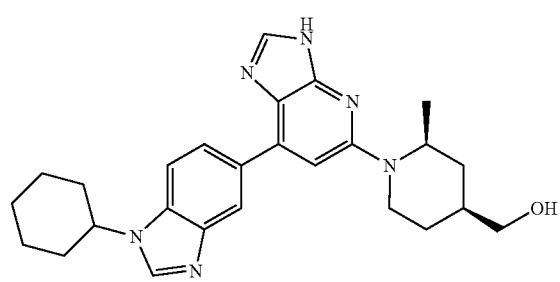

Example 15

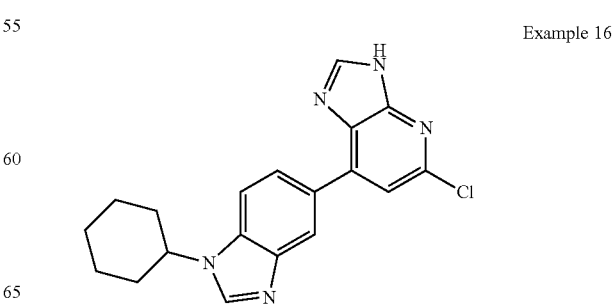

Example 16

According to the procedure described in example 2, step 1, compound (1c) (100 mg, 0.269 mmol) was converted, after purification by preparative TLC on silica gel (DCM/MeOH 9/1+1% NH$_3$ 7M in MeOH), to Example (16) (60 mg, 0.17 mmol, 64%) as a white solid. $^1$H NMR (400 MHz, DMSO-d$_6$) δ 1.26-1.38 (m, 1H), 1.46-1.60 (m, 2H), 1.70-1.78 (m, 1H), 1.83-1.95 (m, 4H), 2.05-2.12 (m, 2H), 4.40-4.50 (m, 1H), 7.67 (bs, 1H), 7.78-7.86 (m, 1H), 8.22 (bs, 1H), 8.44 (s, 1H), 8.52 (s, 1H), 8.77 (bs, 1H). MS m/z ([M+H]$^+$) 352.

Example 17

Synthesis of {(S)-1-[4-(1-Cyclohexyl-3H-benzimidazol-5-yl)-1H-imidazo[4,5-c]pyridin-6-yl]-pyrrolidin-3-yl}-methanol

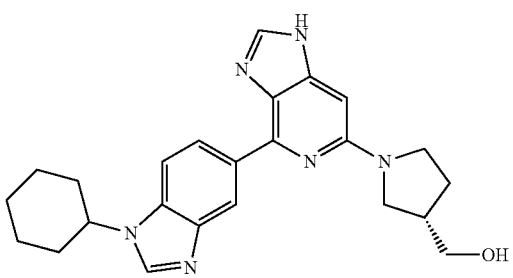

Example 17

Step 1: 2,6-Dichloro-3-nitro-pyridin-4-ylamine (17a)

2,6-Dichloro-pyridin-4-ylamine (2 g, 12.27 mmol) was dissolved in sulfuric acid (26 mL) at 0° C. The solution was stirred 10 minutes at 0° C. until homogenization. Fuming nitric acid (630 μL, 14.72 mmol) was added at 0° C. drop by drop to the middle. The solution was stirred 1 hour at room temperature, then 1 hour at 80° C. The mixture reaction was poured on ice and washed with water. The solid was filtered and dried under reduced pressure at 45° C. with phosphorus pentoxide to afford compound (17a) as a red solid (1.89 g, 9.09 mmol, 74%). MS m/z ([M+H]$^+$) 208/210.

Step 2: 6-Chloro-2-(1-cyclohexyl-1H-benzimidazol-5-yl)-3-nitro-pyridin-4-ylamine (17b)

To a solution of compound (17a) (150 mg, 0.72 mmol) in a mixture of THF (5 mL) and water (1 mL) was dissolved 1-Cyclohexyl-5-(4,4,5,5-tetramethyl-[1,3,2]dioxaborolan-2-yl)-1H-benzimidazole (247 mg, 0.76 mmol) and potassium carbonate (300 mg, 2.16 mmol). The solution was degassed under argon for 10 minutes and bis(triphenylphosphine)palladium(II) dichloride (51 mg, 0.07 mmol) was added. After 16 hours at 80° C., the reaction mixture was concentrated under reduced pressure. The residue was washed with sodium bicarbonate and extracted with ethyl acetate. The organic phase was dried over sodium sulfate, filtered on silica cake and evaporated. The crude was purified by preparative TLC on silica gel (DCM/MeOH 9/1) to afford compound (17b) as a yellow solid (115 mg, 0.31 mmol, 43%). MS m/z ([M+H]$^+$) 372/374.

Step 3: {(S)-1-[4-Amino-6-(1-cyclohexyl-1H-benzimidazol-5-yl)-5-nitro-pyridin-2-yl]-pyrrolidin-3-yl}-methanol (17c)

A solution of compound (17b) (57 mg, 0.15 mmol), (S)-1-Pyrrolidin-3-yl-methanol (20 mg, 0.20 mmol) and DIPEA (107 μL, 0.61 mmol) in n-butanol (2 mL) was stirred at 110° C. for 24 hours. The reaction mixture was then concentrated under reduced pressure. The crude was purified by preparative TLC on silica gel (DCM/MeOH 9/1) to afford compound (17c) (48 mg, 0.11 mmol, 71%). MS m/z ([M+H]$^+$) 437.

Step 4: {(S)-1-[4-(1-Cyclohexyl-3H-benzimidazol-5-yl)-1H-imidazo[4,5-c]pyridin-6-yl]-pyrrolidin-3-yl}-methanol, Example (17)

Compound (17c) (48 mg, 0.11 mmol) was dissolved in a mixture of n-butanol (1 mL) and formic acid (1 mL). Iron (61 mg, 1.10 mmol) and ammonium chloride (59 mg, 1.10 mmol) was added and the solution was stirred 6 hours at 110° C. The reaction mixture was filtered to eliminate salts and filtrate was concentrated under reduced pressure. The crude was purified by preparative TLC on silica gel (DCM/MeOH 9/1 with 1% ammonia) to afford Example (17) (7 mg, 0.02 mmol, 18%). $^1$H NMR (300 MHz, DMSO-d$_6$) δ 1.26-1.39 (m, 1H), 1.46-1.60 (m, 2H), 1.71-1.83 (m, 2H), 1.88-1.95 (m, 4H), 2.08-2.12 (m, 3H), 2.44-2.46 (m, 1H), 3.44-3.52 (m, 3H), 3.55-3.60 (m, 1H), 3.65-3.68 (m, 1H), 4.35-4.44 (m, 1H), 4.74 (t, J=4.5 Hz, 1H), 6.32 (s, 1H), 7.72 (d, J=8.4 Hz, 1H), 8.10 (s, 1H), 8.36 (s, 1H), 8.76 (d, J=7.8 Hz, 1H), 9.18 (s, 1H), 12.26 (bs, 1H). MS m/z ([M+H]$^+$) 417.

Example 18

Synthesis of {anti-1-[4-(1-Cyclohexyl-1H-benzimidazol-5-yl)-1H-imidazo[4,5-c]pyridin-6-yl]-5-methyl-pyrrolidin-3-yl}-methanol

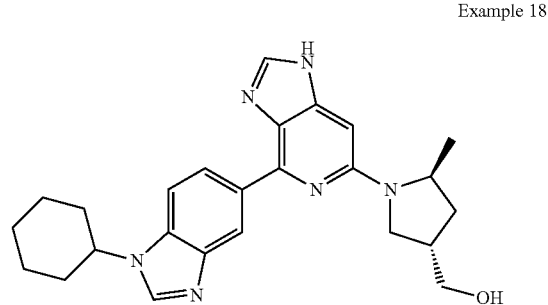 [SMILES: C[C@H]1C[C@H](CO)CN1c1cc2[nH]cnc2c(-c2ccc3c(c2)ncn3C2CCCCC2)n1]

Example 18

Step 1: {anti-1-[4-Amino-6-(1-cyclohexyl-1H-benzimidazol-5-yl)-5-nitro-pyridin-2-yl]-5-methyl-pyrrolidin-3-yl}-methanol (18a)

According to the procedure described in example 17, step 3, compound (17b) (100 mg, 0.27 mmol) was converted, by reaction with compound (8a) (80 mg, 0.70 mmol) and after purification by flash chromatography on silica gel (DCM/MeOH 99/1 to 95/5), to compound (18a) as a orange solid (50 mg, 0.11 mmol, 41%). MS m/z ([M+H]$^+$) 451.

Step 2: {anti-1-[4-(1-Cyclohexyl-1H-benzimidazol-5-yl)-1H-imidazo[4,5-c]pyridin-6-yl]-5-methyl-pyrrolidin-3-yl}-methanol, Example (18)

According to the procedure described in example 17, step 4, compound (18a) (50 mg, 0.11 mmol) was converted, after treatment with NaOH 1N at 80° C., to Example (18) (6.9 mg, 0.02 mmol, 14%). $^1$H NMR (400 MHz, CD$_3$OD) δ 1.26-1.39 (m, 2H), 1.46-1.60 (m, 2H), 1.71-1.83 (m, 2H), 1.88-1.95 (m, 4H), 2.08-2.12 (m, 3H), 2.44-2.46 (m, 1H), 3.44-3.52 (m, 3H), 3.55-3.60 (m, 1H), 3.65-3.68 (m, 1H), 4.35-4.44 (m, 1H), 4.74 (t, J=4.5 Hz, 1H), 6.32 (s, 1H), 7.72 (d, J=8.4 Hz, 1H), 8.10 (s, 1H), 8.36 (s, 1H), 8.76 (d, J=7.8 Hz, 1H), 9.18 (s, 1H), 12.26 (bs, 1H). MS m/z ([M+H]$^+$) 431.

Example 19

Synthesis of (3R,4R)-1-[4-(1-Cyclohexyl-1H-benzimidazol-5-yl)-1H-imidazo[4,5-c]pyridin-6-yl]-4-hydroxymethyl-piperidin-3-ol

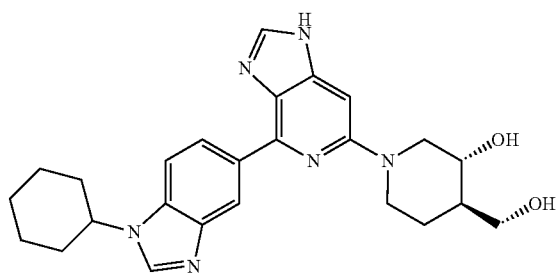

Example 19

Step 1: (3R,4R)-4'-Amino-6'-(1-cyclohexyl-1H-benzimidazol-5-yl)-4-hydroxymethyl-5'-nitro-3,4,5,6-tetrahydro-2H-[1,2']bipyridinyl-3-ol (19a)

According to the procedure described in example 17, step 3, compound (17b) (100 mg, 0.27 mmol) was converted, by reaction with (3R,4R)-4-Hydroxymethyl-piperidin-3-ol (46 mg, 0.35 mmol) and after purification by preparative TLC on silica gel (DCM/MeOH 9/1 with 1% ammonia), to compound (190a) as a orange oil (92 mg, 0.20 mmol, 73%). MS m/z ([M+H]$^+$) 467.

Step 2: (3R,4R)-1-[4-(1-Cyclohexyl-1H-benzimidazol-5-yl)-1H-imidazo[4,5-c]pyridin-6-yl]-4-hydroxymethyl-piperidin-3-ol, Example (19)

According to the procedure described in example 17, step 4, compound (19a) (117 mg, 0.25 mmol) was converted, after purification by preparative TLC on silica gel (DCM/MeOH 9/1 with 1% ammonia), to Example (19) (64 mg, 0.14 mmol, 57%). $^1$H NMR (400 MHz, DMSO-d$_6$) δ 1.26-1.41 (m, 2H), 1.45-1.67 (m, 3H), 1.74 (d, J=12.8 Hz, 1H), 1.84-1.93 (m, 5H), 2.09 (bd, J=9.2 Hz, 2H), 2.52-2.59 (m, 1H), 2.75 (dd, J=12/0.4 Hz, 1H), 3.38-3.44 (m, 2H), 3.67 (qt, J=6 Hz, 1H), 4.32 (d, J=12.8 Hz, 1H), 4.35-4.42 (m, 2H), 4.50 (dd, J=12.4/4.8 Hz, 1H), 4.87 (d, J=4.8 Hz, 1H), 6.87 (s, 1H), 7.72 (d, J=8.8 Hz, 1H), 8.15 (s, 1H), 8.35 (s, 1H), 8.72 (dd, J=8.8/1.6 Hz, 1H), 9.13 (d, J=0.8 Hz, 1H), 12.32 (bs, 1H). MS m/z ([M+H]$^+$) 447.

Example 20

Synthesis of {1-[4-(1-Cyclohexyl-1H-benzimidazol-5-yl)-1H-imidazo[4,5-c]pyridin-6-yl]-4-hydroxymethyl-piperidin-4-yl}-methanol

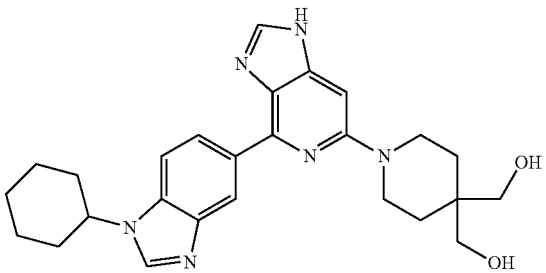

Example 20

Step 1: [4'-Amino-6'-(1-cyclohexyl-1H-benzimidazol-5-yl)-4-hydroxymethyl-5'-nitro-3,4,5,6-tetrahydro-2H-[1,2']bipyridinyl-4-yl]-methanol (20a)

According to the procedure described in example 17, step 3, compound (17b) (90 mg, 0.24 mmol) was converted, by reaction with (4-Hydroxymethyl-piperidin-4-yl)-methanol hydrochloride (66 mg, 0.36 mmol) and after purification by preparative TLC on silica gel (DCM/MeOH 9/1 with 1% ammonia), to compound (20a) as a orange oil (116 mg, 0.24 mmol, 100%). MS m/z ([M+H]$^+$) 481.

Step 2: {1-[4-(1-Cyclohexyl-1H-benzimidazol-5-yl)-1H-imidazo[4,5-c]pyridin-6-yl]-4-hydroxymethyl-piperidin-4-yl}-methanol, Example (20)

According to the procedure described in example 17, step 4, compound (20a) (116 mg, 0.24 mmol) was converted, after purification by preparative TLC on silica gel (DCM/MeOH 9/1 with 1% ammonia), to Example (20) (20 mg, 0.04 mmol, 18%). $^1$H NMR (400 MHz, DMSO-d$_6$) δ 1.33 (t, J=12.8 Hz, 1H), 1.47-1.58 (m, 6H), 1.74 (bd, J=13.6 Hz, 1H), 1.83-1.93 (m, 4H), 2.09 (bd, J=8.4 Hz, 2H), 3.38 (d, J=5.2 Hz, 4H), 3.57 (t, J=5.6 Hz, 4H), 4.39 (t, J=5.2 Hz, 3H), 6.67 (s, 1H), 7.72 (d, J=8.8 Hz, 1H), 8.13 (s, 1H), 8.35 (s, 1H), 8.69 (dd, J=8.8/1.6 Hz, 1H), 9.14 (d, J=0.8 Hz, 1H), 12.31 (bs, 1H). MS m/z ([M+H]$^+$) 461.

Example 21

Synthesis of {1-[4-(1-Cyclohexyl-1H-benzimidazol-5-yl)-1H-imidazo[4,5-c]pyridin-6-yl]-piperidin-4-yl}-methanol

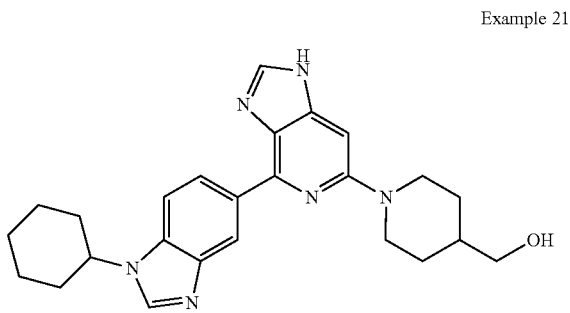 [SMILES: OCC1CCN(c2cc3[nH]cnc3c(-c3ccc4c(c3)ncn4C3CCCCC3)n2)CC1]

Example 21

Step 1: [4'-Amino-6'-(1-cyclohexyl-1H-benzimidazol-5-yl)-5'-nitro-3,4,5,6-tetrahydro-2H-1,2'-bipyridinyl-4-yl]-methanol (21a)

According to the procedure described in example 17, step 3, compound (17b) (90 mg, 0.24 mmol) was converted, by reaction with (piperidin-4-yl)-methanol (42 mg, 0.36 mmol) and after purification by preparative TLC on silica gel (DCM/MeOH 9/1 with 1% ammonia), to compound (21a) as a orange oil (108 mg, 0.24 mmol, 100%). MS m/z ([M+H]$^+$) 451.

Step 2: {1-[4-(1-Cyclohexyl-1H-benzimidazol-5-yl)-1H-imidazo[4,5-c]pyridin-6-yl]-piperidin-4-yl}-methanol, Example (21)

According to the procedure described in example 17, step 4, compound (21a) (108 mg, 0.24 mmol) was converted, after purification by preparative TLC on silica gel (DCM/MeOH 9/1 with 1% ammonia), to Example (21) (29 mg, 0.067 mmol, 28%). $^1$H NMR (400 MHz, DMSO-d$_6$) δ 1.18-1.37 (m, 3H), 1.62-1.45 (m, 3H), 1.71-1.94 (m, 7H), 2.08 (d, J=12.4 Hz, 2H), 2.42-2.45 (m, 2H), 2.80 (t, J=15.6 Hz, 2H), 4.37-4.48 (m. 4H), 6.71 (s, 1H), 7.72 (d, J=11.6 Hz, 1H), 8.14 (s, 1H), 8.35 (s, 1H), 8.67 (bs, 1H), 9.12 (bs, 1H), 12.34 (bs, 1H). MS m/z ([M+H]$^+$) 431.

Example 22

Synthesis of {syn-1-[4-(1-Cyclohexyl-1H-benzimidazol-5-yl)-1H-imidazo[4,5-c]pyridin-6-yl]-5-methyl-pyrrolidin-3-yl}-methanol

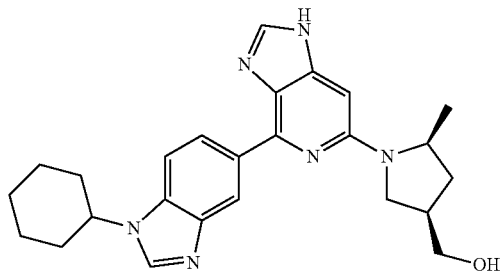

Example 22

Step 1: {syn-1-[4-Amino-6-(1-cyclohexyl-1H-benzimidazol-5-yl)-5-nitro-pyridin-2-yl]-5-methyl-pyrrolidin-3-yl}-methanol (22a)

According to the procedure described in example 17, step 3, compound (17b) (100 mg, 0.27 mmol) was converted, by reaction with compound (7e) (42 mg, 0.36 mmol) and after purification by flash chromatography on silica gel (DCM/MeOH 99/1 to 95/5), to compound (22a) as orange oil (93 mg, 0.21 mmol, 85%). MS m/z ([M+H]$^+$) 451.

Step 2: {syn-1-[4-(1-Cyclohexyl-1H-benzimidazol-5-yl)-1H-imidazo[4,5-c]pyridin-6-yl]-5-methyl-pyrrolidin-3-yl}-methanol, Example (22)

According to the procedure described in example 17, step 4, compound (22a) (50 mg, 0.11 mmol) was converted, after purification by preparative TLC on silica gel (DCM/MeOH 9/1 with 1% ammonia), to Example (22) (42 mg, 0.10 mmol, 47%). $^1$H NMR (400 MHz, DMSO-d$_6$) δ 1.30 (d, J=6 Hz, 4H), 1.52 (q, J=12.8 Hz, 2H), 1.72-1.77 (m, 2H), 1.82-1.93 (m, 5H), 2.08 (d, J=9.2 Hz, 2H), 2.59-2.63 (m, 1H), 3.13 (t, J=9.2 Hz, 1H), 3.44-3.55 (m, 2H), 3.63 (t, J=9.6 Hz, 1H), 4.31-4.41 (m, 2H), 4.68 (t, J=5.2 Hz, 1H), 6.28 (s, 1H), 7.71 (d, J=8.8 Hz, 1H), 8.07 (s, 1H), 8.34 (s, 1H), 8.75 (dd, J=8.4/1.2 Hz, 1H), 9.16 (s, 1H), 12.19 (s, 1H). MS m/z ([M+H]$^+$) 431.

Example 23

Synthesis of 1-[4-(1-Cyclohexyl-1H-benzimidazol-5-yl)-1H-imidazo[4,5-c]pyridin-6-yl]-piperidin-4-ol

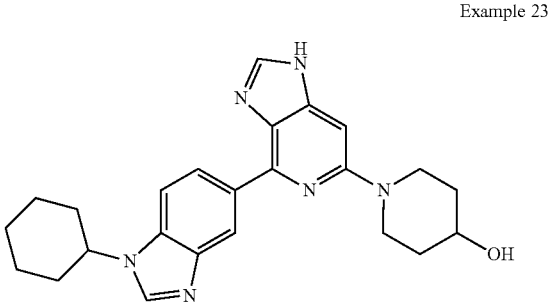

Example 23

Step 1: 4'-Amino-6'-(1-cyclohexyl-1H-benzimidazol-5-yl)-5'-nitro-3,4,5,6-tetrahydro-2H-[1,2']bipyridinyl-4-ol (23a)

According to the procedure described in example 17, step 3, compound (17b) (115 mg, 0.31 mmol) was converted, by reaction with Piperidin-4-ol (47 mg, 0.46 mmol) and after purification by preparative TLC on silica gel (DCM/MeOH 9/1), to compound (23a) as orange oil (52 mg, 0.12 mmol, 38%). MS m/z ([M+H]$^+$) 437.

Step 2: 1-[4-(1-Cyclohexyl-1H-benzimidazol-5-yl)-1H-imidazo[4,5-c]pyridin-6-yl]-piperidin-4-ol, Example (23)

According to the procedure described in example 17, step 4, compound (23a) (52 mg, 0.12 mmol) was converted, after purification by preparative TLC on silica gel (DCM/MeOH 9/1 with 1% ammonia), to Example (23) (7 mg, 0.02 mmol, 14%). $^1$H NMR (400 MHz, CD$_3$OD) δ 1.39 (qt, J=2.8/13.2 Hz, 1H), 1.55-1.70 (m, 4H), 1.82 (d, J=12.8 Hz, 1H), 1.87-2.02 (m, 6H), 2.21 (bd, J=11.6 Hz, 2H), 3.11-3.18 (m, 2H), 3.81-3.85 (m, 1H), 4.15-4.19 (m, 2H), 4.40-4.44 (m, 1H), 6.82 (s, 1H), 7.70 (d, J=8.4 Hz, 1H), 8.10 (s, 1H), 8.33 (s, 1H), 8.42 (d, J=8.4 Hz, 1H), 8.73 (s, 1H). MS m/z ([M+H]$^+$) 417.

Example 24

Synthesis of 4-(1-Cyclohexyl-1H-benzimidazol-5-yl)-6-(hexahydro-pyrrolo[3,4-c]pyrrol-2-yl)-1H-imidazo[4,5-c]pyridine

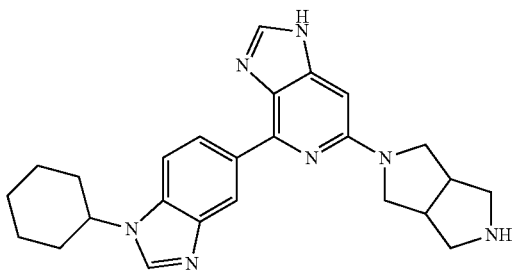

Example 24

Step 1: tert-butyl 5-[4-Amino-6-(1-cyclohexyl-1H-benzimidazol-5-yl)-5-nitro-pyridin-2-yl]-hexahydro-pyrrolo[3,4-c]pyrrole-2-carboxylate (24a)

A solution of compound (17b) (100 mg, 0.27 mmol), tert-butyl Hexahydro-pyrrolo[3,4-c]pyrrole-2-carboxylate (86 mg, 0.40 mmol) and DIPEA (187 µL, 1.08 mmol) in 2 mL of DMSO (2 mL) was stirred for 2 days at 80° C. The reaction mixture was concentrated under reduced pressure. The residue was triturated with diethyl ether to afford compound (24a) as a yellow solid (139 mg, 0.25 mmol, 94%). MS m/z ([M+H]$^+$) 548.

Step 2: 4-(1-Cyclohexyl-1H-benzimidazol-5-yl)-6-(hexahydro-pyrrolo[3,4-c]pyrrol-2-yl)-1H-imidazo[4,5-c]pyridine, Example (24)

According to the procedure described in example 17, step 4, compound (24a) (139 mg, 0.25 mmol) was converted, after purification by preparative TLC on silica gel (DCM/MeOH 8/2 with 5% ammonia), to Example (24) (11 mg, 0.03 mmol, 8%). $^1$H NMR (400 MHz, CD$_3$OD) δ 1.36-1.47 (m, 1H), 1.57-1.67 (m, 2H), 1.83 (bd, J=13.2 Hz, 1H), 1.90-1.94 (m, 1H), 1.95-2.02 (m, 3H), 2.23 (bd, J=10.8 Hz, 2H), 2.85 (dd, J=4/11.6 Hz, 2H), 2.99-3.03 (m, 2H), 3.15-3.20 (m, 2H), 3.54 (dd, J=2.8/10.4 Hz, 2H), 3.60-3.65 (m, 2H), 4.43 (tt, J=3.6/11.6 Hz, 1H), 6.55 (s, 1H), 7.71 (d, J=8.4 Hz, 1H), 8.06 (s, 1H), 8.31 (s, 1H), 8.43 (bd, J=8 Hz, 1H), 8.73 (bs, 1H). MS m/z ([M+H]$^+$) 428.

Example 25

Synthesis of 1-[4-(1-Cyclohexyl-1H-benzimidazol-5-yl)-1H-imidazo[4,5-c]pyridin-6-yl]-piperidin-3-ol

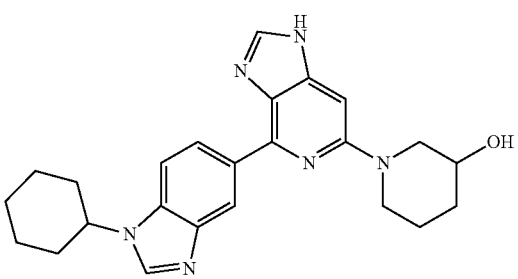

Example 25

Step 1: 4'-Amino-6'-(1-cyclohexyl-1H-benzimidazol-5-yl)-5'-nitro-3,4,5,6-tetrahydro-2H-[1,2']bipyridinyl-3-ol (25a)

According to the procedure described in example 24, step 1, compound (17b) (97 mg, 0.26 mmol) was converted, by reaction with Piperidin-3-ol (40 mg, 0.39 mmol) and without further purification, to compound (25a) as a yellow solid (110 mg, 0.25 mmol, 96%). MS m/z ([M+H]$^+$) 437.

Step 2: 1-[4-(1-Cyclohexyl-1H-benzimidazol-5-yl)-1H-imidazo[4,5-c]pyridin-6-yl]-piperidin-3-ol, Example (25)

According to the procedure described in example 17, step 4, compound (25a) (110 mg, 0.25 mmol) was converted, after purification by preparative TLC on silica gel (DCM/MeOH 9/1), to Example (25) (20 mg, 0.05 mmol, 19%). $^1$H NMR (400 MHz, CD$_3$OD) δ 1.39-1.47 (m, 1H), 1.49-1.57 (m, 1H), 1.60-1.75 (m, 3H), 1.38 (bd, J=13.2 Hz, 1H), 1.88-1.93 (m, 2H), 1.96-2.07 (m, 4H), 2.23 (bd, J=11.2 Hz, 2H), 2.89-2.94 (m, 1H), 2.99-3.06 (m, 1H), 3.79-3.82 (m, 1H), 4.02 (tt, J=4/12.4 Hz, 1H), 4.31 (dd, J=4/12.4 Hz, 1H), 4.43 (tt, J=3.6/12 Hz, 1H), 6.80 (s, 1H), 7.71 (d, J=8.8 Hz, 1H), 8.09 (bs, 1H), 8.31 (s, 1H), 8.48 (bs, 1H), 8.80 (bs, 1H). MS m/z ([M+H]$^+$) 417.

Example 26

Synthesis of 2-[4-(1-Cyclohexyl-1H-benzimidazol-5-yl)-1H-imidazo[4,5-c]pyridin-6-ylamino]-ethanol

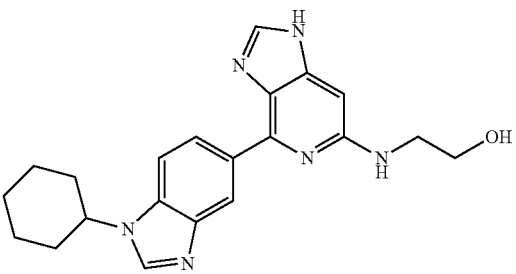

Example 26

Step 1: 2-[4-Amino-6-(1-cyclohexyl-1H-benzimidazol-5-yl)-5-nitro-pyridin-2-ylamino]-ethanol (26a)

According to the procedure described in example 24, step 1, compound (17b) (97 mg, 0.26 mmol) was converted, by reaction with ethanolamine (80 µL, 1.30 mmol) and without further purification, to compound (26a) as a yellow solid (153 mg, 0.26 mmol, 100%). MS m/z ([M+H]$^+$) 397.

Step 2: 2-[4-(1-Cyclohexyl-1H-benzimidazol-5-yl)-1H-imidazo[4,5-c]pyridin-6-ylamino]-ethanol, Example (26)

According to the procedure described in example 17, step 4, compound (26a) (103 mg, 0.26 mmol) was converted, after purification by preparative TLC on silica gel (DCM/MeOH 9/1), to Example (26) (6 mg, 0.02 mmol, 6%). $^1$H NMR (400 MHz, CD$_3$OD) δ 1.41 (qt, J=3.2/13.2 Hz, 1H), 1.62 (qt, J=3.2/13.2 Hz, 2H), 1.83 (bd, J=12.8 Hz, 1H), 1.90

(dd, J=3.2/12.4 Hz, 1H), 1.94-2.01 (m, 3H), 2.22 (bd, J=11.2 Hz, 2H), 3.51 (t, J=5.6 Hz, 2H), 3.81 (t, J=5.6 Hz, 2H), 4.43 (tt, J=3.6/12 Hz, 1H), 6.63 (s, 1H), 7.74 (d, J=8.8 Hz, 1H), 8.10 (s, 1H), 8.24 (dd, J=1.2/8.4 Hz, 1H), 8.36 (bs, 1H), 8.57 (bs, 1H). MS m/z ([M+H]$^+$) 377.

Example 27

Synthesis of 2-{1-[4-(1-Cyclohexyl-1H-benzimidazol-5-yl)-1H-imidazo[4,5-c]pyridin-6-yl]-pyrrolidin-3-yl}-ethanol Example 27

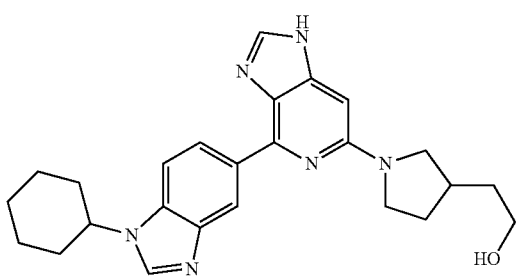

Step 1: 2-{-1-[4-Amino-6-(1-cyclohexyl-1H-benzimidazol-5-yl)-5-nitro-pyridin-2-yl]-pyrrolidin-3-yl}-ethanol (27a)

According to the procedure described in example 21, step 1, compound (14b) (97 mg, 0.26 mmol) was converted, by reaction with 2-Pyrrolidin-3-yl-ethanol (51 mg, 0.39 mmol) and without further purification, to compound (27a) as a yellow solid (114 mg, 0.25 mmol, 94%). MS m/z ([M+H]$^+$) 451.

Step 2: 2-{1-[4-(1-Cyclohexyl-1H-benzimidazol-5-yl)-1H-imidazo[4,5-c]pyridin-6-yl]-pyrrolidin-3-yl}-ethanol, Example (27)

According to the procedure described in example 17, step 4, compound (27a) (114 mg, 0.25 mmol) was converted, after purification by preparative TLC on silica gel (DCM/MeOH 9/1), to Example (27) (19 mg, 0.04 mmol, 17%). $^1$H NMR (400 MHz, CD$_3$OD) δ 1.41 (qt, J=3.2/12.8 Hz, 1H), 1.56-1.68 (m, 2H), 1.70-1.79 (m, 3H), 1.83 (d, J=13.2 Hz, 1H), 1.88-1.93 (m, 1H), 1.95-2.00 (m, 3H), 2.21-2.27 (m, 3H), 2.46 (q, J=7.6 Hz, 1H), 3.16 (t, J=8.4 Hz, 1H), 3.47-3.53 (m, 1H), 3.69 (t, J=6.4 Hz, 3H), 3.80-3.84 (m, 1H), 4.42 (tt, J=3.2/12 Hz, 1H), 6.39 (s, 1H), 7.69 (d, J=8.8 Hz, 1H), 8.01 (s, 1H), 8.30 (s, 1H), 8.43 (bd, J=8 Hz, 1H), 8.72 (bs, 1H). MS m/z ([M+H]$^+$) 431.

Example 28

Synthesis of {1-[4-(1-Cyclohexyl-1H-benzimidazol-5-yl)-1H-imidazo[4,5-c]pyridin-6-yl]-piperidin-3-yl}-methanol Example 28

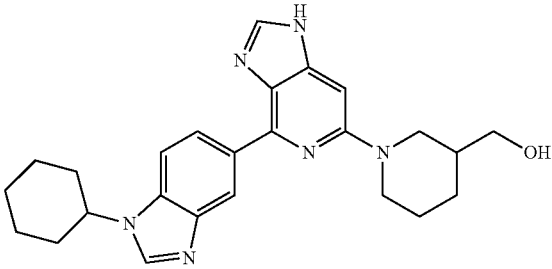

Step 1: [4'-Amino-6'-(1-cyclohexyl-1H-benzimidazol-5-yl)-5'-nitro-3,4,5,6-tetrahydro-2H-[1,2']bipyridinyl-3-yl]-methanol (28a)

According to the procedure described in example 24, step 1, compound (17b) (97 mg, 0.26 mmol) was converted, by reaction with Piperidin-3-yl-methanol (45 mg, 0.39 mmol) and without further purification, to compound (28a) as a yellow solid (117 mg, 0.26 mmol, 100%). MS m/z ([M+H]$^+$) 451.

Step 2: {1-[4-(1-Cyclohexyl-1H-benzimidazol-5-yl)-1H-imidazo[4,5-c]pyridin-6-yl]-piperidin-3-yl}-methanol, Example (28)

According to the procedure described in example 17, step 4, compound (28a) (117 mg, 0.26 mmol) was converted, after purification by preparative TLC on silica gel (DCM/MeOH 9/1), to Example (28) (14 mg, 0.03 mmol, 12%). $^1$H NMR (400 MHz, CD$_3$OD) δ 1.22-1.33 (m, 1H), 1.42 (qt, J=3.6/12.8 Hz, 1H), 1.57-1.76 (m, 3H), 1.82-1.93 (m, 5H), 1.95-2.02 (m, 3H), 2.23 (bd, J=10.4 Hz, 2H), 2.72-2.78 (m, 1H), 2.96 (td, J=2.8/12.4 Hz, 1H), 3.48-3.58 (m, 2H), 4.24-4.34 (m, 2H), 4.43 (tt, J=3.6/12 Hz, 1H), 6.82 (bs, 1H), 7.71 (d, J=8.4 Hz, 1H), 8.09 (s, 1H), 8.31 (s, 1H), 8.45 (bs, 1H), 8.77 (bs, 1H). MS m/z ([M+H]$^+$) 431.

Example 29

Synthesis of [(S)-1-(1'-Cyclohexyl-1H,1'H-[4,5']]bibenzimidazolyl-6-yl)-pyrrolidin-3-yl]-methanol Example 29

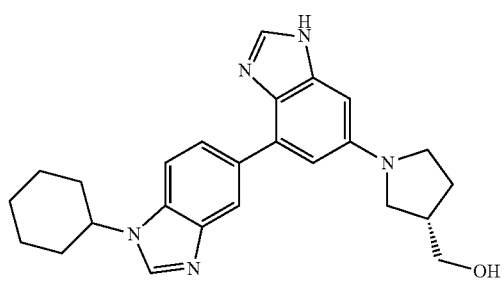

Step 1: 2-(1-Cyclohexyl-1H-benzimidazol-5-yl)-4-fluoro-6-nitro-phenylamine (29a)

A solution of 2-Bromo-4-fluoro-6-nitro-phenylamine (300 mg, 1.27 mmol), potassium carbonate (522 mg, 3.77 mmol) and (1-cyclohexyl-1H-benzimidazol-5-yl) pinacol boronate (486 mg, 1.89 mmol) in DMF (10 mL) and water (2 mL) was degassed under argon for 5 minutes. The catalyst $PdCl_2(PPh_3)_2$ (100 mg, 0.021 mmol) was added to the middle which was stirred for 2 hours at 100° C. The middle was then concentrated and the crude diluted with DCM. The organic layer was washed with water and brine and dried over sodium sulfate, filtered and concentrated. The crude was purified by flash chromatography on silica gel (DCM/MeOH 97.5/2.5) to give compound (29a) (370 mg, 1.04 mmol, 82%). $^1$H NMR (400 MHz, $CDCl_3$) δ 1.31-1.42 (m, 1H), 1.49-1.62 (m, 2H), 1.82-1.93 (m, 3H), 1.99-2.05 (m, 2H), 2.23-2.32 (m, 2H), 4.25-4.32 (s, 1H), 6.19 (bs, 2H), 7.18 (dd, J=3.1/7.8 Hz, 1H), 7.32 (dd, J=1.6/8.4 Hz, 1H), 7.60 (d, J=8.4 Hz, 1H), 7.87 (bs, 1H), 7.90 (d, J=3.0 Hz, 1H), 8.31 (s, 1H). MS m/z ([M+H]$^+$) 355.

Step 1: 1-Cyclohexyl-5-(5-fluoro-2,3-dinitro-phenyl)-1H-benzimidazole (29b)

A solution of hydrogen peroxide (30%, 20 mL) was added to a solution of compound (29a) (310 mg, 0.87 mmol) in acetic acid (30 mL). The middle was heated at 60° C. for 5 hours and then diluted with DCM. The organic layer was washed with a saturated solution of $Na_2CO_3$ and brine and dried over sodium sulfate, filtrated and concentrated under reduced pressure to give compound (29b) (340 mg, 0.78 mmol, 100%). $^1$H NMR (400 MHz, $CDCl_3$) δ 1.29-1.40 (m, 1H), 1.47-1.60 (m, 2H), 1.78-1.88 (m, 3H), 1.97-2.05 (m, 2H), 2.21-2.28 (m, 2H), 4.18-4.26 (s, 1H), 7.23 (dd, J=1.8/8.4 Hz, 1H), 7.49-7.53 (m, 2H), 7.79 (d, J=1.3 Hz, 1H), 7.88 (dd, J=2.7/7.3 Hz, 1H), 8.08 (s, 1H). MS m/z ([M+H]$^+$) 385.

Step 3: {(S)-1-[3-(1-Cyclohexyl-1H-benzimidazol-5-yl)-4,5-dinitro-phenyl]-pyrrolidin-3-yl}-methanol (29c)

A solution of compound (29b) (180 mg, 0.47 mmol), (S)-pyrrolidin-3-yl-methanol (53 mg, 0.51 mmol) and DIPEA (140 μL, 0.78 mmol) in $CH_3CN$ (10 mL) was stirred at 50° C. for 3 hours. The middle was then concentrated under reduced pressure. The crude was purified by flash preparative TLC on silica gel (DCM/MeOH 92/8) to give compound (29c) (100 mg, 0.21 mmol, 46%). MS m/z ([M+H]$^+$) 466.

Step 4: {(S)-1-[3,4-Diamino-5-(1-cyclohexyl-1H-benzimidazol-5-yl)-phenyl]-pyrrolidin-3-yl}-methanol (29d)

A solution of compound (29c) (100 mg, 0.21 mmol) in ethanol (5 mL) was degassed under argon. The catalyst Pd/C (10%, 35 mg) was added followed by addition of hydrazine hydrate (3 mL, 91 mmol). The middle was vigorously stirred for 46 hours, filtrated and concentrated under reduced pressure. The crude was diluted with DCM. The organic layer was washed with water, dried over sodium sulfate, filtrated and concentrated under reduced pressure. The crude was purified by flash chromatography on silica gel (DCM/MeOH 94/6) to give compound (29d) (75 mg, 0.18 mmol, 88%). MS m/z ([M+H]$^+$) 406.

Step 5: [(S)-1-(1'-Cyclohexyl-1H,1'H-[4,5']]bibenzimidazolyl-6-yl)-pyrrolidin-3-yl]-methanol, Example (29)

A solution of compound (29d) (75 mg, 0.18 mmol) in triethylorthoformate (2 mL) was stirred at 110° C. for 17 hours. The middle was concentrated under reduced pressure and the crude was diluted with DCM. The organic layer was washed with water, dried over sodium sulfate, filtrated and concentrated under reduces pressure. The crude was purified by preparative TLC on silica gel (DCM/MeOH 9/1+1% $NH_4OH$) to give Example (29) (13 mg, 0.031 mmol, 17%). $^1$H NMR (400 MHz, $CDCl_3$) δ 1.26-1.40 (m, 1H), 1.47-1.59 (m, 2H), 1.76-1.92 (m, 5H), 1.97-2.05 (m, 2H), 2.14-2.28 (m, 3H), 2.57-2.66 (m, 1H), 3.23 (dd, J=3.1/6.5 Hz, 1H), 3.35-3.40 (m, 1H), 3.44-0.52 (m, 2H), 3.66-3.76 (m, 2H), 4.18-4.26 (s, 1H), 6.72 (bs, 1H), 6.81 (d, J=2.1 Hz, 1H), 7.52 (d, J=8.4 Hz, 2H), 7.80 (bs, 1H), 7.93 (s, 1H), 8.02 (s, 1H), 8.12 (s, 1H). MS m/z ([M+H]$^+$) 416.

Example 30

Synthesis of [1-(1'-Cyclohexyl-1H,1'H-[4,5']bibenzimidazolyl-6-yl)-piperidin-4-yl]-methanol

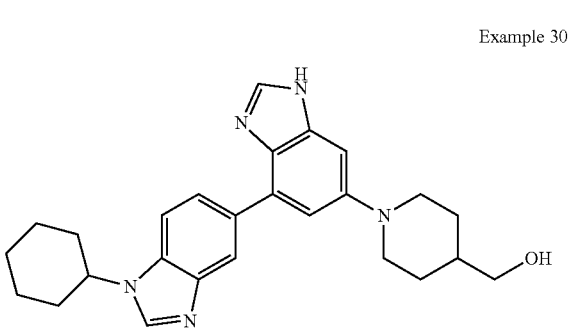 [SMILES: OCC1CCN(c2cc(-c3ccc4c(c3)ncn4C3CCCCC3)c3nc[nH]c3c2)CC1]

Example 30

Step 1: {1-[3-(1-Cyclohexyl-1H-benzimidazol-5-yl)-4,5-dinitro-phenyl]-piperidin-4-yl}-methanol (30a)

Compound (29b) (100 mg, 0.26 mmol) was dissolved in DMSO (1 mL). Piperidin-4-yl-methanol (45 mg, 0.39 mmol) and DIPEA (0.13 mL, 0.78 mmol) were added and the mixture was stirred at room temperature overnight. Water was added and obtained solid was filtered, dissolved in MeOH and concentrated. The crude material was purified by preparative TLC on silica gel (DCM/MeOH 95/5) to give compound (30a) (78 mg, 0.16 mmol, 63%) as an orange solid. $^1$H NMR (400 MHz, $CDCl_3$) δ 1.30-1.43 (m, 4H), 1.46-1.58 (m, 1H), 1.76-1.93 (m, 6H), 1.96-2.04 (m, 2H), 2.20-2.28 (m, 2H), 2.95-3.04 (m, 2H), 3.56 (t, J=5.6 Hz, 2H), 3.89-3.96 (m, 2H), 4.21 (tt, J=11.9/3.6 Hz, 1H), 6.99 (d, J=2.6 Hz, 1H), 7.21 (d, J=8.4 Hz, 1H), 7.38 (d, J=2.5 Hz, 1H), 7.45 (d, J=8.5 Hz, 1H), 7.79 (s, 1H), 8.05 (s, 1H). MS m/z ([M+H]+) 480.

Step 2: {1-[3,4-Diamino-5-(1-cyclohexyl-1H-benzimidazol-5-yl)-phenyl]-piperidin-4-yl}-methanol (30b)

According to the procedure described in example 29, step 4, compound (30a) (30 mg, 0.06 mmol) was converted, without further purification, to compound (30b) (25 mg, 0.06 mmol, 100%). MS m/z ([M+H]+) 420.

Step 3: [1-(1'-Cyclohexyl-1H,1'H-[4,5']bibenzimidazolyl-6-yl)-piperidin-4-yl]-methanol, Example (30)

Compound (30b) (25 mg, 0.06 mmol) was dissolved in formic acid (2 mL) and stirred at 110° C. for 1 hour. The middle was concentrated and the residue was dissolved in MeOH (2 mL). A solution of NaOH 1N (2 mL) was added and the mixture was stirred at room temperature overnight then 1 hour at 60° C. After concentration, DCM, MeOH and a saturated solution of $NH_4Cl$ were added. Organic layer was extracted, dried over sodium sulfate, filtered and concentrated under reduced pressure. The crude was purified by preparative TLC on silica gel (DCM/MeOH 9/1) to give Example (30) (15 mg, 0.035 mmol, 60%). $^1$H NMR (400 MHz, DMSO-$d_6$) δ 1.28-1.40 (m, 3H), 1.46-1.60 (m, 3H), 1.71-1.83 (m, 3H), 1.84-1.94 (m, 4H), 2.05-2.12 (m, 2H), 2.69 (t, J=11.0 Hz, 2H), 3.28-3.34 (m, 2H), 3.69 (d, J=12.0 Hz, 2H), 4.41 (tt, J=11.7/3.8 Hz, 1H), 4.47 (t, J=5.2 Hz, 1H), 6.99 (s, 1H), 7.13 (d, J=1.8 Hz, 1H), 7.72 (d, J=8.5 Hz, 1H), 7.85 (bs, 1H), 8.12 (s, 1H), 8.25 (bs, 1H), 8.37 (s, 1H), 12.39 (bs, 1H). MS m/z ([M+H]+) 430.

Example 31

Synthesis of (3R,4R)-1-(1'-Cyclohexyl-1H,1'H-[4,5']bibenzimidazolyl-6-yl)-4-hydroxymethyl-piperidin-3-ol Example 31

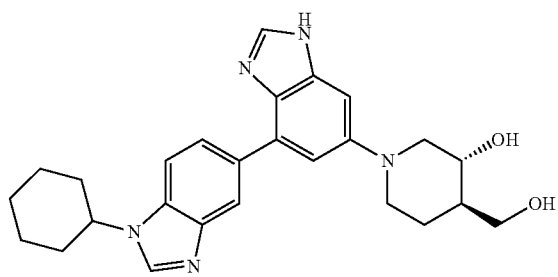

Step 1: (3R,4R)-1-[3-(1-Cyclohexyl-1H-benzimidazol-5-yl)-4,5-dinitro-phenyl]-4-hydroxymethyl-piperidin-3-ol (31a)

According to the procedure described in example 30, step 1, compound (29b) (100 mg, 0.26 mmol) was converted, by reaction with (3R,4R)-4-Hydroxymethyl-piperidin-3-ol (51 mg, 0.39 mmol) and after purification by preparative TLC on silica gel (DCM/MeOH 9/1), to compound (31a) (108 mg, 0.21 mmol, 84%) as a yellow solid. MS m/z ([M+H]+) 496.

Step 2: (3R,4R)-1-[3,4-Diamino-5-(1-cyclohexyl-1H-benzimidazol-5-yl)-phenyl]-4-hydroxymethyl-piperidin-3-ol (31b)

According to the procedure described in example 29, step 4, compound (31a) (105 mg, 0.21 mmol) was converted, without further purification, to compound (31b) (91 mg, 0.21 mmol, 100%). MS m/z ([M+H]+) 436.

Step 3: (3R,4R)-1-(1'-Cyclohexyl-1H,1'H-[4,5']bibenzimidazolyl-6-yl)-4-hydroxymethyl-piperidin-3-ol, Example (31)

According to the procedure described in example 30, step 3, compound (31b) (91 mg, 0.21 mmol) was converted, after purification by preparative TLC on silica gel (DCM/MeOH 85/15+2% $NH_3$ 7M in MeOH), to Example (31) (20 mg, 0.045 mmol, 21%). $^1$H NMR (400 MHz, $CD_3OD$) δ 1.42 (qt, J=12.9/3.3 Hz, 1H), 1.53-1.69 (m, 4H), 1.80-1.88 (m, 1H), 1.90-2.05 (m, 5H), 2.20-2.28 (m, 2H), 2.60 (dd, J=11.0/10.1 Hz, 1H), 2.76 (td, J=11.6/2.5 Hz, 1H), 3.61-3.72 (m, 3H), 3.76-3.81 (m, 1H), 3.86 (dd, J=10.8/4.1 Hz, 1H), 4.44 (tt, J=11.9/3.7 Hz, 1H), 7.15-7.18 (m, 2H), 7.70-7.76 (m, 2H), 8.00 (s, 1H), 8.11 (s, 1H), 8.34 (s, 1H). MS m/z ([M−H]+) 446.

Example 32

Synthesis of [syn-1-(1'-Cyclohexyl-1H,1'H-[4,5']bibenzimidazolyl-6-yl)-5-methyl-pyrrolidin-3-yl]-methanol Example 32

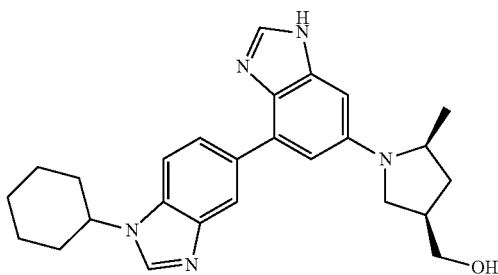

Step 1: {syn-1-[3-(1-Cyclohexyl-1H-benzimidazol-5-yl)-4,5-dinitro-phenyl]-5-methyl-pyrrolidin-3-yl}-methanol (32a)

According to the procedure described in example 30, step 1, compound (29b) (100 mg, 0.26 mmol) was converted, by reaction with compound (7e) (45 mg, 0.39 mmol) and after purification by preparative TLC on silica gel (DCM/MeOH 9/1), to compound (32a) (92 mg, 0.19 mmol, 74%) as an yellow solid. $^1$H NMR (400 MHz, DMSO-$d_6$) δ 1.16 (d, J=6.3 Hz, 3H), 1.25-1.37 (m, 1H), 1.44-1.57 (m, 2H), 1.70-1.79 (m, 2H), 1.81-1.93 (m, 5H), 2.02-2.10 (m, 2H), 3.08-3.14 (m, 1H), 3.17 (d, J=5.3 Hz, 1H), 3.40-3.52 (m, 2H), 3.60 (dd, J=10.6/8.1 Hz, 1H), 4.15-4.23 (m, 1H), 4.40 (tt, J=11.8/3.5 Hz, 1H), 4.70 (t, J=5.2 Hz, 1H), 6.67 (d, J=2.6 Hz, 1H), 7.14 (d, J=2.6 Hz, 1H), 7.17 (dd, J=8.4/1.7 Hz, 1H), 7.65 (d, J=1.4 Hz, 1H), 7.74 (d, J=8.4 Hz, 1H), 8.42 (s, 1H). MS m/z ([M+H]+) 480.

Step 2: {syn-1-[3,4-Diamino-5-(1-cyclohexyl-1H-benzimidazol-5-yl)-phenyl]-5-methyl-pyrrolidin-3-yl}-methanol (32b)

According to the procedure described in example 29, step 4, compound (32a) (90 mg, 0.18 mmol) was converted, without further purification, to compound (32b) (75 mg, 0.18 mmol, 100%). $^1$H NMR (400 MHz, DMSO-$d_6$) δ 1.08 (d, J=6.1 Hz, 3H), 1.22-1.38 (m, 1H), 1.44-1.58 (m, 2H), 1.60-1.68 (m, 1H), 1.69-1.76 (m, 2H), 1.84-1.92 (m, 4H), 2.02-2.10 (m, 2H), 2.78 (t, J=8.6 Hz, 1H), 3.34-3.46 (m, 4H), 3.67-3.74 (m, 1H), 4.33-4.42 (m, 1H), 4.46 (bs, 2H), 4.59 (t, J=5.2 Hz, 1H), 5.68 (d, J=2.6 Hz, 1H), 5.98 (d, J=2.6 Hz, 1H), 7.24 (dd, J=8.4/1.5 Hz, 1H), 7.57 (d, J=1.1 Hz, 1H), 7.68 (d, J=8.3 Hz, 1H), 8.32 (s, 1H). MS m/z ([M+H]+) 420.

Step 3: [syn-1-(1'-Cyclohexyl-1H,1'H-[4,5']bibenzimidazolyl-6-yl)-5-methyl-pyrrolidin-3-yl]-methanol, Example (32)

According to the procedure described in example 30, step 3, compound (32b) (40 mg, 0.095 mmol) was converted, after purification by preparative TLC on silica gel (DCM/MeOH 85/15+2% NH$_3$ 7M in MeOH), to Example (32) (13 mg, 0.030 mmol, 31%). $^1$H NMR (400 MHz, CDCl$_3$) δ 1.20 (d, J=5.8 Hz, 3H), 1.22-1.38 (m, 2H), 1.44-1.58 (m, 2H), 1.72-1.92 (m, 5H), 1.92-2.02 (m, 2H), 2.16-2.27 (m, 2H), 2.68-2.78 (m, 1H), 3.02-3.10 (m, 1H), 3.52-3.60 (m, 1H), 3.62-3.69 (m, 1H), 3.70-3.76 (m, 1H), 3.96-4.05 (m, 1H), 4.13-4.24 (m, 1H), 6.65 (bs, 1H), 6.77 (bs, 1H), 7.48 (d, J=8.5 Hz, 1H), 7.73 (bs, 1H), 7.98-8.10 (m, 3H). MS m/z ([M−H]+) 430.

Example 33

Synthesis of [anti-1-(1'-Cyclohexyl-1H,1'H-[4,5']bibenzimidazolyl-6-yl)-5-methyl-pyrrolidin-3-yl]-methanol Example 33

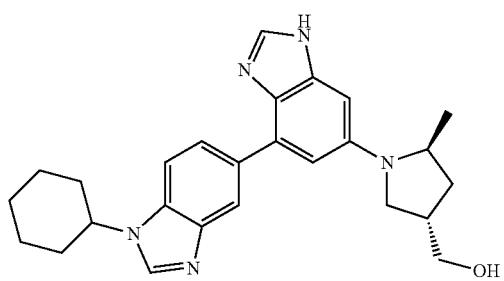

Step 1: {anti-1-[3-(1-Cyclohexyl-1H-benzimidazol-5-yl)-4,5-dinitro-phenyl]-5-methyl-pyrrolidin-3-yl}-methanol (33a)

According to the procedure described in example 30, step 1, compound (29b) (100 mg, 0.26 mmol) was converted, by reaction with compound (8a) (45 mg, 0.39 mmol) and after purification by preparative TLC on silica gel (DCM/MeOH 9/1), to compound (33a) (99 mg, 0.206 mmol, 80%) as an yellow solid. $^1$H NMR (400 MHz, DMSO-d$_6$) δ 1.21 (d, J=6.1 Hz, 3H), 1.24-1.36 (m, 1H), 1.44-1.57 (m, 3H), 1.69-1.76 (m, 1H), 1.82-1.93 (m, 4H), 2.02-2.10 (m, 2H), 2.31-2.38 (m, 2H), 3.17 (d, J=5.2 Hz, 1H), 3.42-3.52 (m, 2H), 3.61 (dd, J=10.7/7.8 Hz, 1H), 4.08-4.14 (m, 1H), 4.40 (tt, J=11.5/3.7 Hz, 1H), 4.74 (t, J=5.2 Hz, 1H), 6.72 (d, J=2.7 Hz, 1H), 7.16-7.20 (m, 2H), 7.65 (d, J=1.4 Hz, 1H), 7.74 (d, J=8.5 Hz, 1H), 8.42 (s, 1H). MS m/z ([M+H]+) 480.

Step 2: {anti-1-[3,4-Diamino-5-(1-cyclohexyl-1H-benzimidazol-5-yl)-phenyl]-5-methyl-pyrrolidin-3-yl}-methanol (33b)

According to the procedure described in example 29, step 4, compound (33a) (97 mg, 0.2 mmol) was converted, without further purification, to compound (33b) (66 mg, 0.2 mmol, 100%). $^1$H NMR (400 MHz, DMSO-d$_6$) δ 1.10 (d, J=6.0 Hz, 3H), 1.28-1.38 (m, 2H), 1.44-1.58 (m, 2H), 1.69-1.76 (m, 1H), 1.84-1.91 (m, 4H), 2.02-2.10 (m, 2H), 2.18-2.28 (m, 2H), 3.06-3.12 (m, 1H), 3.13-3.19 (m, 1H), 3.40-3.48 (m, 4H), 3.60-3.68 (m, 1H), 4.32-4.42 (m, 1H), 4.47 (bs, 2H), 4.60 (t, J=5.3 Hz, 1H), 5.74 (d, J=2.3 Hz, 1H), 6.04 (d, J=2.5 Hz, 1H), 7.25 (dd, J=8.5/1.5 Hz, 1H), 7.57 (s, 1H), 7.68 (d, J=8.4 Hz, 1H), 8.32 (s, 1H). MS m/z ([M+H]+) 420.

Step 3: [anti-1-(1'-Cyclohexyl-1H,1'H-[4,5']bibenzimidazolyl-6-yl)-5-methyl-pyrrolidin-3-yl]-methanol, Example (33)

According to the procedure described in example 30, step 3, compound (33b) (40 mg, 0.095 mmol) was converted, after purification by preparative TLC on silica gel (DCM/MeOH 85/15+2% NH$_3$ 7M in MeOH), to Example (33) (15 mg, 0.035 mmol, 37%). $^1$H NMR (400 MHz, CDCl$_3$) δ 1.24 (d, J=6.3 Hz, 3H), 1.27-1.39 (m, 2H), 1.46-1.58 (m, 2H), 1.76-1.86 (m, 4H), 1.88-1.94 (m, 1H), 1.94-2.02 (m, 2H), 2.20-2.27 (m, 2H), 2.70-2.80 (m, 1H), 3.08 (t, J=8.7 Hz, 1H), 3.60 (t, J=8.3 Hz, 1H), 3.65-3.77 (m, 2H), 4.03 (t, J=6.3 Hz, 1H), 4.16-4.25 (m, 1H), 6.70 (bs, 1H), 6.80 (s, 1H), 7.50 (d, J=8.4 Hz, 1H), 7.78 (bs, 1H), 7.94 (s, 1H), 8.01 (s, 1H), 8.10 (s, 1H). MS m/z ([M−H]+) 430.

Example 34

Synthesis of [1-(1'-Cyclohexyl-1H,1'H-[4,5']bibenzimidazolyl-6-yl)-4-hydroxymethyl-piperidin-4-yl]-methanol Example 34

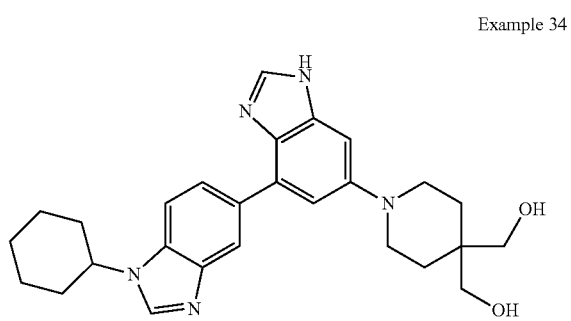 [SMILES: OCC1(CO)CCN(c2cc(-c3ccc4c(c3)ncn4C3CCCCC3)c3nc[nH]c3c2)CC1]

Step 1: {1-[3-(1-Cyclohexyl-1H-benzimidazol-5-yl)-4,5-dinitro-phenyl]-4-hydroxymethyl-piperidin-4-yl}-methanol (34a)

According to the procedure described in example 30, step 1, compound (29b) (100 mg, 0.26 mmol) was converted, by reaction with (4-Hydroxymethyl-piperidin-4-yl)-methanol hydrochloride (62 mg, 0.39 mmol) and after purification by preparative TLC on silica gel (DCM/MeOH 9/1), to compound (34a) (104 mg, 0.204 mmol, 79%) as an yellow solid. $^1$H NMR (400 MHz, DMSO-d$_6$) δ 1.24-1.36 (m, 1H), 1.44-1.56 (m, 6H), 1.69-1.76 (m, 1H), 1.82-1.94 (m, 4H), 2.02-2.09 (m, 2H), 3.33 (d, J=5.4 Hz, 4H), 3.47-3.52 (m, 4H), 4.36-4.44 (m, 1H), 4.46 (t, J=5.4 Hz, 2H), 7.04 (d, J=2.7 Hz, 1H), 7.17 (dd, J=8.4/1.5 Hz, 1H), 7.49 (d, J=2.6

Hz, 1H), 7.65 (d, J=1.2 Hz, 1H), 7.73 (d, J=8.3 Hz, 1H), 8.42 (s, 1H). MS m/z ([M+H]+) 510.

Step 2: {1-[3,4-Diamino-5-(1-cyclohexyl-1H-benzimidazol-5-yl)-phenyl]-4-hydroxymethyl-piperidin-4-yl}-methanol (34b)

According to the procedure described in example 29, step 4, compound (34a) (102 mg, 0.2 mmol) was converted, without further purification, to compound (34b) (90 mg, 0.2 mmol, 100%). $^1$H NMR (400 MHz, DMSO-$d_6$) δ 1.25-1.37 (m, 1H), 1.44-1.58 (m, 7H), 1.70-1.76 (m, 1H), 1.82-1.94 (m, 5H), 2.02-2.10 (m, 2H), 2.90 (t, J=5.5 Hz, 4H), 3.63 (bs, 2H), 4.32 (t, J=5.4 Hz, 2H), 4.33-4.42 (m, 1H), 4.48 (bs, 2H), 5.42 (bs, 2H), 6.02 (d, J=2.6 Hz, 1H), 6.30 (d, J=2.6 Hz, 1H), 7.25 (dd, J=8.4/1.5 Hz, 1H), 7.58 (d, J=1.1 Hz, 1H), 7.68 (d, J=8.4 Hz, 1H), 8.33 (s, 1H). MS m/z ([M+H]+) 450.

Step 3: [1-(1'-Cyclohexyl-1H,1'H-[4,5']bibenzimidazolyl-6-yl)-4-hydroxymethyl-piperidin-4-yl]-methanol, Example (35)

According to the procedure described in example 30, step 3, compound (34b) (40 mg, 0.089 mmol) was converted, after purification by preparative TLC on silica gel (DCM/MeOH 85/15+2% NH$_3$ 7M in MeOH), to Example (34) (8 mg, 0.017 mmol, 19%) as a pink solid. $^1$H NMR (400 MHz, CD$_3$OD) δ 1.36-1.48 (m, 1H), 1.56-1.70 (m, 2H), 1.72 (t, J=5.7 Hz, 4H), 1.80-1.88 (m, 1H), 1.90-2.04 (m, 4H), 2.20-2.28 (m, 2H), 3.24 (t, J=5.7 Hz, 4H), 3.59 (s, 4H), 4.44 (tt, J=11.9/3.6 Hz, 1H), 7.17-7.21 (m, 2H), 7.73 (s, 2H), 8.00 (s, 1H), 8.09 (s, 1H), 8.33 (s, 1H). MS m/z ([M−H]+) 460.

Example 35

Synthesis of 2-[1-(1'-Cyclohexyl-1H,1'H-[4,5']bibenzimidazolyl-6-yl)-pyrrolidin-3-yl]-ethanol Example 35

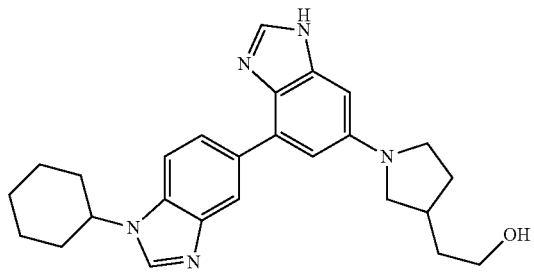

Step 1: 2-{1-[3-(1-Cyclohexyl-1H-benzimidazol-5-yl)-4,5-dinitro-phenyl]-pyrrolidin-3-yl}-ethanol (35a)

According to the procedure described in example 30, step 1, compound (29b) (100 mg, 0.26 mmol) was converted, by reaction with 2-Pyrrolidin-3-yl-ethanol (45 mg, 0.39 mmol) and after purification by preparative TLC on silica gel (DCM/MeOH 92/8), to compound (35a) (120 mg, 0.25 mmol, 97%) as an orange solid. $^1$H NMR (400 MHz, CDCl$_3$) δ 1.34 (qt, J=12.9/3.7 Hz, 1H), 1.46-1.56 (m, 3H), 1.74-1.88 (m, 6H), 1.96-2.04 (m, 2H), 2.21-2.32 (m, 3H), 2.47-2.56 (m, 1H), 3.05 (t, J=9.1 Hz, 1H), 3.34-3.41 (m, 1H), 3.44-3.50 (m, 1H), 3.60 (dd, J=9.7/7.6 Hz, 1H), 3.77 (td, J=6.1/1.9 Hz, 2H), 4.25 (tt, J=12.0/3.7 Hz, 1H), 6.60 (d, J=2.7 Hz, 1H), 6.97 (d, J=2.7 Hz, 1H), 7.21 (dd, J=8.5/1.7 Hz, 1H), 7.44 (dd, J=8.4/0.4 Hz, 1H), 7.80 (d, J=1.2 Hz, 1H), 8.05 (s, 1H). MS m/z ([M+H]+) 480.

Step 2: 2-{1-[3,4-Diamino-5-(1-cyclohexyl-1H-benzimidazol-5-yl)-phenyl]-pyrrolidin-3-yl}-ethanol (35b)

According to the procedure described in example 29, step 4, compound (35a) (117 mg, 0.24 mmol) was converted, without further purification, to compound (35b) (100 mg, 0.24 mmol, 100%). $^1$H NMR (400 MHz, DMSO-$d_6$) δ 1.26-1.36 (m, 1H), 1.45-1.60 (m, 6H), 1.70-1.78 (m, 2H), 1.83-1.94 (m, 5H), 2.02-2.10 (m, 3H), 2.23-2.30 (m, 1H), 2.70-2.78 (m, 1H), 3.06-3.18 (m, 2H), 3.42-3.49 (m, 2H), 4.32-4.40 (m, 1H), 4.41 (t, J=5.1 Hz, 1H), 4.47 (bs, 2H), 5.67 (bs, 1H), 5.96 (d, J=2.3 Hz, 1H), 7.24 (dd, J=8.5/1.3 Hz, 1H), 7.57 (s, 1H), 7.68 (d, J=8.3 Hz, 1H), 8.32 (s, 1H). MS m/z ([M+H]+) 420.5

Step 3: 2-[1-(1'-Cyclohexyl-1H,1'H-[4,5']bibenzimidazolyl-6-yl)-pyrrolidin-3-yl]-ethanol, Example (35)

According to the procedure described in example 30, step 3, compound (35b) (40 mg, 0.095 mmol) was converted, after purification by preparative TLC on silica gel (DCM/MeOH 85/15+2% NH$_3$ 7M in MeOH), to Example (35) (14 mg, 0.032 mmol, 34%) as a pink solid. $^1$H NMR (400 MHz, CD$_3$OD) δ 1.41 (qt, J=12.9/3.4 Hz, 1H), 1.55-1.68 (m, 2H), 1.70-1.80 (m, 3H), 1.80-1.88 (m, 1H), 1.88-1.95 (m, 1H), 1.95-2.04 (m, 3H), 2.19-2.29 (m, 3H), 2.41-2.54 (m, 1H), 3.02 (t, J=8.4 Hz, 1H), 3.35-3.48 (m, 2H), 3.57 (t, J=8.1 Hz, 1H), 3.68 (t, J=6.6 Hz, 2H), 4.42 (tt, J=12.0/3.7 Hz, 1H), 6.68 (d, J=1.9 Hz, 1H), 6.75 (d, J=1.9 Hz, 1H), 7.70 (d, J=8.5 Hz, 1H), 7.75 (d, J=8.5 Hz, 1H), 7.96 (s, 1H), 8.01 (s, 1H), 8.30 (s, 1H). MS m/z ([M−H]+) 430.

Example 36

Synthesis of 1'-Cyclohexyl-6-(hexahydro-pyrrolo[3,4-c]pyrrol-2-yl)-1H,1'H-[4,5']bibenzimidazolyl Example 36

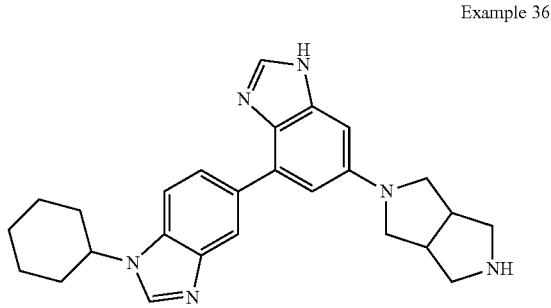 [SMILES: c1nc2c(-c3ccc4c(c3)ncn4C3CCCCC3)cc(N3CC4CNCC4C3)cc2[nH]1]

Step 1: tert-butyl 5-[3-(1-Cyclohexyl-1H-benzimidazol-5-yl)-4,5-dinitro-phenyl]-hexahydro-pyrrolo[3,4-c]pyrrole-2-carboxylate (36a)

According to the procedure described in example 30, step 1, compound (29b) (100 mg, 0.26 mmol) was converted, by reaction with tert-butyl Hexahydro-pyrrolo[3,4-c]pyrrole-2- carboxylate (83 mg, 0.39 mmol) and after purification by preparative TLC on silica gel (DCM/MeOH 94/6), to compound (36a) (125 mg, 0.217 mmol, 84%) as an orange solid. $^1$H NMR (400 MHz, CDCl$_3$) δ 1.34 (qt, J=12.9/3.4 Hz, 1H), 1.45 (s, 9H), 1.46-1.58 (m, 2H), 1.76-1.88 (m, 3H), 1.96-2.04 (m, 2H), 2.20-2.28 (m, 2H), 3.08 (bs, 2H), 3.25-3.40 (m, 4H), 3.62-3.72 (m, 4H), 4.21 (tt, J=12.0/3.8 Hz, 1H), 6.64 (d, J=2.6 Hz, 1H), 7.02 (d, J=2.6 Hz, 1H), 7.21 (dd, J=8.4/1.1 Hz, 1H), 7.44 (d, J=8.4 Hz, 1H), 7.79 (s, 1H), 8.05 (s, 1H). MS m/z ([M+H]+) 577.

Step 2: tert-butyl 5-[3,4-Diamino-5-(1-cyclohexyl-1H-benzimidazol-5-yl)-phenyl]-hexahydro-pyrrolo[3,4-c]pyrrole-2-carboxylate (36b)

According to the procedure described in example 29, step 4, compound (36a) (122 mg, 0.21 mmol) was converted, without further purification, to compound (36b) (84 mg, 0.16 mmol, 78%). $^1$H NMR (400 MHz, DMSO-d$_6$) δ 1.25-1.36 (m, 1H), 1.38 (s, 9H), 1.44-1.57 (m, 2H), 1.70-1.77 (m, 1H), 1.82-1.94 (m, 4H), 2.02-2.10 (m, 2H), 2.91 (bs, 2H), 2.97-3.04 (m, 2H), 3.12-3.20 (m, 2H), 3.23-3.30 (m, 2H), 3.44-3.56 (m, 4H), 4.32-4.42 (m, 1H), 4.50 (bs, 2H), 5.72 (d, J=2.2 Hz, 1H), 6.00 (d, J=2.3 Hz, 1H), 7.25 (dd, J=8.4/1.4 Hz, 1H), 7.58 (d, J=1.1 Hz, 1H), 7.68 (d, J=8.4 Hz, 1H), 8.33 (s, 1H). MS m/z ([M+H]+) 517.

Step 3: 1'-Cyclohexyl-6-(hexahydro-pyrrolo[3,4-c]pyrrol-2-yl)-1H,1'H-[4,5']bibenzimidazolyl, Example (36)

According to the procedure described in example 30, step 3, compound (36b) (45 mg, 0.087 mmol) was converted, after purification by preparative TLC on silica gel (DCM/MeOH 85/15+2% NH$_3$ 7M in MeOH), to Example (36) (10 mg, 0.023 mmol, 27%) as a beige solid. $^1$H NMR (400 MHz, CD$_3$OD) δ 1.42 (qt, J=12.9/3.4 Hz, 1H), 1.56-1.69 (m, 2H), 1.80-1.88 (m, 1H), 1.88-2.04 (m, 4H), 2.20-2.28 (m, 2H), 2.96 (dd, J=11.5/3.8 Hz, 2H), 3.02-3.10 (m, 2H), 3.23-3.30 (m, 2H), 3.39 (d, J=4.6 Hz, 4H), 4.43 (tt, J=11.8/3.6 Hz, 1H), 6.88 (bs, 1H), 6.93 (d, J=2.1 Hz, 1H), 7.74 (bs, 2H), 7.99 (bs, 2H), 8.31 (s, 1H). MS m/z ([M−H]+) 427.

Example 37

Synthesis of [1-(1'-Cyclohexyl-1H,1'H-[4,5']bibenzimidazolyl-6-yl)-piperidin-3-yl]-methanol reaction with Piperidin-3-yl-methanol (45 mg, 0.39 mmol) and after purification by preparative TLC on silica gel (DCM/MeOH 95/5), to compound (37a) (96 mg, 0.20 mmol, 78%) as an orange solid. $^1$H NMR (400 MHz, CDCl$_3$) δ 1.20-1.26 (m, 1H), 1.28-1.40 (m, 2H), 1.44-1.54 (m, 2H), 1.62-1.72 (m, 1H), 1.76-1.94 (m, 6H), 1.96-2.04 (m, 2H), 2.20-2.28 (m, 2H), 2.88 (dd, J=12.9/9.8 Hz, 1H), 2.99-3.07 (m, 1H), 3.51-3.58 (m, 1H), 3.62-3.68 (m, 1H), 3.70-3.80 (m, 1H), 3.87-3.94 (m, 1H), 4.21 (tt, J=11.9/3.6 Hz, 1H), 7.00 (d, J=2.8 Hz, 1H), 7.21 (dd, J=8.5/1.6 Hz, 1H), 7.38 (d, J=2.8 Hz, 1H), 7.45 (d, J=8.4 Hz, 1H), 7.79 (d, J=1.3 Hz, 1H), 8.04 (s, 1H). MS m/z ([M+H]+) 480.

Step 2: {-[3,4-Diamino-5-(1-cyclohexyl-1H-benzimidazol-5-yl)-phenyl]-piperidin-3-yl}-methanol (37b)

According to the procedure described in example 29, step 4, compound (37a) (90 mg, 0.18 mmol) was converted, without further purification, to compound (37b) (75 mg, 0.18 mmol, 100%). $^1$H NMR (400 MHz, DMSO-d$_6$) δ 0.91-1.03 (m, 1H), 1.25-1.37 (m, 1H), 1.45-1.60 (m, 3H), 1.63-1.76 (m, 4H), 1.82-1.94 (m, 4H), 2.02-2.10 (m, 2H), 2.18-2.25 (m, 1H), 2.42-2.48 (m, 1H), 3.22-3.36 (m, 3H), 3.41-3.47 (m, 1H) 3.64 (bs, 2H), 4.33-4.42 (m, 1H), 4.44 (t, J=5.3 Hz, 1H), 4.49 (bs, 2H), 6.02 (d, J=2.6 Hz, 1H), 6.31 (d, J=2.6 Hz, 1H), 7.24 (dd, J=8.4/1.5 Hz, 1H), 7.57 (d, J=1.1 Hz, 1H), 7.69 (d, J=8.4 Hz, 1H), 8.33 (s, 1H). MS m/z ([M+H]+) 420.

Step 3: [1-(1'-Cyclohexyl-1H,1'H-[4,5']bibenzimidazolyl-6-yl)-piperidin-3-yl]-methanol, Example (37)

According to the procedure described in example 30, step 3, compound (37b) (40 mg, 0.095 mmol) was converted, after purification by preparative TLC on silica gel (DCM/MeOH 9/1+2% NH$_3$ 7M in MeOH), to Example (37) (14 mg, 0.032 mmol, 35%) as a beige solid. $^1$H NMR (400 MHz, CD$_3$OD) δ 1.12-1.20 (m, 1H), 1.42 (qt, J=12.9/3.4 Hz, 1H), 1.56-1.68 (m, 2H), 1.76-1.92 (m, 4H), 1.92-2.04 (m, 5H), 2.19-2.27 (m, 2H), 2.50-2.58 (m, 1H), 2.72-2.80 (m, 1H), 3.50 (d, J=7.3 Hz, 1H), 3.53-3.63 (m, 2H), 3.72-3.79 (m, 1H), 4.38-4.48 (m, 1H), 7.16-7.20 (m, 2H), 7.70-7.75 (m, 2H), 8.01 (bs, 1H), 8.05 (s, 1H), 8.31 (s, 1H). MS m/z ([M−H]+) 430.

Example 38

Synthesis of 1-(1'-Cyclohexyl-1H,1'H-[4,5']bibenzimidazolyl-6-yl)-piperidin-4-ol

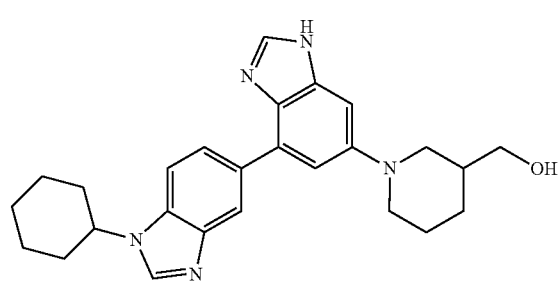

Example 37

Step 1: {1-[3-(1-Cyclohexyl-1H-benzimidazol-5-yl)-4,5-dinitro-phenyl]-piperidin-3-yl}-methanol (37a)

According to the procedure described in example 30, step 1, compound (29b) (100 mg, 0.26 mmol) was converted, by

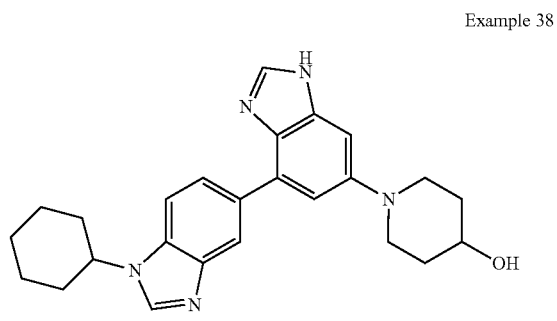 [SMILES: OC1CCN(c2cc(-c3ccc4c(c3)ncn4C3CCCCC3)c3nc[nH]c3c2)CC1]

Example 38

Step 1: 1-[3-(1-Cyclohexyl-1H-benzimidazol-5-yl)-4,5-dinitro-phenyl]-piperidin-4-ol (38a)

According to the procedure described in example 30, step 1, compound (29b) (100 mg, 0.26 mmol) was converted, by reaction with Piperidin-4-ol (40 mg, 0.39 mmol) and after purification by preparative TLC on silica gel (DCM/MeOH 95/5), to compound (38a) (111 mg, 0.24 mmol, 92%) as an orange gum. $^{1}$H NMR (400 MHz, CDCl$_{3}$) δ 1.28-1.40 (m, 1H), 1.46-1.59 (m, 2H), 1.64-1.74 (m, 2H), 1.76-1.88 (m, 3H), 1.93-2.04 (m, 5H), 2.20-2.27 (m, 2H), 3.20-3.29 (m, 2H), 3.69-3.76 (m, 2H), 3.97-4.05 (m, 1H), 4.16-4.26 (m, 1H), 6.99 (d, J=2.8 Hz, 1H), 7.20-7.23 (m, 1H), 7.39 (d, J=2.7 Hz, 1H), 7.45 (d, J=8.4 Hz, 1H), 7.78 (s, 1H), 8.04 (s, 1H). MS m/z ([M+H]+) 466.

Step 2: 1-[3,4-Diamino-5-(1-cyclohexyl-1H-benzimidazol-5-yl)-phenyl]-piperidin-4-ol (38b)

According to the procedure described in example 29, step 4, compound (38a) (105 mg, 0.22 mmol) was converted, without further purification, to compound (38b) (80 mg, 0.19 mmol, 90%). $^{1}$H NMR (400 MHz, DMSO-d$_{6}$) δ 1.24-1.38 (m, 1H), 1.42-1.58 (m, 4H), 1.70-1.82 (m, 3H), 1.82-1.92 (m, 4H), 2.02-2.10 (m, 2H), 2.58-2.66 (m, 2H), 3.23-3.30 (m, 2H), 3.48-3.57 (m, 1H), 3.64 (bs, 2H), 4.32-4.42 (m, 1H), 4.48 (bs, 2H), 4.58 (d, J=4.2 Hz, 1H), 6.02 (d, J=2.7 Hz, 1H), 6.30 (d, J=2.7 Hz, 1H), 7.24 (dd, J=8.4/1.5 Hz, 1H), 7.57 (d, J=1.1 Hz, 1H), 7.68 (d, J=8.4 Hz, 1H), 8.33 (s, 1H). MS m/z ([M+H]+) 406.

Step 3: 1-(1'-Cyclohexyl-1H,1'H-[4,5']bibenzimidazolyl-6-yl)-piperidin-4-ol, Example (38)

According to the procedure described in example 30, step 3, compound (38b) (40 mg, 0.095 mmol) was converted, after purification by preparative TLC on silica gel (DCM/MeOH 9/1+2% NH$_{3}$ 7M in MeOH), to Example (38) (16 mg, 0.038 mmol, 40%) as a beige solid. $^{1}$H NMR (400 MHz, CD$_{3}$OD) δ 1.42 (qt, J=12.9/3.6 Hz, 1H), 1.56-1.69 (m, 2H), 1.70-1.88 (m, 3H), 1.90-2.08 (m, 6H), 2.19-2.28 (m, 2H), 2.91-3.00 (m, 2H), 3.54-3.62 (m, 2H), 3.74-3.82 (m, 1H), 4.38-4.48 (m, 1H), 7.15-7.20 (m, 2H), 7.72 (bs, 2H), 8.00 (bs, 1H), 8.06 (s, 1H), 8.31 (s, 1H). MS m/z ([M−H]+) 416.

Example 39

Synthesis of 1-(1'-Cyclohexyl-1H,1'H-[4,5']bibenzimidazolyl-6-yl)-piperidin-3-ol purification by preparative TLC on silica gel (DCM/MeOH 95/5), to compound (39a) (121 mg, 0.26 mmol, 100%) as an orange gum. $^{1}$H NMR (400 MHz, CDCl$_{3}$) δ 1.28-1.40 (m, 1H), 1.46-1.60 (m, 2H), 1.63-1.70 (m, 2H), 1.76-1.88 (m, 3H), 1.90-2.04 (m, 4H), 2.12 (d, J=5.5 Hz, 1H), 2.20-2.28 (m, 2H), 3.16-3.29 (m, 2H), 3.49-3.55 (m, 1H), 3.66 (dd, J=12.8/3.4 Hz, 1H), 3.87-3.96 (m, 1H), 4.20 (tt, J=12.0/3.6 Hz, 1H), 7.01 (d, J=2.8 Hz, 1H), 7.21 (dd, J=8.4/1.6 Hz, 1H), 7.41 (d, J=2.8 Hz, 1H), 7.44 (d, J=8.4 Hz, 1H), 7.77 (d, J=1.4 Hz, 1H), 8.04 (s, 1H). MS m/z ([M+H]+) 466.

Step 2: 1-[3,4-Diamino-5-(1-cyclohexyl-1H-benzimidazol-5-yl)-phenyl]-piperidin-3-ol (39b)

According to the procedure described in example 29, step 4, compound (39a) (121 mg, 0.26 mmol) was converted, without further purification, to compound (39b) (87 mg, 0.21 mmol, 83%). $^{1}$H NMR (400 MHz, DMSO-d$_{6}$) δ 1.10-1.20 (m, 1H), 1.24-1.38 (m, 1H), 1.44-1.58 (m, 3H), 1.66-1.75 (m, 2H), 1.81-1.92 (m, 5H), 2.02-2.10 (m, 2H), 2.29 (dd, J=11.1/9.2 Hz, 1H), 2.43 (td, J=11.4/2.9 Hz, 1H), 3.18-3.24 (m, 1H), 3.33-3.39 (m, 1H), 3.52-3.62 (m, 1H), 3.65 (bs, 2H), 4.32-4.42 (m, 1H), 4.51 (bs, 2H), 4.67 (d, J=4.8 Hz, 1H), 6.01 (d, J=2.6 Hz, 1H), 6.29 (d, J=2.6 Hz, 1H), 7.25 (dd, J=8.4/1.5 Hz, 1H), 7.58 (d, J=1.1 Hz, 1H), 7.69 (d, J=8.4 Hz, 1H), 8.33 (s, 1H). MS m/z ([M+H]+) 406.

Step 3: 1-(1'-Cyclohexyl-1H,1'H-[4,5']bibenzimidazolyl-6-yl)-piperidin-3-ol, Example (39)

According to the procedure described in example 30, step 3, compound (39b) (40 mg, 0.098 mmol) was converted, after purification by preparative TLC on silica gel (DCM/MeOH 9/1+2% NH$_{3}$ 7M in MeOH), to Example (39) (20 mg, 0.048 mmol, 50%) as a beige solid. $^{1}$H NMR (400 MHz, CD$_{3}$OD) δ 1.38-1.48 (m, 2H), 1.56-1.68 (m, 2H), 1.70-1.80 (m, 1H), 1.80-1.88 (m, 1H), 1.90-2.04 (m, 6H), 2.20-2.27 (m, 2H), 2.74 (dd, J=11.3/8.7 Hz, 1H), 2.83 (td, J=10.5/2.9 Hz, 1H), 3.41-3.46 (m, 1H), 3.57-3.63 (m, 1H), 3.83-3.91 (m, 1H), 4.38-4.47 (m, 1H), 7.14-7.17 (m, 2H), 7.72 (bs, 2H), 8.00 (bs, 1H), 8.06 (s, 1H), 8.31 (s, 1H). MS m/z ([M−H]+) 416.

Example 40

Synthesis of 2-(1'-Cyclohexyl-1H,1'H-[4,5']bibenzimidazolyl-6-ylamino)-ethanol

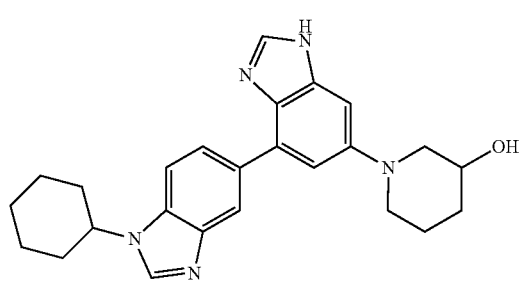

Example 39

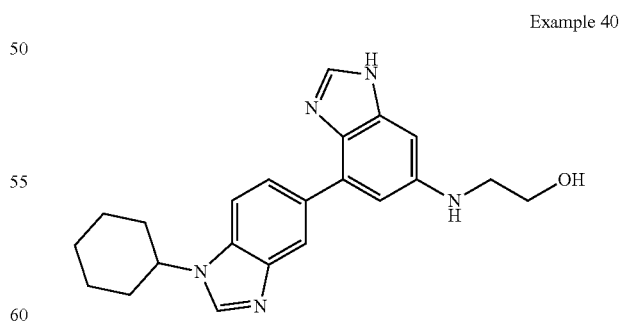

Example 40

Step 1: 1-[3-(1-Cyclohexyl-1H-benzimidazol-5-yl)-4,5-dinitro-phenyl]-piperidin-3-ol (39a)

According to the procedure described in example 30, step 1, compound (29b) (100 mg, 0.26 mmol) was converted, by reaction with Piperidin-3-ol (40 mg, 0.39 mmol) and after Step 1: 2-[3-(1-Cyclohexyl-1H-benzimidazol-5-yl)-4,5-dinitro-phenylamino]-ethanol (40a)

According to the procedure described in example 30, step 1, compound (29b) (80 mg, 0.21 mmol) was converted, by reaction with 2-Amino-ethanol (19 mg, 0.31 mmol) and after purification by preparative TLC on silica gel (DCM/MeOH 9/1), to compound (40a) (58 mg, 0.13 mmol, 65%) as an orange solid. MS m/z ([M+H]+) 426.

Step 2: 2-[3,4-Diamino-5-(1-cyclohexyl-1H-benzimidazol-5-yl)-phenylamino]-ethanol (40b)

According to the procedure described in example 29, step 4, compound (40a) (58 mg, 0.13 mmol) was converted, without further purification, to compound (40b) (41 mg, 0.11 mmol, 84%) as a brown solid. MS m/z ([M+H]+) 366.

Step 3: 2-(1'-Cyclohexyl-1H,1'H-[4,5']bibenzimidazolyl-6-ylamino)-ethanol, Example (40)

According to the procedure described in example 30, step 3, compound (40b) (41 mg, 0.11 mmol) was converted, after purification by preparative TLC on silica gel (DCM/MeOH 9/1+3% NH$_3$ 7M in MeOH), to Example (40) (20 mg, 0.048 mmol, 50%) as a tan solid. $^1$H NMR (400 MHz, CD$_3$OD) δ 1.42 (qt, J=12.9/3.4 Hz, 1H), 1.56-1.69 (m, 2H), 1.80-1.88 (m, 1H), 1.89-2.04 (m, 4H), 2.19-2.27 (m, 2H), 3.31-3.35 (m, 2H), 3.80 (t, J=5.8 Hz, 2H), 4.38-4.48 (m, 1H), 6.83 (d, J=2.0 Hz, 1H), 6.87 (d, J=2.0 Hz, 1H), 7.69-7.76 (m, 2H), 7.96 (s, 1H), 8.00 (bs, 1H), 8.30 (s, 1H). MS m/z ([M–H]+) 376.

Example 41

Synthesis of 1'-Cyclohexyl-6-fluoro-1H,1'H-[4,5']]bibenzimidazolyl

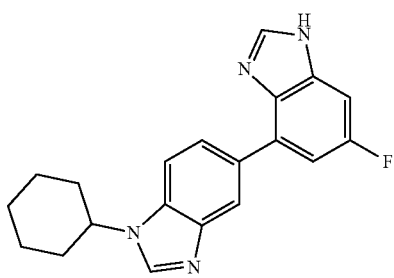

Example 41

To a solution of 4-Bromo-6-fluoro-1H-benzimidazole (200 mg, 0.93 mmol) in dioxane (2 mL) was dissolved 1-Cyclohexyl-5-(4,4,5,5-tetramethyl-[1,3,2]dioxaborolan-2-yl)-1H-benzimidazole (334 mg, 1.02 mmol). A solution of potassium phosphate 1.27 M (1.2 mL) was added and the mixture was degassed 15 minutes in an ultrasonic bath. Dichlorobis(di-tert-butylphenylphosphine)palladium (II) (17 mg, 0.03 mmol) and Tricyclohexylphosphine (13 mg, 0.05 mmol) were added to the middle which was heated at 130° C. for 1 hour under microwave irradiation. The reaction mixture was then concentrated under reduced pressure. The residue was purified by preparative TLC on silica gel (DCM/MeOH 95/5) to give Example (41) (136 mg, 0.41 mmol, 43%). $^1$H NMR (400 MHz, DMSO-d$_6$) δ 1.32 (qt, J=12.8/3.2 Hz, 1H), 1.47-1.58 (m, 2H), 1.74 (bd, J=12.8 Hz, 1H), 1.84-1.94 (m, 4H), 2.08 (bd, J=9.2 Hz, 2H), 4.42 (tt, J=11.6/3.2 Hz, 1H), 7.27-7.33 (m, 2H), 7.76 (d, J=8.4 Hz, 1H), 7.89 (bs, 1H), 8.27 (s, 1H), 8.32 (bs, 1H), 8.39 (s, 1H), 12.64 (s, 1H). MS m/z ([M+H]$^+$) 335.

Example 42

Synthesis of 1'-cyclohexyl-6-Fluoro-7-nitro-1H,1'H-[4,5']bibenzimidazolyl

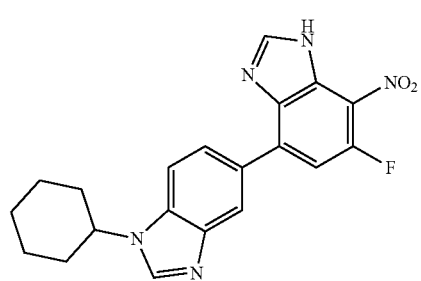

Example 42

Step 1: 4-Bromo-6-fluoro-7-nitro-1H-benzimidazole (42a)

4-Bromo-6-fluoro-1H-benzimidazole (1 g, 4.65 mmol) was dissolved in sulfuric acid (750 μL) at 0° C. Fuming nitric acid (594 μL, 13.95 mmol) was added at 0° C. Then the solution was stirred 4 hours at room temperature. The mixture reaction was poured on ice. The precipitate was filtered and washed with water. The solid was dried under reduced pressure at 45° C. with phosphorus pentoxide to afford compound (42a) as a beige solid (871 mg, 3.35 mmol, 71%). $^1$H NMR (300 MHz, DMSO-d$_6$) δ 7.82 (d, J=12 Hz, 1H), 8.53 (s, 1H). MS m/z ([M+H]$^+$) 260/262.

Step 2: 1'-cyclohexyl-6-Fluoro-7-nitro-1H,1'H-[4,5'] bibenzimidazolyl, Example (42)

To a solution of compound (42a) (20 mg, 0.08 mmol) in a mixture of THF (850 μL) and water (170 μL) was dissolved 1-Cyclohexyl-5-(4,4,5,5-tetramethyl-[1,3,2]dioxaborolan-2-yl)-1H-benzimidazole (26 mg, 0.08 mmol) and potassium carbonate (32 mg, 0.23 mmol). The solution was degassed under argon for 10 minutes and bis(triphenylphosphine)palladium(II) dichloride (10 mg, 0.01 mmol) was added. After 16 hours at 85° C., the reaction mixture was concentrated under reduced pressure. The crude was purified by preparative TLC on silica gel (DCM/MeOH 9/1) to afford Example (42) (16 mg, 0.04 mmol, 55%). $^1$H NMR (400 MHz, DMSO-d$_6$) δ 1.25-1.38 (m, 1H), 1.46-1.60 (m, 2H), 1.70-1.78 (m, 1H), 1.82-1.95 (m, 4H), 2.04-2.12 (m, 2H), 4.39-4.50 (m, 1H), 7.69 (d, J=14.2 Hz, 1H), 7.82 (d, J=8.6 Hz, 1H), 8.08-8.15 (m, 1H), 8.44 (s, 1H), 8.47 (s, 1H), 8.63 (bs, 1H). MS m/z ([M+H]$^+$) 380.

Example 43

Synthesis of [(S)-1-(1'-Cyclohexyl-7-nitro-1H,1'H-[4,5']bibenzimidazolyl-6-yl)-pyrrolidin-3-yl]-methanol

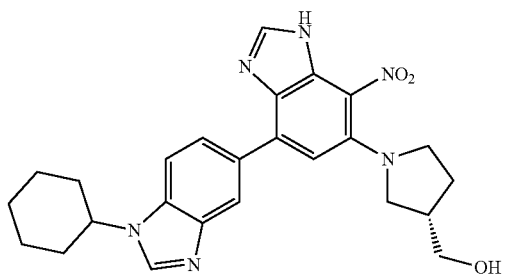

Example 43

According to the procedure described in example 29, step 3, Example (42) (16 mg, 0.04 mmol) was converted, by reaction with (S)-1-Pyrrolidin-3-yl-methanol (6.4 mg, 0.06 mmol) and after trituration in diethyl ether, to Example (43) as a red solid (15 mg, 0.03 mmol, 78%). $^1$H NMR (400 MHz, DMSO-d$_6$) δ 1.28-1.37 (m, 1H), 1.47-1.59 (m, 2H), 1.71-1.76 (m, 2H), 1.84-1.94 (m, 5H), 2.10-2.07 (m, 4H), 2.40-2.50 (m, 1H), 3.24-3.28 (m, 1H), 3.40-3.53 (m, 3H), 4.43 (t, J=11.2 Hz, 1H), 4.73 (t, J=5.2 Hz, 1H), 7.09 (s, 1H), 7.77 (d, J=8.8 Hz, 1H), 8.03 (dd, J=1.6/8.4 Hz, 1H), 8.06 (s, 1H), 8.40 (s, 1H), 8.45 (d, J=1.2 Hz, 1H), 12.63 (bs, 1H). MS m/z ([M+H]$^+$) 461.

Example 44

Synthesis of (3R,4R)-1-(1'-Cyclohexyl-7-nitro-1H,1'H-[4,5']bibenzimidazolyl-6-yl)-4-hydroxymethyl-piperidin-3-ol

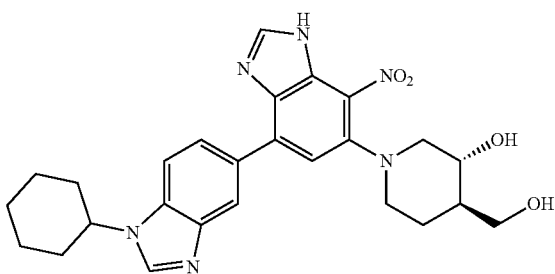

Example 44

According to the procedure described in example 29, step 3, Example (42) (80 mg, 0.21 mmol) was converted, by reaction with (3R,4R)-4-Hydroxymethyl-piperidin-3-ol (36 mg, 0.27 mmol) and after purification by preparative TLC on silica gel (DCM/MeOH 9/1), to Example (44) (7 mg, 0.01 mmol, 6%). $^1$H NMR (400 MHz, CD$_3$OD) δ 1.36-1.46 (m, 1H), 1.53-1.71 (m, 4H), 1.78-1.86 (m, 1H), 1.88-2.01 (m, 5H), 2.18-2.26 (m, 2H), 2.80 (bt, J=10.2 Hz, 1H), 2.99 (bt, J=10.2 Hz, 1H), 3.38-3.46 (bs, 1H), 3.47-3.55 (bs, 1H), 3.65 (dd, J=6.1/10.6 Hz, 1H), 3.77 (bs, 1H), 3.85 (dd, J=4.2/10.6 Hz, 1H), 4.37-4.48 (m, 1H), 7.26 (s, 1H), 7.15 (d, J=8.4 Hz, 1H), 7.87 (bs, 1H), 8.18 (s, 1H), 8.23 (bs, 1H), 8.34 (s, 1H). MS m/z ([M+H]$^+$) 491.

Example 45

Synthesis of (3R,4R)-1-(7-Amino-1'-cyclohexyl-1H,1'H-[4,5']bibenzimidazolyl-6-yl)-4-hydroxymethyl-piperidin-3-ol

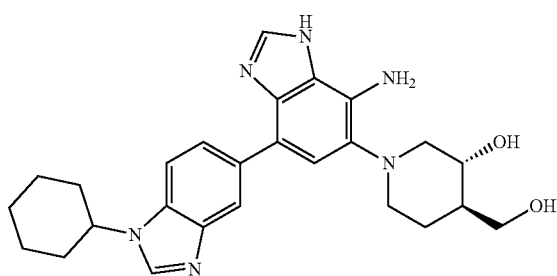

Example 45

A solution of Example (44) (29 mg, 0.06 mmol) in ethanol (2 mL) was purged with nitrogen. Palladium on carbon 10% w (2 mg) was added and the solution was stirred 16 hours at room temperature under hydrogen pressure (1 atm.). The mixture reaction was filtered on PTFE filter and evaporated. The crude was purified by preparative TLC on silica gel (DCM/MeOH 8/2 with 1% ammonia) to afford Example (45) (11 mg, 0.02 mmol, 40%). $^1$H NMR (300 MHz, CD$_3$OD) δ 1.38 (m, 1H), 1.59 (m, 4H), 1.82 (d, J=14.4 Hz, 1H), 1.93 (m, 5H), 2.20 (d, J=11.1 Hz, 2H), 2.58-2.74 (m, 2H), 3.10 (d, J=11.7 Hz, 1H), 3.24-3.28 (m, 1H), 3.64-3.76 (m, 2H), 3.87 (dd, J=4.2/10.8 Hz, 1H), 7.39 (tt, J=3.3/11.7 Hz, 1H), 7.16 (s, 1H), 7.56 (dd, J=1.2/8.4 Hz, 1H), 7.68 (d, J=8.4 Hz, 1H), 7.85 (s, 1H), 8.09 (s, 1H), 8.32 (s, 1H). MS m/z ([M+H]$^+$) 461.

Example 46

Synthesis of [(S)-1-(7-Amino-1'-cyclohexyl-1H,1'H-[4,5']bibenzimidazolyl-6-yl)-pyrrolidin-3-yl]-methanol

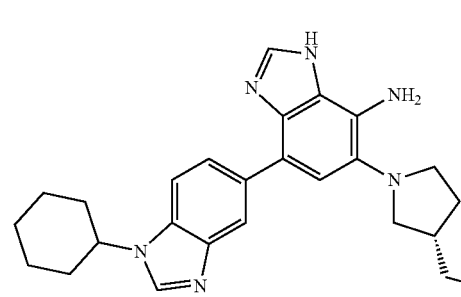

Example 46

According to the procedure described in example 46, Example (43) (44 mg, 0.10 mmol) was converted, after purification by flash chromatography on silica gel (DCM/MeOH 9/1 with 1% ammonia), to Example (46) (6 mg, 0.01 mmol, 14%). $^1$H NMR (300 MHz, CD$_3$OD) δ 1.41 (qt, J=3.0/12.9 Hz, 1H), 1.53-1.74 (m, 3H), 2.83 (bd, J=16.8 Hz, 1H), 1.91-2.01 (m, 4H), 2.07-2.16 (m, 1H), 2.21 (bd, J=12.0 Hz, 2H), 2.46-2.60 (m, 1H), 3.01 (q, J=3.9 Hz, 1H), 3.11-3.22 (m, 3H), 3.63 (d, J=6.9 Hz, 2H), 4.39 (tt, J=3.6/11.7 Hz, 1H), 7.19 (s, 1H), 7.56 (d, J=8.1 Hz, 1H), 7.68 (d, J=8.4 Hz, 1H), 7.85 (bs, 1H), 8.03 (s, 1H), 8.28 (s, 1H). MS m/z ([M+H]+) 431.

Example 47

Synthesis of 1'-Cyclohexyl-6-fluoro-1H,1'H-[4,5']bibenzimidazolyl-7-ylamine

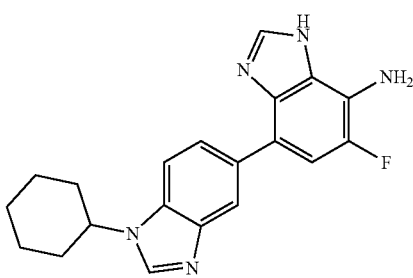

Example 47

Example 42) (90 mg, 0.237 mmol) was dissolved in MeOH (5 mL). The catalyst Pd(C) (20 mg, 20% mass was added and the mixture was stirred under hydrogen atmosphere overnight. The middle was filtered on PTFE filter, concentrated and recrystallized in MeOH to give Example (47) (73 mg, 0.209 mmol, 89%) as a white solid. $^1$H NMR (400 MHz, DMSO-$d_6$) δ 1.25-1.38 (m, 1H), 1.46-1.59 (m, 2H), 1.70-1.78 (m, 1H), 1.81-1.95 (m, 4H), 2.03-2.11 (m, 2H), 4.32-4.46 (m, 1H), 5.20 (d, J=3.1 Hz, 2H), 7.04-7.26 (m, 1H), 7.43-8.42 (m, 5H), 12.19 and 12.37 (2s, 1H). MS m/z ([M+H]+) 350.

Example 48

Synthesis of N-(1'-Cyclohexyl-6-fluoro-1H,1'H-[4,5']bibenzimidazolyl-7-yl)-acetamide

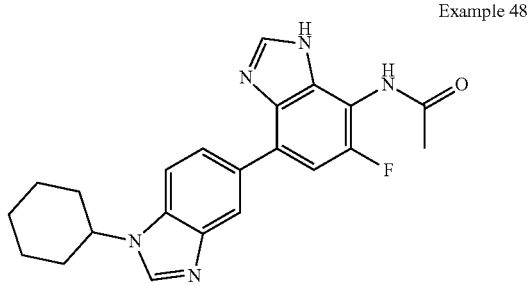 [SMILES: CC(=O)Nc1c(F)cc(-c2ccc3c(c2)ncn3C2CCCCC2)c2nc[nH]c12]

Example 48

Example (47) (27 mg, 0.077 mmol) was dissolved in DCM (5 mL). A catalytic amount of DMAP and acetic anhydride (5 drops) were added. The mixture was stirred at room temperature overnight and then concentrated. The residue was dissolved in EtOH and a solution of NaOH 1N was added. The middle was stirred at room temperature for 1 hour. DCM and water were added. Organic layer was washed with brine, dried over sodium sulfate, filtered and concentrated under reduced pressure. The crude material was purified by chromatography on silica gel (DCM to DCM MeOH 9/1) to give Example (48) (3 mg, 0.007 mmol, 10%). $^1$H NMR (400 MHz, CD$_3$OD) δ 1.35-1.48 (m, 1H), 1.56-1.69 (m, 2H), 1.80-1.88 (m, 1H), 1.89-1.95 (m, 1H), 1.95-2.04 (m, 3H), 2.19-2.26 (m, 2H), 2.28 (s, 3H), 4.39-4.48 (m, 1H), 7.27 (d, J=11.8 Hz, 1H), 7.68-7.80 (m, 2H), 8.04-8.20 (m, 2H), 8.33 (s, 1H). MS m/z ([M+H]+) 392.

Example 49

Synthesis of 1'-Cyclohexyl-1H,1'H-[4,5']]bibenzimidazolyl-6-carbonitrile

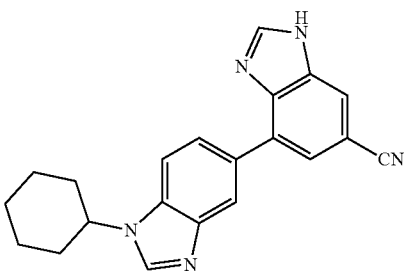

Example 49

According to the procedure described in example 29, step 1, 7-Bromo-3H-benzimidazole-5-carbonitrile (500 mg, 2.25 mmol) was converted, by reaction with 1-Cyclohexyl-5-(4,4,5,5-tetramethyl-[1,3,2]dioxaborolan-2-yl)-1H-benzimidazole (1.21 g, 3.71 mmol) and after purification by flash chromatography on silica gel (DCM/MeOH 95/5 to 92/8), to Example (49) (180 mg, 0.53 mmol, 23%). $^1$H NMR (400 MHz, CDCl$_3$) δ 1.27-1.41 (m, 1H), 1.43-1.91 (m, 5H), 1.93-2.07 (m, 2H), 2.13-2.31 (m, 2H), 4.10-4.26 (m, 1H), 7.47 (d, J=7.3 Hz, 1H), 7.55 (d, J=8.2 Hz, 1H), 7.61 (s, 1H), 7.91 (bs, 1H), 7.97-8.07 (m, 1H), 8.10 (d, J=5.7 Hz, 1H), 8.19 (s, 1H), 11.96 (bs, 1H). MS m/z ([M+H]+) 342.

Example 50

Synthesis of N-(1'-Cyclohexyl-6-fluoro-1H,1'H-[4,5']bibenzimidazolyl-7-yl)-formamide

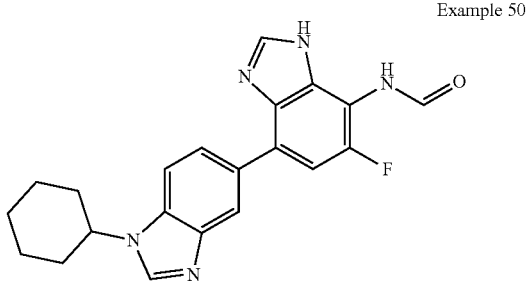 [SMILES: O=CNc1c(F)cc(-c2ccc3c(c2)ncn3C2CCCCC2)c2nc[nH]c12]

Example 50

Example (47) (18 mg, 0.051 mmol) was dissolved in THF (1 mL) and formic acid (10-15 drops). The mixture was stirred at 80° C. for 5 hours and then at room temperature overnight. The middle was concentrated. The residue was purified by preparative TLC on silica gel (DCM to DCM MeOH 9/1+2% NH$_3$ 7M in MeOH) to give Example (50)

(11 mg, 0.029 mmol, 58%). $^1$H NMR (400 MHz, CDCl$_3$) δ 1.27-1.39 (m, 1H), 1.45-1.58 (m, 2H), 1.72-1.88 (m, 3H), 1.94-2.04 (m, 2H), 2.18-2.27 (m, 2H), 4.15-4.25 (m, 1H), 7.22-7.28 (m, 1H), 7.50-7.53 (m, 1H), 7.92-8.40 (m, 5H), 9.63 (bs, 1H), 11.44 (bs, 1H). MS m/z ([M+H]$^+$) 378.

Example 51

Synthesis of Methyl 6-Fluoro-1'-(1-methyl-cyclohexyl)-1H,1'H-[4,5']]bibenzimidazolyl-7-carboxylate

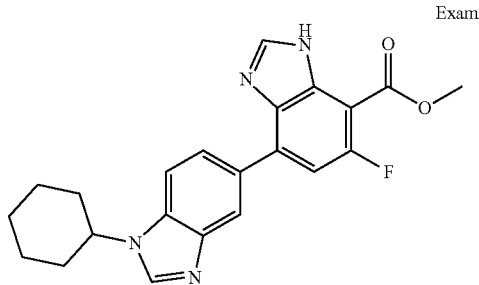

Example 51

Step 1: Methyl 4-Bromo-2,6-difluoro-3-nitro-benzoate (51a)

According to the procedure described in example 42, step 1, Methyl 4-Bromo-2,6-difluoro-benzoate (4 g, 15.93 mmol) was converted to compound (51a) as a white solid (4.66 g, 15.74 mmol, 99%). MS m/z ([M+H]$^+$) 297/298.

Step 2: Methyl 2-Amino-4-bromo-6-fluoro-3-nitro-benzoate (51b)

To a solution of compound (51a) (300 mg, 1.01 mmol) in dioxane (1 mL) at 0° C. was dropped a solution of ammonia 0.5N in dioxane (2 mL, 1.01 mmol). The solution was stirred 15 minutes at room temperature. A solution of ammonia 0.5N in dioxane (4 mL, 2.02 mmol) was added again in the reaction mixture and stirred 20 minutes. The residue was washed with sodium bicarbonate and extracted with DCM. The organic layer was dried on sodium sulfate, filtered and evaporated to afford compound (51b) as a yellow solid (260 mg, 0.88 mmol, 87%). MS m/z ([M+H]$^+$) 293/295.

Step 3: Methyl 7-Bromo-5-fluoro-3H-benzimidazole-4-carboxylate (51c)

According to the procedure described in example 17, step 4, compound (51b) (260 mg, 0.89 mmol) was converted, after trituration with a mixture of cyclohexane and diethyl ether, to compound (51c) as a red solid (153 mg, 0.56 mmol, 63%). MS m/z ([M+H]$^+$) 273/275.

Step 4: Methyl 6-Fluoro-1'-(1-methyl-cyclohexyl)-1H,1'H-[4,5']]bibenzimidazolyl-7-carboxylate, Example (51)

According to the procedure described in example 42, step 2, compound (51c) (50 mg, 0.18 mmol) was converted, by reaction with 1-Cyclohexyl-5-(4,4,5,5-tetramethyl-[1,3,2] dioxaborolan-2-yl)-1H-benzimidazole (62 mg, 0.19 mmol), to Example (51) as a red solid (27 mg, 0.07 mmol, 35%) without further purification. $^1$H NMR (400 MHz, DMSO-d$_6$) δ 1.27-1.37 (m, 1H), 1.53 (q, J=11.6 Hz, 2H), 1.74 (bd, J=13.2 Hz, 1H), 1.86-1.93 (m, 4H), 2.08 (bd, J=9.6 Hz, 2H), 3.96 (s, 3H), 4.43 (t, J=11.2 Hz, 1H), 7.49 (d, J=13.2 Hz, 1H), 7.78 (d, J=8.4 Hz, 1H), 8.09 (bd, J=8.0 Hz, 1H), 8.35 (s, 1H), 8.41 (s, 1H), 8.61 (bs, 1H), 12.68 (bs, 1H). MS m/z ([M+H]$^+$) 393.

Example 52

Synthesis of butyl 1'-Cyclohexyl-6-((S)-3-hydroxymethyl-pyrrolidin-1-yl)-1H,1'H-[4,5']bibenzimidazolyl-7-carboxylate

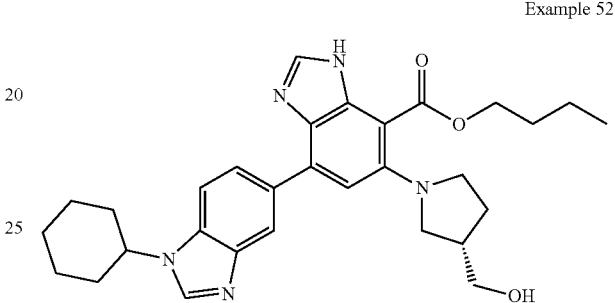

Example 52

A solution of Example (12) (27 mg, 0.07 mmol), (S)-1-Pyrrolidin-3-yl-methanol (10 mg, 0.10 mmol) and DIPEA (48 μL, 0.28 mmol) in n-butanol (1 mL) was stirred at 110° C. for 2 days. The reaction mixture was concentrated under reduced pressure. The crude was purified by preparative TLC on silica gel (DCM/MeOH 9/1) to afford Example (52) (16 mg, 0.03 mmol, 46%). $^1$H NMR (400 MHz, CDCl$_3$) δ 1.00 (t, J=7.2 Hz, 3H), 1.29-1.40 (m, 1H), 1.46-1.59 (m, 5H), 1.80-1.88 (m, 6H), 2.00 (d, J=13.2 Hz, 3H), 2.14 (sex, J=6.4 Hz, 2H), 2.26 (d, J=12.4 Hz, 3H), 2.55 (q, J=6.4 Hz, 1H), 3.34-3.38 (m, 1H), 3.63-3.90 (m, 3H), 4.26 (tt, J=3.2/12.0 Hz, 1H), 4.39-4.48 (m, 2H), 7.07 (s, 1H), 7.56 (d, J=8.4 Hz, 1H), 7.98 (s, 1H), 8.11 (s, 1H), 8.13 (s, 1H), 8.24 (s, 1H). MS m/z ([M+H]$^+$) 516.

Example 53

Synthesis of Methyl 1'-Cyclohexyl-6-((S)-3-hydroxymethyl-pyrrolidin-1-yl)-1H,1'H-[4,5']bibenzimidazolyl-7-carboxylate

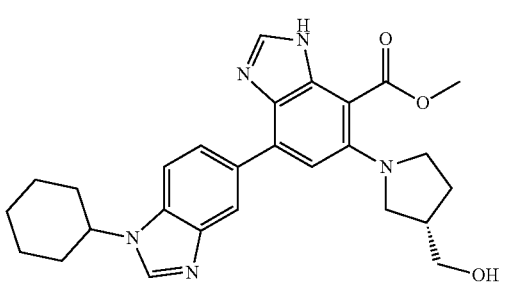

Example 53

According to the procedure described in example 30, step 1, Example (51) (100 mg, 0.26 mmol) was converted, by reaction with (S)-1-Pyrrolidin-3-yl-methanol (39 mg, 0.38 mmol) and after purification by preparative TLC on silica gel (DCM/MeOH 9/1 with 0.1% ammonia), to Example (53) (14 mg, 0.03 mmol, 11%). $^1$H NMR (400 MHz, CD$_3$OD) δ 1.41 (qt, J=3.2/13.2 Hz, 1H), 1.57-1.67 (m, 2H), 1.75-1.85 (m, 2H), 1.89-1.93 (m, 1H), 1.96-2.01 (m, 3H), 1.08-1.16 (m, 1H), 2.23 (bd, J=11.2 Hz, 2H), 2.45-2.56 (m, 1H), 3.26-3.28 (m, 1H), 3.37-3.42 (m, 2H), 3.46-3.53 (m, 1H), 3.56-3.67 (m, 2H), 4.02 (s, 3H), 4.43 (tt, J=3.6/11.6 Hz, 1H), 7.01 (s, 1H), 7.72 (d, J=8.4 Hz, 1H), 7.84 (bd, J=8.8 Hz, 1H), 7.97 (s, 1H), 8.13 (bs, 1H), 8.31 (s, 1H). MS m/z ([M+H]$^+$) 474.

Example 54

Synthesis of [(S)-1-(1'-Cyclohexyl-7-hydroxymethyl-1H,1'H-[4,5']bibenzimidazolyl-6-yl)-pyrrolidin-3-yl]-methanol

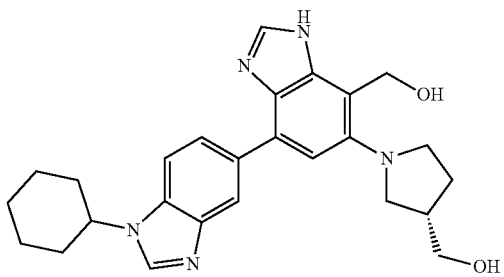

Example 54

A solution of Example (53) (39 mg, 0.08 mmol) and Lithium aluminum hydride (26 mg, 0.68 mmol) in THF (5 mL) was heated 16 hours at 65° C. The reaction mixture was concentrated under reduced pressure. The crude was purified by preparative TLC on silica gel (DCM/MeOH 8/2 with 2% ammonia) to Example (54) (4 mg, 0.009 mmol, 11%). $^1$H NMR (400 MHz, CD$_3$OD) δ 1.47 (qt, J=3.6/13.2 Hz, 1H), 1.62-1.73 (m, 2H), 1.75-1.81 (m, 1H), 1.88 (bd, J=13.2 Hz, 1H), 1.94-2.07 (m, 4H), 2.15-2.23 (m, 1H), 2.28 (bd, J=11.2 Hz, 2H), 2.54-2.63 (m, 1H), 3.18 (q, J=5.2 Hz, 1H), 3.32 (m, 3H), 3.68 (d, J=6.8 Hz, 2H), 4.47 (tt, J=3.2/11.6 Hz, 1H), 5.18 (bs, 2H), 7.29 (s, 1H), 7.76 (d, J=7.2 Hz, 2H), 8.08 (bs, 1H), 8.15 (s, 1H), 8.36 (s, 1H). MS m/z ([M+H]$^+$) 446.

Example 55

Synthesis of 1'-Cyclohexyl-6-((S)-3-hydroxymethyl-pyrrolidin-1-yl)-1H,1'H-[4,5']bibenzimidazolyl-7-carboxylic acid

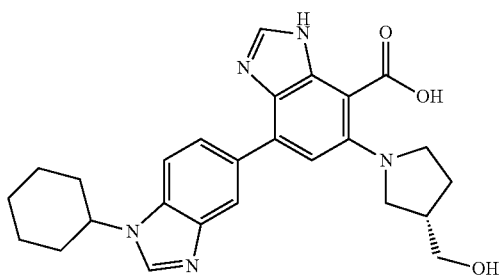

Example 55

A solution of Example (53) (28 mg, 0.06 mmol) in methanol (10 mL) and KOH 0.5M (4 mL) was heated 5 hours at 100° C. The reaction mixture was neutralized with ammonium chloride solution and extracted with DCM. The organic phase was dried over sodium sulfate, filtered and evaporated. Product was purified by preparative TLC on silica gel (DCM/MeOH 8/2 with 3% ammonia) to afford Example (55) (9 mg, 0.02 mmol, 33%). $^1$H NMR (400 MHz, CD$_3$OD) δ 1.42 (tt, J=3.2/12.8 Hz, 1H), 1.58-1.68 (m, 2H), 1.84 (d, J=13.6 Hz, 1H), 1.90-2.02 (m, 4H), 2.05-2.12 (m, 1H), 2.23 (bd, J=10.8 Hz, 2H), 2.38-2.47 (m, 1H), 2.79-2.89 (m, 1H), 3.58 (q, J=6.4 Hz, 1H), 3.67-3.81 (m, 5H), 4.45 (tt, J=3.6/12.0 Hz, 1H), 7.74 (bs, 1H), 7.76 (d, J=8.4 Hz, 1H), 7.96 (dd, J=1.2/8.4 Hz, 1H), 8.26 (s, 1H), 8.32 (s, 1H), 8.35 (s, 1H). MS m/z ([M+H]$^+$) 460.

Example 56

Synthesis of 1'-Cyclohexyl-6-fluoro-1H,1'H-[4,5']bibenzimidazolyl-7-carboxylic acid

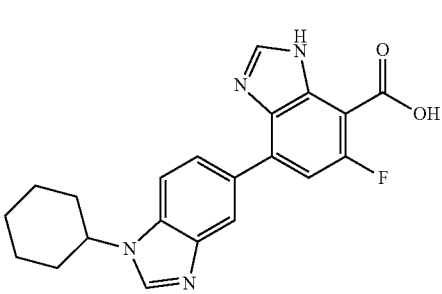

Example 56

According to the procedure described in example 55, Example (51) (50 mg, 0.13 mmol) was converted, after trituration with diethyl ether, to Example (56) (24 mg, 0.06 mmol, 50%). $^1$H NMR (400 MHz, DMSO-d$_6$) δ 1.32 (q, J=13.2 Hz, 1H), 1.53 (q, J=12.8 Hz, 2H), 1.74 (bd, J=14.0 Hz, 1H), 1.88 (q, J=11.2 Hz, 4H), 2.08 (bd, J=9.2 Hz, 2H), 4.42 (t, J=12.0 Hz, 1H), 7.44 (d, J=13.2 Hz, 1H), 7.77 (d, J=8.8 Hz, 1H), 8.07 (d, J=8.4 Hz, 1H), 8.27 (s, 1H), 8.40 (s, 1H), 8.58 (s, 1H), 12.56 (s, 1H). MS m/z ([M+H]$^+$) 379.

Example 57

Synthesis of 1'-Cyclohexyl-6-fluoro-1H,1'H-[4,5']bibenzimidazolyl-7-carbonitrile

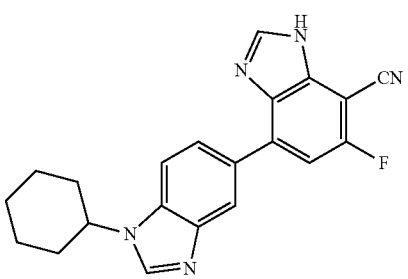

Example 57

Step 1: 4-Bromo-2,6-difluoro-3-nitro-benzonitrile (57a)

According to the procedure described in example 42, step 1, 4-Bromo-2,6-difluoro-benzonitrile (5 g, 22 mmol) was converted, without further purification, to compound (57a) (5.4 g, 20 mmol, 90%) as a yellow oil. $^1$H NMR (400 MHz, DMSO-$d_6$) δ 8.31 (dd, J=8.8/2.1 Hz, 1H).

Step 2: 2-Amino-4-bromo-6-fluoro-3-nitro-benzonitrile (57b)

According to the procedure described in example 51, step 2, compound (57a) (5.4 g, 20 mmol) was converted, after trituration in DCM, to compound (57b) (4.1 g, 16 mmol, 78%) as a yellow solid. $^1$H NMR (400 MHz, DMSO-$d_6$) δ 7.18 (d, J=8.9 Hz, 1H), 7.28 (bs, 2H). MS m/z ([M−H]$^+$) 258/260.

Step 3: 7-Bromo-5-fluoro-3H-benzimidazole-4-carbonitrile (57c)

According to the procedure described in example 17, step 4, compound (57b) (2 g, 7.7 mmol) was converted, after trituration in hot MeOH, to compound (57c) (1.05 g, 4.3 mmol, 57%) as a brown solid. $^1$H NMR (400 MHz, DMSO-$d_6$) δ 7.77 (d, J=9.9 Hz, 1H), 8.58 (s, 1H). MS m/z ([M+H]$^+$) 240/242.

Step 4: 1'-Cyclohexyl-6-fluoro-1H,1'H-[4,5']bibenzimidazolyl-7-carbonitrile, Example (57)

According to the procedure described in example 29, step 1, compound (57c) (1 g, 4.16 mmol) was converted, by reaction with 1-Cyclohexyl-4,4,5,5-tetramethyl-1,3,2-dioxaborolan-2-yl)-1H-benzimidazole (1.63 g, 5 mmol) and after purification by chromatography on silica gel (DCM to DCM/MeOH 9/1), to Example (57) (1.06 g, 2.95 mmol, 72%) as a brown solid. $^1$H NMR (400 MHz, DMSO-$d_6$) δ 1.27-1.37 (m, 1H), 1.53 (q, J=13.6 Hz, 2H), 1.74 (bd, J=12.4 Hz, 1H), 1.82-1.94 (m, 4H), 2.08 (bd, J=9.2 Hz, 2H), 4.40-4.50 (m, 1H), 7.54 (d, J=12.0 Hz, 1H), 7.77 (bs, 1H), 7.85 (d, J=8.0 Hz, 1H), 8.21 (bs, 1H), 8.46 (s, 1H), 8.52 (s, 1H). MS m/z ([M+H]+) 360.

Example 58

Synthesis of 1'-Cyclohexyl-6-((S)-3-hydroxymethyl-pyrrolidin-1-yl)-1H,1'H-[4,5']bibenzimidazolyl-7-carbonitrile

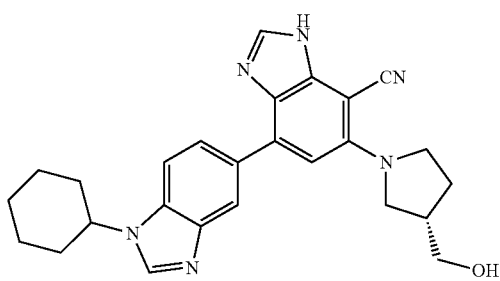

Example 58

Example (57) (200 mg, 0.55 mmol), DIPEA (0.29 mL, 1.65 mmol) and (S)-1-Pyrrolidin-3-yl-methanol (85 mg, 0.83 mmol) were dissolved in DMSO (1 mL). The mixture was stirred at 90° C. for 4 days. Water was then added. Obtained solid was filtered, dissolved in MeOH and concentrated. The crude material was purified by preparative TLC on silica gel (DCM/MeOH 9/1+2% NH3 7M in MeOH). The fraction containing desired product was triturated in hot CH$_3$CN. After cooling the mixture was filtered to give Example (58) (75 mg, 0.17 mmol, 31%) as a beige solid. $^1$H NMR (400 MHz, DMSO-$d_6$) δ 1.25-1.38 (m, 1H), 1.46-1.59 (m, 2H), 1.70-1.82 (m, 2H), 1.83-1.96 (m, 4H), 2.01-2.12 (m, 3H), 2.40-2.50 (m, 1H), 3.41-3.53 (m, 3H), 3.63-3.78 (m, 3H), 4.36-4.50 (m, 1H), 4.71-4.77 (m, 1H), 6.71 and 6.80 (2s, 1H), 7.53-8.46 (m, 5H), 12.65 and 12.80 (2s, 1H). MS m/z ([M+H]$^+$) 441.

Example 59

Synthesis of [(S)-1-(1'-Cyclohexyl-7-trifluoromethyl-1H,1'H-[4,5']]bibenzimidazolyl-6-yl)-pyrrolidin-3-yl]-methanol

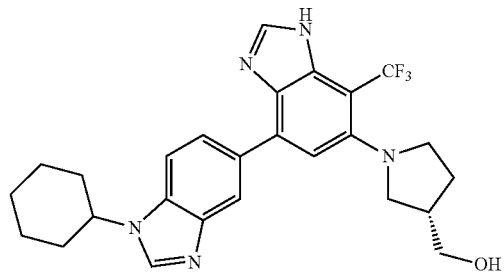

Example 59

Step 1: 1-Bromo-3,5-difluoro-2-nitro-4-trifluoromethyl-benzene (59a)

According to the procedure described in example 42, step 1, 5-Bromo-1,3-difluoro-2-trifluoromethyl-benzene (900 mg, 3.45 mmol) was converted, without further purification, to compound (59a) (850 mg, 2.78 mmol, 80%). $^1$H NMR (400 MHz, CDCl$_3$) δ 7.43 (d, J=9.3 Hz, 1H).

Step 2: 3-Bromo-5-fluoro-2-nitro-6-trifluoromethyl-phenylamine (59b)

According to the procedure described in example 51, step 2, compound (59a) (750 mg, 2.47 mmol) was converted, after purification by column chromatography on silica gel (cyclohexane/DCM 8/2), to compound (59b) (650 mg, 2.14 mmol, 87%). $^1$H NMR (400 MHz, CDCl$_3$) δ 5.48 (bs, 2H), 6.86 (d, J=10.4 Hz, 1H). MS m/z ([M+H]$^+$) 303/305.

Step 3: 3-(1-Cyclohexyl-1H-benzimidazol-5-yl)-5-fluoro-2-nitro-6-trifluoromethyl-phenylamine (59c)

According to the procedure described in example 41, step 2, compound (59b) (380 mg, 1.25 mmol) was converted, by reaction with 1-Cyclohexyl-5-(4,4,5,5-tetramethyl-1,3,2-dioxaborolan-2-yl)-1H-benzimidazole (530 mg, 1.62 mmol) and after purification by preparative TLC on silica gel (DCM/ethyl acetate 7/3), to compound (59c) (170 mg, 0.4 mmol, 32%). $^1$H NMR (400 MHz, CDCl$_3$) δ 1.26-1.41 (m, 1H), 1.45-1.60 (m, 2H), 1.75-1.89 (m, 3H), 1.96-2.04 (m, 2H), 2.18-2.29 (m, 2H), 4.15-4.26 (m, 1H), 5.59 (bs, 2H), 6.59 (d, J=11.3 Hz, 1H), 7.18 (dd, J=1.5/8.5 Hz, 1H), 7.46 (d, J=8.5 Hz, 1H), 7.77 (d, J=1.5 Hz, 1H), 8.05 (s, 1H). MS m/z ([M+H]$^+$) 423.

Step 4: {(S)-1-[3-Amino-5-(1-cyclohexyl-1H-benzimidazol-5-yl)-4-nitro-2-trifluoromethyl-phenyl]-pyrrolidin-3-yl}-methanol (59d)

According to the procedure described in example 58, compound (59c) (85 mg, 0.2 mmol) was converted, by reaction with (S)-1-Pyrrolidin-3-yl-methanol (30 mg, 0.3 mmol) and after purification by preparative TLC on silica gel (DCM/MeOH 93/7), to compound (59d) (90 mg, 0.179 mmol, 89%). $^1$H NMR (400 MHz, CDCl$_3$) δ 1.27-1.39 (m, 1H), 1.44-1.57 (m, 2H), 1.75-1.86 (m, 4H), 1.95-2.03 (m, 2H), 2.05-2.13 (m, 1H), 2.20-2.28 (m, 2H), 2.46-2.53 (m, 1H), 3.32-3.36 (m, 1H), 3.48-3.57 (m, 3H), 3.64-3.74 (m, 2H), 4.15-4.23 (m, 1H), 6.28 (s, 1H), 6.30 (bs, 2H), 7.15 (d, J=8.5 Hz, 1H), 7.40 (d, J=8.5 Hz, 1H), 7.83 (s, 1H), 8.02 (s, 1H). MS m/z ([M+H]$^+$) 504.

Step 5: [(S)-1-(1'-Cyclohexyl-7-trifluoromethyl-1H, 1'H-[4,5']]bibenzimidazolyl-6-yl)-pyrrolidin-3-yl]-methanol, Example (59)

A solution of compound (59d) (50 mg, 0.1 mmol) in MeOH (5 mL) was purged with hydrogen. Catalyst palladium on charcoal 10% (20 mg) was then added and the reaction was stirred under hydrogen atmosphere (1 bar) for 14 hours. The middle was filtrated and concentrated under reduced pressure. The crude material was diluted with triethylorthoformate (1.5 mL) and ethanol (200 μL) and heated at 90° C. for 4 hours. The middle was then diluted with cyclohexane and filtrated. The precipitate was purified by preparative TLC on silica gel (DCM/MeOH 9/1) to give Example (59) (8.6 mg, 0.018 mmol, 18%). $^1$H NMR (400 MHz, CDCl$_3$) δ 1.28-1.40 (m, 1H), 1.45-1.60 (m, 2H), 1.75-1.90 (m, 4H), 1.94-2.04 (m, 2H), 2.10-2.29 (m, 3H), 2.50-2.60 (m, 1H), 3.16-3.27 (m, 2H), 3.33-3.44 (m, 2H), 3.67-3.80 (m, 2H), 4.17-4.28 (m, 1H), 7.39 (s, 1H), 7.50-7.57 (m, 1H), 7.97-8.09 (m, 3H), 8.21 (s, 1H), 10.15 (bs, 1H). MS m/z ([M+H]$^+$) 484.

Example 60

Synthesis of [1-(1'-Cyclohexyl-7-trifluoromethyl-1H,1'H-[4,5']]bibenzimidazolyl-6-yl)-piperidin-4-yl]-methanol Example 60

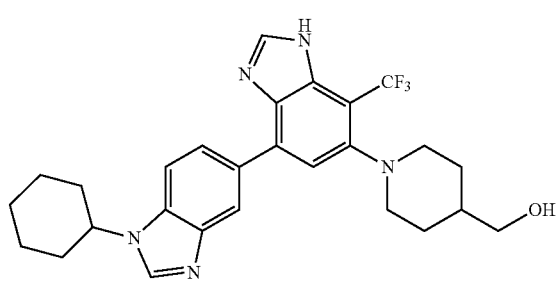

Step 1: {1-[3-Amino-5-(1-cyclohexyl-1H-benzimidazol-5-yl)-4-nitro-2-trifluoromethyl-phenyl]-piperidin-4-yl}-methanol (60a)

According to the procedure described in example 58, compound (59c) (85 mg, 0.2 mmol) was converted, by reaction with Piperidin-4-yl-methanol (35 mg, 0.3 mmol) and after purification by preparative TLC on silica gel (DCM/MeOH 93/7), to compound (60a) (98 mg, 0.19 mmol, 95%). $^1$H NMR (400 MHz, CDCl$_3$) δ 1.29-1.54 (m, 5H), 1.59-1.71 (m, 1H), 1.76-1.89 (m, 5H), 1.95-2.04 (m, 2H), 2.19-2.28 (m, 2H), 2.83 (t, J=11.8 Hz, 2H), 3.33-3.40 (m, 2H), 3.53-3.59 (m, 2H), 4.15-4.25 (m, 1H), 5.75 (bs, 2H), 6.47 (s, 1H), 7.17 (d, J=8.5 Hz, 1H), 7.43 (d, J=8.5 Hz, 1H), 7.79 (s, 1H), 8.03 (s, 1H). MS m/z ([M+H]$^+$) 518.

Step 2: [1-(1'-Cyclohexyl-7-trifluoromethyl-1H,1'H-[4,5']]bibenzimidazolyl-6-yl)-piperidin-4-yl]-methanol, Example (60)

According to the procedure described in example 59, step 5, compound (60a) (50 mg, 0.097 mmol) was converted, after purification by preparative TLC on silica gel (DCM/MeOH 9/1), to Example (60) (14.6 mg, 0.029 mmol, 30%). $^1$H NMR (400 MHz, CDCl$_3$) δ 1.28-1.38 (m, 1H), 1.44-1.59 (m, 4H), 1.60-1.71 (m, 1H), 1.75-1.87 (m, 5H), 1.92-2.04 (m, 3H), 2.19-2.28 (m, 2H), 2.84 (t, J=10.9 Hz, 2H), 3.11-3.20 (m, 2H), 3.58 (d, J=6.3 Hz, 2H), 4.17-4.27 (m, 1H), 7.46 (s, 1H), 7.54 (d, J=8.5 Hz, 1H), 8.01 (bs, 1H), 8.04 (s, 1H), 8.09 (s, 1H), 8.23 (s, 1H), 10.41 (bs, 1H). MS m/z ([M+H]$^+$) 498.

Example 61

Synthesis of 6-(4,4-Bis-hydroxymethyl-piperidin-1-yl)-1'-cyclohexyl-1H,1'H-[4,5']bibenzimidazolyl-7-carbonitrile Example 61

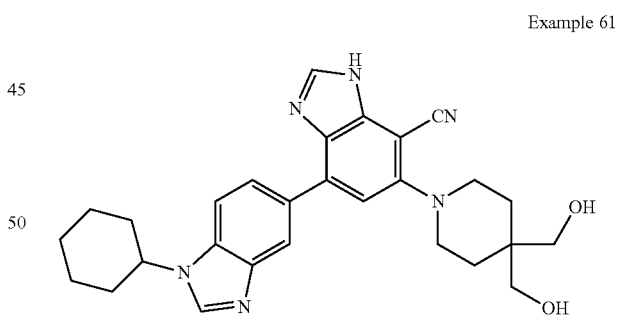

According to the procedure described in example 58, Example (57) (200 mg, 0.55 mmol) was converted, by reaction with (4-Hydroxymethyl-piperidin-4-yl)-methanol hydrochloride (133 mg, 0.83 mmol) and after purification by preparative TLC on silica gel (DCM/MeOH 85/15+3% NH3 7M in MeOH), to Example (61) (55 mg, 0.11 mmol, 21%) as a beige solid. $^1$H NMR (400 MHz, DMSO-d$_6$) δ 1.25-1.39 (m, 1H), 1.46-1.58 (m, 2H), 1.58-1.64 (m, 4H), 1.70-1.78 (m, 1H), 1.83-1.96 (m, 4H), 2.04-2.12 (m, 2H), 3.17-3.22 (m, 2H), 3.23-3.28 (m, 2H), 3.37-3.43 (m, 4H), 4.38-4.50 (m, 3H), 7.11 and 7.22 (2s, 1H), 7.56-8.48 (m, 5H), 12.87 and 13.17 (2s, 1H). MS m/z ([M+H]$^+$) 485.

Example 62

Synthesis of 1'-Cyclohexyl-6-(hexahydro-pyrrolo[3,4-c]pyrrol-2-yl)-1H,1'H-[4,5']bibenzimidazolyl-7-carbonitrile

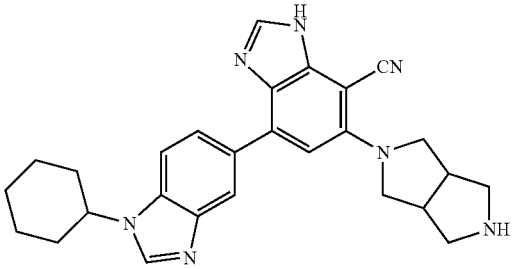

Example 62

Step 1: tert-butyl 5-(7-Cyano-1'-cyclohexyl-1H,1'H-[4,5']bibenzimidazolyl-6-yl)-hexahydro-pyrrolo[3,4-c]pyrrole-2-carboxylate (62a)

According to the procedure described in example 58, Example (57) (200 mg, 0.55 mmol) was converted, by reaction with tert-butyl Hexahydro-pyrrolo[3,4-c]pyrrole-2-carboxylate (176 mg, 0.83 mmol) and after purification by preparative TLC on silica gel (DCM/MeOH 9/1+1% NH$_3$ 7M in MeOH), to compound (62a) (70 mg, 0.127 mmol, 23%) as a beige solid. $^1$H NMR (400 MHz, DMSO-d$_6$) δ 1.25-1.36 (m, 1H), 1.40 (s, 9H), 1.46-1.58 (m, 2H), 1.71-1.78 (m, 1H), 1.83-1.96 (m, 4H), 2.04-2.12 (m, 2H), 3.02 (bs, 2H), 3.20-3.27 (m, 2H), 3.52-3.62 (m, 4H), 3.80-3.92 (m, 2H), 4.36-4.50 (m, 1H), 6.76 and 6.85 (2s, 1H), 7.54-8.44 (m, 5H), 12.69 and 12.85 (2s, 1H). MS m/z ([M+H]$^+$) 552.

Step 2: 1'-Cyclohexyl-6-(hexahydro-pyrrolo[3,4-c]pyrrol-2-yl)-1H,1'H-[4,5']bibenzimidazolyl-7-carbonitrile, Example (62)

Compound (62a) (35 mg, 0.063 mmol) was dissolved in MeOH (1 mL). A solution of HCl 4N in dioxane (0.32 mL, 1.26 mmol) was added and the mixture was stirred at room temperature overnight. After concentration, the residue was dissolved in ammoniac methanol and purified by preparative TLC on silica gel (DCM/MeOH 8/2+3% NH$_3$ 7M in MeOH). The fraction containing desired product was dissolved in a mixture DCM/MeOH and washed with water, Na$_2$CO$_3$ solution and brine. Organic layer was dried over sodium sulfate, filtered and concentrated under reduced pressure to give Example (62) (7 mg, 0.015 mmol, 25%) as a tan solid. $^1$H NMR (400 MHz, CD$_3$OD) δ 1.34-1.46 (m, 1H), 1.55-1.67 (m, 2H), 1.79-1.86 (m, 1H), 1.87-2.02 (m, 4H), 2.17-2.25 (m, 2H), 2.87-2.92 (m, 2H), 2.94-3.01 (m, 2H), 3.17-3.23 (m, 2H), 3.57-3.63 (m, 4H), 4.37-4.47 (m, 1H), 6.94 (s, 1H), 7.68 (dd, J=8.5/1.4 Hz, 1H), 7.74 (d, J=8.5 Hz, 1H), 8.02 (s, 1H), 8.14 (s, 1H), 8.35 (s, 1H). MS m/z ([M+H]$^+$) 452.

Example 63

Synthesis of 1'-Cyclohexyl-6-fluoro-1H,1'H-[4,5']bibenzimidazolyl-7-carboxamide

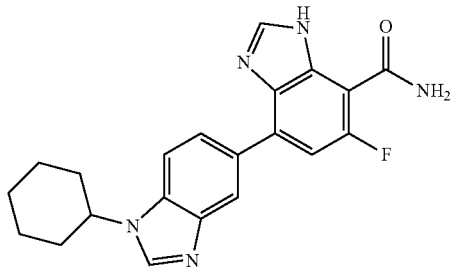

Example 63

A solution of Example (51) (403 mg, 1.03 mmol) in ammonia 7M in methanol (20 mL) was heated 10 hours at 100° C. under microwave irradiation. The solution was evaporated. Then, the residue was washed with water and extracted with DCM. The organic phase was dried on sodium sulfate, filtered and evaporated. The crude was purified by flash chromatography on silica gel (DCM/MeOH 9/1 with 1% ammonia) to give Example (63) as a white solid (122 mg, 0.32 mmol, 31%). $^1$H NMR (400 MHz, DMSO-d$_6$) δ 1.33 (t, J=12.4 Hz, 1H), 1.52 (q, J=13.2 Hz, 2H), 1.74 (d, J=12.0 Hz, 2H), 1.84-1.93 (m, 4H), 2.08 (d, J=9.2 Hz, 2H), 4.38-4.46 (m, 1H), 7.41 (d, J=12.8 Hz, 1H), 7.77 (d, J=8.4 Hz, 2H), 8.02 (bs, 1H), 8.24 (s, 1H), 8.40 (s, 1H), 8.51 (bs, 1H), 12.63 (bs, 1H). MS m/z ([M+H]$^+$) 378.

Example 64

Synthesis of 1'-Cyclohexyl-6-((S)-3-hydroxymethyl-pyrrolidin-1-yl)-1H,1'H-[4,5']bibenzimidazolyl-7-carboxamide

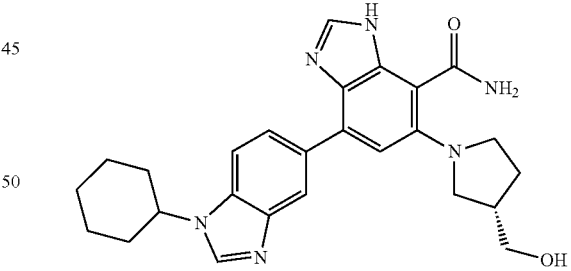

Example 64

According to the procedure described in example 58, Example (63) (50 mg, 0.13 mmol) was converted, by reaction with (S)-1-Pyrrolidin-3-yl-methanol (20 mg, 0.2 mmol) and after purification by preparative TLC on silica gel (DCM/MeOH 9/1+3% NH$_3$ 7M in MeOH), to Example (64) (22 mg, 0.048 mmol, 37%) as a white solid. $^1$H NMR (400 MHz, CD$_3$OD) δ 1.36-1.48 (m, 1H), 1.56-1.70 (m, 2H), 1.74-1.88 (m, 2H), 1.89-1.95 (m, 1H), 1.96-2.04 (m, 3H), 2.13-2.20 (m, 1H), 2.20-2.28 (m, 2H), 2.54-2.64 (m, 1H), 3.16-3.22 (m, 1H), 3.33-3.37 (m, 2H), 3.38-3.45 (m, 1H), 3.57-3.68 (m, 2H), 4.40-4.49 (m, 1H), 7.38 (bs, 1H), 7.74 (d, J=8.5 Hz, 1H), 7.86-7.91 (m, 1H), 8.12-8.18 (m, 2H), 8.32 (s, 1H). MS m/z ([M+H]$^+$) 459.

Example 65

Synthesis of 1'-Cyclohexyl-6-(hexahydro-pyrrolo[3,4-c]pyrrol-2-yl)-1H,1'H-[4,5']bibenzimidazolyl-7-carboxylic acid amide hydrochloride

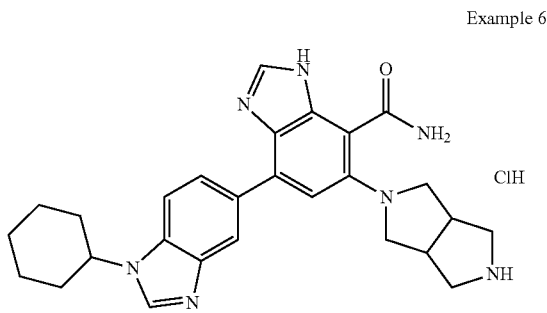

Example 65

Step 1: tert-butyl 5-(7-Carbamoyl-1'-cyclohexyl-1H,1'H-[4,5']bibenzimidazolyl-6-yl)-hexahydro-pyrrolo[3,4-c]pyrrole-2-carboxylate (65a)

According to the procedure described in example 58, Example (63) (100 mg, 0.26 mmol) was converted, by reaction with tert-butyl Hexahydro-pyrrolo[3,4-c]pyrrole-2-carboxylate (83 mg, 0.39 mmol) and after purification by preparative TLC on silica gel (DCM/MeOH 9/1+3% NH$_3$ 7M in MeOH), to compound (65a) (18 mg, 0.031 mmol, 13%) as a brown solid. MS m/z ([M+H]$^+$) 570.

Step 2: 1'-Cyclohexyl-6-(hexahydro-pyrrolo[3,4-c]pyrrol-2-yl)-1H,1'H-[4,5']bibenzimidazolyl-7-carboxylic acid amide hydrochloride salt, Example (65)

According to the procedure described in example 63, compound (65a) (18 mg, 0.031 mmol) was converted, after trituration in a mixture water/CH$_3$CN, to Example (65) (8 mg, 0.016 mmol, 54%). $^1$H NMR (400 MHz, CD$_3$OD) δ 1.38-1.51 (m, 1H), 1.63-1.76 (m, 2H), 1.84-1.92 (m, 1H), 1.93-2.10 (m, 4H), 2.34-2.42 (m, 2H), 3.34-3.39 (m, 2H), 3.46-3.68 (m, 8H), 4.75-4.84 (m, 1H), 7.60 (bs, 1H), 7.99-8.03 (m, 1H), 8.24-8.28 (m, 2H), 9.23 (bs, 1H), 9.66 (s, 1H). MS m/z ([M+H]$^+$) 470.

Example 66

Synthesis of 1'-Cyclohexyl-6-fluoro-7-trifluoromethyl-1H,1'H-[4,5']]bibenzimidazolyl

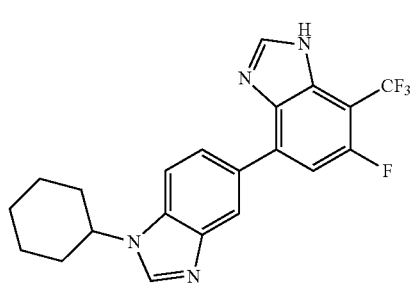

Example 66

Step 1: 4-Bromo-6-fluoro-7-trifluoromethyl-1H-benzimidazole (66a)

According to the procedure described in example 17, step 4, compound (59b) (2.95 g, 9.73 mmol) was converted, after purification by column chromatography on silica gel (DCM/ethyl acetate 7/3), to compound (66a) (2.13 g, 7.52 mmol, 77%). $^1$H NMR (400 MHz, CDCl$_3$) δ 7.43 (d, J=10.6 Hz, 1H), 8.20 (s, 1H), 10.00 (bs, 1H). MS m/z ([M+H]$^+$) 283/285.

Step 2: 1'-Cyclohexyl-6-fluoro-7-trifluoromethyl-1H,1'H-[4,5']]bibenzimidazolyl, Example (66)

A solution of compound (66a) (250 mg, 0.883 mmol), 1-Cyclohexyl-5-(4,4,5,5-tetramethyl-1,3,2-dioxaborolan-2-yl)-1H-benzimidazole (350 mg, 1.072 mmol) and potassium carbonate (360 mg, 2.6 mmol) were dissolved in a mixture of dioxane (10 mL) and water (1.5 mL). The solution was degassed under argon for 5 minutes and bis(triphenylphosphine)palladium (II) dichloride (50 mg, 0,071 mmol) was added. The reaction was heated at 150° C. for 1 hour under microwave irradiation. The middle was then filtered and concentrated under reduced pressure. The crude material was purified by preparative TLC on silica gel (ethyl acetate/MeOH 9/1) to give Example (66) (300 mg, 0.745 mmol, 84%). $^1$H NMR (400 MHz, CDCl$_3$) δ 1.30-1.42 (m, 1H), 1.45-1.61 (m, 2H), 1.74-1.91 (m, 3H), 1.94-2.07 (m, 2H), 2.18-2.30 (m, 2H), 4.18-4.29 (m, 1H), 7.28-7.39 (m, 1H), 7.56 (d, J=8.4 Hz, 1H), 7.99 (bs, 1H), 8.04 (s, 1H), 8.16 (s, 1H), 8.30 (bs, 1H), 9.90 (bs, 1H). MS m/z ([M+H]$^+$) 403.

Example 67

Synthesis of Methyl 7-(3-Cyano-4-methoxy-phenyl)-5-((S)-3-hydroxymethyl-pyrrolidin-1-yl)-3H-benzimidazole-4-carboxylate

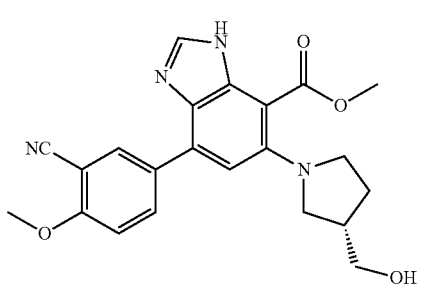

Example 67

Step 1: Methyl 7-Bromo-5-((S)-3-hydroxymethyl-pyrrolidin-1-yl)-3H-benzimidazole-4-carboxylate (67a)

According to the procedure described in example 29, step 3, compound (51c) (307 mg, 1.12 mmol) was converted, by reaction with (S)-1-Pyrrolidin-3-yl-methanol (227 mg, 2.25 mmol) and after purification by column chromatography on silica gel (DCM/MeOH 98/2), to compound (67a) as a beige solid (387 mg, 1.09 mmol, 97%). $^1$H NMR (400 MHz, CDCl$_3$) δ 1.80-1.88 (m, 1H), 2.09-2.17 (m, 1H), 2.54 (sex, J=6.4 Hz, 1H), 3.25-3.30 (m, 1H), 3.35-3.42 (m, 3H), 3.68-3.78 (m, 2H), 3.98 (s, 3H), 7.09 (s, 1H), 7.95 (s, 1H). MS m/z ([M+H]$^+$) 354/356.

Step 2: Methyl 7-(3-Cyano-4-methoxy-phenyl)-5-((S)-3-hydroxymethyl-pyrrolidin-1-yl)-3H-benzimidazole-4-carboxylate, Example (67)

According to the procedure described in example 42, step 2, compound (67a) (100 mg, 0.28 mmol) was converted, by reaction with 3-cyano-4-methoxyphenylboronic acid (77 mg, 0.30 mmol) and after purification by column chromatography on silica gel (DCM/MeOH 9/1), to Example (67) (89 mg, 0.22 mmol, 77%). $^1$H NMR (300 MHz, DMSO-$d_6$) δ 1.63-1.75 (m, 1H), 1.98 (sex, J=5.4 Hz, 1H), 2.36 (qt, J=6.9 Hz, 1H), 3.12-3.18 (m, 1H), 3.25-3.28 (m, 1H), 3.35-3.49 (m, 3H), 3.90 (s, 3H), 3.99 (s, 3H), 4.68 (t, J=5.1 Hz, 1H), 6.96 (s, 1H), 7.36 (d, J=9.0 Hz, 1H), 8.01 (s, 1H), 8.48 (dd, J=9.0/2.1 Hz, 1H), 8.56 (d, J=3.2 Hz, 1H), 11.97 (s, 1H). MS m/z ([M+H]$^+$) 407.

Example 68

Synthesis of Methyl 5-((S)-3-Hydroxymethyl-pyrrolidin-1-yl)-7-(6-methoxy-pyridin-3-yl)-3H-benzimidazole-4-carboxylate

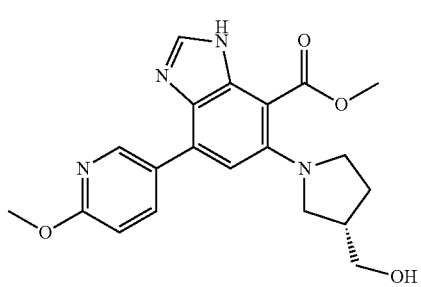

Example 68

According to the procedure described in example 42, step 2, compound (67a) (100 mg, 0.28 mmol) was converted, by reaction with 6-methoxy-pyridin-3-ylboronic acid (45 mg, 0.30 mmol) and after purification by preparative TLC on silica gel (DCM/MeOH 9/1), to Example (68) (69 mg, 0.18 mmol, 63%). $^1$H NMR 400 MHz, DMSO-$d_6$) δ 1.64-1.73 (m, 1H), 1.95-2.03 (m, 1H), 2.34-2.39 (m, 1H), 3.12-3.17 (m, 1H), 3.24-3.29 (m, 2H), 3.45 (qint, J=4.8 Hz, 2H), 3.90 (s, 3H), 3.92 (s, 3H), 4.67 (t, J=5.2 Hz, 1H), 6.91 (s, 1H), 6.94 (d, J=8.4 Hz, 1H), 7.99 (s, 1H), 8.44 (dd, J=8.4/2.0 Hz, 1H), 8.90 (d, J=2.0 Hz, 1H), 11.95 (s, 1H). MS m/z ([M+H]$^+$) 383.

Example 69

Synthesis of Methyl 5-((S)-3-Hydroxymethyl-pyrrolidin-1-yl)-7-(4-methoxy-3-trifluoromethyl-phenyl)-3H-benzimidazole-4-carboxylate

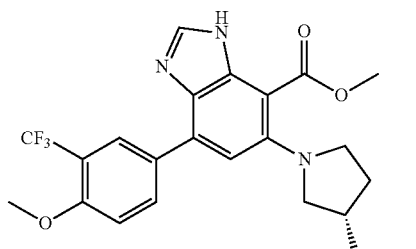

Example 69

According to the procedure described in example 42, step 2, compound (67a) (150 mg, 0.42 mmol) was converted, by reaction with 4-methoxy-3-trifluoromethylbenzene boronic acid (98 mg, 0.44 mmol) and after purification by preparative TLC on silica gel (DCM/MeOH 9/1), to Example (69) (89 mg, 0.20 mmol, 46%). $^1$H NMR (400 MHz, DMSO-$d_6$) δ 1.65-1.74 (m, 1H), 1.99 (sex, J=6.0 Hz, 1H), 2.34-2.40 (m, 1H), 3.13-3.17 (m, 1H), 3.25-3.28 (m, 1H), 3.37-3.48 (m, 3H), 3.90 (s, 3H), 3.96 (s, 3H), 4.68 (t, J=5.2 Hz, 1H), 6.93 (s, 1H), 7.38 (d, J=8.8 Hz, 1H), 8.02 (s, 1H), 8.30 (dd, J=8.4/1.6 Hz, 1H), 8.55 (s, 1H), 11.96 (s, 1H). MS m/z ([M+H]$^+$) 450.

Example 70

Synthesis of Methyl 5-((S)-3-Hydroxymethyl-pyrrolidin-1-yl)-7-(4-methoxy-phenyl)-3H-benzimidazole-4-carboxylate

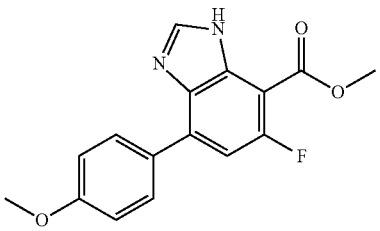

Example 70

According to the procedure described in example 42, step 2, compound (51c) (150 mg, 0.42 mmol) was converted, by reaction with 3-methoxyphenylboronic acid (88 mg, 0.58 mmol) and after purification by preparative TLC on silica gel (DCM/MeOH 9/1), to Example (70) (73 mg, 0.24 mmol, 44%). $^1$H NMR (400 MHz, CD$_3$OD) δ 3.87 (s, 3H), 4.02 (s, 3H), 7.07 (d, J=8.8 Hz, 2H), 7.22 (d, J=13.2 Hz, 1H), 7.92 (d, J=8.4 Hz, 2H), 8.23 (s, 1H). MS m/z ([M+H]$^+$) 301.

Example 71

Synthesis of 5-((S)-3-Hydroxymethyl-pyrrolidin-1-yl)-7-(4-methoxy-phenyl)-3H-benzimidazole-4-carboxylic acid

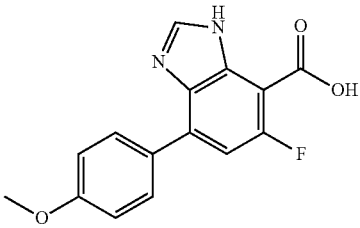

Example 71

According to the procedure described in example 55, Example (70) (30 mg, 0.10 mmol) was converted, after trituration in MeOH and then in diethyl ether, to Example (71) (19 mg, 0.07 mmol, 66%). $^1$H NMR (400 MHz, DMSO-$d_6$) δ 3.32 (bs, 1H), 3.83 (s, 3H), 7.07 (d, J=8.8 Hz, 2H), 7.36 (d, J=13.2 Hz, 1H), 8.22 (s, 1H), 8.24 (s, 2H), 12.55 (s, 1H). MS m/z ([M+H]$^+$) 287.

Example 72

Synthesis of 5-((S)-3-Hydroxymethyl-pyrrolidin-1-yl)-7-(4-methoxy-phenyl)-3H-benzimidazole-4-carboxamide

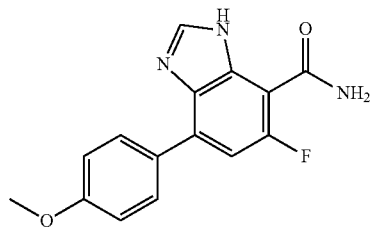

Example 72

A solution of Example (70) (30 mg, 0.10 mmol) in ammonia 7M in methanol (1 mL) and ammonium hydroxide solution (1 mL) was heated 16 hours at 80° C. in a weathon tube under pressure. The solution was evaporated. The residue was triturated with methanol then with diethyl ether to afford Example (72) (14 mg, 0.05 mmol, 50%). $^1$H NMR (400 MHz, DMSO-d$_6$) δ 3.83 (s, 3H), 7.07 (d, J=8.8 Hz, 2H), 7.35 (d, J=13.2 Hz, 1H), 7.70 (bs, 1H), 7.81 (s, 1H), 8.17 (bs, 2H), 8.22 (s, 1H), 12.61 (s, 1H). MS m/z ([M+H]$^+$) 286.

Example 73

Synthesis of 5-((S)-3-Hydroxymethyl-pyrrolidin-1-yl)-7-(6-methoxy-pyridin-3-yl)-3H-benzimidazole-4-carboxamide

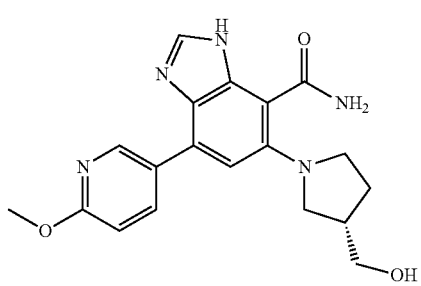

Example 73

According to the procedure described in example 72, Example (68) (18 mg, 0.05 mmol) was converted, after purification by preparative TLC on silica gel (DCM/MeOH 9/1 with 1% ammonia), to Example (73) (8.5 mg, 0.02 mmol, 49%). $^1$H NMR (400 MHz, CD$_3$OD) δ 2.82-2.86 (m, 1H), 2.17-2.26 (m, 1H), 2.61-2.65 (m, 1H), 3.23 (q, J=6.0 Hz, 1H), 3.38-3.41 (m, 2H), 3.42-3.47 (m, 1H), 3.63-3.73 (m, 2H), 4.04 (s, 3H), 6.99 (d, J=8.8 Hz, 1H), 7.34 (s, 1H), 8.19 (s, 1H), 8.27 (dd, J=8.4/2.4 Hz, 1H), 8.72 (d, J=2.4 Hz, 1H). MS m/z ([M+H]$^+$) 368.

Example 74

Synthesis of 5-((S)-3-Hydroxymethyl-pyrrolidin-1-yl)-7-(4-methoxy-phenyl)-3H-benzimidazole-4-carboxamide

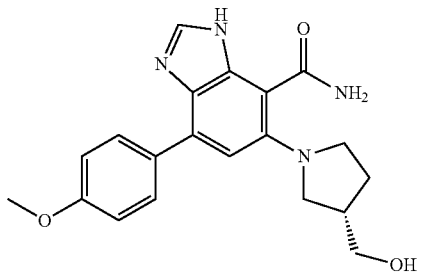

Example 74

Step 1: Methyl 5-((S)-3-Hydroxymethyl-pyrrolidin-1-yl)-7-(4-methoxy-phenyl)-3H-benzimidazole-4-carboxylate (74a)

According to the procedure described in example 42, step 2, compound (67a) (81 mg, 0.23 mmol) was converted, by reaction with 3-methoxyphenylboronic acid (36 mg, 0.24 mmol) and after trituration in diethyl ether, to compound (74a) (87 mg, 0.23 mmol, 100%). MS m/z ([M+H]$^+$) 382.

Step 2: 5-((S)-3-Hydroxymethyl-pyrrolidin-1-yl)-7-(4-methoxy-phenyl)-3H-benzimidazole-4-carboxamide, Example (74)

According to the procedure described in example 63, compound (74a) (40 mg, 0.10 mmol) was converted, after purification by flash chromatography on silica gel (DCM/MeOH 9/1 with 1% ammonia), to Example (74) (11 mg, 0.03 mmol, 28%). $^1$H NMR (400 MHz, CDCl$_3$) δ 1.76-1.85 (m, 2H), 2.13-2.21 (m, 1H), 2.59-2.63 (m, 1H), 3.11-3.15 (m, 1H), 3.20-3.29 (m, 2H), 3.34 (t, J=9.2 Hz, 1H), 3.65-3.77 (m, 2H), 3.87 (s, 3H), 5.82 (bs, 1H), 7.05 (d, J=8.4 Hz, 2H), 7.36 (s, 1H), 7.97 (d, J=8.8 Hz, 2H), 8.12 (s, 1H), 10.12 (bs, 1H), 11.47 (bs, 1H). MS m/z ([M+H]$^+$) 367.

Example 75

Synthesis of 7-(3-Cyano-4-methoxy-phenyl)-5-((S)-3-hydroxymethyl-pyrrolidin-1-yl)-3H-benzimidazole-4-carboxamide Example 75

According to the procedure described in example 72, Example (67) (40 mg, 0.10 mmol) was converted, after purification by preparative TLC on silica gel (DCM/MeOH 9/1 with 1% ammonia), to Example (75) (19 mg, 0.05 mmol, 50%). $^1$H NMR (400 MHz, DMSO-$d_6$) δ 1.66 (sex, J=7.2 Hz, 1H), 2.03 (sex, J=6.4 Hz, 1H), 2.39-2.44 (m, 1H), 3.09-3.13 (m, 1H), 3.26-3.35 (m, 3H), 3.40-3.50 (m, 2H), 3.99 (s, 3H), 4.69 (t, J=5.2 Hz, 1H), 7.25 (s, 1H), 7.37 (d, J=8.8 Hz, 1H), 7.63 (bs, 1H), 8.06 (s, 1H), 8.52 (dd, J=8.8/2.0 Hz, 1H), 8.59 (d, J=2.0 Hz, 1H), 8.70 (s, 1H), 12.19 (s, 1H). MS m/z ([M+H]$^+$) 392.

Example 76

Synthesis of 5-((S)-3-Hydroxymethyl-pyrrolidin-1-yl)-7-(4-methoxy-3-trifluoromethyl-phenyl)-3H-benzimidazole-4-carboxamide

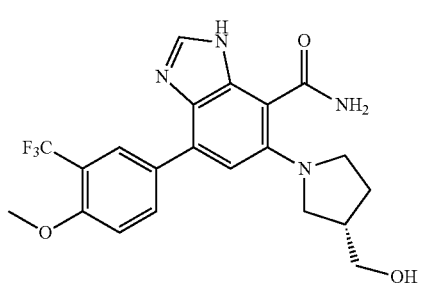

Example 76

According to the procedure described in example 72, Example (69) (40 mg, 0.09 mmol) was converted, after purification by preparative TLC on silica gel (DCM/MeOH 9/1 with 1% ammonia), to Example (76) (16 mg, 0.04 mmol, 42%). $^1$H NMR (400 MHz, DMSO-$d_6$) δ 1.67 (sex, J=6.8 Hz, 1H), 2.03 (sex, J=6.4 Hz, 1H), 2.39-2.44 (m, 1H), 3.10-3.13 (m, 1H), 3.27-3.28 (m, 2H), 3.33-3.35 (m, 1H), 3.40-3.50 (m, 2H), 3.96 (s, 3H), 4.69 (t, J=5.2 Hz, 1H), 7.21 (s, 1H), 7.38 (d, J=8.8 Hz, 1H), 7.62 (s, 1H), 8.06 (s, 1H), 8.32 (dd, J=8.0 Hz, 1H), 8.56 (s, 1H), 8.68 (s, 1H), 12.18 (s, 1H). MS m/z ([M+H]$^+$) 435.

Example 77

Synthesis of 1'-Cyclohexyl-6-[3-(2-hydroxy-ethyl)-pyrrolidin-1-yl]-1H,1'H-[4,5']bibenzimidazolyl-7-carboxamide

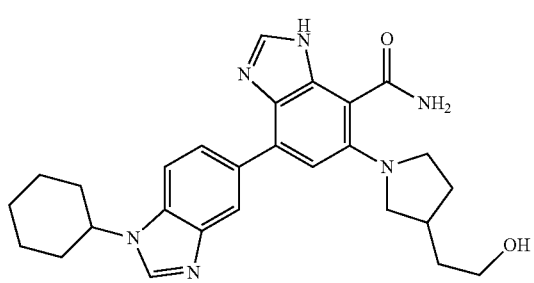

Example 77

According to the procedure described in example 58, Example (63) (55 mg, 0.15 mmol) was converted, by reaction with 2-Pyrrolidin-3-yl-ethanol (25 mg, 0.22 mmol) and after purification by preparative TLC on silica gel (DCM/MeOH 9/1 with 1% ammonia), to Example (77) (22 mg, 0.05 mmol, 31%). $^1$H NMR (400 MHz, CD$_3$OD) δ 1.39-1.43 (m, 1H), 1.56-1.66 (m, 2H), 1.70-1.78 (m, 3H), 1.84 (bd, J=12.0 Hz, 1H), 1.90-2.03 (m, 5H), 2.23 (bd, J=10.4 Hz, 3H), 2.49 (q, J=7.2 Hz, 1H), 3.10 (t, J=8.0 Hz, 1H), 3.42-3.48 (m, 2H), 3.65 (t, J=6.8 Hz, 2H), 4.44 (tt, J=3.6/12.0 Hz, 1H), 7.30 (bs, 1H), 7.73 (d, J=8.4 Hz, 1H), 7.86 (bd, J=7.2 Hz, 1H), 8.11 (s, 1H), 8.14 (bs, 1H), 8.33 (s, 1H). MS m/z ([M+H]$^+$) 473.

Example 78

Synthesis of 1'-Cyclohexyl-6-(2-hydroxy-ethylamino)-1H,1'H-[4,5']]bibenzimidazolyl-7-carbonitrile

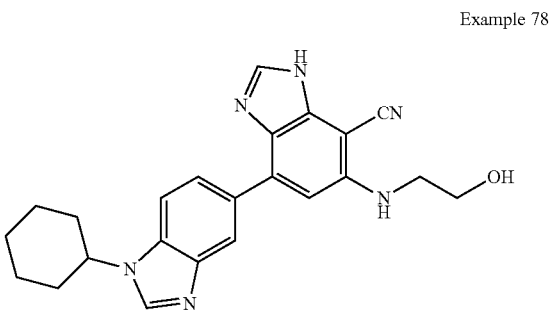 [SMILES: CN(CCO)c1cc(-c2ccc3c(c2)ncn3C2CCCCC2)c2nc[nH]c2c1C#N]

Example 78

According to the procedure described in example 58, Example (57) (100 mg, 0.28 mmol) was converted, by reaction with 2-aminoethan-1-ol (26 mg, 0.42 mmol) and after purification by preparative TLC on silica gel (DCM/MeOH 9/1+1% NH3 7M in MeOH), to Example (78) (34 mg, 0.085 mmol, 30%). $^1$H NMR (400 MHz, DMSO-$d_6$) δ 1.30-1.36 (m, 1H), 1.48-1.58 (m, 2H), 1.74 (d, J=12.8 Hz, 1H), 1.87-1.90 (m, 4H), 2.07 (d, J=9.5 Hz, 2H), 3.37-3.43 (m, 2H), 3.64 (m, 2H), 4.41-4.44 (m, 1H), 4.84-4.91 (m, 1H), 5.64 (t, J=5.8 Hz, 0.5H), 5.84 (t, J=5.4 Hz, 0.5H), 6.80 (s, 0.5H), 6.91 (s, 0.5H), 7.54 (d, J=8.5 Hz, 0.5H), 7.75 (d, J=8.5 Hz, 0.5H), 7.84 (d, J=8.4 Hz, 0.5H), 7.94 (s, 0.5H), 8.00 (d, J=8.5 Hz, 0.5H), 8.07 (s, 0.5H), 8.16 (s, 0.5H), 8.39 (s, 0.5H), 8.41 (s, 0.5H), 8.45 (s, 0.5H), 12.65 (s, 0.5H), 12.89 (s, 0.5H). MS m/z ([M+H]$^+$) 401.

Example 79

Synthesis of 1'-Cyclohexyl-6-(3-hydroxy-piperidin-1-yl)-1H,1'H-[4,5']]bibenzimidazolyl-7-carbonitrile

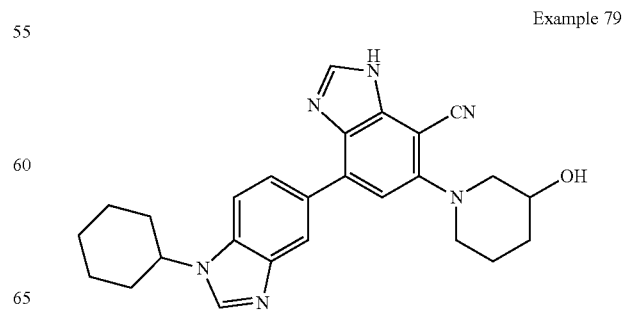

Example 79

According to the procedure described in example 58, Example (57) (50 mg, 0.14 mmol) was converted, by reaction with piperidin-3-ol (21 mg, 0.21 mmol) and after purification by preparative TLC on silica gel (DCM/MeOH 9/1+2% NH3 7M in MeOH), to Example (79) (19 mg, 0.043 mmol, 31%). $^1$H NMR (400 MHz, DMSO-d$_6$) δ 1.25-1.31 (m, 2H), 1.52-1.55 (m, 2H), 1.65-1.99 (m, 8H), 2.08 (m, 2H), 2.64-2.69 (m, 1H), 2.85 (t, J=10.4 Hz, 1H), 3.43 (d, J=12.0 Hz, 1H), 3.57-3.61 (m, 1H), 3.70-3.76 (m, 1H), 4.44 (t, J=11.4 Hz, 1H), 4.89 (d, J=4.7 Hz, 1H), 7.13 (s, 1H), 7.81 (d, J=8.0 Hz, 2H), 8.30 (s, 2H), 8.43 (s, 1H), 13.05 (bs, 1H). MS m/z ([M+H]$^+$) 441.

Example 80

Synthesis of N,N-dimethyl-1'-Cyclohexyl-6-fluoro-1H,1'H-[4,5']bibenzimidazolyl-7-carboxamide

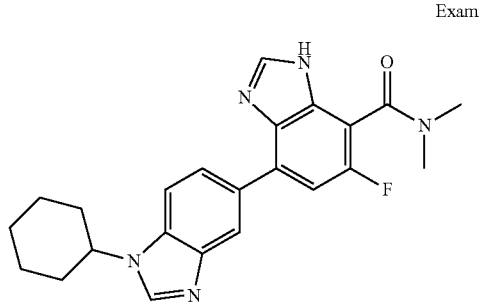

Example 80

HATU (70 mg, 0.185 mmol), DIPEA (71 μL, 0.407 mmol) and a solution of dimethylamine 2M in THF (0.11 mL, 0.222 mmol) were added to a solution of Example (56) (70 mg, 0.185 mmol) in DMF (1 mL). The mixture was stirred at 40° C. for 2 days. After concentration, DCM and water were added. Organic layer was washed with brine, dried over sodium sulfate, filtered and concentrated under reduced pressure. The crude material was purified by preparative TLC on silica gel (DCM/AcOEt/MeOH 8/1/1) to give Example (80) (30 mg, 0.074, 41%) as a white solid. $^1$H NMR (400 MHz, CDCl$_3$) δ 1.30-1.62 (m, 4H), 1.78-1.90 (m, 2H), 1.94-2.06 (m, 2H), 2.21-2.30 (m, 2H), 3.12 (d, J=2.6 Hz, 3H), 3.20 (s, 3H), 4.26 (tt, J=12.0/3.7 Hz, 1H), 7.20-7.26 (m, 1H), 7.58 (d, J=8.5 Hz, 1H), 7.86-7.96 (m, 2H), 8.20 (s, 1H), 8.30 (s, 1H). MS m/z ([M+H]$^+$) 406.

Example 81

Synthesis of N-(2-methoxy-ethyl)-1'-Cyclohexyl-6-fluoro-1H,1'H-[4,5']bibenzimidazolyl-7-carboxamide

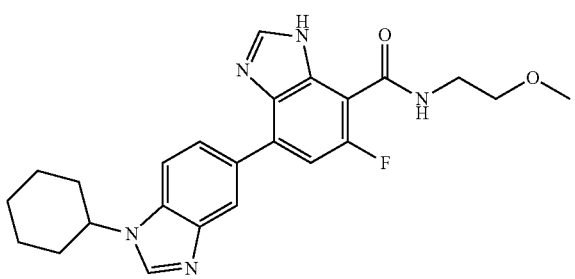

Example 81

According to the procedure described in example 80, Example (56) (70 mg, 0.185 mmol) was converted, by reaction with 2-Methoxy-ethylamine (17 mg, 0.222 mmol) and after purification by preparative TLC on silica gel (DCM/EtOAc/MeOH 45/45/10), to Example (81) (38 mg, 0.087, 48%) as a white solid. $^1$H NMR (400 MHz, CDCl$_3$) δ 1.28-1.62 (m, 4H), 1.80-1.90 (m, 2H), 1.97-2.06 (m, 2H), 2.22-2.32 (m, 2H), 3.43 (s, 3H), 3.60-3.65 (m, 2H), 3.71-3.78 (m, 2H), 4.22-4.34 (m, 1H), 7.26-7.32 (m, 1H), 7.37-7.48 (m, 1H), 7.61 (d, J=8.5 Hz, 1H), 8.12-8.18 (m, 2H), 8.27 (s, 1H), 8.36 (d, J=1.3 Hz, 1H). MS m/z ([M+H]$^+$) 436.

Example 82

Synthesis of N-(2-hydroxy-ethyl)-1'-Cyclohexyl-6-fluoro-1H,1'H-[4,5']bibenzimidazolyl-7-carboxamide

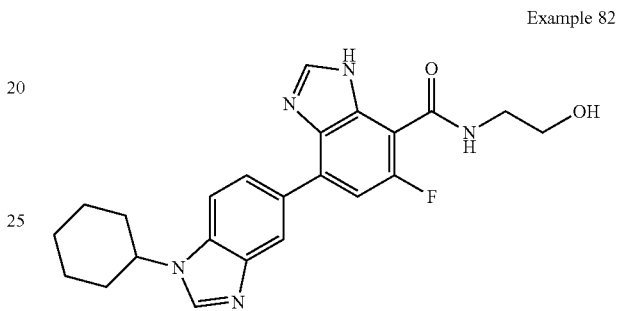

Example 82

Example (81) (30 mg, 0.068 mmol) was dissolved in DCM (2 mL). At 0° C., a solution of boron tribromide 1M in DCM (0.34 mL, 0.34 mmol) was added and the mixture was stirred at room temperature overnight. DCM and water were added. The middle was neutralized by addition of NaOH 1N. Organic layer was washed with brine, dried over sodium sulfate, filtered and concentrated under reduced pressure. The crude material was purified by preparative TLC on silica gel (DCM/MeOH 9/1+2% NH$_3$ 7M in MeOH) to give Example (82) (8 mg, 0.019, 29%) as a white solid. $^1$H NMR (400 MHz, CDCl$_3$) δ 1.28-1.40 (m, 1H), 1.48-1.61 (m, 3H), 1.78-1.90 (m, 3H), 1.96-2.04 (m, 2H), 2.22-2.30 (m, 2H), 3.69-3.75 (m, 2H), 3.89-3.92 (m, 2H), 4.24 (tt, J=12.0/3.7 Hz, 1H), 7.26-7.31 (m, 1H), 7.43-7.55 (m, 1H), 7.57 (d, J=8.5 Hz, 1H), 8.06 (s, 1H), 8.11-8.15 (m, 1H), 8.16 (s, 1H), 8.31 (d, J=1.0 Hz, 1H), 11.35 (bs, 1H). MS m/z ([M+H]$^+$) 422.

Example 83

Synthesis of N-methyl-1'-Cyclohexyl-6-fluoro-1H,1'H-[4,5']bibenzimidazolyl-7-carboxamide

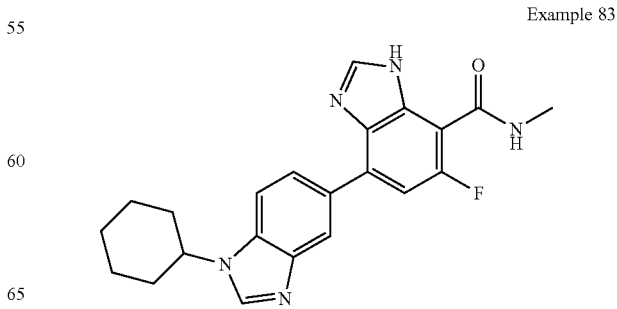

Example 83

According to the procedure described in example 80, Example (56) (70 mg, 0.185 mmol) was converted, by reaction with N-Methylamine (2M in THF, 0.11 mL, 0.222 mmol) and after purification by preparative TLC on silica gel (DCM/MeOH 9/1+1% $NH_3$ 7M in MeOH), to Example (83) (25 mg, 0.064, 35%) as a white solid. $^1$H NMR (400 MHz, DMSO-$d_6$) δ 1.26-1.38 (m, 1H), 1.46-1.59 (m, 2H), 1.70-1.78 (m, 1H), 1.83-1.95 (m, 4H), 2.04-2.12 (m, 2H), 2.90 (d, J=4.6 Hz, 3H), 4.37-4.48 (m, 1H), 7.38-7.45 (m, 1H), 7.77 (d, J=8.6 Hz, 1H), 8.01 (bs, 1H), 8.25 (s, 1H), 8.30 (bs, 1H), 8.39 (s, 1H), 8.50 (bs, 1H), 12.69 (bs, 1H). MS m/z ([M+H]$^+$) 392.

Example 84

Synthesis of 1'-Cyclohexyl-6-pyrrolidin-1-yl-1H,1'H-[4,5']]bibenzimidazolyl-7-carbonitrile

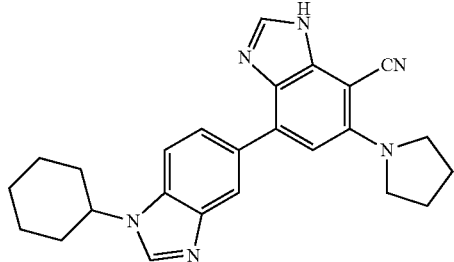

Example 84

According to the procedure described in example 58, Example (57) (50 mg, 0.14 mmol) was converted, by reaction with pyrrolidine (15 mg, 0.24 mmol) and after purification by preparative TLC on silica gel (DCM/MeOH 9/1), to Example (84) (3.5 mg, 0.0085 mmol, 6%). $^1$H NMR (400 MHz, CDCl$_3$) δ 1.32-1.36 (m, 1H), 1.52-1.55 (m, 2H), 1.82-1.84 (m, 3H), 1.97-2.06 (m, 6H), 2.23-2.25 (m, 2H), 3.61-3.86 (m, 4H), 4.18-4.26 (m, 1H), 6.75 (bs, 1H), 7.53 (d, J=6.6 Hz, 1H), 7.95 (bs, 2H), 8.06 (bs, 1H), 8.18 (bs, 1H). MS m/z ([M+H]$^+$) 411.

Example 85

Synthesis of N-[2-(7-Cyano-1'-cyclohexyl-1H,1'H-[4,5']]bibenzimidazolyl-6-ylamino)-ethyl]-acetamide

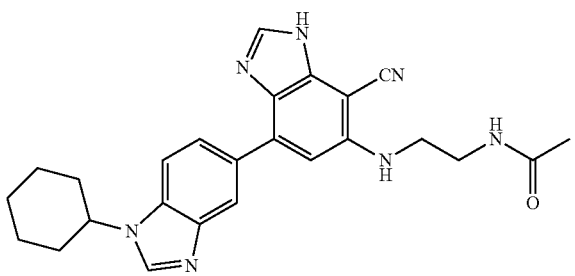

Example 85

According to the procedure described in example 58, Example (57) (200 mg, 0.56 mmol) was converted, by reaction with N-(2-aminoethyl)acetamide (86 mg, 0.84 mmol) and after purification by preparative TLC on silica gel (DCM/MeOH 9/1+2% ammonia 7M in MeOH), to Example (85) (32 mg, 0.072 mmol, 13%). $^1$H NMR (400 MHz, DMSO-$d_6$) δ 1.27-1.37 (m, 1H), 1.48-1.58 (m, 2H), 1.73-1.76 (m, 1H), 1.81 (s, 3H), 1.84-1.94 (m, 4H), 2.07-2.09 (m, 2H), 3.26-3.29 (m, 2H), 3.36-3.39 (m, 2H), 4.41-4.47 (m, 1H), 6.06 (bs, 1H), 6.91 (s, 1H), 7.78-7.80 (m, 2H), 8.05-8.10 (m, 3H), 8.41 (s, 1H), 12.73 (bs, 1H). MS m/z ([M+H]$^+$) 442.

Example 86

Synthesis of (1'-Cyclohexyl-6-fluoro-1H,1'H-[4,5']bibenzimidazolyl-7-yl)-(3-hydroxymethyl-pyrrolidin-1-yl)-methanone

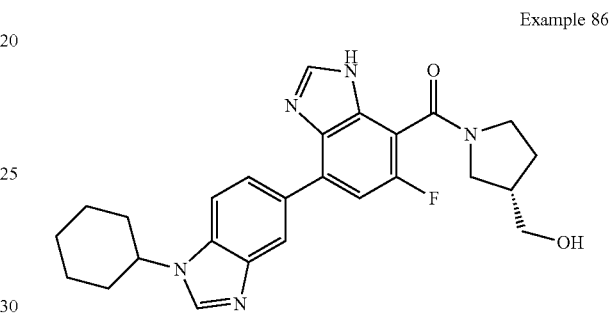

Example 86

Step 1: 3-(tert-Butyl-diphenyl-silanyloxymethyl)-pyrrolidine (86a)

Pyrrolidin-3-yl-methanol (50 mg, 0.49 mmol) was dissolved in DCM (2 mL). A catalytic amount of DMAP, triethylamine (0.2 mL, 1.47 mmol) and tert-butyldiphenylsilyl chloride (148 mg, 0.54 mmol) were added and the mixture was stirred at room temperature for 4 hours. DCM and water were added and organic layer was washed with brine, dried over sodium sulfate, filtered and concentrated under reduced pressure. The crude material was purified by preparative TLC on silica gel (DCM/MeOH 9/1) to give compound (86a) (75 mg, 0.22 mmol, 42%). MS m/z ([M+H]$^+$) 340.

Step 2: [3-(tert-Butyl-diphenyl-silanyloxymethyl)-pyrrolidin-1-yl]-(1'-cyclohexyl-6-fluoro-1H,1'H-[4,5']bibenzimidazolyl-7-yl)-methanone (86b)

According to the procedure described in example 80, (Example 56) (70 mg, 0.185 mmol) was converted, by reaction with compound (86a) (75 mg, 0.22 mmol) and after purification by preparative TLC on silica gel (DCM/MeOH 92/8), to compound (86b) (70 mg, 0.1 mmol, 54%) as a white solid. MS m/z ([M+H]$^+$) 700.

Step 3: (1'-Cyclohexyl-6-fluoro-1H,1'H-[4,5']bibenzimidazolyl-7-yl)-(3-hydroxymethyl-pyrrolidin-1-yl)-methanone, Example (86)

A solution of tetrabutylammonium fluoride 1M in THF (0.09 mL, 0.087 mmol) was added to a solution of compound (86b) (70 mg, 0.1 mmol) in THF (2 mL). The mixture was stirred at room temperature for 4 hours. Ethyl acetate and water were added and organic layer was washed with brine, dried over sodium sulfate, filtered and concentrated under reduced pressure. The crude material was purified by preparative TLC on silica gel (DCM/MeOH 9/1+4% NH$_3$ 7M in MeOH) to give Example (86) (10 mg, 0.022, 25%) as a white solid. $^1$H NMR (400 MHz, CD$_3$OD) δ 1.36-1.49 (m, 1H), 1.57-1.70 (m, 2H), 1.77-1.88 (m, 2H), 1.90-2.20 (m, 5H), 2.20-2.28 (m, 2H), 2.42-2.62 (m, 1H), 3.42-3.76 (m, 5H), 3.84-3.95 (m, 1H), 4.41-4.50 (m, 1H), 7.30 (dd, J=11.0/0.9 Hz, 1H), 7.70-7.82 (m, 2H), 8.06 (bs, 1H), 8.27 (d, J=1.6 Hz, 1H), 8.38 (s, 1H). MS m/z ([M+H]$^+$) 462.

Example 87

Synthesis of 1'-Cyclohexyl-6-fluoro-1H,1'H-[4,5']bibenzimidazolyl-7-carboxylic acid acetamide Example 87

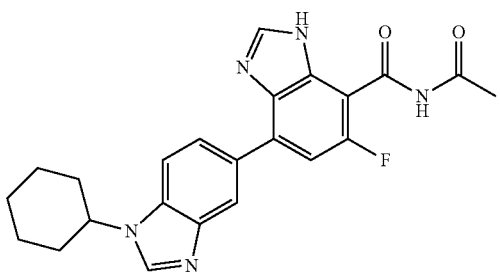

Sulfuric acid (2 drops) was added to a solution of Example (63) (38 mg, 0.1 mmol) in acetic anhydride (0.03 mL, 0.3 mmol). The mixture was stirred at 90° C. for 15 minutes. The middle was poured on ice and DCM was added. The middle was neutralized by addition of NaOH 1N. Organic layer was washed with brine, dried over sodium sulfate, filtered and concentrated under reduced pressure. The crude was purified by preparative TLC on silica gel (DCM/MeOH 9/1) to give Example (87) (6 mg, 0.014 mmol, 15%). $^1$H NMR (400 MHz, CD$_3$OD) δ 1.41 (qt, J=13.0/3.3 Hz, 1H), 1.61 (qt, J=13.0/3.3 Hz, 2H), 1.79-1.86 (m, 1H), 1.88-2.03 (m, 4H), 2.17-2.25 (m, 2H), 2.49 (s, 3H), 4.38-4.47 (m, 1H), 7.24-7.36 (m, 1H), 7.70-7.80 (m, 1H), 7.82-8.00 (m, 1H), 8.20-8.40 (m, 3H). MS m/z ([M+H]$^+$) 420.

Example 88

Synthesis of 6-Methoxy-1'-(1-methyl-cyclohexyl)-1H,1'H-[4,5']bibenzimidazolyl-7-carboxamide Example 88

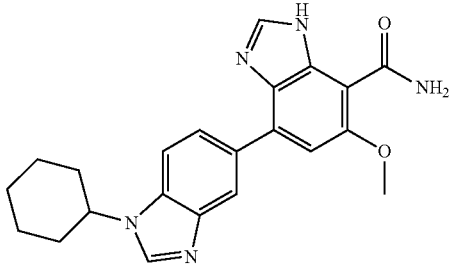

Step 1: Methyl 2-Amino-4-bromo-6-methoxy-3-nitro-benzoate (88a)

A solution of compound (51b) (300 mg, 1.02 mmol) and sodium methanolate (0.5N in methanol, 2.5 mL, 1.23 mmol) in methanol (3.5 mL) was stirred at room temperature for 2 hours. The reaction mixture was then neutralized with HCl 1N solution. Precipitate was filtered, washed with water and dried under reduced pressure to afford compound (88a) as a yellow solid (295 mg, 0.97 mmol, 95%). $^1$H NMR (400 MHz, DMSO-d$_6$) δ 3.79 (s, 3H), 3.81 (s, 3H), 6.31 (bs, 2H), 6.74 (s, 1H). MS m/z ([M+H]$^+$) 305/307.

Step 2: Methyl 2-Amino-4-(1-cyclohexyl-1H-benzimidazol-5-yl)-6-methoxy-3-nitro-benzoate (88b)

According to the procedure described in example 66, step 2, compound (88a) (295 mg, 0.97 mmol) was converted, by reaction with 1-Cyclohexyl-5-(4,4,5,5-tetramethyl-[1,3,2]dioxaborolan-2-yl)-1H-benzimidazole (331 mg, 1.01 mmol) and after trituration in diethyl ether, to compound (88b) as a yellow solid (287 mg, 0.68 mmol, 70%). $^1$H NMR (400 MHz, DMSO-d$_6$) δ 1.25-1.35 (m, 1H), 1.45-1.55 (m, 2H), 1.73 (bd, J=12.0 Hz, 1H), 1.83-1.91 (m, 4H), 2.05 (bd, J=8.8 Hz, 2H), 3.84 (s, 3H), 3.86 (s, 3H), 4.36-4.43 (m, 1H), 6.29 (bs, 2H), 6.40 (s, 1H), 7.16 (dd, J=1.6/8.4 Hz, 1H), 7.64 (d, J=1.6 Hz, 1H), 7.71 (d, J=8.4 Hz, 1H), 8.41 (s, 1H). MS m/z ([M+H]$^+$) 425.

Step 3: Methyl 1'-Cyclohexyl-6-methoxy-1H,1'H-[4,5']bibenzimidazolyl-7-carboxylate (88c)

According to the procedure described in example 17, step 4, compound (88b) (287 mg, 0.68 mmol) was converted, after purification by preparative TLC on silica gel (DCM/MeOH 9/1), to compound (88c) (102 mg, 0.25 mmol, 37%). $^1$H NMR (400 MHz, CD$_3$OD) δ 1.37-1.47 (m, 1H), 1.57-1.68 (m, 2H), 1.84 (bd, J=13.2 Hz, 1H), 1.93-2.02 (m, 4H), 2.23 (bd, J=11.2 Hz, 2H), 4.00 (s, 3H), 4.03 (s, 3H), 4.41-4.47 (m, 1H), 7.22 (s, 1H), 7.75 (d, J=8.4 Hz, 1H), 7.89 (bd, J=8.4 Hz, 1H), 8.14 (s, 1H), 8.21 (bs, 1H), 8.34 (s, 1H). MS m/z ([M+H]$^+$) 405.

Step 4: 6-Methoxy-1'-(1-methyl-cyclohexyl)-1H,1'H-[4,5']bibenzimidazolyl-7-carboxylamide, Example (88)

According to the procedure described in example 72, compound (88c) (40 mg, 0.10 mmol) was converted, after purification by preparative TLC on silica gel (DCM/MeOH 9/1 with 1% ammonia), to Example (88) (21 mg, 0.05 mmol, 55%). $^1$H NMR (400 MHz, DMSO-d$_6$) δ 1.26-1.36 (m, 1H), 1.52 (q, J=12.0 Hz, 2H), 1.74 (d, J=10.4 Hz, 1H), 1.87-1.90 (m, 4H), 2.08 (d, J=9.2 Hz, 2H), 4.10 (s, 3H), 4.35-4.50 (m, 1H), 7.28 (s, 1H), 7.66-7.87 (m, 3H), 8.10 (s, 2H), 8.40 (s, 1H), 8.50 (s, 1H), 12.36 (bs, 1H). MS m/z ([M+H]$^+$) 390.

Example 89

Synthesis of 6-Methoxy-1'-(1-methyl-cyclohexyl)-1H,1'H-[4,5']bibenzimidazolyl-7-carboxylic acid

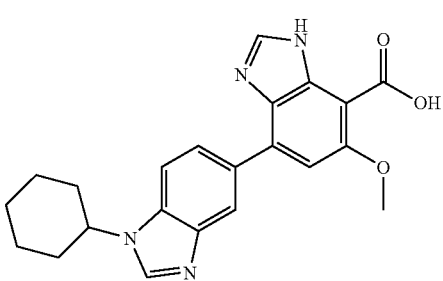

Example 89

According to the procedure described in example 55, compound (88c) (20 mg, 0.05 mmol) was converted, after trituration in MeOH and then in diethyl ether, to Example (89) (20 mg, 0.05 mmol, 36%). $^1$H NMR (400 MHz, CD$_3$OD) δ 1.46-1.50 (m, 1H), 1.64-1.74 (m, 2H), 1.90 (d, J=13.6 Hz, 1H), 2.00-2.08 (m, 4H), 2.29 (d, J=11.2 Hz, 2H), 4.18 (s, 3H), 4.35-4.55 (m, 1H), 7.32 (s, 1H), 7.82 (d, J=8.4 Hz, 1H), 7.98 (dd, J=1.2/8.4 Hz, 1H), 8.23 (s, 1H), 8.28 (d, J=1.2 Hz, 1H), 8.42 (s, 1H). MS m/z ([M+H]$^+$) 391.

Example 90

Synthesis of 6-(2-Amino-ethylamino)-1'-cyclohexyl-1H,1'H-[4,5']]bibenzimidazolyl-7-carbonitrile

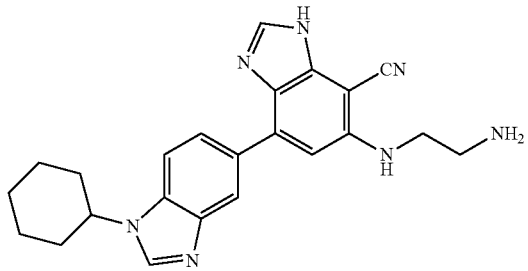

Example 90

At 0° C., hydrochloric acid (4M in dioxane, 0.2 mL, 0.8 mmol) was added to a solution of Example (85) (30 mg, 0.07 mmol) in dioxane (0.2 mL) and the mixture was stirred at room temperature. After 24 hours, methanol (0.4 mL) and hydrochloric acid (4M in dioxane, 0.2 mL, 0.8 mmol) were added and the middle was stirred at 80° C. After 72 hours, methanol (0.5 mL), hydrochloric acid (4M in dioxane, 0.5 mL, 2 mmol) and aqueous hydrochloric acid (6N, 0.5 mL) were added and the middle was stirred at 80° C. for 48 hours. The resulting mixture was concentrated under reduced pressure and the residue was purified by preparative TLC on silica gel (DCM/MeOH 9/1+1% ammonia 7M in MeOH) to give Example (90) (13.5 mg, 0.034 mmol, 48%). $^1$H NMR (400 MHz, DMSO-d$_6$) δ 1.23-1.37 (m, 1H), 1.49-1.59 (m, 2H), 1.75 (d, J=13.3 Hz, 1H), 1.86-1.94 (m, 4H), 2.08-2.11 (m, 2H), 3.02-3.07 (m, 2H), 3.34 (bs, 2H), 3.62-3.64 (m, 2H), 4.48-4.53 (m, 1H), 6.22 (bs, 1H), 6.91 (s, 1H), 7.89 (d, J=8.1 Hz, 1H), 8.07 (bs, 3H), 8.17 (s, 1H), 8.69 (bs, 1H). MS m/z ([M+H]$^+$) 400.

Example 91

Synthesis of 1'-Cyclohexyl-6-propylamino-1H,1'H-[4,5']bibenzimidazolyl-7-carbonitrile

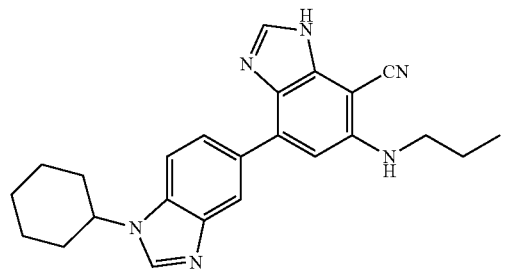

Example 91

Step 1: 2-amino-4-(1-cyclohexyl-1H-benzimidazol-5-yl)-6-fluoro-3-nitrobenzonitrile (91a)

According to the procedure described in example 42, step 2, compound (57b) (2.0 g, 7.6 mmol) was converted, by reaction with 1-Cyclohexyl-5-(4,4,5,5-tetramethyl-1,3,2-dioxaborolan-2-yl)-1H-benzimidazole (2.48 g, 7.6 mmol) and after trituration in DCM, to compound (91a) (1.05 g, 2.77 mmol, 36%). $^1$H NMR (400 MHz, DMSO-d$_6$) δ 1.23-1.34 (m, 1H), 1.43-1.53 (m, 2H), 1.70-1.75 (m, 2H), 1.80-1.90 (m, 2H), 2.02-2.04 (m, 2H), 4.36-4.42 (m, 1H), 6.78 (d, J=9.7 Hz, 1H), 7.05 (s, 2H), 7.17 (dd, J=8.4/1.6 Hz, 1H), 7.61 (d, J=1.4 Hz, 1H), 7.76 (d, J=8.5 Hz, 1H), 8.43 (s, 1H). MS m/z ([M+H]$^+$) 380.

Step 2: 2-amino-4-(1-cyclohexyl-1H-benzimidazol-5-yl)-3-nitro-6-(propylamino)benzonitrile (91b)

According to the procedure described in example 29, step 3, compound (91a) (120 mg, 0.32 mmol) was converted, by reaction with n-propylamine (19 mg, 0.32 mmol) and after purification by preparative TLC on silica gel (DCM/MeOH 95/5), to compound (91b) (47 mg, 0.11 mmol, 35%). $^1$H NMR (400 MHz, DMSO-d$_6$) δ 0.86 (t, J=7.4 Hz, 3H), 1.28-1.35 (m, 1H), 1.48-1.58 (m, 4H), 1.71-1.74 (m, 1H), 1.82-1.92 (m, 4H), 2.04 (m, 2H), 3.26 (m, 2H), 4.35-4.41 (m, 1H), 6.02 (s, 1H), 6.98 (s, 2H), 7.07 (dd, J=8.4/1.6 Hz, 1H), 7.16 (t, J=5.8 Hz, 1H), 7.56 (d, J=1.4 Hz, 1H), 7.66 (d, J=8.4 Hz, 1H), 8.34 (s, 1H). MS m/z ([M+H]$^+$) 419.

Step 3: 1'-Cyclohexyl-6-propylamino-1H,1'H-[4,5']]bibenzimidazolyl-7-carbonitrile, Example (91)

According to the procedure described in example 59, step 5, compound (91b) (46 mg, 0.11 mmol) was converted, after purification by preparative TLC on silica gel (DCM/MeOH 95/5), to Example (91) (7 mg, 0.018 mmol, 16%). $^1$H NMR (400 MHz, CD$_3$OD) δ 1.02 (t, J=7.4 Hz, 3H), 1.28-1.43 (m, 1H), 1.55-1.64 (m, 2H), 1.67-1.77 (m, 2H), 1.80-2.01 (m, 5H), 2.22 (m, 2H), 3.34 (m, 2H), 4.37-4.47 (m, 1H), 6.80 (s, 1H), 7.74 (m, 2H), 8.05 (m, 2H), 8.34 (s, 1H). MS m/z ([M+H]$^+$) 399.

Example 92

Synthesis of 1'-Cyclohexyl-6-[(2-hydroxy-ethyl)-methyl-amino]-1H,1'H-[4,5']]bibenzimidazolyl-7-carbonitrile

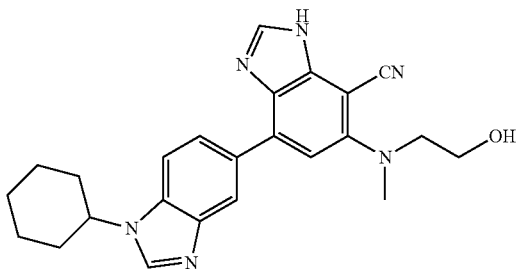

Example 92

Step 1: 2-amino-4-(1-cyclohexyl-1H-benzimidazol-5-yl)-6-[(2-hydroxyethyl)(methyl)amino]-3-nitrobenzonitrile (92a)

According to the procedure described in example 29, step 3, compound (91a) (200 mg, 0.53 mmol) was converted, by reaction with 2-(methylamino)ethan-1-ol (40 mg, 0.53 mmol) and after purification by preparative TLC on silica gel (DCM/MeOH 95/5), to compound (92a) (208 mg, 0.48 mmol, 90%). $^1$H NMR (300 MHz, CDCl$_3$) δ 1.29-1.40 (m, 1H), 1.44-1.56 (m, 2H), 1.79-2.02 (m, 5H), 2.21-2.26 (m, 2H), 3.29 (s, 3H), 3.79 (t, J=5.8 Hz, 2H), 3.95-4.00 (m, 2H), 4.14-4.25 (m, 1H), 6.18 (s, 1H), 6.52 (bs, 2H), 7.11 (dd, J=8.4/1.6 Hz, 1H), 7.40 (d, J=8.4 Hz, 1H), 7.74 (d, J=1.4 Hz, 1H), 8.02 (s, 1H). MS m/z ([M+H]$^+$) 435.

Step 2: 1'-Cyclohexyl-6-[(2-hydroxy-ethyl)-methyl-amino]-1H,1'H-[4,5']]bibenzimidazolyl-7-carbonitrile, Example (92)

According to the procedure described in example 59, step 5, compound (92a) (208 mg, 0.48 mmol) was converted, after purification by preparative TLC on silica gel (DCM/MeOH 95/5), to (Example 92) (4.8 mg, 0.012 mmol, 2.4%). $^1$H NMR (400 MHz, CD$_3$OD) δ 1.38-1.43 (m, 1H), 1.56-1.66 (m, 2H), 1.81-1.84 (m, 1H), 1.91-2.02 (m, 4H), 2.19-2.22 (m, 2H), 3.17 (s, 3H), 3.58 (t, J=6.0 Hz, 2H), 3.87 (t, J=6.2 Hz, 2H), 4.39-4.47 (m, 1H), 7.15 (s, 1H), 7.69-7.77 (m, 2H), 8.02 (bs, 1H), 8.16 (s, 1H), 8.36 (s, 1H). MS m/z ([M+H]$^+$) 415.

Example 93

Synthesis of 1'-Cyclohexyl-6-(2-methanesulfonyl-ethylamino)-1H,1'H-[4,5']]bibenzimidazolyl-7-carbonitrile

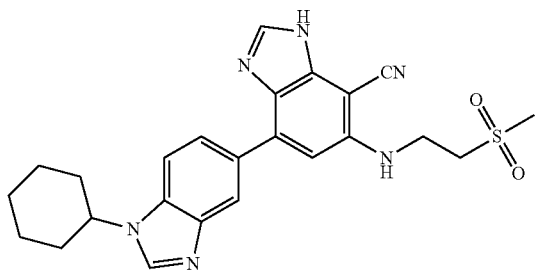

Example 93

Step 1: 2-amino-4-(1-cyclohexyl-1H-benzimidazol-5-yl)-6-[(2-methanesulfonylethyl)amino]-3-nitrobenzonitrile (93a)

According to the procedure described in example 29, step 3, compound (91a) (200 mg, 0.53 mmol) was converted, by reaction with 2-methanesulfonylethan-1-amine (65 mg, 0.53 mmol) and after purification by preparative TLC (DCM/MeOH 95/5), to compound (93a) (203 mg, 0.42 mmol, 80%). MS m/z ([M+H]$^+$) 483.

Step 2: 1'-Cyclohexyl-6-(2-methanesulfonyl-ethylamino)-1H,1'H-[4,5']]bibenzimidazolyl-7-carbonitrile, Example (93)

According to the procedure described in example 59, step 5, compound (93a) (203 mg, 0.42 mmol) was converted, without further purification, to Example (93) (30 mg, 0.064 mmol, 15%). $^1$H NMR (400 MHz, DMSO-d$_6$) δ 1.29-1.32 (m, 1H), 1.50-1.60 (m, 2H), 1.73 (m, 1H), 1.86-1.94 (m, 4H), 2.18 (m, 2H), 3.07 (s, 3H), 3.48 (t, J=6.7 Hz, 2H), 3.80 (m, 2H), 4.66-4.72 (m, 1H), 6.36 (bs, 1H), 6.96 (s, 1H), 8.09 (bs, 1H), 8.16 (d, J=8.6 Hz, 1H), 8.33 (s, 1H), 8.45 (bs, 1H), 9.47 (s, 1H). MS m/z ([M+H]$^+$) 463.

Example 94

Synthesis of 1'-Cyclohexyl-6-piperazin-1-yl-1H,1'H-[4,5']]bibenzimidazolyl-7-carbonitrile

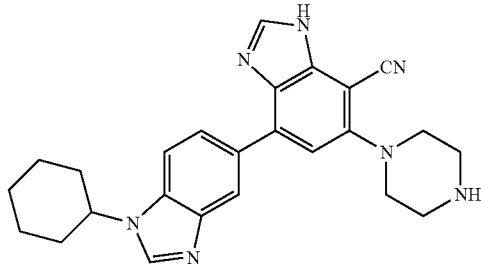

Example 94

Step 1: 2-amino-4-(1-cyclohexyl-1H-benzimidazol-5-yl)-3-nitro-6-(piperazin-1-yl)benzonitrile (95a)

According to the procedure described in example 29, step 3, compound (91a) (300 mg, 0.8 mmol) was converted, by reaction with piperazine (62 mg, 0.72 mmol) and without further purification, to compound (94a) (321 mg, 0.72 mmol, 100%). MS m/z ([M+H]$^+$) 446.

Step 2: 1'-Cyclohexyl-6-piperazin-1-yl-1H,1'H-[4,5']]bibenzimidazolyl-7-carbonitrile, Example (94)

According to the procedure described in example 59, step 5, compound (94a) (321 mg, 0.72 mmol) was converted, after purification by preparative TLC on silica gel (DCM/MeOH 95/5), to Example (94) (11 mg, 0.026 mmol, 3.6%). $^1$H NMR (400 MHz, DMSO-d$_6$) δ 1.25-1.34 (m, 1H), 1.46-1.57 (m, 2H), 1.71-1.74 (m, 1H), 1.86-1.89 (m, 4H), 2.05-2.07 (m, 2H), 2.96 (m, 4H), 3.19 (bs, 4H), 4.42-4.44 (m, 1H), 7.12 (bs, 1H), 7.60 (bs, 1H), 7.84 (bs, 1H), 8.01 (bs, 1H), 8.31-8.42 (m, 3H). MS m/z ([M+H]$^+$) 426.

Example 95

Synthesis of 1'-Cyclohexyl-6-(4-formyl-piperazin-1-yl)-1H,1'H-[4,5']]bibenzimidazolyl-7-carbonitrile

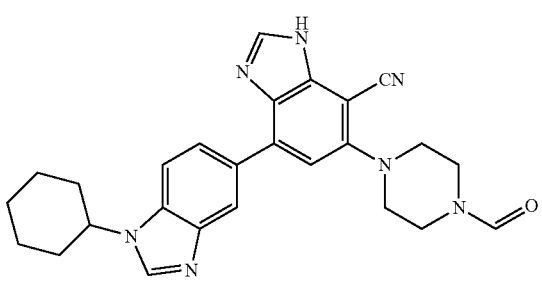

Example 95

According to the procedure described in example 59, step 5, compound (94a) (321 mg, 0.72 mmol) was converted, after purification by preparative TLC on silica gel (DCM/MeOH 95/5), to Example (95) as a byproduct of the reaction (16 mg, 0.035 mmol, 4.9%). $^1$H NMR (400 MHz, DMSO-$d_6$) δ 1.31-1.35 (m, 1H), 1.49-1.59 (m, 2H), 1.74-1.77 (m, 1H), 1.85-1.95 (m, 4H), 2.07-2.09 (m, 2H), 3.21 (m, 2H), 3.27 (m, 2H), 3.60-3.64 (m, 4H), 4.43-4.48 (m, 1H), 7.19 (s, 1H), 7.79 (bs, 1H), 7.83 (d, J=7.7 Hz, 1H), 8.12 (s, 1H), 8.20 (bs, 1H), 8.36 (s, 1H), 8.44 (s, 1H). MS m/z ([M+H]$^+$) 454.

Example 96

Synthesis of 1'-Cyclohexyl-6-(4-methyl-piperazin-1-yl)-1H,1'H-[4,5']]bibenzimidazolyl-7-carbonitrile

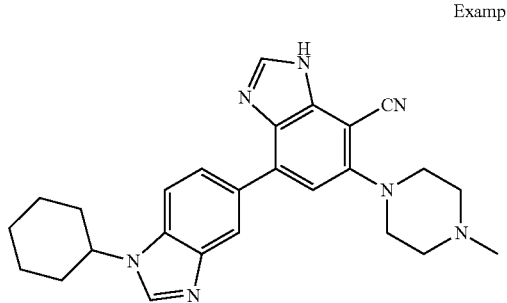

Example 96

Step 1: 2-amino-4-(1-cyclohexyl-1H-benzimidazol-5-yl)-6-(4-methylpiperazin-1-yl)-3-nitrobenzonitrile (96a)

According to the procedure described in example 29, step 3, compound (91a) (200 mg, 0.53 mmol) was converted, by reaction with N-methylpiperazine (79 mg, 0.79 mmol) and after purification by preparative TLC on silica gel (DCM/MeOH 95/5), to compound (96a) (226 mg, 0.49 mmol, 93%). $^1$H NMR (400 MHz, DMSO-$d_6$) δ 1.28-1.34 (m, 1H), 1.44-1.54 (m, 2H), 1.70-1.74 (m, 1H), 1.81-1.90 (m, 4H), 2.03-2.05 (m, 2H), 2.23 (s, 3H), 2.46 (t, J=4.5 Hz, 4H), 3.38 (m, 4H), 4.35-4.41 (m, 1H), 6.26 (s, 1H), 6.73 (s, 2H), 7.11 (dd, J=8.4/1.6 Hz, 1H), 7.62 (d, J=1.4 Hz, 1H), 7.69 (d, J=8.4 Hz, 1H), 8.40 (s, 1H). MS m/z ([M+H]$^+$) 460.

Step 2: 1'-Cyclohexyl-6-(4-methyl-piperazin-1-yl)-1H,1'H-[4,5']]bibenzimidazolyl-7-carbonitrile, Example (96)

According to the procedure described in example 59, step 5, compound (96a) (223 mg, 0.49 mmol) was converted, after purification by preparative TLC on silica gel (DCM/MeOH 9/1+1% NH$_3$ in MeOH), to Example (96) (66 mg, 0.15 mmol, 31%). $^1$H NMR (400 MHz, DMSO-$d_6$) δ 1.28-1.32 (m, 1H), 1.46-1.57 (m, 2H), 1.71-1.74 (m, 1H), 1.83-1.93 (m, 4H), 2.05-2.07 (m, 2H), 2.24 (s, 3H), 2.53 (t, J=4.5 Hz, 4H), 3.24 (m, 4H), 4.39-4.45 (m, 1H), 7.12 (bs, 1H), 7.64 (bs, 1H), 7.80 (d, J=8.2 Hz, 1H), 8.06 (bs, 1H), 8.32 (s, 1H), 8.44 (s, 1H), 13.05 (bs, 1H). MS m/z ([M+H]$^+$) 440.

Example 97

Synthesis of 1'-Cyclohexyl-6-(4-hydroxymethyl-piperidin-1-yl)-1H,1'H-[4,5']]bibenzimidazolyl-7-carbonitrile

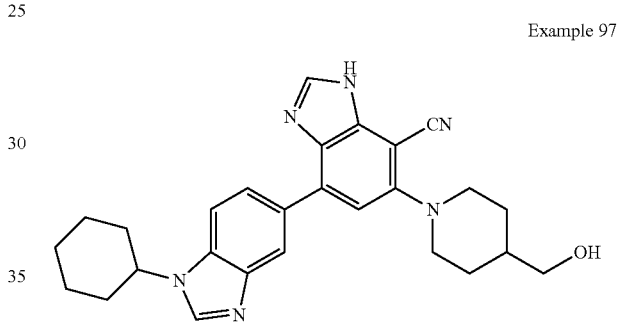

Example 97

Step 1: 2-Amino-4-(1-cyclohexyl-1H-benzimidazol-5-yl)-6-(4-hydroxymethyl-piperidin-1-yl)-3-nitro-benzonitrile (97a)

According to the procedure described in example 29, step 3, compound (91a) (350 mg, 0.92 mmol) was converted, by reaction with piperidin-4-ylmethanol (159 mg, 1.38 mmol) and after purification by preparative TLC on silica gel (DCM/MeOH 95/5), to compound (97a) (103 mg, 0.22 mmol, 24%). MS m/z ([M+H]$^+$) 475.

Step 2: 1'-Cyclohexyl-6-(4-hydroxymethyl-piperidin-1-yl)-1H,1'H-[4,5']]bibenzimidazolyl-7-carbonitrile, Example (97)

According to the procedure described in example 59, step 5, compound (97a) (103 mg, 0.22 mmol) was converted, after purification by preparative TLC on silica gel (DCM/MeOH 95/5), to Example (97) (6 mg, 0.013 mmol, 6%). $^1$H NMR (400 MHz, DMSO-$d_6$) δ 1.38-1.43 (m, 3H), 1.51-1.56 (m, 3H), 1.74-1.77 (m, 1H), 1.82-1.92 (m, 5H), 2.08-2.10 (m, 2H), 2.87-2.93 (m, 2H), 3.30-3.36 (m, 2H), 3.56-3.64 (m, 2H), 4.42-4.50 (m, 1H), 4.51-4.54 (m, 1H), 7.10 and 7.22 (2s, 1H), 7.58 and 8.03 (2dd, J=8.5/1.6 Hz, 1H), 7.78-7.86 (2d, J=8.4 Hz, 1H), 7.99-8.46 (2d, J=1.4 Hz, 1H), 8.29-8.33 (2d, J=1.0 Hz, 1H), 8.41 and 8.47 (2s, 1H), 12.87 and 13.18 (2s, 1H). MS m/z ([M+H]$^+$) 455.

Example 98

Synthesis of 3-[3-Amino-2-cyano-5-(1-cyclohexyl-1H-benzimidazol-5-yl)-4-nitro-phenylamino]-propionic acid

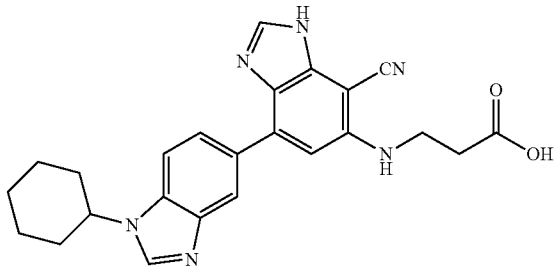

Example 98

Step 1: methyl 3-[3-Amino-2-cyano-5-(1-cyclohexyl-1H-benzimidazol-5-yl)-4-nitro-phenylamino]-propionate (98a)

According to the procedure described in example 29, step 3, compound (91a) (300 mg, 0.8 mmol) was converted, by reaction with methyl 3-aminopropanoate (112 mg, 0.8 mmol) and after purification by preparative TLC on silica gel (DCM/MeOH 95/5), to compound (98a) (332 mg, 0.72 mmol, 90%). MS m/z ([M+H]$^+$) 463.

Step 2: 3-[3-Amino-2-cyano-5-(1-cyclohexyl-1H-benzimidazol-5-yl)-4-nitro-phenylamino]-propionic acid, Example (98)

According to the procedure described in example 59, step 5, compound (98a) (332 mg, 0.72 mmol) was converted, after purification by preparative TLC on silica gel (DCM/MeOH 95/5), to a crude which was treated by NaOH (2M, 1 mL) in MeOH (3 mL) for 48 hours at 80° C. The middle was concentrated under reduced pressure and the crude was purified by preparative TLC on silica gel (DCM/MeOH 9/1+1% AcOH). The product was finally washed with hydrochloric acid 1N and water to give Example (98) (7 mg, 0.016 mmol, 2%). $^1$H NMR (400 MHz, CD$_3$OD) δ 1.43-1.51 (m, 1H), 1.65-1.77 (m, 2H), 1.84-1.90 (m, 1H), 1.93-2.07 (m, 4H), 2.36-2.40 (m, 2H), 2.71 (t, J=6.6 Hz, 2H), 3.77 (t, J=6.6 Hz, 2H), 4.84-4.87 (m, 1H), 7.22 (s, 1H), 7.98 (dd, J=8.7/1.4 Hz, 1H), 8.23 (d, J=1.1 Hz, 1H), 8.29 (d, J=8.7 Hz, 1H), 9.33 (s, 1H), 9.73 (s, 1H). MS m/z ([M+H]$^+$) 429.

Example 99

Synthesis of 1'-Cyclohexyl-6-(anti-4-hydroxymethyl-2-methyl-pyrrolidin-1-yl)-1H,1'H-[4,5']]bibenzimidazolyl-7-carbonitrile

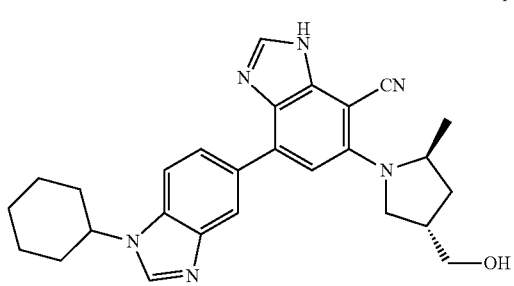

Example 99

Step 1: 2-Amino-4-(1-cyclohexyl-1H-benzimidazol-5-yl)-6-(anti-4-hydroxymethyl-2-methyl-pyrrolidin-1-yl)-3-nitro-benzonitrile (99a)

According to the procedure described in example 29, step 3, compound (91a) (150 mg, 0.39 mmol) was converted, by reaction with compound (8a) (80 mg, 0.69 mmol) and after purification by preparative TLC on silica gel (DCM/MeOH 95/5), to compound (99a) (160 mg, 0.34 mmol, 87%). $^1$H NMR (400 MHz, DMSO-d$_6$) δ 1.23 (d, J=5.9 Hz 3H), 1.30-1.56 (m, 4H), 1.72 (m, 1H), 1.83-1.92 (m, 4H), 2.04-2.07 (m, 2H), 2.22-2.34 (m, 2H), 3.46-3.55 (m, 2H), 3.64-3.72 (m, 2H), 4.29-4.42 (m, 1H), 4.74 (t, J=5.0 Hz, 1H), 6.06 (s, 1H), 6.98 (s, 2H), 7.11 (dd, J=8.4/1.6 Hz, 1H), 7.59 (d, J=1.4 Hz, 1H), 7.67 (d, J=8.5 Hz, 1H), 8.39 (s, 1H). MS m/z ([M+H]$^+$) 475.

Step 2: 1'-Cyclohexyl-6-(anti-4-hydroxymethyl-2-methyl-pyrrolidin-1-yl)-1H,1'H-[4,5']]bibenzimidazolyl-7-carbonitrile, Example (99)

According to the procedure described in example 59, step 5, compound (99a) (160 mg, 0.34 mmol) was converted, after purification by preparative TLC on silica gel (DCM/MeOH 9/1), to Example (99) (12 mg, 0.026 mmol, 8%). $^1$H NMR (400 MHz, DMSO-d$_6$) δ 1.20 (bs, 3H), 1.28-1.57 (m, 4H), 1.72-1.75 (m, 1H), 1.85-1.93 (m, 4H), 2.06-2.08 (m, 2H), 2.25-2.35 (m, 2H), 3.45-3.56 (m, 3H), 3.68 (t, J=9.5 Hz, 1H), 4.27 (bs, 1H), 4.44-4.45 (m, 1H), 4.70 (t, J=5.1 Hz, 1H), 6.86 (bs, 1H), 7.54 and 8.37 (2bs, 1H), 7.79 (bs, 1H), 7.95 (bs, 1H), 8.14 (bs, 1H), 8.42 (bs, 1H), 12.73 and 12.91 (2bs, 1H). MS m/z ([M+H]$^+$) 455.

Example 100

Synthesis of 1'-Cyclohexyl-6-[3-(2-hydroxy-ethyl)-pyrrolidin-1-yl]-1H,1'H-[4,5']]bibenzimidazolyl-7-carbonitrile

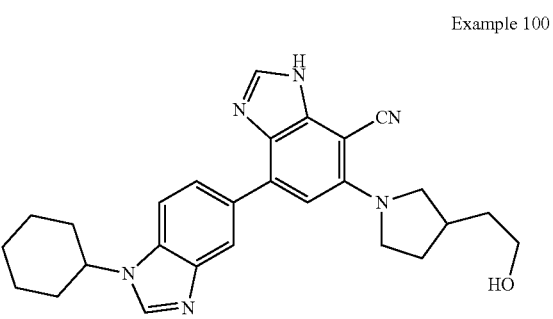 [SMILES: N#Cc1c(N2CCC(CCO)C2)cc(-c2ccc3c(c2)ncn3C2CCCCC2)c2nc[nH]c12]

Example 100

Step 1: 2-Amino-4-(1-cyclohexyl-1H-benzimidazol-5-yl)-6-[3-(2-hydroxy-ethyl)-pyrrolidin-1-yl]-3-nitro-benzonitrile (100a)

According to the procedure described in example 29, step 3, compound (91a) (200 mg, 0.53 mmol) was converted, by reaction with 2-(pyrrolidin-3-yl)ethan-1-ol (91 mg, 0.79 mmol) and after purification by preparative TLC on silica gel (DCM/MeOH 95/5), to compound (100a) (227 mg, 0.48 mmol, 90%). $^1$H NMR (400 MHz, DMSO-d$_6$) δ 1.28-1.31 (m, 1H), 1.48-1.63 (m, 5H), 1.71-1.74 (m, 1H), 1.82-1.90 (m, 4H), 2.03-2.13 (m, 3H), 2.29-2.33 (m, 1H), 3.44-3.49

(m, 2H), 3.63-3.85 (m, 3H), 4.10 (q, J=5.3 Hz, 1H), 4.37-4.39 (m, 1H), 4.49 (t, J=5.1 Hz, 1H), 5.99 (s, 1H), 7.03 (bs, 2H), 7.08 (dd, J=8.4/1.7 Hz, 1H), 7.59 (d, J=1.3 Hz, 1H), 7.65 (d, J=8.5 Hz, 1H), 8.38 (s, 1H). MS m/z ([M+H]$^+$) 475.

Step 2: 1'-Cyclohexyl-6-[3-(2-hydroxy-ethyl)-pyrrolidin-1-yl]-1H,1'H-[4,5']]bibenzimidazolyl-7-carbonitrile, Example (100)

According to the procedure described in example 98, step 2, compound (100a) (227 mg, 0.48 mmol) was converted, after purification by preparative TLC on silica gel (DCM/MeOH 9/1), to Example (100) (4 mg, 0.009 mmol, 1%). $^1$H NMR (400 MHz, DMSO-d$_6$) δ 1.15-1.27 (m, 3H), 1.28-1.45 (m, 2H), 1.45-1.60 (m, 2H), 1.70-1.78 (m, 1H), 1.85-1.94 (m, 4H), 2.07-2.10 (m, 2H), 2.23-2.39 (m, 2H), 3.49-3.54 (m, 2H), 3.71 (t, J=9.5 Hz, 2H), 4.28 (bs, 1H), 4.43 (bs, 1H), 4.70 (t, J=5.1 Hz, 1H), 6.77 (bs, 1H), 7.54 (bs, 1H), 7.79 (bs, 1H), 7.95 (bs, 1H), 8.16 (bs, 1H), 8.42 (bs, 1H), 12.76 and 12.91 (2s, 1H). MS m/z ([M+H]$^+$) 455.

Example 101

Synthesis of 1'-Cyclohexyl-6-(3-dimethylaminomethyl-pyrrolidin-1-yl)-1H,1'H-[4,5']]bibenzimidazolyl-7-carbonitrile

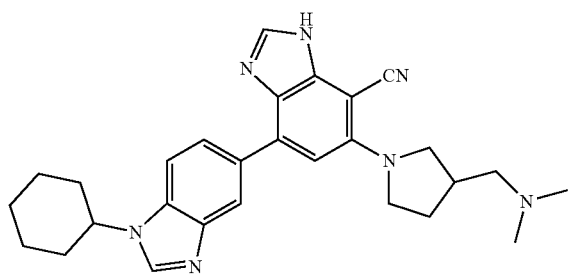

Example 101

Step 1: 2-Amino-4-(1-cyclohexyl-1H-benzimidazol-5-yl)-6-(3-dimethylaminomethyl-pyrrolidin-1-yl)-3-nitro-benzonitrile (101a)

According to the procedure described in example 29, step 3, compound (91a) (150 mg, 0.39 mmol) was converted, by reaction with dimethyl(pyrrolidin-3-ylmethyl)amine (76 mg, 0.59 mmol) and after purification by preparative TLC on silica gel (DCM/MeOH 95/5), to compound (101a) (135 mg, 0.28 mmol, 71%). $^1$H NMR (400 MHz, DMSO-d$_6$) δ 1.22-1.33 (m, 1H), 1.43-1.53 (m, 2H), 1.62-1.72 (m, 2H), 1.80-1.89 (m, 4H), 2.02-2.06 (m, 3H), 2.13 (s, 6H), 2.17-2.28 (m, 2H), 2.44-2.50 (m, 1H), 3.38-3.42 (m, 1H), 3.67-3.80 (m, 3H), 4.32-4.39 (m, 1H), 5.96 (s, 1H), 7.01 (s, 2H), 7.07 (dd, J=8.4/1.7 Hz, 1H), 7.57 (d, J=1.4 Hz, 1H), 7.63 (d, J=8.4 Hz, 1H), 8.36 (s, 1H). MS m/z ([M+H]$^+$) 488.

Step 2: 1'-Cyclohexyl-6-(3-dimethylaminomethyl-pyrrolidin-1-yl)-1H,1'H-[4,5']]bibenzimidazolyl-7-carbonitrile, Example (101)

According to the procedure described in example 59, step 5, compound (101a) (135 mg, 0.28 mmol) was converted, after purification by preparative TLC on silica gel (DCM/MeOH 9/1), to Example (101) (34 mg, 0.073 mmol, 26%). $^1$H NMR (400 MHz, DMSO-d$_6$) δ 1.30-1.37 (m, 1H), 1.48-1.58 (m, 2H), 1.70-1.76 (m, 2H), 1.85-1.92 (m, 4H), 2.07-2.09 (m, 3H), 2.20 (s, 6H), 2.29-2.34 (m, 2H), 2.50-2.59 (m, 1H), 3.38-3.45 (m, 1H), 3.66-3.80 (m, 3H), 4.38-4.48 (m, 1H), 6.71 and 6.80 (2s, 1H), 7.55 and 7.99 (2dd, J=8.5/1.4 Hz, 1H), 7.75-7.83 (2d, J=8.5 Hz, 1H), 7.96-8.41 (2d, J=1.2 Hz, 1H), 8.06-8.39 (2s, 1H), 8.16 and 8.45 (2s, 1H), 12.67 and 12.82 (2s, 1H). MS m/z ([M+H]$^+$) 468.

Example 102

Synthesis of 5-Fluoro-7-(6-methoxy-pyridin-3-yl)-3H-benzimidazole-4-carbonitrile

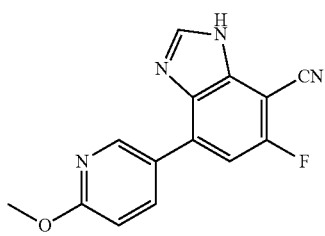

Example 102

According to the procedure described in example 29, step 1, compound (57c) (480 mg, 2 mmol) was converted, by reaction with 2-methoxypyridine-5-boronic acid (470 mg, 2 mmol) and after purification by preparative TLC on silica gel (DCM/MeOH 95/5), to Example (102) (2 mg, 0.0075 mmol, 0.4%). $^1$H NMR (400 MHz, CD$_3$OD) δ 3.99 (s, 3H), 6.97 (d, J=8.7 Hz, 1H), 7.38 (d, J=11.1 Hz, 1H), 8.10 (bs, 1H), 8.38 (s, 1H), 8.57 (bs, 1H). MS m/z ([M+H]$^+$) 269.

Example 103

Synthesis of 1'-Cyclohexyl-6-methoxy-1H,1'H-[4,5']]bibenzimidazolyl-7-carbonitrile

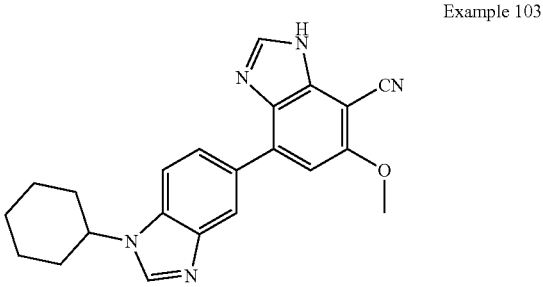 [SMILES: COc1cc(-c2ccc3c(c2)ncn3C2CCCCC2)c2nc[nH]c2c1C#N]

Example 103

Step 1: 2-amino-4-bromo-6-methoxy-3-nitrobenzonitrile (103a)

According to the procedure described in example 88, step 1, compound (57b) (600 mg, 2.3 mmol) was converted, after purification by preparative TLC on silica gel (DCM/MeOH 99/1), to compound (103a) (469 mg, 1.72 mmol, 75%). MS m/z ([M+H]$^+$) 272/274.

Step 2: 2-Amino-4-(1-cyclohexyl-1H-benzimidazol-5-yl)-6-methoxy-3-nitro-benzonitrile (103b)

According to the procedure described in example 29, step 1, compound (103a) (469 mg, 1.72 mmol) was converted, by reaction with (1-cyclohexyl-1H-benzimidazol-5-yl)pinacolboronate (600 mg, 1.83 mmol) and after purification by preparative TLC on silica gel (DCM/MeOH 98/2), to compound (103b) as a crude which was used further purification. MS m/z ([M+H]$^+$) 392.

Step 3: 1'-Cyclohexyl-6-methoxy-1H,1'H-[4,5']]bibenzimidazolyl-7-carbonitrile, Example (103)

According to the procedure described in example 59, step 5, compound (103b) (60 mg, 0.15 mmol) was converted, after purification by preparative TLC on silica gel (DCM/MeOH 95/5), to Example (103) (23 mg, 0.06 mmol, 40%). $^1$H NMR (400 MHz, CD$_3$OD) δ 1.36-1.45 (m, 1H), 1.55-1.66 (m, 2H), 1.81-2.00 (m, 5H), 2.16-2.22 (m, 2H), 4.04 (s, 3H), 4.35-4.43 (m, 1H), 7.14 (s, 1H), 7.70-7.71 (m, 2H), 8.02 (bs, 1H), 8.23 (s, 1H), 8.34 (s, 1H). MS m/z ([M+H]$^+$) 372.

Example 104

Synthesis of 1'-Cyclohexyl-6-(2-dimethylamino-ethoxy)-1H,1'H-[4,5']]bibenzimidazolyl-7-carbonitrile

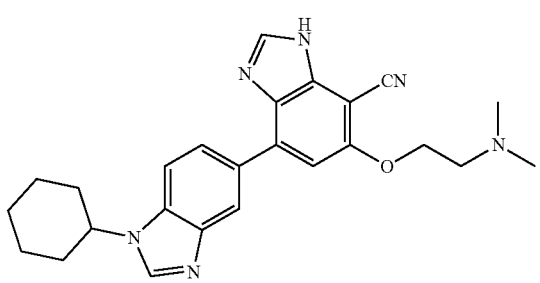

Example 104

Step 1: 2-Amino-4-(1-cyclohexyl-1H-benzimidazol-5-yl)-6-(2-dimethylamino-ethoxy)-3-nitro-benzonitrile (104a)

2-(dimethylamino)ethan-1-ol (0.04 mL, 0.4 mmol) was added slowly to a cooled solution of sodium (92 mg, 4 mmol) in THF (8 mL). At room temperature, compound (91a) (150 mg, 0.4 mmol) was added dropwise and the resulting mixture was stirred at room temperature. After 2 hours, the reaction mixture was diluted with water and ethyl acetate and the aqueous layer was extracted with ethyl acetate. The organic layer was washed with brine, dried over sodium sulfate, filtered and evaporated to dryness to give crude compound (104a) (230 mg) which was used in the next step without further purification. MS m/z ([M+H]$^+$) 449.

Step 2: 1'-Cyclohexyl-6-(2-dimethylamino-ethoxy)-1H,1'H-[4,5']]bibenzimidazolyl-7-carbonitrile, Example (104)

According to the procedure described in example 59, step 5, compound (104a) (202 mg, 0.45 mmol) was converted, after purification by preparative TLC on silica gel (DCM/MeOH 95/5+1% ammonia), to Example (104) (101 mg, 0.24 mmol, 53%). $^1$H NMR (400 MHz, DMSO-d$_6$) δ 1.27-1.35 (m, 1H), 1.49-1.56 (m, 2H), 1.74-1.77 (m, 1H), 1.85-1.95 (m, 4H), 2.08-2.11 (m, 2H), 2.28 (s, 6H), 2.72 (t, J=5.7 Hz, 2H), 4.39 (t, J=5.3 Hz, 2H), 4.45-4.47 (m, 1H), 7.28 (s, 1H), 7.67 (bs, 1H), 7.83-7.85 (m, 1H), 8.08 (bs, 1H), 8.34 (s, 1H), 8.45 (s, 1H), 13.09 (bs, 1H). MS m/z ([M+H]$^+$) 429.

Example 105

Synthesis of 5-Fluoro-7-pyridin-4-yl-3H-benzimidazole-4-carboxamide

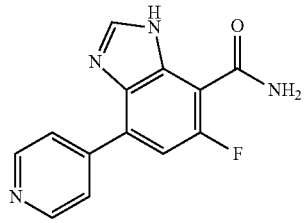

Example 105

Step 1: Methyl 5-Fluoro-7-pyridin-4-yl-3H-benzimidazole-4-carboxylate (105a)

According to the procedure described in example 42, step 2, compound (51c) (200 mg, 0.73 mmol) was converted, by reaction with 4-(4,4,5,5-Tetramethyl-[1,3,2]dioxaborolan-2-yl)-pyridine (158 mg, 0.77 mmol) and after purification by preparative TLC on silica gel (DCM/MeOH 9/1), to compound (105a) (92 mg, 0.34 mmol, 67%). MS m/z ([M+H]$^+$) 272.

Step 2: 5-Fluoro-7-pyridin-4-yl-3H-benzimidazole-4-carboxamide, Example (105)

According to the procedure described in example 72, compound (105a) (60 mg, 0.22 mmol) was converted, after purification by preparative TLC on silica gel (DCM/MeOH 9/1+1% ammonia), to Example (105) (20 mg, 0.08 mmol, 36%). $^1$H NMR (400 MHz, DMSO-d$_6$) δ 7.62 (d, J=12.8 Hz, 1H), 7.82 (bs, 1H), 7.94 (bs, 1H), 8.22 (bs, 2H), 8.31 (s, 1H), 8.70-8.72 (m, 2H), 12.82 (bs, 1H). MS m/z ([M+H]$^+$) 257.

Example 106

Synthesis of 1'-Cyclohexyl-6-(4-methyl-piperazin-1-yl)-1H,1'H-[4,5']bibenzimidazolyl-7-carboxamide

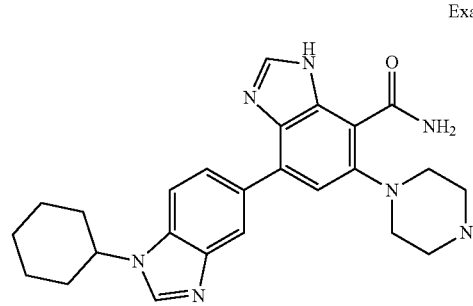

Example 106

Step 1: Methyl 2-Amino-6-fluoro-4-[1-(1-methyl-cyclohexyl)-1H-benzimidazol-5-yl]-3-nitro-benzoate (106a)

A solution of compound (51b) (500 mg, 1.71 mmol) in the mixture of dioxane (2.5 mL) and water (0.85 mL) was dissolved 1-Cyclohexyl-5-(4,4,5,5-tetramethyl-[1,3,2]dioxaborolan-2-yl)-1H-benzimidazole (584 mg, 1.79 mmol) and potassium carbonate (473 mg, 3.42 mmol). The solution was degassed under argon for 10 minutes and Tetrakis(triphenylphosphine)palladium(0) (99 mg, 0.008 mmol) was added. After 1 hour at 120° C. under microwave irradiation, the reaction mixture was concentrated under reduced pressure. The residue was washed with water and extracted with ethyl acetate. The organic phase was dried on sodium sulfate, filtered and evaporated. The product was purified by flash chromatography on silica gel (cyclohexane/EtOAc 9/1 to 7/3) to afford compound (106a) (56 mg, 0.96 mmol, 56%). MS m/z ([M+H]$^+$)(413).

Step 2: Methyl 2-Amino-4-(1-cyclohexyl-1H-benzimidazol-5-yl)-6-(4-methyl-piperazin-1-yl)-3-nitro-benzoate (106b)

According to the procedure described in example 29, step 3, compound (106a) (100 mg, 0.34 mmol) was converted, by reaction with 1-Methyl-piperazine (227 mg, 2.25 mmol) and after trituration in diethyl ether, to compound (106b) (230 mg, 0.47 mmol, 100%). $^1$H NMR (300 MHz, CDCl$_3$) δ 1.31-1.39 (m, 1H), 1.43-1.58 (m, 4H), 1.75-1.88 (m, 4H), 2.00 (bd, J=12.9 Hz, 3H), 2.24 (bd, J=12.9 Hz, 3H), 2.61 (bs, 2H), 3.44-3.57 (m, 4H), 3.94 (s, 3H), 4.16-4.25 (m, 1H), 6.27 (s, 1H), 6.76 (bs, 2H), 7.16 (dd, J=1.5/8.4 Hz, 1H), 7.43 (d, J=8.4 Hz, 1H), 7.76 (d, J=1.5 Hz, 1H), 8.04 (s, 1H). MS m/z ([M+H]$^+$) 493.

Step 3: Methyl 1'-Cyclohexyl-6-(4-methyl-piperazin-1-yl)-1H,1'H-[4,5']bibenzimidazolyl-7-carboxylate (106c)

According to the procedure described in example 17, step 4, compound (106b) (191 mg, 0.39 mmol) was converted, after purification by preparative TLC on silica gel (DCM/MeOH 9/1+1% ammonia), to compound (106c) (181 mg, 0.38 mmol, 98%). $^1$H NMR (400 MHz, CDCl$_3$) δ 1.25-1.39 (m, 1H), 1.47-1.59 (m, 2H), 1.79-1.89 (m, 3H), 2.00 (bd, J=13.6 Hz, 2H), 2.25 (bd, J=11.6 Hz, 2H), 2.41 (s, 3H), 2.68 (bs, 4H), 3.26 (bs, 4H), 4.02 (s, 3H), 4.24 (tt, J=3.6/12.0 Hz, 1H), 7.24 (s, 1H), 7.56 (d, J=8.4 Hz, 1H), 8.03 (s, 1H), 8.04 (s, 1H), 8.13 (dd, J=1.6/8.4 Hz, 1H), 8.27 (d, J=1.2 Hz, 1H), 10.69 (bs, 1H). MS m/z ([M+H]$^+$)473.

Step 4: 1'-Cyclohexyl-6-(4-methyl-piperazin-1-yl)-1H,1'H-[4,5']bibenzimidazolyl-7-carboxamide, Example (106)

According to the procedure described in example 72, compound (106c) (50 mg, 0.11 mmol) was converted, after purification by preparative TLC on silica gel (DCM/MeOH 9/1+1% ammonia), to Example (106) (24 mg, 0.05 mmol, 50%). $^1$H NMR (400 MHz, DMSO-d$_6$) δ 1.26-1.36 (m, 1H), 1.48-1.58 (m, 2H), 1.74 (d, J=12.4 Hz, 1H), 1.84-1.93 (m, 4H), 2.04-2.11 (m, 2H), 2.14 (s, 4H), 2.39 (t, J=6.0 Hz, 2H), 2.73 (s, 3H), 3.20 (t, J=6.4 Hz, 2H), 4.42 (tt, J=3.6/12.0 Hz, 1H), 7.50 (s, 1H), 7.56 (bd, J=3.2 Hz, 1H), 7.75 (d, J=8.4 Hz, 1H), 8.05 (dd, J=1.6/8.8 Hz, 1H), 8.15 (s, 1H), 8.38 (s, 1H), 8.46 (d, J=1.2 Hz, 1H), 10.03 (d, J=4.0 Hz, 1H), 12.39 (s, 1H). MS m/z ([M+H]$^+$) 458.

Example 107

Synthesis of 1'-Cyclohexyl-6-[(2-dimethylamino-ethyl)-methyl-amino]-1H,1'H-[4,5']bibenzimidazolyl-7-carboxamide

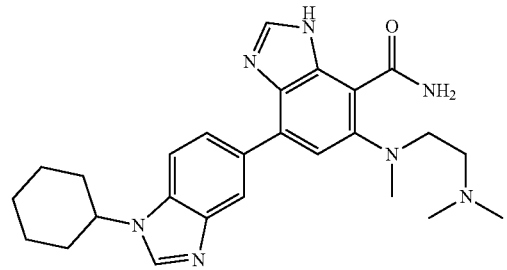

Example 107

Step 1: Methyl 2-Amino-4-(1-cyclohexyl-1H-benzimidazol-5-yl)-6-[(2-dimethylamino-ethyl)-methyl-amino]-3-nitro-benzoate (107a)

According to the procedure described in example 29, step 3, compound (106a) (180 mg, 0.44 mmol) was converted, by reaction with N,N,N'-Trimethylethylenediamine (60 μL, 0.46 mmol) and after purification by preparative TLC on silica gel (DCM/MeOH 9/1), to compound (107a) as an orange solid (217 mg, 0.44 mmol, 100%). MS m/z ([M+H]$^+$) 495.

Step 2: Methyl 1'-Cyclohexyl-6-[(2-dimethylamino-ethyl)-methyl-amino]-1H,1'H-[4,5']bibenzimidazolyl-7-carboxylate (107b)

According to the procedure described in example 17, step 4, compound (107a) (217 mg, 0.44 mmol) was converted, after purification by preparative TLC on silica gel (DCM/MeOH 9/1+1% ammonia), to compound (107b) as a yellow solid (149 mg, 0.31 mmol, 71%). $^1$H NMR (400 MHz, CD$_3$OD) δ 1.25-1.37 (m, 1H), 1.58-1.67 (m, 2H), 1.83 (bd, J=12.4 Hz, 1H), 1.92 (dd, J=3.6/12.4 Hz, 1H), 1.96-2.02 (m, 3H), 2.23 (bd, J=11.6 Hz, 2H), 2.31 (s, 6H), 2.67 (t, J=7.6 Hz, 2H), 2.95 (s, 3H), 3.35-3.42 (m, 2H), 4.04 (s, 3H), 4.44 (tt, J=3.2/11.6 Hz, 1H), 7.28 (s, 1H), 7.75 (d, J=8.4 Hz, 1H), 7.83 (bs, 1H), 8.11 (s, 1H), 8.14 (bs, 1H), 8.34 (s, 1H). MS m/z ([M+H]$^+$) 475.

Step 3: 1'-Cyclohexyl-6-[(2-dimethylamino-ethyl)-methyl-amino]-1H,1'H-[4,5']bibenzimidazolyl-7-carboxamide, Example (107)

According to the procedure described in example 72, compound (107b) (99 mg, 0.21 mmol) was converted, after purification by preparative TLC on silica gel (DCM/MeOH 9/1+2% ammonia), to Example (107) (55 mg, 0.12 mmol, 57%). $^1$H NMR (400 MHz, DMSO-d$_6$) δ 1.26-1.36 (m, 1H), 1.48-1.58 (m, 2H), 1.75 (bd, J=12.8 Hz, 1H), 1.84-1.93 (m, 4H), 2.08 (d, J=9.2 Hz, 2H), 2.15 (s, 6H), 2.41 (t, J=6.0 Hz, 2H), 2.74 (s, 3H), 3.21 (t, J=6.4 Hz, 2H), 4.35-4.50 (m, 1H), 7.50 (s, 1H), 7.57 (bd, J=3.2 Hz, 1H), 7.75 (d, J=8.4 Hz, 1H), 8.06 (dd, J=1.6/8.4 Hz, 1H), 8.15 (bs, 1H), 8.38 (s, 1H), 8.46 (s, J=1.2 Hz, 1H), 10.02 (s, 1H), 12.39 (s, 1H). MS m/z ([M+H]$^+$) 460.

Example 108

Synthesis of 1'-Cyclohexyl-6-[(2-dimethylamino-ethyl)-methyl-amino]-1H,1'H-[4,5']bibenzimidazolyl-7-carboxamide methanesulfonic acid salt Example 108

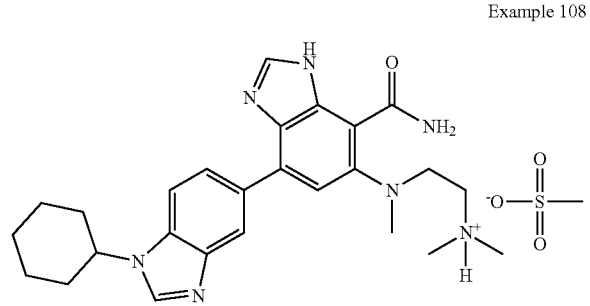

To a solution of Example (107) (961 mg, 2.091 mmol) in DCM (5 mL) and MeOH (5 mL) was added a solution of methanesulfonic acid (0.1N in H$_2$O, 2.091 mL, 2.091 mmol). The middle was concentrated and the residue was triturated in diethyl ether to give Example (108) as white powder (1.116 g, 2.01 mmol, 96%). $^1$H NMR (400 MHz, DMSO-d$_6$) δ 1.27-1.37 (m, 1H), 1.47-1.59 (m, 2H), 1.71-1.78 (m, 1H), 1.82-1.95 (m, 4H), 2.04-2.12 (m, 2H), 2.29 (s, 3H), 2.91-2.95 (m, 9H), 3.13 (bs, 1H), 3.41-3.49 (m, 2H), 4.34-4.49 (m, 1H), 7.57 (s, 1H), 7.76 (d, J=8.6 Hz, 1H), 8.01 (bs, 1H), 8.10 (d, J=8.6 Hz, 1H), 8.24 (s, 1H), 8.41 (s, 1H), 8.47 (s, 1H), 9.10 (bs, 1H), 9.67 (bs, 1H), 12.61 (bs, 1H). MS m/z ([M+H]$^+$) 460.

Example 109

Synthesis of 1'-Cyclohexyl-6-dimethylamino-1H,1'H-[4,5']bibenzimidazolyl-7-carboxamide Example 109

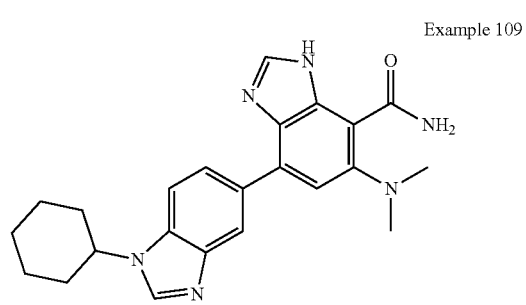 [SMILES: CN(C)c1cc(-c2ccc3c(c2)ncn3C2CCCCC2)c2nc[nH]c2c1C(N)=O]

Step 1: Methyl 2-Amino-4-(1-cyclohexyl-1H-benzimidazol-5-yl)-6-dimethylamino-3-nitro-benzoate (109a)

According to the procedure described in example 29, step 3, compound (106a) (160 mg, 0.39 mmol) was converted, by reaction with dimethylamine (2M in THF, 203 μL, 0.41 mmol) and after trituration in diethyl ether, to compound (109a) (176 mg, 0.40 mmol, 100%). $^1$H NMR (300 MHz, CDCl$_3$) δ 1.25-1.40 (m, 1H), 1.38-1.45 (m, 2H), 1.74-1.87 (m, 3H), 2.00 (bd, J=12.0 Hz, 2H), 2.25 (bd, J=12.0 Hz, 2H), 3.00 (s, 6H), 3.92 (s, 3H), 4.24 (tt, J=3.6/11.7 Hz, 1H), 6.15 (s, 1H), 7.19 (dd, J=1.5/8.4 Hz, 1H), 7.41 (s, 1H), 7.44 (bs, 2H), 7.85 (d, J=1.2 Hz, 1H), 8.18 (s, 1H). MS m/z ([M+H]$^+$) 438.

Step 2: Methyl 1'-Cyclohexyl-6-dimethylamino-1H, 1'H-[4,5']bibenzimidazolyl-7-carboxylate (109b)

According to the procedure described in example 17, step 4, compound (109a) (169 mg, 0.39 mmol) was converted, after purification by preparative TLC on silica gel (DCM/MeOH 9/1), to compound (109b) (75 mg, 0.18 mmol, 46%). MS m/z ([M+H]$^+$) 418.

Step 3: 1'-Cyclohexyl-6-dimethylamino-1H,1'H-[4,5']bibenzimidazolyl-7-carboxamide, Example (109)

According to the procedure described in example 72, compound (109b) (50 mg, 0.11 mmol) was converted, after purification by preparative TLC on silica gel (DCM/MeOH 9/1+1% ammonia), to Example (109) (14.8 mg, 0.04 mmol, 31%). $^1$H NMR (400 MHz, DMSO-d$_6$) δ 1.26-1.36 (m, 1H), 1.48-1.58 (m, 2H), 1.74 (d, J=12.4 Hz, 1H), 1.83-1.93 (m, 4H), 2.08 (d, J=9.2 Hz, 2H), 2.81 (s, 6H), 4.42 (tt, J=3.6/11.6 Hz, 1H), 7.49 (s, 1H), 7.70 (bd, J=4.0 Hz, 1H), 7.75 (d, J=8.4 Hz, 1H), 8.05 (dd, J=1.6/8.8 Hz, 1H), 8.14 (s, 1H), 8.38 (s, 1H), 8.46 (d, J=1.2 Hz, 1H), 9.69 (d, J=4.0 Hz, 1H), 12.38 (s, 1H). MS m/z ([M+H]$^+$) 403.

Example 110

Synthesis of 1'-Cyclohexyl-6-fluoro-1H,1'H-[4,5'] bibenzimidazolyl-N-cyano-7-carboxamide Example 110

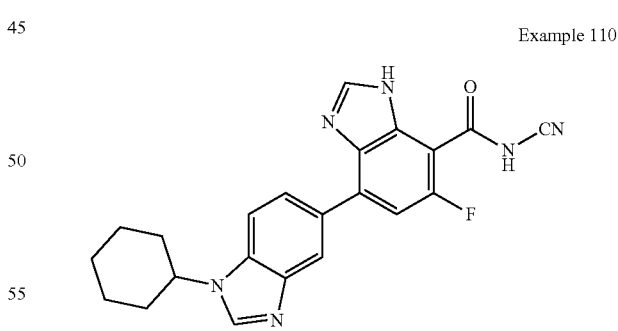

According to the procedure described in example 80, Example (56) (70 mg, 0.185 mmol) was converted, by reaction with cyanamide (12 mg, 0.277 mmol) and after trituration in a mixture of DCM/MeOH, to Example (110) (38 mg, 0.094, 51%) as a brown solid. $^1$H NMR (400 MHz, DMSO-d$_6$) δ 1.22-1.38 (m, 1H), 1.46-1.60 (m, 2H), 1.70-1.79 (m, 1H), 1.82-1.96 (m, 4H), 2.04-2.14 (m, 2H), 4.40-4.50 (m, 1H), 7.70-7.88 (m, 1H), 8.12-8.20 (m, 1H), 8.46 (s, 1H), 8.55-8.70 (m, 2H), 9.08 (s, 1H). MS m/z ([M+H]$^+$) 403.

Example 111

Synthesis of 1'-Cyclohexyl-6-fluoro-1H,1'H-[4,5']bibenzimidazolyl-N-hydroxy-7-carboxamide

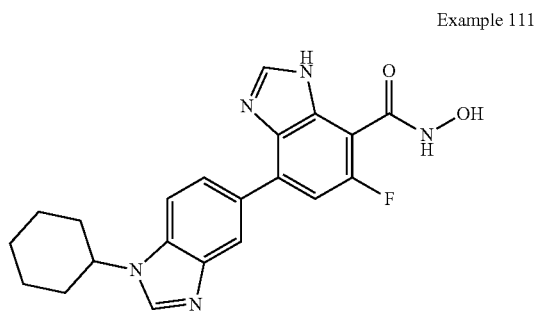 [SMILES: O=C(NO)c1c(F)cc(-c2ccc3c(c2)ncn3C2CCCCC2)c2nc[nH]c12]

Example 111

Step 1: 1'-Cyclohexyl-6-fluoro-1H,1'H-[4,5']bibenzimidazolyl-N-benzyloxy-7-carboxamide (111a)

According to the procedure described in example 80, Example (56) (70 mg, 0.185 mmol) was converted, by reaction with O-Benzyl-hydroxylamine hydrochloride (35 mg, 0.222 mmol) and after purification by preparative TLC on silica gel (DCM/MeOH 9/1+1% NH3 7M in MeOH), to compound (111a) (32 mg, 0.066 mmol, 36%) as a beige solid. MS m/z ([M+H]$^+$) 484.

Step 2: 1'-Cyclohexyl-6-fluoro-1H,1'H-[4,5']bibenzimidazolyl-N-hydroxy-7-carboxamide Example (111)

Compound (111a) (32 mg, 0.066 mmol) was dissolved in a mixture of MeOH (2 mL) and DCM (2 mL). The catalyst Pd(C) (21 mg, 30% mass) was added and the mixture was stirred under hydrogen atmosphere overnight. The middle was filtered on PTFE filter and concentrated. The residue was triturated in DCM to give Example (111) (8.5 mg, 0.021 mmol, 33%) as a beige solid. $^1$H NMR (400 MHz, DMSO-d$_6$) δ 1.24-1.38 (m, 1H), 1.48-1.62 (m, 2H), 1.72-1.80 (m, 1H), 1.86-1.96 (m, 4H), 2.10-2.19 (m, 2H), 4.52-4.62 (m, 1H), 7.45-7.53 (m, 1H), 7.94-8.02 (m, 1H), 8.11 (bs, 1H), 8.33 (s, 1H), 8.60 (bs, 1H), 8.95 (bs, 1H), 9.32 (bs, 1H), 11.11 (s, 1H), 12.88 (bs, 1H). MS m/z ([M+H]+) 394.

Example 112

Synthesis of 1'-Cyclohexyl-6-fluoro-1H,1'H-[4,5']bibenzimidazolyl-N-methoxy-N-methyl-7-carboxamide

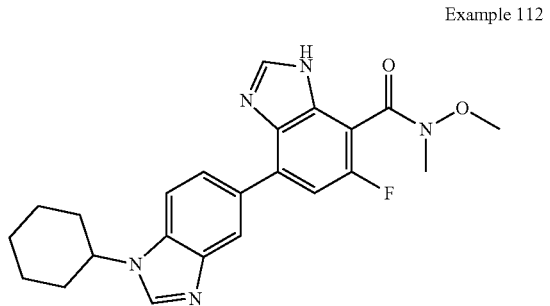 [SMILES: CON(C)C(=O)c1c(F)cc(-c2ccc3c(c2)ncn3C2CCCCC2)c2nc[nH]c12]

Example 112

According to the procedure described in example 80, Example (56) (200 mg, 0.53 mmol) was converted, by reaction with O,N-Dimethyl-hydroxylamine hydrochloride (77 mg, 0.79 mmol) and after purification by preparative TLC on silica gel (DCM/MeOH 9/1), to Example (112) (115 mg, 0.27 mmol, 52%) as a brown solid. $^1$H NMR (300 MHz, CDCl$_3$) δ 1.22-1.60 (m, 3H), 1.76-1.92 (m, 3H), 1.94-2.06 (m, 2H), 2.16-2.30 (m, 2H), 3.41 (s, 3H), 3.71 (s, 3H), 4.16-4.30 (m, 1H), 7.16-7.24 (m, 1H), 7.52-7.60 (m, 1H), 7.87 (bs, 1H), 8.05 (s, 1H), 8.12 (s, 1H), 8.23 (s, 1H). MS m/z ([M+H]$^+$) 422.

Example 113

Synthesis of 1'-Cyclohexyl-6-fluoro-1H,1'H-[4,5']bibenzimidazolyl-7-carboxylhydrazide

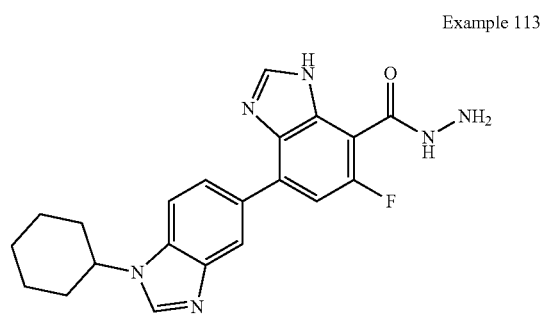 [SMILES: NNC(=O)c1c(F)cc(-c2ccc3c(c2)ncn3C2CCCCC2)c2nc[nH]c12]

Example 113

Step 1: Benzyl N'-(1'-Cyclohexyl-6-fluoro-1H,1'H-[4,5']bibenzimidazolyl-7-carbonyl)-hydrazinecarboxylate (113a)

According to the procedure described in example 80, Example (56) (70 mg, 0.185 mmol) was converted, by reaction with benzyl hydrazinecarboxylate (46 mg, 0.277 mmol) and after purification by preparative TLC on silica gel (DCM/MeOH 9/1+1% NH$_3$ 7M in MeOH), to compound (113a) (47 mg, 0.089 mmol, 49%) as a beige solid. MS m/z ([M+H]$^+$) 527.

Step 2: 1'-Cyclohexyl-6-fluoro-1H,1'H-[4,5']bibenzimidazolyl-7-carboxylhydrazide, Example (113)

According to the procedure described in example 111, step 2, compound (113a) (47 mg, 0.089 mmol) was converted, without further purification, to Example (113) (9 mg, 0.023 mmol, 27%) as a beige solid. $^1$H NMR (400 MHz, CD$_3$OD) δ 1.38-1.50 (m, 1H), 1.61-1.74 (m, 2H), 1.83-1.90 (m, 1H), 1.91-2.08 (m, 4H), 2.30-2.37 (m, 2H), 4.64-4.73 (m, 1H), 7.43 (d, J=12.9 Hz, 1H), 8.06-8.10 (m, 2H), 8.37-8.41 (m, 2H), 9.25 (s, 1H). MS m/z ([M+H]$^+$) 393.

Example 114

Synthesis of 1'-Cyclohexyl-6-fluoro-1H,1'H-[4,5']bibenzimidazolyl-N-hydroxy-N-methyl-7-carboxylamide Example 114

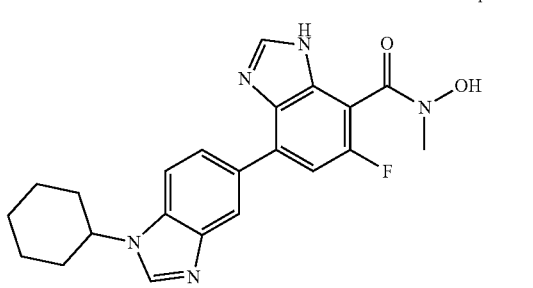

Step 1: 2-{[(benzyloxy)carbamoyl]oxy}-2-methylpropylidyne (114a)

O-Benzyl-hydroxylamine hydrochloride (300 mg, 1.89 mmol) was dissolved in DCM (5 mL). Triethylamine (1.05 mL, 7.56 mmol), DMAP (catalytic amount) and di-tert-butyldicarbonate (617 mg, 2.83 mmol) were added and the mixture was stirred at room temperature overnight. Water and DCM were then added. The organic layer was dried over sodium sulfate, filtered and concentrated under reduced pressure. The crude material was purified by preparative TLC on silica gel (DCM/MeOH 99/1) to give compound (114a) (210 mg, 0.94 mmol, 50%). $^1$H NMR (400 MHz, CDCl$_3$) δ 1.48 (s, 9H), 4.86 (s, 2H), 7.07 (bs, 1H), 7.33-7.42 (m, 5H).

Step 2: N-methyl-2-{[(benzyloxy)carbamoyl]oxy}-2-methylpropylidyne (114b)

Compound (114a) (210 mg, 0.94 mmol) was dissolved in DMF (2 mL). Sodium hydride 60% in mineral oil (42 mg, 1.04 mmol) was added and the mixture was stirred at room temperature for 30 minutes. Iodomethane (146 mg, 1.04 mmol) was added and the mixture was stirred at room temperature overnight. Water and brine were added. The middle was extracted with EtOAc. Organic layer was dried over sodium sulfate, filtered and concentrated. Residue was purified by preparative TLC on silica gel (Cyclohexane/EtOAc 8/2) to give compound (114b) (165 mg, 0.696 mmol, 75%) as a yellow oil. $^1$H NMR (400 MHz, CDCl$_3$) δ 1.49 (s, 9H), 3.05 (s, 3H), 4.02 (s, 2H), 7.31-7.43 (m, 5H).

Step 3: O-Benzyl-N-methyl-hydroxylamine hydrochloride (114c)

According to the procedure described in example 62, step 2, compound (114b) (160 mg, 0.675 mmol) was converted, without further purification, to compound (114c) (105 mg, 0.607 mmol, 91%) as a yellow solid. $^1$H NMR (400 MHz, CDCl$_3$) δ 2.97 (s, 3H), 5.30 (s, 2H), 7.36-7.40 (m, 3H), 7.41-7.46 (m, 2H).

Step 4: 1'-Cyclohexyl-6-fluoro-1H,1'H-[4,5']bibenzimidazolyl-N-benzyloxy-N-methyl-7-carboxamide (114d)

According to the procedure described in example 80, Example (56) (70 mg, 0.185 mmol) was converted, by reaction with compound (114c) (39 mg, 0.222 mmol) and after purification by preparative TLC on silica gel (DCM/MeOH 9/1), to compound (114d) (44 mg, 0.088 mmol, 49%). MS m/z ([M+H]$^+$) 498.

Step 5: 1'-Cyclohexyl-6-fluoro-1H,1'H-[4,5']bibenzimidazolyl-N-hydroxy-N-methyl-7-carboxylamide, Example (114)

According to the procedure described in example 111, step 2, compound (114d) (44 mg, 0.088 mmol) was converted, after trituration in DCM, to Example (114) (13 mg, 0.032 mmol, 37%) as a white solid. $^1$H NMR (400 MHz, DMSO-d$_6$) δ 1.26-1.38 (m, 1H), 1.46-1.60 (m, 2H), 1.70-1.80 (m, 1H), 1.83-1.96 (m, 4H), 2.04-2.13 (m, 2H), 3.32 (s, 3H), 4.37-4.48 (m, 1H), 7.33 (bs, 1H), 7.72-7.81 (m, 1H), 8.00 (bs, 1H), 8.26 (s, 1H), 8.39 (s, 1H), 8.48 (bs, 1H). MS m/z ([M+H]+) 408.

Example 115

Synthesis of 5-Fluoro-7-(3-fluoro-4-methoxy-phenyl)-3H-benzimidazole-4-carboxamide Example 115

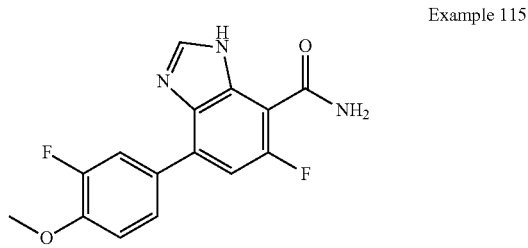 [SMILES: COc1ccc(-c2cc(F)c(C(N)=O)c3[nH]cnc23)cc1F]

Step 1: 7-Bromo-5-fluoro-3H-benzimidazole-4-carboxamide (115a)

In a sealed vial tube was charged compound (51c) (250 mg, 0.91 mmol) and ammonia solution (7M in methanol, 4 mL, 28 mmol). The reaction was stirred at 90° C. for 46 hours. The reaction mixture was cooled to room temperature and a white solid was precipitated. The solid was isolated by filtration, washed with methanol and diethyl ether and dried to give compound (115a) (220 mg, 0.85 mmol, 94%). MS m/z ([M+H]$^+$)259.

Step 2: 5-Fluoro-7-(3-fluoro-4-methoxy-phenyl)-3H-benzimidazole-4-carboxamide, Example (115)

A solution of 3-fluoro-4-methoxybenzene boronic acid (66 mg, 0.38 mmol), compound (115a) (100 mg, 0.38 mmol) and potassium carbonate (157 mg, 1.14 mmol) in 1,4-dioxane (3.8 mL)/water (0.8 mL) was degassed under argon for 10 minutes. The catalyste tetrakis(triphenylphosphine) palladium(0) (88 mg, 0.076 mmol) was then added. After 16 hours at 120° C., the reaction mixture was diluted with ethyl acetate and washed with water. The organic layer was extracted three times with ethyl acetate. The combined organic layers were dried over sodium sulfate, filtered and evaporated. The crude product was triturated with a solution of DCM/MeOH (1/1) to give Example (115) (27.4 mg, 0.09 mmol, 24%). $^1$H NMR (400 MHz, CDCl$_3$) δ 3.92 (s, 3H), 7.31 (t, J=8.9 Hz, 1H), 7.45-7.49 (m, 1H), 7.62 (bs, 1H), 7.86 (bs, 1H), 8.08 (bs, 1H), 8.26 (bs, 2H), 12.69 (s, 1H). MS m/z ([M+H]$^+$) 304.

Example 116

Synthesis of 1-(1'-Cyclohexyl-6-fluoro-1H,1'H-[4,5']bibenzimidazolyl-7-yl)-ethanone

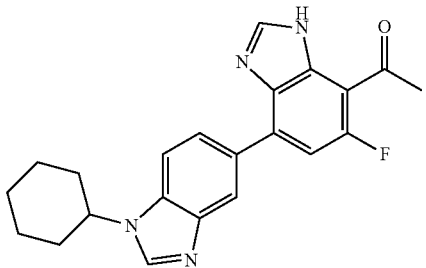

Example 116

Example (112) (105 mg, 0.25 mmol) was dissolved in THF (1 mL). At 0° C. and under argon, a solution of Methyl magnesium bromide (3M in Et$_2$O, 0.4 mL, 1.24 mmol) was added. The mixture was stirred at 0° C. for 2 hours and then at room temperature overnight. The middle was quenched by addition of a solution of ammonium chloride. The middle was extracted with EtOAc. The organic layer was dried over sodium sulfate, filtered and concentrated under reduced pressure. The crude material was purified by preparative TLC on silica gel (DCM/MeOH 9/1). The fraction containing desired product was triturated in MeOH to give Example (116) (55 mg, 0.14 mmol, 59%) as a white solid. $^1$H NMR (300 MHz, CDCl$_3$) δ 1.34 (qt, J=12.7/3.5 Hz, 1H), 1.54 (qt, J=13.0/3.1 Hz, 2H), 1.77-1.92 (m, 3H), 1.95-2.05 (m, 2H), 2.22-2.31 (m, 2H), 2.79 (d, J=5.6 Hz, 3H), 4.24 (tt, J=11.9/3.7 Hz, 1H), 7.33 (d, J=13.5 Hz, 1H), 7.58 (d, J=8.5 Hz, 1H), 8.05 (s, 1H), 8.13-8.18 (m, 2H), 8.36 (d, J=1.4 Hz, 1H), 11.28 (s, 1H). MS m/z ([M+H]$^+$) 377.

Example 117

Synthesis of 1'-Cyclohexyl-6-[(2-hydroxy-ethyl)-methyl-amino]-1H,1'H-[4,5']bibenzimidazolyl-7-carboxamide

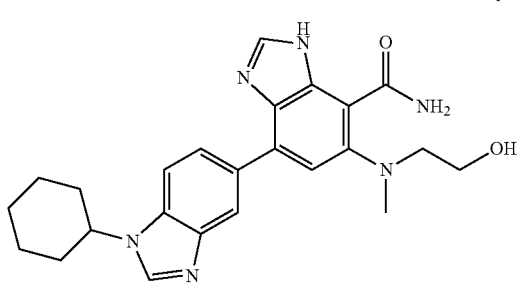

Example 117

Step 1: Methyl 2-Amino-4-(1-cyclohexyl-1H-benzimidazol-5-yl)-6-[(2-hydroxy-ethyl)-methyl-amino]-3-nitro-benzoate (117a)

According to the procedure described in example 29, step 3, compound (106a) (200 mg, 0.48 mmol) was converted, by reaction with 2-Methylamino-ethanol (47 µL, 0.58 mmol) and after purification by preparative TLC on silica gel (DCM/MeOH 9/1), to compound (117a) as an orange solid (226 mg, 0.48 mmol, 99%). MS m/z ([M+H]$^+$) 468.

Step 2: 4-(1-Cyclohexyl-1H-benzimidazol-5-yl)-6-methyl-1,6,7,8-tetrahydro-9-oxa-1,3,6-triaza-cyclohepta[e]inden-10-one (117b)

According to the procedure described in example 17, step 4, compound (117a) (226 mg, 0.48 mmol) was converted, without further purification, to compound (117b) as yellow oil (201 mg, 0.48 mmol, 100%). MS m/z ([M+H]$^+$) 416.

Step 3: 1'-Cyclohexyl-6-[(2-hydroxy-ethyl)-methyl-amino]-1H,1'H-[4,5']bibenzimidazolyl-7-carboxamide, Example (117)

According to the procedure described in example 72, compound (117b) (100 mg, 0.24 mmol) was converted, after purification by preparative TLC on silica gel (DCM/MeOH 9/1+1% ammonia), to Example (117) (23 mg, 0.05 mmol, 22%). $^1$H NMR (300 MHz, DMSO-d$_6$) δ 1.23-1.37 (m, 1H), 1.46-1.59 (m, 2H), 1.74 (d, J=11.7 Hz, 1H), 1.82-1.94 (m, 4H), 2.08 (d, J=8.7 Hz, 2H), 2.75 (s, 3H), 3.17 (t, J=5.1 Hz, 2H), 3.57 (q, J=5.1 Hz, 2H), 4.37-4.45 (m, 1H), 4.75 (t, J=4.8 Hz, 1H), 7.48 (s, 1H), 7.61 (bd, J=3.6 Hz, 1H), 7.74 (d, J=8.4 Hz, 1H), 8.05 (dd, J=8.4/1.5 Hz, 1H), 8.15 (s, 1H), 8.38 (s, 1H), 8.45 (d, J=1.2 Hz, 1H), 9.92 (d, J=3.6 Hz, 1H), 12.40 (bs, 1H). MS m/z ([M+H]$^+$) 433.

Example 118

Synthesis of 1'-Cyclohexyl-6-{[2-(formyl-methyl-amino)-ethyl]-methyl-amino}-1H,1'H-[4,5']bibenzimidazolyl-7-carboxamide

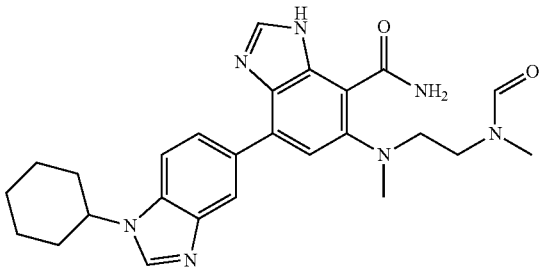

Example 118

Step 1: Methyl 2-Amino-4-(1-cyclohexyl-1H-benzimidazol-5-yl)-6-[methyl-(2-methylamino-ethyl)-amino]-3-nitro-benzoate (118a)

According to the procedure described in example 29, step 3, compound (106a) (200 mg, 0.48 mmol) was converted, by reaction with N,N'-Dimethyl-ethane-1,2-diamine (63 µL, 0.58 mmol) and after trituration in diethyl ether, to compound (118a) as an orange solid (233 mg, 0.48 mmol, 100%). MS m/z ([M+H]$^+$) 481.

Step 2: Methyl 1'-Cyclohexyl-6-{[2-(formyl-methyl-amino)-ethyl]-methyl-amino}-1H,1'H-[4,5']bibenzimidazolyl-7-carboxylate (118b)

According to the procedure described in example 17, step 4, compound (118a) (233 mg, 0.48 mmol) was converted, after purification by preparative TLC on silica gel (DCM/MeOH 9/1), to compound (118b) (80 mg, 0.16 mmol, 33%). MS m/z ([M+H]$^+$) 489.

Step 3: 1'-Cyclohexyl-6-{[2-(formyl-methyl-amino)-ethyl]-methyl-amino}-1H,1'H-[4,5']bibenzimidazolyl-7-carboxamide, Example (118)

According to the procedure described in example 72, compound (118b) (80 mg, 0.16 mmol) was converted, after purification by preparative TLC on silica gel (DCM/MeOH 9/1+1% ammonia), to Example (118) (39 mg, 0.08 mmol, 50%). $^1$H NMR (400 MHz, CD$_3$OD) δ 1.37-1.47 (m, 1H), 1.58-1.69 (m, 2H), 1.84 (bd, J=12.0 Hz, 1H), 1.91-1.95 (m, 1H), 1.97-2.02 (m, 3H), 2.24 (bd, J=10.8 Hz, 2H), 2.84 and 2.87 (2s, 3H), 2.88 and 2.97 (2s, 3H), 3.36 (t, J=6.4 Hz, 1H), 3.43 (t, J=6.0 Hz, 1H), 3.53 (t, J=6.0 Hz, 1H), 3.61 (t, J=6.4 Hz, 1H), 4.40-4.50 (m, 1H), 7.53 (d, J=3.6 Hz, 1H), 7.76 (d, J=8.4 Hz, 1H), 7.86 and 8.04 (2s, 1H), 7.92 (bd, J=8.8 Hz, 1H), 8.21 (bd, J=3.2 Hz, 1H), 8.23 (d, J=4.0 Hz, 1H), 8.34 (d, J=2.4 Hz, 1H). MS m/z ([M+H]$^+$) 474.

Example 119

Synthesis of 1'-Cyclohexyl-6-[methyl-(2-methyl-amino-ethyl)-amino]-1H,1'H-[4,5']bibenzimidazolyl-7-carboxamide

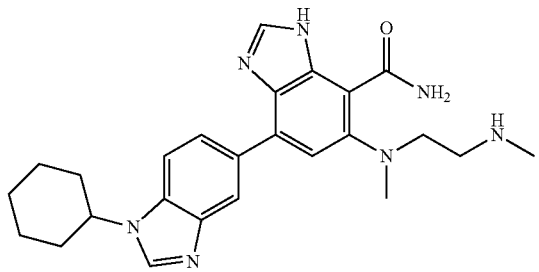

Example 119

A solution of Example (118) (28 mg, 0.06 mmol) in methanol (1 mL) and sodium hydroxide 1N solution (1 mL) was heated 5 hours at 80° C. The solution was evaporated. The residue was extracted with DCM. The organic phase was dried on sodium sulfate, filtered and evaporated. The residue was purified by preparative TLC on silica gel (DCM/MeOH 85/15 with 5% ammonia) to afford Example (119) (13 mg, 0.03 mmol, 50%). $^1$H NMR (400 MHz, CDCl$_3$) δ 1.29-1.40 (m, 1H), 1.49-1.59 (m, 2H), 1.79-1.89 (m, 3H), 2.00 (bd, J=13.6 Hz, 2H), 2.26 (bd, J=10.4 Hz, 2H), 2.44 (s, 3H), 2.82 (bs, 5H), 3.29 (bs, 2H), 4.24 (tt, J=4.0/12.0 Hz, 1H), 5.84 (bs, 1H), 7.45 (bs, 1H), 7.56 (bd, J=8.4 Hz, 1H), 8.04 (s, 1H), 8.14 (bs, 2H), 8.24 (s, 1H), 10.60 (bs, 1H), 11.55 (bs, 1H). MS m/z ([M+H]$^+$) 446.

Example 120

Synthesis of 1'-Cyclohexyl-6-fluoro-1H,1'H-[4,5']bibenzimidazolyl-7-sulfonamide

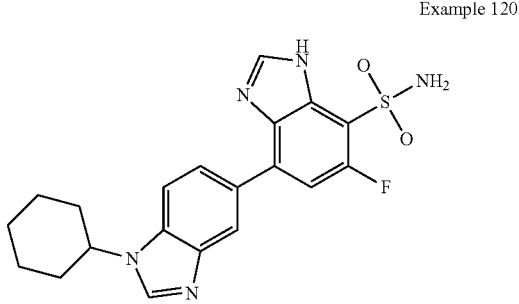 [SMILES: NS(O)(O)c1c(F)cc(-c2ccc3c(c2)ncn3C2CCCCC2)c2nc[nH]c12]

Example 120

Step 1: 7-Bromo-5-fluoro-3H-benzimidazole-4-sulfonyl chloride (120a)

4-Bromo-6-fluoro-1H-benzimidazole (300 mg, 1.39 mmol) was dissolved in thionyl chloride (0.75 mL). Chlorosulfonic acid (1.25 mL) was added and the mixture was stirred at 90° C. for 3 h30. The crude compound (120a) was used without further purification in the next step. MS m/z ([M+H]$^+$) 313/315.

Step 2: 7-Bromo-5-fluoro-3H-benzimidazole-4-sulfonamide (120b)

At 0° C., the solution containing crude compound (120a) (1.39 mmol) was added slowly to a mixture of ammonium hydroxide (28-30%, 6 mL) and acetone (3 mL). The middle was stirred at 0° C. for 10 minutes and at room temperature for 10 minutes. After concentration, water was added and middle was acidified to pH 4-5 by addition of HCl 1N. Obtained solid was filtered and dried under vacuum to give compound (120b) (178 mg, 0.60 mmol, 44% on two steps) as a beige solid. MS m/z ([M+H]$^+$) 294/296.

Step 3: tert-butyl (7-Bromo-5-fluoro-3H-benzimidazole-4-sulfonyl) carbamate (120c)

Compound (120b) (178 mg, 0.60 mmol) was dissolved in DCM (5 mL). Triethylamine (0.25 mL, 1.81 mmol), DMAP (catalytic amount) and di-tert-butyldicarbonate (198 mg, 0.908 mmol) were added. The mixture was stirred at room temperature for 2 hours. Water and DCM were then added. Organic layer was dried over sodium sulfate, filtered and concentrated under reduced pressure. The crude material was purified by preparative TLC on silica gel (DCM/MeOH 9/1) to give compound (120c) (156 mg, 0.39 mmol, 66%). $^1$H NMR (400 MHz, CDCl$_3$) δ 1.10 (s, 9H), 7.24 (d, J=10.4 Hz, 1H), 8.10 (s, 1H), 11.12 (bs, 1H). MS m/z ([M+H]$^+$) 394/396.

Step 4: tert-butyl (1'-Cyclohexyl-6-fluoro-1H,1'H-[4,5']bibenzimidazolyl-7-sulfonyl) carbamate (120d)

According to the procedure described in example 29, step 1, compound (120c) (150 mg, 0.38 mmol) was converted, after purification by preparative TLC on silica gel (DCM/MeOH 9/1+0.5% NH₃ 7M in MeOH), to compound (120d) (39 mg, 0.076 mmol, 20%) as a beige solid. ¹H NMR (400 MHz, DMSO-d₆) δ 1.15 (s, 9H), 1.28-1.39 (m, 1H), 1.47-1.60 (m, 2H), 1.71-1.79 (m, 1H), 1.84-1.96 (m, 4H), 2.06-2.13 (m, 2H), 4.38-4.48 (m, 1H), 7.38-7.50 (m, 1H), 7.78 (d, J=8.6 Hz, 1H), 8.02-8.09 (m, 1H), 8.23 (s, 1H), 8.41 (s, 1H), 8.55 (s, 1H), 12.17 (bs, 1H). MS m/z ([M+H]⁺) 514.

Step 5: 1'-Cyclohexyl-6-fluoro-1H,1'H-[4,5']bibenzimidazolyl-7-sulfonamide, Example (120)

Compound (120d) (39 mg, 0.076 mmol) was dissolved in DCM (2.5 mL). At 0° C., TFA (0.5 mL) was added and the mixture was stirred at room temperature for 2 hours. After concentration, the residue was triturated in MeOH. Obtained solid was filtered and dried under vacuum to give Example (120) (20 mg, 0.048, 69%) as a white solid. ¹H NMR (400 MHz, DMSO-d₆) δ 1.26-1.38 (m, 1H), 1.48-1.64 (m, 2H), 1.72-1.81 (m, 1H), 1.84-1.98 (m, 4H), 2.14-2.24 (m, 2H), 4.59-4.70 (m, 1H), 7.67 (d, J=12.1 Hz, 1H), 7.90 (s, 2H), 8.07-8.14 (m, 1H), 8.21-8.27 (m, 1H), 8.34 (s, 1H), 8.72 (s, 1H), 9.27 (s, 1H), 12.45 (bs, 1H). MS m/z ([M+H]⁺) 414.

Example 121

Synthesis of 1'-Cyclohexyl-6-fluoro-1H,1'H-[4,5'] bibenzimidazolyl-7-thiocarboxamide

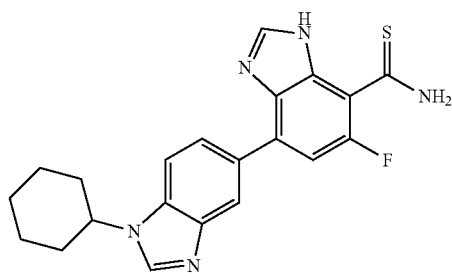

Example 121

A solution of Example (57) (100 mg, 0.278 mmol) and phosphorus pentasulfide (618 mg, 1.39 mmol) in EtOH (3 mL) was refluxed overnight. After concentration, the residue was purified by preparative TLC on silica gel (DCM/MeOH 91/9). The fraction containing desired product was recrystallized in DCM to give Example (121) (10 mg, 0.025 mmol, 10%) as a pale yellow solid. ¹H NMR (400 MHz, DMSO-d⁶) δ 1.26-1.39 (m, 1H), 1.46-1.60 (m, 2H), 1.72-1.79 (m, 1H), 1.84-1.96 (m, 4H), 2.05-2.12 (m, 2H), 4.38-4.48 (m, 1H), 7.41 (d, J=12.5 Hz, 1H), 7.77 (d, J=8.5 Hz, 1H), 8.04 (d, J=8.5 Hz, 1H), 8.24 (s, 1H), 8.39 (s, 1H), 8.52 (s, 1H), 9.78 (bs, 1H), 10.29 (bs, 1H), 12.59 (bs, 1H). MS m/z ([M+H]⁺) 394.

Example 122

Synthesis of 1'-Cyclohexyl-6-[(3-dimethylamino-propyl)-methyl-amino]-1H,1'H-[4,5']bibenzimidazolyl-7-carboxamide

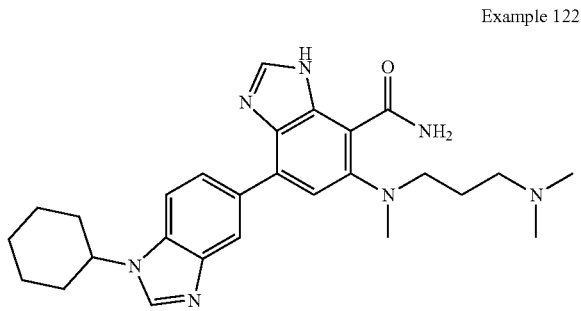 [SMILES: CN(C)CCCN(C)c1cc(-c2ccc3c(c2)ncn3C2CCCCC2)c2nc[nH]c2c1C(N)=O]

Example 122

Step 1: Methyl 2-Amino-4-(1-cyclohexyl-1H-benzimidazol-5-yl)-6-[(3-dimethylamino-propyl)-methylamino]-3-nitro-benzoate (122a)

According to the procedure described in example 29, step 3, compound (106a) (200 mg, 0.48 mmol) was converted, by reaction with N,N'-Dimethyl-propane-1,3-diamine (75 μL, 0.51 mmol), to compound (122a) as an orange solid (244 mg, 0.48 mmol, 99%). MS m/z ([M+H]⁺) 509.

Step 2: Methyl 1'-Cyclohexyl-6-[(3-dimethylamino-propyl)-methyl-amino]-1H,1'H-[4,5']bibenzimidazolyl-7-carboxylate (122b)

According to the procedure described in example 17, step 4, compound (122a) (244 mg, 0.48 mmol) was converted, after purification by preparative TLC on silica gel (DCM/MeOH 9/1 with 1% of ammonia), to compound (122b) as a yellow solid (96 mg, 0.20 mmol, 41%). ¹H NMR (400 MHz, DMSO-d₆) δ 1.25-1.38 (m, 1H), 1.48-1.55 (m, 2H), 1.63-1.77 (m, 3H), 1.84-1.94 (m, 4H), 2.03-2.14 (m, 8H), 2.24 (t, J=7.2 Hz, 2H), 2.86 (s, 3H), 3.20 (t, J=7.2 Hz, 2H), 3.92 (s, 3H), 4.36-4.46 (m, 1H), 7.22 (s, 1H), 7.75 (d, J=8.4 Hz, 1H), 8.00 (dd, J=1.6/8.8 Hz, 1H), 8.12 (s, 1H), 8.39 (s, 1H), 8.41 (d, J=1.6 Hz, 1H), 12.17 (s, 1H). MS m/z ([M+H]⁺) 489.

Step 3: 1'-Cyclohexyl-6-[(3-dimethylamino-propyl)-methyl-amino]-1H,1'H-[4,5']bibenzimidazolyl-7-carboxamide, Example (122)

According to the procedure described in example 72, compound (122b) (93 mg, 0.19 mmol) was converted, after purification by preparative TLC on silica gel (DCM/MeOH 9/1+2% ammonia), to Example (122) (35 mg, 0.07 mmol, 39%). ¹H NMR (400 MHz, DMSO-d₆) δ 1.26-1.36 (m, 1H), 1.48-1.63 (m, 4H), 1.74 (bd, J=12.0 Hz, 1H), 1.84-1.94 (m, 4H), 2.07-2.10 (m, 8H), 2.22 (t, J=6.8 Hz, 2H), 2.76 (s, 3H), 3.11 (t, J=7.2 Hz, 2H), 4.42 (tt, J=4.0/11.6 Hz, 1H), 7.50 (s, 1H), 7.72 (bd, J=4.4 Hz, 1H), 7.75 (d, J=8.4 Hz, 1H), 8.05 (dd, J=1.6/8.8 Hz, 1H), 8.16 (d, J=0.8 Hz, 1H), 8.39 (s, 1H), 8.45 (d, J=1.6 Hz, 1H), 9.98 (d, J=4.4 Hz, 1H), 12.44 (s, 1H). MS m/z ([M+H]⁺) 474.

Example 123

Synthesis of 6-[(2-dimethylamino-ethyl)-methyl-amino]-1'-(tetrahydro-pyran-3-yl)-1H,1'H-[4,5'] bibenzimidazolyl-7-carboxamide

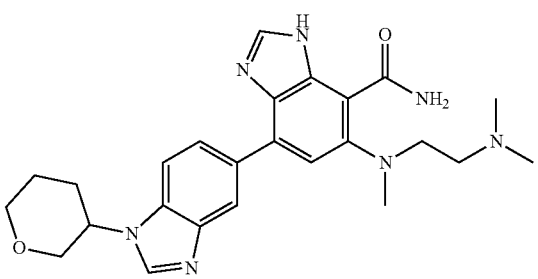

Example 123

Step 1: (4-bromo-2-nitro-phenyl)-(tetrahydro-pyran-3-yl)-amine (123a)

According to the procedure described in example 52, step 5, 4-bromo-1-fluoro-2-nitro-benzene (1.5 g, 6.82 mmol) was converted, by reaction with tetrahydro-2H-pyran-3-amine (0.828 g, 8.18 mmol), to compound (123a) as an orange solid (2.1 g, 6.82 mmol, 100%) without further purification. MS m/z ([M+H]$^+$) 301/303.

Step 2: 4-bromo-N*1*-(tetrahydro-pyran-3-yl)-benzene-1,2-diamine (123b)

A solution of compound (123a) (2.1 g, 6.82 mmol) in a mixture of ethanol/water 2:1 (52 mL) with ammonium chloride (3.65 g, 68.20 mmol) was brought to 60° C. upon which complete dissolution of reagents was achieved and iron (1.14 g, 20.46 mmol) was added. The mixture was heated at 90° C. for 2 hours. After cooling, the solution was filtered through celite, washed with methanol and the filtrate was concentrated under reduced pressure. The residue was diluted with DCM and washed with water. The combined organic phases were dried over sodium sulfate, filtered and evaporated under reduced pressure to afford compound (123b) as brownish oil (1.86 g, 6.82 mmol, 100%) which was used in the next step without further purification. MS m/z ([M+H]$^+$) 271/273.

Step 3: 5-bromo-1-(tetrahydro-pyran-3-yl)-1H-benzimidazole (123c)

To a mixture of compound (123b) (1.86 g, 6.82 mmol) in toluene (45 mL) under nitrogen atmosphere were added trimethyl orthoformate (1.12 mL, 1.023 mmol) and p-toluenesulfonic acid monohydrate (26 mg, 0.136 mmol). The resulting solution was refluxed for 2 hours. The mixture was cooled and concentrated under reduced pressure. The residue was diluted with ethyl acetate and washed with a saturated aqueous solution of sodium hydrogencarbonate. The combined organic phases were dried over sodium sulfate, filtered and concentrated. The crude residue was purified by column chromatography on silica gel (DCM/MeOH 98/2 to 95/5) to afford compound (123c) (1.92 g, 6.82 mmol, 100%) as a brown oil. $^1$H NMR (400 MHz, CDCl$_3$) δ 1.71-1.89 (m, 2H), 2.09-2.18 (m, 1H), 2.23-2.30 (m, 1H), 3.70-3.76 (m, 1H), 3.83-3.93 (m, 2H), 4.11-4.15 (m, 1H), 4.37-4.42 (m, 1H), 7.28 (d, J=8.5 Hz, 1H), 7.41 (dd, J=1.8/8.5 Hz, 1H), 7.96 (d, J=1.8 Hz, 1H), 8.19 (s, 1H). MS m/z ([M+H]$^+$) 281/283.

Step 4: 1-(tetrahydro-pyran-3-yl)-5-(4,4,5,5-tetramethyl-[1,3,2]dioxaborolan-2-yl)-1H-benzimidazole (123d)

A solution of compound (123c) (1.92 g, 6.82 mmol), bis(pinacolato)diboron (2.6 g, 10.24 mmol) and potassium acetate (2.01 g, 20.49 mmol) in dry 1,4-dioxane (45 mL) was degassed under argon for 10 minutes. The Catalyst Pd(dppf)Cl$_2$.CH$_2$Cl$_2$ (279 mg, 0.34 mmol) was added and the reaction mixture was stirred at 85° C. overnight. The reaction mixture was filtered through celite and concentrated under reduced pressure. The residue was diluted with ethyl acetate and washed with a saturated aqueous solution of sodium hydrogencarbonate. The combined organic phases were dried over sodium sulfate, filtered and concentrated. The crude product was triturated in cyclohexane and filtered to afford compound (123d) as a brown solid (1.76 g, 78%) which was engaged in the following step without additional purification. $^1$H NMR (400 MHz, CDCl$_3$) δ 1.37 (s, 12H), 1.73-1.89 (m, 2H), 2.11-2.20 (m, 1H), 2.22-2.30 (m, 1H), 3.68-3.74 (m, 1H), 3.80-3.85 (m, 1H), 3.89-3.94 (m, 1H), 4.12-4.16 (m, 1H), 4.41-4.47 (m, 1H), 7.41 (d, J=8.2 Hz, 1H), 7.75 (dd, J=0.9/8.2 Hz, 1H), 8.19 (s, 1H), 8.29 (bt, 1H). MS m/z ([M+H]$^+$) 329.

Step 5: Methyl 2-amino-6-fluoro-3-nitro-4-[1-(tetrahydro-pyran-3-yl)-1H-benzimidazol-5-yl]-benzoate (123e)

According to the procedure described in example 115, step 2, compound (51b) (350 mg, 1.19 mmol) was converted, by reaction with compound (123d) (412 mg, 1.25 mmol) and after purification by flash column chromatography on silica gel (DCM/MeOH 98/2), to compound (123e) as a beige solid (381 mg, 0.92 mmol, 77%). $^1$H NMR (400 MHz, CDCl$_3$) δ 1.80-1.84 (m, 2H), 2.16-2.20 (m, 1H), 2.26-2.30 (m, 1H), 3.73-3.77 (m, 1H), 3.88-3.92 (m, 2H), 3.97 (s, 3H), 4.14-4.18 (m, 1H), 4.42-4.46 (m, 1H), 6.46 (d, J=11.5 Hz, 1H), 7.21 (bs, 2H), 7.22 (dd, J=1.6/8.4 Hz, 1H), 7.43 (d, J=8.4 Hz, 1H), 7.79 (d, J=1.6 Hz, 1H), 8.27 (s, 1H). MS m/z ([M+H]$^+$) 415.

Step 6: Methyl 2-Amino-6-[(2-dimethylamino-ethyl)-methyl-amino]-3-nitro-4-[1-(tetrahydro-pyran-3-yl)-1H-benzimidazol-5-yl]-benzoate (123f)

According to the procedure described in example 29, step 3, compound (123e) (375 mg, 0.90 mmol) was converted, by reaction with N,N,N'-trimethylethylenediamine (127 μL, 0.99 mmol) and after purification by flash column chromatography on silica gel (DCM/MeOH 95/5), to compound (123f) as an orange solid (318 mg, 0.64 mmol, 71%). $^1$H NMR (400 MHz, CDCl$_3$) δ 1.80 (m, 2H), 2.21 (m, 2H), 2.23 (s, 6H), 2.54 (t, J=7.2 Hz, 2H), 2.99 (s, 3H), 3.42 (t, J=7.2 Hz, 2H), 3.71-3.75 (m, 1H), 3.87-3.91 (m, 2H), 3.90 (s, 3H), 4.14-4.18 (m, 1H), 4.42-4.46 (m, 1H), 6.24 (s, 1H), 7.18 (dd, J=1.6/8.4 Hz, 1H), 7.32 (bs, 2H), 7.38 (dd, J=0.5/8.4 Hz, 1H), 7.80 (dd, J=0.5/1.6 Hz, 1H), 8.22 (s, 1H). MS m/z ([M+H]$^+$) 497.

Step 7: Methyl 6-[(2-Dimethylamino-ethyl)-methyl-amino]-1'-(tetrahydro-pyran-3-yl)-1H,1'H-[4,5'] bibenzimidazolyl-7-carboxylate (123g)

According to the procedure described in example 17, step 4, compound (123f) (318 mg, 0.64 mmol) was converted, after purification by flash column chromatography on silica gel (DCM/MeOH 94/6 to 92/8), to compound (123g) as an orange solid (229 mg, 4.80 mmol, 76%). $^1$H NMR (400 MHz, CDCl$_3$) δ 1.80-1.84 (m, 2H), 2.21-2.25 (m, 2H), 2.25 (s, 6H), 2.59 (t, J=7.2 Hz, 2H), 3.01 (s, 3H), 3.38 (t, J=7.2 Hz, 2H), 3.72-3.76 (m, 1H), 3.89-3.93 (m, 2H), 4.00 (s, 3H), 4.16-4.20 (m, 1H), 4.46-4.50 (m, 1H), 7.25 (d, J=8.4 Hz, 1H), 7.54 (d, J=8.4 Hz, 1H), 8.00 (s, 1H), 8.14 (bd, J=8.8 Hz, 1H), 8.24 (s, 1H), 8.27 (s, 1H). MS m/z ([M+H]$^+$) 477.

Step 8: 6-[(2-dimethylamino-ethyl)-methyl-amino]-1'-(tetrahydro-pyran-3-yl)-1H,1'H-[4,5']bibenzimidazolyl-7-carboxamide, Example (123)

According to the procedure described in example 72, compound (123g) (102 mg, 0.214 mmol) was converted, after purification by flash preparative TLC on silica gel (DCM/MeOH 9/1 with 2% ammonia), to Example (123) as a beige solid (47.8 mg, 0.103 mmol, 48%). $^1$H NMR (400 MHz, CDCl$_3$) δ 1.80-1.84 (m, 2H), 2.22-2.26 (m, 2H), 2.25 (s, 6H), 2.50 (t, J=6.3 Hz, 2H), 2.80 (s, 3H), 3.24 (t, J=6.3 Hz, 2H), 3.72-3.76 (m, 1H), 4.88-4.92 (m, 2H), 4.15-4.19 (m, 1H), 4.47-4.51 (m, 1H), 5.80 (bs, 1H), 7.44 (s, 1H), 7.55 (d, J=8.5 Hz, 1H), 8.14 (s, 1H), 8.19 (dd, J=1.4/8.5 Hz, 1H), 8.25 (m, 2H). MS m/z ([M+H]$^+$) 462.

Example 124

Synthesis of 1'-((1R,2R)-2-fluoro-cyclohexyl)-6-[methyl-(2-methylamino-ethyl)-amino]-1H,1'H-[4,5']bibenzimidazolyl-7-carboxamide Example 124

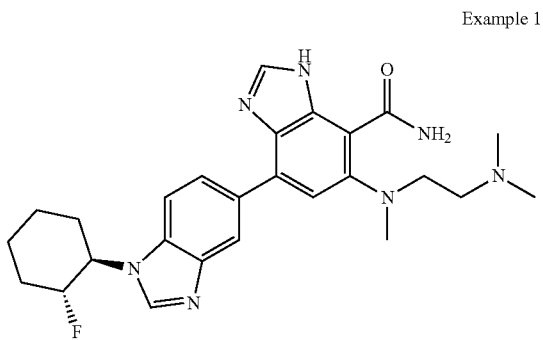

Step 1: (4-bromo-2-nitro-phenyl)-((1R,2R)-2-fluoro-cyclohexyl)-amine (124a)

According to the procedure described in example 52, step 5, 4-bromo-1-fluoro-2-nitro-benzene (1.5 g, 6.82 mmol) was converted, by reaction with (1R,2R)-2-fluoro-cyclohexylamine (0.639 g, 5.45 mmol), to compound (124a) as orange oil (1.61 g, 4.55 mmol, 100%) without further purification. MS m/z ([M+H]$^+$) 317/319.

Step 2: 4-bromo-((1R,2R)-2-fluoro-cyclohexyl)-benzene-1,2-diamine (124b)

According to the procedure described in example 123, step 2, compound (124a) (1.61 g, 4.55 mmol) was converted to compound (124b) as a brownish oil (1.27 g, 4.42 mmol, 97%) which was used in the next step without further purification. MS m/z ([M+H]$^+$) 287/289.

Step 3: 5-bromo-1-((1R,2R)-2-fluoro-cyclohexyl)-1H-benzimidazole (124c)

According to the procedure described in example 123, step 3, compound (124b) (1.27 g, 4.42 mmol) was converted, after purification by column chromatography on silica gel (DCM/MeOH 98/2 to 95/5), to compound (124c) as a brown oil (1.14 g, 3.84 mmol, 84%). $^1$H NMR (400 MHz, CDCl$_3$) δ 1.43-1.51 (m, 2H), 1.62-1.75 (m, 1H), 1.91-2.03 (m, 3H), 2.21-2.30 (m, 1H), 2.32-2.41 (m, 1H), 4.20-4.29 (m, 1H), 4.62-4.81 (m, 1H), 7.31 (d, J=8.6 Hz, 1H), 7.39 (dd, J=1.8/8.6 Hz, 1H), 7.95 (d, J=1.5 Hz, 1H), 7.98 (s, 1H). MS m/z ([M+H]$^+$) 297/299.

Step 4: 1-((1R,2R)-2-fluoro-cyclohexyl)-5-(4,4,5,5-tetramethyl-[1,3,2]dioxaborolan-2-yl)-1H-benzimidazole (124d)

According to the procedure described in example 123, step 4, compound (124c) (1.14 g, 3.83 mmol) was converted, after trituration in cyclohexane, to compound (124d) as a brown solid (1.09 g, 3.18 mmol, 83%) which was engaged in the following step without additional purification. $^1$H NMR (400 MHz, CDCl$_3$) δ 1.37 (s, 12H), 1.44-1.53 (m, 2H), 1.63-1.76 (m, 1H), 1.92-2.01 (m, 3H), 2.21-2.29 (m, 1H), 2.32-2.40 (m, 1H), 4.25-4.33 (m, 1H), 4.68-4.87 (m, 1H), 7.44 (d, J=8.2 Hz, 1H), 7.74 (dd, J=0.9/8.2 Hz, 1H), 8.00 (s, 1H), 8.29 (s, 1H). MS m/z ([M+H]$^+$) 345.

Step 5: Methyl 2-amino-4-bromo-6-[(2-dimethyl-amino-ethyl)-methyl-amino]-3-nitro-benzoate (124e)

Compound (51b) (2.24 g, 7.64 mmol) was dissolved in anhydrous acetonitrile (6.8 mL) under nitrogen atmosphere. The reaction mixture was cooled to −45° C. DIPEA (2.0 mL, 11.47 mmol) and N,N,N'-trimethylethylenediamine (989 µL, 7.64 mmol) were slowly added and the mixture was stirred at −45° C. for 1 hour. N,N,N'-trimethylethylenediamine (198 µL, 1.53 mmol) was still added and the mixture was stirred for an additional 1 hour. Water was added and the organic phase was extracted twice with ethyl acetate. The combined organic layers were dried over sodium sulfate, filtered and evaporated under reduced pressure to afford compound (124e) as an orange oil (2.87 g, 7.64 mmol, 100%) without further purification. $^1$H NMR (400 MHz, CDCl$_3$) δ 2.24 (s, 6H), 2.50 (t, J=6.9 Hz, 2H), 2.94 (s, 3H), 3.37 (t, J=6.9 Hz, 2H), 3.87 (s, 3H), 6.57 (s, 1H), 7.12 (bs, 2H). MS m/z ([M+H]$^+$) 375/377.

Step 6: Methyl 7-bromo-5-[(2-dimethylamino-ethyl)-methyl-amino]-3H-benzimidazole-4-carboxylate (124f)

According to the procedure described in example 17, step 4, compound (124e) (2.87 g, 7.64 mmol) was converted, after purification by flash column chromatography on silica gel (DCM/MeOH 9/1+1% of ammonia), to compound (124f) (2.10 g, 5.91 mmol, 77%) as a yellow oil. $^1$H NMR (400 MHz, CDCl$_3$) δ 2.23 (s, 6H), 2.53 (t, J=7.2 Hz, 2H), 2.94 (s, 3H), 3.31 (t, J=7.2 Hz, 2H), 3.98 (s, 3H), 7.25 (s, 1H), 7.99 (s, 1H). MS m/z ([M+H]$^+$) 355/357.

Step 7: 7-bromo-5-[(2-dimethylamino-ethyl)-methyl-amino]-3H-benzimidazole-4-carboxamide (124g)

According to the procedure described in example 115, step 1, compound (124f) (2.07 g, 5.83 mmol) was converted, without further purification, to compound (124g) (1.98 g, 5.83 mmol, 100%) as a beige solid which was used in the next step without further purification. $^1$H NMR (400 MHz, CDCl$_3$) δ 2.21 (s, 6H), 2.44 (t, J=6.1 Hz, 2H), 2.73 (s, 3H), 3.14 (t, J=6.1 Hz, 2H), 5.73 (bs, 1H), 7.42 (s, 1H), 8.14 (s, 1H). MS m/z ([M+H]$^+$) 340/342.

Step 8: 1'-((1R,2R)-2-fluoro-cyclohexyl)-6-[methyl-(2-methylamino-ethyl)-amino]-1H,1'H-[4,5']bibenzimidazolyl-7-carboxamide, Example (124)

According to the procedure described in example 115, step 2, compound (124g) (102 mg, 0.214 mmol) was converted, by reaction with compound (124d) (101 mg, 0.29 mmol) and after purification by preparative TLC on silica gel (DCM/MeOH 9/1 with 1% of ammonia), to Example (124) (66.7 mg, 0.14 mmol, 48%) as a clear brown solid. $^1$H NMR (400 MHz, CDCl$_3$) δ 1.49-2.38 (m, 8H), 2.22 (s, 6H), 2.47 (t, J=6.2 Hz, 2H), 2.78 (s, 3H), 3.21 (t, J=6.2 Hz, 2H), 4.32 (m, 1H), 4.77, 4.89 (m, 1H), 5.78 (bs, 1H), 7.44 (s, 1H), 7.59 (d, J=8.5 Hz, 1H), 8.04 (s, 1H), 8.14 (s, 1H), 8.17 (dd, J=1.3/8.5 Hz, 1H), 8.26 (bd, J=1.3 Hz, 1H). MS m/z ([M+H]$^+$) 478.

Example 125

Synthesis of 6-[(2-Dimethylamino-ethyl)-methyl-amino]-3'-ethyl-1H,3'H-[4,5']bibenzimidazolyl-7-carboxamide

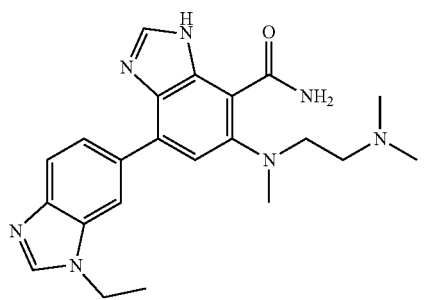

Example 125

Step 1: 5-bromo-N-ethyl-2-nitroaniline (125a)

According to the procedure described in example 29, step 3, 4-bromo-2-fluoro-1-nitrobenzene (220 mg, 1 mmol) was converted, by reaction with Ethylamine hydrochloride (82 mg, 1 mmol) and after purification by preparative TLC on silica gel (DCM), to compound (125a) (244 mg, 1 mmol, 100%). $^1$H NMR (400 MHz, DMSO-d$_6$) δ 1.22 (t, J=7.1 Hz, 3H), 3.36-3.40 (m, 2H), 6.82 (dd, J=9.1/2.0 Hz, 1H), 7.22 (d, J=2.0 Hz, 1H), 7.97 (d, J=9.1 Hz, 1H), 8.12 (bs, 1H). MS m/z ([M+H]$^+$) 245/247.

Step 2: 5-bromo-1-N-ethylbenzene-1,2-diamine (125b)

According to the procedure described in example 123, step 2, compound (125a) (244 mg, 1 mmol) was converted, without further purification, to crude compound (125b). MS m/z ([M+H]$^+$) 215/217.

Step 3: 6-Bromo-1-ethyl-1H-benzimidazole (125c)

To a mixture of crude compound (125b) in toluene (4 mL) under nitrogen atmosphere were added trimethyl orthoformate (0.12 mL, 1.1 mmol) and p-toluenesulfonic acid monohydrate (1 mg, 0.005 mmol). The resulting solution was refluxed for 1 hour. The mixture was cooled and concentrated under reduced pressure. The residue was diluted with water and ethyl acetate. The organic layer was washed with saturated solution of sodium bicarbonate, brine, dried over sodium sulfate, filtered and concentrated under reduced pressure. The crude product was triturated in ethyl acetate and filtered to afford compound (125c) (175 mg, 0.78 mmol, 78% over 2 steps). $^1$H NMR (400 MHz, DMSO-d$_6$) δ 1.40 (t, J=7.3 Hz, 3H), 4.29 (q, J=7.3 Hz, 2H), 7.34 (dd, J=8.6/1.9 Hz, 1H), 7.61 (d, J=8.6 Hz, 1H), 7.92 (d, J=1.9 Hz, 1H), 8.29 (s, 1H). MS m/z ([M+H]$^+$) 225/227.

Step 4: 1-Ethyl-6-(4,4,5,5-tetramethyl-1,3,2-dioxaborolan-2-yl)-1H-benzimidazole (125d)

According to the procedure described in example 123, step 4, compound (125c) (175 mg, 0.78 mmol) was converted, after purification by preparative TLC on silica gel (DCM/MeOH 95/5), to compound (125d) (57 mg, 0.21 mmol, 27%). $^1$H NMR (400 MHz, DMSO-d$_6$) δ 1.33 (s, 12H), 1.42 (t, J=7.3 Hz, 3H), 4.34 (q, J=7.3 Hz, 2H), 7.54 (dd, J=8.1/1.0 Hz, 1H), 7.64 (d, J=8.1 Hz, 1H), 7.88 (s, 1H), 8.31 (s, 1H). MS m/z ([M+H]$^+$) 273.

Step 5: 6-[(2-Dimethylamino-ethyl)-methyl-amino]-3'-ethyl-1H,3'H-[4,5']bibenzimidazolyl-7-carboxamide, Example (125)

According to the procedure described in example 115, step 2, compound (124g) (72 mg, 0.21 mmol) was converted, by reaction with compound (125d) (57 mg, 0.21 mmol) and after purification by preparative TLC on silica gel (DCM/MeOH 9/1+1% of ammonia), to Example (125) (27 mg, 0.067 mmol, 32%). $^1$H NMR (400 MHz, DMSO-d$_6$) δ 1.48 (t, J=7.3 Hz, 3H), 2.15 (s, 6H), 2.40 (t, J=6.3 Hz, 2H), 2.75 (s, 3H), 3.21 (t, J=6.3 Hz, 2H), 4.34 (q, J=7.3 Hz, 2H), 7.53 (s, 1H), 7.58 (d, J=3.3 Hz, 1H), 7.75 (d, J=8.5 Hz, 1H), 7.99 (dd, J=8.5/1.6 Hz, 1H), 8.17 (s, 1H), 8.31 (s, 1H), 8.39 (d, J=1.1 Hz, 1H), 10.03 (d, J=2.2 Hz, 1H), 12.41 (s, 1H). MS m/z ([M−H]$^+$) 406.

Example 126

Synthesis of 1'-Cyclohexyl-6-(2-dimethylaminomethyl-pyrrolidin-1-yl)-1H,1'H-[4,5']bibenzimidazolyl-7-carboxamide

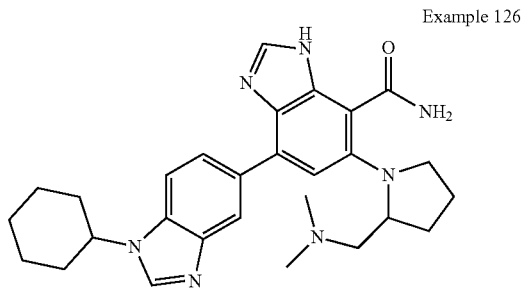 [SMILES: CN(C)CC1CCCN1c1cc(-c2ccc3c(c2)ncn3C2CCCCC2)c2nc[nH]c2c1C(N)=O]

Example 126

Step 1: Methyl 2-Amino-4-(1-cyclohexyl-1H-benzimidazol-5-yl)-6-(2-dimethylaminomethyl-pyrrolidin-1-yl)-3-nitro-benzoate (126a)

According to the procedure described in example 29, step 3, compound (106a) (200 mg, 0.48 mmol) was converted, by reaction with Dimethyl-pyrrolidin-2-ylmethyl-amine (145 mg, 1.13 mmol), to compound (126a) (252 mg, 0.48 mmol, 100%). MS m/z ([M+H]$^+$) 521.

Step 2: Methyl 1'-Cyclohexyl-6-(2-dimethylaminomethyl-pyrrolidin-1-yl)-1H,1'H-[4,5']bibenzimidazolyl-7-carboxylate (126b)

According to the procedure described in example 17, step 4, compound (126a) (252 mg, 0.48 mmol) was converted, after purification by preparative TLC on silica gel (DCM/MeOH 9/1 with 1% of ammonia), to compound (126b) (243 mg, 0.48 mmol, 100%). $^1$H NMR (400 MHz, DMSO-d$_6$) δ 1.09-1.35 (m, 1H), 1.50-1.56 (m, 2H), 1.66-1.79 (m, 3H), 1.82-1.93 (m, 4H), 2.08 (bd, J=9.2 Hz, 2H), 2.23 (m, 6H), 2.76 (q, J=7.2 Hz, 1H), 2.84 (t, J=7.6 Hz, 1H), 3.26-3.30 (m, 1H), 3.57-3.64 (m, 1H), 3.90 (s, 3H), 4.12-4.14 (m, 1H), 4.41 (tt, J=3.2/12.0 Hz, 1H), 7.14 (s, 1H), 7.75 (d, J=8.4 Hz, 1H), 7.95 (bd, J=8.0 Hz, 1H), 8.02 (s, 1H), 8.25 (s, 2H), 8.37 (s, 1H), 8.41 (bs, 1H), 11.96 (bs, 1H). MS m/z ([M+H]$^+$) 501.

Step 3: 1'-Cyclohexyl-6-(2-dimethylaminomethyl-pyrrolidin-1-yl)-1H,1'H-[4,5']bibenzimidazolyl-7-carboxamide, Example (126)

According to the procedure described in example 72, compound (126b) (243 mg, 0.48 mmol) was converted, after purification by preparative TLC on silica gel (DCM/MeOH 9/1+1% ammonia), to Example (126) (46 mg, 0.09 mmol, 19%). $^1$H NMR (400 MHz, DMSO-d$_6$) δ 1.27-1.37 (m, 1H), 1.53 (q, J=12.8 Hz, 2H), 1.70-1.77 (m, 2H), 1.87-1.94 (m, 6H), 2.08 (bs, 8H), 2.22-2.30 (m, 3H), 2.93 (q, J=8.0 Hz, 1H), 3.40-3.45 (m, 1H), 3.87 (quin, J=6.4 Hz, 1H), 4.42 (tt, J=11.6/4.0 Hz, 1H), 7.54 (s, 1H), 7.60 (bs, J=3.6 Hz, 1H), 7.76 (d, J=8.8 Hz, 1H), 8.05 (dd, J=8.4/1.6 Hz, 1H), 8.14 (s, 1H), 8.39 (s, 1H), 8.46 (d, J=1.2 Hz, 1H), 9.50 (d, J=4.0 Hz, 1H), 12.96 (bs, 1H). MS m/z ([M+H]$^+$) 486.

Example 127

Synthesis of 1'-Cyclohexyl-6-[methyl-(2-pyrrolidin-1-yl-ethyl)-amino]-1H,1'H-[4,5']bibenzimidazolyl-7-carboxamide

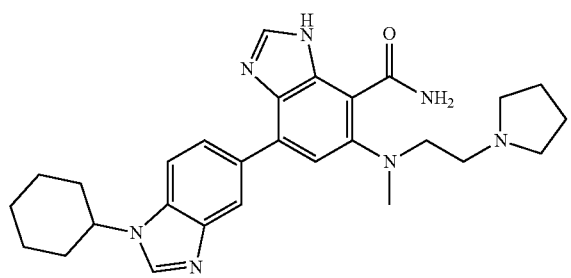

Example 127

Step 1: Methyl 2-Amino-4-(1-cyclohexyl-1H-benzimidazol-5-yl)-6-[methyl-(2-pyrrolidin-1-yl-ethyl)-amino]-3-nitro-benzoate (127a)

According to the procedure described in example 29, step 3, compound (106a) (100 mg, 0.24 mmol) was converted, by reaction with Methyl-(2-pyrrolidin-1-yl-ethyl)-amine (37 mg, 0.29 mmol), to compound (127a) (125 mg, 0.24 mmol, quantitative). MS m/z ([M+H]$^+$) 521.

Step 2: Methyl 1'-Cyclohexyl-6-[methyl-(2-pyrrolidin-1-yl-ethyl)-amino]-1H,1'H[4,5']bibenzimidazolyl-7-carboxylate (127b)

According to the procedure described in example 17, step 4, compound (127a) (125 mg, 0.24 mmol) was converted, after purification by preparative TLC on silica gel (DCM/MeOH 9/1 with 2% of ammonia), to compound (127b) (85 mg, 0.17 mmol, 70%). MS m/z ([M+H]$^+$) 501.

Step 3: 1'-Cyclohexyl-6-[methyl-(2-pyrrolidin-1-yl-ethyl)-amino]-1H,1'H-[4,5']bibenzimidazolyl-7-carboxamide, Example (127)

According to the procedure described in example 115, step 1, compound (127b) (120 mg, 0.24 mmol) was converted, after purification by preparative TLC on silica gel (DCM/MeOH 9/1+2% ammonia), to Example (127) (20 mg, 0.04 mmol, 17%). $^1$H NMR (400 MHz, DMSO-d$_6$) δ 1.26-1.36 (m, 1H), 1.48-1.58 (m, 2H), 1.63-1.69 (m, 4H), 1.74 (bd, J=13.6 Hz, 1H), 1.84-1.93 (m, 4H), 2.08 (bd, J=9.2 Hz, 2H), 2.40-2.42 (m, 4H), 2.59 (t, J=6.4 Hz, 2H), 2.73 (s, 3H), 3.24 (t, J=6.4 Hz, 2H), 4.42 (tt, J=3.6/11.6 Hz, 1H), 7.49 (s, 1H), 7.57 (bd, J=3.2 Hz, 1H), 7.75 (d, J=8.8 Hz, 1H), 8.05 (dd, J=1.6/8.8 Hz, 1H), 8.14 (bs, 1H), 8.38 (s, 1H), 8.46 (d, J=1.2 Hz, 1H), 10.04 (d, J=3.6 Hz, 1H), 12.37 (s, 1H). MS m/z ([M+H]$^+$) 486.

Example 128

Synthesis of 1'-Cyclohexyl-6-[methyl-(1-methyl-pyrrolidin-2-ylmethyl)-amino]-1H,1'H-[4,5']bibenzimidazolyl-7-carboxamide

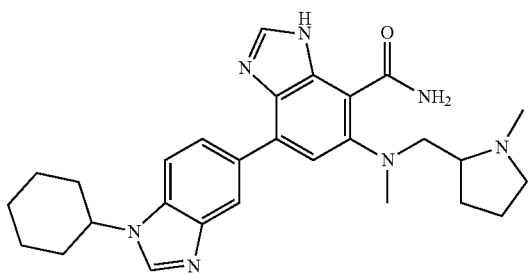

Example 128

Step 1: Methyl 2-Amino-4-(1-cyclohexyl-1H-benzimidazol-5-yl)-6-[methyl-(1-methyl-pyrrolidin-2-ylmethyl)-amino]-3-nitro-benzoate (128a)

According to the procedure described in example 29, step 3, compound (106a) (100 mg, 0.24 mmol) was converted, by reaction with Methyl-(1-methyl-pyrrolidin-2-ylmethyl)- amine (37 mg, 0.29 mmol), to compound (128a) (126 mg, 0.24 mmol, 100%). MS m/z ([M+H]$^+$) 521.

Step 2: Methyl 1'-Cyclohexyl-6-[methyl-(1-methyl-pyrrolidin-2-ylmethyl)-amino]-1H,1'H-[4,5']bibenzimidazolyl-7-carboxylate (128b)

According to the procedure described in example 17, step 4, compound (128a) (126 mg, 0.24 mmol) was converted, after purification by preparative TLC on silica gel (DCM/MeOH 9/1 with 2% of ammonia), to compound (128b) (107 mg, 0.24 mmol, 88%). MS m/z ([M+H]$^+$) 501.

Step 3: 1'-Cyclohexyl-6-[methyl-(1-methyl-pyrrolidin-2-ylmethyl)-amino]-1H,1'H-[4,5']bibenzimidazolyl-7-carboxamide, Example (128)

According to the procedure described in example 115, step 1, compound (128b) (121 mg, 0.24 mmol) was converted, after purification by preparative TLC on silica gel (DCM/MeOH 9/1+2% ammonia), to Example (128) (8 mg, 0.02 mmol, 7%). $^1$H NMR (400 MHz, DMSO-d$_6$) δ 1.30-1.37 (m, 1H), 1.47-1.62 (m, 5H), 1.73-1.76 (bd, J=10.8 Hz, 1H), 1.87-1.91 (m, 5H), 2.03-2.10 (m, 3H), 2.19-2.24 (m, 1H), 2.27 (s, 3H), 2.77 (s, 3H), 2.84-2.92 (m, 2H), 3.45 (dd, J=3.2/12.0 Hz, 1H), 4.42 (tt, J=4.0/12.0 Hz, 1H), 7.57 (s, 1H), 7.72 (bd, J=4.0 Hz, 1H), 7.76 (d, J=8.4 Hz, 1H), 8.05 (dd, J=1.6/8.8 Hz, 1H), 8.16 (s, 1H), 8.38 (s, 1H), 8.47 (d, J=1.2 Hz, 1H), 9.98 (bd, J=4.0 Hz, 1H), 12.44 (bs, 1H). MS m/z ([M+H]$^+$) 486.

Example 129

Synthesis of 1'-Cyclohexyl-6-(3-dimethylaminomethyl-pyrrolidin-1-yl)-1H,1'H-[4,5']bibenzimidazolyl-7-carboxamide

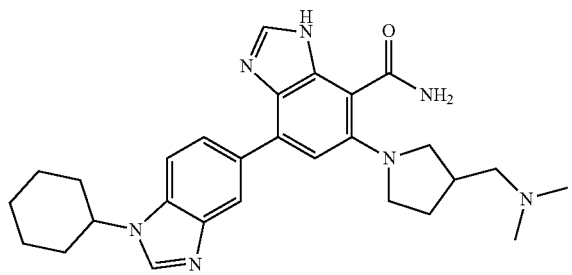

Example 129

Step 1: Methyl 2-Amino-4-(1-cyclohexyl-1H-benzimidazol-5-yl)-6-(3-dimethylaminomethyl-pyrrolidin-1-yl)-3-nitro-benzoate (129a)

According to the procedure described in example 29, step 3, compound (106a) (100 mg, 0.24 mmol) was converted, by reaction with Dimethyl-pyrrolidin-3-ylmethyl-amine (37 mg, 0.29 mmol), to compound (129a) (126 mg, 0.24 mmol, 100%). MS m/z ([M+H]$^+$) 521.

Step 2: Methyl 1'-Cyclohexyl-6-(3-dimethylaminomethyl-pyrrolidin-1-yl)-1H,1'H-[4,5']bibenzimidazolyl-7-carboxylate (129b)

According to the procedure described in example 17, step 4, compound (129a) (126 mg, 0.24 mmol) was converted, after purification by preparative TLC on silica gel (DCM/MeOH 9/1 with 2% of ammonia), to compound (129b) (74 mg, 0.15 mmol, 61%). MS m/z ([M+H]$^+$) 501.

Step 3: 1'-Cyclohexyl-6-(3-dimethylaminomethyl-pyrrolidin-1-yl)-1H,1'H-[4,5']bibenzimidazolyl-7-carboxamide, Example (129)

According to the procedure described in example 115, step 1, compound (129b) (74 mg, 0.15 mmol) was converted, after purification by preparative TLC on silica gel (DCM/MeOH 9/1+2% ammonia), to Example (129) (4.2 mg, 0.01 mmol, 6%). $^1$H NMR (400 MHz, CDCl$_3$) δ 1.32-1.36 (m, 1H), 1.52-1.56 (m, 2H), 1.69-1.77 (m, 1H), 1.80-1.87 (m, 4H), 1.91-2.02 (m, 6H), 2.17-2.27 (m, 4H), 2.40 (d, J=7.5 Hz, 2H), 2.61 (sept, J=7.7 Hz, 1H), 3.03 (dd, J=6.8/9.6 Hz, 1H), 3.21-3.35 (m, 2H), 3.41 (dd, J=7.6/9.6 Hz, 1H), 4.24 (tt, J=3.6/12.0 Hz, 1H), 5.80 (bs, 1H), 7.42 (s, 1H), 7.56 (d, J=8.4 Hz, 1H), 8.04 (s, 1H), 8.12 (s, 1H), 8.16 (dd, J=1.6/8.4 Hz, 1H), 8.24 (d, J=1.2 Hz, 1H), 10.13 (bs, 1H), 11.44 (bs, 1H). MS m/z ([M+H]$^+$) 486.

Example 130

Synthesis of 1'-Cyclohexyl-6-[(2-diethylaminoethyl)-methyl-amino]-1H,1'H-[4,5']bibenzimidazolyl-7-carboxamide

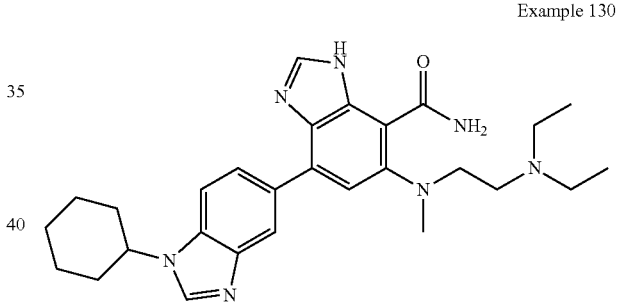

Example 130

Step 1: 4-Bromo-2,6-difluoro-3-nitro-benzoic acid (130a)

According to the procedure described in example 42, step 1, 4-Bromo-2,6-difluoro-benzoic acid (10 g, 42.19 mmol) was converted, without further purification, to compound (130a) as a white solid (10.82 g, 38.37 mmol, 91%). MS m/z ([M+H]$^+$) 282/284.

Step 2: Benzyl 4-Bromo-2,6-difluoro-3-nitro-benzoate (130b)

To a solution of compound (130a) (5 g, 17.73 mmol) in DCM (80 mL) was solubilized N,N'-Dicyclohexylcarbodiimide (4.85 g, 21.28 mmol) and 4-dimethylaminopyridine (217 mg, 1.77 mmol) at 0° C. Benzyl alcohol (2.2 mL, 21.28 mmol) was then added and the mixture was stirred at room temperature for 18 hours. The reaction mixture was filtered and concentrated under reduced pressure. The orange oil was purified by flash chromatography on silica gel (Cyclohexane/DCM 85/15 to 60/40 to afford compound (130b) as a white solid (5.31 g, 14.27 mmol, 80%). $^1$H NMR (400 MHz, CDCl$_3$) δ 5.40 (s, 2H), 7.33-7.43 (m, 6H). MS m/z ([M−H]$^−$) 368/370.

Step 3: Benzyl 2-Amino-4-bromo-6-fluoro-3-nitro-benzoate (130c)

According to the procedure described in example 51, step 2, compound (130b) (5.6 g, 15.05 mmol) was converted, after purification by flash chromatography on silica gel (cyclohexane/DCM 7/3 to 1/1), to compound (130c) as a yellow solid (5.05 g, 13.68 mmol, 91%). $^1$H NMR (400 MHz, CDCl$_3$) δ 5.38 (s, 2H), 6.73 (d, J=10.4 Hz, 1H), 7.09 (bs, 2H), 7.33-7.44 (m, 5H). MS m/z [M−H]$^−$367/369.

Step 4: Benzyl 2-Amino-6-fluoro-4-(1-cyclohexyl-1H-benzimidazol-5-yl)-3-nitro-benzoate (130d)

According to the procedure described in example 115, step 2, compound (130c) (5.05 g, 13.57 mmol) was converted, by reaction with 1-Cyclohexyl-5-(4,4,5,5-tetramethyl-[1,3,2]dioxaborolan-2-yl)-1H-benzimidazole (4.65 g, 14.25 mmol) and after purification by flash chromatography on silica gel (DCM/EtOAc 9/1), to compound (130d) as a yellow solid (4.58 g, 9.37 mmol, 69%). $^1$H NMR (400 MHz, CDCl$_3$) δ 1.30-1.36 (m, 1H), 1.48-1.53 (m, 2H), 1.76-1.86 (m, 3H), 2.00 (bd, J=13.6 Hz, 2H), 2.22 (bd, J=13.2 Hz, 2H), 4.20 (tt, J=4.0/11.6 Hz, 1H), 5.42 (s, 2H), 6.47 (d, J=11.2 Hz, 1H), 7.16-7.19 (m, 3H), 7.34-7.47 (m, 6H), 7.77 (dd, J=0.4/1.6 Hz, 1H), 8.04 (s, 1H). MS m/z ([M+H]$^+$) 489.

Step 5: Benzyl 2-Amino-4-(1-cyclohexyl-1H-benzimidazol-5-yl)-6-[(2-diethylamino-ethyl)-methyl-amino]-3-nitro-benzoate (130e)

According to the procedure described in example 29, step 3, compound (130d) (150 mg, 0.31 mmol) was converted, by reaction with N,N-Diethyl-N'-methyl-ethane-1,2-diamine (34 µL, 0.37 mmol), to compound (130e) as an orange solid (184 mg, 0.31 mmol, 100%). MS m/z ([M+H]$^+$) 599.

Step 6: Benzyl 1'-Cyclohexyl-6-[(2-diethylamino-ethyl)-methyl-amino]-1H,1'H-[4,5']bibenzimidazolyl-7-carboxylate (130f)

According to the procedure described in example 17, step 4, compound (130e) (184 mg, 0.31 mmol) was converted, after purification by flash chromatography on silica gel (DCM/MeOH 9/1 with 1% of ammonia), to compound (130f) (163 mg, 0.28 mmol, 91%). $^1$H NMR (400 MHz, DMSO-d$_6$) δ 0.86 (t, J=6.8 Hz, 6H), 1.26-1.37 (m, 1H), 1.46-1.60 (m, 2H), 1.70-1.78 (1H), 1.84-1.93 (m, 4H), 2.04-2.12 (m, 2H), 2.38-2.50 (m, 5H), 2.55 (bs, 1H), 2.86 (bs, 3H), 3.20-3.26 (m, 2H), 4.41 (t, J=11.6 Hz, 1H), 5.45 (s, 2H), 7.23 (bs, 1H), 7.31-7.35 (m, 1H), 7.37-7.41 (m, 2H), 7.50 (bd, J=7.4 Hz, 2H), 7.75 (bd, J=8.8 Hz, 1H), 7.94-8.01 (m, 1H), 8.14 (bs, 1H), 8.19 (s, 1H), 8.39 (bd, J=10.8 Hz, 1H), 12.23 (bs, 1H). MS m/z ([M+H]$^+$) 579.

Step 7: 1'-Cyclohexyl-6-[(2-diethylamino-ethyl)-methyl-amino]-1H,1'H-[4,5']bibenzimidazolyl-7-carboxamide, Example (130)

According to the procedure described in example 115, step 1, compound (130f) (160 mg, 0.28 mmol) was converted, after purification by preparative TLC on silica gel (DCM/MeOH 9/1 with 1% ammonia), to Example (130) (14 mg, 0.03 mmol, 10%). $^1$H NMR (400 MHz, DMSO-d$_6$) δ 0.9 (bs, 6H), 1.25-1.35 (m, 1H), 1.47-1.57 (m, 2H), 1.74 (bd, J=11.2 Hz, 1H), 1.83-1.94 (m, 4H), 2.08 (bd, J=8.4 Hz, 2H), 2.48-2.54 (m, 6H under solvent), 2.73 (s, 3H), 3.21 (bs, 2H), 4.41 (t, J=11.2 Hz, 1H), 7.49 (s, 1H), 7.63 (bs, 1H), 7.75 (d, J=8.4 Hz, 1H), 8.05 (d, J=8.0 Hz, 1H), 8.15 (s, 1H), 8.38 (s, 1H), 8.46 (s, 1H), 10.00 (bs, 1H), 12.38 (bs, 1H). MS m/z ([M+H]$^+$) 488.

Example 131

Synthesis of 1'-Cyclohexyl-6-[(2-dimethylamino-ethyl)-(2-hydroxy-ethyl)-amino]-1H,1'H-[4,5']bibenzimidazolyl-7-carboxamide Example 131

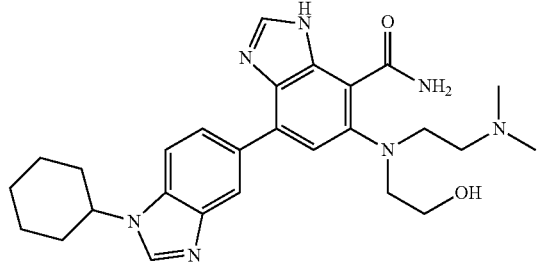

Step 1: Benzyl 2-Amino-4-(1-cyclohexyl-1H-benzimidazol-5-yl)-6-[(2-dimethylamino-ethyl)-(2-hydroxy-ethyl)-amino]-3-nitro-benzoate (131a)

According to the procedure described in example 29, step 3, compound (130d) (100 mg, 0.20 mmol) was converted, by reaction with 2-(2-Dimethylamino-ethylamino)-ethanol (33 µL, 0.25 mmol), to compound (131a) (123 mg, 0.20 mmol, 100%). MS m/z ([M+H]$^+$) 601.

Step 2: Benzyl 1'-Cyclohexyl-6-[(2-dimethylamino-ethyl)-(2-formyloxy-ethyl)-amino]-1H,1'H-[4,5']]bibenzimidazolyl-7-carboxylate (131b)

According to the procedure described in example 17, step 4, compound (131a) (123 mg, 0.20 mmol) was converted, after trituration in DCM, to compound (131b) (119 mg, 0.20 mmol, 100%). MS m/z ([M+H]$^+$) 609.

Step 3: 1'-Cyclohexyl-6-[(2-dimethylamino-ethyl)-(2-hydroxy-ethyl)-amino]-1H,1'H-[4,5']bibenzimidazolyl-7-carboxamide, Example (131)

According to the procedure described in example 115, step 1, compound (131b) (119 mg, 0.20 mmol) was converted, after purification by preparative TLC on silica gel (DCM/MeOH 9/1 with 1% ammonia), to Example (131) (15 mg, 0.03 mmol, 25%). $^1$H NMR (400 MHz, DMSO-d$_6$) δ 1.27-1.37 (m, 1H), 1.48-1.58 (m, 2H), 1.74 (bd, J=12.0 Hz, 1H), 1.83-1.95 (m, 4H), 2.07 (bs, 1H), 2.12 (s, 6H), 2.36 (t, J=6.4 Hz, 2H), 3.19 (t, J=6.0 Hz, 2H), 3.27-3.29 (m, 2H), 3.94 (t, J=6.0 Hz, 2H), 4.42 (tt, J=3.2/11.6 Hz, 1H), 4.68 (bs, 1H), 7.52 (s, 1H), 7.55 (bs, J=4.0 Hz, 1H), 7.75 (d, J=8.4 Hz, 1H), 8.05 (dd, J=1.6/8.4 Hz, 1H), 8.15 (s, 1H), 8.38 (s, 1H), 8.45 (d, J=1.2 Hz, 1H), 9.84 (bs, 1H), 12.36 (bs, 1H). MS m/z ([M+H]$^+$) 490.

Example 132

Synthesis of 1'-Cyclohexyl-6-[methyl-(2-pyrazol-1-yl-ethyl)-amino]-1H,1'H-[4,5']bibenzimidazolyl-7-carboxamide

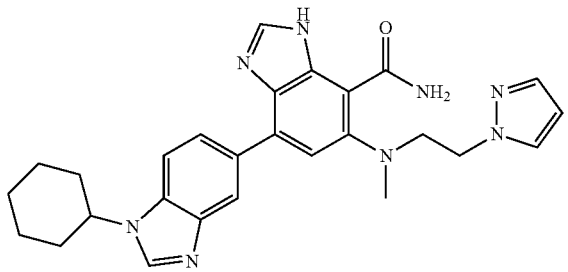

Example 132

Step 1: Benzyl 2-Amino-4-(1-cyclohexyl-1H-benzimidazol-5-yl)-6-[methyl-(2-pyrazol-1-yl-ethyl)-amino]-3-nitro-benzoate (132a)

A solution of compound (130d) (150 mg, 0.31 mmol), Methyl-(2-pyrazol-1-yl-ethyl)-amine (46 mg, 0.37 mmol), triethylamine (428 μL, 2.46 mmol) and magnesium sulfate in DMSO (3 mL) was stirred for 48 hours at 40° C. The reaction mixture was filtered on PTFE and concentrated under reduced pressure. The residue was washed with water and extracted with DCM. The organic layer was dried on sodium sulfate, filtered and evaporated to afford compound (132a) (182 mg, 0.31 mmol, 100%). MS m/z ([M+H]$^+$) 594.

Step 2: Benzyl 1'-Cyclohexyl-6-[methyl-(2-pyrazol-1-yl-ethyl)-amino]-11'H-[4,5']bibenzimidazolyl-7-carboxylate (132b)

According to the procedure described in example 17, step 4, compound (132a) (182 mg, 0.31 mmol) was converted, after purification by preparative TLC on silica gel (DCM/MeOH 9/1 with 1% ammonia), to compound (132b) (69 mg, 0.12 mmol, 39%). MS m/z ([M+H]$^+$) 574.

Step 3: 1'-Cyclohexyl-6-[methyl-(2-pyrazol-1-yl-ethyl)-amino]-1H,1'H-[4,5']bibenzimidazolyl-7-carboxamide, Example (132)

According to the procedure described in example 115, step 1, compound (132b) (69 mg, 0.12 mmol) was converted, after purification by preparative TLC on silica gel (DCM/MeOH 9/1 with 1% ammonia), to Example (132) (11 mg, 0.02 mmol, 18%). $^1$H NMR (400, MHz DMSO-d$_6$) δ 1.27-1.37 (m, 1H), 1.48-1.58 (m, 2H), 1.74 (bd, J=12.4 Hz, 1H), 1.84-1.93 (m, 4H), 2.09 (bs, 2H), 2.78 (s, 3H), 3.59 (bs, 2H), 4.35 (t, J=6.0 Hz, 2H), 4.42 (t, J=11.2 Hz, 1H), 6.21 (s, 1H), 7.39 (bs, 1H), 7.42 (s, 1H), 7.49 (s, 1H), 7.72 (s, 1H), 7.76 (d, J=8.4 Hz, 1H), 8.06 (d, J=8.0 Hz, 1H), 8.16 (s, 1H), 8.41 (s, 1H), 8.47 (s, 1H), 9.02 (bs, 1H), 12.39 (bs, 1H). MS m/z ([M+H]$^+$) 483.

Example 133

Synthesis of 1'-Cyclohexyl-6-[methyl-(tetrahydro-furan-2-ylmethyl)-amino]-1H,1'H-[45']bibenzimidazolyl-7-carboxamide

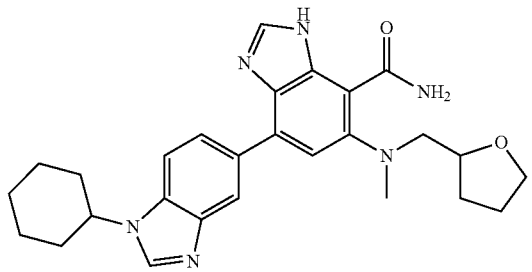

Example 133

Step 1: Benzyl 2-Amino-4-(1-cyclohexyl-1H-benzimidazol-5-yl)-6-[methyl-(tetrahydro-furan-2-ylmethyl)-amino]-3-nitro-benzoate (133a)

According to the procedure described in example 29, step 3, compound (130d) (100 mg, 0.20 mmol) was converted, by reaction with Methyl-(tetrahydro-furan-2-ylmethyl)-amine (28 mg, 0.29 mmol), to compound (133a) (122 mg, 0.24 mmol, 100%). MS m/z ([M+H]$^+$) 508.

Step 2: 1'-Cyclohexyl-6-[methyl-(tetrahydro-furan-2-ylmethyl)-amino]-1H,1'H-[4,5']bibenzimidazolyl-7-carboxylic acid (133b)

According to the procedure described in example 17, step 4, compound (133a) (122 mg, 0.24 mmol) was converted, after trituration in DCM, to compound (133b) (79 mg, 0.17 mmol, 70%). MS m/z ([M+H]$^+$) 474.

Step 3: 1'-Cyclohexyl-6-[methyl-(tetrahydro-furan-2-ylmethyl)-amino]-1H,1'H-[45']bibenzimidazolyl-7-carboxamide, Example (133)

According to the procedure described in example 80, compound (133b) (79 mg, 0.17 mmol) was converted, by reaction with ammonia (0.5M in dioxane, 500 μL, 0.25 mmol) and after purification by preparative TLC on silica gel (DCM/MeOH 9/1), to Example (133) (8 mg, 0.02 mmol, 10%). $^1$H NMR (400 MHz, CDCl$_3$) δ 1.29-1.39 (m, 1H), 1.45-1.59 (m, 2H), 1.80-1.92 (m, 5H), 2.00 (bd, J=13.2 Hz, 4H), 2.26 (bd, J=11.2 Hz, 2H), 2.85 (s, 3H), 3.02-3.07 (m, 1H), 3.18 (bd, J=11.6 Hz, 1H), 3.76 (q, J=7.6 Hz, 1H), 3.85 (q, J=8.0 Hz, 1H), 4.13 (bd, J=4.8 Hz, 1H), 4.24 (tt, J=12.0/3.2 Hz, 1H), 5.84 (bs, 1H), 7.44 (s, 1H), 7.57 (d, J=8.4 Hz, 1H), 8.05 (s, 1H), 8.14 (s, 1H), 8.18 (d, J=8.8 Hz, 1H), 8.24 (s, 1H), 10.59 (bs, 1H), 11.55 (bs, 1H). MS m/z ([M+H]$^+$) 473.

Example 134

Synthesis of 7-Benzothiazol-5-yl-5-[(2-dimethyl-amino-ethyl)-methyl-amino]-3H-benzimidazole-4-carboxamide

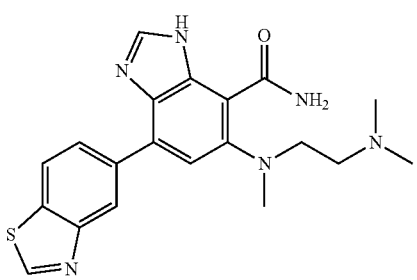

Example 134

According to the procedure described in example 115, step 2, compound (124g) (70 mg, 0.20 mmol) was converted, by reaction with 5-(tetramethyl-1,3,2-dioxaborolan-2-yl)-1,3-benzothiazole (53.80 mg, 0.20 mmol) and after purification by preparative TLC on silica gel (DCM/MeOH 98/2 with 5% of ammonia), to Example (134) as a brown solid (31.3 mg, 0.079 mmol, 38%). $^1$H NMR (400 MHz, DMSO-d6) δ 2.14 (s, 6H), 2.41 (t, J=6.3 Hz, 2H), 2.76 (s, 3H), 3.23 (t, J=6.3 Hz, 2H), 7.62 (s, 2H), 8.20 (s, 1H), 8.29-8.30 (m, 2H), 8.95 (s, 1H), 9.46 (s, 1H), 10.04 (d, J=3.4 Hz, 1H), 12.47 (s, 1H). MS m/z ([M+H]$^+$) 395.

Example 135

Synthesis of 6-[(2-Dimethylamino-ethyl)-methyl-amino]-1'-(2-methoxy-ethyl)-1H,1'H-[4,5']]bibenzimidazolyl-7-carboxamide

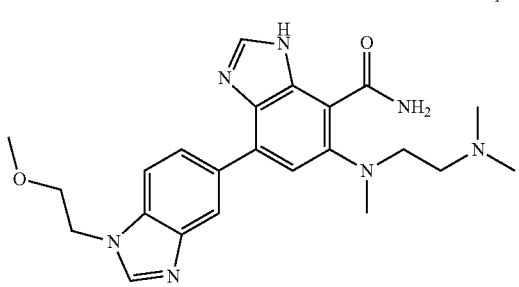

Example 135

Step 1: (4-bromo-2-nitro-phenyl)-(2-methoxy-ethyl)-amine (135a)

According to the procedure described in example 29, step 3, 4-bromo-1-fluoro-2-nitro-benzene (1.4 g, 6.36 mmol) was converted, by reaction with 2-methoxyethylamine (0.956 g, 12.73 mmol), to compound (135a) (1.76 g, 6.36 mmol, 100%) without further purification. MS m/z ([M+H]$^+$) 275/277.

Step 2: 4-bromo-N*1*-(2-methoxy-ethyl)-benzene-1,2-diamine (135b)

According to the procedure described in example 123, step 2, compound (135a) (1.76 g, 6.36 mmol) was converted, without further purification, to compound (135b) as brownish oil (1.52 g, 6.20 mmol, 98%). MS m/z ([M+H]$^+$) 245/247.

Step 3: 5-Bromo-1-(2-methoxy-ethyl)-1H-benzimidazole (135c)

According to the procedure described in example 123, step 3, compound (135b) (1.52 g, 6.20 mmol) was converted, after purification by column chromatography on silica gel (DCM/MeOH 98/2), to compound (135c) (1.45 g, 5.68 mmol, 90%) as a brown oil. $^1$H NMR (400 MHz, CDCl$_3$) δ 3.31 (s, 3H), 3.69 (t, J=5.2 Hz, 2H), 4.29 (t, J=5.2 Hz, 2H), 7.28 (dd, J=1.9/8.5 Hz, 1H), 7.39 (d, J=8.5 Hz, 1H), 7.94 (m, 2H). MS m/z ([M+H]$^+$) 255/257.

Step 4: 1-(2-methoxy-ethyl)-5-(4,4,5,5-tetramethyl-[1,3,2]dioxaborolan-2-yl)-1H-benzimidazole (135d)

According to the procedure described in example 123, step 4, compound (135c) (1.45 g, 5.68 mmol) was converted, after trituration in cyclohexane, to compound (135d) as a beige solid (992 mg, 3.29 mmol, 58%) which was engaged in the following step without additional purification. $^1$H NMR (400 MHz, CDCl$_3$) δ 1.37 (s, 12H), 3.30 (s, 3H), 3.70 (t, J=5.2 Hz, 2H), 4.32 (t, J=5.2 Hz, 2H), 7.40 (dd, J=0.6/8.1 Hz, 1H), 7.75 (dd, J=0.9/8.1 Hz, 1H), 7.98 (s, 1H), 8.29 (bt, 1H). MS m/z ([M+H]$^+$) 303.

Step 5: 6-[(2-Dimethylamino-ethyl)-methyl-amino]-1'-(2-methoxy-ethyl)-1H,1'H-[4,5']]bibenzimidazolyl-7-carboxamide, Example (135)

According to the procedure described in example 115, step 2, compound (124g) (115 mg, 0.34 mmol) was converted, by reaction with compound (135d) (102 mg, 0.34 mmol) and after purification by preparative TLC on silica gel (DCM/MeOH 98/2 with 5% of ammonia), to Example (135) as a beige solid (49.8 mg, 0.114 mmol, 34%). $^1$H NMR (400 MHz, CDCl$_3$) δ 2.20 (s, 6H), 2.47 (t, J=6.2 Hz, 2H), 2.79 (s, 3H), 3.22 (t, J=6.2 Hz, 2H), 3.32 (s, 3H), 3.73 (t, J=5.2 Hz, 2H), 4.37 (t, J=5.2 Hz, 2H), 5.80 (bs, 1H), 7.45 (s, 1H), 7.54 (d, J=8.5 Hz, 1H), 8.01 (s, 1H), 8.14 (s, 1H), 8.19 (dd, J=1.5/8.4 Hz, 1H), 8.25 (d, J=1.5 Hz, 1H). MS m/z ([M+H]$^+$) 436.

Example 136

Synthesis of rac-1'-((trans)-3-methyl-cyclohexyl)-6-[methyl-(2-methylamino-ethyl)-amino]-1H,1'H-[4,5']bibenzimidazolyl-7-carboxamide

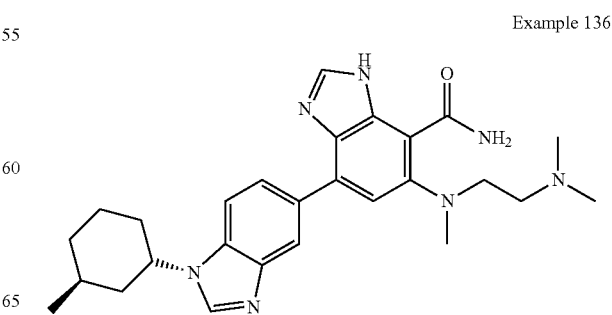

Example 136

According to the procedure described in example 116, step 2, compound (124g) (100 mg, 0.29 mmol) was converted, by reaction with rac-1-((trans)-3-methyl-cyclohexyl)-5-(4,4,5,5-tetramethyl-[1,3,2]dioxaborolan-2-yl)-1H-benzimidazole (100 mg, 0.294 mmol) and after purification by preparative TLC on silica gel (DCM/MeOH 9/1 with 1% of ammonia), to Example (136) as a clear brown solid (59 mg, 0.124 mmol, 42%). $^1$H NMR (400 MHz, CDCl$_3$) δ 1.12 (d, J=7.0 Hz, 3H), 1.47 (m, 1H), 1.74 (m, 3H), 1.96 (m, 2H), 2.15 (m, 3H), 2.22 (s, 6H), 2.47 (t, J=6.2 Hz, 2H), 2.78 (s, 3H), 3.22 (t, J=6.2 Hz, 2H), 4.55 (m, 1H), 5.81 (bs, 1H), 7.45 (s, 1H), 7.56 (d, J=8.4 Hz, 1H), 8.08 (s, 1H), 8.14 (s, 1H), 8.18 (dd, J=1.6/8.5 Hz, 1H), 8.24 (d, J=1.6 Hz, 1H). MS m/z ([M+H]$^+$) 474.

Example 137

Synthesis of 5-[(2-Dimethylamino-ethyl)-methyl-amino]-7-quinolin-7-yl-3H-benzimidazole-4-carboxamide Example 137

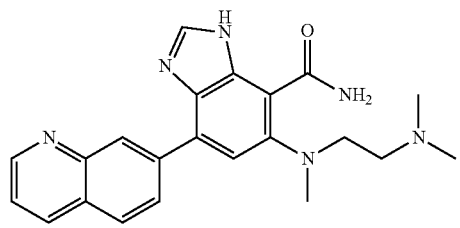

According to the procedure described in example 115, step 2, compound (124g) (102 mg, 0.3 mmol) was converted, by reaction with 7-(tetramethyl-1,3,2-dioxaborolan-2-yl)quinolone (77 mg, 0.3 mmol) and after purification by preparative TLC on silica gel (DCM/MeOH 9/1 with 1% of ammonia), to Example (137) (68 mg, 0175 mmol, 58%). $^1$H NMR (400 MHz, DMSO-d$_6$) δ 2.16 (s, 6H), 2.40.2.48 (m, 2H), 2.76 (s, 3H), 3.25 (t, J=6.3 Hz, 2H), 7.52-7.58 (m, 1H), 7.64 (bs, 1H), 7.67 (s, 1H), 8.09 (d, J=8.6 Hz, 1H), 8.21 (s, 1H), 8.41 (dd, J=8.6/1.6 Hz, 2H), 8.88 (m, 1H), 8.95 (dd, J=4.2/1.7 Hz, 1H), 9.99 (bs, 1H), 12.48 (s, 1H). MS m/z ([M+H]$^+$) 389.

Example 138

Synthesis of 1'-Cyclohexyl-6-(2-dimethylamino-ethoxy)-1H,1'H-[4,5']]bibenzimidazolyl-7-carboxamide Example 138

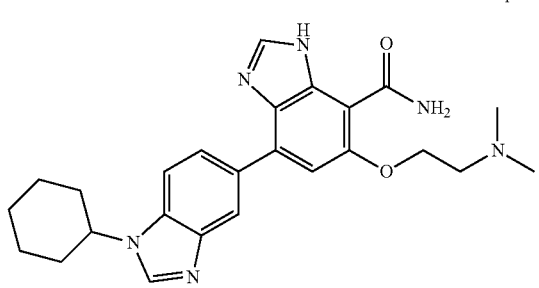

A solution of Example (104) (30 mg, 0.07 mmol) in sulfuric acid (0.1 mL) and trifluoroacetic acid (0.3 mL) was stirred at room temperature. After 24 hours, sulfuric acid (0.2 mL) was added and the mixture was stirred for 2 hours. The middle was diluted in methanol, cooled and neutralized by ammonia 7M in methanol at 0° C. The resulting mixture was filtered and concentrated under reduced pressure. The crude product was purified by preparative TLC on silica gel (DCM/MeOH 9/1+1% ammonia) to provide Example (138) (23 mg, 0.052 mmol, 74%). $^1$H NMR (400 MHz, DMSO-d$_6$) δ 1.28-1.39 (m, 1H), 1.49-1.60 (m, 2H), 1.74-1.78 (m, 2H), 1.85-1.95 (m, 4H), 2.09-2.11 (m, 2H), 2.41 (bs, 6H), 2.89 (bs, 2H), 4.40-4.49 (m, 3H), 7.35 (s, 1H), 7.62 (bs, 1H), 7.77 (d, J=8.6 Hz, 1H), 8.12-8.15 (m, 2H), 8.40 (s, 1H), 8.52 (d, J=1.2 Hz, 1H), 12.36 (s, 1H). MS m/z ([M+H]$^+$) 447.

Example 139

Synthesis of 1'-Cyclohexyl-6-(2-dimethylamino-ethoxy)-1H,1'H-[4,5']bibenzimidazolyl-7-carboxamide methanesulfonic acid salt Example 139

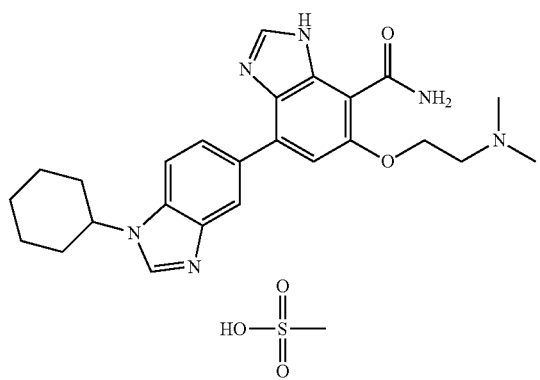

According to the procedure described in example 108, Example (138) (68 mg, 0175 mmol, 58%) was converted, after trituration with ethanol and then diethyl ether, to Example (139) without further purification (47.1 mg, 0.87 mmol, 87%). $^1$H NMR (400 MHz, DMSO-d$_6$) δ 1.26-1.38 (m, 1H), 1.47-1.61 (m, 2H), 1.71-1.79 (m, 1H), 1.83-1.95 (m, 4H), 2.04-2.13 (m, 2H), 2.29 (s, 3H), 2.92 (s, 6H), 3.66 (bs, 2H), 4.38-4.49 (m, 1H), 4.67 (bs, 2H), 7.35 (s, 1H), 7.22-7.85 (m, 3H), 8.11-8.21 (m, 2H), 8.43 (s, 1H), 8.50 (s, 1H), 9.65 (bs, 1H), 12.41 (bs, 1H). MS m/z ([M+H]$^+$) 447.

Example 140

Synthesis of 1'-Cyclohexyl-6-(2-dimethylamino-ethoxy)-1H,1'H-[4,5']]bibenzimidazolyl-7-carboxamide hydrochloride salt Example 140

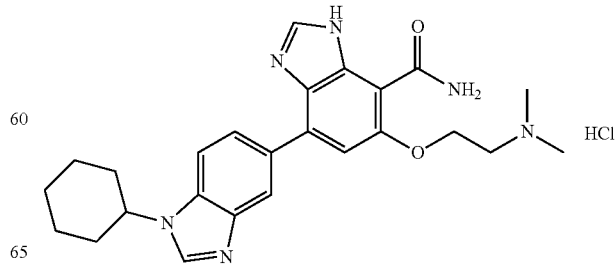

Example (138) (49 mg, 0.11 mmol) was solubilized at room temperature in a mixture of DCM (5 mL) and methanol (5 mL). A solution of hydrochloric acid (0.1N in water, 1.1 mL, 0.11 mmol) was added. The mixture was then concentrated. The residue was triturated with ethanol and then diethyl ether to provide Example (140) without further purification (50.3 mg, 1.04 mmol, 95%). $^1$H NMR (400 MHz, DMSO-$d_6$) δ 1.26-1.39 (m, 1H), 1.49-1.59 (m, 2H), 1.71-1.79 (m, 1H), 1.83-1.97 (m, 4H), 2.04-2.15 (m, 2H), 2.91 (s, 6H), 3.67 (bs, 2H), 4.40-4.51 (m, 1H), 4.72 (bs, 2H), 7.36 (s, 1H), 7.72-7.88 (m, 3H), 8.06-8.25 (m, 2H), 8.51 (m, 2H), 10.25 (bs, 1H), 12.42 (bs, 1H). MS m/z ([M+H]$^+$) 447.

Example 141

Synthesis of 7-(3-Carbamoyl-4-methoxy-phenyl)-5-[(2-dimethylamino-ethyl)-methyl-amino]-3H-benzimidazole-4-carboxamide

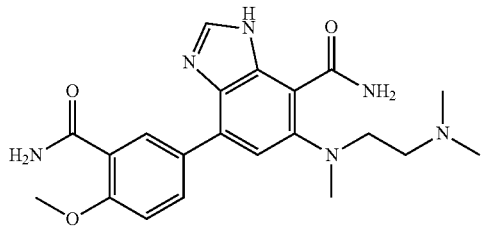

Example 141

Step 1: 2-methoxy-5-(tetramethyl-1,3,2-dioxaborolan-2-yl)benzamide (141a)

According to the procedure described in example 123, step 4, 5-bromo-2-methoxybenzamide (230 mg, 1 mmol) was converted to crude compound (141a) (453 mg) which was used without further purification. MS m/z ([M+H]$^+$) 278.

Step 2: 7-(3-Carbamoyl-4-methoxy-phenyl)-5-[(2-dimethylamino-ethyl)-methyl-amino]-3H-benzimidazole-4-carboxamide, Example (141)

According to the procedure described in example 115, step 2, compound (124g) (102 mg, 0.3 mmol) was converted, by reaction with compound (142a) (83 mg, 0.3 mmol) and after purification by preparative TLC on silica gel (DCM/MeOH 9/1 with 1% of ammonia), to Example (141) (17 mg, 0.041 mmol, 14%). $^1$H NMR (400 MHz, DMSO-$d_6$) δ 2.14 (s, 6H), 2.40 (m, 2H), 2.70 (s, 3H), 3.18 (t, J=6.3 Hz, 2H), 3.93 (s, 3H), 7.24 (d, J=8.8 Hz, 1H), 7.34 (s, 1H), 7.56 (bs, 2H), 7.67 (bs, 1H), 8.12 (s, 1H), 8.29 (dd, J=8.7/2.5 Hz, 1H), 8.53 (d, J=2.5 Hz, 1H), 9.93 (bs, 1H), 12.39 (s, 1H). MS m/z ([M+H]$^+$) 411.

Example 142

Synthesis of 1'-Ethyl-6-[methyl-(2-methylamino-ethyl)-amino]-1H,1'H-[4,5']bibenzimidazolyl-7-carboxamide

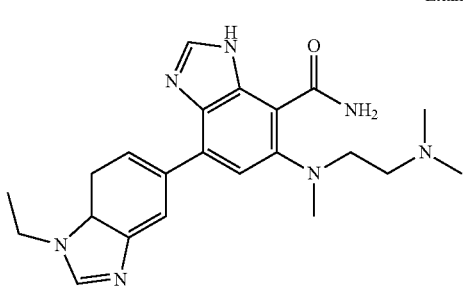

Example 142

According to the procedure described in example 115, step 2, compound (124g) (102 mg, 0.3 mmol) was converted, by reaction with 1-ethyl-5-(4,4,5,5-tetramethyl-[1,3,2]dioxaborolan-2-yl)-1H-benzimidazole (115 mg, 0.39 mmol) and after purification by preparative TLC on silica gel (DCM/MeOH 9/1 with 1% of ammonia), to Example (142) as a beige solid (34.5 mg, 0.085 mmol, 28%). $^1$H NMR (400 MHz, CDCl$_3$) δ 1.56 (t, J=7.3 Hz, 3H), 2.21 (s, 6H), 2.46 (t, J=6.3 Hz, 2H), 2.79 (s, 3H), 3.21 (t, J=6.3 Hz, 2H), 4.27 (q, J=7.3 Hz, 2H), 5.82 (bs, 1H), 7.45 (s, 1H), 7.56 (d, J=8.4 Hz, 1H), 7.96 (s, 1H), 8.14 (s, 1H), 8.19 (dd, J=1.6/8.4 Hz, 1H), 8.24 (dd, J=0.4/1.5 Hz, 1H). MS m/z ([M+H]$^+$) 406.

Example 143

Synthesis of 5-[(2-Dimethylamino-ethyl)-methyl-amino]-7-(1-ethyl-6-oxo-1,6-dihydro-pyridin-3-yl)-3H-benzimidazole-4-carboxamide

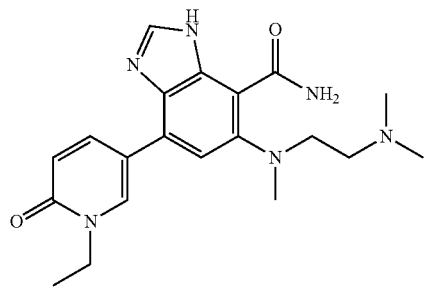

Example 143

Step 1: 5-bromo-1-ethyl-1,2-dihydropyridin-2-one (143a)

A solution of 5-bromo-1,2-dihydropyridin-2-one (1.04 g, 6 mmol) in DMF (12 mL) was treated with sodium hydride (60% dispersion in mineral oil, 960 mg, 24 mmol) at room temperature and then stirred 30 minutes. Iodoethane (0.58 mL, 7.2 mmol) was added to the mixture and the reaction was stirred overnight at room temperature. This operation was repeated twice, until the reaction was completed. The middle was diluted with water and DCM. The organic layer was washed with saturated solution of sodium bicarbonate, brine, dried over sodium sulfate, filtered and concentrated under reduced pressure. The residue was purified by column chromatography on silica gel (DCM/MeOH 98/2) to give compound (143a) (532 mg, 2.63 mmol, 44%). $^1$H NMR (400 MHz, DMSO-$d_6$) δ 1.20 (t, J=7.1 Hz, 3H), 3.88 (q, J=7.1 Hz, 2H), 6.35 (d, J=9.7 Hz, 1H), 7.51 (dd, J=9.7/2.8 Hz, 1H), 8.05 (d, J=2.8 Hz, 1H). MS m/z ([M+H]$^+$) 202-204.

Step 2: 1-ethyl-5-(tetramethyl-1,3,2-dioxaborolan-2-yl)-1,2-dihydropyridin-2-one (143b)

According to the procedure described in example 123, step 4, compound (143a) (303 mg, 1.5 mmol) was converted to crude compound (143b) (697 mg) which was used without further purification. MS m/z ([M+H]$^+$) 250.

Step 3: 5-[(2-Dimethylamino-ethyl)-methyl-amino]-7-(1-ethyl-6-oxo-1,6-dihydro-pyridin-3-yl)-3H-benzimidazole-4-carboxamide, Example (143)

According to the procedure described in example 115, step 2, compound (124g) (272 mg, 0.8 mmol) was converted, by reaction with compound (143b) (300 mg, 0.8 mmol) and after purification by preparative TLC on silica gel (DCM/MeOH 9/1 with 1% of ammonia), to Example (143) (38 mg, 0.1 mmol, 12%). $^1$H NMR (400 MHz, DMSO-$d_6$) δ 1.30 (t, J=7.1 Hz, 3H), 2.11 (s, 6H), 2.37 (t, J=6.3 Hz, 2H), 2.70 (s, 3H), 3.17 (t, J=6.3 Hz, 2H), 4.03 (q, J=7.1 Hz, 2H), 6.52 (d, J=9.5 Hz, 1H), 7.44 (s, 1H), 7.55 (d, J=3.3 Hz, 1H), 8.14 (s, 1H), 8.36 (dd, J=9.5/2.6 Hz, 1H), 8.82 (d, J=2.5 Hz, 1H), 10.00 (d, J=3.3 Hz, 1H), 12.42 (s, 1H). MS m/z ([M+H]$^+$) 383.

Example 144

Synthesis of 7-(3,4-Dihydro-2H-pyrano[2,3-b]pyridin-6-yl)-5-[(2-dimethylamino-ethyl)-methyl-amino]-3H-benzimidazole-4-carboxamide Example 144

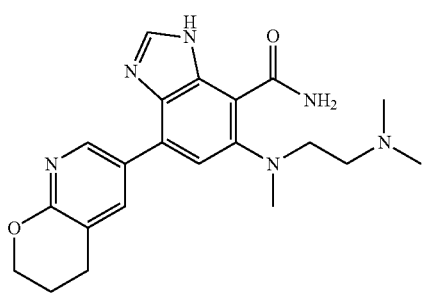

According to the procedure described in example 115, step 2, compound (124g) (70 mg, 0.20 mmol) was converted, by reaction with 6-(tetramethyl-1,3,2-dioxaborolan-2-yl)-2H,3H,4H-pyrano[2,3-b]pyridine (54 mg, 0.20 mmol) and after purification by preparative TLC on silica gel (DCM/MeOH 95/5 with 2% of ammonia), to Example (144) as a brown solid (20.6 mg, 0.052 mmol, 25%). $^1$H NMR (400 MHz, CDCl$_3$) δ 2.08-2.10 (m, 2H), 2.25 (s, 6H), 2.50 (t, J=6.3 Hz, 2H), 2.80 (s, 3H), 2.98 (t, J=6.3 Hz, 2H), 3.24 (t, J=6.3 Hz, 2H), 4.43 (t, J=6.3 Hz, 2H), 5.83-5.84 (m, 1H), 7.36 (s, 1H), 8.17 (s, 1H), 8.32-8.33 (m, 1H), 8.56 (d, J=2.4 Hz, 1H), 10.68 (s, 1H), 11.60 (s, 1H). MS m/z ([M+H]$^+$) 395.

Example 145

Synthesis of [6-Fluoro-1'-(1-methyl-cyclohexyl)-1H,1'H-[4,5']]bibenzimidazolyl-7-yl]-acetonitrile Example 145

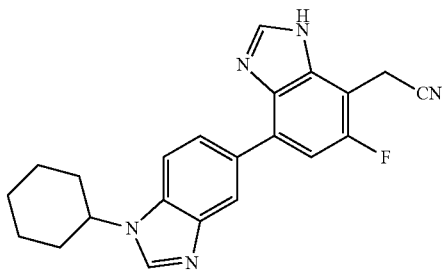

Step 1: 2-(4-bromo-2,6-difluoro-3-nitrophenyl)acetonitrile (145a)

According to the procedure described in example 42, step 1, 4-bromo2,6-difluorophenyl acetonitrile (1 g, 4.3 mmol) was converted, without further purification, to compound (145a) as a yellow oil (1.4 g, 5.0 mmol, 100%). $^1$H NMR (400 MHz, CDCl$_3$) δ 3.82 (s, 2H), 7.43 (dd, J=8.2/2.2 Hz, 1H). MS m/z ([M+H]$^+$) 277/279.

Step 2: 2-(2-amino-4-bromo-6-fluoro-3-nitrophenyl)acetonitrile (145b)

At 0° C., a solution of ammonia (7M in MeOH, 3.20 mL) was added to a solution of compound (145a) (1.4 g, 5.0 mmol) in THF (6.25 mL). The mixture was stirred 16 hours at room temperature and evaporated to afford crude compound (145b) as brown oil (1.4 g) which was used without further purification. MS m/z ([M+H]$^+$) 274/276.

Step 3: (7-Bromo-5-fluoro-3H-benzimidazol-4-yl)-acetonitrile (145c)

According to the procedure described in example 17, step 4, compound (145b) (1.4 g, 5 mmol) was converted, after purification by preparative TLC on silica gel (DCM/MeOH 95/5), to compound (145c) as an orange powder. MS m/z ([M+H]$^+$) 254/256.

Step 4: [6-Fluoro-1'-(1-methyl-cyclohexyl)-1H,1'H-[4,5']]bibenzimidazolyl-7-yl]-acetonitrile, Example (145)

According to the procedure described in example 115, step 2, compound (145c) (100 mg, 0.39 mmol) was converted, by reaction with 1-Cyclohexyl-5-(4,4,5,5-tetramethyl-1,3,2-dioxaborolan-2-yl)-1H-benzimidazole (134 mg, 0.41 mmol) and after purification by preparative TLC on silica gel (DCM/MeOH 95/5 with 2% of ammonia), to Example (145) as an orange powder (80 mg, 0.21 mmol, 55%). $^1$H NMR (400 MHz, CDCl$_3$) δ 1.25-1.33 (m, 1H), 1.45-1.55 (m, 2H), 1.66-1.75 (m, 2H), 1.81-1.85 (m, 1H), 1.95-1.99 (m, 2H), 2.13-2.15 (m, 2H), 4.12-4.15 (m, 3H), 7.16 (d, J=10.8 Hz, 1H), 7.48 (s, 2H), 7.86 (s, 1H), 8.10 (s, 1H), 8.14 (s, 1H), 13.10 (s, 1H). MS m/z ([M+H]⁺) 374.

Example 146

Synthesis of 2-(1'-Cyclohexyl-6-fluoro-1H,1'H-[4,5']]bibenzimidazolyl-7-yl)-acetamide

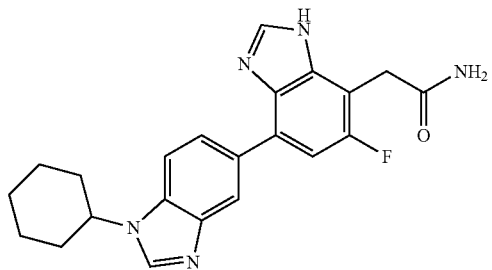

Example 146

A solution of Example (145) (70 mg, 0.18 mmol) in a mixture of sulfuric acid (50 µL) and acetic acid (3.75 mL) was heated to 100° C. for 2 hours. The reaction mixture was then diluted with DCM and neutralized with a solution of sodium hydroxide 1N. The organic layer was extracted two times and the combined organic layers were dried over sodium sulfate, filtered and evaporated under reduced pressure. The crude material was purified by preparative TLC on silica gel (DCM/MeOH 95/5+2% of ammonia) to give Example (146) (11.3 mg, 0.028 mmol, 15%) as a beige powder. ¹H NMR (400 MHz, DMSO-d₆) δ 1.28-1.38 (m, 1H), 1.49-1.59 (m, 2H), 1.73-1.77 (m, 1H), 1.88-1.91 (m, 4H), 2.08-2.10 (m, 2H), 3.77-3.84 (m, 2H), 4.41-4.45 (m, 1H), 6.94 and 7.05 (2bs, 1H), 7.17 and 7.32 (2d, J=11.5 Hz, 1H), 7.46 and 7.52 (2bs, 1H), 7.74 and 7.84 (2m, 1H), 7.92 and 8.01 (2m, 1H), 8.23 and 8.29 (s, 1H), 8.36 and 7.52 (2bs, 1H), 8.43 and 8.48 (bs, 1H). MS m/z ([M+H]⁺) 392.

Example 147

Synthesis of 6-[(2-dimethylamino-ethyl)-methyl-amino]-1H,1'H-[4,5']bibenzimidazolyl-7-carboxamide

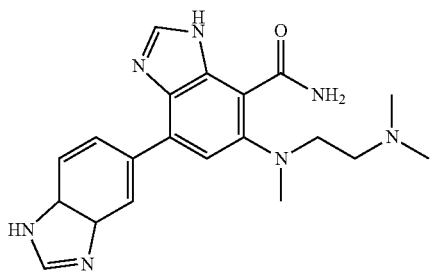

Example 147

Step 1: 5-bromo-1-(2-trimethylsilanyl-ethoxymethyl)-1H-benzimidazole (147a)

At 0° C. under nitrogen atmosphere, Sodium hydride 60% in mineral oil (101 mg, 2.54 mmol) washed with pentane was added to a solution of 5-bromo-1H-benzimidazole (500 mg, 2.54 mmol) in anhydrous DMF (5 mL). After 15 minutes, 2-(trimethylsilyl)ethoxymethyl chloride (477 µL, 2.69 mmol) was added and the mixture was stirred for one hour. A saturated solution of ammonium chloride was added to the middle. The aqueous layer was extracted with AcOEt and the combined organic layers were dried over sodium sulfate and concentrated under reduced pressure. The crude was purified by flash chromatography on silica gel (cyclohexane/AcOEt 6/4) to provide compound (147a) as uncoloured oil (370 mg, 1.13 mmol, 44%). MS m/z ([M+H]⁺) 327/329.

Step 2: 5-(4,4,5,5-tetramethyl-[1,3,2]dioxaborolan-2-yl)-1-(2-trimethylsilanyl-ethoxymethyl)-1H-benzimidazole (147b)

According to the procedure described in example 123, step 4, compound (147a) (119 mg, 0.36 mmol) was converted, after purification by flash chromatography on silica gel (DCM/MeOH 97/3), to compound (147b) as a yellow oil (133 mg, 0.35 mmol, 97%). MS m/z ([M+H]⁺) 375.

Step 3: 6-[(2-dimethylamino-ethyl)-methyl-amino]-1'-(2-trimethylsilanyl-ethoxymethyl)-1H,1'H-[4,5']bibenzimidazolyl-7-carboxamide (147c)

According to the procedure described in example 115, step 2, compound (124g) (167 mg, 0.45 mmol) was converted, by reaction with compound (147b) (238 mg, 0.64 mmol) and after purification by column chromatography on silica gel (DCM/MeOH 9/1 with 1% of ammonia), to compound (147c) as a colorless oil (177 mg, 0.35 mmol, 71%). MS m/z ([M−H]⁻) 506.

Step 4: 6-[(2-dimethylamino-ethyl)-methyl-amino]-1H,1'H-[4,5']bibenzimidazolyl-7-carboxamide, Example (147)

A solution of compound (147c) (177 mg, 0.35 mmol) and TBAF (1M in THF, 420 µL) in THF (3.2 mL) was refluxed for 24 hours. The mixture was then cooled and concentrated to dryness. The crude product was purified by preparative TLC on silica gel (DCM/MeOH 9/1 with 4% of ammonia) to afford Example (147) (18 mg, 0.048 mmol, 14%) as a white solid. ¹H NMR (300 MHz, CD₃OD) δ 2.26 (s, 6H), 2.53 (t, J=7.2 Hz, 2H), 2.85 (s, 3H), 3.34 (m, 2H), 7.52 (s, 1H), 7.80 (m, 2H), 8.21 (bs, 1H), 8.25 (s, 1H), 8.27 (s, 1H). MS m/z ([M+H]⁺) 378.

Example 148

Synthesis of 5-[(2-Dimethylamino-ethyl)-methyl-amino]-7-(1-ethyl-2-oxo-1,2-dihydro-pyridin-4-yl)-3H-benzimidazole-4-carboxamide

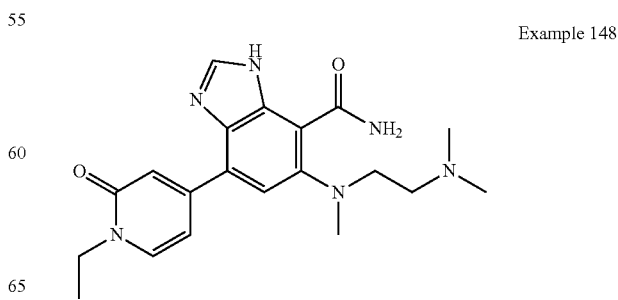

Example 148

Step 1: 4-bromo-1-ethyl-1,2-dihydropyridin-2-one (148a)

Under argon atmosphere, a solution of 4-bromo-1,2-dihydropyridin-2-one (1.00 g, 5.75 mmol) in THF (20 mL) was treated with sodium hydride (60% dispersion in mineral oil, 230 mg, 5.75 mmol) at 0° C. and then stirred 30 minutes at room temperature. Iodoethane (1.39 mL, 17.25 mmol) was added to the mixture and the reaction was stirred for 16 hours at room temperature and then heated at 50° C. for 24 hours. The middle was diluted with water and ethyl acetate. The organic layer was washed with water, brine, dried over sodium sulfate, filtered and concentrated under reduced pressure. The residue was purified by column chromatography on silica gel (DCM/EtOAc 100/0 to 85/15) to give compound (148a) (981 mg, 4.86 mmol, 84%). $^1$H NMR (300 MHz, CDCl$_3$) δ 1.33 (t, J=7.2 Hz, 3H), 3.94 (q, J=7.2 Hz, 2H), 6.33 (dd, J=7.2/2.1 Hz, 1H), 6.82 (d, J=2.1 Hz, 1H), 7.13 (d, J=7.2 Hz, 1H). MS m/z ([M+H]$^+$) 202-204.

Step 2: 1-ethyl-4-(tetramethyl-1,3,2-dioxaborolan-2-yl)-1,2-dihydropyridin-2-one (148b)

A solution of compound (148a) (202 mg, 1.0 mmol), bis pinacol diboron (381 mg, 1.5 mmol) and potassium acetate (294 mg, 3 mmol) in N,N'-dimethylacetamide (0.7 mL) was degassed with argon for 10 minutes and tris(dibenzylideneacetone)dipalladium(0) (Pd$_2$dba$_3$, 9 mg, 0.01 mmol) and Di(1-adamantyl)-n-butylphosphine (11 mg, 0.03 mmol) were then added. The mixture was heated at 90° C. overnight and then concentrated. The residue was diluted with ethyl acetate. The organic layer was washed with saturated solution of sodium bicarbonate, brine, dried over sodium sulfate, filtered and concentrated under reduced pressure to give crude compound (148b) (800 mg) which was used in the next step without further purification. MS m/z ([M+H]$^+$) 250.

Step 3: 5-[(2-Dimethylamino-ethyl)-methyl-amino]-7-(1-ethyl-2-oxo-1,2-dihydro-pyridin-4-yl)-3H-benzimidazole-4-carboxamide, Example (148)

According to the procedure described in example 115, step 2, compound (124g) (340 mg, 1 mmol) was converted, by reaction with crude compound (148b) (800 mg) and after purification by column chromatography on silica gel (DCM/MeOH 9/1 with 1% of ammonia), to Example (148) (60 mg, 0.16 mmol, 16%). $^1$H NMR (400 MHz, DMSO-d$_6$) δ 1.23 (t, J=7.1 Hz, 3H), 2.17 (bs, 6H), 2.25 (bs, 2H), 2.70 (s, 3H), 3.18 (t, J=6.2 Hz, 2H), 3.94 (q, J=7.1 Hz, 2H), 7.01 (dd, J=7.1/2.0 Hz, 1H), 7.26 (d, J=1.9 Hz, 1H), 7.50 (s, 1H), 7.75 (bs, 1H), 7.77 (d, J=7.1 Hz, 1H), 8.16 (s, 1H), 9.85 (bs, 1H), 12.48 (s, 1H). MS m/z ([M+H]$^+$)383.

Example 149

Synthesis of 1'-Cyclohexyl-6-[(2-dimethylamino-ethyl)-methyl-amino]-1H,1'H-[4,5']bibenzimidazolyl-7-carboxylic acid

Step 1: Benzyl 2-Amino-4-(1-cyclohexyl-1H-benzimidazol-5-yl)-6-[(2-dimethylamino-ethyl)-methyl-amino]-3-nitro-benzoate (149a)

According to the procedure described in example 29, step 3, compound (130d) (200 mg, 0.41 mmol) was converted, by reaction with N,N,N'-Trimethyl-ethane-1,2-diamine (55 μL, 0.43 mmol), to compound (149a) as an orange solid (184 mg, 0.32 mmol, 78%). $^1$H NMR (400 MHz, CDCl$_3$) δ 1.25-1.34 (m, 1H), 1.45-1.53 (m, 2H), 1.76-1.86 (m, 3H), 2.00 (bd, J=12.8 Hz, 2H), 2.13 (s, 6H), 2.24 (bd, J=12.0 Hz, 2H), 2.37 (t, J=7.6 Hz, 2H), 2.93 (s, 3H), 3.33 (t, J=7.2 Hz, 2H), 4.19 (tt, J=3.6/12.0 Hz, 1H), 5.34 (s, 2H), 6.24 (s, 1H), 7.18 (dd, J=1.6/8.4 Hz, 1H), 7.28 (bs, 2H), 7.33-7.44 (m, 6H), 7.78 (d, J=1.2 Hz, 1H), 8.00 (s, 1H). MS m/z ([M+H]$^+$) 571.

Step 2: Benzyl 1'-Cyclohexyl-6-[(2-dimethylamino-ethyl)-methyl-amino]-1H,1'H-[4,5']bibenzimidazolyl-7-carboxylate (149b)

According to the procedure described in example 17, step 4, compound (149a) (180 mg, 0.31 mmol) was converted, after purification by preparative TLC on silica gel (DCM/MeOH 9/1 with 2% of ammonia), to compound (149b) (106 mg, 0.19 mmol, 61%). $^1$H NMR (400 MHz, CDCl$_3$) δ 128-1.38 (m, 1H), 1.45-1.54 (m, 2H), 1.82-1.88 (m, 3H), 2.00 (bd, J=13.6 Hz, 2H), 2.25 (bd, J=11.2 Hz, 2H), 2.47 (bs, 6H), 2.93 (bs, 5H), 3.50 (t, J=6.8 Hz, 2H), 4.24 (tt, J=3.6/12.0 Hz, 1H), 5.45 (s, 2H), 7.22 (s, 1H), 7.37-7.45 (m, 3H), 7.48-7.51 (m, 2H), 7.57 (d, J=8.0 Hz, 1H), 8.03-8.07 (m, 3H), 8.26 (d, J=1.2 Hz, 1H), 8.41 (s, 1H). MS m/z ([M+H]$^+$) 551.

Step 3: 1'-Cyclohexyl-6-[(2-dimethylamino-ethyl)-methyl-amino]-1H,1'H-[4,5']bibenzimidazolyl-7-carboxylic acid, Example (149)

A solution of compound (149b) (106 mg, 0.18 mmol) in ethanol (2 mL) with Palladium on carbon 10% (10 mg, 10% w) was stirred under hydrogen. After 3 hours, the solution was filtered on PTFE filter and evaporated. The residue was purified by preparative TLC on silica gel (DCM/MeOH/ammonia 7M in MeOH 8/1/1) to afford Example (149) (25.5 mg, 0.06 mmol, 30%). $^1$H NMR (300 MHz, CDCl$_3$) δ 1.25-1.38 (m, 1H), 1.45-1.58 (m, 2H), 1.82-1.88 (m, 3H), 2.00 (bd, J=13.6 Hz, 2H), 2.28 (bs, 7H), 2.25 (bs, 1H), 2.54 (t, J=6.6 Hz, 2H), 2.94 (s, 3H), 3.33 (t, J=6.6 Hz, 2H), 4.26 (tt, J=3.6/12.0 Hz, 1H), 7.51 (s, 1H), 7.60 (d, J=8.4 Hz, 1H), 8.07 (s, 1H), 8.17 (dd, J=1.8/8.7 Hz, 1H), 8.23 (s, 1H), 8.25 (d, J=1.8 Hz, 1H), 11.20 (bs, 1H). MS m/z ([M+H]$^+$) 461.

Example 150

Synthesis of 5-[(2-Dimethylamino-ethyl)-methyl-amino]-7-quinoxalin-6-yl-3H-benzimidazole-4-carboxamide

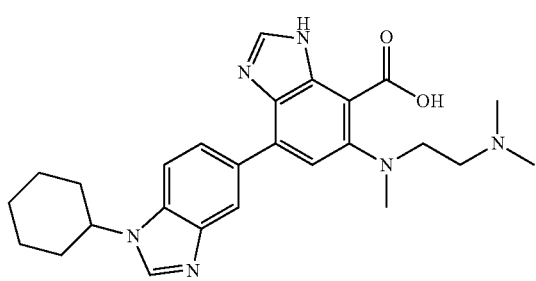

Example 149

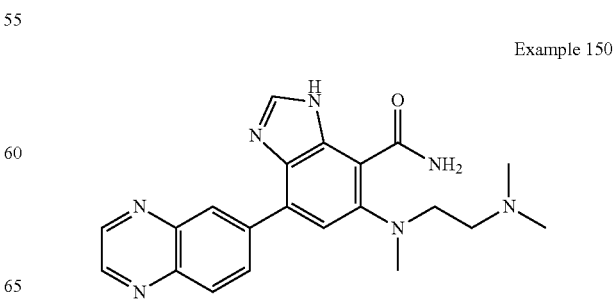

Example 150

Step 1: Synthesis of 6-(tetramethyl-1,3,2-dioxaborolan-2-yl)quinoxaline (150a)

According to the procedure described in example 123, step 4, 6-bromoquinoxaline (210 mg, 1.0 mmol) was converted, after purification by preparative TLC on silica gel (DCM/MeOH 95/5), to compound (150a) (130 mg, 0.50 mmol, 50%) as a yellow oil which was engaged in the following step without additional purification. MS m/z ([M+H]$^+$) 257.

Step 2: 5-[(2-Dimethylamino-ethyl)-methyl-amino]-7-quinoxalin-6-yl-3H-benzimidazole-4-carboxamide, Example (150)

According to the procedure described in example 115, step 2, compound (124g) (75.7 mg, 0.22 mmol) was converted, by reaction with compound (150a) (57 mg, 0.22 mmol) and after purification by preparative TLC on silica gel (DCM/MeOH 98/2 with 5% of ammonia), to Example (150) as a yellow powder (16.2 mg, 0.04 mmol, 19%). $^1$H NMR (400 MHz, CDCl$_3$) δ 2.26 (s, 6H), 2.52 (t, J=6.2 Hz, 2H), 2.84 (s, 3H), 3.28 (t, J=6.2 Hz, 2H), 5.87-5.88 (m, 1H), 7.58 (s, 1H), 8.22 (s, 1H), 8.28-8.30 (m, 1H), 8.67-8.69 (m, 2H), 8.90-8.92 (m, 2H), 10.74 (d, J=3.2 Hz, 1H), 11.65 (s, 1H). MS m/z ([M+H]$^+$) 390.

Example 151

Synthesis of 5-[(2-Dimethylamino-ethyl)-methyl-amino]-7-(8-oxo-5,6,7,8-tetrahydro-naphthalen-2-yl)-3H-benzimidazole-4-carboxamide

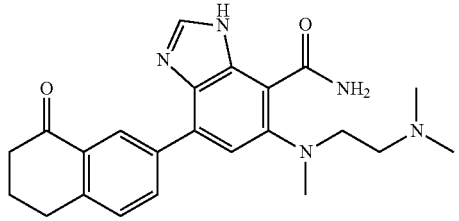

Example 151

Step 1: 7-(tetramethyl-1,3,2-dioxaborolan-2-yl)-1,2,3,4-tetrahydronaphthalen-1-one (151a)

According to the procedure described in example 123, step 4, 7-bromo-1,2,3,4-tetrahydronaphthalen-1-one (225 mg, 1 mmol) was converted to crude compound (151a) (428 mg) which was used in the next step without further purification. $^1$H NMR (400 MHz, DMSO-d$_6$) δ 1.29 (s, 12H), 2.02 (m, 2H), 2.60 (m, 2H), 2.95 (t, J=6.0 Hz, 2H), 7.36 (d, J=7.6 Hz, 1H), 7.78 (dd, J=7.6/1.4 Hz, 1H), 8.18 (d, J=1.1 Hz, 1H). MS m/z ([M+H]$^+$) 273.

Step 2: 5-[(2-Dimethylamino-ethyl)-methyl-amino]-7-(8-oxo-5,6,7,8-tetrahydro-naphthalen-2-yl)-3H-benzimidazole-4-carboxamide, Example (151)

According to the procedure described in example 115, step 2, compound (124g) (170 mg, 0.5 mmol) was converted, by reaction with crude compound (151a) (214 mg) and after purification by preparative TLC on silica gel (DCM/MeOH 9/1 with 1% of ammonia), to Example (151) (80 mg, 0.2 mmol, 40%). $^1$H NMR (400 MHz, DMSO-d$_6$) δ 2.04-2.09 (m, 2H), 2.11 (s, 6H), 2.36 (t, J=6.3 Hz, 2H), 2.63 (m, 2H), 2.70 (s, 3H), 2.99 (t, J=5.9 Hz, 2H), 3.16 (t, J=6.3 Hz, 2H), 7.44 (s, 1H), 7.47 (d, J=8.8 Hz, 1H), 7.59 (d, J=3.2 Hz, 1H), 8.14 (s, 1H), 8.27 (dd, J=8.0/2.0 Hz, 1H), 8.64 (d, J=2.0 Hz, 1H), 9.97 (d, J=3.0 Hz, 1H), 12.42 (s, 1H). MS m/z ([M+H]$^+$) 406.

Example 152

Synthesis of 6-[(2-Dimethylamino-ethyl)-methyl-amino]-1'-ethyl-7'-methoxy-1H,1'H-[4,5']]bibenzimidazolyl-7-carboxamide

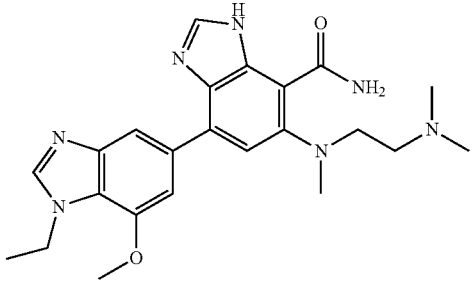

Example 152

Step 1: N-ethyl-2-methoxy-6-nitroaniline (152a)

A solution of ethylamine 2M in THF (5.4 mL, 10.77 mmol) was added in a weathon tube under pressure with 2-bromo-1-methoxy-3-nitrobenzene (500 mg, 2.15 mmol) in dioxane (7.5 mL). The mixture was stirred at 100° C. for 3 days and evaporated to give compound (152a) as orange oil (250 mg, 1.27 mmol, 60%). $^1$H NMR (400 MHz, CDCl$_3$) δ 1.28 (t, J=7.2 Hz, 3H), 3.58-3.64 (m, 2H), 3.88 (s, 3H), 6.65 (m, 1H), 6.94 (dd, J=7.8/1.4 Hz, 1H), 7.52 (bs, 1H), 7.74 (dd, J=8.7 Hz, J=1.4 Hz, 1H). MS m/z ([M+H]$^+$) 197.

Step 2: 4-bromo-N-ethyl-2-methoxy-6-nitroaniline (152b)

Bromine (230 µl, 4.5 mmol) was introduced to a solution of compound (152a) (880 mg, 4.5 mmol) in acetic acid (4.5 mL). The mixture was stirred at room temperature for 5 hours. After addition of ice water, the reaction mixture was stirred for 1 hour, filtered and washed with water to give compound (152b) as a red powder (1.1 g, 4 mmol, 90%). $^1$H NMR (400 MHz, CDCl$_3$) δ 1.30 (t, J=7.2 Hz, 3H), 3.62 (q, J=7.2 Hz, 2H), 3.90 (s, 3H), 7.00 (d, J=2.2 Hz, 1H), 7.90 (d, J=2.2 Hz, 1H). MS m/z ([M+H]$^+$) 275/277.

Step 3: 4-bromo-1-N-ethyl-6-methoxybenzene-1,2-diamine (152c)

Tin chloride dihydrate (4.95 g, 0.022 mol) was introduced to a solution of compound (152b) (1.2 g, 4.4 mmol) in methanol (20 mL). The mixture was stirred at 70° C. for 3 hours. A solution of sodium hydroxide 30% was added and the organic layer was extracted twice with ethyl acetate. The combined organic phases were dried over sodium sulfate, filtered and concentrated. The crude product was purified by column chromatography on silica gel (cyclohexane/EtOAc 9/1) to give compound (152c) as yellow oil (850 mg, 3.5 mmol, 79%). $^1$H NMR (400 MHz, CDCl$_3$) δ 1.16 (t, J=7.1 Hz, 3H), 2.91 (q, J=7.1 Hz, 2H), 3.90 (bs, 2H) 3.91 (s, 3H), 6.47 (d, J=2.0 Hz, 1H), 6.55 (d, J=2.0 Hz, 1H). MS m/z ([M+H]$^+$) 245/247.

Step 4:
5-Bromo-1-ethyl-7-methoxy-1H-benzimidazole (152d)

According to the procedure described in example 125, step 3, compound (152c) (850 mg, 3.5 mmol) was converted, after purification by preparative TLC on silica gel (DCM/MeOH 95/5), to compound (152d) as a beige powder (300 mg, 1.18 mmol, 34%). $^1$H NMR (400 MHz, CDCl$_3$) δ 1.51 (t, J=7.2 Hz, 3H), 3.98 (s, 3H), 4.42 (q, J=7.2 Hz, 2H), 6.84 (d, J=1.5 Hz, 1H), 7.57 (d, J=1.5 Hz, 1H), 7.75 (s, 1H). MS m/z ([M+H]$^+$) 255/257.

Step 5: 1-Ethyl-7-methoxy-5-(4,4,5,5-tetramethyl-1,3,2-dioxaborolan-2-yl)-1H-benzimidazole (152e)

According to the procedure described in example 125, step 4, compound (152d) (236 mg, 0.92 mmol) was converted to crude compound (152e) (300 mg) which was used in the next step without further purification. MS m/z ([M+H]$^+$) 303.

Step 6: 6-[(2-Dimethylamino-ethyl)-methyl-amino]-1'-ethyl-7'-methoxy-1H,1'H-[4,5']]bibenzimidazolyl-7-carboxamide, Example (152)

According to the procedure described in example 115, step 2, compound (124g) (70 mg, 0.20 mmol) was converted, by reaction with crude compound (152e) (60.4 mg, 0.20 mmol) and after purification by preparative TLC on silica gel (DCM/MeOH 95/5 with 2% of ammonia), to Example (152) as a colorless oil (5.3 mg, 0.012 mmol, 6%). $^1$H NMR (400 MHz, CDCl$_3$) δ 1.55 (t, J=7.2 Hz, 3H), 2.26 (s, 6H), 2.51 (t, J=6.2 Hz, 2H), 2.83 (s, 3H), 3.25 (t, J=6.2 Hz, 2H), 4.09 (s, 3H), 4.49 (q, J=7.2 Hz, 2H), 5.78-5.79 (m, 1H), 7.49 (s, 1H), 7.75 (d, J=1.2 Hz, 1H), 7.83 (d, J=1.2 Hz, 1H), 7.85 (s, 1H), 8.16 (s, 1H), 10.7 (bs, 1H), 11.57 (bs, 1H). MS m/z ([M+H]$^+$) 436.

Example 153

Synthesis of 5-[(2-Dimethylamino-ethyl)-methyl-amino]-7-{8-(methoxyimino)-5,6,7,8-tetrahydro-naphthalen-2-yl}-3H-benzimidazole-4-carboxamide Example 153

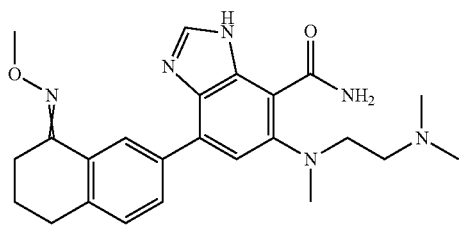

A solution of Example (151) (80 mg, 0.2 mmol), O-Methylhydroxylamine hydrochloride (50 mg, 0.6 mmol) and sodium acetate (98 mg, 1.2 mmol) in ethanol (4 mL) and THF (1 mL) was stirred overnight at 50° C. and then concentrated. The residue was diluted with ethyl acetate. The organic layer was washed with saturated solution of bicarbonate, brine, dried over sodium sulfate, filtered and concentrated under reduced pressure. The crude product was purified by preparative TLC on silica gel (DCM/MeOH 95/5) to afford Example (153) (23 mg, 0.053 mmol, 27%). $^1$H NMR (400 MHz, DMSO-d$_6$) δ 1.78-1.81 (m, 2H), 2.13 (s, 6H), 2.38 (t, J=6.4 Hz, 2H), 2.69-2.72 (m, 5H), 2.78 (t, J=6.9 Hz, 2H), 3.17 (t, J=6.4 Hz, 2H), 3.91 (s, 3H), 7.33 (d, J=8.0 Hz, 1H), 7.37 (s, 1H), 7.58 (d, J=3.5 Hz, 1H), 7.96 (dd, J=7.9/1.8 Hz, 1H), 8.14 (s, 1H), 8.50 (d, J=1.8 Hz, 1H), 9.97 (d, J=3.5 Hz, 1H), 12.39 (s, 1H). MS m/z ([M+H]$^+$) 435.

Example 154

Synthesis of 5-[(2-Dimethylamino-ethyl)-methyl-amino]-7-(8-hydroxy-5,6,7,8-tetrahydro-naphthalen-2-yl)-3H-benzimidazole-4-carboxamide Example 154

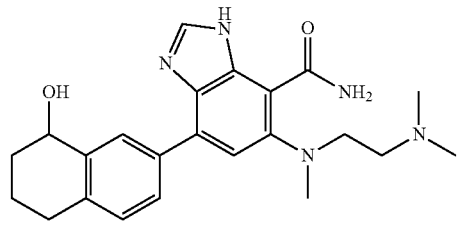

Step 1: 7-bromo-1,2,3,4-tetrahydronaphthalen-1-ol (154a)

To a cold solution of 7-bromo-1,2,3,4-tetrahydronaphthalen-1-one (225 mg, 1 mmol) in DCM (1.5 ml) and methanol (3 ml) was added dropwise NaBH$_4$ (95 mg, 2.5 mmol). The reaction mixture was stirred 1 hour at room temperature and quenched with water. The aqueous layer was extracted with DCM. The organic layer was dried over sodium sulfate, filtered and concentrated under reduced pressure to give compound (154a) (229 mg, 1 mmol, 100%) $^1$H NMR (400 MHz, CDCl$_3$) δ 1.73-1.87 (m, 2H), 1.92-2.02 (m, 2H), 2.61-2.68 (m, 1H), 2.72-2.79 (m, 1H), 4.73 (m, 1H), 6.96 (d, J=8.2 Hz, 1H), 7.29 (dd, J=8.2/2.1 Hz, 1H), 7.58 (d, J=2.1 Hz, 1H). MS m/z ([M−H$_2$O+H]$^+$) 209-211.

Step 2: 7-(tetramethyl-1,3,2-dioxaborolan-2-yl)-1,2,3,4-tetrahydronaphthalen-1-ol (154b)

According to the procedure described in example 123, step 4, compound (154a) (229 mg, 1 mmol) was converted to crude compound (154b) (730 mg) which was used in the next step without further purification. $^1$H NMR (400 MHz, DMSO-d$_6$) δ 1.15 (s, 12H), 1.62-1.67 (m, 2H), 1.84-1.88 (m, 2H), 2.64-2.75 (m, 2H), 4.53-4.57 (m, 1H), 5.13 (d, J=5.9

Hz, 1H), 7.04 (d, J=7.6 Hz, 1H), 7.41 (d, J=7.5 Hz, 1H), 7.75 (s, 1H). MS m/z ([M–H$_2$O+H]$^+$) 257.

Step 3: 5-[(2-Dimethylamino-ethyl)-methyl-amino]-7-(8-hydroxy-5,6,7,8-tetrahydro-naphthalen-2-yl)-3H-benzimidazole-4-carboxamide, Example (154)

According to the procedure described in example 115, step 2, compound (124g) (170 mg, 0.5 mmol) was converted, by reaction with crude compound (154b) (365 mg) and after purification by preparative TLC on silica gel (DCM/MeOH 95/5 with 1% of ammonia), to Example (145) (33 mg, 0.081 mmol, 16%). $^1$H NMR (400 MHz, DMSO-d$_6$) δ 1.69-1.78 (m, 2H), 1.90-1.95 (m, 2H), 2.12 (s, 6H), 2.37 (t, J=6.3 Hz, 2H), 2.66-2.81 (m, 5H), 3.15 (t, J=6.3 Hz, 2H), 4.64-4.69 (m, 1H), 5.13 (d, J=5.8 Hz, 1H), 7.17 (d, J=8.0 Hz, 1H), 7.39 (s, 1H), 7.55 (d, J=3.5 Hz, 1H), 7.95 (dd, J=7.9/1.8 Hz, 1H), 8.09 (d, J=1.6 Hz, 1H), 8.12 (s, 1H), 9.99 (d, J=3.5 Hz, 1H), 12.37 (s, 1H). MS m/z ([M+H]$^+$) 408.

Example 155

Synthesis of 5-[(2-Dimethylamino-ethyl)-methyl-amino]-7-(3-oxo-indan-5-yl)-3H-benzimidazole-4-carboxamide

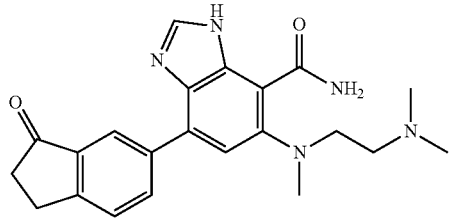

Example 155

Step 1: 6-(tetramethyl-1,3,2-dioxaborolan-2-yl)-2,3-dihydro-1H-inden-1-one (155a)

According to the procedure described in example 123, step 4, 6-bromo-2,3-dihydro-1H-inden-1-one (211 mg, 1 mmol) was converted to crude compound (155a) (584 mg) which was used in the next step without further purification. $^1$H NMR (400 MHz, DMSO-d$_6$) δ 1.31 (s, 12H), 2.64 (m, 2H), 3.14 (m, 2H), 7.78 (dd, J=7.6/0.5 Hz, 1H), 7.90 (d, J=2.9 Hz, 1H), 7.92 (s, 1H). MS m/z ([M+H]$^+$) 259.

Step 2: 5-[(2-Dimethylamino-ethyl)-methyl-amino]-7-(3-oxo-indan-5-yl)-3H-benzimidazole-4-carboxamide, Example (155)

According to the procedure described in example 115, step 2, compound (124g) (340 mg, 1 mmol) was converted, by reaction with crude compound (155a) (584 mg) and after purification by preparative TLC on silica gel (DCM/MeOH 9/1), to Example (155) (163 mg, 0.42 mmol, 42%). $^1$H NMR (400 MHz, DMSO-d$_6$) δ 2.14 (s, 6H), 2.37-2.41 (m, 2H), 2.72-2.74 (m, 5H), 3.17-3.22 (m, 4H), 7.55 (s, 1H), 7.62 (s, 1H), 7.71 (d, J=8.0 Hz, 1H), 8.18 (s, 1H), 8.47 (dd, J=8.0/1.7 Hz, 1H), 8.49 (s, 1H), 10.01 (s, 1H), 12.46 (s, 1H). MS m/z ([M+H]$^+$) 392.

Example 156

Synthesis of 5-[(2-Dimethylamino-ethyl)-methyl-amino]-7-(3-hydroxy-indan-5-yl)-3H-benzimidazole-4-carboxamide

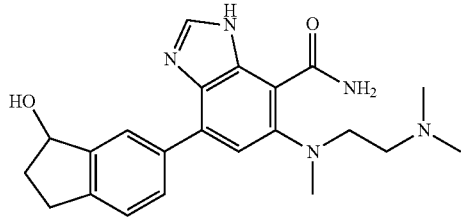

Example 156

Step 1: 6-bromo-2,3-dihydro-1H-inden-1-ol (157a)

According to the procedure described in example 154, step 1, 6-bromo-2,3-dihydro-1H-inden-1-one (211 mg, 1 mmol) was converted to compound (156a) (206 mg, 0.97 mmol, 97%) without further purification. $^1$H NMR (400 MHz, DMSO-d$_6$) δ 1.74-1.79 (m, 1H), 2.29-2.36 (m, 1H), 2.61-2.69 (m, 1H), 2.81-2.88 (m, 1H), 5.02-5.05 (m, 1H), 5.34 (d, J=5.8 Hz, 1H), 7.17 (d, J=8.0 Hz, 1H), 7.35 (dd, J=8.0/1.9 Hz, 1H), 7.44 (d, J=1.4 Hz, 1H). MS m/z ([M–H$_2$O+H]$^+$) 195-197.

Step 2: 6-(tetramethyl-1,3,2-dioxaborolan-2-yl)-2,3-dihydro-1H-inden-1-ol (156b)

According to the procedure described in example 123, step 4, compound (156a) (206 mg, 0.97 mmol) was converted to crude compound (156b) (580 mg) which was used in the next step without further purification. $^1$H NMR (400 MHz, DMSO-d$_6$) δ 1.30 (s, 12H), 1.71-1.80 (m, 1H), 2.29-2.37 (m, 1H), 2.68-2.77 (m, 1H), 2.89-2.95 (m, 1H), 5.04 (m, 1H), 5.22 (d, J=5.7 Hz, 1H), 7.23 (d, J=7.5 Hz, 1H), 7.52 (d, J=7.5 Hz, 1H), 7.94 (s, 1H). MS m/z ([M–H$_2$O+H]$^+$) 243.

Step 3: 5-[(2-Dimethylamino-ethyl)-methyl-amino]-7-(3-hydroxy-indan-5-yl)-3H-benzimidazole-4-carboxamide, Example (156)

According to the procedure described in example 115, step 2, compound (124g) (170 mg, 0.5 mmol) was converted, by reaction with crude compound (156b) (300 mg) and after purification by preparative TLC on silica gel (DCM/MeOH 9/1), to Example (156) (34 mg, 0.086 mmol, 17%). $^1$H NMR (400 MHz, DMSO-d$_6$) δ 1.83-1.87 (m, 1H), 2.16 (s, 6H), 2.36-2.41 (m, 3H), 2.73 (s, 3H), 2.76-2.82 (m, 1H), 2.95-3.02 (m, 1H), 3.17-3.22 (m, 2H), 5.12-5.16 (m, 1H), 5.29 (d, J=6.0 Hz, 1H), 7.35 (d, J=7.8 Hz, 1H), 7.43 (s, 1H), 7.59 (d, J=2.6 Hz, 1H), 7.99 (d, J=7.8 Hz, 1H), 8.10 (s, 1H), 8.15 (s, 1H), 9.99 (d, J=2.6 Hz, 1H), 12.40 (s, 1H). MS m/z ([M+H]$^+$) 394.

Example 157

Synthesis of 5-[(2-Dimethylamino-ethyl)-methyl-amino]-7-{3-(methoxyimino)-indan-5-yl}-3H-benzimidazole-4-carboxylic acid amide Example 157

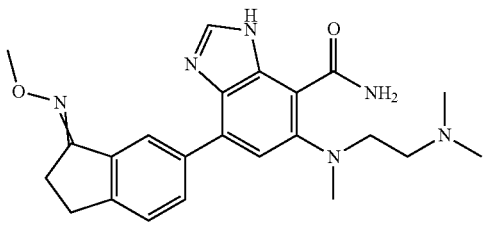

According to the procedure described in example 153, Example (155) (79 mg, 0.2 mmol) was converted, by reaction with Methylhydroxylamine hydrochloride (50 mg, 0.6 mmol) and after purification by preparative TLC on silica gel (DCM/MeOH 85/15), to Example (157) as a mixture of both isomers (ratio E/Z 66/34, 29 mg, 0.069 mmol, 34%). $^1$H NMR (400 MHz, DMSO-$d_6$) δ 1.86 (bs, 2H), 2.14 (s, 6H), 2.38-2.42 (m, 2H), 2.74 (s, 3H), 2.83-2.91 (m, 2H), 3.07-3.12 and 3.17-3.22 (2m, 2H), 3.89 and 3.94 (2s, 3H), 7.38 and 7.48 (2s, 1H), 7.53 and 7.54 (2d, J=8.0 Hz, 1H), 7.61 (bs, 1H), 8.12 and 8.14 (2dd, J=8.0/1.5 Hz, 1H), 8.16 and 8.18 (2s, 1H), 8.40 and 8.86 (2bs, 1H), 9.98 and 10.02 (2bs, 1H), 12.42 and 12.44 (2s, 1H). MS m/z ([M+H]$^+$) 421.

Example 158

Synthesis of 5-[(2-Dimethylamino-ethyl)-methyl-amino]-7-(1-ethyl-4-oxo-1,4-dihydro-quinolin-6-yl)-3H-benzimidazole-4-carboxamide Example 158

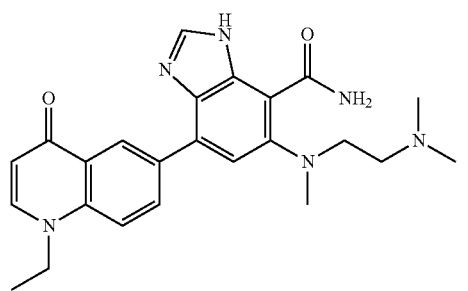

Step 1: 5-[(4-Bromo-phenylamino)-methylene]-2,2-dimethyl-1,3-dioxinane-4,6-dione (158a)

Under argon atmosphere, a solution of Meldrum's acid (432 mg, 3 mmol) in trimethyl orthoformate (5.5 mL, 50 mmol) was heated to reflux for 2 hours. At room temperature, 4-bromoaniline (344 mg, 2 mmol) was added and the reaction mixture was heated under reflux overnight. The precipitate was filtered and washed with diethyl ether to give compound (158a) (535 mg, 1.64 mmol, 82%) $^1$H NMR (400 MHz, DMSO-$d_6$) δ 1.68 (s, 6H), 7.55 (d, J=8.9 Hz, 2H), 7.62 (d, J=8.9 Hz, 2H), 8.55 (s, 1H), 11.25 (s, 1H). MS m/z ([M−H]$^−$) 324-326.

Step 2: 6-bromo-1,4-dihydroquinolin-4-one (158b)

Compound (158a) (535 mg, 1.64 mmol) was dissolved in hot diphenyl ether (10 mL) and heated under reflux for 30 minutes until the formation of gaseous products ceased. After cooling, pentane (8 mL) was added and the mixture was stirred 48 hours at room temperature. The precipitate was isolated by filtration and washed with pentane to afford compound (158b) (258 mg, 1.15 mmol, 70%). $^1$H NMR (400 MHz, DMSO-$d_6$) δ 6.08 (d, J=7.4 Hz, 1H), 7.53 (d, J=8.8 Hz, 1H), 7.79 (dd, J=8.8/2.3 Hz, 1H), 7.96 (d, J=7.4 Hz, 1H), 8.17 (d, J=2.3 Hz, 1H), 11.9 (bs, 1H). MS m/z ([M+H]$^+$) 224-226.

Step 3: 6-bromo-1-ethyl-1,4-dihydroquinolin-4-one (158c)

Under argon atmosphere, ethyl iodide (0.23 mL, 2.85 mmol) was added to a solution of compound (158b) (255 mg, 1.14 mmol) and potassium carbonate (472 mg, 3.42 mmol) in DMF (2 mL). The mixture was heated at 80° C. overnight. The middle was poured over ice and the aqueous layer was extracted with ethyl acetate. The organic layer was washed with water, brine, dried over sodium sulfate, filtered and concentrated under reduced pressure. The residue was purified by column chromatography on silica gel (DCM/MeOH 95/5) to give compound (158c) (144 mg, 0.57 mmol, 50%). $^1$H NMR (400 MHz, DMSO-$d_6$) δ 1.33 (t, J=7.1 Hz, 3H), 4.28 (q, J=7.1 Hz, 2H), 6.11 (d, J=7.7 Hz, 1H), 7.75 (d, J=9.1 Hz, 1H), 7.86 (dd, J=9.1/2.5 Hz, 1H), 8.05 (d, J=7.7 Hz, 1H), 8.25 (d, J=2.5 Hz, 1H). MS m/z ([M+H]$^+$) 252-254.

Step 4: 1-ethyl-6-(tetramethyl-1,3,2-dioxaborolan-2-yl)-1,4-dihydroquinolin-4-one (158d)

According to the procedure described in example 148, step 2, compound (158c) (189 mg, 0.75 mmol) was converted to crude compound (158d) (976 mg) which was used in the next step without further purification. MS m/z ([M+H]$^+$) 300.

Step 5: 5-[(2-Dimethylamino-ethyl)-methyl-amino]-7-(1-ethyl-4-oxo-1,4-dihydro-quinolin-6-yl)-3H-benzimidazole-4-carboxamide, Example (158)

According to the procedure described in example 115, step 2, compound (124g) (255 mg, 0.75 mmol) was converted, by reaction with crude compound (158d) (976 mg) and after purification by preparative TLC on silica gel (DCM/MeOH 9/1+1% of ammonia), to Example (158) (45 mg, 0.104 mmol, 14%). $^1$H NMR (400 MHz, DMSO-$d_6$) δ 1.40 (t, J=7.1 Hz, 3H), 2.19 (s, 6H), 2.45-2.50 (m, 2H), 2.77 (s, 3H), 3.22-3.28 (m, 2H), 4.36 (q, J=7.1 Hz, 2H), 6.12 (d, J=7.7 Hz, 1H), 7.55 (s, 1H), 7.67 (bs, 1H), 7.88 (d, J=9.1 Hz, 1H), 8.04 (d, J=7.7 Hz, 1H), 8.20 (s, 1H), 8.58 (dd, J=9.0/2.2 Hz, 1H), 8.94 (d, J=2.2 Hz, 1H), 9.91 (bs, 1H), 12.48 (s, 1H). MS m/z ([M+H]$^+$) 433.

Example 159

Synthesis of 1'-Cyclohexyl-6-(2-pyrrolidin-1-yl-ethoxy)-1H,1'H-[4,5']]bibenzimidazolyl-7-carboxamide methanesulfonic acid salt

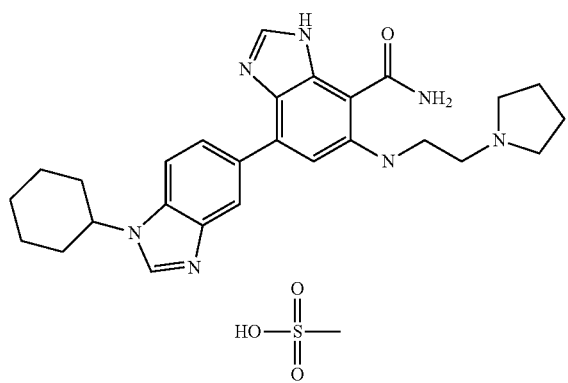

Example 159

Step 1: 2-Amino-4-bromo-3-nitro-6-(2-pyrrolidin-1-yl-ethoxy)-benzonitrile (159a)

According to the procedure described in example 104, step 1, compound (57b) (1 g, 3.84 mmol) was converted, by reaction with 2-Pyrrolidin-1-yl-ethanol (840 µL, 7 mmol) and after purification by column chromatography on silica gel (DCM/MeOH 95/5), to compound (159a) (820 mg, 2.31 mmol, 60%). $^1$H NMR (400 MHz, DMSO-$d_6$) δ 1.62-1.71 (m, 4H), 2.50-2.60 (m, 4H), 2.73-2.85 (m, 2H), 4.27 (t, J=5.6 Hz, 2H), 6.84 (bs, 2H), 6.85 (s, 1H). MS m/z ([M+H]$^+$) 355/357.

Step 2: 7-Bromo-5-(2-pyrrolidin-1-yl-ethoxy)-3H-benzimidazole-4-carbonitrile (159b)

According to the procedure described in example 17, step 4, compound (159a) (820 mg, 2.31 mmol) was converted, after purification by column chromatography on silica gel (DCM/MeOH 9/1+0.5% of Methanol ammonia 7M), to compound (159b) (320 mg, 0.955 mmol, 41%). $^1$H NMR (400 MHz, DMSO-$d_6$) δ 1.64-1.72 (m, 4H), 2.53-2.59 (m, 4H), 2.84 (t, J=5.6 Hz, 2H), 4.29 (t, J=5.6 Hz, 2H), 7.45 (s, 1H), 8.39 (s, 1H), 13.36 (bs, 1H). MS m/z ([M+H]$^+$) 335/337.

Step 3: 1'-Cyclohexyl-6-(2-pyrrolidin-1-yl-ethoxy)-1H,1'H-[4,5']]bibenzimidazolyl-7-carbonitrile (159c)

Under argon atmosphere, compound (159b) (320 mg, 0.95 mmol), 1-Cyclohexyl-5-(4,4,5,5-tetramethyl-1,3,2-dioxaborolan-2-yl)-1H-benzimidazole (404 mg, 1.24 mmol) and potassium carbonate (404 mg, 2.92 mmol) were dissolved in a mixture of DMF (7 mL) and water (1.5 mL). The solution was degassed under argon for 5 minutes and [1,1'-Bis(diphenylphosphino)ferrocene]dichloropalladium(II) (109 mg, 0.133 mmol) was added. The reaction was heated at 100° C. After 1 hour, the middle was concentrated. The residue was triturated with a mixture of DCM/MeOH (9/1) to eliminate residual salts. The filtrate was concentrated and triturated with diethyl ether to eliminate residual DMF. The crude material was purified by preparative TLC (DCM/MeOH ammonia 7M 9/1) to give compound (159c) (140 mg, 0.308 mmol, 32%). $^1$H NMR (400 MHz, DMSO-$d_6$) δ 1.25-1.39 (m, 1H), 1.47-1.60 (m, 2H), 1.65-1.79 (m, 5H), 1.83-1.97 (m, 4H), 2.04-2.12 (m, 2H), 2.53-2.64 (m, 4H), 2.88 (t, J=5.6 Hz, 2H), 4.33-4.52 (m, 3H), 7.17-7.38 (m, 1H), 7.56-7.67 (m, 1H), 7.74-7.92 (m, 1H), 7.98-8.19 (m, 1H), 8.28-8.59 (m, 2H), 12.96 and 13.28 (2bs, 1H). MS m/z ([M+H]$^+$) 455.

Step 4: 1'-Cyclohexyl-6-(2-pyrrolidin-1-yl-ethoxy)-1H,1'H-[4,5']]bibenzimidazolyl-7-carboxamide (159d)

According to the procedure described in example 138, compound (159c) (140 mg, 0.308 mmol) was converted, after purification by preparative TLC (DCM/MeOH ammonia 7M 9/1), to compound (159d) (89 mg, 0.188 mmol, 61%). $^1$H NMR (400 MHz, DMSO-$d_6$) δ 1.26-1.37 (m, 1H), 1.46-1.60 (m, 2H), 1.69-1.79 (m, 5H), 1.84-1.94 (m, 4H), 2.04-2.13 (m, 2H), 2.50-2.58 (m, 4H), 2.88 (t, J=5.2 Hz, 2H), 4.37-4.48 (m, 3H), 7.34 (s, 1H), 7.56 (bs, 1H), 7.75 (d, J=8.6 Hz, 1H), 8.10 (s, 1H), 8.11 (dd, J=1.5/8.6 Hz, 1H), 8.38 (s, 1H), 8.51 (d, J=1.5 Hz, 1H), 8.67 (bs, 1H), 12.33 (bs, 1H). MS m/z ([M+H]$^+$) 473. MS m/z ([M−H]$^-$) 471.

Step 5: 1'-Cyclohexyl-6-(2-pyrrolidin-1-yl-ethoxy)-1H,1'H-[4,5']]bibenzimidazolyl-7-carboxamide methanesulfonic acid salt, Example (159)

According to the procedure described in example 108, compound (159d) (89 mg, 0.188 mmol) was converted, after trituration in diethyl ether, to Example (159) (88 mg, 0.155 mmol, 82%). $^1$H NMR (400 MHz, DMSO-$d_6$) δ 1.26-1.39 (m, 1H), 1.47-1.61 (m, 2H), 1.71-1.79 (m, 1H), 1.84-1.98 (m, 6H), 2.01-2.13 (m, 4H), 2.29 (s, 3H), 3.10-3.24 (m, 2H), 3.61-3.81 (m, 4H), 4.38-4.49 (m, 1H), 4.65 (bs, 2H), 7.36 (s, 1H), 7.74-7.91 (m, 3H), 8.11-8.21 (m, 2H), 8.43 (bs, 1H), 8.50 (bs, 1H), 9.76 (bs, 1H), 12.42 (bs, 1H). MS m/z ([M+H]$^+$) 473. MS m/z ([M−H]$^-$) 471.

Example 160

Synthesis of 1'-Cyclohexyl-6-(2-dimethylamino-ethylsulfanyl)-1H,1'H-[4,5']bibenzimidazolyl-7-carboxamide

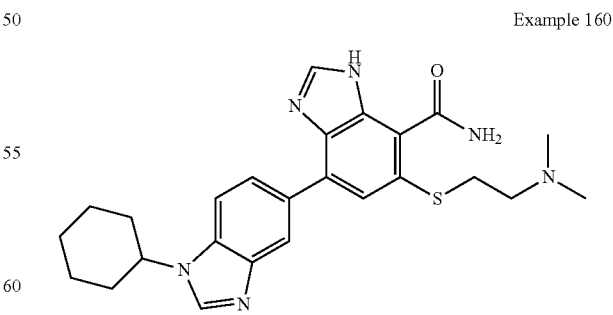

Example 160

Step 1: 4-Bromo-2,6-difluoro-benzamide (160a)

According to the procedure described in example 80, 4-Bromo-2,6-difluoro-benzoic acid (1 g, 4.22 mmol) was converted, by reaction with ammonia (0.5M in dioxane, 12.7 mL, 6.33 mmol), to compound (160a) (726 mg, 3.08 mmol, 72%). MS m/z ([M+H]⁺) 236/238.

Step 2: 4-Bromo-2,6-difluoro-3-nitro-benzamide (160b)

According to the procedure described in example 42, step 1, compound (160a) (726 mg, 3.08 mmol) was converted to compound (160b) as a beige solid (165 mg, 0.59 mmol, 19%). MS m/z ([M+H]⁺) 281/283.

Step 3: 2-Amino-4-bromo-6-fluoro-3-nitro-benzamide (160c)

According to the procedure described in example 51, step 2, compound (160b) (165 mg, 0.59 mmol) was converted, after purification by preparative TLC on silica gel (DCM/MeOH 9/1), to compound (160c) as a yellow solid (119 mg, 0.43 mmol, 73%). ¹H NMR (300 MHz, DMSO-d₆) δ 7.98 (d, J=6.9 Hz, 2H), 7.02 (d, J=9.2 Hz, 1H), 6.68 (bs, 2H). MS m/z ([M+H]⁺) 278/280.

Step 4: 2-Amino-4-(1-cyclohexyl-1H-benzimidazol-5-yl)-6-fluoro-3-nitro-benzamide (160d)

According to the procedure described in example 115, step 2, compound (160c) (119 mg, 0.43 mmol) was converted, by reaction with 1-Cyclohexyl-5-(4,4,5,5-tetramethyl-[1,3,2]dioxaborolan-2-yl)-1H-benzimidazole (146 mg, 0.45 mmol) and after purification by preparative TLC on silica gel (DCM/MeOH 9/1), to compound (160d) (113 mg, 0.28 mmol, 66%). ¹H NMR (400 MHz, DMSO-d₆) δ 1.24-1.34 (m, 1H), 1.45-1.55 (m, 2H), 1.73 (bd, J=12.0 Hz, 1H), 1.81-1.91 (m, 4H), 2.05 (bd, J=9.2 Hz, 2H), 4.39 (tt, J=3.6/11.6 Hz, 1H), 6.61-6.64 (m, 3H), 7.16 (dd, J=1.6/8.4 Hz, 1H), 7.58 (d, J=1.6 Hz, 1H), 7.74 (d, J=8.4 Hz, 1H), 7.98 (d, J=10.8 Hz, 2H), 8.42 (s, 1H). MS m/z ([M+H]⁺) 398.

Step 5: 2-Amino-4-(1-cyclohexyl-1H-benzimidazol-5-yl)-6-(2-dimethylamino-ethylsulfanyl)-3-nitro-benzamide (160e)

According to the procedure described in example 29, step 3, compound (160d) (111 mg, 0.28 mmol) was converted, by reaction with 2-Dimethylamino-ethanethiol chlorhydrate (47 mg, 0.33 mmol), to compound (160e) (134 mg, 0.28 mmol, 100%). MS m/z ([M+H]⁺) 483.

Step 6: 2,3-Diamino-4-(1-cyclohexyl-1H-benzimidazol-5-yl)-6-(2-dimethylamino-ethylsulfanyl)-benzamide (160f)

Compound (160e) (134 mg, 0.28 mmol) was dissolved in ethanol (4 mL). Tin chloride (526 mg, 2.78 mmol) was added and the solution was stirred for 16 hours at 50° C. The reaction mixture was filtered on PTFE filter to eliminate salts and concentrated under reduced pressure to afford compound (160f) (125 mg, 0.28 mmol, 100%). MS m/z ([M+H]⁺) 453.

Step 7: 1'-Cyclohexyl-6-(2-dimethylamino-ethylsulfanyl)-1H,1'H-[4,5']bibenzimidazolyl-7-carboxamide, Example (160)

A solution of compound (160f) (125 mg, 0.28 mmol) in formic acid (10 mL) was heated 4 hours at 110° C. The solution was concentrated. The residue was triturated with DCM. The solid was purified by preparative TLC on silica gel (DCM/MeOH 9/1) to afford Example (160) (31 mg, 0.07 mmol, 24%). ¹H NMR (300 MHz, CD₃OD) δ 1.37-1.48 (m, 1H), 1.57-1.69 (m, 3H), 1.84 (d, J=12.4 Hz, 1H), 1.90-2.02 (m, 4H), 2.20-2.35 (m, 7H), 2.66 (bs, 2H), 3.19 (t, 2H), 4.45 (tt, J=3.6/11.6 Hz, 1H), 7.63 (bs, 1H), 7.78 (d, J=6.4 Hz, 2H), 8.09 (bs, 1H), 8.24 (s, 1H), 8.36 (bs, 1H). MS m/z ([M+H]⁺) 463.

Example 161

Synthesis of 1'-(4,4-Difluoro-cyclohexyl)-6-[(2-dimethylamino-ethyl)-methyl-amino]-1H,1'H-[4,5'] bibenzimidazolyl-7-carboxamide

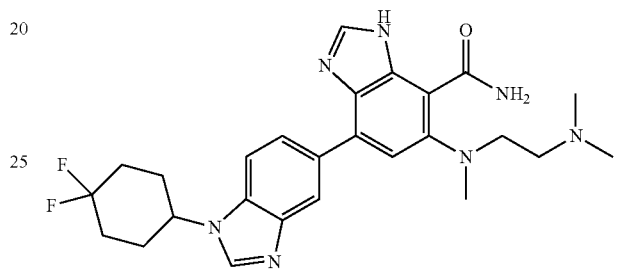

Example 161

Step 1: (4-Bromo-2-nitro-phenyl)-(4,4-difluoro-cyclohexyl)-amine (161a)

4,4-difluorocyclohexylamine hydrochloride (470 mg, 2.7 mmol) and 5-bromo-2-fluoronitrobenzene (500 mg, 2.3 mmol) were added to a solution of acetonitrile (3 mL) and triethylamine (315 µL, 2.7 mmol). The mixture was stirred at 85° C. for 16 hours. Water was added and the organic layer was extracted twice with ethyl acetate. The combined organic phases were dried over sodium sulfate, filtered and concentrated to give compound (161a) as orange powder (780 mg, 2.3 mmol, 100%). MS m/z ([M+H]⁺) 336.

Step 2: 4-Bromo-N*1*-(4,4-difluoro-cyclohexyl)-benzene-1,2-diamine (161b)

According to the procedure described in example 123, step 2, compound (161a) (780 mg, 2.3 mmol) was converted to crude compound (161b) (500 mg, 1.6 mmol) which was used in the next step without further purification. MS m/z ([M+H]⁺) 306.

Step 3: 5-Bromo-1-(4,4-difluoro-cyclohexyl)-1H-benzimidazole (161c)

According to the procedure described in example 125, step 3, crude compound (161b) (500 mg, 1.6 mmol) was converted, after purification by preparative TLC on silica gel (DCM/MeOH 95/5), to compound (161c) as a brown oil (250 mg, 0.8 mmol, 50%). MS m/z ([M+H]⁺) 315/317.

Step 4: 1-(4,4-Difluoro-cyclohexyl)-5-(4,4,5,5-tetramethyl-[1,3,2]dioxaborolan-2-yl)-1H-benzimidazole (161d)

According to the procedure described in example 123, step 4, compound (161c) (250 mg, 0.8 mmol) was converted to crude compound (161d) (500 mg) as a brown oil which was engaged in the following step without further purification. MS m/z ([M+H]⁺) 362.

Step 5: 1'-(4,4-Difluoro-cyclohexyl)-6-[(2-dimethyl-amino-ethyl)-methyl-amino]-1H,1'H-[4,5']bibenz-imidazolyl-7-carboxamide, Example (161)

According to the procedure described in example 115, step 2, compound (124g) (102 mg, 0.3 mmol) was converted, by reaction with compound (161d) (286 mg, 0.8 mmol) and after purification by preparative TLC on silica gel (DCM/MeOH 95/5 with 3% of ammonia), to Example (161) as a colorless oil (12 mg, 0.024 mmol, 9%). ¹H NMR (400 MHz, CDCl₃) δ 2.05-2.15 (m, 2H), 2.26 (s, 6H), 2.28-2.42 (m, 6H), 2.50 (t, J=6.1 Hz, 2H), 2.82 (s, 3H), 3.25 (t, J=6.1 Hz, 2H), 4.40-4.44 (m, 1H), 5.83 (d, J=4.2 Hz, 1H), 7.47 (s, 1H), 7.59 (d, J=8.5 Hz, 1H), 8.06 (s, 1H), 8.18 (s, 1H), 8.23 (dd, J=8.5/1.5 Hz, 1H), 8.30 (d, J=1.1 Hz, 1H), 10.73 (d, J=3.8 Hz, 1H), 11.59 (s, 1H). MS m/z ([M+H]⁺) 496.

Example 162

Synthesis of 5-[(2-Dimethylamino-ethyl)-methyl-amino]-7-(5-nitro-3,4-dihydro-2H-1,4-benzoxazin-7-yl)-3H-benzimidazole-4-carboxamide

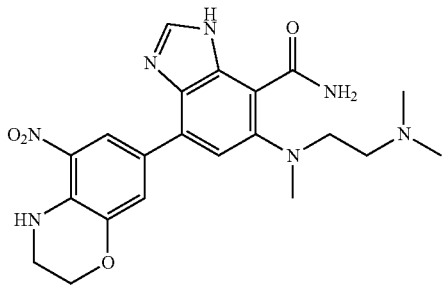

Example 162

Step 1: 5-Nitro-7-(4,4,5,5-tetramethyl-1,3,2-dioxaborolan-2-yl)-3,4-dihydro-2H-1,4-benzoxazine (162a)

According to the procedure described in example 123, step 4, 7-Bromo-5-nitro-3,4-dihydro-2H-1,4-benzoxazine (100 mg, 0.4 mmol) was converted to crude compound (162a) (268 mg) which was used in the next step without further purification. MS m/z ([M+H]⁺) 307.

Step 2: 5-[(2-Dimethylamino-ethyl)-methyl-amino]-7-(5-nitro-3,4-dihydro-2H-1,4-benzoxazin-7-yl)-3H-benzimidazole-4-carboxamide, Example (162)

According to the procedure described in example 115, step 2, compound (124g) (136 mg, 0.4 mmol) was converted, by reaction with crude compound (162a) (268 mg) and after purification by preparative TLC on silica gel (DCM/MeOH 9/1 with 1% of ammonia), to Example (162) (79 mg, 0.18 mmol, 45% over 2 steps). ¹H NMR (400 MHz, DMSO-d₆) δ 2.27 (bs, 6H), 2.45-2.50 (m, 2H), 2.73 (s, 3H), 3.26 (bs, 2H), 3.61-3.68 (m, 2H), 4.27 (t, J=4.4 Hz, 2H), 7.50 (s, 1H), 7.67 (bs, 1H), 7.96 (d, J=1.9 Hz, 1H), 8.20 (s, 1H), 8.53 (s, 1H), 8.86 (d, J=2.1 Hz, 1H), 9.84 (bs, 1H), 12.48 (s, 1H). MS m/z ([M+H]⁺) 440.

Example 163

Synthesis of 1'-(2,2-Difluoro-ethyl)-6-[(2-dimethyl-amino-ethyl)-methyl-amino]-1H,1'H-[4,5']bibenz-imidazolyl-7-carboxamide

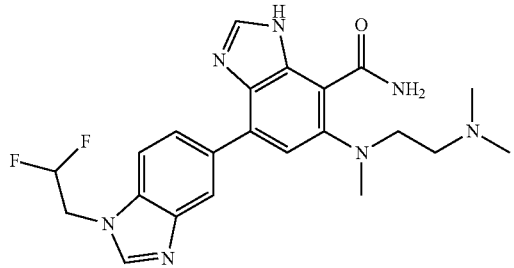

Example 163

Step 1: (4-Bromo-2-nitro-phenyl)-(2,2-difluoro-ethyl)-amine (164a)

According to the procedure described in example 161, step 1, 5-bromo-2-fluoronitrobenzene (500 mg, 2.3 mmol) was converted, by reaction with 2,2-difluoroethylamine (200 µL, 1.2 mmol), to compound (163a) as orange powder (600 mg, 2.1 mmol, 94%). MS m/z ([M+H]⁺) 282.

Step 2: 4-Bromo-N*1*-(2,2-difluoro-ethyl)-benzene-1,2-diamine (163b)

According to the procedure described in example 123, step 5, compound (163a) (600 mg, 2.1 mmol) was converted to crude compound (163b) (430 mg) which was used in the next step without further purification. MS m/z ([M+H]⁺) 252.

Step 3: 5-Bromo-1-(2,2-difluoro-ethyl)-1H-benzimi-dazole (163c)

According to the procedure described in example 125, step 3, crude compound (163b) (430 mg, 1.7 mmol) was converted, after purification by preparative TLC on silica gel (DCM/MeOH 95/5), to compound (163c) as a brown powder (371 mg, 1.4 mmol, 80%). MS m/z ([M+H]⁺) 262.

Step 4: 1-(2,2-Difluoro-ethyl)-5-(4,4,5,5-tetram-ethyl-[1,3,2]dioxaborolan-2-yl)-1H-benzimidazole (163d)

According to the procedure described in example 123, step 4, compound (163c) (371 mg, 1.4 mmol) was converted, after purification by preparative TLC on silica gel (DCM/MeOH 95/5), to compound (163d) as a white powder (200 mg, 0.6 mmol, 50%). MS m/z ([M+H]⁺) 309.

Step 5: 1'-(2,2-Difluoro-ethyl)-6-[(2-dimethylamino-ethyl)-methyl-amino]-1H,1'H-[4,5']bibenzimida-zolyl-7-carboxamide, Example (163)

According to the procedure described in example 115, step 2, compound (124g) (100 mg, 0.3 mmol) was converted, by reaction with compound (163d) (109 mg, 0.3 mmol) and after purification by preparative TLC on silica gel (DCM/MeOH 9/1 with 3% of ammonia), to Example (163) as a colorless oil (3.1 mg, 0.007 mmol, 2.4%). $^1$H NMR (400 MHz, CDCl$_3$) δ 2.27 (s, 6H), 2.52 (t, J=6.2 Hz, 2H), 2.83 (s, 3H), 3.26 (t, J=6.3 Hz, 2H), 4.60 (td, J=14.2/3.7 Hz, 2H), 5.80 (d, J=3.9 Hz, 1H), 6.12-6.26 (m, 1H), 7.47 (s, 1H), 7.59 (d, J=8.4 Hz, 1H), 8.01 (s, 1H), 8.18 (s, 1H), 8.26 (dd, J=1.5/8.4 Hz, 1H), 8.33 (d, J=1.1 Hz, 1H), 10.72 (s, 1H), 11.58 (s, 1H). MS m/z ([M+H]$^+$) 442.

Example 164

Synthesis of 1'-Cyclohexyl-6-[(2-dimethylamino-ethyl)-methyl-amino]-7'-methoxy-1H,1'H-[4,5']]bibenzimidazolyl-7-carboxamide

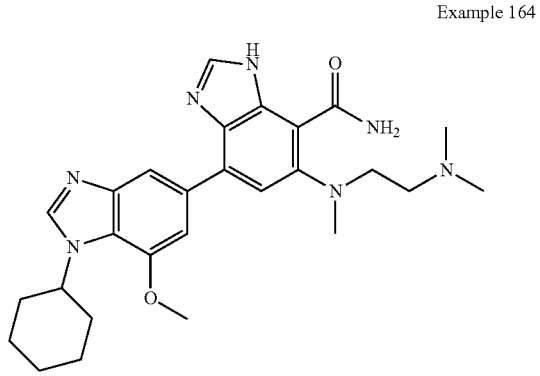 [SMILES: COc1cc(-c2cc(N(C)CCN(C)C)c(C(N)=O)c3[nH]cnc23)cc2ncn(C3CCCCC3)c12]

Example 164

Step 1: (4-Bromo-2-methoxy-6-nitro-phenyl)-cyclohexyl-amine (164a)

In a sealed vial, a solution of 2-bromo-3-nitroanisole (700 mg, 3.02 mmol) in cyclohexylamine (6 mL) was stirred overnight at 100° C. and then concentrated. The residue was diluted with water and DCM. The organic layer was washed with saturated NaHCO$_3$, brine, dried over sodium sulfate, filtered and concentrated under reduced pressure. The crude product was purified by preparative TLC on silica gel (cyclohexane/EtOAc 7/3) to afford compound (164a) (715 mg, 2.86 mmol, 95%). $^1$H NMR (400 MHz, CDCl$_3$) δ 1.24-1.32 (m, 5H), 1.5-1.65 (m, 1H), 1.75-1.79 (m, 2H), 1.98-2.01 (m, 2H), 3.91 (s, 3H), 3.99 (m, 1H), 6.73 (m, 1H), 6.98 (dd, J=7.9/1.3 Hz, 1H), 7.77 (dd, J=8.7/1.4 Hz, 1H). MS m/z ([M+H]$^+$) 251.

Step 2: (4-Bromo-2-methoxy-6-nitro-phenyl)-cyclohexyl-amine (164b)

According to the procedure described in example 152, step 2, compound (164a) (715 mg, 2.86 mmol) was converted to compound (164b) (287 mg, 0.87 mmol, 30%). $^1$H NMR (400 MHz, CDCl$_3$) δ 1.24-1.39 (m, 5H), 1.61-1.64 (m, 1H), 1.75-1.79 (m, 2H), 1.97-2.00 (m, 2H), 3.91 (s, 3H), 3.98-4.02 (m, 1H), 7.00 (d, J=2.2 Hz, 1H), 7.94 (d, J=2.2 Hz, 1H). MS m/z ([M+H]$^+$) 329/331.

Step 3: 5-Bromo-N*2*-cyclohexyl-3-methoxy-benzene-1,2-diamine (164c)

According to the procedure described in example 152, step 3, compound (164b) (580 mg, 1.76 mmol) was converted to compound (164c) (344 mg, 1.76 mmol, 100%) which was used in the next step without further purification. MS m/z ([M+H]$^+$) 299/301.

Step 4: 5-Bromo-1-cyclohexyl-7-methoxy-1H-benzimidazole (164d)

According to the procedure described in example 125, step 3, compound (164c) (344 mg, 1.76 mmol) was converted, after purification by preparative TLC on silica gel (DCM/MeOH 95/5), to compound (164d) (383 mg, 1.24 mmol, 70%). $^1$H NMR (400 MHz, DMSO-d$_6$) δ 1.21-1.33 (m, 1H), 1.37-1.52 (m, 2H), 1.69-1.88 (m, 5H), 1.98-2.02 (m, 1H), 2.06-2.10 (m, 1H), 3.94 and 3.95 (2s, 3H), 4.34 and 4.66 (2m, 1H), 6.85 and 6.94 (2d, J=1.6 Hz, 1H),), 7.43 and 7.54 (2d, J=1.6 Hz, 1H), 8.25 and 8.30 (2s, 1H). MS m/z ([M+H]$^+$) 309/311.

Step 5: 1-Cyclohexyl-7-methoxy-5-(4,4,5,5-tetramethyl-[1,3,2]dioxaborolan-2-yl)-1H-benzimidazole (164e)

According to the procedure described in example 123, step 4, compound (164d) (380 mg, 1.23 mmol) was converted to compound (164e) (383 mg, 1.24 mmol, 70%) which was used in the next step without further purification. MS m/z ([M+H]$^+$) 357.

Step 6: 1'-Cyclohexyl-6-[(2-dimethylamino-ethyl)-methyl-amino]-7'-methoxy-1H,1'H-[4,5']]bibenzimidazolyl-7-carboxamide, Example (164)

According to the procedure described in example 115, step 2, compound (124g) (136 mg, 0.4 mmol) was converted, by reaction with compound (164e) (142 mg, 0.4 mmol) and after purification by preparative TLC on silica gel (DCM/MeOH 9/1+1% NH$_3$), to Example (164) (19 mg, 0.039 mmol, 10%). $^1$H NMR (400 MHz, DMSO-d$_6$) δ 1.24-1.34 (m, 1H), 1.50-1.54 (m, 2H), 1.72-1.76 (m, 1H), 1.86-1.91 (m, 4H), 2.08-2.09 (m, 2H), 2.15 (s, 6H), 2.41 (t, J=6.4 Hz, 2H), 2.76 (s, 3H), 3.23 (t, J=6.4 Hz, 2H), 4.04 (s, 3H), 4.38 (m, 1H), 7.46 (d, J=1.0 Hz, 1H), 7.51 (s, 1H), 7.59 (d, J=3.8 Hz, 1H), 7.91 (d, J=1.2 Hz, 1H), 8.18 (s, 1H), 8.29 (s, 1H), 10.04 (d, J=3.8 Hz, 1H), 12.41 (s, 1H). MS m/z ([M+H]$^+$) 490. MS m/z ([M−H]$^−$) 488.

Example 165

Synthesis of 7-(3,4-Dihydro-5-oxa-1.2a-diaza-acenaphthylen-7-yl)-5-[(2-dimethylamino-ethyl)-methyl-amino]-3H-benzimidazole-4-carboxamide

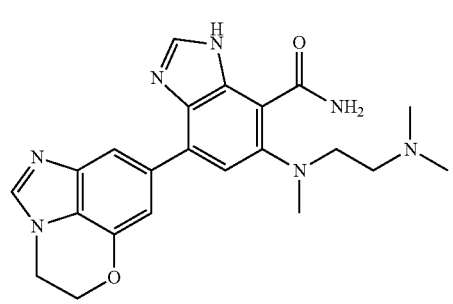

Example 165

According to the procedure described in example 59, step 5, Example (162) (79 mg, 0.18 mmol) was converted, after purification by preparative TLC on silica gel (DCM/MeOH 95/5+1% of ammonia), to Example (165) (7.8 mg, 0.019 mmol, 10%). $^1$H NMR (400 MHz, DMSO-d$_6$) δ 2.29 (s, 6H), 2.47-2.50 (m, 2H), 2.76 (s, 3H), 3.25-3.30 (m, 2H), 4.50-4.20 (m, 2H), 4.54-4.56 (m, 2H), 7.11 and 7.13 (2s, 1H), 7.47 (s, 1H), 7.49 (s, 1H), 7.56 (d, J=0.7 Hz, 1H), 7.69 (bs, 1H), 8.03 (d, J=0.9 Hz, 1H), 9.79 (bs, 1H), 12.44 (s, 1H). MS m/z ([M+H]$^+$) 420.

Example 166

Synthesis of 1'-Cyclohexyl-6-[methyl-(2-piperidin-1-yl-ethyl)-amino]-1H,1'H-[4,5']bibenzimidazolyl-7-carboxamide

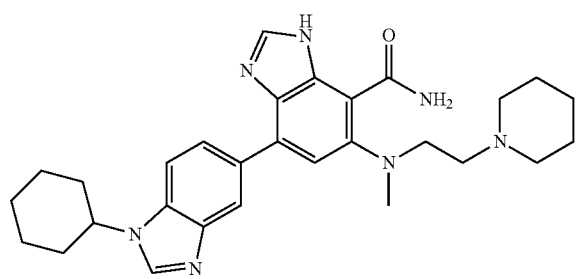

Example 166

Step 1: 2-Amino-4-(1-cyclohexyl-1H-benzimidazol-5-yl)-6-[methyl-(2-piperidin-1-yl-ethyl)-amino]-3-nitro-benzamide (166a)

According to the procedure described in example 29, step 3, compound (160d) (100 mg, 0.25 mmol) was converted, by reaction with Methyl-(2-piperidin-1-yl-ethyl)-amine (43 mg, 0.30 mmol), to compound (166a) (108 mg, 0.28 mmol, 20%). MS m/z ([M+H]$^+$) 520.

Step 2: 2,3-Diamino-4-(1-cyclohexyl-1H-benzimidazol-5-yl)-6-[methyl-(2-piperidin-1-yl-ethyl)-amino]-benzamide (166b)

According to the procedure described in example 160, step 6, compound (166a) (108 mg, 0.208 mmol) was converted to compound (166b) (102 mg, 0.208 mmol, 100%). MS m/z ([M+H]$^+$) 490.

Step 3: 1'-Cyclohexyl-6-[methyl-(2-piperidin-1-yl-ethyl)-amino]-1H,1'H-[4,5']bibenzimidazolyl-7-carboxamide, Example (166)

According to the procedure described in example 160, step 7, compound (166b) (102 mg, 0.208 mmol) was converted, after purification by preparative TLC on silica gel (DCM/MeOH 9/1+1% of ammonia), to Example (166) (21 mg, 0.04 mmol, 23%). $^1$H NMR (300 MHz, CDCl$_3$) δ 1.29-1.40 (m, 1H), 1.45-1.60 (m, 4H), 1.72-1.80 (m, 4H), 1.81-1.90 (m, 3H), 2.01 (d, J=13.6 Hz, 2H), 2.26 (d, J=12.0 Hz, 2H), 2.76 (bs, 4H), 2.82-2.85 (m, 5H), 3.47 (t, J=6.8 Hz, 2H), 4.26 (tt, J=3.6/12.0 Hz, 1H), 6.04 (bd, J=3.6 Hz, 1H), 7.44 (bs, 1H), 7.59 (d, J=8.4 Hz, 1H), 8.10 (bs, 1H), 8.16 (dd, J=1.6/8.4 Hz, 1H), 8.18 (s, 1H), 8.25 (bs, 1H), 8.41 (bs, 1H), 10.33 (d, J=3.6 Hz, 1H). MS m/z ([M+H]$^+$) 500.

Example 167

Synthesis of 5-[(2-Dimethylamino-ethyl)-methyl-amino]-7-(6-ethoxy-5-methyl-pyridin-3-yl)-3H-benzimidazole-4-carboxamide

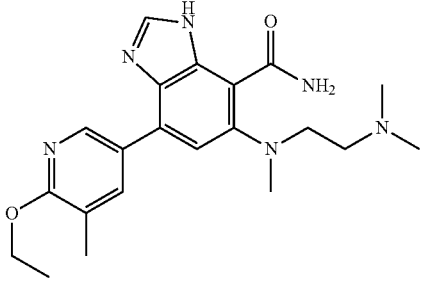

Example 167

Step 1: 5-bromo-2-ethoxy-3-methylpyridine (167a)

Sodium hydride (22.4 mg, 0.56 mmol, 60% in oil) was added in portions to a solution of ethanol (0.05 mL, 0.8 mmol) in THF (0.5 ml). The mixture was stirred at room temperature for 30 minutes. 5-bromo-2-chloro-3-picoline (103 mg, 0.5 mmol) was added and the resulting solution was refluxed 72 hours. A solution of sodium ethoxide (prepared with 40 mg sodium hydride added in a solution of 0.06 mL of ethanol in THF) was added and the mixture was refluxed overnight. The middle was then diluted with water and ethyl acetate. The organic layer was washed with water, brine, dried over sodium sulfate, filtered and concentrated under reduced pressure to give compound (167a) (109 mg, 0.5 mmol, 100%), which was used in the next step without further purification. $^1$H NMR (400 MHz, DMSO-d$_6$) δ 1.32 (t, J=7.0 Hz, 3H), 2.13 (s, 3H), 4.31 (q, J=7.0 Hz, 2H), 7.78 (dd, J=0.9/2.5 Hz, 1H), 8.08 (dd, J=0.6 Hz, J=2.5 Hz, 1H). MS m/z ([M+H]$^+$)216/218.

Step 2: 2-ethoxy-3-methyl-5-pyridinylboronic acid (167b)

According to the procedure described in example 126, step 4, compound (167a) (109 mg, 0.5 mmol) was converted to crude compound (167b) (132 mg), which was used in the next step without further purification. MS m/z ([M+H]$^+$) 182.

Step 3: 5-[(2-Dimethylamino-ethyl)-methyl-amino]-7-(6-ethoxy-5-methyl-pyridin-3-yl)-3H-benzimidazole-4-carboxamide, Example (167)

According to the procedure described in example 115, step 2, compound (124g) (170 mg, 0.5 mmol) was converted, by reaction with (167b) (132 mg, 0.5 mmol) and after purification by two successive preparative TLC on silica gel (DCM/MeOH 9/1+1% ammonia then DCM/MeOH 9/1), to Example (167) (9 mg, 0.023 mmol, 4,5% over 2 steps). $^1$H NMR (400 MHz, CD$_3$OD) δ 1.46 (t, J=7.2 Hz, 3H), 2.27 (bs, 6H), 2.31 (s, 3H), 2.50-2.56 (m, 2H), 2.83 (s, 3H), 3.29-3.35

(m, 2H), 4.47 (q, J=7.0 Hz, 2H), 7.46 (s, 1H), 8.09 (s, 1H), 8.24 (s, 1H), 8.51 (bs, 1H). MS m/z ([M+H]$^+$) 397.

Example 168

Synthesis of 6-[(2-Dimethylamino-ethyl)-methyl-amino]-1'-ethyl-2'-oxo-2',3'-dihydro-1H,1'H-[4,5']]bibenzimidazolyl-7-carboxamide

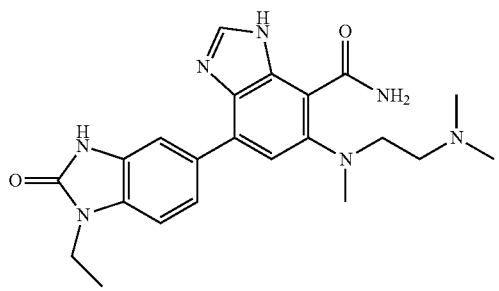

Example 168

Step 1: (4-Bromo-2-nitro-phenyl)-ethyl-amine (168a)

Ethylamine (2M in THF, 1.37 mL, 2.7 mmol) and 5-bromo-2-fluoronitrobenzene (500 mg, 2.3 mmol) was added in a solution of acetonitrile (3 mL) and triethylamine (315 µL, 2.7 mmol). The mixture was stirred at 85° C. for 16 hours. Water was added and the organic layer was extracted twice with ethyl acetate. The combined organic phases were dried over sodium sulfate, filtered and concentrated to give compound (168a) as orange powder (550 mg, 2.2 mmol, 98%). MS m/z ([M+H]$^+$) 246.

Step 2: 4-Bromo-N*1*-ethyl-benzene-1,2-diamine (168b)

According to the procedure described in example 123, step 2, compound (168a) (550 mg, 2.2 mmol) was converted to compound (168b) (260 mg, 1.2 mmol, 54%) which was used in the next step without further purification. MS m/z ([M+H]$^+$) 216.

Step 3: 5-Bromo-1-ethyl-1,3-dihydro-benzimidazol-2-one (168c)

Carbonyldiimidazole (200 mg, 1.2 mmol) was introduced to a solution of compound (168b) (260 mg, 1.2 mmol) in THF (3 mL). The mixture was stirred at 50° C. for 16 hours. Carbonyldiimidazole (200 mg, 1.2 mmol) was added to the mixture to complete the reaction. The mixture was stirred at 65° C. for 16 hours. Water was added and the organic layer was extracted, dried over sodium sulfate, filtered and concentrated. The crude product was purified by preparative TLC on silica gel (DCM/MeOH 95/5), to give compound (168c) as a powder (180 mg, 0.7 mmol, 62%). MS m/z ([M+H]$^+$) 242.

Step 4: 1-Ethyl-5-(4,4,5,5-tetramethyl-1,3,2-dioxaborolan-2-yl)-1,3-dihydro-benzimidazol-2-one (168d)

According to the procedure described in example 123, step 4, compound (168c) (180 mg, 0.7 mmol) was converted to crude compound (168d) (215 mg) as a brown oil which was engaged in the following step without additional purification. MS m/z ([M+H]$^+$) 288.

Step 5: 6-[(2-Dimethylamino-ethyl)-methyl-amino]-1'-ethyl-2'-oxo-2',3'-dihydro-1H,1'H-[4,5']]bibenzimidazolyl-7-carboxamide, Example (168)

According to the procedure described in example 115, step 2, compound (124g) (252 mg, 0.7 mmol) was converted, by reaction with compound (168d) (213 mg, 0.7 mmol) and after purification by preparative TLC on silica gel (DCM/MeOH 9/1 with 5% of ammonia), to Example (168) as an uncolorless powder (60 mg, 0.14 mmol, 20%). $^1$H NMR (400 MHz, DMSO-d$_6$) δ 1.26 (t, J=7.1 Hz, 3H), 2.16 (bs, 6H), 2.42 (bs, 2H), 2.73 (s, 3H), 3.20 (t, J=5.9 Hz, 2H), 3.87 (q, J=7.1 Hz, 2H), 7.26 (d, J=8.3 Hz, 1H), 7.45 (s, 1H), 7.60 (bs, 1H), 7.76 (dd, J=1.6/8.2 Hz, 1H), 8.01 (d, J=1.6 Hz, 1H), 8.15 (s, 1H), 9.98 (bs, 1H), 10.92 (s, 1H), 12.42 (s, 1H). MS m/z ([M+H]$^+$) 422.

Example 169

Synthesis of 1'-Cyclohexyl-6-(2-hydroxy-ethoxy)-1H,1'H-[4,5']bibenzimidazolyl-7-carboxamide

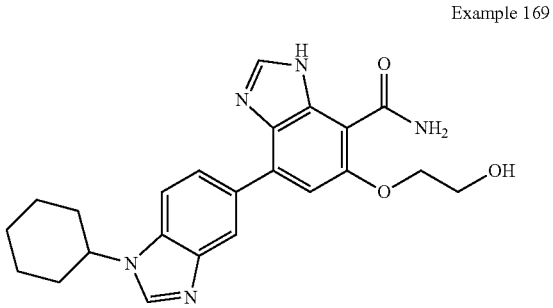

Example 169

Step 1: 2-Amino-6-(2-benzyloxy-ethoxy)-4-(1-cyclohexyl-1H-benzimidazol-5-yl)-3-nitro-benzamide (169a)

According to the procedure described in example 104, step 1, compound (160d) (200 mg, 0.50 mmol) was converted, by reaction with 2-Benzyloxy-ethanol (143 µL, 1.00 mmol), to compound (169a) (264 mg, 0.50 mmol, 100%). MS m/z ([M+H]$^+$) 530.

Step 2: 2,3-Diamino-6-(2-benzyloxy-ethoxy)-4-(1-cyclohexyl-1H-benzimidazol-5-yl)-benzamide (169b)

Compound (169a) (264 mg, 0.50 mmol) was dissolved in ethanol (5 mL). Palladium on carbon 10% (132 mg) was added and the solution was stirred 16 hours under hydrogen (5 bars). The reaction mixture was filtered on PTFE filter to eliminate salts and concentrated under reduced pressure to afford compound (169b) (248 mg, 0.50 mmol, 100%). MS m/z ([M+H]$^+$) 500.

Step 3: 6-(2-Benzyloxy-ethoxy)-1'-cyclohexyl-1H,1'H-[4,5']bibenzimidazolyl-7-carboxamide (169c)

According to the procedure described in example 160, step 7, compound (169b) (200 mg, 0.50 mmol) was converted, after purification by preparative TLC on silica gel (DCM/MeOH 9/1), to compound (169c) (35 mg, 0.08 mmol, 14%). MS m/z ([M+H]+) 510.

Step 4: 1'-Cyclohexyl-6-(2-hydroxy-ethoxy)-1H, 1'H-[4,5']bibenzimidazolyl-7-carboxamide, Example (169)

A solution of boron tribromide (1N in DCM, 75 µL, 0.075 mmol) was added at 0° C. to a solution of compound (169c) (35 mg, 0.08 mmol). After 16 hours at room temperature, the mixture was quenched with water and NaOH 1N (75 µL). The residue was purified by preparative TLC on silica gel (DCM/MeOH 9/1 with 2% of ammonia) to afford Example (169) (9 mg, 0.02 mmol, 31%). $^1$H NMR (400 MHz, CD$_3$OD) δ 1.36-1.47 (m, 1H), 1.58-1.68 (m, 2H), 1.84 (bd, J=12.4 Hz, 1H), 1.89-2.02 (m, 4H), 2.24 (bd, J=11.2 Hz, 2H), 4.01 (t, J=4.4 Hz, 2H), 4.41 (t, J=4.4 Hz, 2H), 4.44-4.51 (m, 1H), 7.29 (s, 1H), 7.79 (d, J=8.8 Hz, 1H), 7.93 (dd, J=2.4/8.4 Hz, 1H), 8.22 (bs, 1H), 8.23 (bs, 1H), 8.50 (bs, 1H). MS m/z ([M+H]+) 420.

Example 170

Synthesis of 1'-((1R,2R)-2-Fluoro-cyclohexyl)-6-[methyl-(2-pyrrolidin-1-yl-ethyl)-amino]-1H,1'H-[4,5']]bibenzimidazolyl-7-carboxamide

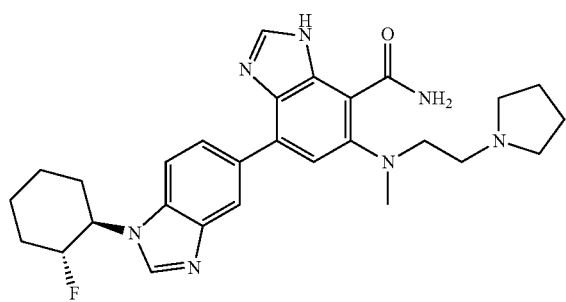

Example 170

Step 1: 2-Amino-6-fluoro-4-[1-((1R,2R)-2-fluoro-cyclohexyl)-1H-benzimidazol-5-yl]-3-nitro-benzamide (170a)

According to the procedure described in example 115, step 2, compound (160c) (600 mg, 2.16 mmol) was converted, by reaction with compound (124d) (781 mg, 2.27 mmol) and after purification by preparative TLC on silica gel (DCM/MeOH 96/4), to compound (170a) (498 mg, 1.2 mmol, 56%). $^1$H NMR (400 MHz, DMSO-d$_6$) δ 1.47-1.52 (m, 2H), 1.64-1.70 (m, 1H), 1.78-1.87 (m, 2H), 2.05-2.09 (m, 2H), 2.22-2.28 (m, 1H), 4.61 (m, 1H), 4.95 and 5.08 (2m, 1H), 6.64 (s, 2H), 6.67 (s, 1H), 7.18 (dd, J=1.0/8.4 Hz, 1H), 7.60 (bs, 1H), 7.79 (d, J=8.4 Hz, 1H), 8.03 (m, 2H), 8.53 (s, 1H). MS m/z ([M+H]+) 416.

Step 2: 2-Amino-4-[1-((1R,2R)-2-fluoro-cyclohexyl)-1H-benzimidazol-5-yl]-6-[methyl-(2-pyrrolidin-1-yl-ethyl)-amino]-3-nitro-benzamide (170b)

According to the procedure described in example 29, step 3, compound (170a) (150 mg, 0.36 mmol) was converted, by reaction with methyl[2-(pyrrolidin-1-yl)ethyl]amine (55 mg, 0.43 mmol) and after purification by preparative TLC on silica gel (DCM/MeOH 9/1), to compound (170b) (112 mg, 0.21 mmol, 59%). $^1$H NMR (400 MHz, DMSO-d$_6$) δ 1.48-1.54 (m, 2H), 1.63 (bs, 5H), 1.80-1.85 (m, 2H), 2.05-2.10 (m, 2H), 2.22-2.28 (m, 1H), 2.43 (s, 4H), 2.62 (t, J=6.0 Hz, 2H), 2.93 (s, 3H), 3.47 (t, J=5.9 Hz, 2H), 4.58-4.64 (m, 1H), 4.95 and 5.08 (2m, 1H), 6.36 (s, 1H), 7.08 (bs, 2H), 7.11 (dd, J=1.5/8.4 Hz, 1H), 7.56 (d, J=1.3 Hz, 1H), 7.70 (d, J=8.5 Hz, 1H), 7.74 (bs, 1H), 8.38 (bs, 1H), 8.47 (s, 1H). MS m/z ([M+H]+) 524.

Step 3: 1'-((1R,2R)-2-Fluoro-cyclohexyl)-6-[methyl-(2-pyrrolidin-1-yl-ethyl)-amino]-1H,1'H-[4,5']]bibenzimidazolyl-7-carboxamide, Example (170)

A solution of compound (170b) (112 mg, 0.21 mmol) in methanol (4 mL), was purged with hydrogen. Catalyst Pd/C 10% (21 mg) was then added and the reaction was stirred under hydrogen atmosphere (1 bar) overnight. The middle was filtered and concentrated under reduced pressure. The crude material was diluted in formic acid (3 ml) then heated at 110° C. After 3 hours, the middle was concentrated and the crude product was purified by preparative TLC on silica gel (DCM/MeOH 95/5+1% NH$_3$) to afford Example (170) (60 mg, 0.12 mmol, 57%). $^1$H NMR (400 MHz, DMSO-d$_6$) δ 1.48-1.54 (m, 2H), 1.66-1.71 (bs, 4H), 1.83-1.88 (m, 2H), 2.08-2.13 (m, 2H), 2.24-2.30 (m, 1H), 2.45 (bs, 4H), 2.60 (t, J=6.3 Hz, 2H), 2.74 (s, 3H), 3.26 (t, J=6.3 Hz, 2H), 4.62-4.65 (m, 1H), 4.98 and 5.10 (2m, 1H), 7.50 (s, 1H), 7.61 (bs, 1H), 7.79 (d, J=8.6 Hz, 1H), 8.06 (d, J=8.8 Hz, 1H), 8.16 (s, 1H), 8.29 (bs, 1H), 8.48 (m, 2H), 10.02 (bs, 1H), 12.41 (s, 1H). MS m/z ([M+H]+) 504.

Example 171

Synthesis of 1'-((1R,2R)-2-Fluoro-cyclohexyl)-6-[(2-hydroxy-ethyl)-methyl-amino]-1H,1'H-[4,5']]bibenzimidazolyl-7-carboxamide

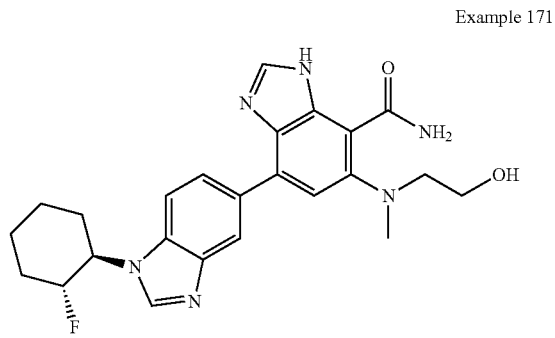 [SMILES: CN(CCO)c1cc(-c2ccc3c(c2)ncn3[C@@H]2CCCC[C@H]2F)c2nc[nH]c2c1C(N)=O]

Example 171

Step 1: 2-Amino-4-[1-((1R,2R)-2-fluoro-cyclohexyl)-1H-benzimidazol-5-yl]-6-[(2-hydroxy-ethyl)-methyl-amino]-3-nitro-benzamide (171a)

According to the procedure described in example 29, step 3, compound (170a) (150 mg, 0.36 mmol) was converted, by reaction with 2-(methylamino)ethanol (0.035 mL, 0.43 mmol) and after purification by preparative TLC on silica gel (DCM/MeOH 9/1), to compound (171a) (127 mg, 0.27 mmol, 75%). $^1$H NMR (400 MHz, DMSO-d$_6$) δ 1.46-1.54

(m, 2H), 1.60-1.72 (m, 1H), 1.80-1.85 (m, 2H), 2.05-2.09 (m, 2H), 2.22-2.28 (m, 1H), 2.97 (s, 3H), 3.38 (t, J=5.5 Hz, 2H), 3.62 (q, J=5.5 Hz, 2H), 4.60 (m, 1H), 4.95 and 5.08 (2m, 1H), 6.32 (s, 1H), 6.82 (bs, 2H), 7.10 (dd, J=1.6/8.4 Hz, 1H), 7.56 (d, J=1.5 Hz, 1H), 7.70 (d, J=8.4 Hz, 1H), 7.79 (m, 2H), 8.47 (s, 1H). MS m/z ([M+H]$^+$) 471.

Step 2: 1'-((1R,2R)-2-Fluoro-cyclohexyl)-6-[(2-hydroxy-ethyl)-methyl-amino]-1H,1'H-[4,5']]bibenzimidazolyl-7-carboxamide, Example (171)

A solution of compound (171a) (127 mg, 0.27 mmol) in methanol (4 mL) was purged with hydrogen. Catalyst Pd/C 10% (27 mg) was then added and the reaction was stirred under hydrogen atmosphere (1 bar) overnight. The middle was filtered and concentrated under reduced pressure. The crude material was diluted in formic acid (3 mL) then heated at 110° C. After 3 hours, the middle was concentrated and the crude product was purified by preparative TLC on silica gel (DCM/MeOH 95/5+1% NH$_3$). The yellow powder was diluted in methanol (2 mL) and sodium hydroxide 5M was added. The resulting mixture was stirred at 40° C. for 2 hours. The crude material was concentrated under reduced pressure and poured into water. The precipitate was filtered and washed with diethyl ether to afford Example (171) (20 mg, 0.044 mmol, 16%). $^1$H NMR (400 MHz, DMSO-d$_6$) δ 1.50-1.55 (m, 2H), 1.65-1.70 (m, 2H), 1.80-1.85 (m, 2H), 2.24-2.29 (m, 1H), 2.77 (s, 3H), 3.17-3.22 (m, 2H), 3.55-3.61 (m, 2H), 4.61-4.67 (m, 1H), 4.98 and 5.10 (2m, 1H), 7.79 (s, 1H), 7.61 (bs, 1H), 7.79 (d, J=8.6 Hz, 1H), 8.06 (d, J=8.3 Hz, 1H), 8.16 (s, 1H), 8.48 (m, 2H), 9.95 (bs, 1H), 12.42 (s, 1H). MS m/z ([M+H]$^+$) 451.

Example 172

Synthesis of 5-[(2-Dimethylamino-ethyl)-methyl-amino]-7-(8-fluoro-1-benzopyran-6-yl)-3H-benzimidazole-4-carboxamide

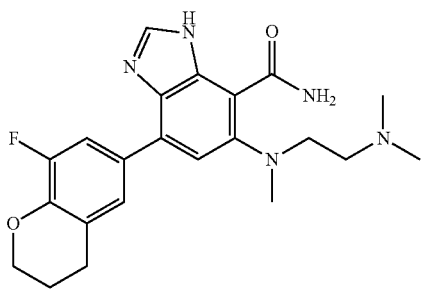

Example 172

Step 1: 3-(2-fluorophenoxy)propanoic acid (172a)

To a suspension of 2-fluorophenol (3.0 g, 26.8 mmol) in THF (30 mL) at 0-5° C. was dropped a solution of potassium tert-butoxide (1N in THF, 28.1 mL, 28.1 mmol), followed by β-propiolactone (1.85 mL, 29.4 mmol) in one portion. The mixture was warmed to room temperature for 1 hour and then heated at 50° C. for 2 hours. After cooling to room temperature, the mixture was quenched with a saturated solution of sodium hydrogenocarbonate and diluted with water. The aqueous layer was washed with ethyl acetate, acidified with 1M hydrochloric acid until pH 2 and extracted with ethyl acetate. The organic layer was dried over sodium sulfate and concentrated under reduced pressure to give compound (172a) (3.73 g, 20.3 mmol, 76%) which was used without further purification. MS m/z ([M−H]$^-$) 183.

Step 2: 8-fluoro-3,4-dihydro-2H-1-benzopyran-4-one (172b)

A mixture of compound (172a) (3.7 g, 20.3 mmol) in polyphosphoric acid (59.5 g, 607.6 mmol) was stirred at 100° C. for 2 hours. After cooling to room temperature, the mixture was diluted with water and extracted with ethyl acetate. The organic layers were combined, washed with brine, dried over sodium sulfate, and concentrated under reduced pressure. The residue was triturated in diethyl ether and filtered. The filtrate was concentrated to provide compound (172b) (1.80 g, 10.8 mmol, 53%) which was used without further purification. $^1$H NMR (300 MHz, CDCl$_3$) δ 2.83-2.90 (m, 2H), 4.60-4.68 (m, 2H), 6.95 (td, J=8.0/4.4 Hz, 1H), 7.30 (ddd, J=1.4/8.0/10.6 Hz, 1H), 7.67 (td, J=1.4/8.0 Hz, 1H). MS m/z ([M+H]$^+$) 167.

Step 3: 8-fluoro-3,4-dihydro-2H-1-benzopyran (172c)

A solution of compound (172b) (1.80 g, 10.83 mmol) in acetic acid (14 mL) was added to a suspension of zinc dust (9.21 g, 140.8 mmol) in acetic acid (14 mL). The reaction mixture was heated at 100° C. for 5 hours. After cooling to room temperature, the mixture was filtered through a pad of Celite® and successively rinsed with ethyl acetate (80 mL) and toluene (80 mL). The filtrate was concentrated under reduced pressure. The residue was purified purification by flash chromatography on silica gel (cyclohexane/ethyl acetate 100/0 to 95/5), to provide compound (172c) (827 mg, 5.43 mmol, 50%). $^1$H NMR (300 MHz, CDCl$_3$) δ 1.99-2.08 (m, 2H), 2.81 (t, J=6.5 Hz, 2H), 4.23-4.29 (m, 2H), 6.69-6.93 (m, 3H).

Step 4: 6-bromo-8-fluoro-3,4-dihydro-2H-1-benzopyran (172d)

A mixture of compound (172c) (820 mg, 5.39 mmol) and acetic acid (8.5 mL) is treated with bromine (0.33 mL, 6.47 mmol) in acetic acid (5 mL). The mixture was stirred at room temperature for 20 minutes and then diluted with toluene (20 mL). The mixture was concentrated under reduced pressure. The residue was dissolved in ethyl acetate and successively washed with a 15% sodium thiosulfate solution and a saturated solution of sodium hydrogenocarbonate. The organic layer was dried over sodium sulfate and concentrated to provide compound (172d) (1.21 g, 5.24 mmol, 92%) which was used without further purification. $^1$H NMR (300 MHz, CDCl$_3$) δ 1.97-2.07 (m, 2H), 2.78 (t, J=6.5 Hz, 2H), 4.21-4.27 (m, 2H), 6.95-6.98 (m, 1H), 7.05 (dd, J=2.3/10.2 Hz, 1H).

Step 5: 2-(8-fluoro-3,4-dihydro-2H-1-benzopyran-6-yl)-4,4,5,5-tetramethyl-1,3,2-dioxaborolane (172e)

[1,1'-Bis(diphenylphosphino)ferrocene]dichloropalladium(II) (318 mg, 0.39 mmol) was added to a previously degassed solution of compound (173f) (900 mg, 3.89 mmol), bis(pinacolato)diboron (1.48 g, 5.84 mmol) and potassium acetate (1.34 g, 13.63 mmol) in anhydrous DMF (30 mL). The reaction mixture was heated at 95° C. for 16 hours. Water (30 mL) was added and the reaction mixture was concentrated under reduced pressure. The residue was taken in water and extracted with ethyl acetate. The organic layer was washed with brine then dried over sodium sulfate, concentrated under reduced pressure by co-evaporating with toluene. The crude was purified by flash chromatography on silica gel (cyclohexane/ethyl acetate 100/0 to 95/5). The product was triturated in pentane and filtered to provide compound (172e) (515 mg, 1.85 mmol, 47%) as a white powder. $^1$H NMR (400 MHz, CDCl$_3$) δ 1.32 (s, 12H), 1.99-2.06 (m, 2H), 2.80 (t, J=6.4 Hz, 2H), 4.25-4.31 (m, 2H), 7.26-7.35 (m, 2H). MS m/z ([M+H]$^+$) 279.

Step 6: 5-[(2-Dimethylamino-ethyl)-methyl-amino]-7-(8-fluoro-1-benzopyran-6-yl)-3H-benzimidazole-4-carboxamide, Example (172)

According to the procedure described in example 115, step 2, compound (124g) (119 mg, 0.35 mmol) was converted, by reaction with compound (172e) (97 mg, 0.35 mmol) and after purification by preparative TLC on silica gel (DCM/MeOH 9/1+1% of ammonia), to Example (172) (47 mg, 0.114 mmol, 33%). $^1$H NMR (400 MHz, DMSO-d$_6$) δ 2.01 (m, 2H), 2.14 (s, 6H), 2.39 (t, J=6.2 Hz, 2H), 2.72 (s, 3H), 2.88 (t, J=6.3 Hz, 2H), 3.19 (m, 2H), 4.27 (m, 2H), 7.47 (s, 1H), 7.57 (d, J=2.9 Hz, 1H), 7.79 (bs, 1H), 8.03 (dd, J=13.0/1.8 Hz, 1H), 8.16 (bs, 1H), 10.02 (d, J=2.9 Hz, 1H), 12.41 (s, 1H). MS m/z ([M+H]$^+$) 412.

Example 173

Synthesis of 1'-Ethyl-7'-methoxy-6-[methyl-(2-pyrrolidin-1-yl-ethyl)-amino]-1H,1'H-[4,5']]bibenzimidazolyl-7-carboxamide Example 173

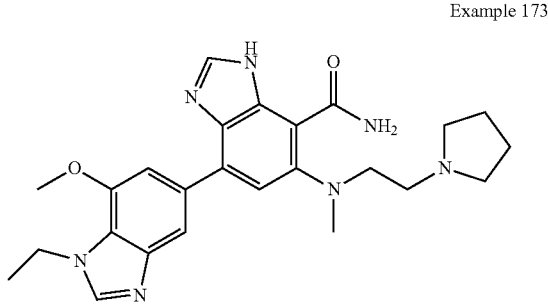 [SMILES: CCn1cnc2cc(-c3cc(N(C)CCN4CCCC4)c(C(N)=O)c4[nH]cnc34)cc(OC)c21]

Step 1: 2-Amino-4-(1-ethyl-7-methoxy-1H-benzimidazol-5-yl)-6-fluoro-3-nitro-benzamide (174a)

According to the procedure described in example 115, step 2, compound (160c) (600 mg, 2.16 mmol) was converted, by reaction with compound (152e) (686 mg, 2.27 mmol) and after purification by preparative TLC on silica gel (DCM/MeOH 95/5), to compound (173a) as a yellow powder (450 mg, 1.2 mmol, 56%). MS m/z ([M+H]$^+$) 374.

Step 2: 2-Amino-4-(1-ethyl-7-methoxy-1H-benzimidazol-5-yl)-6-[methyl-(2-pyrrolidin-1-yl-ethyl)-amino]-3-nitro-benzamide (173)

According to the procedure described in example 29, step 3, compound (173a) (140 mg, 0.37 mmol) was converted, by reaction with methyl-[2-(pyrrolidin-1-yl)ethyl]amine (55 mg, 0.43 mmol), to crude compound (173b) (178 mg, 0.37 mmol) which was used in the following step without additional purification. MS m/z ([M+H]$^+$) 482.

Step 3: 2,3-Diamino-4-(1-ethyl-7-methoxy-1H-benzimidazol-5-yl)-6-[methyl-(2-pyrrolidin-1-yl-ethyl)-amino]-benzamide (173c)

Compound (173b) (178 mg, 0.37 mmol) was dissolved in methanol (4 mL). Palladium on carbon 10% (37 mg) was added and the solution was stirred for 16 hours under hydrogen (1 bar). The reaction mixture was filtered on PTFE filter to eliminate salts and concentrated under reduced pressure to afford compound (173c) (167 mg, 0.37 mmol, 100%). MS m/z ([M+H]$^+$) 452.

Step 4: 1'-Ethyl-7'-methoxy-6-[methyl-(2-pyrrolidin-1-yl-ethyl)-amino]-1H,1'H-[4,5']]bibenzimidazolyl-7-carboxamide, Example (173)

According to the procedure described in example 125, step 3, compound (173c) (167 mg, 0.37 mmol) was converted, after purification by preparative TLC on silica gel (DCM/MeOH 95/5+2% of ammonia), to Example (173) (36.3 mg, 0.078 mmol, 22%). $^1$H NMR (400 MHz, CDCl$_3$) δ 1.54 (t, J=7.1 Hz, 3H), 1.72-1.82 (m, 5H), 2.48-2.58 (m, 4H), 2.66-2.74 (m, 2H), 2.82 (s, 3H), 3.24-3.32 (m, 2H), 4.09 (s, 3H), 4.48 (q, J=7.1 Hz, 2H), 7.48 (s, 1H), 7.74 (s, 1H), 7.82 (s, 1H), 7.85 (s, 1H), 8.16 (s, 1H), 10.73 (s, 1H), 11.58 (s, 1H). MS m/z ([M+H]$^+$) 462.

Example 174

Synthesis of 1'-Ethyl-6-[(2-hydroxy-ethyl)-methyl-amino]-7'-methoxy-1H,1'H-[4,5']]bibenzimidazolyl-7-carboxamide Example 174

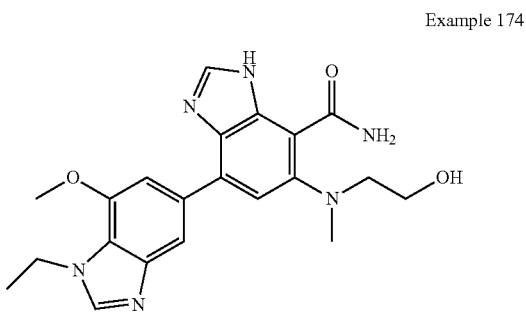 [SMILES: CCn1cnc2cc(-c3cc(N(C)CCO)c(C(N)=O)c4[nH]cnc34)cc(OC)c21]

Step 1: 2-Amino-4-(1-ethyl-7-methoxy-1H-benzimidazol-5-yl)-6-[(2-hydroxy-ethyl)-methyl-amino]-3-nitro-benzamide (174a)

According to the procedure described in example 29, step 3, compound (173a) (180 mg, 0.48 mmol) was converted, by reaction with 2-Methylamino-ethanol (46.5 µL, 0.58 mmol), to crude compound (174a) (137 mg, 0.32 mmol) which was used in the next step without additional purification. MS m/z ([M+H]$^+$) 429.

Step 2: 2,3-Diamino-4-(1-ethyl-7-methoxy-1H-benzimidazol-5-yl)-6-[(2-hydroxy-ethyl)-methyl-amino]-benzamide (174b)

According to the procedure described in example 173, step 3, compound (174a) (205 mg, 0.48 mmol) was converted to compound (174b) (191 mg, 0.48 mmol, 100%) which was used in the next step without additional purification. MS m/z ([M+H]$^+$) 399.

Step 3: 1'-Ethyl-6-[(2-hydroxy-ethyl)-methyl-amino]-7'-methoxy-1H,1'H-[4,5']]bibenzimidazolyl-7-carboxamide, Example (174)

According to the procedure described in example 125, step 3, compound (174a) (191 mg, 0.48 mmol) was converted, after purification by preparative TLC on silica gel (DCM/MeOH 95/5+2% of ammonia), to Example (174) (45.8 mg, 0.11 mmol, 24%). H NMR (400 MHz, CDCl$_3$) δ 1.50 (t, J=7.1 Hz, 3H), 2.75 (s, 3H), 3.12-3.23 (m, 2H), 3.60-3.70 (m, 2H), 4.05 (s, 3H), 4.43 (q, J=7.1 Hz, 2H), 6.44-6.54 (m, 1H), 7.34 (s, 1H), 7.61 (s, 1H), 7.74 (s, 1H), 7.86 (s, 1H), 8.16 (s, 1H), 10.67 (s, 1H). MS m/z ([M+H]$^+$) 409.

Example 175

Synthesis of 6-(2-Dimethylamino-ethoxy)-1'-ethyl-7'-methoxy-1H,1'H-[4,5']]bibenzimidazolyl-7-carboxamide p-toluenesulfonic acid salt

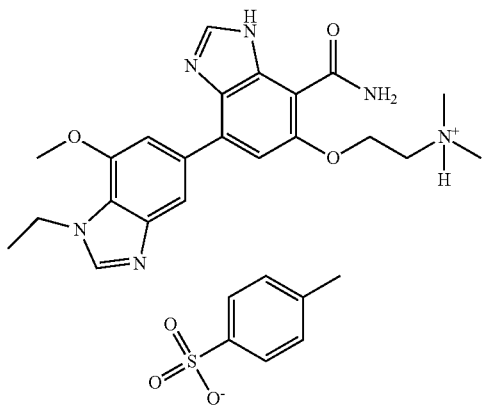

Example 175

Step 1: 2-Amino-6-(2-dimethylamino-ethoxy)-4-(1-ethyl-7-methoxy-1H-benzimidazol-5-yl)-3-nitro-benzamide (175a)

According to the procedure described in example 104, step 7, compound (173a) (130 mg, 0.35 mmol) was converted, by reaction with 2-dimethylamino-ethanol (70 µL, 0.70 mmol), to crude compound (175a) (100 mg, 0.22 mmol) which was used in the next step without additional purification. MS m/z ([M+H]$^+$) 443.

Step 2: 2,3-Diamino-6-(2-dimethylamino-ethoxy)-4-(1-ethyl-7-methoxy-1H-benzimidazol-5-yl)-benzamide (175b)

According to the procedure described in example 173, step 3, compound (175a) (100 mg, 0.22 mmol) was converted to compound (175b) (144 mg, 0.35 mmol, 100%) which was used in the next step without additional purification. MS m/z ([M+H]$^+$) 413.

Step 3: 6-(2-Dimethylamino-ethoxy)-1'-ethyl-7'-methoxy-1H,1'H-[4,5']]bibenzimidazolyl-7-carboxamide p-toluenesulfonic acid salt, Example (175)

According to the procedure described in example 125, step 3, compound (175b) (144 mg, 0.35 mmol) was converted, after purification by preparative TLC on silica gel (DCM/MeOH 9/1+2% of ammonia), to Example (175) (6.8 mg, 0.016 mmol, 3.5%). $^1$H NMR (400 MHz, CD$_3$OD) δ 1.56 (t, J=7.1 Hz, 3H), 2.35 (s, 3H), 3.05 (s, 6H), 3.68-3.75 (m, 2H), 4.12 (s, 3H), 4.58 (q, J=7.1 Hz, 2H), 4.60-4.70 (m, 2H), 7.20 (d, J=7.9 Hz, 2H), 7.36 (s, 1H), 7.39 (s, 1H), 7.69-7.72 (m, 3H), 8.29 (s, 1H), 8.39 (s, 1H). MS m/z ([M+H]$^+$) 423.

Example 176

Synthesis of 1'-Cyclohexyl-6-[(2-methoxy-ethyl)-methyl-amino]-1H,1'H-[4,5']bibenzimidazolyl-7-carboxamide

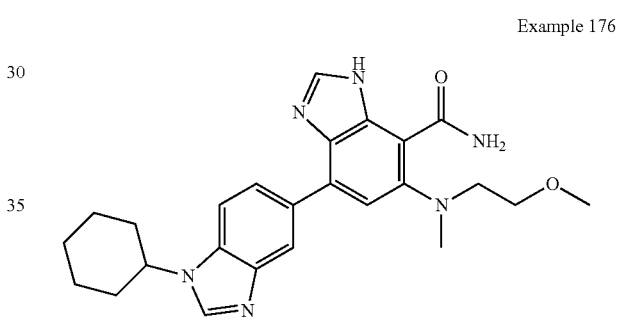

Example 176

Step 1: 2-Amino-4-(1-cyclohexyl-1H-benzimidazol-5-yl)-6-[(2-methoxy-ethyl)-methyl-amino]-3-nitro-benzamide (176a)

According to the procedure described in example 30, step 1, compound (160d) (100 mg, 0.25 mmol) was converted, by reaction with (2-Methoxy-ethyl)-methyl-amine (55 µL, 0.50 mmol) and after purification by preparative TLC on silica gel (DCM/MeOH 9/1), to compound (176a) (73 mg, 0.16 mmol, 62%). MS m/z ([M+H]$^+$) 467.

Step 2: 2,3-Diamino-4-(1-cyclohexyl-1H-benzimidazol-5-yl)-6-[(2-methoxy-ethyl)-methyl-amino]-benzamide (176b)

According to the procedure described in example 160, step 6, compound (176a) (73 mg, 0.16 mmol) was converted to compound (176b) (68 mg, 0.16 mmol, 100%). MS m/z ([M+H]$^+$) 437.

Step 3: 1'-Cyclohexyl-6-[(2-methoxy-ethyl)-methyl-amino]-1H,1'H-[4,5']bibenzimidazolyl-7-carboxamide, Example (176)

According to the procedure described in example 160, step 7, compound (176b) (68 mg, 0.16 mmol) was converted, after purification by preparative TLC on silica gel (DCM/MeOH 9/1+1% of ammonia), to Example (176) (17 mg, 0.04 mmol, 29%). $^1$H NMR (400 MHz, DMSO-d$_6$) δ 1.25-1.38 (m, 1H), 1.46-1.60 (m, 2H), 1.71-1.78 (m, 1H), 1.82-1.95 (m, 4H), 2.05-2.13 (m, 2H), 2.75 (s, 3H), 3.23 (s, 3H), 3.27 (t, J=5.4 Hz, 2H), 3.48 (t, J=5.4 Hz, 2H), 4.37-4.46 (m, 1H), 7.51 (s, 1H), 7.62 (bd, J=3.7 Hz, 1H), 7.75 (d, J=8.5 Hz, 1H), 8.06 (dd, J=1.4/8.4 Hz, 1H), 8.16 (s, 1H), 8.38 (s, 1H), 8.46 (d, J=1.4 Hz, 1H), 9.87 (d, J=4.0 Hz, 1H), 12.41 (bs, 1H). MS m/z ([M+H]$^+$) 447.

Example 177

Synthesis of 7-(3,4-Dihydro-2H-pyrano[2,3-b]pyridin-6-yl)-5-[(2-hydroxy-ethyl)-methyl-amino]-3H-benzimidazole-4-carboxamide

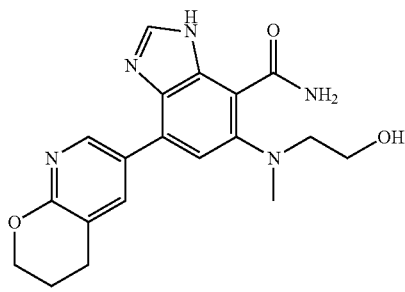

Example 177

Step 1: 2-Amino-4-(3,4-dihydro-2H-pyrano[2,3-b]pyridin-6-yl)-6-fluoro-3-nitro-benzamide (177a)

According to the procedure described in example 115, step 2, compound (160c) (800 mg, 2.88 mmol) was converted, by reaction with 6-(4,4,5,5-Tetramethyl-1,3,2-dioxaborolan-2-yl)-3,4-dihydro-2H-pyrano[2,3-b]pyridine (789 mg, 3.02 mmol) and after purification by preparative TLC on silica gel (DCM/MeOH 95/5), to compound (177a) (723 mg, 2.17 mmol, 75%). $^1$H NMR (400 MHz, DMSO-d$_6$) δ 1.91-1.95 (m, 2H), 2.81 (t, J=6.2 Hz, 2H), 4.34 (t, J=5.1 Hz, 2H), 6.62 (d, J=10.4 Hz, 1H), 6.73 (s, 1H), 7.50 (d, J=2.5 Hz, 2H), 7.91 (d, J=2.5 Hz, 1H), 8.00 (bs, 1H), 8.03 (bs, 1H). MS m/z ([M+H]$^+$) 333.

Step 2: 2-Amino-4-(3,4-dihydro-2H-pyrano[2,3-b]pyridin-6-yl)-6-[(2-hydroxy-ethyl)-methyl-amino]-3-nitro-benzamide (177b)

According to the procedure described in example 29, step 3, compound (177a) (133 mg, 0.4 mmol) was converted, by reaction with 2-(methylamino)ethanol (0.038 mL, 0.48 mmol) and after purification by preparative TLC on silica gel (DCM/MeOH 95/5), to compound (177b) (135 mg, 0.35 mmol, 88%). $^1$H NMR (400 MHz, DMSO-d$_6$) δ 1.93 (m, 2H), 2.80 (t, J=6.4 Hz, 2H), 2.97 (s, 3H), 3.39 (t, J=5.7 Hz, 2H), 3.58-3.64 (m, 2H), 4.30 (t, J=5.1 Hz, 2H), 4.83-4.89 (m, 1H), 6.25 (s, 1H), 6.99 (s, 2H), 7.41 (d, J=2.5 Hz, 1H), 7.73 (bs, 1H), 7.78 (bs, 1H), 7.85 (d, J=2.5 Hz, 1H). MS m/z ([M+H]$^+$) 388.

Step 3: 7-(3,4-Dihydro-2H-pyrano[2,3-b]pyridin-6-yl)-5-[(2-hydroxy-ethyl)-methyl-amino]-3H-benzimidazole-4-carboxamide, Example (177)

A solution of compound (177b) (135 mg, 0.35 mmol) in methanol (4 mL), was purged with hydrogen. Catalyst Pd/C 10% (35 mg) was then added and the reaction was stirred under hydrogen atmosphere (1 bar) overnight. The middle was filtered and concentrated under reduced pressure. The crude material was diluted in toluene (3 mL) and ethanol (1 mL). Triethyl orthoformate (0.07 ml, 0.42 mmol) was then added and the mixture was heated at 110° C. for 2 hours. The middle was concentrated and the crude product was purified by preparative TLC on silica gel (DCM/MeOH 9/1) to afford Example (177) (44 mg, 0.12 mmol, 34%). $^1$H NMR (400 MHz, DMSO-d$_6$) δ 1.95-2.00 (m, 2H), 2.74 (s, 3H), 2.90 (t, J=6.3 Hz, 2H), 3.15 (t, J=5.6 Hz, 2H), 3.56 (q, J=5.4 Hz, 2H), 4.34 (t, J=5.2 Hz, 2H), 4.74 (t, J=4.9 Hz, 1H), 7.48 (s, 1H), 7.63 (d, J=3.8 Hz, 1H), 8.16 (s, 1H), 8.33 (d, J=2.4 Hz, 1H), 8.81 (d, J=2.4 Hz, 1H), 9.91 (d, J=3.7 Hz, 1H), 12.44 (s, 1H). MS m/z ([M+H]$^+$) 368.

Example 178

Synthesis of 7-(3,4-Dihydro-2H-pyrano[2,3-b]pyridin-6-yl)-5-dimethylamino-3H-benzimidazole-4-carboxamide

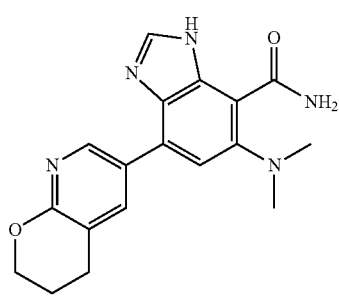

Example 178

Step 1: 2-Amino-4-(3,4-dihydro-2H-pyrano[2,3-b]pyridin-6-yl)-6-dimethylamino-3-nitro-benzamide (178a)

According to the procedure described in example 29, step 3, compound (177a) (166 mg, 0.5 mmol) was converted, by reaction with dimethylamine (2M in THF, 0.3 mL, 0.6 mmol), to compound (178a) (186 mg) which was used in the next step without further purification. MS m/z ([M+H]$^+$)358.

Step 2: 7-(3,4-Dihydro-2H-pyrano[2,3-b]pyridin-6-yl)-5-dimethylamino-3H-benzimidazole-4-carboxamide, Example (178)

According to the procedure described in example 177, step 3, compound (178a) (179 mg, 0.5 mmol) was converted, after purification by preparative TLC on silica gel (DCM/MeOH 9/1), to Example (178) (87 mg, 0.26 mmol, 52%). $^1$H NMR (400 MHz, DMSO-d$_6$) δ 1.98 (m, 2H), 2.79 (s, 6H), 2.90 (t, J=6.3 Hz, 2H), 4.34 (t, J=5.1 Hz, 2H), 7.47 (s, 1H), 7.71 (d, J=3.9 Hz, 1H), 8.16 (s, 1H), 8.33 (d, J=2.4 Hz, 1H), 8.81 (d, J=2.4 Hz, 1H), 9.66 (d, J=3.8 Hz, 1H), 12.42 (s, 1H). MS m/z ([M+H]$^+$) 338.

Example 179

Synthesis of 1'-Ethyl-6-methoxy-1H,1'H-[4,5']]bibenzimidazolyl-7-carboxamide

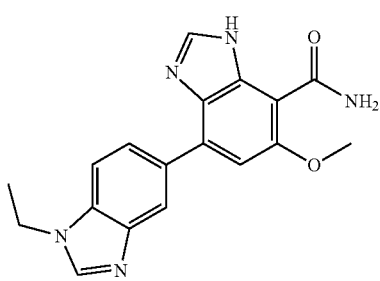

Example 179

Step 1: Methyl 2-Amino-4-bromo-6-methoxy-3-nitro-benzoate (179a)

According to the procedure described in example 88, step 1, compound (51b) (1 g, 3 mmol) was converted, by reaction with methanol and after purification by preparative TLC on silica gel (cyclohexane/EtOAc 7/3), to compound (179a) (450 mg, 1.47 mmol, 43%). $^1$H NMR (400 MHz, DMSO-$d_6$) δ 3.81 (s, 3H), 3.91 (s, 3H), 6.32 (bs, 2H), 6.75 (s, 1H). MS m/z ([M+H]$^+$) 306/308.

Step 2: Methyl 7-Bromo-5-methoxy-3H-benzimidazole-4-carboxylate (179b)

According to the procedure described in example 17, step 4, compound (179a) (450 mg, 1.47 mmol) was converted, after purification by preparative TLC on silica gel (DCM/MeOH 98/2 with 5% of ammonia), to compound (179b) (223 mg, 0.78 mmol) as a yellow oil. $^1$H NMR (400 MHz, DMSO-$d_6$) δ 3.88 (s, 3H), 3.90 (s, 3H), 7.33 (s, 1H), 8.22 (s, 1H), 12.40 (bs, 1H). MS m/z ([M+H]$^+$) 285/287.

Step 3: Methyl 1'-Ethyl-6-methoxy-1H,1'H-[4,5'] bibenzimidazolyl-7-carboxylate (179c)

A solution of compound (179b) (223 mg, 0.78 mmol), 1-Ethyl-5-(4,4,5,5-tetramethyl-[1,3,2]dioxaborolan-2-yl)-1Hbenzimidazole (223 mg, 0.82 mmol) and potassium carbonate (323 mg, 2.34 mmol) in a mixture of tetrahydrofuran (4 mL) and water (1 mL) was degassed under argon for 10 minutes. The catalyst bis(triphenylphosphine)palladium(II) dichloride (98.5 mg, 0.14 mmol) was then added. After 16 hours at 85° C., the reaction mixture was concentrated under reduced pressure. The residue was washed with water and extracted with ethyl acetate. The organic phase was dried on sodium sulfate, filtered and evaporated. The solid was purified by preparative TLC on silica gel (DCM/MeOH 95/5 with 3% of ammonia) to afford compound (179c) (70 mg, 0.2 mmol) as a brown oil. $^1$H NMR (400 MHz, CDCl$_3$) δ 1.47 (t, J=7.3 Hz, 3H), 3.93 (s, 3H), 3.98 (s, 3H), 4.20 (q, J=7.3 Hz, 2H), 7.10 (s, 1H), 7.45 (d, J=8.5 Hz, 1H), 7.89 (s, 1H), 7.99 (s, 1H), 8.08 (d, J=8.5 Hz, 1H), 8.22 (s, 1H), 10.81 (bs, 1H). MS m/z ([M+H]$^+$) 351.

Step 4: 1'-Ethyl-6-methoxy-1H,1'H-[4,5']]bibenzimidazolyl-7-carboxamide, Example (179)

According to the procedure described in example 115, step 1, compound (179c) (70 mg, 0.2 mmol) was converted, after purification by preparative TLC on silica gel (DCM/MeOH 95/5 with 2% of ammonia), to Example (179) (23.2 mg, 0.07 mmol, 35%) as a white powder. $^1$H NMR (400 MHz, DMSO-$d_6$) δ 1.46 (t, J=7.2 Hz, 3H), 4.11 (s, 3H), 4.33 (q, J=7.2 Hz, 2H), 7.30 (s, 1H), 7.68 (s, 1H), 7.72 (d, J=8.5 Hz, 1H), 7.88 (bs, 1H), 8.10 (s, 1H), 8.14 (d, J=8.5 Hz, 1H), 8.31 (s, 1H), 8.53 (s, 1H), 12.35 (s, 1H). MS m/z ([M+H]$^+$) 336.

Example 180

Synthesis of 6-(2-Dimethylamino-ethoxy)-1'-((1R,2R)-2-fluoro-cyclohexyl)-1H,1'H-[4,5']]bibenzimidazolyl-7-carboxamide methanesulfonic acid salt

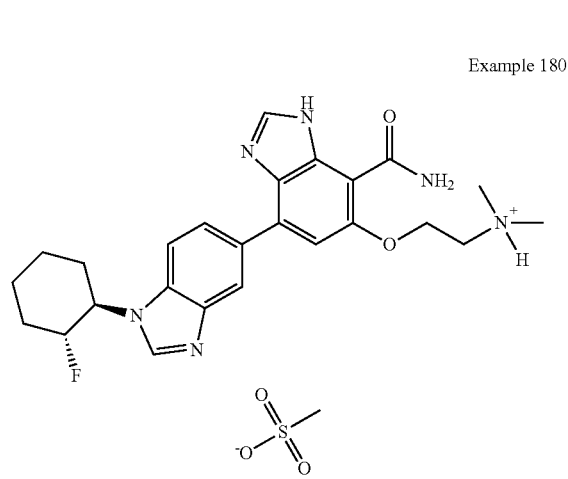

Example 180

Step 1: 2-Amino-6-(2-dimethylamino-ethoxy)-4-[1-((1R,2R)-2-fluoro-cyclohexyl)-1H-benzimidazol-5-yl]-3-nitro-benzamide (180a)

According to the procedure described in example 104, step 1, compound (170a) (180 mg, 0.43 mmol) was converted, by reaction with N,N-dimethylethanolamine (0.09 mL, 0.9 mmol), to compound (180a) (207 mg, 0.43 mmol, 100%) which was used without further purification. MS m/z ([M+H]$^+$) 485.

Step 2: 6-(2-Dimethylamino-ethoxy)-1'-((1R,2R)-2-fluoro-cyclohexyl)-1H,1'H-[4,5']]bibenzimidazolyl-7-carboxamide (180b)

According to the procedure described in example 170, step 3, compound (180a) (277 mg, 0.43 mmol) was converted, after purification by preparative TLC on silica gel (DCM/MeOH 9/1+1% of ammonia), to compound (180b) (170 mg, 0.36 mmol, 84%).
MS m/z ([M+H]$^+$) 465.

Step 3: 6-(2-Dimethylamino-ethoxy)-1'-((1R,2R)-2-fluoro-cyclohexyl)-1H,1'H-[4,5']]bibenzimidazolyl-7-carboxamide methanesulfonic acid salt, Example (180)

According to the procedure described in example 108, compound (180b) (27 mg, 0.058 mmol) was converted to Example (180) without further purification (29 mg, 0.052 mmol, 90%). $^1$H NMR (400 MHz, DMSO-$d_6$) δ 1.48-1.55 (m, 2H), 1.70-1.76 (m, 1H), 1.84-1.91 (m, 2H), 2.15-2.22 (m, 2H), 2.29-2.35 (m, 4H), 2.90-2.98 (m, 6H), 3.64-3.70 (m, 2H), 4.67-4.73 (m, 2H), 4.82-4.89 (m, 1H), 5.12 and 5.00 (2m, 1H), 7.47 (s, 1H), 7.92-7.97 (m, 2H), 8.05 (s, 1H), 8.65 (bs, 1H), 9.11 (bs, 1H), 9.81 (bs, 1H). MS m/z ([M+H]$^+$) 465.

Example 181

Synthesis of 7-(3,4-Dihydro-2H-pyrano[2,3-b]pyridin-6-yl)-5-[methyl-(2-pyrrolidin-1-yl-ethyl)-amino]-3H-benzimidazole-4-carboxamide Example 181

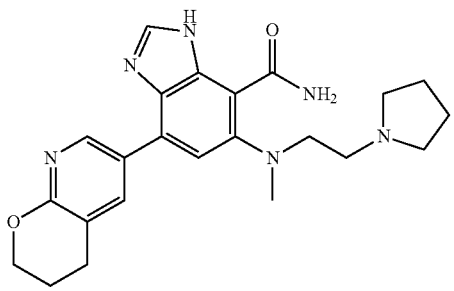

Step 1: 2-Amino-4-(3,4-dihydro-2H-pyrano[2,3-b]pyridin-6-yl)-6-[methyl-(2-pyrrolidin-1-yl-ethyl)-amino]-3-nitro-benzamide (181a)

According to the procedure described in example 29, step 3, compound (177a) (133 mg, 0.4 mmol) was converted, by reaction with methyl[2-(pyrrolidin-1-yl)ethyl]amine (62 mg, 0.48 mmol) and after purification by preparative TLC on silica gel (DCM/methanol 95/5), to compound (181a) (155 mg, 0.35 mmol, 88%). $^1$H NMR (400 MHz, DMSO-$d_6$) δ 1.62 (bs, 4H), 1.90-1.97 (m, 2H), 2.42 (bs, 4H), 2.62 (t, J=5.8 Hz, 2H), 2.80 (t, J=6.3 Hz, 2H), 2.94 (s, 3H), 3.49 (t, J=6.0 Hz, 2H), 4.30 (t, J=5.1 Hz, 2H), 6.31 (s, 1H), 7.19 (bs, 2H), 7.42 (d, J=2.5 Hz, 1H), 7.76 (bs, 1H), 7.86 (d, J=2.5 Hz, 1H), 8.35 (bs, 1H). MS m/z ([M+H]$^+$) 441.

Step 2: 7-(3,4-Dihydro-2H-pyrano[2,3-b]pyridin-6-yl)-5-[methyl-(2-pyrrolidin-1-yl-ethyl)-amino]-3H-benzimidazole-4-carboxamide, Example (181)

According to the procedure described in example 177, step 3, compound (181a) (155 mg, 0.35 mmol) was converted, after twice purification by preparative TLC on silica gel (DCM/MeOH 9/1 then DCM/MeOH 9/1+1% NH$_3$), to Example (181) (36 mg, 0.086 mmol, 24%). $^1$H NMR (400 MHz, DMSO-$d_6$) δ 1.76 (bs, 4H), 1.95-2.01 (m, 2H), 2.40-2.47 (m, 4H), 2.58-2.64 (m, 2H), 2.72 (s, 3H), 2.90 (t, J=6.3 Hz, 2H), 3.23 (t, J=6.2 Hz, 2H), 4.34 (t, J=5.1 Hz, 2H), 7.48 (s, 1H), 7.61 (bs, 1H), 8.16 (s, 1H), 8.33 (d, J=2.4 Hz, 1H), 8.81 (d, J=2.4 Hz, 1H), 10.0 (bs, 1H), 12.42 (s, 1H). MS m/z ([M+H]$^+$) 421.

Example 182

Synthesis of 7-(3,4-Dihydro-2H-pyrano[2,3-b]pyridin-6-yl)-5-(2-dimethylamino-ethoxy)-3H-benzimidazole-4-carboxamide methanesulfonic acid salt Example 182

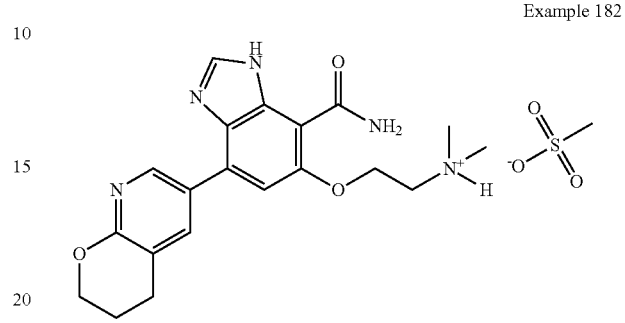

Step 1: 2-Amino-4-(3,4-dihydro-2H-pyrano[2,3-b]pyridin-6-yl)-6-(2-dimethylamino-ethoxy)-3-nitro-benzamide (182a)

According to the procedure described in example 104, step 1, compound (177a) (150 mg, 0.45 mmol) was converted, by reaction with N,N-dimethylethanolamine (0.09 mL, 0.9 mmol) and after purification by preparative TLC on silica gel (DCM/MeOH 95/5), to compound (182a) (78 mg, 0.19 mmol, 42%). $^1$H NMR (400 MHz, DMSO-$d_6$) δ 1.90-1.96 (m, 2H), 2.20 (s, 6H), 2.61 (t, J=5.4 Hz, 2H), 2.82 (t, J=6.3 Hz, 2H), 4.28 (t, J=5.4 Hz, 2H), 4.32 (t, J=5.1 Hz, 2H), 6.40 (s, 1H), 7.27 (s, 2H), 7.51 (d, J=2.5 Hz, 1H), 7.72 (bs, 1H), 7.93 (d, J=2.5 Hz, 1H), 8.34 (bs, 1H). MS m/z ([M+H]$^+$) 402.

Step 2: 7-(3,4-Dihydro-2H-pyrano[2,3-b]pyridin-6-yl)-5-(2-dimethylamino-ethoxy)-3H-benzimidazole-4-carboxamide (182b)

According to the procedure described in example 177, step 3, compound (182a) (78 mg, 0.19 mmol) was converted, twice purification by preparative TLC on silica gel (DCM/MeOH 9/1+1% NH$_3$), to compound (182b) (51 mg, 0.13 mmol, 68%). $^1$H NMR (400 MHz, DMSO-$d_6$) δ 1.95-2.02 (m, 2H), 2.26 (s, 6H), 2.69-2.75 (m, 2H), 2.90 (t, J=6.4 Hz, 2H), 4.34 (t, J=5.1 Hz, 2H), 4.39 (t, J=5.2 Hz, 2H), 7.32 (s, 1H), 7.59 (bs, 1H), 8.11 (s, 1H), 8.39 (d, J=2.4 Hz, 1H), 8.52 (bs, 1H), 8.86 (d, J=2.4 Hz, 1H), 12.38 (s, 1H). MS m/z ([M+H]$^+$) 382.

Step 3: 7-(3,4-Dihydro-2H-pyrano[2,3-b]pyridin-6-yl)-5-(2-dimethylamino-ethoxy)-3H-benzimidazole-4-carboxamide methanesulfonic acid salt, Example (182)

According to the procedure described in example 108, compound (182b) (51 mg, 0.13 mmol) was converted to Example (182) (63 mg, 0.13 mmol, 100%). $^1$H NMR (400 MHz, DMSO-$d_6$) δ 1.95-2.01 (m, 2H), 2.32 (s, 3H), 2.86-2.90 (m, 2H), 2.91-2.95 (m, 6H), 3.65-3.69 (m, 2H), 4.34-4.39 (m, 2H), 4.63-4.70 (m, 2H), 7.39 (s, 1H), 7.86 (bs, 1H), 7.91 (s, 1H), 8.29 (s, 1H), 8.54 (bs, 1H), 8.72 (s, 1H), 9.75 (bs, 1H). MS m/z ([M+H]$^+$) 382.

Example 183

Synthesis of 5-[(2-Dimethylamino-ethyl)-methyl-amino]-7-(2-oxo-1,2,3,4-tetrahydro-quinolin-7-yl)-3H-benzimidazole-4-carboxamide Example 183

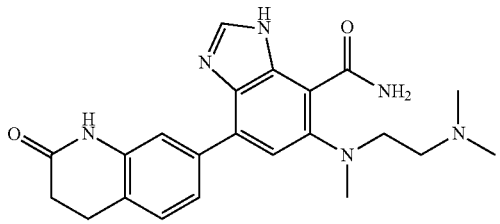

Step 1: 7-(4,4,5,5-Tetramethyl-1,3,2-dioxaborolan-2-yl)-3,4-dihydro-1H-quinolin-2-one (183a)

According to the procedure described in example 123, step 4, 7-bromo-3,4-dihydroquinolin-2(1H)-one (100 mg, 0.44 mmol) was converted to compound (183a) (63 mg, 0.13 mmol, 100%) which was used in the next step without further purification. $^1$H NMR (300 MHz, CDCl$_3$) δ 1.34 (s, 12H), 2.63 (dd, J=8.6/6.4 Hz, 2H), 2.90-3.04 (m, 2H), 7.13 (s, 1H), 7.18 (d, J=7.3 Hz, 1H), 7.44 (dd, J=7.5/1.2 Hz, 1H). MS m/z ([M+H]$^+$) 274.

Step 2: 5-[(2-Dimethylamino-ethyl)-methyl-amino]-7-(2-oxo-1,2,3,4-tetrahydro-quinolin-7-yl)-3H-benzimidazole-4-carboxamide, Example (183)

According to the procedure described in example 115, step 2, compound (124g) (150 mg, 0.44 mmol) was converted, by reaction with compound (183a) (121 mg, 0.44 mmol) and after purification by preparative TLC on silica gel (DCM and 10% NH$_4$OH in MeOH), to Example (183) (120 mg, 0.29 mmol, 67%). $^1$H NMR (300 MHz, CDCl$_3$) δ 2.21 (s, 6H), 2.45 (t, J=6.3 Hz, 2H), 2.67 (t, J=8.7/6.4 Hz, 2H), 2.77 (s, 3H), 3.03 (t, J=7.6 Hz, 2H), 3.20 (t, J=6.3 Hz, 2H), 5.99 (s, 1H), 7.26-7.39 (m, 2H), 7.52 (dd, J=7.7/1.6 Hz, 1H), 7.59 (d, J=1.6 Hz, 1H), 8.12 (s, 2H), 10.67 (s, 1H), 11.61 (s, 1H). MS m/z ([M+H)$^+$] 407.

Example 184

Synthesis of 5-[(2-Dimethylamino-ethyl)-methyl-amino]-7-(1-oxo-1,2,3,4-tetrahydro-isoquinolin-7-yl)-3H-benzimidazole-4-carboxamide Example 184

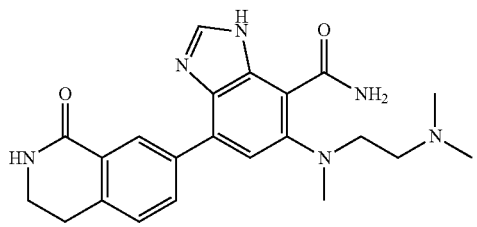

Step 1: 7-(4,4,5,5-Tetramethyl-1,3,2-dioxaborolan-2-yl)-3,4-dihydro-2H-isoquinolin-1-one (184a)

According to the procedure described in example 123, step 4, 7-bromo-3,4-dihydroisoquinolin-1(2H)-one (100 mg, 0.44 mmol) was converted to crude compound (184a) (121 mg, 0.44 mmol, 100%) which was used in the next step without further purification. MS m/z ([M+H]$^+$) 274.

Step 2: 5-[(2-Dimethylamino-ethyl)-methyl-amino]-7-(1-oxo-1,2,3,4-tetrahydro-isoquinolin-7-yl)-3H-benzimidazole-4-carboxamide, Example (184)

According to the procedure described in example 115, step 2, compound (124g) (150 mg, 0.44 mmol) was converted, by reaction with compound (184a) (121 mg, 0.44 mmol) and after purification by preparative TLC on silica gel (DCM and 10% NH$_4$OH in MeOH), to Example (184) (100 mg, 0.246 mmol, 56%). $^1$H NMR (300 MHz, CDCl$_3$) δ 2.15 (s, 6H), 2.39 (t, J=6.3 Hz, 2H), 2.71 (s, 3H), 3.01 (t, J=6.4 Hz, 2H), 3.15 (t, J=6.2 Hz, 2H), 3.55 (td, J=6.5/2.6 Hz, 2H), 5.72 (s, 1H), 6.07 (s, 1H), 7.27-7.42 (m, 2H), 8.07 (s, 1H), 8.31 (dt, J=7.9/1.6 Hz, 1H), 8.44 (d, J=1.8 Hz, 1H), 10.66 (s, 1H), 11.47 (s, 1H). MS m/z ([M+H]$^+$) 407.

Example 185

Synthesis of 5-[(2-Dimethylamino-ethyl)-methyl-amino]-7-(4-methoxy-3-trifluoromethoxy-phenyl)-3H-benzimidazole-4-carboxamide Example 185

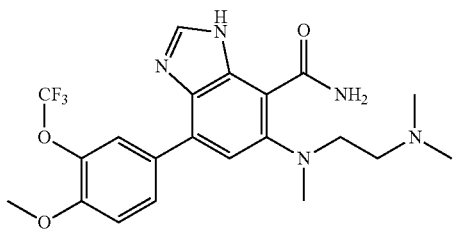

Step 1: 2-(4-Methoxy-3-trifluoromethoxy-phenyl)-4,4,5,5-tetramethyl-1,3,2-dioxaborolane (185a)

According to the procedure described in example 123, step 4, 4-bromo-1-methoxy-2-(trifluoromethoxy)benzene (100 mg, 0.37 mmol) was converted to crude compound (185a) (117 mg, 0.37 mmol, 100%) which was used in the next step without further purification. $^1$H NMR (300 MHz, CDCl$_3$) δ 1.33 (s, 12H), 3.89 (s, 3H), 6.97 (d, J=8.3 Hz, 1H), 7.59-7.79 (m, 2H).

Step 2: 5-[(2-Dimethylamino-ethyl)-methyl-amino]-7-(4-methoxy-3-trifluoromethoxy-phenyl)-3H-benzimidazole-4-carboxamide, Example (185)

According to the procedure described in example 115, step 2, compound (124g) (126 mg, 0.369 mmol) was converted, by reaction with compound (185a) (117 mg, 0.369 mmol) and after purification by preparative TLC on silica gel (DCM and 10% NH$_4$OH in MeOH), to Example (185) (154 mg, 0.34 mmol, 92%). $^1$H NMR (300 MHz, CDCl$_3$) δ 2.21 (s, 6H), 2.46 (t, J=6.4 Hz, 2H), 2.77 (s, 3H), 3.20 (t, J=6.3 Hz, 2H), 3.95 (s, 3H), 5.72 (s, 1H), 7.15 (d, J=8.7 Hz, 1H), 7.30 (s, 1H), 7.88 (d, J=2.1 Hz, 1H), 8.07 (dt, J=8.5/2.2 Hz, 1H), 8.14 (s, 1H), 10.68 (s, 1H), 11.52 (s, 1H). MS m/z ([M+H]⁺) 452.

Example 186

Synthesis of 7-1,3-Benzodioxol-5-yl-5-[(2-dimethylamino-ethyl)-methyl-amino]-3H-benzimidazole-4-carboxamide

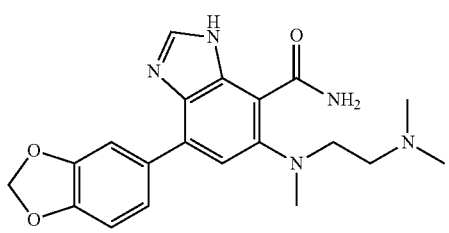

Example 186

Step 1: 5-(4,4,5,5-Tetramethyl-1,3,2-dioxaborolan-2-yl)-1,3-benzodioxole (186a)

According to the procedure described in example 123, step 4, 5-bromobenzo[d][1,3]dioxole (100 mg, 0.50 mmol) was converted to crude compound (186a) (123 mg, 0.50 mmol, 100%) which was used in the next step without further purification. ¹H NMR (300 MHz, CDCl₃) δ 1.32 (s, 12H), 5.95 (s, 2H), 6.83 (d, J=7.7, Hz, 1H), 7.24 (s, 1H), 7.29-7.41 (m, 1H).

Step 2: 7-1,3-Benzodioxol-5-yl-5-[(2-dimethyl-amino-ethyl)-methyl-amino]-3H-benzimidazole-4-carboxamide, Example (186)

According to the procedure described in example 115, step 2, compound (124g) (169 mg, 0.50 mmol) was converted, by reaction with compound (186a) (123 mg, 0.50 mmol) and after purification by preparative TLC on silica gel (DCM and 10% NH₄OH in MeOH), to Example (186) (84 mg, 0.220 mmol, 44%). ¹H NMR (300 MHz, CDCl₃) δ 2.21 (s, 6H), 2.44 (t, 2H), 2.77 (s, 3H), 3.18 (d, J=6.5 Hz, 2H), 5.69 (s, 1H), 6.02 (s, 2H), 6.87-7.02 (m, 1H), 7.30 (d, J=1.0 Hz, 1H), 7.43-7.60 (m, 2H), 8.13 (s, 1H), 10.68 (s, 1H), 11.50 (s, 1H). MS m/z ([M+H]⁺) 382.

Example 187

Synthesis of 7-1-Benzopyran-6-yl-5-[(2-dimethyl-amino-ethyl)-methyl-amino]-3H-benzimidazole-4-carboxamide

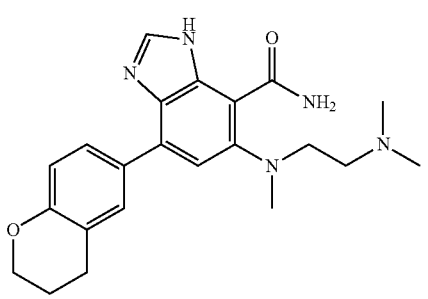

Example 187

According to the procedure described in example 115, step 2, compound (124g) (100 mg, 0.294 mmol) was converted, by reaction with 2-(chroman-7-yl)-4,4,5,5-tetramethyl-1,3,2-dioxaborolane (76 mg, 0.294 mmol) and after purification by column chromatography and preparative TLC on silica gel (DCM and 10% NH₄OH in MeOH), to Example (187) (68 mg, 0.173 mmol, 59%). ¹H NMR (300 MHz, CDCl₃) δ 1.93-2.13 (m, 2H), 2.21 (s, 6H), 2.44 (t, 2H), 2.76 (s, 3H), 2.92 (t, J=6.6 Hz, 2H), 3.19 (t, 2H), 4.13-4.30 (m, 2H), 5.69 (s, 1H), 6.93 (d, J=8.5 Hz, 1H), 7.31 (d, J=1.7 Hz, 1H), 7.71 (d, J=8.7 Hz, 1H), 7.77 (s, 1H), 8.12 (s, 1H), 10.68 (s, 1H), 11.50 (s, 1H). MS m/z ([M+H]⁺) 394.

Example 188

Synthesis of 7-Benzoxazol-5-yl-5-[(2-dimethyl-amino-ethyl)-methyl-amino]-3H-benzimidazole-4-carboxamide

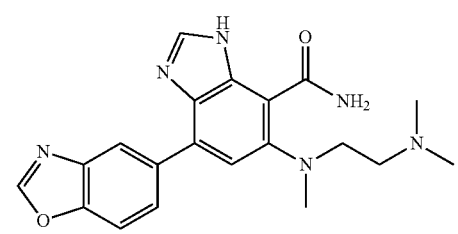

Example 188

Step 1: 5-(4,4,5,5-Tetramethyl-1,3,2-dioxaborolan-2-yl)-benzoxazole (188a)

According to the procedure described in example 123, step 4, 5-bromobenzo[d]oxazole (100 mg, 0.505 mmol) was converted to crude compound (188a) (124 mg, 0.505 mmol, 100%) which was used in the next step without further purification. ¹H NMR (300 MHz, CDCl₃) δ 1.37 (s, 12H), 7.58 (dd, J=8.3/1.4 Hz, 1H), 7.78-7.90 (m, 1H), 8.10 (d, J=1.5 Hz, 1H), 8.26 (s, 1H).

Step 2: 7-Benzoxazol-5-yl-5-[(2-dimethylamino-ethyl)-methyl-amino]-3H-benzimidazole-4-carboxamide, Example (188)

According to the procedure described in example 115, step 2, compound (124g) (172 mg, 0.505 mmol) was converted, by reaction with compound (188a) (124 mg, 0.505 mmol) and after purification by preparative TLC on silica gel (DCM and 10% NH₄OH in MeOH), to Example (188) (84 mg, 0.222 mmol, 44%). ¹H NMR (300 MHz, CDCl₃) δ 2.22 (s, 6H), 2.44 (t, 2H), 2.80 (s, 3H), 3.22 (t, 2H), 5.72 (s, 1H), 7.24 (s, 1H), 7.41 (s, 1H), 7.74 (d, 1H), 8.14-8.18 (m, 2H), 8.33 (s, 1H), 10.70 (s, 1H), 11.52 (s, 1H). MS m/z ([M+H]⁺) 379.

Example 189

Synthesis of 5-[(2-Dimethylamino-ethyl)-methyl-amino]-7-(5-fluoro-6-methoxy-pyridin-3-yl)-3H-benzimidazole-4-carboxamide

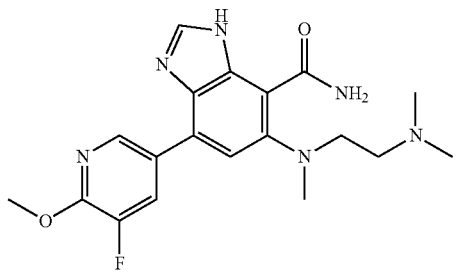

Example 189

Step 1: 3-Fluoro-2-methoxy-5-(4,4,5,5-tetramethyl-1,3,2-dioxaborolan-2-yl)-pyridine (189a)

According to the procedure described in example 123, step 4, 5-bromo-3-fluoro-2-methoxypyridine (100 mg, 0.485 mmol) was converted to crude compound (189a) (123 mg, 0.485 mmol, 100%) which was used in the next step without further purification. $^1$H NMR (300 MHz, CDCl$_3$) δ 1.33 (s, 12H), 4.04 (s, 3H), 7.54-7.68 (m, 1H), 8.27 (s, 1H).

Step 2: 5-[(2-Dimethylamino-ethyl)-methyl-amino]-7-(5-fluoro-6-methoxy-pyridin-3-yl)-3H-benzimidazole-4-carboxamide, Example (189)

According to the procedure described in example 115, step 2, compound (124g) (165 mg, 0.485 mmol) was converted, by reaction with compound (189a) (123 mg, 0.485 mmol) and after purification by preparative TLC on silica gel (DCM and 10% NH$_4$OH in MeOH), to Example (189) (82 mg, 0.212 mmol, 44%). $^1$H NMR (300 MHz, CDCl$_3$) δ 2.20 (s, 6H), 2.45 (t, 2H), 2.77 (s, 3H), 3.19 (t, J=6.3 Hz, 2H), 4.10 (s, 3H), 5.72 (s, 1H), 7.33 (s, 1H), 8.14 (d, J=2.9 Hz, 1H), 8.23 (dd, J=11.3/2.2 Hz, 1H), 8.54 (d, J=2.1 Hz, 1H), 10.66 (s, 1H), 11.51 (s, 1H). MS m/z ([M+H]$^+$) 387.

Example 190

Synthesis of 5-[(2-Dimethylamino-ethyl)-methyl-amino]-7-(7-oxo-5,6,7,8-tetrahydro-1,8-naphthyridin-3-yl)-3H-benzimidazole-4-carboxamide

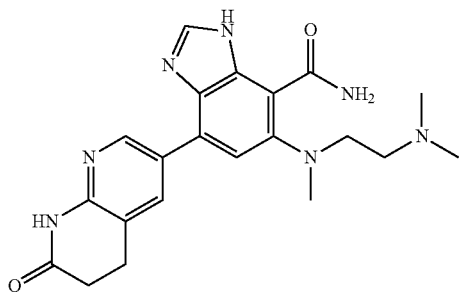

Example 190

Step 1: 6-(4,4,5,5-Tetramethyl-1,3,2-dioxaborolan-2-yl)-3,4-dihydro-1H-1,8-naphthyridin-2-one (190a)

According to the procedure described in example 123, step 4, 6-bromo-3,4-dihydro-1,8-naphthyridin-2(1H)-one (100 mg, 0.440 mmol) was converted to crude compound (190a) (121 mg, 0.440 mmol, 100%) which was used in the next step without further purification. $^1$H NMR (300 MHz, CDCl$_3$) δ 1.34 (s, 12H), 2.63 (dd, J=8.6/6.4 Hz, 2H), 2.87-3.06 (m, 2H), 7.06-7.22 (m, 2H), 7.44 (dd, J=7.5/1.2 Hz, 1H).

Step 2: 5-[(2-Dimethylamino-ethyl)-methyl-amino]-7-(7-oxo-5,6,7,8-tetrahydro-1,8-naphthyridin-3-yl)-3H-benzimidazole-4-carboxamide, Example (190)

According to the procedure described in example 115, step 2, compound (124g) (150 mg, 0.440 mmol) was converted, by reaction with compound (190a) (121 mg, 0.440 mmol) and after purification by preparative TLC on silica gel (DCM and 10% NH$_4$OH in MeOH), to Example (190) (86 mg, 0.211 mmol, 48%). $^1$H NMR (300 MHz, CDCl$_3$) δ 2.22 (s, 6H), 2.47 (t, J=7.7 Hz, 2H), 2.63-2.85 (m, 5H), 3.11 (t, J=7.7 Hz, 2H), 3.20 (d, J=6.3 Hz, 2H), 5.75 (s, 1H), 7.34 (s, 1H), 8.02 (s, 1H), 8.15 (s, 1H), 8.36 (s, 1H), 8.65 (s, 1H), 10.68 (s, 1H), 11.55 (s, 1H). MS m/z ([M+H]$^+$) 408.

Example 191

Synthesis of 7-(2,3-Dihydro-benzofuran-6-yl)-5-[(2-dimethylamino-ethyl)-methyl-amino]-3H-benzimidazole-4-carboxamide

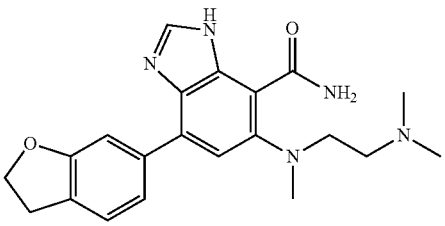

Example 191

Step 1: 6-(4,4,5,5-Tetramethyl-1,3,2-dioxaborolan-2-yl)-2,3-dihydro-benzofuran (191a)

According to the procedure described in example 123, step 4, 6-bromo-2,3-dihydrobenzofuran (100 mg, 0.502 mmol) was converted to crude compound (191a) (124 mg, 0.502 mmol, 100%) which was used in the next step without further purification. $^1$H NMR (300 MHz, CDCl$_3$) δ 1.33 (s, 12H), 3.21 (t, J=8.9 Hz, 2H), 4.54 (t, J=8.7 Hz, 2H), 7.20 (t, J=3.4 Hz, 2H), 7.31 (d, J=7.2 Hz, 1H).

Step 2: 7-(2,3-Dihydro-benzofuran-6-yl)-5-[(2-dimethylamino-ethyl)-methyl-amino]-3H-benzimidazole-4-carboxamide, Example (191)

According to the procedure described in example 115, step 2, compound (124g) (171 mg, 0.502 mmol) was converted, by reaction with compound (191a) (124 mg, 0.502 mmol) and after purification by preparative TLC on silica gel (DCM and 10% NH$_4$OH in MeOH), to Example (191) (79 mg, 0.208 mmol, 41%). $^1$H NMR (300 MHz, CDCl$_3$) δ 2.21 (s, 6H), 2.45 (t, J=6.4 Hz, 2H), 2.76 (s, 3H), 3.18 (t, J=6.4 Hz, 2H), 3.27 (t, J=8.6 Hz, 2H), 4.63 (td, J=8.7, 1.3

Hz, 2H), 5.71 (s, 1H), 7.30-7.40 (m, 3H), 7.56 (dt, J=7.5/1.5 Hz, 1H), 8.12 (d, J=1.5 Hz, 1H), 10.69 (s, 1H), 11.49 (s, 1H). MS m/z ([M+H]$^+$) 380.

Example 192

Synthesis of 5-[(2-Dimethylamino-ethyl)-methyl-amino]-7-quinolin-3-yl-3H-benzimidazole-4-carboxamide

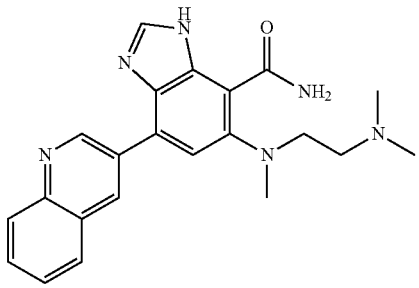

Example 192

Step 1: 3-(4,4,5,5-Tetramethyl-1,3,2-dioxaborolan-2-yl)-quinoline (192a)

According to the procedure described in example 123, step 4, 3-bromoquinoline (100 mg, 0.481 mmol) was converted to crude compound (192a) (123 mg, 0.481 mmol, 100%) which was used in the next step without further purification.

Step 2: 5-[(2-Dimethylamino-ethyl)-methyl-amino]-7-quinolin-3-yl-3H-benzimidazole-4-carboxamide, Example (192)

According to the procedure described in example 115, step 2, compound (124g) (164 mg, 0.481 mmol) was converted, by reaction with compound (192a) (123 mg, 0.481 mmol) and after purification by preparative TLC on silica gel (DCM and 10% NH$_4$OH in MeOH), to Example (192) (74 mg, 0.190 mmol, 40%). $^1$H NMR (300 MHz, CDCl$_3$) δ 2.08-2.33 (s, 6H), 2.47 (t, J=6.5 Hz, 2H), 2.69-2.90 (m, 3H), 3.23 (t, J=6.4 Hz, 2H), 5.76 (s, 1H), 7.51 (d, J=1.9 Hz, 1H), 7.60 (d, J=7.5 Hz, 1H), 7.75 (t, J=7.7 Hz, 1H), 7.98 (d, J=8.2 Hz, 1H), 8.08-8.33 (m, 2H), 8.98 (s, 1H), 9.44 (d, J=2.4 Hz, 1H), 10.72 (s, 1H), 11.57 (s, 1H). MS m/z ([M+H]$^+$) 389.

Example 193

Synthesis of 7-(2,3-Dihydro-furo[2,3-b]pyridin-5-yl)-5-[(2-dimethylamino-ethyl)-methyl-amino]-3H-benzimidazole-4-carboxamide

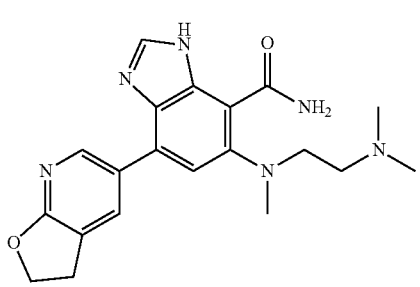

Example 193

Step 1: 5-(4,4,5,5-Tetramethyl-1,3,2-dioxaborolan-2-yl)-2,3-dihydro-furo[2,3-b]pyridine (193a)

According to the procedure described in example 123, step 4, 5-bromo-2,3-dihydrofuro[2,3-b]pyridine (55.0 mg, 0.275 mmol) was converted to crude compound (193a) (67.8 mg, 0.275 mmol, 100%) which was used in the next step without further purification. $^1$H NMR (300 MHz, CDCl$_3$) δ 1.33 (s, 12H), 3.22 (t, J=8.6 Hz, 2H), 4.63 (t, J=8.7 Hz, 2H), 7.83 (d, J=1.9 Hz, 1H), 8.40 (s, 1H).

Step 2: 7-(2,3-Dihydro-furo[2,3-b]pyridin-5-yl)-5-[(2-dimethylamino-ethyl)-methyl-amino]-3H-benzimidazole-4-carboxamide, Example (193)

According to the procedure described in example 115, step 2, compound (124g) (93 mg, 0.2745 mmol) was converted, by reaction with compound (193a) (67.8 mg, 0.275 mmol) and after purification by preparative TLC on silica gel (DCM and 10% NH$_4$OH in MeOH), to Example (193) (65 mg, 0.171 mmol, 62%). $^1$H NMR (300 MHz, CDCl$_3$) δ 2.20 (s, 6H), 2.45 (t, J=6.4 Hz, 2H), 2.65-2.85 (s, 3H), 3.19 (t, J=6.3 Hz, 2H), 3.36 (t, J=8.5 Hz, 2H), 4.69 (td, J=8.7/1.9 Hz, 2H), 5.81 (s, 1H), 7.31 (d, J=1.7 Hz, 1H), 8.13 (d, J=1.8 Hz, 1H), 8.28-8.52 (m, 2H), 10.67 (s, 1H), 11.58 (s, 1H). MS m/z ([M+H]$^+$) 381.

Example 194

Synthesis of 5-[(2-Dimethylamino-ethyl)-methyl-amino]-7-(2-methoxy-pyrimidin-5-yl)-3H-benzimidazole-4-carboxamide

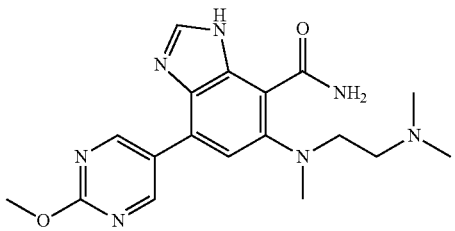

Example 194

According to the procedure described in example 115, step 2, compound (124g) (100 mg, 0.294 mmol) was converted, by reaction with (2-methoxypyrimidin-5-yl)boronic acid (45.2 mg, 0.294 mmol) and after purification by preparative TLC on silica gel (DCM and 10% NH$_4$OH in MeOH), to Example (194) (87 mg, 0.236 mmol, 80%). $^1$H NMR (300 MHz, CDCl$_3$) δ 2.22 (s, 6H), 2.46 (t, J=6.3 Hz, 2H), 2.79 (s, 3H), 3.20 (t, J=6.2 Hz, 2H), 4.10 (s, 3H), 5.75 (s, 1H), 7.32 (s, 1H), 8.15 (s, 1H), 9.21 (d, J=1.4 Hz, 2H), 10.67 (s, 1H), 11.52 (s, 1H). MS m/z ([M+H]$^+$) 370.

Example 195

Synthesis of 5-[(2-Dimethylamino-ethyl)-methyl-amino]-7-(6-trifluoromethyl-pyridin-3-yl)-3H-benzimidazole-4-carboxamide

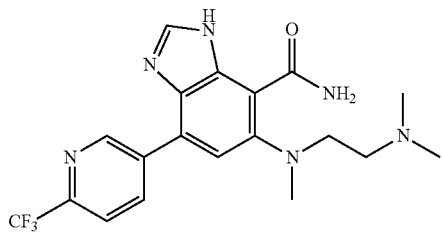

Example 195

According to the procedure described in example 115, step 2, compound (124g) (100 mg, 0.294 mmol) was converted, by reaction with (6-(trifluoromethyl)pyridin-3-yl) boronic acid (56.1 mg, 0.294 mmol) and after purification by preparative TLC on silica gel (DCM and 10% NH$_4$OH in MeOH), to Example (195) (66 mg, 0.162 mmol, 55%). $^1$H NMR (300 MHz, CDCl$_3$) δ 2.22 (s, 6H), 2.47 (t, J=6.1 Hz, 2H), 2.79 (s, 3H), 3.21 (t, J=6.3 Hz, 2H), 5.84 (s, 1H), 7.40 (d, J=1.5 Hz, 1H), 7.83 (dd, J=8.3/0.9 Hz, 1H), 8.16 (d, J=1.7 Hz, 1H), 8.68 (dd, J=8.3/2.4 Hz, 1H), 9.21 (d, J=2.2 Hz, 1H), 10.68 (s, 1H), 11.60 (s, 1H). MS m/z ([M+H]$^+$) 407.

Example 196

Synthesis of 5-[(2-Dimethylamino-ethyl)-methyl-amino]-7-imidazo[1,2-a]pyridin-7-yl-3H-benzimidazole-4-carboxamide

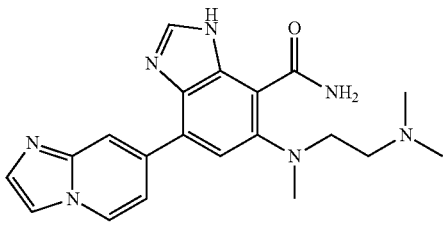

Example 196

According to the procedure described in example 115, step 2, compound (124g) (80 mg, 0.235 mmol) was converted, by reaction with 7-(4,4,5,5-tetramethyl-1,3,2-dioxaborolan-2-yl)imidazo[1,2-a]pyridine (68.9 mg, 0.282 mmol) and after purification by preparative TLC on silica gel (DCM and 10% NH$_4$OH in MeOH), to Example (196) (41 mg, 0.109 mmol, 46%). $^1$H NMR (300 MHz, CDCl$_3$) δ 2.22 (s, 6H), 2.47 (t, J=6.2 Hz, 2H), 2.79 (s, 3H), 3.21 (t, J=6.3 Hz, 2H), 5.75 (s, 1H), 7.48 (d, J=1.4 Hz, 1H), 7.64 (d, J=1.2 Hz, 1H), 7.71 (d, J=1.2 Hz, 1H), 7.86 (dd, J=7.1/1.8 Hz, 1H), 8.10-8.19 (m, 2H), 8.25 (d, J=7.2 Hz, 1H), 10.69 (s, 1H), 11.55 (s, 1H). MS m/z ([M+H]$^+$) 378.

Example 197

Synthesis of 7-(3,4-Dihydro-2H-pyrano[23-b]pyridin-6-yl)-5-methoxy-3H-benzimidazole-4-carboxamide

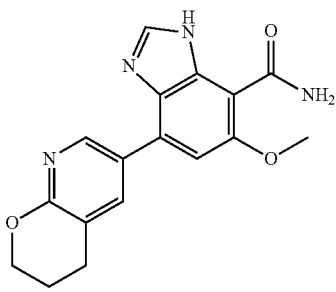

Example 197

Step 1: 2-Amino-4-(3,4-dihydro-2H-pyrano[2,3-b]pyridin-6-yl)-6-methoxy-3-nitro-benzamide (197a)

According to the procedure described in example 88, step 1, compound (177a) (130 mg, 0.39 mmol) was converted, by reaction with sodium methoxide (49 mg, 0.9 mmol) and after purification by preparative TLC on silica gel (DCM/MeOH 95/5), to compound (197a) (35 mg, 0.102 mmol, 26%). MS m/z ([M+H]$^+$) 345.

Step 2: 7-(3,4-Dihydro-2H-pyrano[2,3-b]pyridin-6-yl)-5-methoxy-3H-benzimidazole-4-carboxamide, Example (197)

According to the procedure described in example 177, step 3, compound (197a) (78 35 mg, 0.102 mmol) was converted, after purification by preparative TLC on silica gel (DCM/MeOH 9/1+1% NH$_3$), to Example (197) (16 mg, 0.049 mmol, 48%). $^1$H NMR (400 MHz, DMSO-d$_6$) δ 1.95-1.99 (m, 2H), 2.89 (t, J=6.3 Hz, 2H), 4.07 (s, 3H), 4.34 (t, J=5.2 Hz, 2H), 7.26 (s, 1H), 7.68 (d, J=1.3 Hz, 1H), 7.86 (d, J=1.2 Hz, 1H), 8.10 (s, 1H), 8.38 (d, J=2.2 Hz, 1H), 8.84 (d, J=2.3 Hz, 1H), 12.38 (s, 1H). MS m/z ([M+H]$^+$) 325.

Example 198

Synthesis of 6-(2-Dimethylamino-ethoxy)-1'-ethyl-1H,1'H-[4,5']]bibenzimidazolyl-7-carboxamide methanesulfonic acid salt

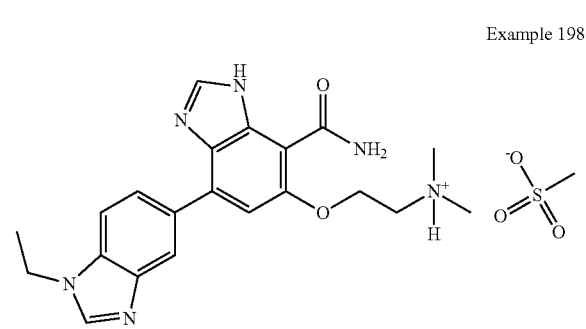

Example 198

Step 1: 2-Amino-4-bromo-6-(2-dimethylamino-ethoxy)-3-nitro-benzonitrile (198a)

According to the procedure described in example 104, step 1, compound (57b) (2 g, 7.69 mmol) was converted, by reaction with N,N-dimethylethanolamine (1 mL, 9.94 mmol), to compound (198a) (2.3 g, 6.99 mmol, 91%) without further purification. MS m/z ([M+H]$^+$) 329/331.

Step 2: 7-Bromo-5-(2-dimethylamino-ethoxy)-3H-benzimidazole-4-carbonitrile (198b)

According to the procedure described in example 19, step 4, compound (198a) (2.3 g, 6.99 mmol) was converted, after purification by column chromatography on silica gel (DCM/MeOH 9/1+2% of ammonia), to compound (198b) (1.2 g, 3.88 mmol, 50%). MS m/z ([M+H]$^+$) 309/311.

Step 3: 6-(2-Dimethylamino-ethoxy)-1'-ethyl-1H,1'H-[4,5']]bibenzimidazolyl-7-carbonitrile (198c)

According to the procedure described in example 29, step 1, compound (198b) (180 mg, 0.58 mmol) was converted, by reaction with 1-Ethyl-5-(4,4,5,5-tetramethyl-[1,3,2]dioxaborolan-2-yl)-1H-benzoimidazole (175 mg, 0.64 mmol) and after purification by preparative TLC on silica gel (DCM/MeOH 9/1+1% of ammonia), to compound (198c) (90 mg, 0.24 mmol, 41%). MS m/z ([M+H]$^+$) 375.

Step 4: 6-(2-Dimethylamino-ethoxy)-1'-ethyl-1H,1'H-[4,5']]bibenzimidazolyl-7-carboxamide (198d)

According to the procedure described in example 138, compound (198c) (90 mg, 0.24 mmol) was converted, after purification by preparative TLC on silica gel (DCM/MeOH/NH$_3$ 7M in MeOH 94/4/2), to compound (198d) (24 mg, 0.061 mmol, 25%). $^1$H NMR (400 MHz, CD$_3$OD) δ 1.61 (t, J=7.3 Hz, 3H), 3.05 (s, 6H), 3.70 (t, J=5.0 Hz, 2H), 4.46 (q, J=7.3 Hz, 2H), 4.70 (t, J=5.0 Hz, 2H), 7.37 (s, 1H), 7.83 (d, J=8.5 Hz, 1H), 7.90 (dd, J=8.5/1.2 Hz, 1H), 8.19 (bs, 1H), 8.29 (s, 1H), 8.49 (s, 1H). MS m/z ([M+H]$^+$) 393.

Step 5: 6-(2-Dimethylamino-ethoxy)-1'-ethyl-1H,1'H-[4,5']]bibenzimidazolyl-7-carboxamide methanesulfonic acid salt, Example (198)

According to the procedure described in example 108, compound (198d) (24 mg, 0.061 mmol) was converted to Example (198) without further purification (29 mg, 0.06 mmol, 100%). $^1$H NMR (400 MHz, CD$_3$OD) δ 1.74 (t, J=7.3 Hz, 3H), 2.75 (s, 3H), 3.09 (s, 6H), 3.83-3.86 (m, 2H), 4.71 (q, J=7.3 Hz, 2H), 4.83-4.85 (m, 2H), 7.74 (s, 1H), 8.09 (dd, J=8.7/1.5 Hz, 1H), 8.27 (dd, J=8.7/0.4 Hz, 1H), 8.35 (bs, 1H), 9.50 (bs, 1H), 9.65 (s, 1H). MS m/z ([M+H]$^+$) 393.

Example 199

Synthesis of 1'-Ethyl-6-[(2-hydroxy-ethyl)-methyl-amino]-1H,1'H-[4,5']]bibenzimidazolyl-7-carboxamide Example 199

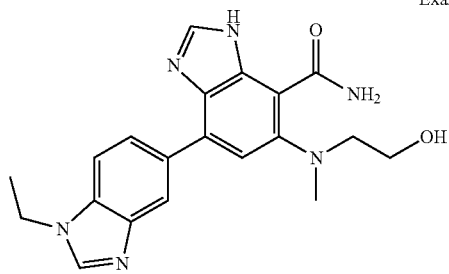

Step 1: Methyl 2-Amino-4-bromo-6-[(2-hydroxy-ethyl)-methyl-amino]-3-nitro-benzoate (199a)

According to the procedure described in example 124, step 5, compound (51) (1 g, 3.4 mmol) was converted, by reaction with 2-Methylamino-ethanol (0.3 mL, 3.75 mmol), to compound (199a) (1.16 g, 3.33 mmol, 98%) was used in the next step without purification. $^1$H NMR (400 MHz, DMSO-d$_6$) δ 2.89 (s, 3H), 3.29-3.31 (m, 2H), 3.55-3.60 (m, 2H), 3.82 (s, 3H), 4.75-4.78 (t, J=5.4 Hz, 1H), 6.69 (s, 1H), 6.79 (bs, 2H). MS m/z ([M+H]$^+$) 348/350.

Step 2: Methyl 7-Bromo-5-[(2-hydroxy-ethyl)-methyl-amino]-3H-benzimidazole-4-carboxylate (199b)

According to the procedure described in example 19, step 4, compound (199a) (1.16 g, 3.33 mmol) was converted, after purification by column chromatography on silica gel (DCM/MeOH 95/5), to compound (199b) (180 mg, 0.55 mmol, 16%). $^1$H NMR (400 MHz, DMSO-d$_6$) δ 2.85 (s, 3H), 3.20 (t, J=6.1 Hz, 2H), 3.55-3.56 (m, 2H), 3.90 (s, 3H), 4.51 (bs, 1H), 7.26 (s, 1H), 8.12 (s, 1H), 12.34 (s, 1H). MS m/z ([M+H]$^+$) 328/330.

Step 3: 4-(1-Ethyl-1H-benzimidazol-5-yl)-6-methyl-1,6,7,8-tetrahydro-9-oxa-1,36-triaza-cyclohept[e]inden-10-one (199c)

According to the procedure described in example 42, step 2, compound (199b) (180 mg, 0.55 mmol) was converted, by reaction with 1-Ethyl-5-(4,4,5,5-tetramethyl-[1,3,2]dioxaborolan-2-yl)-1H-benzoimidazole (164 mg, 0.60 mmol) and after purification by preparative TLC on silica gel (DCM/MeOH 92/8), to compound (199c) (34 mg, 0.094 mmol, 17%) $^1$H NMR (400 MHz, DMSO-d$_6$) δ 1.46 (t, J=7.2 Hz, 3H), 3.04 (s, 3H), 3.52-3.55 (m, 2H), 4.35 (q, J=7.2 Hz, 2H), 4.48-4.50 (m, 2H), 7.03 (s, 1H), 7.72 (d, J=8.5 Hz, 1H), 8.06 (s, 1H), 8.07 (dd, J=1.5/8.4 Hz, 1H), 8.32 (s, 1H), 8.46 (d, J=1.1 Hz, 1H), 12.20 (s, 1H). MS m/z ([M+H]$^+$) 362.

Step 4: 1'-Ethyl-6-[(2-hydroxy-ethyl)-methyl-amino]-1H,1'H-[4,5']]bibenzimidazolyl-7-carboxamide, Example (199)

According to the procedure described in example 115, step 1, compound (199c) (34 mg, 0.094 mmol) was converted, after purification by preparative TLC on silica gel (DCM/MeOH 9/1+1% of ammonia), to Example (199) (11 mg, 0.029 mmol, 31%). $^1$H NMR (400 MHz, DMSO-d$_6$) δ 1.46 (t, J=7.2 Hz, 3H), 2.77 (s, 3H), 3.17-3.20 (m, 2H), 3.56-3.60 (m, 2H) 4.35 (q, J=7.2 Hz, 2H), 4.75 (t, J=5.0 Hz, 1H), 7.51 (s, 1H), 7.62 (d, J=3.7 Hz, 1H), 7.72 (d, J=8.5 Hz, 1H), 8.09 (dd, J=1.5/8.5 Hz, 1H), 8.16 (s, 1H), 8.31 (s, 1H), 8.48 (d, J=1.1 Hz, 1H), 9.94 (d, J=3.9 Hz, 1H), 12.41 (s, 1H). MS m/z ([M+H]$^+$) 379.

Example 200

Synthesis of 6-[2-(dimethylamino)ethyl-methyl-amino]-4-(1-ethylbenzimidazol-5-yl)-1H-imidazo[4,5-c]pyridine-7-carboxamide

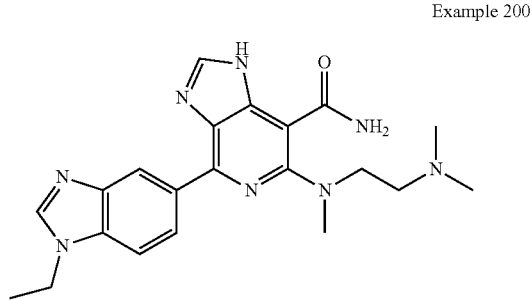 [SMILES: CCn1cnc2cc(-c3nc(N(C)CCN(C)C)c(C(N)=O)c4[nH]cnc34)ccc21]

Example 200

Step 1: 3-bromo-2,6-dichloro-5-nitro-pyridin-4-amine (200a)

Compound (17a) (3.80 g, 18.3 mmol) was suspended in acetic acid (80 mL) at room temperature under nitrogen and treated with NBS (3.58 g, 2.01 mmol). The suspension was stirred for 3 hours at 60° C. The solvent was evaporated and the residue was co-evaporated with toluene. Ethyl acetate (200 mL) was added and the solution was washed with saturated NaHCO$_3$ and brine. The organic phase was dried over sodium sulfate and evaporated. Compound (200a) (4.85 g, 92%) was obtained as a yellow solid and used without further purification in the next step.

Step 2: 2-benzyloxy-5-bromo-6-chloro-3-nitro-pyridin-4-amine (200b)

Benzyl alcohol (2.38 g, 2.2 mmol) was dissolved in toluene (160 mL) at 0° C. under nitrogen and treated with NaH (60% oil dispersion, 845 mg, 2.11 mmol). After 30 minutes, compound (200a) (4.85 g, 16.9 mmol) was added by portions and the red suspension was stirred for 48 hours at room temperature. Then, toluene was removed and the residue was portioned between ethyl acetate and saturated NH$_4$Cl. The organic phase was washed with brine, dried over sodium sulfate and evaporated. The crude material was purified by chromatography on silica gel (petroleum ether/DCM 1/0 to 3/7) to give compound (200b) as a yellow powder (5.46 g, 15.2 mmol, 90%). $^1$H NMR (400 MHz, DMSO-d$_6$) δ 5.38 (s, 2H), 7.33-7.46 (m, 5H), 7.62 (bs, 2H).

Step 3: 2-benzyloxy-5-bromo-6-chloro-pyridine-3,4-diamine (200c)

Compound (200b) (2.52 g, 7 mmol) and ammonium chloride (3.77 g, 70 mmol) were dissolved in a mixture of ethanol (34 mL) and water (17 mL). The middle was heated at 60° C. for 20 minutes and Iron (1.74 g, 3.08 mmol) was then added. The mixture was stirred at 90° C. for 2 hours. The resulting dark solution was filtered over Celite and diluted with DCM (200 mL). The organic phase was washed with water, dried over sodium sulfate and evaporated to give compound (200c) (2.27 g, 6.91 mmol, 98%) which was used in the next step without further purification.

Step 4: 4-benzyloxy-7-bromo-6-chloro-1H-imidazo[4,5-c]pyridine (200d)

A solution of compound (200c) (2.26 g, 6.88 mmol) in triethyl orthoformate (7.5 mL) and acetic anhydride (4 mL) was heated at 120° C. for 4 hours. The resulting solution was evaporated and the residue co-evaporated twice with ethanol. The crude material was purified by chromatography on silica gel (petroleum ether/ethyl acetate 4/1 to 1/4) to give compound (200d) as a beige solid (1.89 g, 5.58 mmol, 81%). $^1$H NMR (400 MHz, DMSO-d$_6$) δ 5.49 (s, 2H), 7.33-7.44 (m, 3H), 7.52-7.55 (m, 2H), 8.40 (s, 1H).

Step 5: dimethyl 4-benzyloxy-6-chloro-imidazo[4,5-c]pyridine-1,7-dicarboxylate (200e)

Compound (200d) (335 mg, 0.99 mmol) was dissolved in THF (10 mL) at room temperature under nitrogen and cooled to −78° C. Butyllithium (1.6 M, 1.36 mL, 1.18 mmol) was added drop-wise over 5 minutes and the mixture was stirred at −78° C. for 10 minutes. Methyl chloroformate (775 µL, 9.9 mmol) was added drop-wise over 2 minutes. The mixture was warmed to 0° C. and stirred for 1 hour at this temperature. The reaction was quenched by addition of saturated ammonium chloride (2 mL). The mixture was diluted with ethyl acetate (50 mL) and the organic phase was washed with saturated ammonium chloride and brine. The organic phase was dried over sodium sulfate and evaporated. The crude material was purified by chromatography on silica gel (petroleum ether/ethyl acetate 1/0 to 1/1) to give compound (200e) as a pale yellow solid (124 g, 0.33 mmol, 33%). $^1$H NMR (400 MHz, CDCl$_3$) δ 3.92 (s, 3H), 4.04 (s, 3H), 5.57 (s, 2H), 7.32-7.44 (m, 3H), 7.52-7.55 (m, 2H), 8.56 (s, 1H).

Step 6: methyl 4-benzyloxy-6-[2-(dimethylamino)ethyl-methyl-amino]-1H-imidazo[4,5-c]pyridine-7-carboxylate (200f)

A mixture of compound (200e) (360 mg, 0.96 mmol), N,N',N'-trimethylethane-1,2-diamine (750 µl, 5.76 mmol) and diisopropylethylamine (370 µL, 2.22 mmol) in dioxane (13 mL) was stirred for 24 hours at 100° C. The mixture was cooled to room temperature and diluted with ethyl acetate (80 mL). The organic phase was washed with water and brine. The organic phase was dried over sodium sulfate and evaporated. The crude material was purified by chromatography on silica gel (DCM/Methanol 1/0 to 8/2) to give compound (200f) as a yellow oil (301 g, 0.78 mmol, 82%). $^1$H NMR (400 MHz, CDCl$_3$) δ 2.37 (s, 6H), 2.67 (t, J=6.9 Hz, 2H), 3.02 (s, 3H), 3.77 (t, J=6.9 Hz, 2H), 3.92 (s, 3H), 5.61 (s, 2H), 7.32-7.44 (m, 3H), 7.52-7.55 (m, 2H), 7.80 (s, 1H), 10.22 (bs, 1H).

Step 7: methyl 4-benzyloxy-6-[2-(dimethylamino)ethyl-methyl-amino]-1-(2-trimethylsilylethoxymethyl)imidazo[4,5-c]pyridine-7-carboxylate (200g)

At 0° C., 2-(Trimethylsilyl)ethoxymethyl chloride (143 µL, 0.8 mmol) was added to a solution of compound (200f) (255 mg, 0.67 mmol) and triethylamine (187 µL, 1.34 mmol) in THF (3 mL) under nitrogen. The solution was then stirred for 2 hours at room temperature. The mixture was concentrated. The crude material was quickly purified on a pad of silica gel (DCM/MeOH 1/1+1% NEt₃) to give crude compound (200g) as a yellow solid (182 mg) which was used in the next step without further purification.

Step 8: methyl 6-[2-(dimethylamino)ethyl-methylamino]-4-hydroxy-1-(2-trimethylsilylethoxymethyl)imidazo[4,5-c]pyridine-7-carboxylate (200h)

At room temperature, a solution of crude compound (200g) (180 mg) in Methanol (10 mL) was degassed with nitrogen. Palladium catalyst (Pd/C 10%, 100 mg) was added. The mixture was purged with hydrogen and stirred for 15 hours at room temperature. The suspension was filtered and evaporated to give crude compound (200h) (146 mg) which was used in the next step without further purification.

Step 9: methyl 6-[2-(dimethylamino)ethyl-methylamino]-4-(trifluoromethylsulfonyloxy)-1-(2-trimethylsilylethoxymethyl)imidazo[4,5-c]pyridine-7-carboxylate (200i)

At 0° C., triflic anhydride (49 µL, 0.29 mmol) was slowly added to a solution of crude compound (200h) (143 mg) and 2,6-lutidine (57 µL, 0.48 mmol) in DCM (2 mL). The mixture was stirred at 0° C. for 2 hours and diluted with DCM (10 mL). The solution was washed twice with brine, dried over sodium sulfate and evaporated to give crude compound (200i) (200 mg) which was used in the next step without further purification.

Step 10: methyl 6-[2-(dimethylamino)ethyl-methylamino]-4-(1-ethylbenzimidazol-5-yl)-1-(2-trimethylsilylethoxymethyl)imidazo[4,5-c]pyridine-7-carboxylate (200j)

A solution of crude compound (200i) (200 mg), 1-ethyl-5-(4,4,5,5-tetramethyl-1,3,2-dioxaborolan-2-yl)benzimidazole (72 mg, 0.264 mmol) and NaHCO₃ (60 mg, 0.72 mmol) in a mixture of THF (1.5 mL) and water (100 µL) was degassed with nitrogen. Tetrakis(triphenylphosphine)palladium (55 mg, 0.048 mmol) was added. The mixture was stirred at 85° C. for 2 hours and then filtrated. The crude was quickly purified on a pad of silica gel (DCM/MeOH 7/3+1% NEt₃) to give crude compound (200j) (77 mg) which was used in the next step without further purification.

Step 11: 6-[2-(dimethylamino)ethyl-methyl-amino]-4-(1-ethylbenzimidazol-5-yl)-1H-imidazo[4,5-c]pyridine-7-carboxamide, Example (200)

A solution of tetrabutylammonium fluoride (1M in THF, 1 mL, 1 mmol) and crude compound (200j) (77 mg) in THF (1 mL) was stirred at 60° C. for 2 hours. The mixture was cooled to room temperature and then transferred into a steel container, diluted with methanol (10 mL) and treated with ammonium hydroxide (30%, 5 mL). The mixture was stirred at 70° C. for 15 hours and then concentrated. The crude was purified by chromatography on reverse phase (H₂O/MeOH 1/0 to 0/1) to afford Example (200) as an oil (8 mg, 0.02 mmol, 3% yield over 5 last steps). ¹H NMR (400 MHz, CD₃OD) δ 1.57 (t, J=7.3 Hz, 3H), 2.28 (s, 6H), 2.63 (t, J=6.8 Hz, 2H), 2.96 (s, 3H), 3.65 (t, J=6.8 Hz, 2H), 4.40 (q, J=7.3 Hz, 2H), 7.72 (d, J=8.6 Hz, 1H), 8.23 (s, 1H), 8.27 (s, 1H), 8.67 (d, J=9.1 Hz, 1H), 9.02 (s, 1H). MS m/z ([M+H]⁺) 407. MS m/z ([M−H]⁻) 405.

Example 201

Synthesis of 4-(1-ethylbenzimidazol-5-yl)-6-[methyl(2-pyrrolidin-1-ylethyl)amino]-1H-imidazo[4,5-c]pyridine-7-carboxamide Example 201

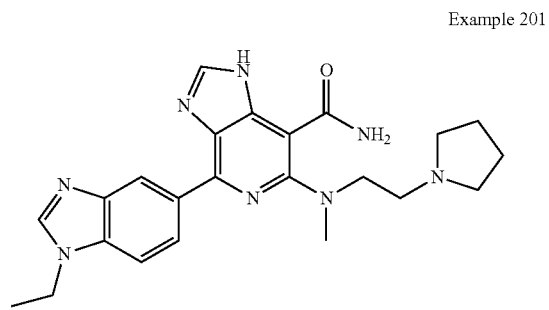 [SMILES: CCn1cnc2cc(-c3nc(N(C)CCN4CCCC4)c(C(N)=O)c4[nH]cnc34)ccc21]

Step 1: methyl 4-benzyloxy-6-[methyl(2-pyrrolidin-1-ylethyl)amino]-1H-imidazo[4,5-c]pyridine-7-carboxylate (201a)

A mixture of compound (200e) (400 mg, 1.06 mmol), N-Methyl-2-(1-pyrrolidinyl)ethanamine (750 µl, 6.36 mmol) and diisopropylethylamine (460 µL, 3.18 mmol) in dioxane (15 mL) was stirred for 24 hours at 100° C. The mixture was cooled to room temperature and diluted with ethyl acetate (80 mL). The organic phase was washed with water and brine. The organic phase was dried over sodium sulfate and evaporated. The crude material was purified by chromatography on silica gel (DCM/Methanol 1/0 to 4/1+1% NEt₃) to give compound (201a) as a orange oil (379 g, 0.92 mmol, 87%). ¹H NMR (400 MHz, DMSO-d₆) δ 1.59-1.67 (m, 4H), 2.38-2.46 (m, 4H), 2.63-2.68 (m, 2H), 2.91 (s, 3H), 3.59-3.64 (m, 2H), 3.82 (s, 3H), 5.54 (s, 2H), 7.32-7.41 (m, 3H), 7.44-7.57 (m, 2H), 7.88 (s, 1H), 12.07 (bs, 1H).

Step 2: methyl 4-benzyloxy-6-[methyl(2-pyrrolidin-1-ylethyl)amino]-1-(2-trimethylsilylethoxymethyl)imidazo[4,5-c]pyridine-7-carboxylate (201b)

At 0° C., 2-(Trimethylsilyl)ethoxymethyl chloride (98 µL, 0.55 mmol) was added to a solution of compound (201a) (190 mg, 0.46 mmol) and triethylamine (128 µL, 0.92 mmol) in THF (3 mL) under nitrogen. The solution was then stirred for 2 hours at room temperature. The mixture was concentrated. The crude material was quickly purified on a pad of silica gel (DCM/MeOH 3/1+1% NEt₃) to give crude compound (201b) as a yellow oil (120 mg) which was used in the next step without further purification.

Step 3: methyl 4-hydroxy-6-[methyl(2-pyrrolidin-1-ylethyl)amino]-1-(2-trimethylsilylethoxymethyl)imidazo[4,5-c]pyridine-7-carboxylate (201c)

At room temperature, a solution of crude compound (201b) (116 mg) in Methanol (8 mL) was degassed with nitrogen. Palladium catalyst (Pd/C 10%, 80 mg) was added. The mixture was purged with hydrogen and stirred for 15 hours at room temperature. The suspension was filtered and evaporated to give crude compound (201c) (95 mg) which was used in the next step without further purification.

Step 4: methyl 6-[methyl(2-pyrrolidin-1-ylethyl) amino]-4-(trifluoromethylsulfonyloxy)-1-(2-trimethylsilylethoxymethyl)imidazo[4,5-c]pyridine-7-carboxylate (201d)

At 0° C., triflic anhydride (31 µL, 0.18 mmol) was slowly added to a solution of crude compound (201c) (92 mg) and 2,6-lutidine (36 µL, 0.3 mmol) in DCM (1.5 mL). The mixture was stirred at 0° C. for 2 hours and diluted with DCM (10 mL). The solution was washed twice with brine, dried over sodium sulfate and evaporated to give crude compound (201d) (170 mg) which was used in the next step without further purification.

Step 5: methyl 4-(1-ethylbenzimidazol-5-yl)-6-[methyl(2-pyrrolidin-1-ylethyl)amino]-1-(2-trimethylsilylethoxymethyl)imidazo[4,5-c]pyridine-7-carboxylate (201e)

A solution of crude compound (201d) (170 mg), 1-ethyl-5-(4,4,5,5-tetramethyl-1,3,2-dioxaborolan-2-yl)benzimidazole (45 mg, 0.165 mmol) and NaHCO₃ (38 mg, 0.45 mmol) in a mixture of THF (1.5 mL) and water (100 µL) was degassed with nitrogen. Tetrakis(triphenylphosphine)palladium (35 mg, 0.03 mmol) was added. The mixture was stirred at 85° C. for 2 hours and then filtrated. The crude was quickly purified on a pad of silica gel (DCM/MeOH 7/3+1% NEt₃) to give crude compound (201e) (52 mg) which was used in the next step without further purification.

Step 6: 4-(1-ethylbenzimidazol-5-yl)-6-[methyl(2-pyrrolidin-1-ylethyl)amino]-1H-imidazo[4,5-c]pyridine-7-carboxamide, Example (201)

A solution of tetrabutylammonium fluoride (1M in THF, 700 µL, 0.7 mmol) and crude compound (201e) (52 mg) in THF (1 mL) was stirred at 60° C. for 2 hours. The mixture was cooled to room temperature and then transferred into a steel container, diluted with methanol (8 mL) and treated with ammonium hydroxide (30%, 4 mL). The mixture was stirred at 70° C. for 15 hours and then concentrated. The crude was purified at first by chromatography on silica gel (DCM/MeOH 1/0 to 7/3+1% NEt₃) and then on reverse phase (H₂O/MeOH 1/0 to 0/1) to afford Example (201) as an oil (5 mg, 0.011 mmol, 3% yield over 5 last steps). $^1$H NMR (300 MHz, CD₃OD) δ 1.56 (t, J=7.3 Hz, 3H), 1.75-1.78 (m, 4H), 2.64-2.68 (m, 4H), 2.84 (t, J=6.8 Hz, 2H), 2.97 (s, 3H), 3.69 (t, J=6.9 Hz, 2H), 4.39 (q, J=7.3 Hz, 2H), 7.72 (d, J=8.6 Hz, 1H), 8.23 (s, 1H), 8.27 (s, 1H), 8.65 (d, J=8.5 Hz, 1H), 8.99 (s, 1H). MS m/z ([M+H]⁺) 433. MS m/z ([M−H]⁻) 431.

Example 202

Synthesis of 4-(5-cyclopropylpyridin-3-yl)-6-((2-(dimethylamino)ethyl)-(methyl)amino)-1H-benzo[d]imidazole-7-carboxamide Example 202

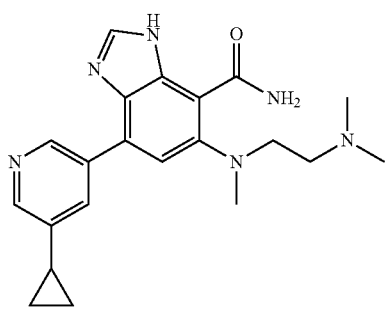

According to the procedure described in Example 115, Step 2, compound (124g) (100 mg, 0.294 mmol) was converted, by reaction with (5-cyclopropylpyridin-3-yl)boronic acid (57.5 mg, 0.35 mmol) and after purification by preparative TLC on silica gel (DCM/10% NH₄OH in MeOH 9/1), to Example (202) (25 mg, 0.066 mmol, 22%). $^1$H NMR (300 MHz, CDCl₃) δ 0.83 (dt, J=4.1/2.0 Hz, 2H), 1.06 (ddd, J=8.5/4.0/2.2 Hz, 2H), 2.01 (dd, J=8.7/4.7 Hz, 1H), 2.13-2.23 (s, 6H), 2.45 (t, J=6.2 Hz, 2H), 2.77 (s, 3H), 3.20 (t, J=6.3 Hz, 2H), 5.82 (s, 1H), 7.34 (d, J=1.6 Hz, 1H), 8.01-8.22 (m, 2H), 8.43 (d, J=2.3 Hz, 1H), 8.86 (s, 1H), 10.68 (s, 1H), 11.57 (s, 1H). MS m/z ([M+H]⁺) 379. MS m/z ([M−H]⁻) 377.

Example 203

Synthesis of 7-(1-butylbenzimidazol-5-yl)-5-[2-(dimethylamino)ethyl-methyl-amino]-3H-benzimidazole-4-carboxamide Example 203

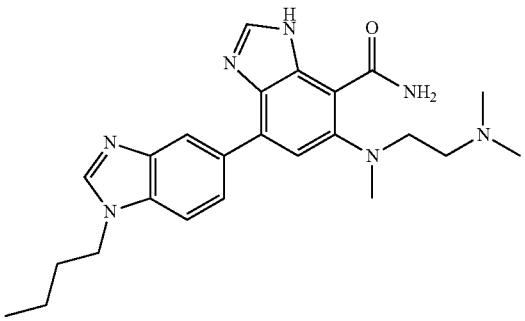

According to the procedure described in Example 115, Step 2, compound (124g) (100 mg, 0.294 mmol) was converted, by reaction with 1-butyl-5-(4,4,5,5-tetramethyl-1,3,2-dioxaborolan-2-yl)benzimidazole (290 mg, 0.97 mmol) and after purification by column chromatography on silica gel (DCM/MeOH 9/1 to 8/2+1% NEt₃), to Example (203) (223 mg, 0.54 mmol, 55%). $^1$H NMR (400 MHz, CDCl₃) δ 0.89 (t, J=7.4 Hz, 3H), 1.20-1.38 (m, 2H), 1.77-1.88 (m, 2H), 2.24 (s, 6H), 2.50 (t, J=6.3 Hz, 2H), 2.75 (s, 3H), 3.22 (t, J=6.4 Hz, 2H), 4.15 (t, J=7.0 Hz, 2H), 5.83 (d, J=4.5 Hz, 1H), 7.38 (s, 1H), 7.48 (dd, J=8.5/0.6 Hz, 1H), 7.87 (s, 1H), 8.09 (s, 1H), 8.12 (dd, J=8.4, 1.6 Hz, 1H), 8.18 (d, J=1.0 Hz, 1H), 10.52 (bs, 1H), 11.55 (bs, 1H). MS m/z ([M+H]⁺) 434. MS m/z ([M−H]⁻) 432.

Example 204

Synthesis of 5-[2-(dimethylamino)ethyl-methyl-amino]-7-(1-phenylbenzimidazol-5-yl)-3H-benzimidazole-4-carboxamide Example 204

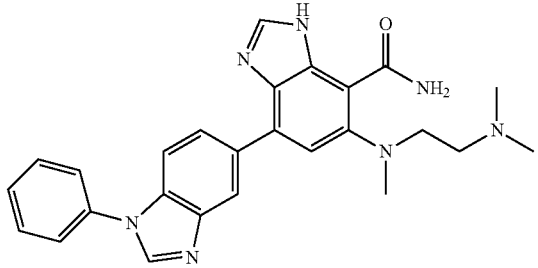

Step 1: 1-phenyl-5-(4,4,5,5-tetramethyl-1,3,2-dioxaborolan-2-yl)benzimidazole (204a)

According to the procedure described in Example 123, Step 4, 5-bromo-1-phenyl-1H-benzoimidazole (950 mg, 3.45 mmol) was converted to compound (204a) as a brown oil (223 mg, 0.54 mmol, 55%) which was used as crude without further purification. MS m/z ([M+H]$^+$) 321.

Step 2: 5-[2-(dimethylamino)ethyl-methyl-amino]-7-(1-phenylbenzimidazol-5-yl)-3H-benzimidazole-4-carboxamide, Example (204)

According to the procedure described in Example 115, Step 2, compound (124g) (170 mg, 0.5 mmol) was converted, after purification by preparative TLC on silica gel (DCM/methanol 9/1+1% of ammonia) to Example (204) (11.5 mg, 0.025 mmol, 5%). $^1$H NMR (400 MHz, DMSO-d$_6$) δ 2.15 (s, 6H), 2.42 (t, J=6.3 Hz, 2H), 2.76 (s, 3H), 3.23 (t, J=6.4 Hz, 2H), 7.51-7.57 (m, 2H), 7.59 (d, J=3.9 Hz, 1H), 7.65-7.71 (m, 2H), 7.72-7.77 (m, 3H), 8.19 (bs, 2H), 8.63 (dd, J=1.7/0.6 Hz, 1H), 8.64 (s, 1H), 10.03 (d, J=3.9 Hz, 1H), 12.42 (s, 1H). MS m/z ([M+H]$^+$) 454. MS m/z ([M−H]$^-$) 452.

Example 205

5-[2-(dimethylamino)ethyl-methyl-amino]-7-[6-(dimethylamino)-3-pyridyl]-3H-benzimidazole-4-carboxamide

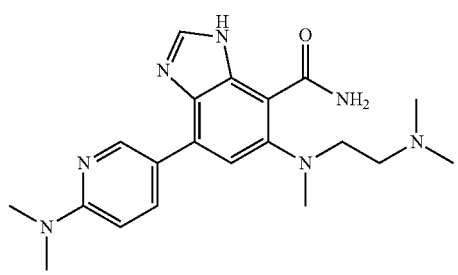

Example 205

According to the procedure described in Example 115, Step 2, compound (124g) (50 mg, 0.15 mmol) was converted, by reaction with N,N-dimethyl-5-(4,4,5,5-tetramethyl-1,3,2-dioxaborolan-2-yl)pyridin-2-amine (30 mg, 0.17 mmol) and after purification by preparative TLC on silica gel (DCM/methanol 9/1+2% of ammonia) to Example (205) (14.2 mg, 0.037 mmol, 25%). $^1$H NMR (400 MHz, CDCl$_3$) δ 2.27 (s, 6H), 2.51 (t, J=6.4 Hz, 2H), 2.80 (s, 3H), 3.19 (s, 6H), 3.24 (t, J=6.4 Hz, 2H), 5.88 (d, J=4.1 Hz, 1H), 6.70 (dd, J=8.9/0.9 Hz, 1H), 7.36 (d, J=1.0 Hz, 1H), 8.15 (d, J=1.0 Hz, 1H), 8.42 (bs, 1H), 8.77 (dd, J=2.5/0.9 Hz, 1H), 10.62 (d, J=4.6 Hz, 1H), 11.60 (s, 1H). MS m/z ([M+H]$^+$) 382.

Example 206

Synthesis of 5-[2-(dimethylamino)ethyl-methyl-amino]-7-(1-methylpyrrolo[3,2-b]pyridin-6-yl)-3H-benzimidazole-4-carboxamide

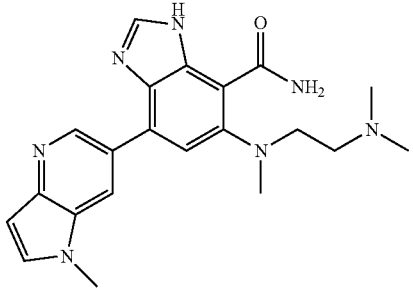

Example 206

Step 1: 6-bromo-1-methyl-pyrrolo[3,2-b]pyridine (206a)

6-bromo-1H-pyrrolo[3,2-b]pyridine (250 mg, 1.27 mmol) was added slowly to a cooled solution of sodium hydride (60% in mineral oil, 52 mg, 1.02 mmol) in DMF (1.5 mL). The reaction was stirred at 0° C. for 30 minutes and methyl iodide (80 μL, 1.02 mmol) was added dropwise. The resulting mixture was stirred at 0° C. for 1 hour then at room temperature for 2 hours. The reaction mixture was diluted with water and ethyl acetate and the aqueous layer was extracted with ethyl acetate. The organic layer was washed with brine, dried over sodium sulfate, filtered and concentrated under reduced pressure. The crude product was purified by preparative TLC on silica gel (DCM/ethyl acetate 50/50) to provide compound (206a) (250 mg, 1.18 mmol, 93%). $^1$H NMR (400 MHz, DMSO-d$_6$) δ 3.82 (s, 3H), 6.58 (dd, J=3.2/0.9 Hz, 1H), 7.67 (d, J=3.2 Hz, 1H), 8.24 (dd, J=2.1/0.9 Hz, 1H), 8.39 (d, J=2.0 Hz, 1H). MS m/z ([M+H]$^+$) 212.

Step 2: 1-methyl-6-(4,4,5,5-tetramethyl-1,3,2-dioxaborolan-2-yl)pyrrolo[3,2-b]pyridine (206b)

According to the procedure described in Example 123, Step 4, compound (206a) (250 mg, 1.18 mmol) was converted to compound (206b) as a brown oil (250 mg) which was used as crude without further purification. MS m/z ([M+H]$^+$) 259.

Step 3: 5-[2-(dimethylamino)ethyl-methyl-amino]-7-(1-methylpyrrolo[3,2-b]pyridin-6-yl)-3H-benzimidazole-4-carboxamide, Example (206)

According to the procedure described in Example 115, Step 2, compound (124g) (371 mg, 1.09 mmol) was converted, by reaction with crude compound (206b) (250 mg) and after purification by preparative TLC on silica gel (DCM/methanol 9/1+5% of ammonia) to Example (206) (9.4 mg, 0.024 mmol, 2.2%). $^1$H NMR (400 MHz, CDCl$_3$) δ 2.28 (s, 6H), 2.53 (t, J=6.3 Hz, 2H), 2.84 (s, 3H), 3.28 (t, J=6.3 Hz, 2H), 3.95 (s, 3H), 5.74-5.86 (m, 1H), 6.77 (dd, J=3.2/0.9 Hz, 1H), 7.39 (d, J=3.2 Hz, 1H), 7.51 (s, 1H), 8.20

(s, 1H), 8.65 (dd, J=1.9/1.0 Hz, 1H), 8.92 (d, J=1.9 Hz, 1H), 10.73 (s, 1H), 11.61 (s, 1H). MS m/z ([M+H]⁺) 392. MS m/z ([M−H]⁻) 390.

Example 207

7-[1-[(1R,2R)-2-fluorocyclohexyl]benzimidazol-5-yl]-5-[[(2R)-1-methylpyrrolidin-2-yl]methoxy]-3H-benzimidazole-4-carboxamide methanesulfonic acid salt

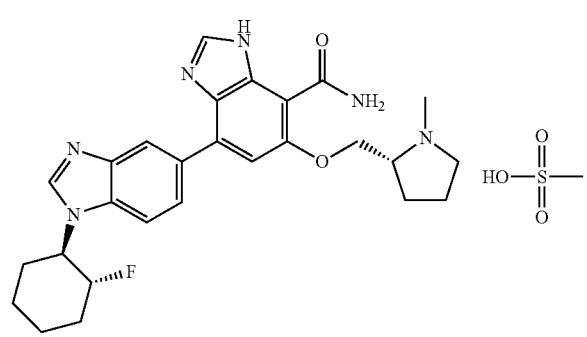

Example 207

Step 1: 2-amino-4-[1-[(1R,2R)-2-fluorocyclohexyl]benzimidazol-5-yl]-6-[[(2R)-1-ethylpyrrolidin-2-yl]methoxy]-3-nitro-benzamide (207a)

According to the procedure described in Example 104, Step 1, compound (170a) (1.5 g, 3.61 mmol) was converted, by reaction with [(2R)-1-methylpyrrolidin-2-yl]methanol (1.18 g, 10.2 mmol) and after purification by chromatography on silica gel (DCM/MeOH 95/5 to 9/1), to compound (207a) (1.41 g, 2.76 mmol, 76%). ¹H NMR (400 MHz, DMSO-d₆) δ 1.42-1.56 (m, 2H), 1.59-1.75 (m, 4H), 1.76-1.87 (m, 2H), 1.88-1.97 (m, 1H), 2.03-2.11 (m, 2H), 2.16-2.29 (m, 2H), 2.30 (s, 3H), 2.52-2.58 (m, 1H), 2.94-3.01 (m, 1H), 4.09 (dd, J=4.5/9.9 Hz, 1H), 4.23 (dd, J=3.7/9.9 Hz, 1H), 4.54-4.66 (m, 1H), 4.90-5.11 (m, 1H), 6.42 (s, 1H), 7.08 (s, 2H), 7.17 (dd, J=1.5/8.4 Hz, 1H), 7.65 (d, J=1.5 Hz, 1H), 7.74 (s, 1H), 7.75 (d, J=8.4 Hz, 1H), 8.18 (s, 1H), 8.49 (s, 1H). MS m/z ([M+H]⁺) 511.

Step 2: 7-[1-[(1R,2R)-2-fluorocyclohexyl]benzimidazol-5-yl]-5-[[(2R)-1-methylpyrrolidin-2-yl]methoxy]-3H-benzimidazole-4-carboxamide (207b)

A solution of compound (207a) (1.41 g, 2.76 mmol) in ethanol (20 mL) was purged with nitrogen. Catalyst Pd/C 10% (200 mg) was then added and the reaction was stirred under hydrogen atmosphere (1 bar) overnight. The middle was filtered and concentrated under reduced pressure. The crude material was diluted in toluene (30 mL) and ethanol (5 mL). Triethyl orthoformate (2 ml, 12.02 mmol) was then added and the mixture was heated at 110° C. for 1 hour. The middle was concentrated and the crude product was purified by preparative TLC on silica gel (DCM/MeOH 9/1+1% NH₃ 7M in MeOH) to afford compound (207b) (827 mg, 1.68 mmol, 61%). ¹H NMR (400 MHz, DMSO-d₆) δ 1.44-1.59 (m, 2H), 1.63-1.91 (m, 6H), 1.94-2.03 (m, 1H), 2.07-2.14 (m, 2H), 2.20-2.28 (m, 2H), 2.34 (s, 3H), 2.56-2.66 (m, 1H), 3.00-3.08 (m, 1H), 4.21 (dd, J=4.1/9.8 Hz, 1H), 4.48 (dd, J=2.9/9.8 Hz, 1H), 4.58-4.67 (m, 1H), 4.94-5.13 (m, 1H), 7.34 (s, 1H), 7.62 (s, 1H), 7.79 (d, J=8.6 Hz, 1H), 8.10 (s, 1H), 8.13 (dd, J=1.3/8.6 Hz, 1H), 8.45 (s, 1H), 8.48 (s, 1H), 8.53 (d, J=1.3 Hz, 1H), 12.34 (s, 1H). MS m/z ([M+H]⁺) 491. MS m/z ([M−H]⁻) 489.

Step 3: 7-[1-[(1R,2R)-2-fluorocyclohexyl]benzimidazol-5-yl]-5-[[(2R)-1-methylpyrrolidin-2-yl]methoxy]-3H-benzimidazole-4-carboxamide methanesulfonic acid salt, Example (207)

To a solution of compound (207b) (827 mg, 1.68 mmol) in DCM (2 mL) and MeOH (10 mL) was added a solution of methanesulfonic acid (0.1N in H₂O, 16.8 mL, 1.68 mmol). The middle was concentrated to eliminate DCM and MeOH, frozen and lyophilized to give Example (207) as white powder (920 mg, 1.57 mmol, 93%). ¹H NMR (400 MHz, DMSO-d₆) δ 1.43-1.59 (m, 2H), 1.62-1.74 (m, 1H), 1.78-1.90 (m, 2H), 1.92-2.03 (m, 2H), 2.04-2.16 (m, 3H), 2.21-2.30 (m, 2H), 2.31 (s, 3H), 3.00 (s, 3H), 3.12-3.24 (m, 1H), 3.61-3.96 (m, 1H), 3.95-4.07 (m, 1H), 4.49-4.58 (m, 1H), 4.61-4.73 (m, 2H), 4.92-5.14 (m, 1H), 7.35 (s, 1H), 7.71-7.80 (m, 1H), 7.83 (m, 1H), 7.85 (s, 1H), 8.09 (bs, 1H), 8.23 (s, 1H), 8.44 (bs, 1H), 8.57 (s, 1H), 9.89 (bs, 1H), 12.49 (bs, 1H). MS m/z ([M+H]⁺) 491. MS m/z ([M−H]⁻) 489.

Example 208

Synthesis of 7-(3,4-dihydro-2H-pyrano[2,3-b]pyridin-6-yl)-5-[(1-methyl-3-piperidyl)oxy]-3H-benzimidazole-4-carboxamide methanesulfonic acid salt

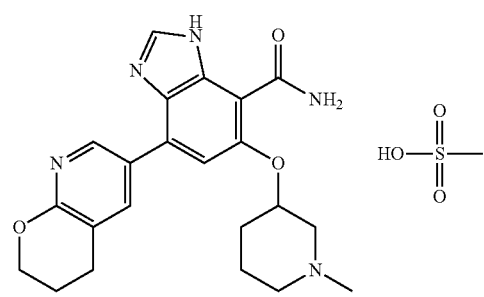

Example 208

Step 1: 2-amino-4-(3,4-dihydro-2H-pyrano[2,3-b]pyridin-6-yl)-6-[(1-methyl-3-piperidyl)oxy]-3-nitro-benzamide (208a)

According to the procedure described in Example 104, Step 1, compound (177a) (166 mg, 0.5 mmol) was converted, by reaction with 1-methylpiperidin-3-ol (0.12 mL, 1 mmol) and after purification by preparative TLC on silica gel (DCM/methanol 95/5), to compound (208a) (129 mg, 0.30 mmol, 60%). ¹H NMR (400 MHz, DMSO-d₆) δ 1.49-1.55 (m, 1H), 1.62-1.87 (m, 3H), 1.91-1.96 (m, 2H), 2.14 (s, 4H), 2.27-2.33 (m, 1H), 2.63 (s, 1H), 2.81 (t, J=6.4 Hz, 2H), 4.29-4.34 (m, 2H), 4.58 (s, 1H), 4.92 (s, 1H), 6.46 (s, 1H), 7.14 (s, 2H), 7.49 (dd, J=2.3/1.2 Hz, 1H), 7.73 (s, 1H), 7.91 (d, J=2.5 Hz, 1H), 8.55 (s, 1H). MS m/z ([M+H]⁺) 428.

Step 2: 7-(3,4-dihydro-2H-pyrano[2,3-b]pyridin-6-yl)-5-[(1-methyl-3-piperidyl)oxy]-3H-benzimidazole-4-carboxamide (208b)

According to the procedure described in Example 177, Step 3, compound (208a) (129 mg, 0.30 mmol) was converted, after purification by preparative TLC on silica gel (dichloromethane/methanol 9/1+1% of ammonia), to compound (208b) (80 mg, 0.20 mmol, 65%). $^1$H NMR (400 MHz, CDCl$_3$) δ 1.57 (dt, J=13.4/4.3 Hz, 1H), 1.75 (d, J=12.4 Hz, 1H), 1.82-2.02 (m, 4H), 2.02-2.09 (m, 2H), 2.28 (s, 4H), 2.50 (d, J=11.7 Hz, 1H), 2.64 (d, J=11.1 Hz, 1H), 2.81 (d, J=11.8 Hz, 1H), 2.94 (t, J=6.4 Hz, 2H), 4.37-4.43 (m, 2H), 4.85 (dt, J=5.2/2.6 Hz, 1H), 5.81 (s, 1H), 7.05 (s, 1H), 8.08 (s, 1H), 8.28 (dt, J=2.2/1.0 Hz, 1H), 8.51 (d, J=2.4 Hz, 1H), 9.03 (s, 1H), 11.52 (s, 1H). MS m/z ([M+H]$^+$) 408.

Step 3: 7-(3,4-dihydro-2H-pyrano[2,3-b]pyridin-6-yl)-5-[(1-methyl-3-piperidyl)oxy]-3H-benzimidazole-4-carboxamide methanesulfonic acid salt, Example (208)

According to the procedure described in Example 207, Step 3, compound (208b) (80 mg, 0.20 mmol) was converted to Example (208) (97 mg, 0.19 mmol, 98%). $^1$H NMR (400 MHz, CD$_3$OD) δ 1.88-1.97 (m, 2H), 2.10 (dt, J=10.5/6.1 Hz, 2H), 2.21-2.37 (m, 2H), 2.69 (s, 3H), 2.84 (s, 3H), 2.98 (t, J=6.4 Hz, 2H), 3.09 (d, J=12.8 Hz, 1H), 3.23 (d, J=13.3 Hz, 1H), 3.60-3.66 (m, 2H), 4.46 (t, J=5.1 Hz, 2H), 5.16 (s, 1H), 7.38 (s, 1H), 8.10 (s, 1H), 8.38 (s, 1H), 8.43 (s, 1H). MS m/z ([M+H]$^+$) 408. MS m/z ([M−H]$^-$) 406.

Example 209

Synthesis of 7-(3,4-dihydro-2H-pyrano[2,3-b]pyridin-6-yl)-5-(1-methylpyrrolidin-3-yl)oxy-3H-benzimidazole-4-carboxamide methanesulfonic acid salt

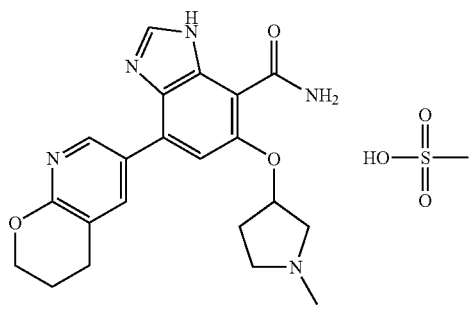

Example 209

Step 1: 2-amino-4-(3,4-dihydro-2H-pyrano[2,3-b]pyridin-6-yl)-6-(1-methylpyrrolidin-3-yl)oxy-3-nitro-benzamide (209a)

According to the procedure described in Example 104, Step 1, compound (177a) (166 mg, 0.5 mmol) was converted, by reaction with 1-methyl-3-pyrrolidinol (0.11 mL, 1 mmol) and after purification by preparative TLC on silica gel (DCM/methanol 95/5), to compound (209a) (166 mg, 0.401 mmol, 80%) $^1$H NMR (400 MHz, CDCl$_3$) δ 2.00-2.10 (m, 3H), 2.25-2.35 (m, 2H), 2.37 (s, 3H), 2.50 (dd, J=10.9/4.5 Hz, 1H), 2.82 (t, J=6.4 Hz, 2H), 2.98-3.03 (m, 2H), 4.36-4.41 (m, 2H), 5.01-5.05 (m, 1H), 5.66 (s, 1H), 6.04 (s, 1H), 7.25 (d, J=1.1 Hz, 1H), 7.90 (s, 2H), 8.04 (d, J=2.5 Hz, 1H), 8.24 (s, 1H). MS m/z ([M+H]$^+$) 414.

Step 2: 7-(3,4-dihydro-2H-pyrano[2,3-b]pyridin-6-yl)-5-(1-methylpyrrolidin-3-yl)oxy-3H-benzimidazole-4-carboxamide (209b)

According to the procedure described in Example 177, Step 3, compound (209a) (164 mg, 0.40 mmol) was converted, after purification by preparative TLC on silica gel (DCM/methanol 9/1+1% of ammonia), to compound (209b) (59 mg, 0.15 mmol, 38%). $^1$H NMR (400 MHz, CDCl$_3$) δ 2.02-2.17 (m, 3H), 2.32-2.39 (m, 2H), 2.41 (s, 3H), 2.66 (dd, J=10.8/4.9 Hz, 1H), 2.94 (t, J=6.4 Hz, 2H), 2.97-3.08 (m, 2H), 4.37-4.43 (m, 2H), 5.17 (dd, J=7.7/3.9 Hz, 1H), 5.81-5.86 (m, 1H), 7.00 (s, 1H), 8.08 (s, 1H), 8.30 (d, J=2.4 Hz, 1H), 8.45 (s, 1H), 8.50 (d, J=2.3 Hz, 1H), 11.51 (s, 1H). MS m/z ([M+H]$^+$) 394.

Step 3: 7-(3,4-dihydro-2H-pyrano[2,3-b]pyridin-6-yl)-5-(1-methylpyrrolidin-3-yl)oxy-3H-benzimidazole-4-carboxamide methanesulfonic acid salt, Example (209)

According to the procedure described in Example 207, Step 3, compound (209b) (59 mg, 0.15 mmol) was converted to Example (209) (65 mg, 0.13 mmol, 89%). $^1$H NMR (400 MHz, CD$_3$OD) δ 2.10-2.12 (m, 2H), 2.42-2.60 (m, 2H), 2.71 (s, 3H), 2.85-2.85 (m, 1H), 2.99 (t, J=6.4 Hz, 2H), 3.04-3.10 (m, 4H), 3.45-3.53 (m, 1H), 3.92-4.08 (m, 1H), 4.47 (t, J=5.2 Hz, 2H), 5.55-5.56 (m, 1H), 7.23 (s, 1H), 8.17 (s, 1H), 8.36 (s, 1H), 8.48 (d, J=2.4 Hz, 1H). MS m/z ([M+H]$^+$) 394. MS m/z ([M−H]$^-$) 392.

Example 210

Synthesis of 7-(3,4-dihydro-2H-pyrano[2,3-b]pyridin-6-yl)-5-[[(2R)-1-methylpyrrolidin-2-yl]methoxy]-3H-benzimidazole-4-carboxamide methanesulfonic acid salt

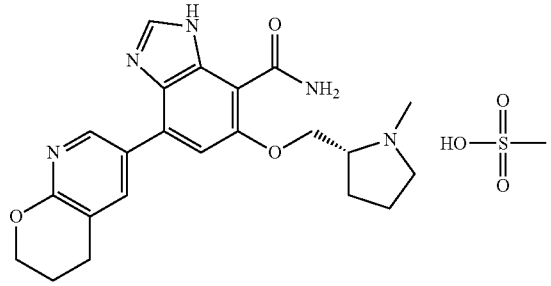

Example 210

Step 1: 2-amino-4-(3,4-dihydro-2H-pyrano[2,3-b]pyridin-6-yl)-6-[[(2R)-1-methylpyrrolidin-2-yl]methoxy]-3-nitro-benzamide (210a)

According to the procedure described in Example 104, Step 1, compound (177a) (166 mg, 0.5 mmol) was converted, by reaction with N-Methyl-D-prolinol (1.07 mL, 9 mmol) and after trituration in Ethyl acetate, to compound (210a) (1.474 g, 3.45 mmol, 77%). $^1$H NMR (400 MHz, DMSO-$d_6$) δ 1.68 (q, J=9.2, 6.8 Hz, 3H), 1.92 (q, J=5.8 Hz, 4H), 2.20 (q, J=8.5 Hz, 1H), 2.29 (s, 3H), 2.54 (d, J=11.1 Hz, 1H), 2.80 (t, J=6.4 Hz, 2H), 2.96 (d, J=7.4 Hz, 1H), 4.06 (dd, J=9.8/4.5 Hz, 1H), 4.20 (dd, J=9.9/3.8 Hz, 1H), 4.28-4.33 (m, 2H), 6.37 (s, 1H), 7.15 (s, 2H), 7.50 (d, J=2.4 Hz, 1H), 7.75 (s, 1H), 7.90 (d, J=2.5 Hz, 1H), 8.15 (s, 1H). MS m/z ([M+H]$^+$) 428.

Step 2: 7-(3,4-dihydro-2H-pyrano[2,3-b]pyridin-6-yl)-5-[[(2R)-1-methylpyrrolidin-2-yl]methoxy]-3H-benzimidazole-4-carboxamide (210b)

According to the procedure described in Example 177, Step 3, compound (210a) (1.474 g, 3.45 mmol) was converted, after purification by preparative TLC on silica gel (DCM/methanol 9/1+1% of ammonia), to compound (210b) (309 mg, 0.76 mmol, 22%). $^1$H NMR (400 MHz, CDCl$_3$) δ 1.78 (s, 2H), 1.91-2.10 (m, 4H), 2.35 (td, J=9.4/7.6 Hz, 1H), 2.40 (s, 3H), 2.64 (d, J=9.8 Hz, 1H), 2.95 (t, J=6.4 Hz, 2H), 3.08/3.16 (m, 1H), 4.15 (dd, J=9.4/4.3 Hz, 1H), 4.36-4.43 (m, 3H), 5.69 (s, 1H), 7.08 (s, 1H), 8.08 (d, J=0.6 Hz, 1H), 8.31 (dt, J=2.2/1.0 Hz, 1H), 8.55 (d, J=2.4 Hz, 1H), 8.91 (s, 1H), 11.46 (s, 1H). MS m/z ([M+H]$^+$) 408.

Step 3: 7-(3,4-dihydro-2H-pyrano[2,3-b]pyridin-6-yl)-5-[[(2R)-1-methylpyrrolidin-2-yl]methoxy]-3H-benzimidazole-4-carboxamide methanesulfonic acid salt, Example (210)

According to the procedure described in Example 207, Step 3, compound (211b) (158 mg, 0.39 mmol) was converted to Example (210) (190 mg, 0.38 mmol, 97%). $^1$H NMR (400 MHz, CD$_3$OD) δ 2.08-2.21 (m, 4H), 2.21-2.32 (m, 1H), 2.45-2.51 (m, 1H), 2.71 (s, 3H), 3.00 (t, J=6.4 Hz, 2H), 3.11 (s, 3H), 3.28-3.30 (m, 1H), 3.82 (dt, J=11.9/6.2 Hz, 1H), 4.00-4.06 (m, 1H), 4.45-4.50 (m, 2H), 4.56 (dd, J=11.3/6.3 Hz, 1H), 4.64 (dd, J=11.1/3.4 Hz, 1H), 7.32 (s, 1H), 8.14 (s, 1H), 8.36 (s, 1H), 8.45-8.49 (m, 1H). MS m/z ([M+H]$^+$) 408. MS m/z ([M–H]$^-$) 406.

Example 211

Synthesis of 5-[4,4-bis(hydroxymethyl)-1-piperidyl]-7-(1-cyclohexylbenzimidazol-5-yl)-3H-benzimidazole-4-carboxamide

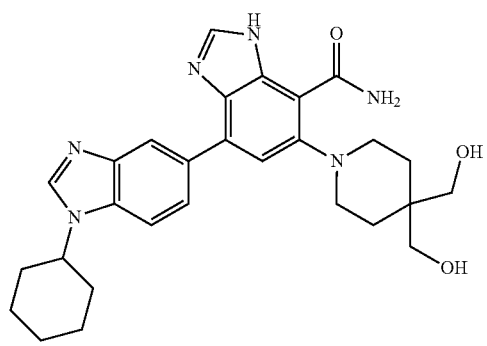

Example 211

Step 1: 2-amino-6-[4,4-bis(hydroxymethyl)-1-piperidyl]-4-(1-cyclohexylbenzimidazol-5-yl)-3-nitrobenzamide (211a)

According to the procedure described in Example 29, Step 3, compound (160d) (155 mg, 0.39 mmol) was converted, by reaction with [4-(hydroxymethyl)-4-piperidyl]methanol (87 mg, 0.48 mmol), to compound (211b) (168 mg, 0.322 mmol, 81%) which was used in the next without further purification. MS m/z ([M+H]$^+$) 523.

Step 2: 5-[4,4-bis(hydroxymethyl)-1-piperidyl]-7-(1-cyclohexylbenzimidazol-5-yl)-3H-benzimidazole-4-carboxamide, Example (211)

According to the procedure described in Example 177, Step 3, compound (211a) (168 mg, 0.32 mmol) was converted, after purification by preparative TLC on silica gel (DCM/methanol 8/2+1% ammonia), to Example (211) (42 mg, 0.083 mmol, 26%). $^1$H NMR (400 MHz, CD$_3$OD) δ 1.39-1.49 (m, 1H), 1.58-1.68 (m, 2H), 1.78-1.86 (m, 5H), 1.96-2.05 (m, 4H), 2.24 (d, J=11.8 Hz, 2H), 3.12 (bs, 4H), 3.63 (bs, 4H), 4.40-4.50 (m, 1H), 7.50 (s, 1H), 7.76 (d, J=8.6 Hz, 1H), 7.90 (d, J=8.5 Hz, 1H), 8.18 (s, 1H), 8.21 (s, 1H), 8.35 (s, 1H). MS m/z ([M+H]$^+$) 503. MS m/z ([M–H]$^-$) 501.

Example 212

Synthesis of 7-(3,4-dihydro-2H-pyrano[2,3-b]pyridin-6-yl)-5-(2-pyridylmethoxy)-3H-benzimidazole-4-carboxamide methanesulfonic acid salt

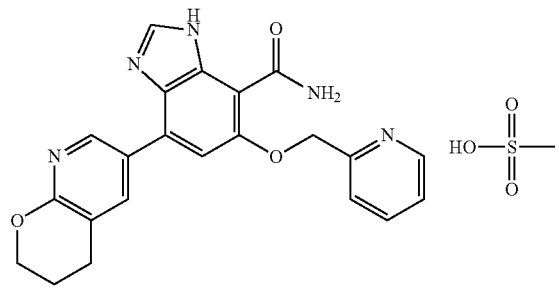

Example 212

Step 1: 2-amino-4-(3,4-dihydro-2H-pyrano[2,3-b]pyridin-6-yl)-3-nitro-6-(2-pyridylmethoxy)benzamide (212a)

According to the procedure described in Example 104, Step 1, compound (177a) (166 mg, 0.5 mmol) was converted, by reaction with 2-(hydroxymethyl)pyridine (0.95 mL, 1 mmol) and after purification by preparative TLC on silica gel (DCM/methanol 95/5), to compound (212a) (160 mg, 0.38 mmol, 76%). $^1$H NMR (400 MHz, DMSO-$d_6$) δ 1.90-1.99 (m, 2H), 2.81 (t, J=6.4 Hz, 2H), 4.28-4.36 (m, 2H), 4.56 (d, J=5.5 Hz, 2H), 6.50 (s, 1H), 6.87 (s, 2H), 7.24 (bs, 1H), 7.38 (bs, 1H), 7.43-7.50 (m, 2H), 7.53-7.60 (m, 1H), 8.27 (s, 1H), 8.48 (bs, 1H), 8.57 (bs, 1H). MS m/z ([M+H]$^+$) 422.

Step 2: 7-(3,4-dihydro-2H-pyrano[2,3-b]pyridin-6-yl)-5-(2-pyridylmethoxy)-3H-benzimidazole-4-carboxamide (212b)

According to the procedure described in Example 19, Step 4, compound (212a) (160 mg, 0.38 mmol) was converted, after purification by preparative TLC on silica gel (DCM/methanol 9/1) and trituration in DCM, to compound (212b) (33.1 mg, 0.08 mmol, 22%). $^1$H NMR (400 MHz, DMSO-$d_6$) δ 1.99 (dt, J=10.5/6.1 Hz, 2H), 2.90 (t, J=6.4 Hz, 2H), 4.31-4.38 (m, 2H), 5.58 (s, 2H), 7.35-7.44 (m, 2H), 7.59 (d, J=7.8 Hz, 1H), 7.70-7.76 (m, 1H), 7.88 (bs, 1H), 8.13 (s, 1H), 8.38 (d, J=2.4 Hz, 1H), 8.49 (d, J=2.7 Hz, 1H), 8.63 (bs, 1H), 8.82 (d, J=2.4 Hz, 1H), 12.43 (s, 1H). MS m/z ([M+H]$^+$) 402.

Step 3: 7-(3,4-dihydro-2H-pyrano[2,3-b]pyridin-6-yl)-5-(2-pyridylmethoxy)-3H-benzimidazole-4-carboxamide methanesulfonic acid salt, Example (212)

According to the procedure described in Example 207, Step 3, compound (212b) (33.1 mg, 0.08 mmol) was converted to Example (212) (39.7 mg, 0.079 mmol, 99%). $^1$H NMR (400 MHz, DMSO-$d_6$) δ 1.99-2.03 (m, 2H), 2.32 (s, 3H), 2.92 (t, J=6.4 Hz, 2H), 4.40 (t, J=5.1 Hz, 2H), 5.64 (s, 2H), 7.40-7.48 (m, 1H), 7.55 (s, 1H), 7.61 (d, J=7.8 Hz, 1H), 7.89-8.01 (m, 2H), 8.11-8.16 (m, 1H), 8.54-8.60 (m, 2H), 8.61-8.67 (m, 1H), 9.03 (s, 1H). MS m/z ([M+H]$^+$) 402. MS m/z ([M–H]$^-$) 400.

Example 213

Synthesis of 7-(3,4-dihydro-2H-pyrano[2,3-b]pyridin-6-yl)-5-[2-(dimethylamino)propoxy]-3H-benzimidazole-4-carboxamide methanesulfonic acid salt Example 213

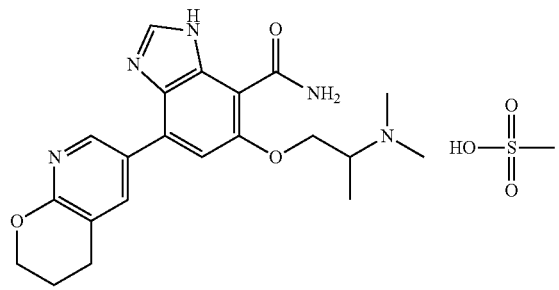

Step 1: 2-amino-4-(3,4-dihydro-2H-pyrano[2,3-b]pyridin-6-yl)-6-[2-(dimethylamino)propoxy]-3-nitro-benzamide (213a)

According to the procedure described in Example 104, Step 1, compound (177a) (166 mg, 0.5 mmol) was converted, by reaction with dimethylamino-1-propanol (103 mg, 1 mmol) and after purification by preparative TLC on silica gel (DCM/methanol 95/5), to compound (213a) (90 mg, 0.21 mmol, 44%). $^1$H NMR (400 MHz, DMSO-$d_6$) δ 0.93 (d, J=6.7 Hz, 3H), 1.89-2.02 (m, 2H), 2.17 (s, 6H), 2.82 (t, J=6.4 Hz, 2H), 2.93-3.06 (m, 1H), 4.00-4.11 (m, 1H), 4.21 (dd, J=10.5/4.8 Hz, 1H), 4.28-4.36 (m, 2H), 6.41 (s, 1H), 7.36 (s, 2H), 7.51 (dd, J=2.5/1.1 Hz, 1H), 7.69 (s, 1H), 7.93 (d, J=2.5 Hz, 1H), 8.65 (s, 1H). MS m/z ([M+H]$^+$) 416.

Step 2: 7-(3,4-dihydro-2H-pyrano[2,3-b]pyridin-6-yl)-5-[2-(dimethylamino)propoxy]-3H-benzimidazole-4-carboxamide (213b)

According to the procedure described in Example 19, Step 4, compound (213a) (90 mg, 0.21 mmol) was converted, after purification by preparative TLC on silica gel (DCM/methanol 80/20+2% ammonia), to compound (213b) (10.1 mg, 0.025 mmol, 12%). $^1$H NMR (400 MHz, CD$_3$OD) δ 1.22 (d, J=6.6 Hz, 3H), 2.10-2.15 (m, 2H), 2.49 (s, 6H), 2.99 (t, J=6.4 Hz, 2H), 4.28 (dd, J=10.5/8.4 Hz, 1H), 4.41-4.49 (m, 3H), 7.25 (s, 1H), 8.20 (s, 2H), 8.54 (s, 1H). MS m/z ([M+H]$^+$) 396.

Step 3: 7-(3,4-dihydro-2H-pyrano[2,3-b]pyridin-6-yl)-5-[2-(dimethylamino)propoxy]-3H-benzimidazole-4-carboxamid methanesulfonic acid salt, Example (213)

According to the procedure described in Example 207, Step 3, compound (213b) (10.1 mg, 0.025 mmol) was converted to Example (213) (8.9 mg, 0.018 mmol, 72%). $^1$H NMR (400 MHz, DMSO-$d_6$) δ 1.36 (d, J=6.8 Hz, 3H), 1.95-2.04 (m, 2H), 2.31 (s, 3H), 2.84 (d, J=4.9 Hz, 3H), 2.88-2.93 (m, 6H), 3.98 (bs, 1H), 4.32-4.41 (m, 2H), 4.54 (d, J=5.5 Hz, 2H), 7.39 (s, 1H), 7.93 (s, 1H), 8.36 (bs, 2H), 8.41 (bs, 1H), 8.73 (bs, 1H), 9.91 (bs, 1H). MS m/z ([M+H]$^+$) 396. MS m/z ([M–H]$^-$) 394.

Example 214

Synthesis of 7-[1-[(1R,2R)-2-fluorocyclohexyl]benzimidazol-5-yl]-5-[[(2R)-pyrrolidin-2-yl]methoxy]-3H-benzimidazole-4-carboxamide methanesulfonic acid salt Example 214

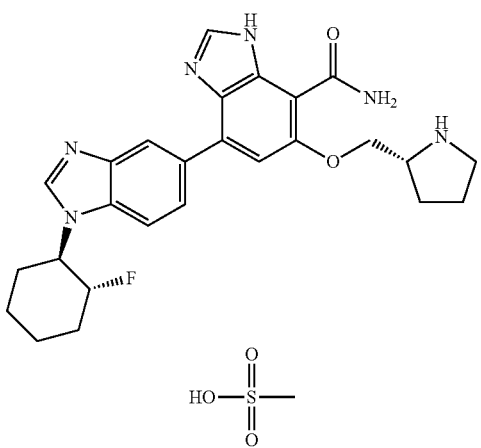

Step 1: tert-butyl (2R)-2-[[3-amino-2-carbamoyl-5-[1-[(1R,2R)-2-fluorocyclohexyl]benzimidazol-5-yl]-4-nitro-phenoxy]methyl]pyrrolidine-1-carboxylate (214a)

According to the procedure described in Example 104, Step 1, compound (170a) (300 mg, 0.722 mmol) was converted, by reaction with tert-butyl (2R)-2-(hydroxymethyl)pyrrolidine-1-carboxylate (435 mg, 2.17 mmol) and after purification by chromatography on silica gel (AcOEt isochratic), to compound (214a) (420 mg, 0.7 mmol, 97%). MS m/z ([M+H]$^+$) 597.

Step 2: tert-butyl (2R)-2-[[4-carbamoyl-7-[1-[(1R,2R)-2-fluorocyclohexyl]benzimidazol-5-yl]-3H-benzimidazol-5-yl]oxymethyl]pyrrolidine-1-carboxylate (214b)

According to the procedure described in Example 177, Step 3, compound (214a) (420 mg, 0.7 mmol) was converted, after purification by preparative TLC on silica gel (DCM/MeOH 9/1), to compound (214b) (220 mg, 0.38 mmol, 54%). $^1$H NMR (400 MHz, CDCl$_3$) δ 1.47 (s, 9H), 1.55-1.79 (m, 4H), 1.85-2.18 (m, 6H), 2.23-2.33 (m, 1H), 2.44-2.50 (m, 1H), 3.44-3.55 (m, 1H), 3.46-3.59 (m, 1H), 4.03-4.44 (m, 4H), 4.67-4.97 (m, 1H), 5.74 (bs, 1H), 7.17 (s, 1H), 7.61 (d, J=9.9 Hz, 1H), 8.09 (s, 1H), 8.14-8.38 (m, 3H), 8.62 (bs, 1H), 11.56 (bs, 1H). MS m/z ([M+H]$^+$) 577.

Step 3: 7-[1-[(1R,2R)-2-fluorocyclohexyl]benzimidazol-5-yl]-5-[[(2R)-pyrrolidin-2-yl]methoxy]-3H-benzimidazole-4-carboxamide (214c)

According to the procedure described in Example 62, Step 2, compound (214c) (220 mg, 0.38 mmol) was converted to compound (214c) (70 mg, 0.147 mmol, 39%) without further purification. $^1$H NMR (400 MHz, DMSO-d$_6$) δ 1.47-1.59 (m, 3H), 1.62-1.94 (m, 7H), 2.07-2.16 (m, 2H), 2.23-2.31 (m, 1H), 2.83-2.90 (m, 2H), 3.53-3.61 (m, 1H), 4.09-4.13 (m, 1H), 4.29-4.33 (m, 1H), 4.60-4.69 (m, 1H), 4.95-5.15 (m, 1H), 7.34 (s, 1H), 7.63 (bs, 1H), 7.80 (d, J=8.6 Hz, 1H), 8.11 (s, 1H), 8.14 (dd, J=1.5/8.6 Hz, 1H), 8.44 (bs, 1H), 8.49 (s, 1H), 8.52 (d, J=1.5 Hz, 1H), 12.35 (bs, 1H). MS m/z ([M+H]$^+$) 477.

Step 4: 7-[1-[(1R,2R)-2-fluorocyclohexyl]benzimidazol-5-yl]-5-[[(2R)-pyrrolidin-2-yl]methoxy]-3H-benzimidazole-4-carboxamide methanesulfonic acid salt, Example (214)

According to the procedure described in Example 207, Step 3, compound (214c) (10.1 mg, 0.025 mmol) was converted to Example (214) as white powder (81 mg, 0.141 mmol, 96%). $^1$H NMR (400 MHz, DMSO-d$_6$) δ 1.44-1.58 (m, 2H), 1.62-2.21 (m, 9H), 2.22-2.28 (m, 1H), 2.30 (s, 3H), 3.24 (t, J=7.0 Hz, 2H), 4.00-4.11 (m, 1H), 4.46 (t, J=7.0 Hz, 1H), 4.55-4.67 (m, 2H), 4.94-5.13 (m, 1H), 7.35 (s, 1H), 7.72-7.81 (m, 3H), 8.14 (s, 1H), 8.16 (dd, J=1.3/8.6 Hz, 1H), 8.49 (s, 2H), 8.86 (bs, 2H), 12.39 (s, 1H). MS m/z ([M+H]$^+$) 477. MS m/z ([M−H]$^−$) 475.

Example 215

5-[[(2R)-1-methylpyrrolidin-2-yl]methoxy]-7-(1-tetrahydropyran-3-ylbenzimidazol-5-yl)-3H-benzimidazole-4-carboxamide methanesulfonic acid salt Example 215

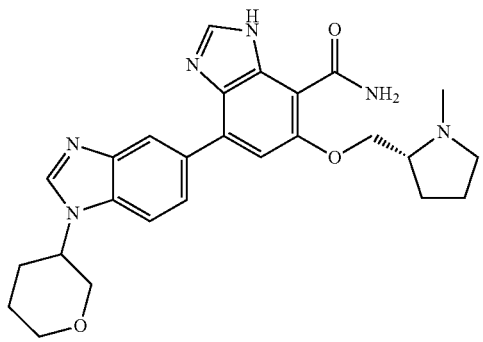

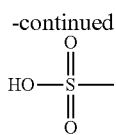

Step 1: 2-amino-6-fluoro-3-nitro-4-(1-tetrahydropyran-3-ylbenzimidazol-5-yl)benzamide (215a)

According to the procedure described in Example 115, Step 2, compound (160c) (2 g, 7.2 mmol) was converted, by reaction with compound (123d) (2.6 g, 7.92 mmol) and after purification by chromatography on silica gel (DCM/Acetone 1/1 to 0/1), to compound (215a) (2 g, 5 mmol, 70%). 1H NMR (400 MHz, DMSO-d$_6$) δ 1.68-1.80 (m, 2H), 2.12-2.24 (m, 2H), 3.55-3.61 (m, 1H), 3.77-3.87 (m, 2H), 4.01 (dd, J=3.9/11.1 Hz, 1H), 4.57-4.64 (m, 1H), 6.61-6.64 (m, 3H), 7.18 (dd, J=1.5/8.4 Hz, 1H), 7.60 (d, J=1.5 Hz, 1H), 7.77 (d, J=8.4 Hz, 1H), 7.99 (d, J=11.6 Hz, 2H), 8.47 (s, 1H). MS m/z ([M+H]$^+$) 400.

Step 2: 2-amino-6-[[(2R)-1-methylpyrrolidin-2-yl]methoxy]-3-nitro-4-(1-tetrahydropyran-3-ylbenzimidazol-5-yl)benzamide (215b)

According to the procedure described in Example 104, Step 1, compound (215a) (2.28 g, 5.72 mmol) was converted, by reaction with [(2R)-1-methylpyrrolidin-2-yl]methanol (2.14 g, 18.55 mmol) and after trituration in diethyl ether, to compound (215b) (2.8 g, 5.66 mmol, 99%) which was used in the step without further purification. $^1$H NMR (400 MHz, DMSO-d$_6$) δ 1.63-1.79 (m, 5H), 1.87-1.97 (m, 1H), 2.13-2.24 (m, 3H), 2.30 (s, 3H), 2.51-2.60 (m, 1H), 2.94-3.02 (m, 1H), 3.55-3.61 (m, 1H), 3.79 (dd, J=8.9/11.1 Hz, 1H), 3.82-3.88 (m, 1H), 4.01 (dd, J=3.9/11.1 Hz, 1H), 4.08 (dd, J=4.6/9.9 Hz, 1H), 4.22 (dd, J=3.9/9.9 Hz, 1H), 4.56-4.64 (m, 1H), 6.41 (s, 1H), 7.07 (s, 2H), 7.18 (dd, J=1.5/8.4 Hz, 1H), 7.65 (d, J=1.5 Hz, 1H), 7.73 (s, 1H), 7.74 (d, J=8.4 Hz, 1H), 8.18 (s, 1H), 8.45 (s, 1H). MS m/z ([M+H]$^+$) 495.

Step 3: 5-[[(2R)-1-methylpyrrolidin-2-yl]methoxy]-7-(1-tetrahydropyran-3-ylbenzimidazol-5-yl)-3H-benzimidazole-4-carboxamide (215c)

According to the procedure described in Example 177, Step 3, compound (215b) (2.8 g, 5.66 mmol) was converted, after purification by preparative TLC on silica gel (DCM/MeOH 9/1+1% NH$_3$ 7M in MeOH) followed by a second one (Acetone/Methanol 7/3) and finally by trituration in acetone, to compound (215c) (370 mg, 0.78 mmol, 14%). $^1$H NMR (400 MHz, DMSO-d$_6$) δ 1.70-1.81 (m, 4H), 1.83-1.89 (m, 1H), 1.94-2.03 (m, 1H), 2.19-2.29 (m, 3H), 2.34 (s, 3H), 2.61 (bs, 1H), 3.04 (bs, 1H), 3.56-3.62 (m, 1H), 3.81 (dd, J=8.9/11.0 Hz, 1H), 3.86-3.89 (m, 1H), 4.04 (dd, J=4.0/11.0 Hz, 1H), 4.21 (dd, J=3.8/9.6 Hz, 1H), 4.48 (dd, J=2.8/9.9 Hz, 1H), 4.59-4.66 (m, 1H), 7.34 (s, 1H), 7.63 (bs, 1H), 7.79 (d, J=8.6 Hz, 1H), 8.10 (s, 1H), 8.15 (dd, J=1.5/8.6 Hz, 1H), 8.44 (s, 1H), 8.45 (bs, 1H), 8.55 (d, J=1.3 Hz, 1H), 12.35 (s, 1H). MS m/z ([M+H]$^+$) 475.

Step 4: 5-[[(2R)-1-methylpyrrolidin-2-yl]methoxy]-7-(1-tetrahydropyran-3-ylbenzimidazol-5-yl)-3H-benzimidazole-4-carboxamide methanesulfonic acid salt, Example (215)

To a suspension of compound (215c) (370 mg, 0.78 mmol) in water (5 mL) was added a solution of methanesulfonic acid (0.1N in H$_2$O, 7.8 mL, 0.78 mmol). The middle was frozen and lyophilized to give Example (215) as white powder (425 mg, 0.745 mmol, 95%). $^1$H NMR (400 MHz, DMSO-d$_6$) δ 1.72-1.82 (m, 2H), 1.91-2.03 (m, 2H), 2.06-2.16 (m, 1H), 2.19-2.25 (m, 2H), 2.30 (s, 3H), 2.31-2.36 (m, 1H), 2.96 (s, 3H), 3.13-3.24 (m, 1H), 3.55-3.70 (m, 2H), 3.77-3.92 (m, 2H), 3.96-4.09 (m, 2H), 4.48-4.57 (m, 1H), 4.61-4.73 (m, 2H), 7.35 (s, 1H), 7.72 (bs, 1H), 7.81-7.91 (m, 2H), 8.18 (bs, 2H), 8.51 (s, 2H), 9.80 (bs, 1H), 12.43 (bs, 1H). MS m/z ([M+H]$^+$) 475. MS m/z ([M−H]$^−$) 473.

Example 216

Synthesis of 7-(3,4-dihydro-2H-pyrano[2,3-b]pyridin-6-yl)-5-[3-(dimethylamino)propoxy]-3H-benzimidazole-4-carboxamide 4-methylbenzenesulfonic acid salt

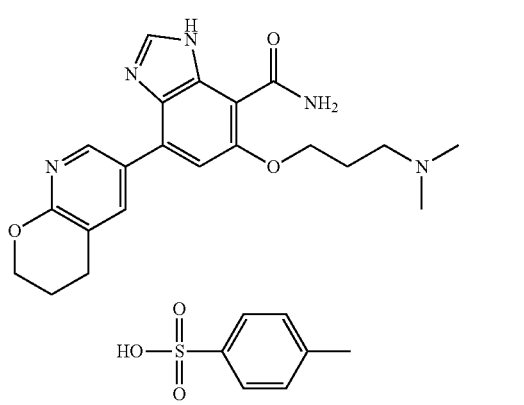

Example 216

Step 1: 2-amino-4-(3,4-dihydro-2H-pyrano[2,3-b] pyridin-6-yl)-6-[3-(dimethylamino)propoxy]-3-nitro-benzamide (216a)

According to the procedure described in Example 104, Step 1, compound (177a) (83 mg, 0.25 mmol) was converted, by reaction with 3-dimethylamino-1-propanol (90 µL, 0.75 mmol) and after purification by preparative TLC on silica gel (DCM/methanol 80/20+1% ammonia), to compound (216a) (20 mg, 0.048 mmol, 19%). $^1$H NMR (400 MHz, CDCl$_3$) δ 2.07 (m, 4H), 2.28 (s, 6H), 2.53 (t, J=6.5 Hz, 2H), 2.85 (t, J=6.5 Hz, 2H), 4.27 (t, J=6.0 Hz, 2H), 4.38-4.45 (m, 2H), 5.87 (s, 1H), 6.15 (s, 1H), 7.30 (d, J=2.3 Hz, 1H), 8.01-8.10 (m, 3H), 8.20 (s, 1H). MS m/z ([M+H]$^+$) 416.

Step 2: 7-(3,4-dihydro-2H-pyrano[2,3-b]pyridin-6-yl)-5-[3-(dimethylamino)propoxy]-3H-benzimidazole-4-carboxamide 4-methylbenzenesulfonic acid salt, Example (216)

A solution of compound (216a) (42 mg, 0.10 mmol) in methanol (2 mL) was purged with hydrogen. Catalyst Pd/C 10% (10 mg) was then added and the reaction was stirred under hydrogen atmosphere (1 bar) overnight. The middle was filtered and diluted in methanol (3 mL) then triethyl orthoformate (1 mL) and a catalytic amount of 4-methyl-benzenesulfonic acid were added. The mixture was heated at 110° C. After 3 hours, the middle was concentrated and the crude product was purified twice by preparative TLC on silica gel (DCM/MeOH 90/10+2% ammonia) to afford Example (216) (6.4 mg, 0.011 mmol, 11%). $^1$H NMR (400 MHz, CDCl$_3$) δ 2.09 (m, 2H), 2.38 (s, 3H), 2.54 (m, 2H), 2.89-3.05 (m, 8H), 3.32 (m, 2H), 4.44 (m, 4H), 6.12 (s, 1H), 7.03 (d, J=5.3 Hz, 1H), 7.21 (d, J=7.7 Hz, 2H), 7.80 (d, J=7.7 Hz, 2H), 8.02 (s, 1H), 8.13 (s, 1H), 8.33 (s, 1H), 8.54 (s, 1H), 11.58 (s, 1H). MS m/z ([M+H]$^+$) 396.

Example 217

Synthesis of 7-(3,4-dihydro-2H-pyrano[2,3-b]pyridin-6-yl)-5-[(1-methylazetidin-2-yl)methoxy]-3H-benzimidazole-4-carboxamide methanesulfonic acid salt

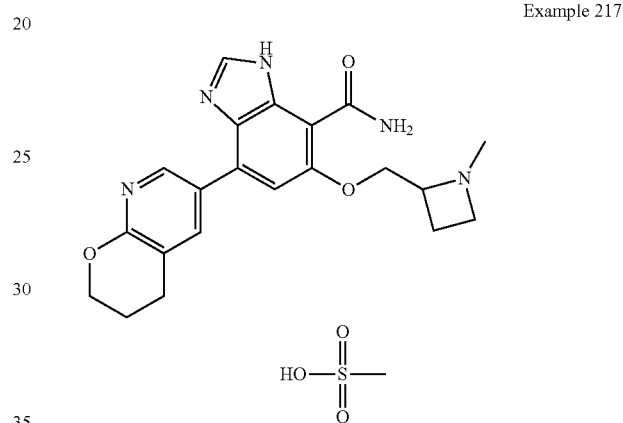

Example 217

Step 1: 2-amino-4-(3,4-dihydro-2H-pyrano[2,3-b] pyridin-6-yl)-6-[(1-methylazetidin-2-yl)methoxy]-3-nitro-benzamide (217a)

According to the procedure described in Example 104, Step 1, compound (177a) (200 mg, 0.6 mmol) was converted, by reaction with 1-methyl-2-azetidine methanol (243 mg, 2.4 mmol) and after purification by preparative TLC on silica gel (DCM/methanol 95/5), to compound (217a) (80 mg, 0.19 mmol, 32%). $^1$H NMR (400 MHz, DMSO-d$_6$) δ 1.89-2.08 (m, 4H), 2.25 (s, 3H), 2.75-2.90 (m, 3H), 3.25-3.32 (m, 2H), 4.08-4.21 (m, 2H), 4.27-4.36 (m, 2H), 6.36 (s, 1H), 7.08-7.15 (m, 2H), 7.50 (d, J=2.4 Hz, 1H), 7.83 (s, 1H), 7.91 (d, J=2.5 Hz, 1H), 8.28 (s, 1H). MS m/z ([M+H]$^+$) 414.

Step 2: 7-(3,4-dihydro-2H-pyrano[2,3-b]pyridin-6-yl)-5-[(1-methylazetidin-2-yl)methoxy]-3H-benzimidazole-4-carboxamide (217b)

A solution of compound (217a) (80 mg, 0.19 mmol) in a mixture of DCM (1.5 mL) and methanol (1.5 mL) was purged with hydrogen. Catalyst Pd/C 10% (19 mg) was then added and the reaction was stirred under hydrogen atmosphere (1 bar) overnight. The middle was filtered and diluted in methanol (2 mL) then triethyl orthoformate (2 mL) and a catalytic amount of APTS were added. The mixture was heated at 110° C. for 3 hours. The middle was then concentrated and the crude product was purified twice by column chromatography on silica gel (DCM/methanol 80/20+2% ammonia) and (DCM/MeOH 90/10+2% ammonia) to afford compound (217b) (14 mg, 0.035 mmol, 19%). $^1$H NMR (400 MHz, CDCl$_3$) δ 2.06-2.19 (m, 3H), 2.30-2.37 (m, 1H), 2.40 (s, 3H), 2.95-3.02 (m, 3H), 3.44-3.54 (m, 2H), 4.17 (dd, J=10.2/3.4 Hz, 1H), 4.37 (dd, J=10.2/3.4 Hz, 1H), 4.40-4.47 (m, 2H), 5.90 (bs, 1H), 7.10 (s, 1H), 8.12 (s, 1H), 8.34 (dd, J=2.3/1.1 Hz, 1H), 8.56 (d, J=2.4 Hz, 1H), 9.08 (bs, 1H), 11.55 (bs, 1H). MS m/z ([M+H]$^+$) 394.

Step 3: 7-(3,4-dihydro-2H-pyrano[2,3-b]pyridin-6-yl)-5-[(1-methylazetidin-2-yl)methoxy]-3H-benzimidazole-4-carboxamide methanesulfonic acid salt, Example (217)

According to the procedure described in Example 207, Step 3, compound (217b) (14 mg, 0.035 mmol) was converted to Example (217) (17.9 mg, 0.03 mmol, 86%). $^1$H NMR (400 MHz, DMSO-d$_6$) δ 1.98-2.02 (m, 2H), 2.31 (s, 3H), 2.37-2.50 (m, 2H), 2.78-2.98 (m, 5H), 3.89 (bs, 1H), 4.08 (bs, 1H), 4.30-4.41 (m, 2H), 4.56-4.85 (m, 3H), 7.31 (s, 1H), 7.80-7.85 (m, 2H), 8.15 (s, 1H), 8.42 (d, J=2.3 Hz, 1H), 8.84 (d, J=2.4 Hz, 1H), 10.14 (bs, 1H), 12.44 (s, 1H). MS m/z ([M+H]$^+$) 394. MS m/z ([M−H]$^-$) 392.

Example 218

Synthesis of 7-(3,4-dihydro-2H-pyrano[2,3-b]pyridin-6-yl)-5-[4-[(dimethylamino)methyl]-1-piperidyl]-3H-benzimidazole-4-carboxamide

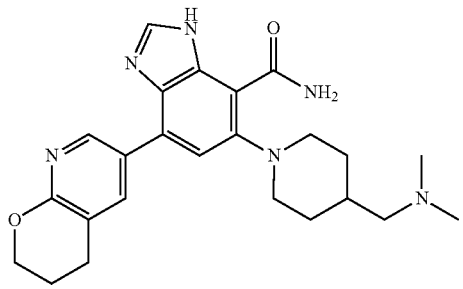

Example 218

Step 1: 2-amino-4-(3,4-dihydro-2H-pyrano[2,3-b]pyridin-6-yl)-6-[4-[(dimethylamino)methyl]-1-piperidyl]-3-nitro-benzamide (218a)

According to the procedure described in Example 29, Step 3, compound (177a) (323 mg, 0.75 mmol) was converted, by reaction with N,N-dimethyl-1-piperidine-4-yl-methanamine (128 mg, 0.90 mmol) and after purification by preparative TLC on silica gel (DCM/methanol 95/5+1% ammonia), to compound (218a) (90 mg, 0.19 mmol, 21%). $^1$H NMR (400 MHz, DMSO-d$_6$) δ 1.22-1.28 (m 2H), 1.59 (dt, J=11.3/6.6 Hz, 1H), 1.68-1.77 (m, 2H), 1.90-1.96 (m, 2H), 2.07 (d, J=7.2 Hz, 2H), 2.12 (s, 6H), 2.77-2.88 (m, 4H), 3.47 (d, J=12.2 Hz, 2H), 4.27-4.34 (m, 2H), 6.20 (s, 1H), 6.79 (s, 2H), 7.45 (d, J=2.5 Hz, 1H), 7.79-7.91 (m, 3H). MS m/z ([M+H]$^+$) 455.

Step 2: 7-(3,4-dihydro-2H-pyrano[2,3-b]pyridin-6-yl)-5-[4-[(dimethylamino)methyl]-1-piperidyl]-3H-benzimidazole-4-carboxamide, Example (218)

A solution of compound (218a) (90 mg, 0.19 mmol) in methanol (2 mL), was purged with hydrogen. Catalyst Pd/C 10% (20 mg) was then added and the reaction was stirred under hydrogen atmosphere (1 bar) overnight. The middle was filtered and diluted in methanol (2 mL) then triethyl orthoformate (2 mL) and a catalytic amount of APTS were added. The mixture was heated at 110° C. for 2 hours. The middle was then concentrated and the crude product was purified by preparative TLC on silica gel (DCM/MeOH 90/10+2% ammonia) to afford Example (218) (23.8 mg, 0.055 mmol, 28%). $^1$H NMR (400 MHz, CDCl$_3$) δ 1.48-1.55 (m, 2H), 1.80-1.86 (m, 1H), 1.98-2.13 (m, 4H), 2.57 (s, 6H), 2.59-2.67 (m, 2H), 2.83-2.92 (m, 4H), 3.17 (d, J=11.1 Hz, 2H), 4.38-4.46 (m, 2H), 6.43 (bs, 1H), 7.12 (d, J=7.9 Hz, 1H), 7.79 (d, J=7.9 Hz, 1H), 8.13 (s, 1H), 8.25 (d, J=2.4 Hz, 1H), 8.54 (d, J=2.4 Hz, 1H), 11.76 (s, 1H). MS m/z ([M+H]$^+$) 435. MS m/z ([M−H]$^-$) 433.

Example 219

Synthesis of 7-(3,4-dihydro-2H-pyrano[2,3-b]pyridin-6-yl)-5-[4-(dimethylamino)-1-piperidyl]-3H-benzimidazole-4-carboxamide

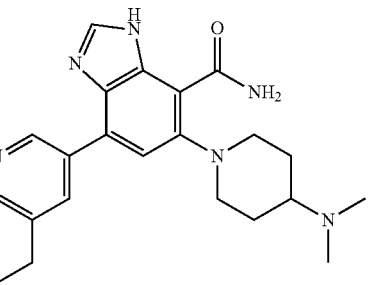

Example 219

Step 1: 2-amino-4-(3,4-dihydro-2H-pyrano[2,3-b]pyridin-6-yl)-6-[4-(dimethylamino)-1-piperidyl]-3-nitro-benzamide (219a)

According to the procedure described in Example 29, Step 3, compound (177a) (233 mg, 0.7 mmol) was converted, by reaction with 4-Dimethylaminopiperidine (108 mg, 0.84 mmol), to compound (219a) (258 mg, 0.59 mmol, 84%) which was used in the next step without further purification. MS m/z ([M+H]$^+$) 441.

Step 2: synthesis of 7-(3,4-dihydro-2H-pyrano[2,3-b]pyridin-6-yl)-5-[4-(dimethylamino)-1-piperidyl]-3H-benzimidazole-4-carboxamide, Example (219)

According to the procedure described in Example 218, Step 2, compound (219a) (258 mg, 0.59 mmol) was converted, after purification by preparative TLC on silica gel (DCM/MeOH 9/1+1% NH$_3$), to Example (219) (62 mg, 0.15 mmol, 26%). $^1$H NMR (400 MHz, CDCl$_3$) δ 1.70-1.85 (m, 2H), 2.05 (dt, J=10.9/5.1 Hz, 2H), 2.15 (d, J=12.7 Hz, 2H), 2.44 (s, 6H), 2.90-3.02 (m, 5H), 3.25-3.32 (m, 2H), 4.36-4.42 (m, 2H), 6.09 (d, J=5.5 Hz, 1H), 7.32 (s, 1H), 8.14 (s, 1H), 8.29 (d, J=2.3 Hz, 1H), 8.52 (d, J=2.4 Hz, 1H), 10.35 (d, J=5.4 Hz, 1H), 11.60 (s, 1H). MS m/z ([M+H]$^+$) 421. MS m/z ([M−H]$^-$) 419.

Example 220

Synthesis of 7-(3,4-dihydro-2H-pyrano[2,3-b]pyridin-6-yl)-5-[3-[(dimethylamino)methyl]-1-piperidyl]-3H-benzimidazole-4-carboxamide Example 220

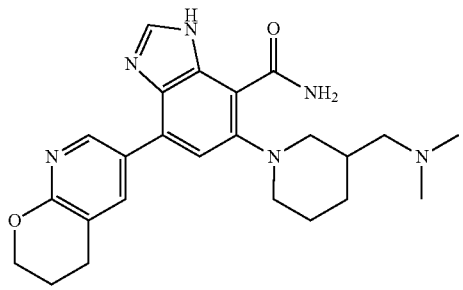

Step 1: 2-amino-4-(3,4-dihydro-2H-pyrano[2,3-b]pyridin-6-yl)-6-[3-[(dimethylamino)methyl]-1-piperidyl]-3-nitro-benzamide (220a)

According to the procedure described in Example 29, Step 3, compound (177a) (200 mg, 0.60 mmol) was converted, by reaction with N,N-dimethyl-1-(3-piperidyl)methanamine (103 mg, 0.72 mmol), to compound (220a) (228 mg, 0.50 mmol, 84%) which was used in the next step without further purification. $^1$H NMR (400 MHz, DMSO-$d_6$) δ 1.00-1.05 (m, 1H), 1.58-1.80 (m, 3H), 1.84-1.89 (m, 1H), 1.90-1.98 (m, 2H), 2.10 (s, 6H), 2.77-2.85 (m, 3H), 3.44-3.51 (m, 2H), 4.11 (q, J=5.2 Hz, 3H), 4.31 (t, J=5.1 Hz, 2H), 6.19 (s, 1H), 6.81 (s, 2H), 7.44 (d, J=2.5 Hz, 1H), 7.79-7.91 (m, 3H). MS m/z ([M+H]$^+$) 455.

Step 2: 7-(3,4-dihydro-2H-pyrano[2,3-b]pyridin-6-yl)-5-[3-[(dimethylamino)methyl]-1-piperidyl]-3H-benzimidazole-4-carboxamide, Example (220)

According to the procedure described in Example 216, Step 2, compound (220a) (228 mg, 0.50 mmol) was converted, after purification by preparative TLC on silica gel (DCM/MeOH 9/1+2% NH$_3$), to Example (220) (42.1 mg, 0.09 mmol, 19%). $^1$H NMR (300 MHz, CDCl$_3$) δ 1.05-1.16 (m, 1H), 1.69-1.86 (m, 1H), 1.90-2.02 (m, 2H), 2.03-2.14 (m, 2H), 2.15-2.31 (m, 8H), 2.57 (t, J=10.8 Hz, 2H), 2.83-2.92 (m, 1H), 2.97 (t, J=6.4 Hz, 2H), 3.15-3.25 (m, 1H), 3.30-3.40 (m, 1H), 4.37-4.49 (m, 2H), 6.09 (d, J=5.7 Hz, 1H), 7.38 (s, 1H), 8.16 (s, 1H), 8.30-8.32 (m, 1H), 8.53-8.58 (m, 1H), 10.61 (d, J=5.7 Hz, 1H), 11.66 (s, 1H). MS m/z ([M+H]$^+$) 435. MS m/z ([M−H]$^-$) 433.

Example 221

Synthesis of 7-(3,4-dihydro-2H-pyrano[2,3-b]pyridin-6-yl)-5-[3-[(dimethylamino)methyl]pyrrolidin-1-yl]-3H-benzimidazole-4-carboxamide Example 221

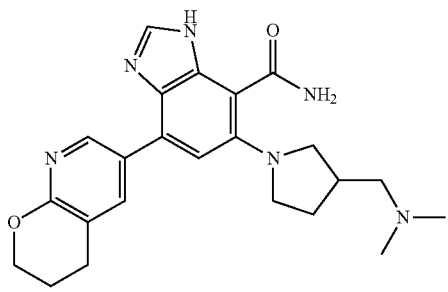

Step 1: 2-amino-4-(3,4-dihydro-2H-pyrano[2,3-b]pyridin-6-yl)-6-[3-[(dimethylamino)methyl]pyrrolidin-1-yl]-3-nitro-benzamide (221a)

According to the procedure described in Example 29, Step 3, compound (177a) (200 mg, 0.60 mmol) was converted, by reaction with N,N-dimethyl-1-pyrrolidin-3-yl-methanamine (92 mg, 0.72 mmol), to compound (221a) (250 mg, 0.56 mmol, 94%) which was used in the next step without further purification. $^1$H NMR (400 MHz, CDCl$_3$) δ 1.62-1.69 (m, 6H), 2.03-2.10 (m, 3H), 2.32 (d, J=7.4 Hz, 2H), 2.44-2.50 (m, 1H), 2.84 (t, J=6.4 Hz, 2H), 3.27 (dd, J=10.2/7.9 Hz, 1H), 3.45-3.67 (m, 4H), 4.36-4.44 (m, 2H), 5.92 (s, 1H), 6.02 (s, 1H), 6.47 (s, 1H), 7.10 (s, 2H), 7.27 (dd, J=2.3/1.2 Hz, 1H), 7.94 (d, J=2.4 Hz, 1H). MS m/z ([M+H]$^+$) 441.

Step 2: 7-(3,4-dihydro-2H-pyrano[2,3-b]pyridin-6-yl)-5-[3-[(dimethylamino)methyl]pyrrolidin-1-yl]-3H-benzimidazole-4-carboxamide, Example (221)

According to the procedure described in example 218, Step 2, compound (221a) (250 mg, 0.56 mmol) was converted, after purification by preparative TLC on silica gel (DCM/MeOH 90/10+2% ammonia), to Example (221) (8.6 mg, 0.02 mmol, 3.6%). $^1$H NMR (400 MHz, CDCl$_3$) δ 1.70-1.81 (m, 1H), 2.05-2.15 (m, 2H), 2.22-2.29 (m, 1H), 2.33 (s, 6H), 2.45 (d, J=7.6 Hz, 2H), 2.65 (hept, J=7.7 Hz, 1H), 2.98 (t, J=6.4 Hz, 2H), 3.04-3.10 (m, 1H), 3.21-3.30 (m, 1H), 3.31-3.38 (m, 1H), 3.40-3.46 (m, 1H), 4.40-4.48 (m, 2H), 5.87 (bs, 1H), 7.38 (s, 1H), 8.15 (s, 1H), 8.31 (d, J=2.3 Hz, 1H), 8.56 (d, J=2.4 Hz, 1H), 10.07 (bs, 1H), 11.50 (bs, 1H). MS m/z ([M+H]$^+$) 421. MS m/z ([M−H]$^-$) 419.

Example 222

Synthesis of 7-(3,4-dihydro-2H-pyrano[2,3-b]pyridin-6-yl)-5-[3-(dimethylamino)-1-piperidyl]-3H-benzimidazole-4-carboxamide Example 222

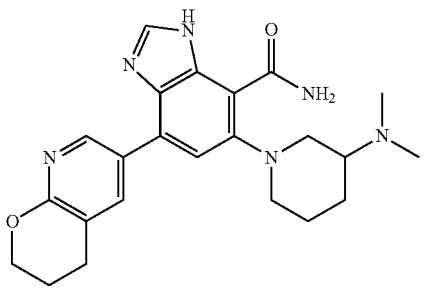

Step 1: 2-amino-4-(3,4-dihydro-2H-pyrano[2,3-b]pyridin-6-yl)-6-[3-(dimethylamino)-1-piperidyl]-3-nitro-benzamide (223a)

According to the procedure described in Example 29, Step 3, compound (177a) (233 mg, 0.7 mmol) was converted, by reaction with 3-dimethylaminopiperidine (135 mg, 1.05 mmol) and after purification by preparative TLC on silica gel (DCM/methanol 95/5), to compound (222a) (224 mg, 0.51 mmol, 73%). $^1$H NMR (400 MHz, DMSO-$d_6$) δ

1.26-1.42 (m, 1H), 1.53-1.67 (m, 1H), 1.67-1.77 (m, 1H), 1.87-1.99 (m, 3H), 2.30 (bs, 6H), 2.68-2.76 (m, 2H), 2.81 (t, J=6.4 Hz, 2H), 3.36 (m, 2H), 3.58 (m, 1H), 4.31 (t, J=5.1 Hz, 2H), 6.24 (s, 1H), 6.72 (s, 2H), 7.45 (d, J=2.5 Hz, 1H), 7.83 (bs, 1H), 7.88 (d, J=2.5 Hz, 1H), 7.93 (bs, 1H). MS m/z ([M+H]⁺) 441.

Step 2: 7-(3,4-dihydro-2H-pyrano[2,3-b]pyridin-6-yl)-5-[3-(dimethylamino)-1-piperidyl]-3H-benzimidazole-4-carboxamide, Example (222)

According to the procedure described in example 218, Step 2, compound (222a) (224 mg, 0.51 mmol) was converted, after purification by preparative TLC on silica gel (DCM/MeOH 9/1+1% ammonia), to Example (222) (69 mg, 0.16 mmol, 32%). ¹H NMR (400 MHz, CDCl₃) δ 1.51-1.77 (m, 2H), 1.98-2.06 (m, 4H), 2.40 (s, 6H), 2.54-2.73 (m, 1H), 2.87-2.92 (m, 4H), 3.03 (bs, 1H), 3.34 (m, 1H), 4.32-4.43 (m, 2H), 6.25 (bs, 1H), 7.29 (s, 1H), 8.14 (s, 1H), 8.23 (d, J=2.4 Hz, 1H), 8.54 (d, J=2.4 Hz, 1H), 10.36 (bs, 1H), 11.72 (bs, 1H). MS m/z ([M+H]⁺) 421. MS m/z ([M–H]⁻) 419.

Example 223

Synthesis of 7-(3,4-dihydro-2H-pyrano[2,3-b]pyridin-6-yl)-5-[3-(dimethylamino)pyrrolidin-1-yl]-3H-benzimidazole-4-carboxamide

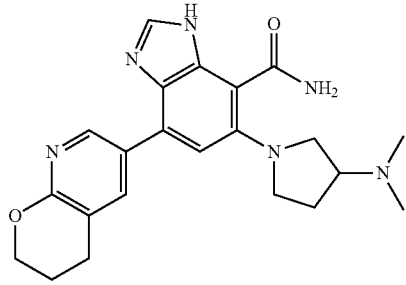

Example 223

Step 1: 2-amino-4-(3,4-dihydro-2H-pyrano[2,3-b]pyridin-6-yl)-6-[3-(dimethylamino)pyrrolidin-1-yl]-3-nitro-benzamide (223a)

According to the procedure described in Example 29, Step 3, compound (177a) (233 mg, 0.7 mmol) was converted, by reaction with 3-(Dimethylamino)pyrrolidine (96 mg, 0.84 mmol), to compound (223a) (249 mg, 0.58 mmol, 83%) which was used in the next without further purification. ¹H NMR (400 MHz, DMSO-d₆) δ 1.72 (p, J=10.4 Hz, 1H), 1.88-1.99 (m, 2H), 2.06-2.15 (m, 1H), 2.18 (s, 6H), 2.60-2.69 (m, 1H), 2.80 (t, J=6.4 Hz, 2H), 3.34-3.42 (m, 2H), 3.43-3.62 (m, 2H), 4.26-4.34 (m, 2H), 6.03 (s, 1H), 6.76 (s, 2H), 7.41 (d, J=2.5 Hz, 1H), 7.77-7.84 (m, 2H), 7.85 (d, J=2.5 Hz, 1H). MS m/z ([M+H]⁺) 427.

Step 2: 7-(3,4-dihydro-2H-pyrano[2,3-b]pyridin-6-yl)-5-[3-(dimethylamino)pyrrolidin-1-yl]-3H-benzimidazole-4-carboxamide, Example (223)

According to the procedure described in example 218, Step 2, compound (223a) (249 mg, 0.58 mmol) was converted, after purification by preparative TLC on silica gel (DCM/MeOH 9/1+1% ammonia), to Example (223) (69 mg, 0.16 mmol, 32%). ¹H NMR (400 MHz, CDCl₃) δ 2.00-2.08 (m, 3H), 2.20-2.28 (m, 1H), 2.32 (s, 6H), 2.90-2.97 (m, 3H), 3.25-3.40 (m, 4H), 4.37-4.45 (m, 2H), 5.80 (d, J=4.7 Hz, 1H), 7.37 (s, 1H), 8.12 (s, 1H), 8.28 (dt, J=2.3/1.1 Hz, 1H), 8.54 (d, J=2.4 Hz, 1H), 9.96 (bs, 1H), 11.46 (bs, 1H). MS m/z ([M+H]⁺) 407. MS m/z ([M–H]⁻) 405.

Example 224

Synthesis of 7-(3,4-dihydro-2H-pyrano[2,3-b]pyridin-6-yl)-5-[2-(dimethylamino)-1-methyl-ethoxy]-3H-benzimidazole-4-carboxamide methanesulfonic acid salt

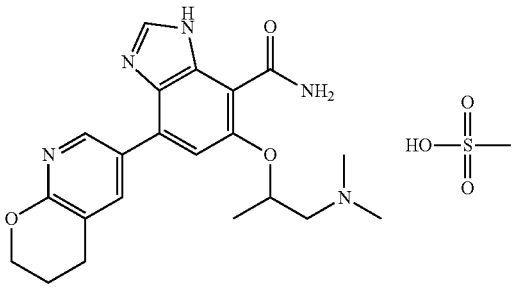

Example 224

Step 1: 2-amino-4-(3,4-dihydro-2H-pyrano[2,3-b]pyridin-6-yl)-6-[2-(dimethylamino)-1-methyl-ethoxy]-3-nitro-benzamide (224a)

According to the procedure described in Example 104, Step 1, compound (177a) (200 mg, 0.6 mmol) was converted, by reaction with 1-dimethylamino-2-propanol (150 µL, 1.2 mmol) and after purification by preparative TLC on silica gel (DCM/methanol 95/5), to compound (224a) (70 mg, 0.17 mmol, 28%). ¹H NMR (400 MHz, CDCl₃) δ 1.42 (d, J=6.1 Hz, 3H), 2.00-2.10 (m, 2H), 2.24 (s, 6H), 2.29 (dd, J=13.0/3.0 Hz, 1H), 2.67-2.98 (m, 3H), 4.31-4.52 (m, 2H), 4.60 (m, 1H), 5.32 (s, 1H), 6.11 (s, 1H), 7.29 (dd, J=2.3/1.1 Hz, 1H), 7.73 (s, 2H), 8.07 (d, J=2.5 Hz, 1H), 9.15-9.36 (m, 1H). MS m/z ([M+H]⁺) 416.

Step 2: 7-(3,4-dihydro-2H-pyrano[2,3-b]pyridin-6-yl)-5-[2-(dimethylamino)-1-methyl-ethoxy]-3H-benzimidazole-4-carboxamide (224b)

According to the procedure described in Example 218, Step 2, compound (224a) (70 mg, 0.17 mmol) was converted, after purification by preparative TLC on silica gel (DCM/MeOH 9/1+2% ammonia), to compound (224b) (14 mg, 0.035 mmol, 20%). ¹H NMR (400 MHz, CDCl₃) δ 1.53 (d, J=6.1 Hz, 3H), 2.03-2.15 (m, 2H), 2.32 (s, 6H), 2.46 (dd, J=13.0/3.9 Hz, 1H), 2.86 (dd, J=13.0/8.7 Hz, 1H), 2.99 (t, J=6.4 Hz, 2H), 4.35-4.51 (m, 2H), 4.70-4.80 (m, 1H), 5.78 (s, 1H), 7.14 (s, 1H), 8.11 (s, 1H), 8.36 (d, J=2.4 Hz, 1H), 8.55 (d, J=2.4 Hz, 1H), 9.08 (s, 1H), 11.45 (s, 1H). MS m/z ([M+H]⁺) 396.

Step 3: 7-(3,4-dihydro-2H-pyrano[2,3-b]pyridin-6-yl)-5-[2-(dimethylamino)-1-methyl-ethoxy]-3H-benzimidazole-4-carboxamide methanesulfonic acid salt, Example (224)

According to the procedure described in Example 207, Step 3, compound (224b) (14 mg, 0.035 mmol) was converted to Example (224) (12.6 mg, 0.025 mmol, 73%) without further purification. ¹H NMR (400 MHz, DMSO-$d_6$) δ 1.08-1.40 (m, 4H), 1.96-2.02 (m, 2H), 2.31 (s, 3H), 2.83-2.95 (m, 8H), 3.65-3.80 (m, 1H), 4.35 (t, J=4.9 Hz, 2H), 5.28 (bs, 1H), 7.40 (bs, 1H), 7.72-7.91 (m, 2H), 8.21 (bs, 1H), 8.40 (bs, 1H), 8.80 (bs, 1H), 9.61 (bs, 1H), 12.53 (bs, 1H). MS m/z ([M+H]⁺) 396. MS m/z ([M−H]⁻) 394.

Example 225

Synthesis of 7-(3,4-dihydro-2H-pyrano[2,3-b]pyridin-6-yl)-5-[(2S)-2-(dimethylamino)propoxy]-3H-benzimidazole-4-carboxamide methanesulfonic acid salt Example 225

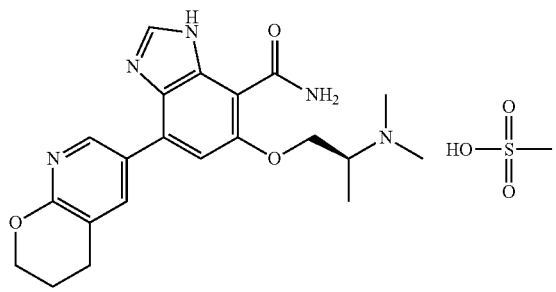

Step 1: 2-amino-4-(3,4-dihydro-2H-pyrano[2,3-b]pyridin-6-yl)-6-[(2S)-2-(dimethylamino)propoxy]-3-nitro-benzamide (225a)

According to the procedure described in Example 104, Step 1, compound (177a) (200 mg, 0.6 mmol) was converted, by reaction with (2S)-2-(dimethylamino)propan-1-ol (150 μL, 1.2 mmol) and after purification by preparative TLC on silica gel (DCM/methanol 95/5), to compound (225a) (130 mg, 0.31 mmol, 52%). ¹H NMR (400 MHz, CDCl₃) δ 1.01 (d, J=6.7 Hz, 3H), 1.99-2.08 (m, 2H), 2.25 (s, 6H), 2.83 (t, J=6.4 Hz, 2H), 3.09-3.16 (m, 1H), 3.92 (t, J=9.8 Hz, 1H), 4.16 (dd, J=10.0/4.3 Hz, 1H), 4.35-4.43 (m, 2H), 5.80 (s, 1H), 6.08 (s, 1H), 7.30 (d, J=2.8 Hz, 1H), 8.03-8.10 (m, 3H), 9.31 (s, 1H). MS m/z ([M+H]⁺) 416.

Step 2: 7-(3,4-dihydro-2H-pyrano[2,3-b]pyridin-6-yl)-5-[(2S)-2-(dimethylamino)propoxy]-3H-benzimidazole-4-carboxamide (225b)

According to the procedure described in Example 218, Step 2, compound (225a) (130 mg, 0.31 mmol) was converted, after purification by preparative TLC on silica gel (DCM/MeOH 9/1+2% ammonia), to compound (225b) (35 mg, 0.09 mmol, 28%). ¹H NMR (400 MHz, CDCl₃) δ 1.09 (d, J=6.7 Hz, 3H), 2.02-2.11 (m, 2H), 2.32 (s, 6H), 2.97 (t, J=6.5 Hz, 2H), 3.20 (bs, 1H), 4.04 (t, J=9.3 Hz, 1H), 4.31 (dd, J=9.7/4.4 Hz, 1H), 4.42 (t, J=5.1 Hz, 2H), 5.78 (bs, 1H), 7.06 (s, 1H), 8.10 (s, 1H), 8.33 (d, J=2.4 Hz, 1H), 8.55 (d, J=2.4 Hz, 1H), 9.35 (bs, 1H), 11.51 (bs, 1H). MS m/z ([M+H]⁺) 396.

Step 3: 7-(3,4-dihydro-2H-pyrano[2,3-b]pyridin-6-yl)-5-[(2S)-2-(dimethylamino)propoxy]-3H-benzimidazole-4-carboxamide methanesulfonic acid salt, Example (225)

According to the procedure described in Example 207, Step 3, compound (225b) (35 mg, 0.09 mmol) was converted to Example (225) (35 mg, 0.07 mmol, 89%) without further purification. ¹H NMR (400 MHz, DMSO-$d_6$) δ 1.37 (d, J=6.8 Hz, 3H), 1.96-2.09 (m, 2H), 2.34 (s, 3H), 2.83-2.95 (m, 8H), 3.97-4.04 (m, 1H), 4.35-4.38 (m, 2H), 4.52-4.59 (m, 2H), 7.41 (s, 1H), 7.95 (s, 2H), 8.27 (s, 1H), 8.55 (s, 1H), 8.70 (s, 1H), 9.85 (bs, 1H). MS m/z ([M+H]⁺) 396. MS m/z ([M−H]⁻) 394.

Example 226

Synthesis of 7-(3,4-dihydro-2H-pyrano[2,3-b]pyridin-6-yl)-5-[(2R)-2-(dimethylamino)propoxy]-3H-benzimidazole-4-carboxamide methanesulfonic acid salt Example 226

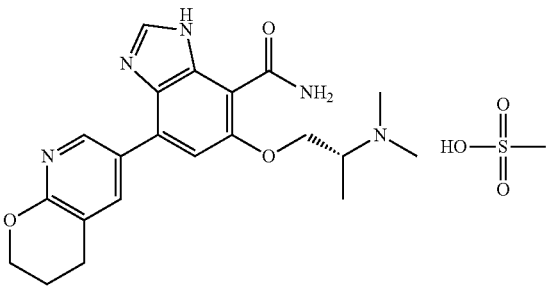

Step 1: 2-amino-4-(3,4-dihydro-2H-pyrano[2,3-b]pyridin-6-yl)-6-[(2R)-2-(dimethylamino)propoxy]-3-nitro-benzamide (226a)

According to the procedure described in Example 104, Step 1, compound (177a) (233 mg, 0.7 mmol) was converted, by reaction with (2R)-2-(dimethylamino)propan-1-ol (145 mg, 1.4 mmol) and after purification by preparative TLC on silica gel (DCM/methanol 95/5), to compound (226a) (167 mg, 0.402 mmol, 57%). MS m/z ([M+H]⁺) 416.

Step 2: 7-(3,4-dihydro-2H-pyrano[2,3-b]pyridin-6-yl)-5-[(2R)-2-(dimethylamino)propoxy]-3H-benzimidazole-4-carboxamide (226b)

According to the procedure described in Example 218, Step 2, compound (226a) (167 mg, 0.402 mmol) was converted, after purification by preparative TLC on silica gel (DCM/MeOH 9/1+1% ammonia), to compound (226b) (54 mg, 0.14 mmol, 35%). ¹H NMR (400 MHz, DMSO-$d_6$) δ 0.99 (d, J=6.7 Hz, 3H), 1.95-2.02 (m, 2H), 2.22 (s, 6H), 2.90 (t, J=6.4 Hz, 2H), 3.09 (bs, 1H), 4.07 (t, J=9.6 Hz, 1H), 4.31-4.37 (m, 2H), 4.41 (dd, J=10.2/4.4 Hz, 1H), 7.31 (s, 1H), 7.54 (bs, 1H), 8.11 (d, J=0.9 Hz, 1H), 8.40 (d, J=2.4 Hz, 1H), 8.86 (d, J=2.4 Hz, 1H), 8.90 (bs, 1H), 12.37 (s, 1H). MS m/z ([M+H]⁺) 396.

Step 3: 7-(3,4-dihydro-2H-pyrano[2,3-b]pyridin-6-yl)-5-[(2R)-2-(dimethylamino)propoxy]-3H-benzimidazole-4-carboxamide methanesulfonic acid salt, Example (226)

According to the procedure described in Example 207, Step 3, compound (226b) (52 mg, 0.131 mmol) was converted to Example (226) (64 mg, 0.130 mmol, 99%) without further purification. $^1$H NMR (400 MHz, CD$_3$OD) δ 1.45 (d, J=6.8 Hz, 3H), 2.06-2.17 (m, 2H), 2.71 (s, 3H), 2.88-2.97 (m, 3H), 2.98-3.09 (m, 5H), 3.97-4.02 (m, 1H), 4.45-4.54 (m, 3H), 4.65 (dd, J=11.8/3.9 Hz, 1H), 7.36 (s, 1H), 8.14 (s, 1H), 8.40 (s, 1H), 8.48 (d, J=2.3 Hz, 1H). MS m/z ([M+H]$^+$) 396. MS m/z ([M–H]$^-$) 394.

Example 227

Synthesis of 5-[2-(dimethylamino)ethyl-methyl-amino]-7-(1-ethyl-7-fluoro-benzimidazol-5-yl)-3H-benzimidazole-4-carboxamide

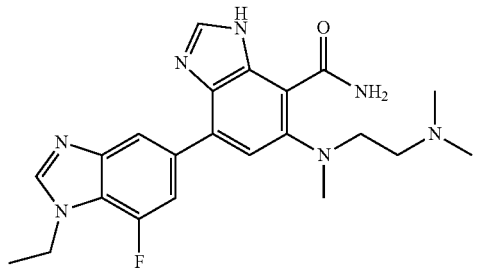

Example 227

According to the procedure described in Example 156, Step 2, compound (124g) (234 mg, 0.69 mmol) was converted, by reaction with 1-ethyl-7-fluoro-5-(4,4,5,5-tetramethyl-1,3,2-dioxaborolan-2-yl)-1H-benzo[d]imidazole (200 mg, 0.69 mmol) and after purification by chromatography on silica gel (DCM/MeOH 8/2+1% ammonia), to Example (227) (161 mg, 0.38 mmol, 55%) as a yellow glassy oil. $^1$H NMR (400 MHz, CDCl$_3$) δ 1.57 (t, J=7.2 Hz, 3H), 2.24 (s, 6H), 2.50 (t, J=6.3 Hz, 2H), 2.80 (s, 3H), 3.24 (t, J=6.4 Hz, 2H), 4.41 (q, J=7.3 Hz, 2H), 5.98 (bs, 1H), 7.45 (s, 1H), 7.91 (s, 1H), 7.96 (dd, J=12.7/1.3 Hz, 1H), 8.09 (d, J=1.3 Hz, 1H), 8.18 (s, 1H), 10.57-10.76 (m, 1H), 11.68 (bs, 1H). MS m/z ([M+H]$^+$) 424. MS m/z ([M–H]$^-$) 422.

Example 228

Synthesis of 5-[2-(dimethylamino)ethyl-methyl-amino]-7-(6-methoxy-3-pyridyl)-3H-benzimidazole-4-carboxamide

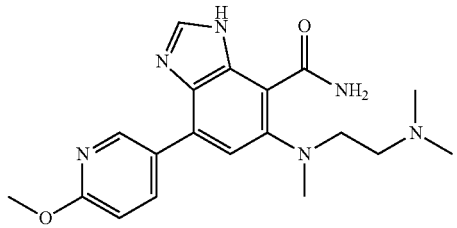

Example 228

According to the procedure described in Example 115, Step 2, compound (124g) (276 mg, 0.81 mmol) was converted, by reaction with 6-methoxy-3-pyridinylboronic acid (124 mg, 0.81 mmol) and after purification by chromatography on silica gel (DCM/MeOH 8/2+1% ammonia), to Example (228) (104 mg, 0.28 mmol, 35%) as a yellow glassy oil. $^1$H NMR (400 MHz, CD$_3$OD) δ 2.25 (s, 6H), 2.52 (t, J=7.0 Hz, 2H), 2.81 (d, J=3.1 Hz, 3H), 3.28 (t, J=7.0 Hz, 2H), 3.98 (s, 3H), 6.93 (d, J=8.9 Hz, 1H), 7.44 (s, 1H), 8.22 (s, 1H), 8.24 (d, J=5.8 Hz, 1H), 8.71 (d, J=2.4 Hz, 1H). MS m/z ([M+H]$^+$) 369. MS m/z ([M–H]$^-$) 367.

Example 229

Synthesis of 5-[2-(dimethylamino)ethyl-methyl-amino]-7-(3-pyridyl)-3H-benzimidazole-4-carboxamide

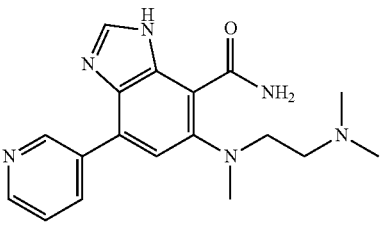

Example 229

According to the procedure described in Example 115, Step 2, compound (124g) (276 mg, 0.81 mmol) was converted, by reaction with 3-pyridinylboronic acid (100 mg, 0.81 mmol) and after purification by chromatography on silica gel (DCM/MeOH 8/2+1% ammonia), to Example (229) (91 mg, 0.27 mmol, 33%) as a yellow glassy oil. $^1$H NMR (400 MHz, CD$_3$OD) δ 2.36 (s, 6H), 2.62-2.66 (m, 2H), 2.85 (s, 3H), 3.32-3.38 (m, 2H), 7.55 (s, 1H), 7.60 (dd, J=8.0/4.9 Hz, 1H), 8.27 (s, 1H), 8.39 (d, J=8.0 Hz, 1H), 8.60 (dd, J=4.9/1.6 Hz, 1H), 9.10 (bs, 1H). MS m/z ([M+H]$^+$) 339. MS m/z ([M–H]$^-$) 337.

Example 230

Synthesis of 5-[2-(dimethylamino)ethyl-methyl-amino]-7-(5-pyrrolidin-1-yl-3-pyridyl)-3H-benzimidazole-4-carboxamide

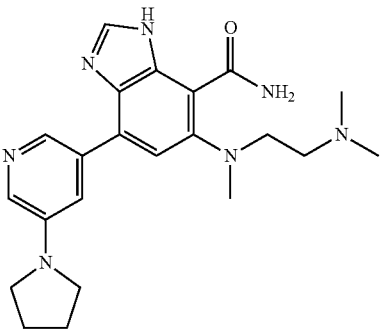

Example 230

According to the procedure described in Example 115, Step 2, compound (124g) (177 mg, 0.52 mmol) was converted, by reaction with 5-pyrrolidinopyridine-3-boronic acid (100 mg, 0.52 mmol) and after purification by chromatography on silica gel (DCM/MeOH 8/2+1% ammonia), to Example (230) (135 mg, 0.33 mmol, 64%) as a yellow glassy oil. $^1$H NMR (400 MHz, CDCl$_3$) δ 2.04-2.09 (m, 4H), 2.27 (s, 6H), 2.52 (t, J=6.4 Hz, 2H), 2.80 (s, 3H), 3.25 (t, J=6.4 Hz, 2H), 3.38-3.45 (m, 4H), 5.93-6.04 (m, 1H), 7.40 (s, 1H), 7.65 (dd, J=2.9/1.8 Hz, 1H), 8.03 (d, J=2.9 Hz, 1H), 8.16 (s, 1H), 8.33 (d, J=1.8 Hz, 1H), 10.67 (d, J=4.5 Hz, 1H), 11.65 (bs, 1H). MS m/z ([M+H]$^+$) 408. MS m/z ([M−H]$^−$) 406.

Example 231

Synthesis of 7-(1-cyclopentylbenzimidazol-5-yl)-5-[2-(dimethylamino)ethyl-methyl-amino]-3H-benzimidazole-4-carboxamide

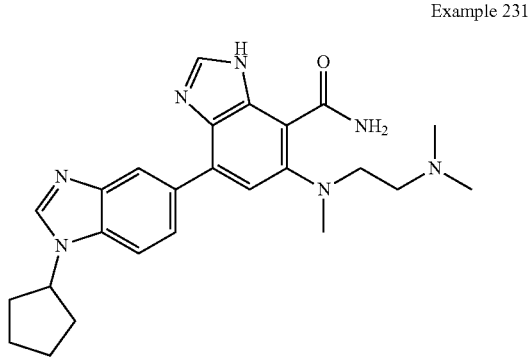 [SMILES: CN(C)CCN(C)c1cc(-c2ccc3c(c2)ncn3C2CCCC2)c2nc[nH]c2c1C(N)=O]

Example 231

Step 1: 4-bromo-N-cyclopentyl-2-nitroaniline (231a)

Cyclopentylamine (1.35 ml, 13.6 mmol) then K$_2$CO$_3$ (3.8 g, 27.3 mmol) were added to a stirred solution of 4-Bromo-1-fluoro-2-nitrobenzene (3.0 g, 13.6 mmol) in DMF (30 ml) under a nitrogen atmosphere. The solution was allowed to cool to room temperature and water was added. The mixture was extracted with EtOAc, dried over sodium sulfate and concentrated to give an orange oily solid. This was triturated with hexane to give compound (231a) (2.74 g, 9.6 mmol, 71%) as an orange solid. $^1$H NMR (400 MHz, CDCl$_3$) δ 1.62-1.76 (m, 4H), 1.77-1.89 (m, 2H), 2.10-2.14 (m, 2H), 3.96 (d, J=5.8 Hz, 1H), 6.82 (d, J=9.2 Hz, 1H), 7.49 (dd, J=9.2/2.4 Hz, 1H), 8.11 (s, 1H), 8.33 (d, J=2.4 Hz, 1H). MS m/z ([M+H]$^+$) 285/287.

Step 2: 4-bromo-N1-cyclopentyl-benzene-1,2-diamine (231b)

According to the procedure described in Example 123, Step 2, compound (231a) (2.74 g, 9.6 mmol) was converted to compound (231b) (2.6 g, 10.2 mmol, 100%) as a brown oil which was used in the next step without further purification. MS m/z ([M+H]$^+$) 255/257.

Step 3: 5-bromo-1-cyclopentyl-benzimidazole (231c)

According to the procedure described in Example 125, Step 3, compound (231b) (2.6 g, 10.2 mmol) was converted, after purification by chromatography on silica gel (AcOEt/Petroleum Ether 7/2) to compound (231c) (1.91 g, 7.21 mmol, 71%) as a grey oil. $^1$H NMR (400 MHz, CDCl$_3$) δ 1.82-1.98 (m, 4H), 2.01-2.10 (m, 2H), 2.25-2.39 (m, 2H), 4.67-4.82 (m, 1H), 7.35 (dd, J=8.6/0.5 Hz, 1H), 7.43 (dd, J=8.6/1.8 Hz, 1H), 7.99 (dd, J=1.8/0.5 Hz, 1H), 8.09 (s, 1H). MS m/z ([M+H]$^+$) 265/267.

Step 4: 1-cyclopentyl-5-(4,4,5,5-tetramethyl-1,3,2-dioxaborolan-2-yl)benzimidazole (231d)

According to the procedure described in Example 123, Step 4, compound (231c) (1.29 g, 5.1 mmol) was converted, after trituration in hexane, to compound (231d) (140 mg, 0.45 mmol, 13%) as an off-white solid. $^1$H NMR (400 MHz, CDCl$_3$) δ 1.28 (s, 12H), 1.78-2.47 (m, 8H), 4.86 (bs, 1H), 7.53 (bs, 1H), 7.83 (bs, 1H), 8.38 (bs, 2H). MS m/z ([M+H]$^+$) 313.

Step 5: 7-(1-cyclopentylbenzimidazol-5-yl)-5-[2-(dimethylamino)ethyl-methyl-amino]-3H-benzimidazole-4-carboxamide, Example (231)

According to the procedure described in Example 115, Step 2, compound (124g) (153 mg, 0.45 m mol) was converted, by reaction with compound (231d) (140 mg, 0.45 mmol) and after purification by chromatography on silica gel (DCM/MeOH 8/2+1% ammonia), to Example (231) (98 mg, 0.22 mmol, 49%) as a yellow oily solid. $^1$H NMR (400 MHz, CDCl$_3$) δ 1.74-1.80 (m, 2H), 1.85-1.92 (m, 2H), 1.97-2.08 (m, 2H), 2.18-2.26 (m, 8H), 2.45-2.50 (m, 2H), 2.74 (s, 3H), 3.17-3.22 (m, 2H), 4.73 (q, J=7.1 Hz, 1H), 5.83 (bs, 1H), 7.38 (s, 1H), 7.52 (d, J=8.5 Hz, 1H), 7.95 (s, 1H), 8.05-8.15 (m, 2H), 8.17 (d, J=1.6 Hz, 1H), 10.58 (bs, 1H), 11.54 (bs, 1H). MS m/z ([M+H]$^+$) 446. MS m/z ([M−H]$^−$) 444.

Example 232

Synthesis of 7-(1-cyclohexylbenzimidazol-5-yl)-5-[(1-methylpyrrolidin-2-yl)methoxy]-3H-benzimidazole-4-carboxamide methanesulfonic acid salt

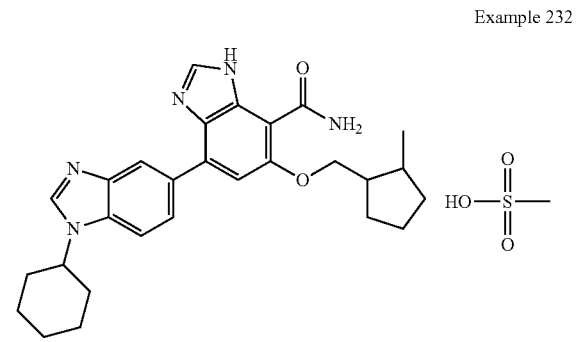

Example 232

Step 1: 2-amino-4-(1-cyclohexylbenzimidazol-5-yl)-6-[(1-methylpyrrolidin-2-yl)methoxy]-3-nitro-benzamide (232a)

According to the procedure described in Example 104, Step 1, compound (160d) (600 mg, 1.5 mmol) was converted, by reaction with N-Methyl prolinol (313 mg, 2.7 mmol), to compound (232a) (620 mg, 1.26 mmol, 83%) as an orange solid. $^1$H NMR (400 MHz, CDCl$_3$) δ 1.38-1.50

(m, 4H), 1.69-1.77 (m, 6H), 1.88-1.96 (m, 4H), 2.11-2.22 (m, 2H), 2.27 (s, 3H), 2.42-2.54 (m, 1H), 2.95-3.15 (m, 1H), 4.08-4.19 (m, 2H), 5.58-5.68 (m, 1H), 6.16 (s, 1H), 7.12 (dd, J=8.4/1.7 Hz, 1H), 7.33-7.38 (m, 1H), 7.74 (dd, J=1.7/0.6 Hz, 1H), 7.88 (d, J=7.9 Hz, 2H), 7.96 (s, 1H), 8.70 (s, 1H). MS m/z ([M+H]$^+$) 473.

Step 2: 7-(1-cyclohexylbenzimidazol-5-yl)-5-[(1-methylpyrrolidin-2-yl)methoxy]-3H-benzimidazole-4-carboxamide (232b)

According to the procedure described in Example 170, Step 3, compound (232a) (620 mg, 1.26 mmol) was converted, after purification by chromatography on silica gel (DCM/MeOH 9/1) and trituration in ethyl acetate, to compound (232b) (328 mg, 0.69 mmol, 55%) as a light brown/orange solid. $^1$H NMR (400 MHz, DMSO-d$_6$) δ 1.20-1.36 (m, 1H), 1.47-1.57 (m, 2H), 1.66-1.79 (m, 3H), 1.84-2.01 (m, 8H), 2.07-2.10 (m, 2H), 2.35 (s, 3H), 3.05 (s, 1H), 4.20-4.23 (m, 1H), 4.35-4.57 (m, 2H), 7.34 (s, 1H), 7.63 (s, 1H), 7.75 (d, J=8.7 Hz, 1H), 8.13 (d, J=5.2 Hz, 2H), 8.39 (s, 1H), 8.46 (s, 1H), 8.53 (s, 1H), 12.35 (s, 1H). MS m/z ([M+H]$^+$) 473.

Step 3: 7-(1-cyclohexylbenzimidazol-5-yl)-5-[(1-methylpyrrolidin-2-yl)methoxy]-3H-benzimidazole-4-carboxamide methanesulfonic acid salt, Example (232)

According to the procedure described in Example 207, Step 3, compound (232b) (308 mg, 0.65 mmol) was converted, after trituration in ethyl acetate, to Example (232) (320 mg, 0.56 mmol, 86%) as a beige solid. $^1$H NMR (400 MHz, DMSO-d$_6$) δ 1.22-1.39 (m, 1H), 1.49-1.64 (m, 2H), 1.75-1.78 (m, 1H), 1.84-2.04 (m, 7H), 2.10-2.18 (m, 3H), 2.30-2.34 (m, 1H), 2.35 (s, 3H), 3.01 (s, 3H), 3.19-3.21 (m, 1H), 3.99-4.06 (m, 1H), 4.53-4.73 (m, 3H), 7.41 (s, 1H), 7.90 (s, 2H), 8.05 (d, J=8.7 Hz, 1H), 8.18 (d, J=8.6 Hz, 1H), 8.38 (s, 1H), 8.59 (s, 1H), 9.11 (s, 1H), 9.95 (bs, 1H). MS m/z ([M+H]$^+$) 473. MS m/z ([M−H]$^-$) 471.

Example 233

Synthesis of 7-(3,4-dihydro-2H-pyrano[2,3-b]pyridin-6-yl)-5-[(1-methylpyrrolidin-2-yl)methoxy]-3H-benzimidazole-4-carboxamide methanesulfonic acid salt Example 233

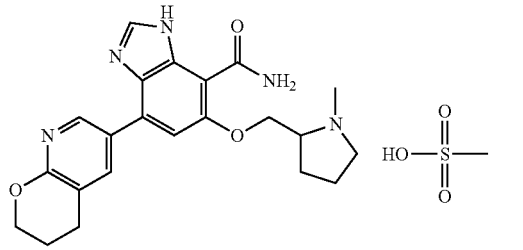

Step 1: 2-amino-4-(3,4-dihydro-2H-pyrano[2,3-b]pyridin-6-yl)-6-[(1-methylpyrrolidin-2-yl)methoxy]-3-nitro-benzamide (233a)

According to the procedure described in Example 104, Step 1, compound (177a) (550 mg, 1.66 mmol) was converted, by reaction with N-Methyl prolinol (400 mg, 3.48 mmol), to compound (233a) (900 mg, 2.1 mmol, 100%) which was used in the next step without further purification. $^1$H NMR (400 MHz, CDCl$_3$) δ 1.66-1.87 (m, 6H), 1.92-2.02 (m, 4H), 2.52 (s, 1H), 2.71-2.78 (m, 2H), 3.01 (d, J=8.1 Hz, 1H), 3.97-4.11 (m, 1H), 4.15 (dd, J=9.6/2.4 Hz, 1H), 4.24-4.40 (m, 1H), 5.56 (s, 1H), 6.02 (s, 1H), 7.21 (dd, J=2.3/1.1 Hz, 1H), 7.85-8.18 (m, 3H), 8.72 (s, 1H). MS m/z ([M+H]$^+$) 428.

Step 2: 7-(3,4-dihydro-2H-pyrano[2,3-b]pyridin-6-yl)-5-[(1-methylpyrrolidin-2-yl)methoxy]-3H-benzimidazole-4-carboxamide (233b)

According to the procedure described in Example 170, Step 3, compound (233a) (900 mg, 2.1 mmol) was converted, after purification by chromatography on silica gel (DCM/MeOH 85/15+1% ammonia), to compound (233b) (300 mg, 0.74 mmol, 44%) as a light brown/orange solid. $^1$H NMR (400 MHz, DMSO-d$_6$) δ 1.72-1.89 (m, 3H), 1.95-2.05 (m, 3H), 2.25-2.45 (m, 4H), 2.89 (t, J=6.4 Hz, 2H), 3.03-3.19 (m, 2H), 4.20-4.28 (m, 1H), 4.34 (dd, J=5.8/4.4 Hz, 2H), 4.47 (dd, J=10.1/3.5 Hz, 1H), 7.32 (s, 1H), 7.67 (bs, 1H), 8.12 (d, J=0.9 Hz, 1H), 8.40 (d, J=2.4 Hz, 2H), 8.86 (d, J=2.4 Hz, 1H), 12.40 (s, 1H). MS m/z ([M+H]$^+$) 408.

Step 3: 7-(3,4-dihydro-2H-pyrano[2,3-b]pyridin-6-yl)-5-[(1-methylpyrrolidin-2-yl)methoxy]-3H-benzimidazole-4-carboxamide methanesulfonic acid salt, Example (233)

According to the procedure described in Example 215, Step 4, compound (233b) (176 mg, 0.433 mmol) was converted to Example (233) (204 mg, 0.405 mmol, 80%) without further purification. $^1$H NMR (400 MHz, DMSO-d$_6$) δ 1.89-2.03 (m, 4H), 2.07-2.15 (m, 1H), 2.27-2.36 (m, 4H), 2.89 (m, 2H), 2.98 (t, J=4.4 Hz, 3H), 3.14-3.25 (m, 1H), 3.60-3.71 (m, 1H), 3.97-4.06 (m, 1H), 4.35 (m, 2H), 4.49 (dd, J=3.2/11.5 Hz, 1H), 4.66 (dd, J=3.2/11.5 Hz, 1H), 7.33 (s, 1H), 7.71-7.88 (m, 1H), 7.93 (s, 1H), 8.33 (s, 2H), 8.75 (s, 1H), 9.84 (bs, 1H), 12.65 (bs, 1H). MS m/z ([M+H]$^+$) 408. MS m/z ([M−H]$^-$) 406.

Example 234

Synthesis of 7-(1-cyclohexyl-7-fluoro-benzimidazol-5-yl)-5-[2-(dimethylamino)ethyl-methyl-amino]-3H-benzimidazole-4-carboxamide Example 234

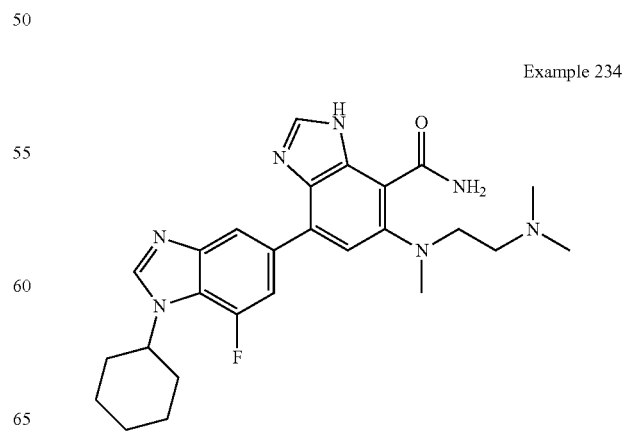

Step 1:
4-bromo-N-cyclohexyl-2-fluoro-6-nitro-aniline (234a)

Cyclohexylamine (2.75 ml, 24 mmol) was added to a stirred solution of 4-bromo-2-fluoro-6-nitroanisole (3.0 g, 12 mmol) in DMF (20 ml) under a nitrogen atmosphere. The mixture was stirred for 3 hours at room temperature then at 50° C. overnight. The mixture was concentrated. Hexane was added to the residue and the precipitate filtered off. The filtrate was concentrated to give compound (234a) (3.0 g, 9.46 mmol, 79%) as an orange oil. $^1$H NMR (400 MHz, CDCl$_3$) δ 1.23-1.48 (m, 5H), 1.60-1.69 (m, 1H), 1.72-1.84 (m, 2H), 2.02-2.06 (m, 2H), 3.80-3.88 (m, 1H), 7.31 (dd, J=13.2/2.4 Hz, 1H), 8.14 (dd, J=2.4/1.8 Hz, 1H). MS m/z ([M+H]$^+$) 317.

Step 2:
5-bromo-N2-cyclohexyl-3-fluoro-benzene-1,2-diamine (234b)

According to the procedure described in Example 123, Step 2, compound (234a) (3.0 g, 9.46 mmol) was converted to (234b) (2.3 g, 8.0 mmol, 85%) as a brown oil. MS m/z ([M+H]$^+$) 288.

Step 3:
5-bromo-1-cyclohexyl-7-fluoro-benzimidazole (234c)

According to the procedure described in Example 125, Step 3, compound (234b) (2.3 g, 8.0 mmol) was converted, after purification by chromatography on silica gel (EtOAc/Petroleum ether 6/4), to compound (234c) (2.0 g, 6.7 mmol, 84%) as a pale brown oily solid. $^1$H NMR (400 MHz, CDCl$_3$) δ 1.24-1.40 (m, 1H), 1.49-1.54 (m, 2H), 1.70-1.89 (m, 3H), 1.95-2.05 (m, 2H), 2.22-2.35 (m, 2H), 4.40-4.48 (m, 1H), 7.18 (dd, J=11.0/1.6 Hz, 1H), 7.77 (d, J=1.6 Hz, 1H), 8.07 (s, 1H). MS m/z ([M+H]$^+$) 298.

Step 4: 1-cyclohexyl-7-fluoro-5-(4,4,5,5-tetramethyl-1,3,2-dioxaborolan-2-yl)benzimidazole (234d)

According to the procedure described in Example 123, Step 4, compound (234c) (1.0 g, 3.37 mmol) was converted, after trituration in hexane, to compound (234d) (680 mg, 1.98 mmol, 59%) as an off-white solid. $^1$H NMR (400 MHz, CDCl$_3$) δ 1.29-1.35 (m, 1H), 1.38 (s, 12H), 1.45-1.61 (m, 2H), 1.75-1.80 (m, 3H), 1.94-2.05 (m, 2H), 2.29 (d, J=12.1 Hz, 2H), 4.49-4.54 (m, 1H), 7.42 (d, J=12.2 Hz, 1H), 8.07 (s, 2H). MS m/z ([M+H]$^+$) 345.

Step 5: 7-(1-cyclohexyl-7-fluoro-benzimidazol-5-yl)-5-[2-(dimethylamino)ethyl-methyl-amino]-3H-benzimidazole-4-carboxamide, Example (234)

According to the procedure described in Example 115, Step 2, compound (124g) (198 mg, 0.58 mmol) was converted, by reaction with compound (234d) (200 mg, 0.58 mmol) and after purification by preparative TLC (DCM/MeOH 9/1+1% ammonia), to Example (234) (28 mg, 0.058 mmol, 10%) was obtained as a white solid. $^1$H NMR (400 MHz, CD$_3$OD) δ 1.29-1.45 (m, 1H), 1.51-1.63 (m, 2H), 1.78-2.04 (m, 5H), 2.25-2.30 (m, 8H), 2.54-2.58 (m, 2H), 2.84 (s, 3H), 3.32-3.38 (m, 2H), 4.59 (tt, J=11.7, 3.8 Hz, 1H), 7.52 (s, 1H), 7.72 (d, J=13.0 Hz, 1H), 8.03 (s, 1H), 8.24 (s, 1H), 8.37 (s, 1H). MS m/z ([M+H]$^+$) 478. MS m/z ([M−H]$^-$) 476.

Example 235

Synthesis of 7-(1-cyclohexylbenzimidazol-5-yl)-5-[[(2S)-1-methylpyrrolidin-2-yl]methoxy]-3H-benzimidazole-4-carboxamide methanesulfonic acid salt

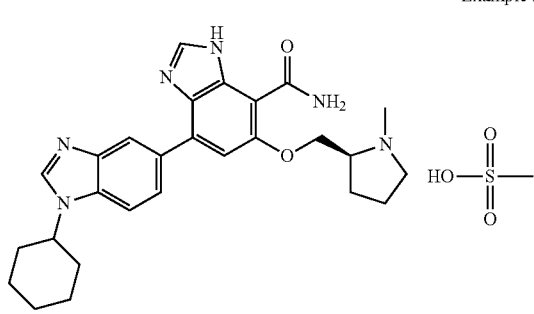

Example 235

Step 1: 2-amino-4-(1-cyclohexylbenzimidazol-5-yl)-6-[[(2S)-1-methylpyrrolidin-2-yl]methoxy]-3-nitro-benzamide (235a)

According to the procedure described in Example 104, Step 1, compound (160d) (600 mg, 1.5 mmol) was converted, by reaction with (S)-N-Methylprolinol (313 mg, 2.7 mmol), to compound (235a) (740 mg, 1.5 mmol, 100%) as an orange solid. $^1$H NMR (400 MHz, CDCl$_3$) δ 1.46-1.62 (m, 4H), 1.77-1.88 (m, 6H), 1.99-2.03 (m, 4H), 2.23-2.28 (m, 2H), 2.37 (s, 3H), 2.59 (s, 1H), 3.05-3.15 (m, 1H), 4.18-4.27 (m, 2H), 5.67 (s, 1H), 6.25 (s, 1H), 7.21 (dd, J=8.4/1.7 Hz, 1H), 7.45 (dd, J=8.4/0.7 Hz, 1H), 7.84 (dd, J=1.7/0.6 Hz, 1H), 7.98 (d, J=11.0 Hz, 1H), 8.06 (bs, 2H), 8.82 (s, 1H). MS m/z ([M+H]$^+$) 493.

Step 2: 7-(1-cyclohexylbenzimidazol-5-yl)-5-[[(2S)-1-methylpyrrolidin-2-yl]methoxy]-3H-benzimidazole-4-carboxamide (235b)

According to the procedure described in Example 170, Step 3, compound (235a) (740 mg, 1.5 mmol) was converted, after purification by chromatography on silica gel (DCM/MeOH 9/1+1% of ammonia) and recrystallization in MeOH, to compound (235b) (280 mg, 0.59 mmol, 40%) as a pale yellow solid. $^1$H NMR (400 MHz, DMSO-d$_6$) δ 1.25-1.35 (m, 1H), 1.45-1.61 (m, 2H), 1.67-1.80 (m, 3H), 1.80-2.03 (m, 6H), 2.02-2.12 (m, 2H), 2.25 (q, J=8.6 Hz, 1H), 2.34 (s, 3H), 2.58-2.65 (m, 1H), 3.00-3.08 (m, 1H), 4.18-4.23 (m, 1H), 4.35-4.53 (m, 2H), 7.34 (s, 1H), 7.62 (d, J=2.7 Hz, 1H), 7.76 (d, J=8.6 Hz, 1H), 8.09-8.16 (m, 2H), 8.39 (s, 1H), 8.46 (d, J=2.7 Hz, 1H), 8.54 (d, J=1.7 Hz, 1H), 12.35 (s, 1H). MS m/z ([M+H]$^+$) 473.

Step 3: 7-(1-cyclohexylbenzimidazol-5-yl)-5-[[(2S)-1-methylpyrrolidin-2-yl]methoxy]-3H-benzimidazole-4-carboxamide methanesulfonic acid salt, Example (235)

According to the procedure described in Example 207, Step 3, compound (235b) (256 mg, 0.54 mmol) was converted, after trituration in ethyl acetate, to Example (235) (349 mg, 0.61 mmol, 100%) as a beige solid. $^1$H NMR (400 MHz, DMSO-d$_6$) δ 1.25-1.35 (m, 1H), 1.51-1.67 (m, 2H), 1.77 (d, J=13.0 Hz, 1H), 1.88-2.04 (m, 6H), 2.05-2.15 (m, 1H), 2.20-2.28 (m, 2H), 2.37 (s, 3H), 3.02 (s, 3H), 3.61-3.75 (m, 2H), 4.00-4.10 (m, 2H), 4.55-4.60 (m, 1H), 4.68-4.85 (m, 2H), 7.51 (s, 1H), 7.91 (s, 1H), 8.03 (s, 1H), 8.11-8.20 (m, 1H), 8.28 (d, J=8.7 Hz, 1H), 8.54 (s, 1H), 8.89 (s, 1H), 9.66 (s, 1H), 9.94 (s, 1H). MS m/z ([M+H]$^+$) 473. MS m/z ([M−H]$^−$) 471.

Example 236

Synthesis of 7-(1-cyclohexylbenzimidazol-5-yl)-5-[[(2R)-1-methylpyrrolidin-2-yl]methoxy]-3H-benzimidazole-4-carboxamide methanesulfonic acid salt

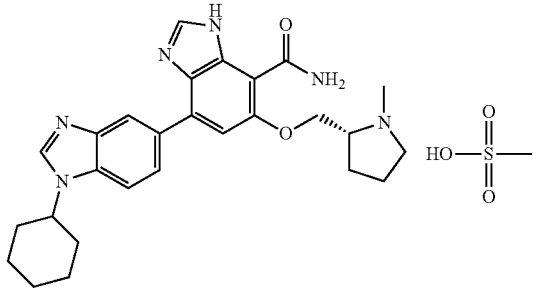

Example 236

Step 1: 2-amino-4-(1-cyclohexylbenzimidazol-5-yl)-6-[[(2R)-1-methylpyrrolidin-2-yl]methoxy]-3-nitrobenzamide (236a)

According to the procedure described in Example 104, Step 1, compound (160d) (600 mg, 1.5 mmol) was converted, by reaction with (R)-N-Methylprolinol (313 mg, 2.7 mmol), to compound (236a) (740 mg, 1.5 mmol, 100%) as an orange solid. $^1$H NMR (400 MHz, CDCl$_3$) δ 1.48-1.55 (m, 4H), 1.78-1.89 (m, 6H), 1.98-2.05 (m, 4H), 2.26 (d, J=12.3 Hz, 2H), 2.37 (s, 3H), 2.58-2.65 (m, 1H), 3.00-3.15 (m, 1H), 4.18-4.28 (m, 2H), 5.66 (s, 1H), 6.25 (s, 1H), 7.21 (dd, J=8.4/1.7 Hz, 1H), 7.42-7.47 (m, 1H), 7.84 (d, J=1.8 Hz, 1H), 8.03 (d, J=26.5 Hz, 3H), 8.82 (s, 1H). MS m/z ([M+H]$^+$) 493.

Step 2: 7-(1-cyclohexylbenzimidazol-5-yl)-5-[[(2R)-1-methylpyrrolidin-2-yl]methoxy]-3H-benzimidazole-4-carboxamide (236b)

According to the procedure described in Example 170, Step 3, compound (236a) (740 mg, 1.5 mmol) was converted, after purification by chromatography on silica gel (DCM/MeOH 9/1+1% of ammonia) and recrystallization in MeOH, to compound (236b) (181 mg, 0.38 mmol, 25%) as a beige solid. $^1$H NMR (400 MHz, DMSO-d$_6$) δ 1.23-1.41 (m, 1H), 1.45-1.62 (m, 2H), 1.68-1.78 (m, 3H), 1.83-2.02 (m, 6H), 2.04-2.15 (m, 2H), 2.25 (q, J=8.7 Hz, 1H), 2.34 (s, 3H), 2.58-2.64 (m, 1H), 2.99-3.09 (m, 1H), 4.15-4.26 (m, 1H), 4.36-4.53 (m, 2H), 7.34 (s, 1H), 7.59-7.66 (m, 1H), 7.76 (d, J=8.6 Hz, 1H), 8.13 (d, J=10.1 Hz, 2H), 8.39 (s, 1H), 8.46 (d, J=2.7 Hz, 1H), 8.54 (d, J=1.7 Hz, 1H), 12.35 (s, 1H). MS m/z ([M+H]$^+$) 473.

Step 3: 7-(1-cyclohexylbenzimidazol-5-yl)-5-[[(2R)-1-methylpyrrolidin-2-yl]methoxy]-3H-benzimidazole-4-carboxamide methanesulfonic acid salt, Example (236)

According to the procedure described in Example 207, Step 3, compound (236b) (163 mg, 0.34 mmol) was converted, after trituration in ethyl acetate, to Example (236) (178 mg, 0.31 mmol, 91%) as a beige solid. $^1$H NMR (400 MHz, DMSO-d$_6$) δ 1.25-1.32 (m, 1H), 1.45-1.60 (m, 2H), 1.70-1.80 (m 1H), 1.85-2.00 (m, 6H), 2.10-2.14 (m, 3H), 2.34 (s, 3H), 3.01 (s, 3H), 3.17-3.24 (m, 2H), 3.65-3.69 (m, 2H), 4.50-4.59 (m, 2H), 4.65-4.70 (m, 1H), 7.40 (s, 1H), 7.89 (s, 2H), 8.00 (d, J=8.7 Hz, 1H), 8.16 (d, J=8.6 Hz, 1H), 8.34 (s, 1H), 8.56 (s, 1H), 9.00 (s, 1H), 9.90 (s, 1H). MS m/z ([M+H]$^+$) 473. MS m/z ([M−H]$^−$) 471.

Example 237

Synthesis of 5-[2-(dimethylamino)ethyl-methylamino]-7-(5-propyl-3-pyridyl)-3H-benzimidazole-4-carboxamide

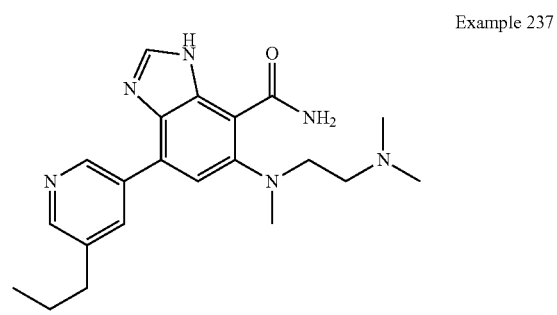 [SMILES: CCCc1cncc(-c2cc(N(C)CCN(C)C)c(C(N)=O)c3[nH]cnc23)c1]

Example 237

Step 1: 3-propyl-5-(4,4,5,5-tetramethyl-1,3,2-dioxaborolan-2-yl)pyridine (237a)

According to the procedure described in Example 123, Step 4, 3-bromo-5-(n-propyl)pyridine (500 mg, 2.5 mmol) was converted, after trituration in hexane, to compound (237a) (165 mg, 0.67 mmol, 27%) as an off-white solid. $^1$H NMR (400 MHz, CDCl$_3$) δ 0.97 (t, J=7.3 Hz, 3H), 1.37 (s, 12H), 1.57-1.80 (m, 2H), 2.53-2.69 (m, 2H), 7.94 (s, 1H), 8.52 (s, 1H), 8.80 (s, 1H). MS m/z ([M+H]$^+$) 248.

Step 2: 5-[2-(dimethylamino)ethyl-methyl-amino]-7-(5-propyl-3-pyridyl)-3H-benzimidazole-4-carboxamide, Example (237)

According to the procedure described in Example 115, Step 2, compound (124g) (227 mg, 0.67 mmol) was converted, by reaction with compound (237a) (165 mg, 0.67 mmol) and after purification by flash chromatography on silica gel (DCM/MeOH 9/1+1% ammonia), to Example (237) (67 mg, 0.18 mmol, 26%) as a white solid. $^1$H NMR (400 MHz, CD$_3$OD) δ 1.02 (t, J=7.3 Hz, 3H), 1.69-1.82 (m, 2H), 2.24 (s, 6H), 2.43-2.55 (m, 2H), 2.72-2.80 (m, 2H), 2.84 (s, 3H), 3.26-3.34 (m, 2H), 7.53 (s, 1H), 8.25 (t, J=2.1 Hz, 1H), 8.27 (d, J=1.9 Hz, 1H), 8.45 (d, J=2.1 Hz, 1H), 8.92 (d, J=2.1 Hz, 1H). MS m/z ([M+H]$^+$) 381. MS m/z ([M−H]$^−$) 379.

Example 238

Synthesis of 5-[2-(dimethylamino)ethyl-methyl-amino]-7-(5-ethoxy-3-pyridyl)-3H-benzimidazole-4-carboxamide Example 238

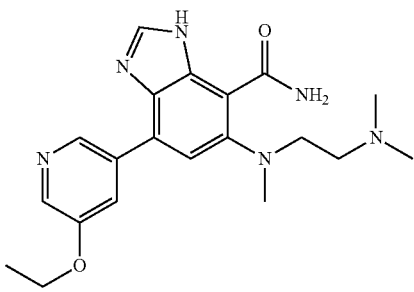

Step 1: 3-ethoxy-5-(4,4,5,5-tetramethyl-1,3,2-dioxaborolan-2-yl)pyridine (238a)

According to the procedure described in Example 123, Step 4, 3-bromo-5-ethoxypyridine (500 mg, 2.5 mmol) was converted, after trituration in hexane, to compound (238a) (320 mg, 1.29 mmol, 51%) as a brown solid. $^1$H NMR (400 MHz, CDCl$_3$) δ 1.33 (s, 12H), 1.39-1.46 (m, 3H), 4.09-4.13 (m, 2H), 7.58 (d, J=3.3 Hz, 1H), 8.28 (t, J=3.3 Hz, 1H), 8.46 (d, J=3.6 Hz, 1H). MS m/z ([M+H]$^+$) 250.

Step 2: 5-[2-(dimethylamino)ethyl-methyl-amino]-7-(5-ethoxy-3-pyridyl)-3H-benzimidazole-4-carboxamide, Example (238)

According to the procedure described in Example 115, Step 2, compound (124g) (290 mg, 0.90 mmol) was converted, by reaction with compound (238a) (305 mg, 1.2 mmol) and after purification by flash chromatography on silica gel (DCM/MeOH 9/1+1% ammonia), to Example (238) (65 mg, 0.17 mmol, 19%) as a pale brown oily foam. $^1$H NMR (400 MHz, CDCl$_3$) δ 1.48 (t, J=7.0 Hz, 3H), 2.26 (s, 6H), 2.52 (t, J=6.5 Hz, 2H), 2.81 (s, 3H), 3.25 (t, J=6.5 Hz, 2H), 4.21 (q, J=7.0 Hz, 2H), 6.17 (s, 1H), 7.40 (s, 1H), 8.03 (dd, J=2.8/1.8 Hz, 1H), 8.18 (s, 1H), 8.32 (d, J=2.8 Hz, 1H), 8.66 (d, J=1.9 Hz, 1H), 10.63 (s, 1H), 11.74 (s, 1H). MS m/z ([M+H]$^+$) 383. MS m/z ([M−H]$^-$) 381.

Example 239

Synthesis of 7-(3,4-dihydro-2H-pyrano[2,3-b]pyridin-6-yl)-5-[(1-methyl-2-piperidyl)methoxy]-3H-benzimidazole-4-carboxamide methanesulfonic acid salt

Step 1: 2-amino-4-(3,4-dihydro-2H-pyrano[2,3-b]pyridin-6-yl)-6-[(1-methyl-2-piperidyl)methoxy]-3-nitro-benzamide (239a)

According to the procedure described in Example 104, Step 1, compound (177a) (166 mg, 0.5 mmol) was converted, by reaction with 2-methyl-2-piperidine methanol (0.13 mL, 1 mmol) and after purification by preparative TLC on silica gel (DCM/methanol 95/5), to compound (239a) (190 mg, 0.43 mmol, 86%). $^1$H NMR (400 MHz, DMSO-d$_6$) δ 1.18-1.33 (m, 1H), 1.42-1.60 (m, 3H), 1.63-1.76 (m, 2H), 1.89-1.99 (m, 2H), 2.07 (m, 1H), 2.18 (s, 4H), 2.81 (m, 3H), 4.17 (dd, J=10.4/2.6 Hz, 1H), 4.26-4.36 (m, 3H), 6.36 (s, 1H), 7.42 (s, 2H), 7.52 (d, J=2.5 Hz, 1H), 7.73 (s, 1H), 7.93 (d, J=2.5 Hz, 1H), 8.41 (s, 1H). MS m/z ([M+H]$^+$) 442.

Step 2: 7-(3,4-dihydro-2H-pyrano[2,3-b]pyridin-6-yl)-5-[(1-methyl-2-piperidyl)methoxy]-3H-benzimidazole-4-carboxamide (239b)

According to the procedure described in Example 19, Step 4, compound (239a) (190 mg, 0.43 mmol) was converted, after purification by preparative TLC on silica gel twice (DCM/methanol 80/20), to compound (239b) (30 mg, 0.071 mmol, 16%). $^1$H NMR (400 MHz, DMSO-d$_6$) δ 1.25-1.35 (m, 1H), 1.50 (d, J=12.7 Hz, 1H), 1.61 (d, J=12.6 Hz, 1H), 1.66-1.80 (m, 3H), 1.96-2.02 (m, 2H), 2.12-2.17 (m, 1H), 2.20-2.29 (m, 4H), 2.85-2.93 (m, 3H), 4.29-4.37 (m, 3H), 4.41-4.48 (m, 1H), 7.60 (s, 1H), 8.11 (s, 2H), 8.40 (d, J=2.4 Hz, 1H), 8.57 (s, 1H), 8.86 (d, J=2.4 Hz, 1H), 12.37 (s, 1H). MS m/z ([M+H]$^+$) 422.

Step 3: 7-(3,4-dihydro-2H-pyrano[2,3-b]pyridin-6-yl)-5-[(1-methyl-2-piperidyl)methoxy]-3H-benzimidazole-4-carboxamide methanesulfonic acid salt, Example (239)

According to the procedure described in Example 207, Step 3, compound (239b) (30 mg, 0.07 mmol) was converted to Example (239) (15.3 mg, 0.029 mmol, 41%) without further purification. $^1$H NMR (400 MHz, DMSO-d$_6$) δ 1.45-1.90 (m, 4H), 1.96-2.10 (m, 2H), 2.32 (s, 3H), 2.74 (s, 3H), 2.90 (m, 6H), 3.15-3.22 (m, 1H), 3.48-3.65 (m, 1H), 4.34-4.48 (m, 2H), 4.75 (m, 1H), 7.04 (s, 1H), 7.16 (s, 1H), 7.29 (s, 1H), 7.89 (bs, 1H), 7.96 (s, 1H), 8.38 (bs, 1H), 8.73 b (s, 1H). MS m/z ([M+H]$^+$) 422. MS m/z ([M−H]$^-$) 420.

Example 240

Synthesis of 5-[2-(dimethylamino)ethyl-methyl-amino]-7-(5,6,7,8-tetrahydroquinolin-3-yl)-3H-benzimidazole-4-carboxamide Example 239

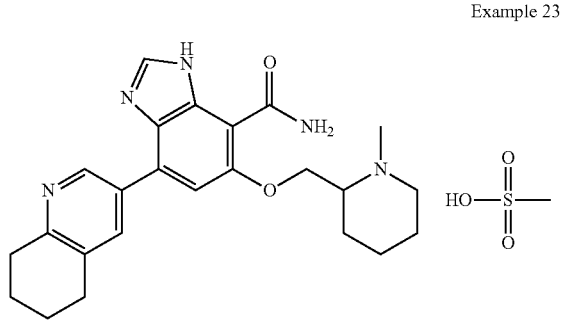

Example 240

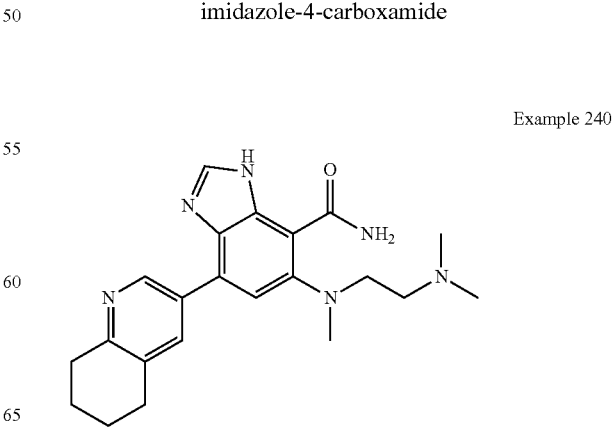

Step 1: 3-(4,4,5,5-tetramethyl-1,3,2-dioxaborolan-2-yl)-5,6,7,8-tetrahydroquinoline (240a)

According to the procedure described in Example 123, Step 4, 3-bromo-5,6,7,8-tetrahydroquinoline (250 mg, 1.18 mmol) was converted to compound (240a) (250 mg, >100%) which was used as crude in the next without further purification. MS m/z ([M+H]$^+$) 260.

Step 2: 5-[2-(dimethylamino)ethyl-methyl-amino]-7-(5,6,7,8-tetrahydroquinolin-3-yl)-3H-benzimidazole-4-carboxamide, Example (240)

According to the procedure described in Example 115, Step 2, compound (124g) (340 mg, 1.10 mmol) was converted, by reaction with compound (240a) (250 mg, 1.18 mmol) and after purification by preparative TLC on silica gel (DCM/Methanol 90/10+2% ammonia), to Example (240) (18.11 mg, 0.046 mmol, 5%). $^1$H NMR (400 MHz, CDCl$_3$) δ 1.79-1.89 (m, 2H), 1.89-1.97 (m, 2H), 2.21 (s, 6H), 2.46 (t, J=6.3 Hz, 2H), 2.77 (s, 3H), 2.89 (t, J=6.3 Hz, 2H), 2.98 (t, J=6.4 Hz, 2H), 3.20 (t, J=6.3 Hz, 2H), 5.99 (bs, 1H), 7.33 (s, 1H), 8.12 (d, J=2.2 Hz, 1H), 8.14 (s, 1H), 8.80 (d, J=2.2 Hz, 1H), 10.66 (bs, 1H), 11.66 (bs, 1H). MS m/z ([M+H]$^+$) 393. MS m/z ([M−H]$^-$) 391.

Examples of Pharmaceutical Compositions:

Solutions for IV administration have been prepared by diluting the compounds of examples 2, 6, 20, 24, 96, 123, 173, 182, 200, 203, 210, 214 and 215 at 1-20 mg/mL in a 10% solution of Hydroxypropyl-beta-cyclodextrine in sterile water, with or without addition of vancomycin (dose 5 mg/mL) or colistin (dose 75 mg/ml).

Solutions for IV administration have been prepared by diluting 500 mg of compound of examples 96, 123, 173, 182, 200, 203, 210, 214 and 215 in 100 mL of a 10% solution of Hydroxypropyl-beta-cyclodextrine in sterile water.

Pharmacological Study of the Compounds of the Invention

The effect of the compounds of the invention on DltA enzymes has been based on the measure of their inhibition of DltA activity in vitro. To this end, recombinant proteins DltA were expressed and purified after cloning of the genes of *S. aureus, E. faecalis, E. faecium* and *S. agalactiae* as described thereafter. The capacity of the compounds of the invention to inhibit DltA enzymatic activity was assessed using the DltA assays as described below:

The dltA gene was amplified from chromosomal DNA of *S. aureus, E. faecalis, E. faecium* and *S. agalactiae* and introduced into *E. coli* BL21 (Invitrogen, Carlsbad, Calif.) following manufacturer's instruction. Bacteria were grown at 37° C. under aerobic conditions and isopropyl-beta-D-thiogalactopyranoside (IPTG) was added to 0.5-1 mM when OD$_{600}$ of the bacterial culture had reached 0.5. After a further incubation for 3 hours, cells were harvested by centrifugation. Purification of the recombinant DltA protein was performed by affinity chromatography on nickel-nitrilotriacetic acid (Ni-NTA) column following manufacturer's instructions (Qiagen). Fractions containing recombinant DltA protein were adjusted to 50% glycerol and stored at −20° C. until use.

The binding potency of the inhibitors against DltA enzyme was assessed by IC$_{50}$ determination in an in vitro DltA activity assay. The assay buffer "AB" contained 50 mM Hepes pH8.0, 10 mM MgCl$_2$, 50 mM KCl, 0.012% Triton-X100, 10 mM DTT and 100 nM Myelin-basic protein. The following components were added in a white polystyrene Costar plate up to a final volume of 30 μL: 3 μL DMSO, or inhibitor dissolved in DMSO and 27 μL DltA enzyme in AB. After 30 min of pre-incubation at room temperature, 30 μL of Substrates mix in AB were added in each well to a final volume of 60 μL. This reaction mixture was then composed of DltA (produced in house from *S. aureus, E. faecalis, E. faecium* and *S. agalactiae*), 0.5 mM D-Alanine (Sigma), 0.5-5 μM ATP (Sigma) and 0.05 u/ml inorganic pyrophosphatase (Sigma) in assay buffer. After typically 1-2 hours of incubation at room temperature (conversion rate around 30%), 30 μL of the revelation mix were added to a final volume of 90 μL, including the following constituents at the respective final concentrations: 10000 u/ml luciferase (Sigma), 30 μM D-luciferin (Sigma), 100 μM N-acetylcysteamine (Aldrich). Luminescence intensity was immediately measured on a Fluostar Optima (BMG) (excitation 360 nm, emission 520 nm) and converted into inhibition percentages. For IC$_{50}$ determinations (Inhibitory Concentration 50%) the inhibitor was added at 6 to 10 different concentrations and the related inhibitions were fitted to a classical Langmuir equilibrium model using XLFIT (IDBS).

For compounds interfering with the luminescent signal (quenching), the same experiment without DltA enzyme was performed to allow quenching determination and correction.

The effect of the compounds of the invention on controlling the bacterial D-alanylation of the wall teichoic acids (WTA) and lipoteichoic acids (LTA) has been based on the measure of their inhibition of bacterial D-alanylation in vitro. The strains used in this study were: *S. aureus* SA113, *E. faecalis* ATCC 29212, *E. faecium* (VRE) SF090703 and *S. agalactiae* NEM316.

To this end, the compounds to be tested were prepared in deionised water/DMSO (60/40) solutions and distributed (75 μl) in a sterile deep-well culture microplate.

The bacteria were grown on tryptic soy agar (TSA) over-night. Isolated colonies were cultured in 10 ml of cation-adjusted Mueller-Hinton broth (ca-MHB) for the staphylococci and Todd-Hewitt+0.5% yeast extracts (THYE) for the streptococci and the enterococci up to an optical density (OD) typically of 0.15. These exponentially growing bacteria were finally diluted to 5e5 cfu/ml and added in each well (1.425 ml) for incubation with the compounds at 37° C., with 5% CO2 for streptococci and enterococci. After 16-20H culture, bacteria were pelleted, heat inactivated in 0.5 ml MES 0.1M pH6.0+TritonX100 0.1% for 30 min at 100° C. Resulting mixture was centrifuged/washed 3 times in 0.25 ml of MES 0.1M pH6.0. The resulting pellet of cell-wall extracts was resuspended in 0.5 ml of a mild alkaline buffer TRIS 0.2M pH8.5+200 μM TritonX100 and heated for 3H at 60° C. in an air oven to allow D-Alanine (D-Ala) hydrolysis from the teichoic acids. The mixture was finally centrifuged to perform D-Ala titration in the supernatant, and phosphate titration in the pellet.

D-Ala content was measured with a coupled enzymatic assay using D-amino acid oxidase (DAAO) and peroxidase (HRP) associated with Amplex-Red® as fluorophore (method modified from Kontinen et al., J. Biol. Chem 2000). Dosages were carried out in black polystyrene 96-well microplates in 100 μl final volume. Assay buffer was TRIS 0.2M pH8.5+200 μM TritonX100. Reagents were added in the microplate in the following order: D-Ala samples (50 μl) or DAla scale for reference, Revelation mix (40 μl) containing FAD 5 μM, HRP 1 u/ml, 5 μM Amplex Red (final concentrations). Background signal was read at this point, followed by addition of 0.15 u/ml DAAO (10 μl). Plate was finally read approximately 90 min later (Fluostar Optima from BMG, excitation at 544 nm, emission at 590 nm). Data treatment: background was subtracted from 90 min-signal, then a D-Ala standard curve was established with the references, and used to convert signals into D-Ala concentrations for each sample. Finally, results were expressed in nmol DAla/sample.

Phosphate (Pi) titration was adapted from Zhou et al. (J. Lipid Res., 1992, 33, 1233) and started by Pi hydrolysis from cell wall extracts: pellets coming from DAla hydrolysis were incubated for 2.5 hours in 1 ml 0.9M $H_2SO_4$/0.16M $HClO_4$. Titrations were carried out in clear polystyrene plates in 200 µl final volume. Reagents were added in the microplate in the following order: Pi hydrolysed samples or KH2PO4 scale for reference (100 µl), Ammonium molybdate 6 mM (50 µl), and Malachite green 0.12 mM+Tween20 0.06% (50 µl). The OD at 620 nm was read 20 min later (Fluostar Optima from BMG). A Pi standard curve was established with the references, and used to convert samples signals into Pi concentrations. Finally, results were expressed in nmol Pi/sample.

Final treatment: for each sample (treated and untreated), the normalised ratio DAla/Pi was calculated and used to calculate the inhibition percentages of D-Alanylation in the treated samples compared to the untreated ones. The $EC_{50}$ was defined as the dose of DltA inhibitor leading to 50% inhibition of teichoic acids D-Alanylation for the considered strain.

Inhibitory Activities of the Compounds of Formula (I)
$IC_{50}$ of the compounds of formula (I) on *S. aureus* DltA, *E. feacalis* DltA, *E. feacium* DltA and *S. Agalactiae* DltA

| Examples | S. aureus DltA $IC_{50}$ (µM) | E. feacalis DltA $IC_{50}$ (µM) | E. feacium DltA $IC_{50}$ (µM) | S. Agalactiae DltA $IC_{50}$ (µM) |
|---|---|---|---|---|
| 2 | 0.066 | 0.018 | 0.086 | 0.50 |
| 3 | 0.20 | 0.052 | 0.10 | 1.4 |
| 4 | 0.52 | 0.38 | 2.2 | 3.1 |
| 6 | 0.011 | 0.018 | 0.029 | 0.18 |
| 10 | 0.16 | 0.072 | 0.12 | 3.8 |
| 11 | 0.0014 | 0.019 | 0.03 | 0.26 |
| 19 | 0.033 | 0.46 | 1.8 | 1.9 |
| 20 | 0.012 | 0.056 | 0.17 | 0.29 |
| 24 | 0.038 | 0.57 | 3.7 | 5.2 |
| 34 | 0.11 | 0.079 | 0.17 | 0.38 |
| 36 | 0.08 | 0.17 | 1.1 | 3.8 |
| 43 | 0.085 | 0.03 | 0.17 | 6.3 |
| 44 | 0.049 | 0.071 | 0.096 | 1.5 |
| 55 | 0.25 | 0.15 | 0.36 | 0.76 |
| 58 | 0.18 | 0.12 | 0.23 | 8.6 |
| 61 | 0.24 | 0.11 | 0.23 | 4.7 |
| 63 | 0.049 | 0.043 | 0.083 | 2.0 |
| 64 | 0.065 | 0.027 | 0.068 | 0.71 |
| 65 | 0.066 | 0.036 | 0.14 | 1.8 |
| 77 | 0.077 | 0.041 | 0.11 | 1.3 |
| 78 | 0.21 | 0.17 | 0.59 | 5.4 |
| 88 | 0.033 | 0.026 | 0.079 | 0.69 |
| 92 | 0.19 | 0.24 | 0.60 | 8.2 |
| 104 | 0.053 | 0.084 | 0.39 | 2.4 |
| 106 | 0.034 | 0.018 | 0.076 | 0.50 |
| 111 | 0.28 | 0.61 | 1.1 | 11 |
| 117 | 0.023 | 0.016 | 0.027 | 0.56 |
| 122 | 0.059 | 0.031 | 0.082 | 1.8 |
| 123 | 0.0069 | 0.0082 | 0.041 | 0.97 |
| 126 | 0.057 | 0.056 | 0.24 | 1.8 |
| 127 | 0.025 | 0.0029 | 0.018 | 0.14 |
| 130 | 0.073 | 0.036 | 0.17 | 0.79 |
| 131 | 0.075 | 0.04 | 0.23 | 1.9 |
| 134 | 0.25 | 0.024 | 0.12 | 1.1 |
| 135 | 0.017 | 0.069 | 0.045 | 0.84 |
| 136 | 0.0057 | 0.0043 | 0.025 | 0.36 |
| 142 | 0.016 | 0.015 | 0.073 | 0.92 |
| 144 | 0.039 | 0.017 | 0.12 | 0.63 |
| 152 | 0.013 | 0.016 | 0.058 | 2.2 |
| 161 | 0.013 | 0.0081 | 0.069 | 1.2 |
| 163 | 0.014 | 0.0054 | 0.034 | 0.78 |
| 165 | 0.029 | 0.026 | 0.09 | 2.2 |
| 171 | 0.015 | 0.0067 | 0.04 | 0.35 |
| 176 | 0.94 | 0.035 | 0.19 | 2.3 |
| 177 | 0.17 | 0.045 | 0.32 | 1.1 |
| 181 | 0.051 | 0.0092 | 0.16 | 0.18 |
| 182 | 0.0048 | 0.0045 | 0.059 | 0.48 |
| 198 | 0.0068 | 0.0083 | 0.073 | 1.4 |
| 200 | 0.022 | 0.071 | 0.8 | 5.4 |
| 202 | 0.11 | 0.095 | 0.19 | 2 |
| 203 | 0.028 | 0.0073 | 0.11 | 0.35 |
| 204 | 0.017 | 0.012 | 0.058 | 1.4 |
| 205 | 0.14 | 0.0092 | 0.03 | 4.3 |
| 208 | 0.23 | 0.061 | 0.28 | 1.9 |
| 210 | 0.0062 | 0.0051 | 0.036 | 0.15 |
| 211 | 0.024 | 0.0068 | 0.002 | 0.47 |
| 214 | 0.004 | 0.004 | 0.032 | 0.39 |
| 215 | 0.0008 | 0.0014 | 0.0057 | 0.086 |
| 222 | 0.047 | 0.009 | 0.067 | 0.18 |
| 227 | 0.032 | 0.03 | 0.083 | 1.3 |
| 230 | 0.064 | 0.03 | 0.28 | 2.1 |
| 233 | 0.0065 | 0.0047 | 0.024 | 0.13 |
| 236 | 0.0004 | 0.0014 | 0.0036 | 0.091 |

The invention claimed is:
1. A compound selected from the group consisting of:
{(S)-1-[7-(1-Cyclohexyl-1H-benzimidazol-5-yl)-3H-imidazo[4,5-b]pyridin-5-yl]-pyrrolidin-3-yl}-methanol,
(3R,4R)-1-[7-(1-Cyclohexyl-1H-benzimidazol-5-yl)-3H-imidazo[4,5-b]pyridin-5-yl]-4-hydroxymethyl-piperidin-3-ol,
{1-[7-(1-Cyclohexyl-1H-benzimidazol-5-yl)-3H-imidazo[4,5-b]pyridin-5-yl]-piperidin-4-yl}-methanol,
2-[7-(1-Cyclohexyl-1H-benzimidazol-5-yl)-3H-imidazo[4,5-b]pyridin-5-ylamino]-ethanol,
{1-[7-(1-Cyclohexyl-1H-benzimidazol-5-yl)-3H-imidazo[4,5-b]pyridin-5-yl]-azetidin-3-yl}-methanol,
{1-[7-(1-Cyclohexyl-1H-benzimidazol-5-yl)-3H-imidazo[4,5-b]pyridin-5-yl]-4-hydroxymethyl-piperidin-4-yl}-methanol,
7-(1-Cyclohexyl-1H-benzimidazol-5-yl)-5-(hexahydro-pyrrolo[3,4-c]pyrrol-2-yl)-3H-imidazo[4,5-b]pyridine,
{(S)-1-[4-(1-Cyclohexyl-3H-benzimidazol-5-yl)-1H-imidazo[4,5-c]pyridin-6-yl]-pyrrolidin-3-yl}-methanol,
{1-[4-(1-Cyclohexyl-1H-benzimidazol-5-yl)-1H-imidazo[4,5-c]pyridin-6-yl]-4-hydroxymethyl-piperidin-4-yl}-methanol,
{1-[4-(1-Cyclohexyl-1H-benzimidazol-5-yl)-1H-imidazo[4,5-c]pyridin-6-yl]-piperidin-4-yl}-methanol,
4-(1-cyclohexyl-1H-benzimidazol-5-yl)-1H-imidazo[4,5-c]pyridine-7-carboxamide,
[(S)-1-(1'-Cyclohexyl-7-nitro-1H,1'H-[4,5']bibenzimidazolyl-6-yl)-pyrrolidin-3-yl]-methanol,
(3R,4R)-1-(1'-Cyclohexyl-7-nitro-1H,1'H-[4,5']bibenzimidazolyl-6-yl)-4-hydroxymethyl-piperidin-3-ol,
(3R,4R)-1-(7-Amino-1'-cyclohexyl-1H,1'H-[4,5']bibenzimidazolyl-6-yl)-4-hydroxymethyl-piperidin-3-ol,
Methyl 1'-Cyclohexyl-6-((S)-3-hydroxymethyl-pyrrolidin-1-yl)-1H,1'H-[4,5']bibenzimidazolyl-7-carboxylate,
1'-Cyclohexyl-6-((S)-3-hydroxymethyl-pyrrolidin-1-yl)-1H,1'H-[4,5']bibenzimidazolyl-7-carboxylic acid,
1'-Cyclohexyl-6-((S)-3-hydroxymethyl-pyrrolidin-1-yl)-1H,1'H-[4,5']bibenzimidazolyl-7-carbonitrile,
[(S)-1-(1'-Cyclohexyl-7-trifluoromethyl-1H,1'H-[4,5']]bibenzimidazolyl-6-yl)-pyrrolidin-3-yl]-methanol,

[1-(1'-Cyclohexyl-7-trifluoromethyl-1H,1'H-[4,5']]bibenzimidazolyl-6-yl)-piperidin-4-yl]-methanol, 1'-Cyclohexyl-6-(hexahydro-pyrrolo[3,4-c]pyrrol-2-yl)-1H,1'H-[4,5']bibenzimidazolyl-7-carbonitrile, 1'-Cyclohexyl-6-((S)-3-hydroxymethyl-pyrrolidin-1-yl)-1H,1'H-[4,5']bibenzimidazolyl-7-carboxamide, 1'-Cyclohexyl-6-[3-(2-hydroxy-ethyl)-pyrrolidin-1-yl]-1H,1'H-[4,5']bibenzimidazolyl-7-carboxamide, 1'-Cyclohexyl-6-(2-hydroxy-ethylamino)-1H,1'H-[4,5']]bibenzimidazolyl-7-carbonitrile, N-[2-(7-Cyano-1'-cyclohexyl-1H,1'H-[4,5']]bibenzimidazolyl-6-ylamino)-ethyl]-acetamide, 1'-Cyclohexyl-6-piperazin-1-yl-1H,1'H-[4,5']]bibenzimidazolyl-7-carbonitrile, 1'-Cyclohexyl-6-(4-methyl-piperazin-1-yl)-1H,1'H-[4,5']]bibenzimidazolyl-7-carbonitrile, 1'-Cyclohexyl-6-(2-dimethylamino-ethoxy)-1H,1'H-[4,5']]bibenzimidazolyl-7-carbonitrile, 1'-Cyclohexyl-6-[(2-dimethylamino-ethyl)-methyl-amino]-1H,1'H-[4, 5']bibenzimidazolyl-7-carboxamide, 1'-Cyclohexyl-6-[(2-hydroxy-ethyl)-methyl-amino]-1H,1'H-[4,5']bibenzimidazolyl-7-carboxamide, 6-[(2-dimethylamino-ethyl)-methyl-amino]-1'-(tetrahydro-pyran-3-yl)-1H,1'H-[4,5']bibenzimidazolyl-7-carboxamide, 1'-((1R,2R)-2-fluoro-cyclohexyl)-6-[methyl-(2-methylamino-ethyl)-amino]-1H,1'H-[4,5']bibenzimidazolyl-7-carboxamide, 1'-Cyclohexyl-6-[methyl-(2-pyrrolidin-1-yl-ethyl)-amino]-1H,1'H-[4,5']bibenzimidazolyl-7-carboxamide, 1'-Cyclohexyl-6-[methyl-(1-methyl-pyrrolidin-2-ylmethyl)-amino]-1H,1'H-[4,5']bibenzimidazolyl-7-carboxamide, 1'-Cyclohexyl-6-[(2-diethylamino-ethyl)-methyl-amino]-1H,1'H-[4,5']bibenzimidazolyl-7-carboxamide, 1'-Cyclohexyl-6-[(2-dimethylamino-ethyl)-(2-hydroxy-ethyl)-amino]-1H,1'H-[4,5']bibenzimidazolyl-7-carboxamide, 1'-Cyclohexyl-6-[methyl-(tetrahydro-furan-2-ylmethyl)-amino]-1H,1'H-[45']bibenzimidazolyl-7-carboxamide, 6-[(2-Dimethylamino-ethyl)-methyl-amino]-1'-(2-methoxy-ethyl)-1H,1'H-[4,5']]bibenzimidazolyl-7-carboxamide, rac-1'-((trans)-3-methyl-cyclohexyl)-6-[methyl-(2-methylamino-ethyl)-amino]-1H,1'H-[4,5']bibenzimidazolyl-7-carboxamide, 5-[(2-Dimethylamino-ethyl)-methyl-amino]-7-quinolin-7-yl-3H-benzimidazole-4-carboxamide, 1'-Cyclohexyl-6-(2-dimethylamino-ethoxy)-1H,1'H-[4,5']]bibenzimidazolyl-7-carboxamide, 7-(3-Carbamoyl-4-methoxy-phenyl)-5-[(2-dimethylamino-ethyl)-methyl-amino]-3H-benzimidazole-4-carboxamide, 1'-Ethyl-6-[methyl-(2-methylamino-ethyl)-amino]-1H,1'H-[4,5']bibenzimidazolyl-7-carboxamide, 7-(3,4-Dihydro-2H-pyrano[2,3-b]pyridin-6-yl)-5-[(2-dimethylamino-ethyl)-methyl-amino]-3H-benzimidazole-4-carboxamide, 6-[(2-dimethylamino-ethyl)-methyl-amino]-1H,1'H-[4,5'] bibenzimidazolyl-7-carboxamide, 5-[(2-Dimethylamino-ethyl)-methyl-amino]-7-(1-ethyl-2-oxo-1,2-dihydro-pyridin-4-yl)-3H-benzimidazole-4-carboxamide, 6-[(2-Dimethylamino-ethyl)-methyl-amino]-1'-ethyl-7'-methoxy-1H,1'H-[4,5']]bibenzimidazolyl-7-carboxamide, 1'-Cyclohexyl-6-(2-pyrrolidin-1-yl-ethoxy)-1H,1'H-[4,5']]bibenzimidazolyl-7-carboxamide, 1'-(4,4-Difluoro-cyclohexyl)-6-[(2-dimethylamino-ethyl)-methyl-amino]-1H,1'H-[4,5']bibenzimidazolyl-7-carboxamide, 1'-(2,2-Difluoro-ethyl)-6-[(2-dimethylamino-ethyl)-methyl-amino]-1H,1'H-[4,5']bibenzimidazolyl-7-carboxamide, 7-(3,4-Dihydro-5-oxa-1,2a-diaza-acenaphthylen-7-yl)-5-[(2-dimethylamino-ethyl)-methyl-amino]-3H-benzimidazole-4-carboxamide, 1'-Cyclohexyl-6-[methyl-(2-piperidin-1-yl-ethyl)-amino]-1H,1'H-[4,5']bibenzimidazolyl-7-carboxamide, 1'-Cyclohexyl-6-(2-hydroxy-ethoxy)-1H,1'H-[4,5']bibenzimidazolyl-7-carboxamide, 1'-((1R,2R)-2-Fluoro-cyclohexyl)-6-[(2-hydroxy-ethyl)-methyl-amino]-1H,1'H-[4,5']]bibenzimidazolyl-7-carboxamide, 1'-Ethyl-7'-methoxy-6-[methyl-(2-pyrrolidin-1-yl-ethyl)-amino]-1H,1'H-[4,5']]bibenzimidazolyl-7-carboxamide, 7-(3,4-Dihydro-2H-pyrano[2,3-b]pyridin-6-yl)-5-[methyl-(2-pyrrolidin-1-yl-ethyl)-amino]-3H-benzimidazole-4-carboxamide, 7-(3,4-Dihydro-2H-pyrano[2,3-b]pyridin-6-yl)-5-(2-dimethylamino-ethoxy)-3H-benzimidazole-4-carboxamide, 6-(2-Dimethylamino-ethoxy)-1'-ethyl-1H,1'H-[4,5']] bibenzimidazolyl-7-carboxamide, 4-(5-cyclopropylpyridin-3-yl)-6-((2-(dimethylamino)ethyl)-(methyl)amino)-1H-benzo[d]imidazole-7-carboxamide, 7-(1-butylbenzimidazol-5-yl)-5-[2-(dimethylamino)ethyl-methyl-amino]-3H-benzimidazole-4-carboxamide, 5-[2-(dimethylamino)ethyl-methyl-amino]-7-(1-ethyl-7-fluoro-benzimidazol-5-yl)-3H-benzimidazole-4-carboxamide, 5-[2-(dimethylamino)ethyl-methyl-amino]-7-(5-pyrrolidin-1-yl-3-pyridyl)-3H-benzimidazole-4-carboxamide, 6-[2-(dimethylamino)ethyl-methyl-amino]-4-(1-ethylbenzimidazol-5-yl)-1H-imidazo[4,5-c]pyridine-7-carboxamide, 7-(3,4-dihydro-2H-pyrano[2,3-b]pyridin-6-yl)-5-[(1-methylpyrrolidin-2-yl)methoxy]-3H-benzimidazole-4-carboxamide, 5-[2-(dimethylamino)ethyl-methyl-amino]-7-(1-phenylbenzimidazol-5-yl)-3H-benzimidazole-4-carboxamide, 7-(3,4-dihydro-2H-pyrano[2,3-b]pyridin-6-yl)-5-[(1-methyl-3-piperidyl)oxy]-3H-benzimidazole-4-carboxamide, 7-(3,4-dihydro-2H-pyrano[2,3-b]pyridin-6-yl)-5-[[(2R)-1-methylpyrrolidin-2-yl]methoxy]-3H-benzimidazole-4-carboxamide, 5-[4,4-bis(hydroxymethyl)-1-piperidyl]-7-(1-cyclohexylbenzimidazol-5-yl)-3H-benzimidazole-4-carboxamide, 7-(3,4-dihydro-2H-pyrano[2,3-b]pyridin-6-yl)-5-(2-pyridylmethoxy)-3H-benzimidazole-4-carboxamide, 5-[2-(dimethylamino)ethyl-methyl-amino]-7-[6-(dimethylamino)-3-pyridyl]-3H-benzimidazole-4-carboxamide, 7-[1-[(1R,2R)-2-fluorocyclohexyl]benzimidazol-5-yl]-5-[[(2R)-pyrrolidin-2-yl]methoxy]-3H-benzimidazole-4-carboxamide, 5-[[(2R)-1-methylpyrrolidin-2-yl]methoxy]-7-(1-tetrahydropyran-3-ylbenzimidazol-5-yl)-3H-benzimidazole-4-carboxamide, and 7-(3,4-dihydro-2H-pyrano[2,3-b]pyridin-6-yl)-5-[3-(dimethylamino)-1-piperidyl]-3H-benzimidazole-4-carboxamide, or their salts.

2. A compound and pharmaceutically acceptable addition salts thereof with acids and bases, as defined in claim 1, for use as drug.

3. A compound and pharmaceutically acceptable addition salts thereof with acids and bases, as defined in claim 1, for use as drug for treatment of human or animal Gram-positive bacterial infections.

4. A compound and pharmaceutically acceptable addition salts thereof with acids and bases, as defined in claim 1, for use as drug for treatment of human or animal Gram-positive bacterial infections, in combination with an antibacterial, an antivirulence agent, a drug reinforcing the host innate immunity or a combination of any of them.

5. A compounds and pharmaceutically acceptable addition salts thereof with acids and bases, as defined in claim 1, for use as drugs for treatment of human or animal Gram-positive bacterial infections, in combination with an antibacterial targeting the bacterial cell wall and/or membrane, an antibacterial of the CAMP type, an antibacterial of the glycopeptides type, an antibacterial of the lipopeptides type, and /or in association with immunomodulatory peptide, and/or in association with GM-CSF.

6. Pharmaceutical compositions containing, as active principle, a therapeutically effective amount of at least one compound or a pharmaceutically acceptable addition salt thereof with an acid or a base, as defined in claim 1.

7. Mixtures or pharmaceutical associations comprising, as active principles, at least a compound or a pharmaceutically acceptable addition salt thereof with an acid or a base, as defined in claim 1, and at least an antibacterial, an antivirulence agent or a drug reinforcing the host innate immunity or a combination of any of them.

8. Mixtures or pharmaceutical associations comprising, as active principles, at least a compound or a pharmaceutically acceptable addition salt thereof with an acid or a base, as defined in claim 1, and at least an antibacterial targeting the bacterial cell wall and/or membrane, an antibacterial of the CAMP type, of the glycopeptides type, or of the lipopeptides type, and/or an immunomodulatory peptide, and/or a GM-CSF.

9. A compound of claim 1, wherein the salt is a hydrochloride salt.

10. A compound of claim 1, wherein the salt is amethanasulfonate salt.

* * * * *